United States Patent
Kumaravel et al.

(10) Patent No.: US 10,144,732 B2
(45) Date of Patent: Dec. 4, 2018

(54) ATX MODULATING AGENTS

(71) Applicant: BIOGEN MA INC., Cambridge, MA (US)

(72) Inventors: Gnanasambandam Kumaravel, Cambridge, MA (US); Hairuo Peng, Cambridge, MA (US); Zhili Xin, Cambridge, MA (US)

(73) Assignee: BIOGEN MA INC., Cambridge, MA (US)

( * ) Notice: Subject to any disclaimer, the term of this patent is extended or adjusted under 35 U.S.C. 154(b) by 0 days.

(21) Appl. No.: 15/316,534

(22) PCT Filed: Jun. 5, 2015

(86) PCT No.: PCT/US2015/034388
§ 371 (c)(1),
(2) Date: Dec. 6, 2016

(87) PCT Pub. No.: WO2015/188051
PCT Pub. Date: Dec. 10, 2015

(65) Prior Publication Data
US 2017/0197960 A1   Jul. 13, 2017

Related U.S. Application Data

(60) Provisional application No. 62/008,951, filed on Jun. 6, 2014.

(51) Int. Cl.
*C07D 471/04* (2006.01)
*C07D 487/04* (2006.01)
*C07D 519/00* (2006.01)

(52) U.S. Cl.
CPC .......... *C07D 471/04* (2013.01); *C07D 487/04* (2013.01); *C07D 519/00* (2013.01)

(58) Field of Classification Search
CPC .................................................. C07D 471/04
See application file for complete search history.

(56) References Cited

FOREIGN PATENT DOCUMENTS

| | | |
|---|---|---|
| EP | 2 269 990 A1 | 1/2011 |
| WO | 1996/12720 A1 | 5/1996 |
| WO | 2002/00655 A1 | 1/2002 |

OTHER PUBLICATIONS

Hausmann "Structural basis of substrate discrimination and integrin binding by autotaxin" Nature Structural & Molecular Biology 2011, 18(2), 198-205.*
Pozharskii et. al. Heterocycles in Life and Society Wiley, 1997, pp. 1-6.*
Pitt "Heteroaromatic Rings of the Future" J. Med. Chem. 2009, 52, 2952-2963.*
Ashton et al.; "Dipeptidyl Peptidase IV Inhibitors Derived from Beta-aminoacylpiperidines Bearing a Fused Thiazole, Oxazole, Isoxazole, or Pyrazole"; Bioorganic & Medicinal Chemistry Letters; 15(9):2253-2258 (May 2, 2005).

* cited by examiner

*Primary Examiner* — David K O'Dell
(74) *Attorney, Agent, or Firm* — McCarter & English, LLP; Steven G. Davis; Xin Zhang

(57) ABSTRACT

Compounds of formula (I) can modulate the activity of autotaxin (ATX).

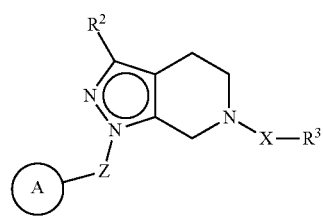

21 Claims, No Drawings

ATX MODULATING AGENTS

RELATED APPLICATIONS

This application is a 35 U.S.C. § 371 national stage filing of International Application No. PCT/US2015/034388, filed Jun. 5, 2015, which claims the benefit of U.S. Provisional Patent Application No. 62/008,951, filed Jun. 6, 2014. The entire contents of each of these application are hereby incorporated by reference.

TECHNICAL FIELD

This invention relates to compounds that are ATX modulating agents, especially ATX inhibitors, and methods of making and using such compounds.

BACKGROUND

Autotaxin (ATX, ENPP2) is a secreted glycoprotein widely present in biological fluids, including blood, cancer ascites, synovial, pleural and cerebrospinal fluids, originally isolated from the supernatant of melanoma cells as an autocrine motility stimulation factor (Stracke, M. L., et al. Identification, purification, and partial sequence analysis of autotaxin, a novel motility-stimulating protein. J Biol Chem 267, 2524-2529 (1992), which is incorporated by reference in its entirety). ATX is encoded by a single gene on human chromosome 8 (mouse chromosome 15) whose transcription, regulated by diverse transcription factors (Hoxa13, NFAT-1 and v-jun), results in four alternatively spliced isoforms ($\alpha$, $\beta$, $\gamma$ and $\delta$). See, for example, Giganti, A., et al Murine and Human Autotaxin alpha, beta, and gamma Isoforms: Gene organization, tissue distribution and biochemical characterization. J Biol Chem 283, 7776-7789 (2008); and van Meeteren, L. A. & Moolenaar, W. H. Regulation and biological activities of the autotaxin-LPA axis. Prog Lipid Res 46, 145-160 (2007); Hashimoto, et al, "Identification and Biochemical Charaterization of a Novel Autotaxin Isoform, ATX$\delta$," J. of Biochemistry Advance Access (Oct. 11, 2011); each of which is incorporated by reference in its entirety.

ATX is synthesized as a prepro-enzyme, secreted into the extracellular space after the proteolytic removal of its N-terminal signal peptide (Jansen, S., el al Proteolytic maturation and activatio of autotaxin (NPP2), a secreted metastasis-enhancing lysophospho lipase D. J Cell Sci 118, 3081-3089 (2005), which is incorporated by reference in its entirety). ATX is a member of the ectonucleotide pyrophosphatase/phosphodiesterase family of ectoenzymes (E-NPP) that hydrolyze phosphodiesterase (PDE) bonds of various nucleotides and derivatives (Stefan, C, Jansen, S. & Bollen, M. NPP-type ectophosphodiesterases: unity in diversity. Trends Biochem Sci 30, 542-550 (2005), which is incorporated by reference in its entirety). The enzymatic activity of ATX was enigmatic, until it was shown to be identical to lysophospholipase D (lysoPLD) (Umezu-Goto, M., et al. Autotaxin has lysophospholipase D activity leading to tumor cell growth and motility by lysophosphatidic acid production. J Cell Biol 158, 227-233 (2002), which is incorporated by reference in its entirety), which is widely present in biological fluids. Since ATX is a constitutively active enzyme, the biological outcome of ATX action will largely depend on its expression levels and the local availability of its substrates. The major lysophospholipid substrate for ATX, lysophosphatidylcholine (LPC), is secreted by the liver and is abundantly present in plasma (at about 100 µM) as a predominantly albumin bound form (Croset, M., Brossard, N., Polette, A. & Lagarde, M. Characterization of plasma unsaturated lysophosphatidylcholines in human and rat Biochem J 345 Pt 1, 61-67 (2000), which is incorporated by reference in its entirety). LPC is also detected in tumor-cell conditioned media (Umezu-Goto, M., et al.), presumably as a constituent of shed microvesicles. ATX, through its lysoPLD activity converts LPC to lysophosphatidic acid (LPA).

LPC is an important inflammatory mediator with recognized effects in multiple cell types and pathophysiological processes. It is a major component of oxidized low density lipoprotein (oxLDL) and it can exist in several other forms including free, micellar, bound to hydrophobic proteins such as albumin and incorporated in plasma membranes. It is produced by the hydrolysis of phosphatidylcholine (PC) by PLA2 with concurrent release of arachidonic acid and in turn of other pro-inflammatory mediators (prostaglandins and leukotrienes). Moreover, LPC externalization constitutes a chemotactic signal to phagocytic cells, while interaction with its receptors can also stimulate lymphocytic responses. LPC has been shown to have therapeutic effects in experimental sepsis, possibly by suppressing endotoxin-induced HMGB1 release from macrophages/monocytes.

LPA is a bioactive phospholipid with diverse functions in almost every mammalian cell line (Moolenaar, W. H., van Meeteren, L. A. & Giepmans, B. N. The ins and outs of lysophosphatidic acid signaling. Bioessays 28, 870-881 (2004), which is incorporated by reference in its entirety). LPA is a major constituent of serum bound tightly to albumin, gelsolin and possibly other as yet unidentified proteins. See, e.g., Goetzl, E. J., et al Gelsolin binding and. cellular presentation of lysophosphatidic acid. J Biol Chem 275, 14573-14578 (2000); and Tigyi, G. & Miledi, R, Lysophosphatidates bound to serum albumin activate membrane currents in *Xenopus* oocytes and neurite retraction in PC12 pheochromocytoma cells. J Biol Chem 267, 21360-21367 (1992); each of which is incorporated by reference in its entirety.

LPA is also found in other biofluids, such as saliva and follicular fluid, and has been implicated in a wide array of functions, such as wound healing, tumor invasion and metastasis, neurogenesis, myelination, astrocytes outgrowth and neurite retraction. The long list of LPA functions was also explained with the discovery that it signals through G-protein coupled receptors (GPCRs), via classical second messenger pathways. Five mammalian cell-surface LPA receptors have been identified so far. The best known are LPA1-3 (namely Edg-2, Edg-4 and Edg7) which are all members of the so-called 'endothelial differentiation gene' (EDG) family of GPCRs (Contos, J. J., Ishii, I. & Chun, J. Lysophosphatidic acid receptors. Mol Pharmacol 58, 1188-1196 (2000), which is incorporated by reference in its entirety). LPA receptors can couple to at least three distinct G proteins ($G_q$, $G_i$ and $G_{12/13}$), which, in turn, feed into multiple effector systems. LPA activates $G_q$ and thereby stimulates phospholipase C (PLC), with subsequent phosphatidylinositol-bisphosphate hydrolysis and generation of multiple second messengers leading to protein kinase C activation and changes in cytosolic calcium. LPA also activates $G_i$, which leads to at least three distinct signaling routes: inhibition of adenylyl cyclase with inhibition of cyclic AMP accumulation; stimulation of the mitogenic RAS-MAPK (mitogen-activated protein kinase) cascade; and activation of phosphatidylinositol 3-kinase (PI3K), leading to activation of the guanosine diphosphate/guanosine triphosphate (GDP/GTP) exchange factor TIAM1 and the downstream RAC GTPase, as well as to activation of the AKT/PKB antiapoptotic pathway. Finally, LPA activates $G_{12/13}$, leading to activation of the small GTPase RhoA, which drives cytoskeletal contraction and cell rounding. So, LPA not only signals via classic second messengers such as calcium, diacylglycerol and cAMP, but it also activates RAS- and RHO-family GTPases, the master switches that control cell proliferation, migration and morphogenesis.

LPA signaling through the RhoA-Rho kinase pathway mediates neurite retraction and inhibition of axon growth. Interfering with LPA signaling has been shown to promote axonal regeneration and functional recovery after CNS injury or cerebral ischemia. (See Broggini, et al., *Molecular Biology of the Cell* (2010), 21:521-537.) It has been reported that addition of LPA to dorsal root fibers in ex vivo culture causes demyelination, whereas LPC fails to cause significant demyelination of nerve fibers in ex vivo cultures without further addition of recombinant ATX to the culture which when added caused significant demyelination at equivalent levels to LPA presumable due to conversion of LPC to LPA through the enzymatic activity of ATX. Moreover, injury induced demyelination was attenuated by about 50% in atx$^{+/-}$ mice (Nagai, et al., *Molecular Pain* (2010), 6:78).

A number of diseases or disorders involve demyelination of the central or peripheral nervous system which can occur for a number of reasons such as immune dysfunction as in multiple sclerosis, encephalomyelitis, Guillain-Barre Syndrome, chronic inflammatory demyelinating polyneuropathy (CIDP), transverse myelitis, and optic neuritis; demyelination due to injury such as spinal cord injury, traumatic brain injury, stroke, acute ischemic optic neuropathy, or other ischemia, cerebral palsy, neuropathy (e.g. neuropathy due to diabetes, chronic renal failure, hypothyroidism, liver failure, or compression of the nerve (e.g. in Bell's palsy)), post radiation injury, and central pontine myelolysis (CPM); inherited conditions such as Charcot-Marie-Tooth disease (CMT), Sjogren-Larsson syndrome, Refsum disease, Krabbe disease, Canavan disease, Alexander disease, Friedreich's ataxia, Pelizaeus-Merzbacher disease, Bassen-Kornzweig syndrome, metachromatic leukodystrophy (MLD), adrenoleukodystrophy, and nerve damage due to pernicious anemia; viral infection such as progressive multifocal leukoencephalopathy (PML), Lyme disease, or tabes *dorsalis* due to untreated syphilis; toxic exposure due to chronic alcoholism (which is a possible cause of Marchiafava-Bignami disease), chemotherapy, or exposure to chemicals such as organophosphates; or dietary deficiencies such as vitamin B12 deficiency, vitamin E deficiency and copper deficiency. Other demyelination disorders may have unknown causes or multiple causes such as trigeminal neuralgia, Marchiafava-Bignami disease and Bell's palsy. One practically successful approach to treating demyelination disorders which are caused by autoimmune dysfunction has been to attempt to limit the extent of demyelination by treating the patient with immunoregulatory drugs. However, typically this approach has merely postponed but not avoided the onset of disability in these patients. Patients with demyelination due to other causes have even fewer treatment options. Therefore, the need exists to develop new treatments for patients with demyelination diseases or disorders.

SUMMARY

The present invention relates to compounds, or pharmaceutically acceptable salts thereof, which inhibit ATX. Without wishing to be bound by any theory, it is believed that LPA inhibits remyelination of neurons that have suffered demyelination due to injury or disease and that inhibition of ATX will prevent the conversion of LPC to LPA and thus allow remyelination to occur. In addition, activation of PLC, ERK and Rho via LPA receptors results in cell proliferation, cell survival and changes in cell morphology. Therefore, inhibition of ATX is expected to be useful for treating demyelination due to injury or disease, as well as for treating proliferative disorders such as cancer.

In one aspect, a compound, or a pharmaceutically acceptable salt thereof, is represented by structural formula (I):

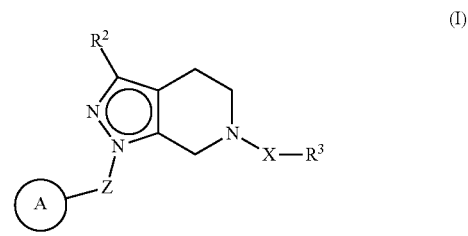

(I)

or a pharmaceutically acceptable salt thereof, wherein:

X is selected from —C(O)—, —C(O)$_2$—, and —C(O)NR$^X$—;

Z is a bond or C$_{1-5}$alkylene;

Ring A is selected from cyclohexyl, phenyl, and 5- or 6-membered heteroaryl, wherein Ring A is optionally substituted with one or more R$^1$;

R$^L$ is selected from H and C$_{1-3}$alkyl;

R$^X$ is selected from H and C$_{1-3}$alkyl;

R$^1$ in each occurrence is independently selected from C$_{1-6}$alkyl, C$_{2-6}$alkenyl, C$_{2-6}$alkynyl, 3- to 6-membered monocyclic carbocyclyl, 3- to 6-membered monocyclic heterocyclyl, halo, —CN, —C(O)R$^{1a}$, —C(O)$_2$R$^{1a}$, —C(O)N(R$^{1a}$)$_2$, —N(R$^{1a}$)$_2$, —N(R$^{1a}$)C(O)R$^{1a}$, —N(R$^{1a}$)N(R$^{1a}$)$_2$, —NO$_2$, —N(R$^{1a}$)C(O)$_2$R$^{1a}$, —N(R$^{1a}$)C(O)N(R$^{1a}$)$_2$, —N(R$^{1a}$)S(O)$_2$R$^{1a}$, —OR$^{1a}$, —SR$^{1a}$, —S(O)R$^{1a}$, —S(O)$_2$R$^{1a}$, —S(O)N(R$^{1a}$)$_2$, and —S(O)$_2$N(R$^{1a}$)$_2$, wherein said C$_{1-6}$alkyl, C$_{2-6}$alkenyl, C$_{2-6}$alkynyl, 3- to 6-membered monocyclic carbocyclyl, and 3- to 6-membered monocyclic heterocyclyl are optionally substituted with one or more R$^{10}$;

R$^{1a}$ in each occurrence is independently selected from H, C$_{1-6}$alkyl, 3- to 6-membered monocyclic carbocyclyl, and 3- to 6-membered monocyclic heterocyclyl;

R$^{10}$ in each occurrence is independently selected from halo, alkyl, —OR$^{10a}$; and —N(R$^{10a}$);

R$^{10a}$ in each occurrence is independently selected from H and C$_{1-6}$alkyl;

R$^2$ is selected from H, C$_{1-6}$alkyl, C$_{2-6}$alkenyl, C$_{2-6}$alkynyl, 3- to 6-membered monocyclic carbocyclyl, 3- to 6-membered monocyclic heterocyclyl, halo, —CN, —C(O)R$^{2a}$, —C(O)$_2$R$^{2a}$, —C(O)N(R$^{2a}$)$_2$, —OR$^{2a}$, —N(R$^{2a}$)$_2$, —N(R$^{2a}$)C(O)R$^{2a}$, —N(R$^{2a}$)N(R$^{2a}$)$_2$, —NO$_2$, —N(R$^{2a}$)C(O)$_2$R$^{2a}$, —N(R$^{2a}$)C(O)N(R$^{2a}$)$_2$, —N(R$^{2a}$)S(O)$_2$R$^{2a}$, —SR$^{2a}$, —S(O)R$^{2a}$, —S(O)$_2$R$^{2a}$, —S(O)N(R$^{2a}$)$_2$, and —S(O)$_2$N(R$^{2a}$)$_2$, wherein said C$_{1-6}$alkyl, C$_{2-6}$alkenyl, C$_{2-6}$alkynyl, 3- to 6-membered monocyclic carbocyclyl, and 3- to 6-membered monocyclic heterocyclyl are optionally substituted with one or more R$^{20}$;

R$^{2a}$ in each occurrence is independently selected from H, C$_{1-6}$alkyl, 3- to 6-membered monocyclic carbocyclyl, and 3- to 6-membered monocyclic heterocyclyl;

R$^{20}$ in each occurrence is independently selected from halo, alkyl, —OR$^{20a}$, and —N(R$^{20a}$);

$R^{20a}$ in each occurrence is independently selected from H and $C_{1-6}$alkyl;

$R^3$ is selected from:
i. —$[CHR^{3a}]_z$—$R^4$;
ii. —$[CHR^{3a}]_x$-L-$[CHR^{3a}]_y$—$R^4$;
iii. —$[CHR^{3a}]_z$-(L)$_m$-$R^5$;
iv. —$[CHR^{3a}]_x$-L-$[CHR^{3a}]_y$—$R^5$; and
v. $R^5$, m is 0 or 1;
L is selected from —N($R^L$)— and —O—;
$R^{3a}$ is hydrogen or $C_{1-3}$alkyl;
x and y are each independently selected from 1, 2, or 3;
z is 1, 2, 3, 4, 5, or 6;
$R^4$ is selected from —C(O)$_2R^{4a}$, —C(O)N($R^{4a}$)$_2$, —O$R^{4a}$, —N($R^{4a}$)$_2$, CN, —S(O)$_2$N($R^{4a}$)$_2$, —S(O)$_2$N($R^{4a}$)C(O)$R^{4a}$, —S$R^{4a}$, —S(O)$R^{4a}$, —S(O)$_2R^{4a}$, —S(O)$_2$O$R^{4a}$, —C(O)N($R^{4a}$)S(O)$_2R^{4a}$, —C(O)N($R^{4a}$)S(O)$_2R^{4a}$, —C(O)N($R^{4a}$)O$R^{4a}$, —C(O)N($R^{4a}$)CN, —C$R^{4a}$(CF$_3$)O$R^{4a}$, —C(CF$_3$)$_2$O$R^{4a}$, —P(O)(O$R^{4a}$)$_2$, and —B(O$R^{4a}$)$_2$;

$R^{4a}$ in each occurrence is independently selected from H and $C_{1-6}$alkyl;

$R^5$ is selected from 3- to 12-membered carbocyclyl and 3- to 12-membered heterocyclyl, wherein $R^5$ is optionally substituted with one or more $R^{30}$;

$R^{30}$ in each occurrence is independently selected from 3- to 6-membered monocyclic carbocyclyl, 3- to 6-membered monocyclic heterocyclyl, $C_{1-6}$alkyl, halo, CN, —S(O)$_2$O$R^{30a}$, —S(O)$_2$N($R^{30a}$)$_2$, —S(O)$_2$N($R^{30a}$)C(O)$R^{30a}$, —C(O)N($R^{30a}$)S(O)$_2R^{30a}$, —C(O)N($R^{30a}$)S(O)$_2R^{30a}$, —C(O)N($R^{30a}$)O$R^{30a}$, —C(O)N($R^{30a}$)CN, —CH(CF$_3$)O$R^{30a}$, —C(CF$_3$)$_2$O$R^{30a}$, —P(O)(O$R^{30a}$)$_2$, —B(O$R^{30a}$)$_2$, —C(O)$_2R^{30a}$, —C(O)N($R^{30a}$)$_2$, —O$R^{30a}$, —N($R^{30a}$)$_2$, and —C(O)$R^{30a}$, wherein said 3- to 6-membered monocyclic carbocyclyl, 3- to 6-membered monocyclic heterocyclyl, and $C_{1-6}$alkyl in each occurrence are optionally and independently substituted with one or more $R^{35}$; and $R^{30a}$ in each occurrence is independently selected from H, $C_{1-6}$alkyl, 3- to 6-membered monocyclic carbocyclyl, and 3- to 6-membered monocyclic heterocyclyl;

$R^{35}$ in each occurrence is independently selected from halo, —O$R^{35a}$, —C(O)$_2R^{35a}$, —C(O)N($R^{35a}$)$_2$, —S(O)$_2R^{30a}$, and —N($R^{35a}$)$_2$; and $R^{35a}$ in each occurrence is independently selected from H and $C_{1-6}$alkyl.

Also provided is a pharmaceutical composition comprising at least one compound or a pharmaceutically acceptable salt thereof described herein, and at least one pharmaceutically acceptable carrier.

Also provided is a method of treating, or reducing symptoms of a condition mediated by ATX activity in a mammal comprising administering to said mammal an effective amount of at least one compound or a pharmaceutically acceptable salt thereof described herein.

Also provided is a method of promoting myelination or remyelination in a mammal in need thereof, comprising administering to cells an effective amount of at least one compound or a pharmaceutically acceptable salt thereof described herein.

Also provided is a method of treating, or reducing chronic pain in a mammal comprising administering to said mammal an effective amount of at least one compound or a pharmaceutically acceptable salt thereof described herein.

Other features or advantages will be apparent from the following detailed description of several embodiments, and also from the appended claims.

DETAILED DESCRIPTION

The compounds or pharmaceutically acceptable salts thereof as described herein, can have activity as ATX modulators. In particular, compounds or pharmaceutically acceptable salts thereof as described herein, can be ATX inhibitors.

A first embodiment of the invention is a compound of Formula (I):

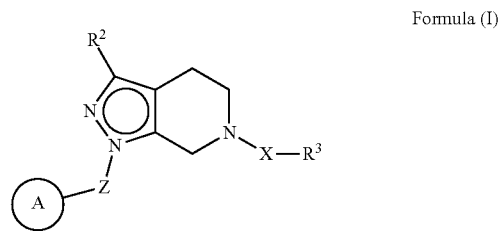

Formula (I)

or a pharmaceutically acceptable salt thereof, wherein:
X is selected from —C(O)—, —C(O)$_2$—, and —C(O)N$R^X$—;
Z is a bond or $C_{1-5}$alkylene;
Ring A is selected from cyclohexyl, phenyl, and 5- or 6-membered heteroaryl, wherein Ring A is optionally substituted with one or more $R^1$;
$R^L$ is selected from H and $C_{1-3}$alkyl;
$R^X$ is selected from H and $C_{1-3}$alkyl;
$R^1$ in each occurrence is independently selected from $C_{1-6}$alkyl, $C_{2-6}$alkenyl, $C_{2-6}$alkynyl, 3- to 6-membered monocyclic carbocyclyl, 3- to 6-membered monocyclic heterocyclyl, halo, —CN, —C(O)$R^{1a}$, —C(O)$_2R^{1a}$, —C(O)N($R^{1a}$)$_2$, —N($R^{1a}$)$_2$, —N($R^{1a}$)C(O)$R^{1a}$, —N($R^{1a}$)N($R^{1a}$)$_2$, —NO$_2$, —N($R^{1a}$)C(O)$_2R^{1a}$, —N($R^{1a}$)C(O)N($R^{1a}$)$_2$, —N($R^{1a}$)S(O)$_2R^{1a}$, —O$R^{1a}$, —S$R^{1a}$, —S(O)$R^{1a}$, —S(O)$_2R^{1a}$, —S(O)N($R^{1a}$)$_2$, and —S(O)$_2$N($R^{1a}$)$_2$, wherein said $C_{1-6}$alkyl, $C_{2-6}$alkenyl, $C_{2-6}$alkynyl, 3- to 6-membered monocyclic carbocyclyl, and 3- to 6-membered monocyclic heterocyclyl are optionally substituted with one or more $R^{10}$;

$R^{1a}$ in each occurrence is independently selected from H, $C_{1-6}$alkyl, 3- to 6-membered monocyclic carbocyclyl, and 3- to 6-membered monocyclic heterocyclyl;

$R^{10}$ in each occurrence is independently selected from halo, alkyl, —O$R^{10a}$ and —N($R^{10a}$);

$R^{10a}$ in each occurrence is independently selected from H and $C_{1-6}$alkyl;

$R^2$ is selected from H, $C_{1-6}$alkyl, $C_{2-6}$alkenyl, $C_{2-6}$alkynyl, 3- to 6-membered monocyclic carbocyclyl, 3- to 6-membered monocyclic heterocyclyl, halo, —CN, —C(O)$R^{2a}$, —C(O)$_2R^{2a}$, —C(O)N($R^{2a}$)$_2$, —O$R^{2a}$, —N($R^{2a}$)$_2$, —N($R^{2a}$)C(O)$R^{2a}$, —N($R^{2a}$)N($R^{2a}$)$_2$, —NO$_2$, —N($R^{2a}$)C(O)$_2R^{2a}$, —N($R^{2a}$)C(O)N($R^{2a}$)$_2$, —N($R^{2a}$)S(O)$_2R^{2a}$, —S$R^{2a}$, —S(O)$R^{2a}$, —S(O)$_2R^{2a}$, —S(O)N($R^{2a}$)$_2$, and —S(O)$_2$N($R^{2a}$)$_2$, wherein said $C_{1-6}$alkyl, $C_{2-6}$alkenyl, $C_{2-6}$alkynyl, 3- to 6-membered monocyclic carbocyclyl, and 3- to 6-membered monocyclic heterocyclyl are optionally substituted with one or more $R^{20}$;

$R^{2a}$ in each occurrence is independently selected from H, $C_{1-6}$alkyl, 3- to 6-membered monocyclic carbocyclyl, and 3- to 6-membered monocyclic heterocyclyl;

$R^{20}$ in each occurrence is independently selected from halo, alkyl, —O$R^{20a}$, and —N($R^{20a}$);

$R^{20a}$ in each occurrence is independently selected from H and $C_{1-6}$alkyl;

$R^3$ is selected from:
i. —$[CHR^{3a}]_z$—$R^4$;
ii. —$[CHR^{3a}]_x$-L-$[CHR^{3a}]_y$—$R^4$;
iii. —$[CHR^{3a}]_z$-(L)$_m$-$R^5$;

iv. —[CHR$^{3a}$]$_x$-L-[CHR$^{3a}$]$_y$—R$^5$; and v. R$^5$, m is 0 or 1;

L is selected from —N(R$^L$)— and —O—;

R$^{3a}$ is hydrogen or C$_{1-3}$alkyl;

x and y are each independently 1, 2, or 3;

z is 1, 2, 3, 4, 5, or 6;

R$^4$ is selected from —C(O)$_2$R$^{4a}$, —C(O)N(R$^{4a}$)$_2$, —OR$^{4a}$, —N(R$^{4a}$)$_2$, CN, —S(O)$_2$N(R$^{4a}$)$_2$, —S(O)$_2$N(R$^{4a}$)C(O)R$^{4a}$, —SR$^{4a}$, —S(O)R$^{4a}$, —S(O)$_2$R$^{4a}$, —S(O)$_2$OR$^{4a}$, —C(O)N(R$^{4a}$)S(O)$_2$R$^{4a}$, —C(O)N(R$^{4a}$)S(O)$_2$R$^{4a}$, —C(O)N(R$^{4a}$)OR$^{4a}$, —C(O)N(R$^{4a}$)CN, —CR$^{4a}$(CF$_3$)OR$^{4a}$, —C(CF$_3$)$_2$OR$^{4a}$, —P(O)(OR$^{4a}$)$_2$, and —B(OR$^{4a}$)$_2$;

R$^{4a}$ in each occurrence is independently selected from H and C$_{1-6}$alkyl;

R$^5$ is selected from 3- to 12-membered carbocyclyl and 3- to 12-membered heterocyclyl, wherein R$^5$ is optionally substituted with one or more R$^{30}$;

R$^{30}$ in each occurrence is independently selected from 3- to 6-membered monocyclic carbocyclyl, 3- to 6-membered monocyclic heterocyclyl, C$_{1-6}$alkyl, halo, CN, —S(O)$_2$OR$^{30a}$, —S(O)$_2$N(R$^{30a}$)$_2$, —S(O)$_2$N(R$^{30a}$)C(O)R$^{30a}$, —C(O)N(R$^{30a}$)S(O)$_2$R$^{30a}$, —C(O)N(R$^{30a}$)S(O)$_2$R$^{30a}$, —C(O)N(R$^{30a}$)OR$^{30a}$, —C(O)N(R$^{30a}$)CN, —CH(CF$_3$)OR$^{30a}$, —C(CF$_3$)$_2$OR$^{30a}$, —P(O)(OR$^{30a}$)$_2$, —B(OR$^{30a}$)$_2$, —C(O)$_2$R$^{30a}$, —C(O)N(R$^{30a}$)$_2$, —OR$^{30a}$, —N(R$^{30a}$)$_2$, and —C(O)R$^{30a}$, wherein said 3- to 6-membered monocyclic carbocyclyl, 3- to 6-membered monocyclic heterocyclyl, and C$_{1-6}$alkyl in each occurrence are optionally and independently substituted with one or more R$^{35}$; and R$^{30a}$ in each occurrence is independently selected from H, C$_{1-6}$alkyl, 3- to 6-membered monocyclic carbocyclyl, and 3- to 6-membered monocyclic heterocyclyl;

R$^{35}$ in each occurrence is independently selected from halo, —OR$^{35a}$, —C(O)$_2$R$^{35a}$, —C(O)N(R$^{35a}$)$_2$, —S(O)$_2$R$^{30a}$, and —N(R$^{35a}$)$_2$; and R$^{35a}$ in each occurrence is independently selected from H and C$_{1-6}$alkyl.

A second embodiment of the invention is a compound of Formula (II):

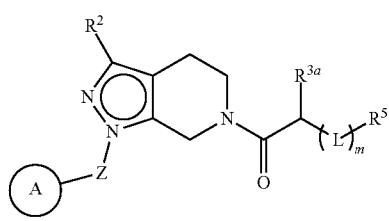

Formula (II)

or a pharmaceutically acceptable salt thereof, wherein the values of the variables are as defined for the first embodiment.

A third embodiment of the invention is a compound of Formula (III):

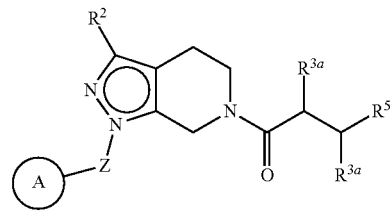

Formula (III)

or a pharmaceutically acceptable salt thereof, wherein the values of the variables are as defined for the first embodiment.

A fourth embodiment of the invention is a compound of Formula (IV):

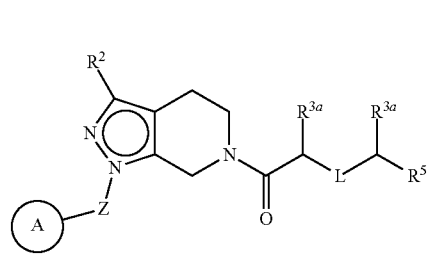

Formula (IV)

or a pharmaceutically acceptable salt thereof, wherein the values of the variables are as defined for the first embodiment.

A fifth embodiment of the invention is a compound of Formula (V):

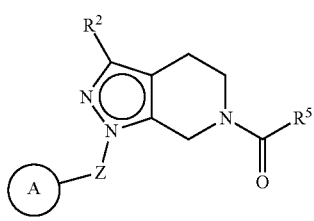

Formula (V)

or a pharmaceutically acceptable salt thereof, wherein the values of the variables are as defined for the first embodiment.

A sixth embodiment of the invention is a compound of Formula (VI):

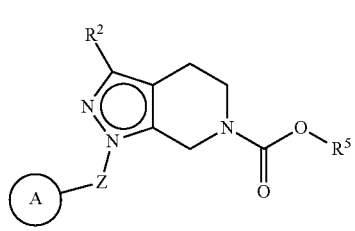

Formula (VI)

or a pharmaceutically acceptable salt thereof, wherein the values of the variables are as defined for the first embodiment.

A seventh embodiment of the invention is a compound of Formula (VII):

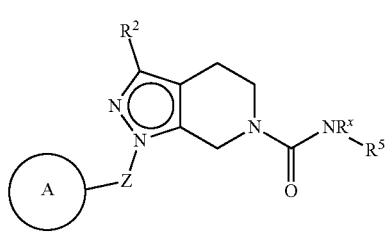

Formula (VII)

or a pharmaceutically acceptable salt thereof, wherein $R^x$ is hydrogen or methyl and wherein the values of the other variables are as defined for the first embodiment.

An eighth embodiment of the invention is a compound of Formula (VIII):

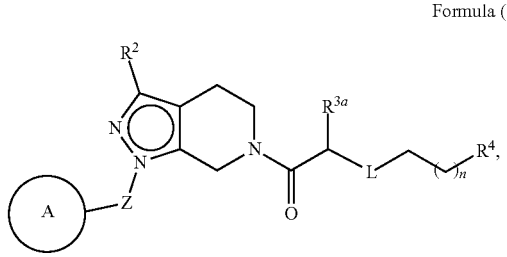

Formula (VIII)

or a pharmaceutically acceptable salt thereof, and n is 0, 1, or 2, and wherein the values of the other variables are as defined for the first embodiment.

A ninth embodiment of the invention is a compound of Formula (IX):

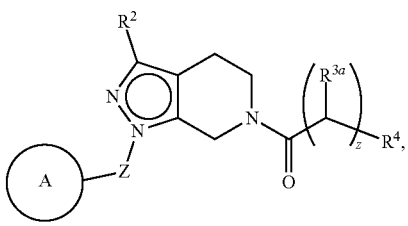

Formula (IX)

or a pharmaceutically acceptable salt thereof, and z is 1, 2, 3, or 4 and wherein the values of the other variables are as defined for the first embodiment.

In a tenth embodiment of the invention, the compound is represented by the formula (I), (II), (III), (IV), (V), (VI), (VII), (VIII) or (IX), wherein Ring A is phenyl optionally substituted with one to three $R^1$; $R^1$ is selected from $C_{1-4}$alkyl, halo, —CN, —$OR^{1a}$, —$S(O)_2R^{1a}$, —$C(O)_2R^{1a}$, —$NO_2$, —$N(R^{1a})C(O)_2R^{1a}$, —$N(R^{1a})S(O)_2R^{1a}$, and —$SR^{1a}$, wherein said $C_{1-4}$alkyl is optionally substituted with one to three $R^{10}$; $R^{1a}$ in each occurrence is independently selected from H and $C_{1-4}$alkyl; $R^{10}$ in each occurrence is independently selected from halo, —$OR^{10a}$, and —$N(R^{10a})$; and $R^{10a}$ in each occurrence is independently selected from H and $C_{1-4}$alkyl, wherein the values of the other variables are as defined for the first embodiment.

In an eleventh embodiment of the invention, the compound is represented by the formula (I), (II), (III), (IV), (V), (VI), (VII), (VIII) or (IX), wherein Ring A is cyclohexyl optionally substituted with one to three $R^1$, $R^1$ is selected from $C_{1-4}$alkyl, halo, —CN, —$OR^{1a}$, —$S(O)_2R^{1a}$, —$C(O)_2R^{1a}$, —$NO_2$, —$N(R^{1a})C(O)_2R^{1a}$, —$N(R^{1a})S(O)_2R^{1a}$, and —$SR^{1a}$, wherein said $C_{1-4}$alkyl is optionally substituted with one to three $R^{10}$; $R^{1a}$ in each occurrence is independently selected from H and $C_{1-4}$alkyl; $R^{10}$ in each occurrence is independently selected from halo, —$OR^{10a}$, and —$N(R^{10a})$; and $R^{10a}$ in each occurrence is independently selected from H and $C_{1-4}$alkyl, wherein the values of the other variables are as defined for the first embodiment.

In a twelfth embodiment of the invention, the compound is represented by the formula (I), (II), (III), (IV), (V), (VI), (VII), (VIII) or (IX), wherein Ring A is 5- or 6-membered heteroaryl optionally substituted with one to three $R^1$, wherein the 5- or 6-membered heteroaryl is selected from pyrrolyl, furanyl, thiophenyl, imidazolyl, pyrazolyl, oxazolyl, isoxazolyl, thiazolyl, isothiazolyl, triazolyl, furazanyl, oxadiazolyl, thiadiazolyl, thiadiazolyl, tetrazolyl, pyridinyl, pyranyl, pyrimidinyl, thiopyranyl, diazinyl, oxazinyl, thiazinyl, dioxinyl, dithiinyl, triazinyl, and tetrazinyl; $R^1$ is selected from $C_{1-4}$alkyl, halo, —CN, —$OR^{1a}$, —$S(O)_2R^{1a}$, —$C(O)_2R^{1a}$, —$NO_2$, —$N(R^{1a})C(O)_2R^{1a}$, —$N(R^{1a})S(O)_2R^{1a}$, and —$SR^{1a}$, wherein said $C_{1-4}$alkyl is optionally substituted with one to three $R^{10}$; $R^{1a}$ in each occurrence is independently selected from H and $C_{1-4}$alkyl; $R^{10}$ in each occurrence is independently selected from halo, —$OR^{10a}$, and —$N(R^{10a})$; and $R^{10a}$ in each occurrence is independently selected from H and $C_{1-4}$alkyl, wherein the values of the other variables are as defined for the first embodiment.

In a thirteenth embodiment of the invention, the compound is represented by the formula (I), (II), (III), (IV), (V), (VI), (VII), (VIII) or (IX), wherein Ring A is either unsubstituted or substituted with 1, 2 or 3 groups independently selected from methyl, ethyl, propyl, isopropyl, butyl, tert-butyl, isobutyl, sec-butyl, fluoro, chloro, methyoxy, ethoxy, and trifluoromethyl, wherein the values of the other variables are as defined for the first, tenth, eleventh, and twelfth embodiments. In an alternative aspect, Ring A is either unsubstituted or substituted with 1, 2 or 3 groups independently selected from methyl, ethyl, propyl, isopropyl, butyl, tert-butyl, isobutyl, sec-butyl, fluoro, chloro, cyano, methyoxy, ethoxy, and trifluoromethyl, wherein the values of the other variables are as defined for the first, tenth, eleventh, and twelfth embodiments. In a particular aspect of this embodiment, Ring A is phenyl substituted with 1, 2, or 3 groups selected from fluoro, chloro and cyano. In a particular aspect of this embodiment, Ring A is phenyl substituted with 1 or 2 groups selected from fluoro and chloro. In another particular aspect, Ring A is cyclohexyl optionally substituted with methyl. In another particular aspect, Ring A is thiophenyl, thiazoyl, pyridinyl, pyrimidinyl, optionally substituted with chloro.

In a fourteenth embodiment of the invention, the compound is represented by the formula (I), (II), (III), (IV), (V), (VI), (VII), (VIII) or (IX), wherein Z is a bond, —$CH_2$—, —$CH(CH_3)$—, or —$CH_2CH_2$—, wherein the values of the other variables are as defined for the first, tenth, eleventh, twelfth, and thirteenth embodiments.

In a fifteenth embodiment of the invention, the compound is represented by the formula (I), (II), (III), (IV), (V), (VI), (VII), (VIII) or (IX), wherein $R^2$ is H, halo, or $C_{1-4}$alkyl optionally substituted with 1 to 3 halo, wherein the values of the other variables are as defined for the first, tenth, eleventh, twelfth, thirteenth, and fourteenth embodiments. In an alternative fifteenth embodiment of the invention, the compound is represented by the formula (I), (II), (III), (IV), (V), (VI), (VII), (VIII) or (IX), wherein $R^2$ is H, halo, phenyl, cyclopropyl, pyridinyl, —CN, $C(O)_2R^{2a}$, $C(O)N(R^{2a})_2$, —$OR^{2a}$, $N(R^{2a})_2$, or $C_{1-4}$alkyl optionally substituted with 1 to 3 halo or $OR^{20}$; $R^{2a}$ is H or $C_{1-4}$alkyl; and $R^{20}$ is H or $C_{1-4}$alkyl, wherein the values of the other variables are as defined for the first, tenth, eleventh, twelfth, thirteenth, and fourteenth embodiments. In a particular aspect of the fifteenth embodiment, $R^2$ is $CF_3$ or $CF_2$.

In a sixteenth embodiment of the invention, the compound is represented by the formula (I), (II), (III), (IV), (V), (VI), or (VII), wherein $R^5$ is 3- to 12-membered carbocyclyl or 3- to 12-membered heterocyclyl, each optionally substituted with 1, 2 or 3 groups selected from $R^{30}$, wherein the 3- to 12-membered carbocyclyl is selected from cyclopropyl, cyclobutyl, cyclopentyl, cyclopentenyl, cyclohexyl, cyclohexenyl, bornyl, spiro[3.3]heptanyl, tricyclo[2.2.1.0$^{2,6}$]heptanyl, phenyl, bicyclo[2.1.1]hexyl, bicyclo[2.2.1]heptyl, bicyclo[2.2.1]heptenyl, bicyclo[2.2.2]octanyl, bicyclo[3.2.1]octanyl, bicyclo[3.3.1]nonanyl, and bicyclo[3.2.2]nonanyl and the 3- to 12-membered heterocyclyl is selected from 8-azabicyclo[3.2.1]octanyl, 9-azabicyclo[3.3.1]nonanyl, 3-azabicyclo[3.1.0]hexanyl, azepinyl, azetidinyl, aziridinyl, 3,8-diazabicyclo[3.2.1]octanyl, 3,9-diazabicyclo[3.3.1]nonanyl, 4,7-diazaspiro[2.5]octanyl, benzofuran, benzo[d]oxazolyl, benzothiazolyl, benzothiophenyl, diazepinyl, dihydrofuranyl, dihydropyranyl, dioxanyl, dioxolanyl, dithianyl, dithiolanyl, imidazolidinyl, imidazolinyl, indolyl, morpholinyl, octahydro-1H-pyrido[1,2-a]pyrazinyl, octahydrocyclopenta[c]pyrrolyl, octahydropyrrolo[1,2-a]pyrazinyl, octahydro-1H-pyrido[1,2-a]pyrrolyl, octahydropyrrolo[3,4-c]pyrrolyl, oxapinyl, oxathianyl, oxathiolanyl, oxadiazolyl, oxazepinyl, oxetanyl, oxiranyl, piperazinyl, piperidinyl, pyridinyl, pyrimidinyl, pyrrolidinyl, tetrahydrofuranyl, tetrahydropyranyl, 5,6,7,8-tetrahydroimidazo[1,5-a]pyridinyl and thiomorpholinyl;

$R^{30}$ in each occurrence is independently selected from 5- or 6-membered heteroaryl, $C_{1-4}$alkyl, halo, CN, —$S(O)_2R^{30a}$, —$S(O)_2N(R^{30a})_2$, —$S(O)_2N(R^{30a})C(O)R^{30a}$, —$C(O)N(R^{30a})S(O)_2R^{30a}$, —$C(O)N(R^{30a})OR^{30a}$, —$C(O)N(R^{30a})CN$, —$CH(CF_3)OR^{30a}$, —$C(CF_3)_2OR^{30a}$, —$P(O)(OR^{30a})_2$, —$B(OR^{30a})_2$, —$C(O)_2R^{30a}$, —$C(O)N(R^{30a})_2$, —$OR^{30a}$, —$N(R^{30a})_2$, and —$C(O)R^{30a}$, wherein said 5- or 6-membered heteroaryl and $C_{1-4}$alkyl in each occurrence are optionally and independently substituted with 1, 2, or 3 $R^{35}$, and the 5- or 6-membered heteroaryl is selected from pyrrolyl, furanyl, thiophenyl, imidazolyl, pyrazolyl, oxazolyl, isoxazolyl, thiazolyl, isothiazolyl, triazolyl, furazanyl, oxadiazolyl, thiadiazolyl, thiadiazolyl, tetrazolyl, pyridinyl, pyranyl, pyrimidinyl, thiopyranyl, diazinyl, oxazinyl, thiazinyl, dioxinyl, dithiinyl, triazinyl, and tetrazinyl and $R^{30a}$ in each occurrence is independently selected from H and $C_{1-4}$alkyl;

$R^{35}$ in each occurrence is independently selected from halo, $C_{1-4}$alkyl, $OR^{35a}$, —$C(O)_2R^{35a}$, —$C(O)N(R^{35a})_2$, —$S(O)_2R^{30a}$, and —$N(R^{35a})_2$; and $R^{35a}$ in each occurrence is independently selected from H and $C_{1-4}$alkyl; wherein the values of the other variables are as defined for the first, tenth, eleventh, twelfth, thirteenth, fourteenth, and fifteenth embodiments.

In an alternative sixteenth embodiment of the invention, the compound is represented by the formula (I), (II), (III), (IV), (V), (VI), or (VII), wherein $R^5$ is 3- to 12-membered carbocyclyl or 3- to 12-membered heterocyclyl, each optionally substituted with 1, 2 or 3 groups selected from $R^{30}$, wherein the 3- to 12-membered carbocyclyl is selected from cyclopropyl, cyclobutyl, cyclopentyl, cyclopentenyl, cyclohexyl, cyclohexenyl, bornyl, spiro[3.3]heptanyl, tricyclo[2.2.1.0$^{2,6}$]heptanyl, phenyl, bicyclo[2.1.1]hexyl, bicyclo[2.2.1]heptyl, bicyclo[2.2.1]heptenyl, bicyclo[2.2.2]octanyl, bicyclo[3.2.1]octanyl, bicyclo[3.3.1]nonanyl, bicyclo[3.2.2]nonanyl, and adamantanyl, and the 3- to 12-membered heterocyclyl is selected from 8-azabicyclo[3.2.1]octanyl, 9-azabicyclo[3.3.1]nonanyl, 3-azabicyclo[3.1.0]hexanyl, azepinyl, azetidinyl, aziridinyl, azepanyl, 3,8-diazabicyclo[3.2.1]octanyl, 3,9-diazabicyclo[3.3.1]nonanyl, 4,7-diazaspiro[2.5]octanyl, benzofuran, benzo[d]oxazolyl, benzothiazolyl, benzothiophenyl, diazepinyl, dihydrofuranyl, dihydropyranyl, dioxanyl, dioxolanyl, dithianyl, dithiolanyl, imidazolidinyl, imidazolinyl, indolyl, morpholinyl, octahydro-1H-pyrido[1,2-a]pyrazinyl, octahydrocyclopenta[c]pyrrolyl, octahydropyrrolo[1,2-a]pyrazinyl, octahydro-1H-pyrido[1,2-a]pyrrolyl, octahydropyrrolo[3,4-c]pyrrolyl, oxapinyl, oxathianyl, oxathiolanyl, oxadiazolyl, oxazepinyl, oxetanyl, oxiranyl, piperazinyl, piperidinyl, pyridinyl, pyrimidinyl, pyrrolidinyl, tetrahydrofuranyl, tetrahydropyranyl, 5,6,7,8-tetrahydroimidazo[1,5-a]pyridinyl, thiomorpholinyl, tetrazolyl, octahydroindolizinyl, quinuclidinyl, 3-oxa-9-azabicyclo[3.3.1]nonanyl, and 2-azaspiro[3.3]heptanyl;

$R^{30}$ in each occurrence is independently selected from 5- or 6-membered heterocyclyl, $C_{1-4}$alkyl, halo, CN, —$S(O)_2OR^{30a}$, —$S(O)_2N(R^{30a})_2$, —$S(O)_2N(R^{30a})C(O)R^{30a}$, —$C(O)N(R^{30a})S(O)_2R^{30a}$, —$C(O)N(R^{30}a)OR^{30a}$, —$C(O)N(R^{30a})CN$, —$CH(CF_3)OR^{30a}$, —$C(CF_3)_2OR^{30a}$, —$P(O)(OR^{30a})_2$, —$B(OR^{30a})_2$, —$C(O)_2R^{30a}$, —$C(O)N(R^{30a})_2$, —$OR^{30a}$, —$N(R^{30a})_2$, and —$C(O)R^{30a}$, wherein said 5- or 6-membered heterocyclyl and $C_{1-4}$alkyl in each occurrence are optionally and independently substituted with 1, 2, or 3 $R^{35}$, and the 5- or 6-membered heterocyclyl is selected from pyrrolyl, furanyl, thiophenyl, imidazolyl, pyrazolyl, oxazolyl, isoxazolyl, thiazolyl, isothiazolyl, triazolyl, furazanyl, oxadiazolyl, thiadiazolyl, thiadiazolyl, tetrazolyl, pyridinyl, pyranyl, pyrimidinyl, thiopyranyl, diazinyl, oxazinyl, thiazinyl, dioxinyl, dithiinyl, triazinyl, and tetrazinyl and $R^{30a}$ in each occurrence is independently selected from H and $C_{1-4}$alkyl;

$R^{35}$ in each occurrence is independently selected from halo, $C_{1-4}$alkyl, $OR^{35a}$, —$C(O)_2R^{35a}$, —$C(O)N(R^{35a})_2$, —$S(O)_2R^{30a}$, and —$N(R^{35a})_2$; and $R^{35a}$ in each occurrence is independently selected from H and $C_{1-4}$alkyl; wherein the values of the other variables are as defined for the first, tenth, eleventh, twelfth, thirteenth, fourteenth, and fifteenth embodiments.

In a seventeenth embodiment of the invention, the compound is represented by the formula (I), (II), (III), (IV), (V), (VI), or (VII), wherein $R^5$ is a cyclobutyl, cyclopentyl, cyclohexyl, spiro[3.3]heptanyl, tricyclo[2.2.1.0$^{2,6}$]heptanyl, phenyl, bicyclo[2.1.1]hexyl, bicyclo[2.2.1]heptyl, bicyclo[2.2.1]heptenyl, bicyclo[2.2.2]octanyl, bicyclo[3.2.1]octanyl, bicyclo[3.3.1]nonanyl, bicyclo[3.2.2]nonanyl, 8-azabicyclo[3.2.1]octanyl, 9-azabicyclo[3.3.1]nonanyl, 3-azabicyclo[3.1.0]hexanyl, azetidinyl, 3,8-diazabicyclo[3.2.1]octanyl, 3,9-diazabicyclo[3.3.1]nonanyl, 4,7-diazaspiro[2.5]octanyl, benzofuran, benzo[d]oxazolyl, benzothiazolyl, benzothiophenyl, diazepinyl, morpholinyl, octahydro-1H-pyrido[1,2-a]pyrazinyl, octahydrocyclopenta[c]pyrrolyl, octahydropyrrolo[1,2-a]pyrazinyl, piperazinyl, piperidinyl, pyridinyl, pyrimidinyl, pyrrolidinyl, and 5,6,7, 8-tetrahydroimidazo[1,5-a]pyridinyl, wherein $R^5$ is substituted with 1, 2 or 3 groups selected from $R^{30}$;

$R^{30}$ in each occurrence is independently selected from 5- or 6-membered heteroaryl, $C_{1-4}$alkyl, halo, CN, —S(O)$_2$OR$^{30a}$, —C(O)N(R$^{30a}$)S(O)$_2$R$^{30a}$, —C(O)N(R$^{30a}$)S(O)$_2$R$^{30a}$, —P(O)(OR$^{30a}$)$_2$, —C(O)$_2$R$^{30a}$, —OR$^{30a}$, and —C(O)R$^{30a}$, wherein said 5- or 6-membered heteroaryl and $C_{1-4}$alkyl in each occurrence are optionally and independently substituted with 1, 2, or 3 $R^{35}$, and the 5- or 6-membered heteroaryl is selected from pyrrolyl, imidazolyl, pyrazolyl, triazolyl, pyridinyl, pyranyl, and pyrimidinyl, and $R^{30a}$ in each occurrence is independently selected from H and methyl, ethyl, propyl, isopropyl, butyl, tert-butyl, isobutyl, sec-butyl;

$R^{35}$ in each occurrence is independently selected from halo, $C_{1-4}$alkyl, and —C(O)$_2$R$^{35a}$; and $R^{35a}$ in each occurrence is independently selected from H and methyl, ethyl, propyl, isopropyl, butyl, tert-butyl, isobutyl, sec-butyl, wherein the values of the other variables are as defined for the first, tenth, eleventh, twelfth, thirteenth, fourteenth, fifteenth, and sixteenth embodiments.

In an alternative seventeenth embodiment of the invention, the compound is represented by the formula (I), (II), (III), (IV), (V), (VI), or (VII), wherein $R^5$ is a cyclobutyl, cyclopentyl, cyclohexyl, spiro[3.3]heptanyl, tricyclo[2.2.1.0$^{2,6}$]heptanyl, phenyl, bicyclo[2.1.1]hexyl, bicyclo[2.2.1]heptyl, bicyclo[2.2.1]heptenyl, bicyclo[2.2.2]octanyl, bicyclo[3.2.1]octanyl, bicyclo[3.3.1]nonanyl, bicyclo[3.2.2]nonanyl, adamantanyl, 8-azabicyclo[3.2.1]octanyl, 9-azabicyclo[3.3.1]nonanyl, 3-azabicyclo[3.1.0]hexanyl, azetidinyl, 3,8-diazabicyclo[3.2.1]octanyl, 3,9-diazabicyclo[3.3.1]nonanyl, 4,7-diazaspiro[2.5]octanyl, benzofuran, benzo[d]oxazolyl, benzothiazolyl, benzothiophenyl, diazepinyl, morpholinyl, octahydro-1H-pyrido[1,2-a]pyrazinyl, octahydrocyclopenta[c]pyrrolyl, octahydropyrrolo[1,2-a]pyrazinyl, piperazinyl, piperidinyl, pyridinyl, pyrimidinyl, pyrrolidinyl, 5,6,7,8-tetrahydroimidazo[1,5-a]pyridinyl, tetrahydropyranyl, tetrazolyl, octahydroindolizinyl, quinuclidinyl, azepanyl, 3-oxa-9-azabicyclo[3.3.1]nonanyl, 2-azaspiro[3.3]heptanyl, wherein $R^5$ is substituted with 1, 2 or 3 groups selected from $R^{30}$;

$R^{30}$ in each occurrence is independently selected from 5- or 6-membered heterocyclyl, $C_{1-4}$alkyl, halo, CN, —S(O)$_2$OR$^{30a}$, —C(O)N(R$^{30a}$)S(O)$_2$R$^{30a}$, —P(O)(OR$^{30a}$)$_2$, —C(O)$_2$R$^{30a}$, —C(O)N(R$^{30a}$)$_2$, —OR$^a$, —N(R$^{30a}$)$_2$, and —C(O)R$^{30a}$, wherein the 5- or 6-membered heterocyclyl is selected from pyrrolyl, imidazolyl, pyrazolyl, triazolyl, pyridinyl, pyranyl, pyrimidinyl, azetindinyl, pyrrolidinyl, piperidinyl, and morpholinyl, wherein the 5- or 6-membered heterocyclyl and $C_{1-4}$alkyl are each independently optionally substituted with 1, 2 or 3 groups selected from $R^{35}$;

$R^{30a}$ in each occurrence is independently selected from H and $C_{1-4}$alkyl;

$R^{35}$ in each occurrence is independently selected from halo, $C_{1-4}$alkyl, and —C(O)$_2$R$^{35a}$; and $R^{35a}$ in each occurrence is independently selected from H and $C_{1-4}$alkyl, wherein the values of the other variables are as defined for the first, tenth, eleventh, twelfth, thirteenth, fourteenth, fifteenth, and sixteenth embodiments.

In an eighteenth embodiment of the invention, the compound is represented by the formula (I), (II), (III), (IV), (V), (VI), or (VII), wherein $R^5$ is cyclohexyl, cyclopentyl, cyclobutyl, bicyclo[2.2.2]octanyl, bicyclo[3.2.1]octanyl, spiro[3.3]heptanyl, tricyclo[2.2.1.0$^{2,6}$]heptanyl, phenyl, piperidinyl, pyridinyl, pyrrolidinyl, azetidinyl, 8-azabicyclo[3.2.1]octanyl, 9-azabicyclo[3.3.1]nonanyl, octahydrocyclopenta[c]pyrrolyl, 5,6,7,8-tetrahydroimidazo[1,5-a]pyridinyl, or benzothiazolyl, each of which is optionally substituted with 1 to 3 groups selected from —CO—CH$_3$, —CO$_2$H, —CH$_2$—CO$_2$H, —CH$_2$—CH$_2$—CO$_2$H, —CO$_2$—(C$_{1-4}$alkyl), —CO$_2$—(C$_{1-4}$alkyl), $C_{1-4}$alkyl optionally substituted with 1, 2, or 4 halo, halo, hydroxyl, and pyrimidinyl, wherein the values of the other variables are as defined for the first, tenth, eleventh, twelfth, thirteenth, fourteenth, fifteenth, sixteenth, and seventeenth embodiments. In an alterntive eighteenth embodiment of the invention, the compound is represented by the formula (I), (II), (III), (IV), (V), (VI), or (VII), wherein $R^5$ is cyclohexyl, cyclopentyl, cyclobutyl, bicyclo[2.2.2]octanyl, bicyclo[3.2.1]octanyl, bicyclo[2.2.1]heptyl, spiro[3.3]heptanyl, tricyclo[2.2.1.0$^{2,6}$]heptanyl, phenyl, piperidinyl, pyridinyl, pyrrolidinyl, azetidinyl, 8-azabicyclo[3.2.1]octanyl, 9-azabicyclo[3.3.1]nonanyl, octahydrocyclopenta[c]pyrrolyl, 5,6,7,8-tetrahydroimidazo[1,5-a]pyridinyl, benzothiazolyl, tetrahydropyranyl, tetrazolyl, octahydroindolizinyl, quinuclidinyl, adamantanyl, morpholinyl, azepanyl, 3-oxa-9-azabicyclo[3.3.1]nonanyl, or 2-azaspiro[3.3]heptanyl, each of which is optionally substituted with 1 to 3 groups selected from —CO$_2$H, —CH$_2$—CO$_2$H, —CH$_2$—CH$_2$—CO$_2$H, —CO—(C$_{1-4}$alkyl), —CO$_2$—(C$_{1-4}$alkyl), $C_{1-4}$alkyl, halo, hydroxyl, pyrimidinyl, —N(R$^{30a}$)$_2$, CN, pyridinyl, —C(O)N(R$^{30a}$)S(O)$_2$R$^{30a}$, —C(O)N(R$^{30a}$)$_2$, azetindinyl, pyrrolidinyl, piperidinyl, morpholinyl, wherein the $C_{1-4}$alkyl, pyrimidinyl, pyridinyl, azetindinyl, pyrrolidinyl, piperidinyl, morpholinyl each are optionally substituted with 1, 2 or 3 halo, and $R^{30a}$ is selected from H or $C_{1-4}$alkyl; wherein the values of the other variables are as defined for the first, tenth, eleventh, twelfth, thirteenth, fourteenth, fifteenth, sixteenth, and seventeenth embodiments.

In a nineteenth embodiment of the invention, the compound is represented by the formula (I), (II), (III), (IV), (V), (VI), or (VII), wherein $R^5$ is cyclohexyl, cyclopentyl, cyclobutyl, bicyclo[2.2.2]octanyl, bicyclo[3.2.1]octanyl, spiro[3.3]heptanyl, tricyclo[2.2.1.0$^{2,6}$]heptanyl, phenyl, piperidinyl, pyridinyl, pyrrolidinyl, azetidinyl, 8-azabicyclo[3.2.1]octanyl, 9-azabicyclo[3.3.1]nonanyl, octahydrocyclopenta[c]pyrrolyl, 5,6,7,8-tetrahydroimidazo[1,5-a]pyridinyl, or benzothiazolyl, each of which is optionally substituted with 1 to 3 groups selected from —CO—CH$_3$, —CO$_2$H, —CO$_2$—CH$_3$, —CO$_2$—CH$_2$CH$_3$, —CO$_2$—C(CH$_3$)$_3$, —CH$_2$—CO$_2$H, —CH$_2$—CH$_2$—CO$_2$H, methyl, ethyl, isopropyl, fluoro, hydroxyl, —CF$_3$ and pyrimidinyl, wherein the values of the other variables are as defined for the first, tenth, eleventh, twelfth, thirteenth, fourteenth, fifteenth, sixteenth, seventeenth, and eighteenth embodiments. In an alternate nineteenth embodiment of the invention, the compound is represented by the formula (I), (II), (III), (IV), (V), (VI), or (VII), wherein $R^5$ is cyclohexyl, cyclopentyl, cyclobutyl, bicyclo[2.2.2]octanyl, bicyclo[3.2.1]octanyl, bicyclo[2.2.1]heptyl, spiro[3.3]heptanyl, tricyclo[2.2.1.0$^{2,6}$]heptanyl, phenyl, piperidinyl, pyridinyl, pyrrolidinyl, azetidinyl, 8-azabicyclo[3.2.1]octanyl, 9-azabicyclo[3.3.1]nonanyl, octahydrocyclopenta[c]pyrrolyl, 5,6,7,8-tetrahydroimidazo[1,5-a]pyridinyl, benzothiazolyl, tetrahydropyranyl, tetrazolyl, octahydroindolizinyl, quinuclidinyl, adamantanyl, morpholinyl, azepanyl, 3-oxa-9-azabicyclo[3.3.1]nonanyl, and 2-azaspiro[3.3]heptanyl, each of which is optionally substituted with 1 to 3 groups selected from —CO—CH$_3$, —CO$_2$H, —CO$_2$—CH$_3$, —CO$_2$—CH$_2$CH$_3$, —CO$_2$—C(CH$_3$)$_3$, —CH$_2$—CO$_2$H, —CH$_2$—CH$_2$—CO$_2$H, methyl, ethyl, propyl, isopropyl, fluoro, hydroxyl, —CF$_3$, pyrimidinyl, —N(R$^{30a}$)$_2$, CN, pyridinyl, —C(O)N(R$^{30a}$)S(O)$_2$R$^{30a}$, —C(O)N(R$^{30a}$)$_2$, azetindinyl, pyrrolidinyl, piperidinyl, morpholinyl, wherein the pyrimidinyl, pyridinyl, azetindinyl, pyrrolidinyl, piperidinyl, morpholinyl each are optionally substituted with 1 or 2 fluoro, and $R^{30a}$ is selected from H or $C_{1-4}$alkyl; wherein the values of the other variables are as defined for the first, tenth, eleventh, twelfth, thirteenth, fourteenth, fifteenth, sixteenth, seventeenth, and eighteenth embodiments. In particular aspect of the nineteenth embodiment of the invention, the compound is represented by the formula (I), (II), (III), (IV), (V), (VI), or (VII), wherein $R^5$ is cyclohexyl, cyclopentyl, cyclobutyl, piperidinyl, 9-azabicyclo[3.3.1]nonanyl, tetrahydropyranyl, bicyclo[2.2.1]heptyl, morpholinyl, and 3-oxa-9-azabicyclo[3.3.1]nonanyl, each of which is optionally substituted with 1 to 3 groups selected from —$CO_2$H, —$CO_2$—$CH_3$, —$CO_2$—$CH_2CH_3$, —$CO_2$—$C(CH_3)_3$, —$CH_2$—$CO_2$H, methyl, ethyl, propyl, isopropyl, —$CF_3$, CN, pyridinyl, and —C(O)N($R^{30a}$)S(O)$_2R^{30a}$, and $R^{30a}$ is selected from H or $C_{1-4}$alkyl; wherein the values of the other variables are as defined for the first, tenth, eleventh, twelfth, thirteenth, fourteenth, fifteenth, sixteenth, seventeenth, and eighteenth embodiments.

In a twentieth embodiment of the invention, the compound is represented by the formula (I), (II), (IV), or (VIII), wherein m is 1 and L is —NH—, —N(CH$_3$)— or —O—, wherein the values of the other variables are as defined for the first, tenth, eleventh, twelfth, thirteenth, fourteenth, fifteenth, sixteenth, seventeenth, eighteenth, and nineteenth embodiments.

In a twenty-first embodiment of the invention, the compound is represented by the formula (I), (VIII) or (IX), wherein $R^4$ is —C(O)$_2R^{4a}$, —CN, —SO$_3R^{4a}$, —S(O)$_2R^{4a}$, —CR$^{4a}$(CF$_3$)OR$^{4a}$, or —C(CF$_3$)$_2$OR$^{4a}$; and $R^{4a}$ in each occurrence is independently selected from H and $C_{1-4}$alkyl, wherein the values of the other variables are as defined for the first, tenth, eleventh, twelfth, thirteenth, fourteenth, fifteenth, sixteenth, seventeenth, eighteenth, nineteenth, and twentieth embodiments.

In a twenty-second embodiment of the invention, the compound is represented by the formula (I), (VIII) or (IX), wherein $R^4$ is —CO$_2$H, —CO$_2$—CH$_3$, or —CO$_2$—CH$_2$CH$_3$, wherein the values of the other variables are as defined for the first, tenth, eleventh, twelfth, thirteenth, fourteenth, fifteenth, sixteenth, seventeenth, eighteenth, nineteenth, twentieth, and twenty-first embodiments.

In a twenty-third embodiment of the invention, the compound is represented by the formula (X):

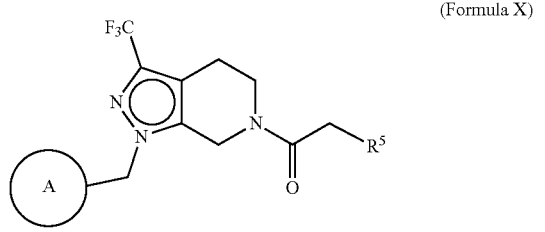

(Formula X)

or a pharmaceutically acceptable salt thereof, wherein
Ring A is phenyl, optionally substituted with one or more halo;
$R^5$ is selected from 4- to 10-membered carbocyclyl and 4- to 10-membered heterocyclyl, wherein $R^5$ optionally substituted with one or more $R^{30}$;
$R^{30}$ in each occurrence is independently selected from $C_{1-4}$alkyl optionally substituted with 1, 2, or 3 halo and —C(O)$_2R^{30a}$; and $R^{30a}$ in each occurrence is independently selected from H and $C_{1-4}$alkyl.

In one aspect of the twenty-third embodiment, Ring A is phenyl, optionally substituted with one or two halo; $R^5$ is selected from 9-azabicyclo[3.3.1]nonanyl, piperidinyl, and cyclohexyl, each of which is optionally substituted with 1, 2, or 3 groups independently selected from methyl, —CO$_2$H and —CF$_3$.

In an alternative twenty-third embodiment of the invention, the compound is represented by the formula (X*):

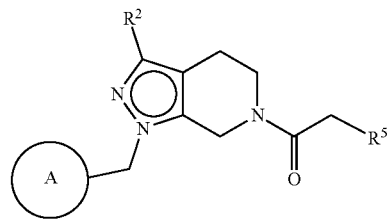

(Formula X*)

or a pharmaceutically acceptable salt thereof, wherein
Ring A is phenyl, optionally substituted with one or two halo;
$R^2$ is CF$_3$ or CHF$_2$;
$R^5$ is selected from 9-azabicyclo[3.3.1]nonanyl, piperidinyl, and cyclohexyl, tetrahydropyranyl, bicyclo[2.2.1]heptyl, morpholinyl, and 3-oxa-9-azabicyclo[3.3.1]nonanyl, wherein $R^5$ optionally substituted with one to three $R^{30}$;
$R^{30}$ in each occurrence is independently selected from —CH$_2$C(O)$_2R^{30a}$, —C(O)$_2R^{30a}$, pyridinyl, C(O)NR$^{30a}$S(O)$_2R^{30a}$, CN, and $C_{1-4}$alkyl optionally substituted with 1, 2, or 3 halo, and
$R^{30a}$ in each occurrence is independently selected from H and $C_{1-4}$alkyl.

In a twenty-fourth embodiment of the invention, the compound is represented by the formula (XI):

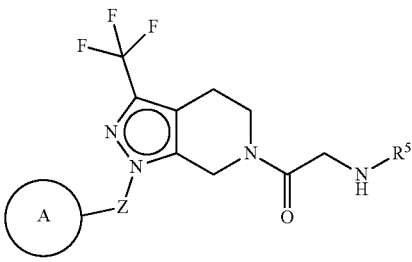

(Formula XI)

or a pharmaceutically acceptable salt thereof, Ring A is phenyl, optionally substituted with one or more halo;
$R^5$ is selected from 4- to 10-membered carbocyclyl and 4- to 10-membered heterocyclyl, wherein $R^5$ optionally substituted with one or more $R^{30}$;
$R^{30}$ in each occurrence is independently selected from $C_{1-4}$alkyl optionally substituted with 1, 2, or 3 halo, and —C(O)$_2R^{30a}$; and
$R^{30a}$ in each occurrence is independently selected from H and $C_{1-4}$alkyl.

In one aspect of the twenty-fourth embodiment, Ring A is phenyl, optionally substituted with one or two halo; $R^5$ is cyclobutyl optionally substituted with 1, 2, or 3 groups independently selected from methyl and —CO$_2$H.

In a twenty-fifth embodiment of the invention, the compound is represented by the formula (XII):

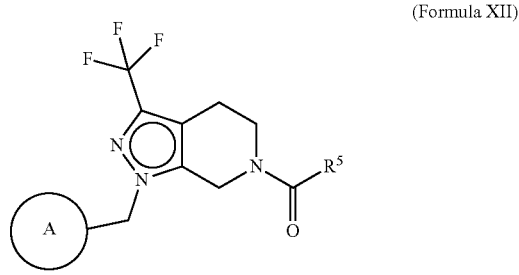

(Formula XII)

or a pharmaceutically acceptable salt thereof, Ring A is phenyl, optionally substituted with one or more halo;

R$^5$ is selected from 4- to 10-membered carbocyclyl and 4- to 10-membered heterocyclyl, wherein R$^5$ optionally substituted with one or more R$^{30}$;

R$^{30}$ in each occurrence is independently selected from C$_{1-4}$alkyl optionally substituted with 1, 2, or 3 halo and —C(O)$_2$R$^{30a}$; and R$^{30a}$ in each occurrence is independently selected from H and C$_{1-4}$alkyl.

In one aspect of the twenty-fifth embodiment, Ring A is phenyl, optionally substituted with one or two halo; R$^5$ is selected from 9-azabicyclo[3.3.1]nonanyl, piperidinyl, pyrrolidinyl, tetrahydroimidazo[1,5-a]pyridinyl, bicyclo[2.2.2]octanyl, cyclobutyl, and cyclohexyl, each of which is optionally substituted with 1, 2, or 3 groups independently selected from methyl, —CO$_2$H, —CO$_2$CH$_3$, —CH$_2$CH$_2$CO$_2$H, and —CF$_3$.

In a twenty-sixth embodiment of the invention, the compound is represented by the formula (XIII):

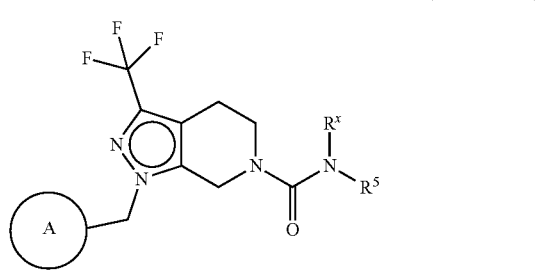

(Formula XIII)

or a pharmaceutically acceptable salt thereof, Ring A is phenyl, optionally substituted with one or more halo;

R$^5$ is selected from 4- to 10-membered carbocyclyl and 4- to 10-membered heterocyclyl, wherein R$^5$ optionally substituted with one or more R$^{30}$;

R$^{30}$ in each occurrence is independently selected from C$_{1-4}$alkyl optionally substituted with 1, 2, or 3 halo and —C(O)$_2$R$^{30a}$; and R$^{30a}$ in each occurrence is independently selected from H and C$_{1-4}$alkyl.

In one aspect of the twenty-sixth embodiment, Ring A is phenyl, optionally substituted with one or two halo; R$^5$ is selected from 9-azabicyclo[3.3.1]nonanyl, piperidinyl, bicyclo[2.2.2]octanyl, cyclobutyl, and cyclohexyl, each of which is optionally substituted with 1, 2, or 3 groups independently selected from methyl, —CO$_2$H, —CO$_2$CH$_3$, and —CF$_3$.

In a twenty-seventh embodiment of the invention, the compound is represented by the formula (XIV):

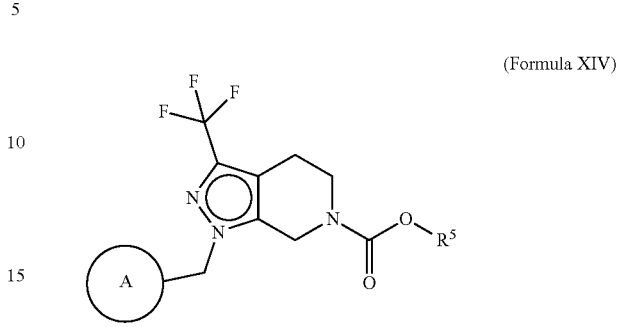

(Formula XIV)

or a pharmaceutically acceptable salt thereof, Ring A is phenyl, optionally substituted with one or more halo;

R$^5$ is selected from 4- to 10-membered carbocyclyl and 4- to 10-membered heterocyclyl, wherein R$^5$ optionally substituted with one or more R$^{30}$;

R$^{30}$ in each occurrence is independently selected from C$_{1-4}$alkyl optionally substituted with 1, 2, or 3 halo and —C(O)$_2$R$^{30a}$; and R$^{30a}$ in each occurrence is independently selected from H and C$_{1-4}$alkyl.

In one aspect of the twenty-seventh embodiment, Ring A is phenyl, optionally substituted with one or two halo; R$^5$ is selected from 9-azabicyclo[3.3.1]nonanyl, piperidinyl, bicyclo[2.2.2]octanyl, cyclobutyl, and cyclohexyl, each of which is optionally substituted with 1, 2, or 3 groups independently selected from methyl, —CO$_2$H, —CO$_2$CH$_3$, and —CF$_3$.

In one embodiment of the invention, there is provided a compound selected from:

Ethyl 4-(2-(1-(4-fluorobenzyl)-3-(trifluoromethyl)-4,5-dihydro-1H-pyrazolo[3,4-c]pyridin-6 (7H)-yl)-2-oxoethyl) cyclohexanecarboxylate, 1-(1-(4-Chloro-2-fluorobenzyl)-3-(trifluoromethyl)-4,5-dihydro-1H-pyrazolo[3,4-c]pyridin-6 (7H)-yl)-2-(1-methylpiperidin-4-yl)ethanone, 1-(1-(4-Chloro-2-fluorobenzyl)-3-(trifluoromethyl)-4,5-dihydro-1H-pyrazolo[3,4-c]pyridin-6(7H)-yl)-2-phenylethanone, Ethyl 4-(2-(1-(4-chloro-2-fluorobenzyl)-4,5-dihydro-1H-pyrazolo[3,4-c]pyridin-6(7H)-yl)-2-oxoethyl)cyclohexanecarboxylate, 1-(1-(4-Chloro-2-fluorobenzyl)-3-(trifluoromethyl)-4,5-dihydro-1H-pyrazolo[3,4-c]pyridin-6(7H)-yl)-2-cyclohexylethanone, (1-(4-Chloro-2-fluorobenzyl)-3-(trifluoromethyl)-4,5-dihydro-1H-pyrazolo[3,4-c]pyridin-6(7H)-yl) (cyclohexyl) methanone, 1-(1-(4-Chloro-2-fluorobenzyl)-3-(trifluoromethyl)-4,5-dihydro-1H-pyrazolo[3,4-c]pyridin-6(7H)-yl)-2-(pyridin-4-yl)ethanone, Ethyl 4-(2-(1-(4-chlorobenzyl)-3-(trifluoromethyl)-4,5-dihydro-1H-pyrazolo[3,4-c]pyridin-6(7H)-yl)-2-oxoethyl) cyclohexanecarboxylate, Ethyl 4-(2-(1-(2,4-dichlorobenzyl)-3-(trifluoromethyl)-4,5-dihydro-1H-pyrazolo[3,4-c]pyridin-6(7H)-yl)-2-oxoethyl)cyclohexanecarboxylate, Ethyl 4-(2-oxo-2-(3-(trifluoromethyl)-1-(4-(trifluoromethyl)benzyl)-4,5-dihydro-1H-pyrazolo[3,4-c]pyridin-6 (7H)-yl)ethyl)cyclohexanecarboxylate, Methyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)benzoate, 1-(1-(4-Chloro-2-fluorobenzyl)-3-(trifluoromethyl)-4,5-dihydro-1H-pyrazolo[3,4-c]pyridin-6(7H)-yl)-2-(4-fluorophenyl)ethanone, Ethyl 4-(2-(1-benzyl-3-(trifluoromethyl)-4,5-dihydro-1H-pyrazolo[3,4-c]pyridin-6(7H)-yl)-2-oxoethyl)cyclohexanecarboxylate, 3-(Benzo[d]thiazol-2-yl)-1-(1-(4-fluorobenzyl)-3-(trifluoromethyl)-4,5-dihydro-1H-pyrazolo[3,4-c]pyridin-6(7H)-yl)propan-1-one, 1-(1-(4-Chloro-2-fluorobenzyl)-3-(trifluoromethyl)-4,5-dihydro-1H-pyrazolo[3,4-c]pyridin-6(7H)-yl)-2-(4-hydroxycyclohexyl)ethanone, Ethyl 4-(2-(1-(cyclohexylmethyl)-3-(trifluoromethyl)-4,5-dihydro-1H-pyrazolo[3,4-c]pyridin-6(7H)-yl)-2-oxoethyl)cyclohexanecarboxylate, Ethyl 4-(2-(1-(4-fluorobenzyl)-4,5-dihydro-1H-pyrazolo[3,4-c]pyridin-6(7H)-yl)-2-oxoethyl)cyclohexanecarboxylate, Ethyl 4-(2-(1-(3-fluorobenzyl)-3-(trifluoromethyl)-4,5-dihydro-1H-pyrazolo[3,4-c]pyridin-6(7H)-yl)-2-oxoethyl)cyclohexanecarboxylate, Ethyl 4-(2-(1-(2-fluorobenzyl)-3-(trifluoromethyl)-4,5-dihydro-1H-pyrazolo[3,4-c]pyridin-6(7H)-yl)-2-oxoethyl)cyclohexanecarboxylate, (1-(4-Fluorobenzyl)-3-(trifluoromethyl)-4,5-dihydro-1H-pyrazolo[3,4-c]pyridin-6(7H)-yl)(5,6,7,8-tetrahydroimidazo[1,5-a]pyridin-7-yl)methanone, 1-(1-(4-Chloro-2-fluorobenzyl)-3-(trifluoromethyl)-4,5-dihydro-1H-pyrazolo[3,4-c]pyridin-6(7H)-yl)-2-(4-methylcyclohexyl)ethanone, Methyl 4-(1-(4-fluorobenzyl)-3-(trifluoromethyl)-4,5,6,7-tetrahydro-1H-pyrazolo[3,4-c]pyridine-6-carbonyl)cyclohexanecarboxylate, Methyl 4-(1-(4-fluorobenzyl)-3-(trifluoromethyl)-4,5,6,7-tetrahydro-1H-pyrazolo[3,4-c]pyridine-6-carbonyl)bicyclo[2.2.2]octane-1-carboxylate, trans-Ethyl 4-(2-(1-cyclohexyl-3-(trifluoromethyl)-4,5-dihydro-1H-pyrazolo[3,4-c]pyridin-6(7H)-yl)-2-oxoethyl)cyclohexanecarboxylate, trans-Ethyl 4-(2-(1-(4-methylbenzyl)-3-(trifluoromethyl)-4,5-dihydro-1H-pyrazolo[3,4-c]pyridin-6(7H)-yl)-2-oxoethyl)cyclohexanecarboxylate, trans-Ethyl 4-(2-(1-(4-methoxylbenzyl)-3-(trifluoromethyl)-4,5-dihydro-1H-pyrazolo[3,4-c]pyridin-6(7H)-yl)-2-oxoethyl)cyclohexanecarboxylate, Methyl 8-(2-(1-(4-chloro-2-fluorobenzyl)-3-(trifluoromethyl)-4,5-dihydro-1H-pyrazolo[3,4-c]pyridin-6(7H)-yl)-2-oxoethyl)bicyclo[3.2.1]octane-3-carboxylate, trans-Ethyl 4-(2-oxo-2-(1-phenethyl-3-(trifluoromethyl)-4,5-dihydro-1H-pyrazolo[3,4-c]pyridin-6(7H)-yl)ethyl)cyclohexanecarboxylate, trans-Ethyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)cyclohexanecarboxylate, cis-Ethyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)cyclohexanecarboxylate, trans-Ethyl 4-(2-(1-(3-chloro-5-fluorobenzyl)-3-(trifluoromethyl)-4,5-dihydro-1H-pyrazolo[3,4-c]pyridin-6(7H)-yl)-2-oxoethyl)cyclohexanecarboxylate, cis-ethyl 4-(2-(1-(3-chloro-5-fluorobenzyl)-3-(trifluoromethyl)-4,5-dihydro-1H-pyrazolo[3,4-c]pyridin-6(7H)-yl)-2-oxoethyl)cyclohexanecarboxylate, cis-Methyl 4-(1-(4-chloro-2-fluorobenzyl)-3-(trifluoromethyl)-4,5,6,7-tetrahydro-1H-pyrazolo[3,4-c]pyridine-6-carboxamido)cyclohexanecarboxylate, trans-Methyl 4-(1-(4-chloro-2-fluorobenzyl)-3-(trifluoromethyl)-4,5,6,7-tetrahydro-1H-pyrazolo[3,4-c]pyridine-6-carboxamido)cyclohexanecarboxylate, cis-Methyl 4-(1-(4-chloro-2-fluorobenzyl)-N-methyl-3-(trifluoromethyl)-4,5,6,7-tetrahydro-1H-pyrazolo[3,4-c]pyridine-6-carboxamido)cyclohexanecarboxylate, trans-Methyl 4-(1-(4-chloro-2-fluorobenzyl)-N-methyl-3-(trifluoromethyl)-4,5,6,7-tetrahydro-1H-pyrazolo[3,4-c]pyridine-6-carboxamido)cyclohexanecarboxylate, 4-(Ethoxycarbonyl)cyclohexyl1-(4-chloro-2-fluorobenzyl)-3-(trifluoromethyl)-4,5-dihydro-1H-pyrazolo[3,4-c]pyridine-6(7H)-carboxylate, trans-4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)cyclohexanecarboxylic acid, cis-4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)cyclohexanecarboxylic acid, trans-4-(2-(1-(3-chloro-5-fluorobenzyl)-3-(trifluoromethyl)-4,5-dihydro-1H-pyrazolo[3,4-c]pyridin-6(7H)-yl)-2-oxoethyl)cyclohexanecarboxylic acid, cis-4-(2-(1-(3-chloro-5-fluorobenzyl)-3-(trifluoromethyl)-4,5-dihydro-1H-pyrazolo[3,4-c]pyridin-6(7H)-yl)-2-oxoethyl)cyclohexanecarboxylic acid, 4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)benzoic acid, cis-4-(1-(4-chloro-2-fluorobenzyl)-3-(trifluoromethyl)-4,5,6,7-tetrahydro-1H-pyrazolo[3,4-c]pyridine-6-carboxamido)cyclohexanecarboxylic acid, trans-4-(1-(4-Chloro-2-fluorobenzyl)-3-(trifluoromethyl)-4,5,6,7-tetrahydro-1H-pyrazolo[3,4-c]pyridine-6-carboxamido)cyclohexanecarboxylic acid, 4-(1-(4-Chloro-2-fluorobenzyl)-3-(trifluoromethyl)-4,5,6,7-tetrahydro-1H-pyrazolo[3,4-c]pyridine-6-carboxamido)bicyclo[2.2.2]octane-1-carboxylic acid, cis-4-(1-(4-Chloro-2-fluorobenzyl)-N-methyl-3-(trifluoromethyl)-4,5,6,7-tetrahydro-1H-pyrazolo[3,4-c]pyridine-6-carboxamido)cyclohexanecarboxylic acid, trans-4-(1-(4-Chloro-2-fluorobenzyl)-N-methyl-3-(trifluoromethyl)-4,5,6,7-tetrahydro-1H-pyrazolo[3,4-c]pyridine-6-carboxamido)cyclohexanecarboxylic acid, 4-(1-(4-Fluorobenzyl)-3-(trifluoromethyl)-4,5,6,7-tetrahydro-1H-pyrazolo[3,4-c]pyridine-6-carbonyl)bicyclo[2.2.2]octane-1-carboxylic acid, 4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)bicyclo[2.2.2]octane-1-carboxylic acid, 4-(2-(1-(4-Fluorobenzyl)-3-(trifluoromethyl)-4,5-dihydro-1H-pyrazolo[3,4-c]pyridin-6(7H)-yl)-2-oxoethyl)bicyclo[2.2.2]octane-1-carboxylic acid, trans-4-(2-(1-(4-Methylbenzyl)-3-(trifluoromethyl)-4,5-dihydro-1H-pyrazolo[3,4-c]pyridin-6(7H)-yl)-2-oxoethyl)cyclohexanecarboxylic acid, trans-4-(2-(1-(4-Methoxylbenzyl)-3-(trifluoromethyl)-4,5-dihydro-1H-pyrazolo[3,4-c]pyridin-6(7H)-yl)-2-oxoethyl)cyclohexanecarboxylic acid, trans-4-(2-Oxo-2-(1-phenethyl-3-(trifluoromethyl)-4,5-dihydro-1H-pyrazolo[3,4-c]pyridin-6(7H)-yl)ethyl)cyclohexanecarboxylic acid, trans-4-(2-(1-((5-chlorothiophen-2-yl)methyl)-3-(trifluoromethyl)-4,5-dihydro-1H-pyrazolo[3,4-c]pyridin-6(7H)-yl)-2-oxoethyl)cyclohexanecarboxylic acid, (2S)-1-(tert-Butoxycarbonyl)-4-(2-(1-(4-chloro-2-fluorobenzyl)-3-(trifluoromethyl)-4,5-dihydro-1H-pyrazolo[3,4-c]pyridin-6(7H)-yl)-2-oxoethyl)pyrrolidine-2-carboxylic acid, trans-4-(2-(1-(1-(4-Fluorophenyl)ethyl)-3-(trifluoromethyl)-4,5-dihydro-1H-pyrazolo[3,4-c]pyridin-6(7H)-yl)-2-oxoethyl)cyclohexanecarboxylic acid, cis-4-(2-(1-(1-(4-Fluorophenyl)ethyl)-3-(trifluoromethyl)-4,5-dihydro-1H-pyrazolo[3,4-c]pyridin-6(7H)-yl)-2-oxoethyl)cyclohexanecarboxylic acid, cis-4-(2-Oxo-2-(1-phenyl-3-(trifluoromethyl)-4,5-dihydro-1H-pyrazolo[3,4-c]pyridin-6(7H)-yl)ethyl)cyclohexanecarboxylic acid, 4-(2-(1-(3-Fluorobenzyl)-3-(trifluoromethyl)-4,5-dihydro-1H-pyrazolo[3,4-c]pyridin-6(7H)-yl)-2-oxoethyl)cyclohexanecarboxylic acid, 4-(2-Oxo-2-(3-(trifluoromethyl)-1-(4-(trifluoromethyl)benzyl)-4,5-dihydro-1H-pyrazolo[3,4-c]pyridin-6(7H)-yl)ethyl)cyclohexanecarboxylic acid, 4-(2-(1-(2-Fluorobenzyl)-3-(trifluoromethyl)-4,5-dihydro-1H-pyrazolo[3,4-c]pyridin-6(7H)-yl)-2-oxoethyl)cyclohexanecarboxylic acid, 4-(1-(1-(4-Chloro-2-fluorobenzyl)-3-(trifluoromethyl)-4,5-dihydro-1H-pyrazolo[3,4-c]pyridin-6(7H)-yl)-1-oxopropan-2-yl)cyclohexanecarboxylic acid, 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)-1-methylcyclohexanecarboxylic acid, 3-(2-(1-(4-Chloro-2-fluorobenzyl)-3-(trifluoromethyl)-4,5-dihydro-1H-pyrazolo[3,4-c]pyridin-6(7H)-yl)-2-oxoethyl)cyclopentanecarboxylic acid, 3-(2-(1-(4-Fluorobenzyl)-3-(trifluoromethyl)-4,5-dihydro-1H-pyrazolo[3,4-c]pyridin-6(7H)-yl)-2-oxoethyl)cyclopentanecarboxylic acid, 3-(2-(1-(4-Chloro-2-fluorobenzyl)-3-(trifluoromethyl)-4,5-dihydro-1H-pyrazolo[3,4-c]pyridin-6(7H)-yl)-2-oxoethyl)cyclobutanecarboxylic acid, 3-(2-(1-(4-Fluorobenzyl)-3-(trifluoromethyl)-4,5-dihydro-1H-pyrazolo[3,4-c]pyridin-6(7H)-yl)-2-oxoethyl)cyclobutanecarboxylic acid, 8-(2-(1-(4-Chloro-2-fluorobenzyl)-3-(trifluoromethyl)-4,5-dihydro-1H-pyrazolo[3,4-c]pyridin-6(7H)-yl)-2-oxoethyl)bicyclo[3.2.1]octane-3-carboxylic acid, 4-(2-(1-(4-Fluorobenzyl)-3-(trifluoromethyl)-4,5-dihydro-1H-pyrazolo[3,4-c]pyridin-6(7H)-yl)-2-oxoethyl)-1-methylcyclohexanecarboxylic acid, 6-(2-(1-(4-Chloro-2-fluorobenzyl)-3-(trifluoromethyl)-4,5-dihydro-1H-pyrazolo[3,4-c]pyridin-6(7H)-yl)-2-oxoethyl)spiro[3.3]heptane-2-carboxylic acid, 6-(2-(1-(4-Fluorobenzyl)-3-(trifluoromethyl)-4,5-dihydro-1H-pyrazolo[3,4-c]pyridin-6(7H)-yl)-2-oxoethyl)spiro[3.3]heptane-2-carboxylic acid, 3-(2-(1-(4-Chloro-2-fluorobenzyl)-3-(trifluoromethyl)-4,5-dihydro-1H-pyrazolo[3,4-c]pyridin-6(7H)-yl)-2-oxoethyl)-2,2-dimethylcyclobutanecarboxylic acid, 3-(2-(1-(4-Fluorobenzyl)-3-(trifluoromethyl)-4,5-dihydro-1H-pyrazolo[3,4-c]pyridin-6(7H)-yl)-2-oxoethyl)-2,2-dimethylcyclobutanecarboxylic acid, (3R,4R)-5-(2-(1-(4-Chloro-2-fluorobenzyl)-3-(trifluoromethyl)-4,5-dihydro-1H-pyrazolo[3,4-c]pyridin-6(7H)-yl)-2-oxoethyl)tricyclo[2.2.1.02,6]heptane-3-carboxylic acid, (3R,4R)-5-(2-(1-(4-Fluorobenzyl)-3-(trifluoromethyl)-4,5-dihydro-1H-pyrazolo[3,4-c]pyridin-6(7H)-yl)-2-oxoethyl)tricyclo[2.2.1.02,6]heptane-3-carboxylic acid, trans-4-(2-(1-(4-Fluorobenzyl)-3-(trifluoromethyl)-4,5-dihydro-1H-pyrazolo[3,4-c]pyridin-6(7H)-yl)-2-oxoethyl)cyclohexanecarboxylic acid, cis-4-(2-(1-(4-fluorobenzyl)-3-(trifluoromethyl)-4,5-dihydro-1H-pyrazolo[3,4-c]pyridin-6(7H)-yl)-2-oxoethyl)cyclohexanecarboxylic acid, trans-4-(2-(1-(4-Chloro-2-fluorobenzyl)-4,5-dihydro-1H-pyrazolo[3,4-c]pyridin-6(7H)-yl)-2-oxoethyl)cyclohexanecarboxylic acid, cis-4-(2-(1-(4-chloro-2-fluorobenzyl)-4,5-dihydro-1H-pyrazolo[3,4-c]pyridin-6(7H)-yl)-2-oxoethyl)cyclohexanecarboxylic acid, trans-4-(2-(1-(4-CXhlorobenzyl)-3-(trifluoromethyl)-4,5-dihydro-1H-pyrazolo[3,4-c]pyridin-6(7H)-yl)-2-oxoethyl)cyclohexanecarboxylic acid, cis-4-(2-(1-(4-chlorobenzyl)-3-(trifluoromethyl)-4,5-dihydro-1H-pyrazolo[3,4-c]pyridin-6(7H)-yl)-2-oxoethyl)cyclohexanecarboxylic acid, trans-4-(2-(1-(2,4-Dichlorobenzyl)-3-(trifluoromethyl)-4,5-dihydro-1H-pyrazolo[3,4-c]pyridin-6(7H)-yl)-2-oxoethyl)cyclohexanecarboxylic acid, cis-4-(2-(1-(2,4-dichlorobenzyl)-3-(trifluoromethyl)-4,5-dihydro-1H-pyrazolo[3,4-c]pyridin-6(7H)-yl)-2-oxoethyl)cyclohexanecarboxylic acid, cis-4-((1-(4-Chloro-2-fluorobenzyl)-3-(trifluoromethyl)-4,5,6,7-tetrahydro-1H-pyrazolo[3,4-c]pyridine-6-carbonyl)oxy)cyclohexanecarboxylic acid, trans-4-((1-(4-chloro-2-fluorobenzyl)-3-(trifluoromethyl)-4,5,6,7-tetrahydro-1H-pyrazolo[3,4-c]pyridine-6-carbonyl)oxy)cyclohexanecarboxylic acid, trans-4-(2-(1-Benzyl-3-(trifluoromethyl)-4,5-dihydro-1H-pyrazolo[3,4-c]pyridin-6(7H)-yl)-2-oxoethyl)cyclohexanecarboxylic acid, cis-4-(2-(1-benzyl-3-(trifluoromethyl)-4,5-dihydro-1H-pyrazolo[3,4-c]pyridin-6(7H)-yl)-2-oxoethyl)cyclohexanecarboxylic acid, trans-4 4-(2-(1-(cyclohexylmethyl)-3-(trifluoromethyl)-4,5-dihydro-1H-pyrazolo[3,4-c]pyridin-6(7H)-yl)-2-oxoethyl)cyclohexanecarboxylic acid, cis-4 4-(2-(1-(cyclohexylmethyl)-3-(trifluoromethyl)-4,5-dihydro-1H-pyrazolo[3,4-c]pyridin-6(7H)-yl)-2-oxoethyl)cyclohexanecarboxylic acid, trans-4-(2-(1-(4-Fluorobenzyl)-4,5-dihydro-1H-pyrazolo[3,4-c]pyridin-6(7H)-yl)-2-oxoethyl)cyclohexanecarboxylic acid, cis-4-(2-(1-(4-Fluorobenzyl)-4,5-dihydro-1H-pyrazolo[3,4-c]pyridin-6(7H)-yl)-2-oxoethyl)cyclohexanecarboxylic acid, trans-4-(1-(4-Fluorobenzyl)-3-(trifluoromethyl)-4,5,6,7-tetrahydro-1H-pyrazolo[3,4-c]pyridine-6-carbonyl)cyclohexanecarboxylic acid, cis-4-(1-(4-fluorobenzyl)-3-(trifluoromethyl)-4,5,6,7-tetrahydro-1H-pyrazolo[3,4-c]pyridine-6-carbonyl)cyclohexanecarboxylic acid, trans-4-(2-(1-cyclohexyl-3-(trifluoromethyl)-4,5-dihydro-1H-pyrazolo[3,4-c]pyridin-6(7H)-yl)-2-oxoethyl)cyclohexanecarboxylic acid, cis-4-(2-(1-cyclohexyl-3-(trifluoromethyl)-4,5-dihydro-1H-pyrazolo[3,4-c]pyridin-6(7H)-yl)-2-oxoethyl)cyclohexanecarboxylic acid, cis-4-(2-(1-(2-Cyclohexylethyl)-3-(trifluoromethyl)-4,5-dihydro-1H-pyrazolo[3,4-c]pyridin-6(7H)-yl)-2-oxoethyl)cyclohexanecarboxylic acid, trans-4-(2-(1-(2-cyclohexylethyl)-3-(trifluoromethyl)-4,5-dihydro-1H-pyrazolo[3,4-c]pyridin-6(7H)-yl)-2-oxoethyl)cyclohexanecarboxylic acid, tert-Butyl 3-(2-(1-(4-chloro-2-fluorobenzyl)-3-(trifluoromethyl)-4,5-dihydro-1H-pyrazolo[3,4-c]pyridin-6(7H)-yl)-2-oxoethyl)-8-azabicyclo[3.2.1]octane-8-carboxylate, tert-Butyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)piperidine-1-carboxylate,
tert-Butyl 3-(2-(1-(4-chloro-2-fluorobenzyl)-3-(trifluoromethyl)-4,5-dihydro-1H-pyrazolo[3,4-c]pyridin-6(7H)-yl)-2-oxoethyl)azetidine-1-carboxylate,
tert-Butyl 3-(2-(1-(4-fluorobenzyl)-3-(trifluoromethyl)-4,5-dihydro-1H-pyrazolo[3,4-c]pyridin-6(7H)-yl)-2-oxoethyl)piperidine-1-carboxylate,
tert-Butyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)-2-methylpiperidine-1-carboxylate,
tert-Butyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)-2,2-dimethylpiperidine-1-carboxylate,
tert-Butyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)-2-(trifluoromethyl)piperidine-1-carboxylate,
2-(8-Aza-bicyclo[3.2.1]octan-3-yl)-1-(1-(4-chloro-2-fluorobenzyl)-3-(trifluoromethyl)-4,5-dihydro-1H-pyrazolo[3,4-c]pyridin-6(7H)-yl)ethanone,
1-(1-(4-Chloro-2-fluorobenzyl)-3-(trifluoromethyl)-4,5-dihydro-1H-pyrazolo[3,4-c]pyridin-6(7H)-yl)-2-(piperidin-4-yl)ethanone,
2-(Azetidin-3-yl)-1-(1-(4-chloro-2-fluorobenzyl)-3-(trifluoromethyl)-4,5-dihydro-1H-pyrazolo[3,4-c]pyridin-6(7H)-yl)ethanone,
1-(1-(4-Fluorobenzyl)-3-(trifluoromethyl)-4,5-dihydro-1H-pyrazolo[3,4-c]pyridin-6(7H)-yl)-2-(piperidin-3-yl)ethanone,
1-(1-(4-Chloro-2-fluorobenzyl)-3-(trifluoromethyl)-4,5-dihydro-1H-pyrazolo[3,4-c]pyridin-6(7H)-yl)-2-(2-methylpiperidin-4-yl)ethanone,
1-(1-(4-Chloro-2-fluorobenzyl)-3-(trifluoromethyl)-4,5-dihydro-1H-pyrazolo[3,4-c]pyridin-6(7H)-yl)-2-(2,2-dimethylpiperidin-4-yl)ethanone,
1-(1-(4-Chloro-2-fluorobenzyl)-3-(trifluoromethyl)-4,5-dihydro-1H-pyrazolo[3,4-c]pyridin-6(7H)-yl)-2-(2-(trifluoromethyl)piperidin-4-yl)ethanone,
(2s)-4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)pyrrolidine-2-carboxylic acid,
1-(1-(4-Chloro-2-fluorobenzyl)-3-(trifluoromethyl)-4,5-dihydro-1H-pyrazolo[3,4-c]pyridin-6(7H)-yl)-2-(8-methyl-8-aza-bicyclo[3.2.1]octan-3-yl)ethanone,
1-(1-(4-Chloro-2-fluorobenzyl)-3-(trifluoromethyl)-4,5-dihydro-1H-pyrazolo[3,4-c]pyridin-6(7H)-yl)-2-(1,2-dimethylpiperidin-4-yl)ethanone,
1-(1-(4-Chloro-2-fluorobenzyl)-3-(trifluoromethyl)-4,5-dihydro-1H-pyrazolo[3,4-c]pyridin-6(7H)-yl)-2-(1,2,2-timethylpiperidin-4-yl)ethanone,
1-(1-(4-Chloro-2-fluorobenzyl)-3-(trifluoromethyl)-4,5-dihydro-1H-pyrazolo[3,4-c]pyridin-6(7H)-yl)-2-(1-methyl-2-(trifluoromethyl)piperidin-4-yl)ethanone,
1-(1-(4-Fluorobenzyl)-3-(trifluoromethyl)-4,5-dihydro-1H-pyrazolo[3,4-c]pyridin-6(7H)-yl)-2-(1-methylpiperidin-3-yl)ethanone formate,
1-(1-(4-Chloro-2-fluorobenzyl)-3-(trifluoromethyl)-4,5-dihydro-1H-pyrazolo[3,4-c]pyridin-6(7H)-yl)-2-(1-isopropylpiperidin-4-yl)ethanone,
1-(1-(4-Chloro-2-fluorobenzyl)-3-(trifluoromethyl)-4,5-dihydro-1H-pyrazolo[3,4-c]pyridin-6(7H)-yl)-2-(1-ethylpiperidin-4-yl)ethanone,
1-(1-(4-Fluorobenzyl)-3-(trifluoromethyl)-4,5-dihydro-1H-pyrazolo[3,4-c]pyridin-6(7H)-yl)-2-(1-isopropylpiperidin-3-yl)ethanone formate,
Methyl 1-(2-(1-(4-fluorobenzyl)-3-(trifluoromethyl)-4,5-dihydro-1H-pyrazolo[3,4-c]pyridin-6(7H)-yl)-2-oxoethyl)piperidine-4-carboxylate,
1-(1-(4-Chloro-2-fluorobenzyl)-3-(trifluoromethyl)-4,5-dihydro-1H-pyrazolo[3,4-c]pyridin-6(7H)-yl)-2-(piperidin-1-yl)ethanone,
Ethyl 1-(2-(1-(4-chloro-2-fluorobenzyl)-3-(trifluoromethyl)-4,5-dihydro-1H-pyrazolo[3,4-c]pyridin-6(7H)-yl)-2-oxoethyl)piperidine-3-carboxylate,
Methyl 8-(2-(1-(4-chloro-2-fluorobenzyl)-3-(trifluoromethyl)-4,5-dihydro-1H-pyrazolo[3,4-c]pyridin-6(7H)-yl)-2-oxoethyl)-8-azabicyclo[3.2.1]octane-3-carboxylate,
Ethyl 1-(2-(1-(4-fluorobenzyl)-3-(trifluoromethyl)-4,5-dihydro-1H-pyrazolo[3,4-c]pyridin-6(7H)-yl)-2-oxoethyl)piperidine-3-carboxylate,
Ethyl 1-(1-(1-(4-chloro-2-fluorobenzyl)-3-(trifluoromethyl)-4,5-dihydro-1H-pyrazolo[3,4-c]pyridin-6(7H)-yl)-1-oxopropan-2-yl)piperidine-4-carboxylate,
Methyl 1-(2-(1-(4-fluorobenzyl)-3-(trifluoromethyl)-4,5-dihydro-1H-pyrazolo[3,4-c]pyridin-6(7H)-yl)-2-oxoethyl)pyrrolidine-3-carboxylate,
1-(1-(4-Chloro-2-fluorobenzyl)-3-(trifluoromethyl)-4,5-dihydro-1H-pyrazolo[3,4-c]pyridin-6(7H)-yl)-2-(4-(trifluoromethyl)piperidin-1-yl)ethanone,
Ethyl 3-(2-(1-(4-fluorobenzyl)-3-(trifluoromethyl)-4,5-dihydro-1H-pyrazolo[3,4-c]pyridin-6(7H)-yl)-2-oxoethylamino)propanoate,
1-(2-(1-(4-Fluorobenzyl)-3-(trifluoromethyl)-4,5-dihydro-1H-pyrazolo[3,4-c]pyridin-6(7H)-yl)-2-oxoethyl)piperidine-4-carboxylic acid,
1-(2-(1-(4-Chloro-2-fluorobenzyl)-3-(trifluoromethyl)-4,5-dihydro-1H-pyrazolo[3,4-c]pyridin-6(7H)-yl)-2-oxoethyl)piperidine-4-carboxylic acid,
1-(2-(1-(4-Chloro-2-fluorobenzyl)-3-(trifluoromethyl)-4,5-dihydro-1H-pyrazolo[3,4-c]pyridin-6(7H)-yl)-2-oxoethyl)piperidine-3-carboxylic acid,
8-(2-(1-(4-Chloro-2-fluorobenzyl)-3-(trifluoromethyl)-4,5-dihydro-1H-pyrazolo[3,4-c]pyridin-6(7H)-yl)-2-oxoethyl)-8-azabicyclo[3.2.1]octane-3-carboxylic acid,
8-(2-(1-(4-Fluorobenzyl)-3-(trifluoromethyl)-4,5-dihydro-1H-pyrazolo[3,4-c]pyridin-6(7H)-yl)-2-oxoethyl)-8-azabicyclo[3.2.1]octane-3-carboxylic acid,
9-(2-(1-(4-Fluorobenzyl)-3-(trifluoromethyl)-4,5-dihydro-1H-pyrazolo[3,4-c]pyridin-6(7H)-yl)-2-oxoethyl)-9-azabicyclo[3.3.1]nonane-3-carboxylic acid,
1-(2-(1-(4-Fluorobenzyl)-3-(trifluoromethyl)-4,5-dihydro-1H-pyrazolo[3,4-c]pyridin-6(7H)-yl)-2-oxoethyl)piperidine-3-carboxylic acid,
1-(1-(1-(4-Chloro-2-fluorobenzyl)-3-(trifluoromethyl)-4,5-dihydro-1H-pyrazolo[3,4-c]pyridin-6(7H)-yl)-1-oxopropan-2-yl)piperidine-4-carboxylic acid,
2-(2-(1-(4-Chloro-2-fluorobenzyl)-3-(trifluoromethyl)-4,5-dihydro-1H-pyrazolo[3,4-c]pyridin-6(7H)-yl)-2-oxoethyl)octahydrocyclopenta[c]pyrrole-5-carboxylic acid,
2-(2-(1-(4-Fluorobenzyl)-3-(trifluoromethyl)-4,5-dihydro-1H-pyrazolo[3,4-c]pyridin-6(7H)-yl)-2-oxoethyl)octahydrocyclopenta[c]pyrrole-5-carboxylic acid,
3-((2-(1-(4-Chloro-2-fluorobenzyl)-3-(trifluoromethyl)-4,5-dihydro-1H-pyrazolo[3,4-c]pyridin-6(7H)-yl)-2-oxoethyl)amino)-2,2-dimethylcyclobutanecarboxylic acid,
1-(2-(1-(4-Fluorobenzyl)-3-(trifluoromethyl)-4,5-dihydro-1H-pyrazolo[3,4-c]pyridin-6(7H)-yl)-2-oxoethyl)pyrrolidine-3-carboxylic acid,
2-(1-(2-(1-(4-Chloro-2-fluorobenzyl)-3-(trifluoromethyl)-4,5-dihydro-1H-pyrazolo[3,4-c]pyridin-6(7H)-yl)-2-oxoethyl)piperidin-4-yl)acetic acid, 3-((2-(1-(4-Fluorobenzyl)-3-(trifluoromethyl)-4,5-dihydro-1H-pyrazolo[3,4-c]pyridin-6(7H)-yl)-2-oxoethyl)amino)-2,2-dimethylcyclobutanecarboxylic acid,
2-(1-(2-(1-(4-Fluorobenzyl)-3-(trifluoromethyl)-4,5-dihydro-1H-pyrazolo[3,4-c]pyridin-6(7H)-yl)-2-oxoethyl)piperidin-4-yl)acetic acid,
3-(2-(1-(4-Fluorobenzyl)-3-(trifluoromethyl)-4,5-dihydro-1H-pyrazolo[3,4-c]pyridin-6(7H)-yl)-2-oxoethylamino)propanoic acid,
6-(1-(4-Chloro-2-fluorobenzyl)-3-(trifluoromethyl)-4,5-dihydro-1H-pyrazolo[3,4-c]pyridin-6(7H)-yl)-6-oxohexanoic acid,
5-(1-(4-Chloro-2-fluorobenzyl)-3-(trifluoromethyl)-4,5-dihydro-1H-pyrazolo[3,4-c]pyridin-6(7H)-yl)-5-oxopentanoic acid,
4-(1-(4-Chloro-2-fluorobenzyl)-3-(trifluoromethyl)-4,5-dihydro-1H-pyrazolo[3,4-c]pyridin-6(7H)-yl)-4-oxobutanoic acid,
2-(4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)piperidin-1-yl)acetic acid,
3-(3-(1-(4-Fluorobenzyl)-3-(trifluoromethyl)-4,5,6,7-tetrahydro-1H-pyrazolo[3,4-c]pyridine-6-carbonyl)pyrrolidin-1-yl)propanoic acid,
3-(3-(1-(4-chloro-2-fluorobenzyl)-3-(trifluoromethyl)-4,5,6,7-tetrahydro-1H-pyrazolo[3,4-c]pyridine-6-carbonyl)pyrrolidin-1-yl)propanoic acid,
Methyl 3-(2-(1-(4-fluorobenzyl)-3-(trifluoromethyl)-4,5-dihydro-1H-pyrazolo[3,4-c]pyridin-6(7H)-yl)-2-oxoethyl)piperidine-1-carboxylate,
Methyl 3-(2-(1-(4-fluorobenzyl)-3-(trifluoromethyl)-4,5-dihydro-1H-pyrazolo[3,4-c]pyridin-6(7H)-yl)-2-oxoethyl)piperidine-1-carboxylate, and
1-(1-(4-Fluorobenzyl)-3-(trifluoromethyl)-4,5-dihydro-1H-pyrazolo[3,4-c]pyridin-6(7H)-yl)-2-(1-(pyrimidin-2-yl)piperidin-4-yl)ethanone,
or a pharmaceutically acceptable salt thereof.

In one embodiment of the invention, there is provided a compound selected from:
1-(1-(4-Chloro-2-fluorobenzyl)-3-(trifluoromethyl)-4,5-dihydro-1H-pyrazolo[3,4-c]pyridin-6(7H)-yl)-2-(tetrahydro-2H-pyran-4-yl)ethanone;
1-(1-(4-Fluorobenzyl)-3-(trifluoromethyl)-4,5-dihydro-1H-pyrazolo[3,4-c]pyridin-6(7H)-yl)-2-(tetrahydro-2H-pyran-4-yl)ethanone;
1-(1-(4-Chloro-2-fluorobenzyl)-3-(trifluoromethyl)-4,5-dihydro-1H-pyrazolo[3,4-c]pyridin-6(7H)-yl)-3-(1H-tetrazol-5-yl)propan-1-one;
1-(1-(4-Fluorobenzyl)-3-(trifluoromethyl)-4,5-dihydro-1H-pyrazolo[3,4-c]pyridin-6(7H)-yl)-3-(1H-tetrazol-5-yl)propan-1-one;
1-(1-(4-Chloro-2-fluorobenzyl)-3-(trifluoromethyl)-4,5-dihydro-1H-pyrazolo[3,4-c]pyridin-6(7H)-yl)-2-(octahydroindolizin-7-yl)ethanone;
1-(1-(4-Fluorobenzyl)-3-(trifluoromethyl)-4,5-dihydro-1H-pyrazolo[3,4-c]pyridin-6(7H)-yl)-2-(octahydroindolizin-7-yl)ethanone;
(1-(4-Fluorobenzyl)-3-(trifluoromethyl)-4,5-dihydro-1H-pyrazolo[3,4-c]pyridin-6(7H)-yl)(quinuclidin-3-yl)methanone;
(1-(4-Fluorobenzyl)-3-(trifluoromethyl)-4,5-dihydro-1H-pyrazolo[3,4-c]pyridin-6(7H)-yl)(quinuclidin-4-yl)methanone;
1-(1-(4-Fluorobenzyl)-3-(trifluoromethyl)-4,5-dihydro-1H-pyrazolo[3,4-c]pyridin-6(7H)-yl)-2-(quinuclidin-3-yl)ethanone;
trans-Ethyl 4-(2-(3-(difluoromethyl)-1-(4-fluorobenzyl)-4,5-dihydro-1H-pyrazolo[3,4-c]pyridin-6(7H)-yl)-2-oxoethyl)cyclohexanecarboxylate;
trans-Ethyl 4-(2-(3-cyclopropyl-1-(4-fluorobenzyl)-4,5-dihydro-1H-pyrazolo[3,4-c]pyridin-6(7H)-yl)-2-oxoethyl)cyclohexanecarboxylate;
Ethyl 6-(2-(trans-4-(ethoxycarbonyl)cyclohexyl)acetyl)-1-(4-fluorobenzyl)-4,5,6,7-tetrahydro-1H-pyrazolo[3,4-c]pyridine-3-carboxylate;
trans-Ethyl-4-(2-(1-(4-fluorobenzyl)-3-(hydroxymethyl)-4,5-dihydro-1H-pyrazolo[3,4-c]pyridin-6(7H)-yl)-2-oxoethyl)cyclohexanecarboxylate;
trans-Ethyl 4-(2-(3-carbamoyl-1-(4-fluorobenzyl)-4,5-dihydro-1H-pyrazolo[3,4-c]pyridin-6(7H)-yl)-2-oxoethyl)cyclohexanecarboxylate;
trans-Ethyl 4-(2-(3-cyano-1-(4-fluorobenzyl)-4,5-dihydro-1H-pyrazolo[3,4-c]pyridin-6(7H)-yl)-2-oxoethyl)cyclohexanecarboxylate;
trans-Ethyl 4-(2-(1-(4-fluorobenzyl)-3-phenyl-4,5-dihydro-1H-pyrazolo[3,4-c]pyridin-6(7H)-yl)-2-oxoethyl)cyclohexanecarboxylate;
trans-Ethyl-4-(2-oxo-2-(1-(thiophen-3-ylmethyl)-3-(trifluoromethyl)-4,5-dihydro-1H-pyrazolo[3,4-c]pyridin-6(7H)-yl)ethyl)cyclohexanecarboxylate;
trans-Ethyl-4-(2-oxo-2-(1-(thiophen-2-ylmethyl)-3-(trifluoromethyl)-4,5-dihydro-1H-pyrazolo[3,4-c]pyridin-6(7H)-yl)ethyl)cyclohexanecarboxylate;
trans-Ethyl 4-(2-oxo-2-(1-(thiazol-5-ylmethyl)-3-(trifluoromethyl)-4,5-dihydro-1H-pyrazolo[3,4-c]pyridin-6(7H)-yl)ethyl)cyclohexanecarboxylate;
trans-Ethyl 4-(2-(1-((4-methylcyclohexyl)methyl)-3-(trifluoromethyl)-4,5-dihydro-1H-pyrazolo[3,4-c]pyridin-6(7H)-yl)-2-oxoethyl)cyclohexanecarboxylate;
trans-Ethyl 4-(2-(1-(2,4-difluorobenzyl)-3-(trifluoromethyl)-4,5-dihydro-1H-pyrazolo[3,4-c]pyridin-6(7H)-yl)-2-oxoethyl)cyclohexanecarboxylate;
trans-4-(2-Oxo-2-(1-(pyridin-3-ylmethyl)-3-(trifluoromethyl)-4,5-dihydro-1H-pyrazolo[3,4-c]pyridin-6(7H)-yl)ethyl)cyclohexanecarboxylic acid;
trans-4-(2-Oxo-2-(1-(pyridin-2-ylmethyl)-3-(trifluoromethyl)-4,5-dihydro-1H-pyrazolo[3,4-c]pyridin-6(7H)-yl)ethyl)cyclohexanecarboxylic acid;
trans-4-(2-Oxo-2-(1-(pyridin-4-ylmethyl)-3-(trifluoromethyl)-4,5-dihydro-1H-pyrazolo[3,4-c]pyridin-6(7H)-yl)ethyl)cyclohexanecarboxylic acid;
cis-4-(2-(1-((5-Chlorothiophen-2-yl)methyl)-3-(trifluoromethyl)-4,5-dihydro-1H-pyrazolo[3,4-c]pyridin-6(7H)-yl)-2-oxoethyl)cyclohexanecarboxylic acid;
trans-4-(2-Oxo-2-(1-(thiophen-2-ylmethyl)-3-(trifluoromethyl)-4,5-dihydro-1H-pyrazolo[3,4-c]pyridin-6(7H)-yl)ethyl)cyclohexanecarboxylic acid;
trans-4-(2-Oxo-2-(1-(thiophen-3-ylmethyl)-3-(trifluoromethyl)-4,5-dihydro-1H-pyrazolo[3,4-c]pyridin-6(7H)-yl)ethyl)cyclohexanecarboxylic acid;
trans-4-(2-Oxo-2-(1-(thiazol-5-ylmethyl)-3-(trifluoromethyl)-4,5-dihydro-1H-pyrazolo[3,4-c]pyridin-6(7H)-yl)ethyl)cyclohexanecarboxylic acid;
trans-4-(2-Oxo-2-(1-(pyrimidin-5-ylmethyl)-3-(trifluoromethyl)-4,5-dihydro-1H-pyrazolo[3,4-c]pyridin-6(7H)-yl)ethyl)cyclohexanecarboxylic acid;
trans-4-(2-(1-(2,4-Difluorobenzyl)-3-(trifluoromethyl)-4,5-dihydro-1H-pyrazolo[3,4-c]pyridin-6(7H)-yl)-2-oxoethyl)cyclohexanecarboxylic acid;
trans-4-(2-(1-(3,4-Difluorobenzyl)-3-(trifluoromethyl)-4,5-dihydro-1H-pyrazolo[3,4-c]pyridin-6(7H)-yl)-2-oxoethyl)cyclohexanecarboxylic acid;

trans-4-(2-(1-(2,4,5-Trifluorobenzyl)-3-(trifluoromethyl)-4,5-dihydro-1H-pyrazolo[3,4-c]pyridin-6(7H)-yl)-2-oxoethyl)cyclohexanecarboxylic acid;

trans-4-(2-(1-(3,4,5-Trifluorobenzyl)-3-(trifluoromethyl)-4,5-dihydro-1H-pyrazolo[3,4-c]pyridin-6(7H)-yl)-2-oxoethyl)cyclohexanecarboxylic acid;

cis-4-(2-(1-(2,4-Difluorobenzyl)-3-(trifluoromethyl)-4,5-dihydro-1H-pyrazolo[3,4-c]pyridin-6(7H)-yl)-2-oxoethyl)cyclohexanecarboxylic acid;

cis-4-(2-(1-(4-Cyanobenzyl)-3-(trifluoromethyl)-4,5-dihydro-1H-pyrazolo[3,4-c]pyridin-6(7H)-yl)-2-oxoethyl)cyclohexanecarboxylic acid;

trans-4-(2-(1-((4-Methylcyclohexyl)methyl)-3-(trifluoromethyl)-4,5-dihydro-1H-pyrazolo[3,4-c]pyridin-6(7H)-yl)-2-oxoethyl)cyclohexanecarboxylic acid;

trans-4-(2-(3-Cyclopropyl-1-(4-fluorobenzyl)-4,5-dihydro-1H-pyrazolo[3,4-c]pyridin-6(7H)-yl)-2-oxoethyl)cyclohexanecarboxylic acid;

trans-4-(2-(1-(4-Fluorobenzyl)-3-phenyl-4,5-dihydro-1H-pyrazolo[3,4-c]pyridin-6(7H)-yl)-2-oxoethyl)cyclohexanecarboxylic acid;

trans-4-(2-(1-(4-Fluorobenzyl)-3-(pyridin-3-yl)-4,5-dihydro-1H-pyrazolo[3,4-c]pyridin-6(7H)-yl)-2-oxoethyl)cyclohexanecarboxylic acid;

trans-4-(2-(1-(4-Fluorobenzyl)-3-(pyridin-3-yl)-4,5-dihydro-1H-pyrazolo[3,4-c]pyridin-6(7H)-yl)-2-oxoethyl)cyclohexanecarboxylic acid;

trans-4-(2-(3-Ethoxy-1-(4-fluorobenzyl)-4,5-dihydro-1H-pyrazolo[3,4-c]pyridin-6(7H)-yl)-2-oxoethyl)cyclohexanecarboxylic acid;

trans-4-(2-(3-(Dimethylamino)-1-(4-fluorobenzyl)-4,5-dihydro-1H-pyrazolo[3,4-c]pyridin-6 (7H)-yl)-2-oxoethyl)cyclohexanecarboxylic acid;

trans-4-(2-(3-(Difluoromethyl)-1-(4-fluorobenzyl)-4,5-dihydro-1H-pyrazolo[3,4-c]pyridin-6(7H)-yl)-2-oxoethyl)cyclohexanecarboxylic acid;

trans-4-(2-(1-(4-Fluorobenzyl)-3-(hydroxymethyl)-4,5-dihydro-1H-pyrazolo[3,4-c]pyridin-6(7H)-yl)-2-oxoethyl)cyclohexanecarboxylic acid;

trans-4-(2-(3-Cyano-1-(4-fluorobenzyl)-4,5-dihydro-1H-pyrazolo[3,4-c]pyridin-6(7H)-yl)-2-oxoethyl)cyclohexanecarboxylic acid;

trans-4-(2-(3-Carbamoyl-1-(4-fluorobenzyl)-4,5-dihydro-1H-pyrazolo[3,4-c]pyridin-6(7H)-yl)-2-oxoethyl)cyclohexanecarboxylic acid;

2-(trans-4-(2-(1-(4-Fluorobenzyl)-3-(trifluoromethyl)-4,5-dihydro-1H-pyrazolo[3,4-c]pyridin-6(7H)-yl)-2-oxoethyl)cyclohexyl)acetic acid;

2-(cis-4-(2-(1-(4-Fluorobenzyl)-3-(trifluoromethyl)-4,5-dihydro-1H-pyrazolo[3,4-c]pyridin-6(7H)-yl)-2-oxoethyl)cyclohexyl)acetic acid;

4-(1-(4-Fluorobenzyl)-3-(trifluoromethyl)-4,5,6,7-tetrahydro-1H-pyrazolo[3,4-c]pyridine-6-carbonyl)bicyclo[2.2.1]heptane-1-carboxylic acid;

4-(1-(4-Fluorobenzyl)-3-(trifluoromethyl)-4,5,6,7-tetrahydro-1H-pyrazolo[3,4-c]pyridine-6-carbonyl)bicyclo[2.2.1]heptane-1-carboxylic acid;

4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)bicyclo[2.2.1]heptane-1-carboxylic acid;

4-(2-(1-(4-Fluorobenzyl)-3-(trifluoromethyl)-4,5-dihydro-1H-pyrazolo[3,4-c]pyridin-6(7H)-yl)-2-oxoethyl)bicyclo[2.2.1]heptane-1-carboxylic acid;

4-(2-(1-(4-Chloro-2-fluorobenzyl)-3-(trifluoromethyl)-4,5-dihydro-1H-pyrazolo[3,4-c]pyridin-6(7H)-yl)-2-oxoethyl) adamantancarboxylic acid;

1-(1-(4-Fluorobenzyl)-3-(trifluoromethyl)-4,5-dihydro-1H-pyrazolo[3,4-c]pyridin-6(7H)-yl)-2-(2-azaspiro[3.3]heptan-6-yl)adamantane carboxylic acid;

(2R)-1-(tert-Butoxycarbonyl)-4-(2-(1-(4-chloro-2-fluorobenzyl)-3-(trifluoromethyl)-4,5-dihydro-1H-pyrazolo[3,4-c]pyridin-6(7H)-yl)-2-oxoethyl)pyrrolidine-2-carboxylic acid;

3-(2-(1-(4-Chloro-2-fluorobenzyl)-3-(trifluoromethyl)-4,5-dihydro-1H-pyrazolo[3,4-c]pyridin-6(7H)-yl)-2-oxoethyl)-1-methylcyclobutanecarboxylic acid;

cis-3-(2-(1-(4-Fluorobenzyl)-3-(trifluoromethyl)-4,5-dihydro-1H-pyrazolo[3,4-c]pyridin-6(7H)-yl)-2-oxoethyl)-1-methylcyclobutanecarboxylic acid;

trans-3-(2-(1-(4-fluorobenzyl)-3-(trifluoromethyl)-4,5-dihydro-1H-pyrazolo[3,4-c]pyridin-6(7H)-yl)-2-oxoethyl)-1-methylcyclobutanecarboxylic acid;

cis-4-(2-(1-(4-fluorobenzyl)-3-(trifluoromethyl)-4,5-dihydro-1H-pyrazolo[3,4-c]pyridin-6(7H)-yl)-2-oxoethyl)-1-methylcyclohexanecarboxylic acid;

trans-4-(2-(1-(4-fluorobenzyl)-3-(trifluoromethyl)-4,5-dihydro-1H-pyrazolo[3,4-c]pyridin-6(7H)-yl)-2-oxoethyl)-1-methylcyclohexanecarboxylic acid;

trans-4-(2-(1-(4-fluorobenzyl)-3-(trifluoromethyl)-4,5-dihydro-1H-pyrazolo[3,4-c]pyridin-6(7H)-yl)-2-oxoethyl)-1-methylcyclohexanecarboxylic acid;

tert-Butyl 2-ethyl-4-(2-(1-(4-fluorobenzyl)-3-(trifluoromethyl)-4,5-dihydro-1H-pyrazolo[3,4-c]pyridin-6(7H)-yl)-2-oxoethyl)piperidine-1-carboxylate;

tert-Butyl 4-(2-(1-(4-fluorobenzyl)-3-(trifluoromethyl)-4,5-dihydro-1H-pyrazolo[3,4-c]pyridin-6(7H)-yl)-2-oxoethyl)-2-propylpiperidine-1-carboxylate;

tert-Butyl 4-(1-(4-fluorobenzyl)-3-(trifluoromethyl)-4,5,6,7-tetrahydro-1H-pyrazolo[3,4-c]pyridine-6-carbonyl)bicyclo[2.2.2]octan-1-ylcarbamate;

(4-Aminobicyclo[2.2.2]octan-1-yl) (1-(4-fluorobenzyl)-3-(trifluoromethyl)-4,5-dihydro-1H-pyrazolo[3,4-c]pyridin-6(7H)-yl)methanone;

2-(4-Aminobicyclo[2.2.2]octan-1-yl)-1-(1-(4-fluorobenzyl)-3-(trifluoromethyl)-4,5-dihydro-1H-pyrazolo[3,4-c]pyridin-6(7H)-yl)ethanone;

2-(2-Ethylpiperidin-4-yl)-1-(1-(4-fluorobenzyl)-3-(trifluoromethyl)-4,5-dihydro-1H-pyrazolo[3,4-c]pyridin-6(7H)-yl)ethanone;

1-(1-(4-Fluorobenzyl)-3-(trifluoromethyl)-4,5-dihydro-1H-pyrazolo[3,4-c]pyridin-6(7H)-yl)-2-(2-propylpiperidin-4-yl)ethanone acid;

1-(1-(4-Fluorobenzyl)-3-(trifluoromethyl)-4,5-dihydro-1H-pyrazolo[3,4-c]pyridin-6(7H)-yl)-2-(2-(trifluoromethyl)piperidin-4-yl)ethanone;

(2R)-4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)pyrrolidine-2-carboxylic acid;

1-(1-(4-Chloro-2-fluorobenzyl)-3-(trifluoromethyl)-4,5-dihydro-1H-pyrazolo[3,4-c]pyridin-6(7H)-yl)-2-(morpholin-2-yl)ethanone;

1-(1-(4-Fluorobenzyl)-3-(trifluoromethyl)-4,5-dihydro-1H-pyrazolo[3,4-c]pyridin-6(7H)-yl)-2-(morpholin-2-yl)ethanone;

2-(cis-4-Aminocyclohexyl)-1-(1-(4-chloro-2-fluorobenzyl)-3-(trifluoromethyl)-4,5-dihydro-1H-pyrazolo[3,4-c]pyridin-6(7H)-yl)ethanone;

2-(cis-4-Aminocyclohexyl)-1-(1-(4-fluorobenzyl)-3-(trifluoromethyl)-4,5-dihydro-1H-pyrazolo[3,4-c]pyridin-6 (7H)-yl)ethanone;

2-(trans-4-aminocyclohexyl)-1-(1-(4-chloro-2-fluorobenzyl)-3-(trifluoromethyl)-4,5-dihydro-1H-pyrazolo[3,4-c]pyridin-6(7H)-yl)ethanone;

2-(trans-4-Aminocyclohexyl)-1-(1-(4-fluorobenzyl)-3-(trifluoromethyl)-4,5-dihydro-1H-pyrazolo[3,4-c]pyridin-6(7H)-yl)ethanone;
1-(1-(4-Chloro-2-fluorobenzyl)-3-(trifluoromethyl)-4,5-dihydro-1H-pyrazolo[3,4-c]pyridin-6(7H)-yl)-2-(octahydrocyclopenta[c]pyrrol-5-yl)ethanone;
(1-(4-Fluorobenzyl)-3-(trifluoromethyl)-4,5-dihydro-1H-pyrazolo[3,4-c]pyridin-6(7H)-yl)(4-(methylamino)bicyclo[2.2.2]octan-1-yl)methanone;
1-(1-(4-Fluorobenzyl)-3-(trifluoromethyl)-4,5-dihydro-1H-pyrazolo[3,4-c]pyridin-6(7H)-yl)-2-(pyrrolidin-3-yl)ethanone;
1-(1-(4-Fluorobenzyl)-3-(trifluoromethyl)-4,5-dihydro-1H-pyrazolo[3,4-c]pyridin-6(7H)-yl)-2-(1-methylpyrrolidin-3-yl)ethanone;
1-(1-(4-Fluorobenzyl)-3-(trifluoromethyl)-4,5-dihydro-1H-pyrazolo[3,4-c]pyridin-6(7H)-yl)-2-(1-isopropylpyrrolidin-3-yl)ethanone;
2-(2-Ethyl-1-methylpiperidin-4-yl)-1-(1-(4-fluorobenzyl)-3-(trifluoromethyl)-4,5-dihydro-1H-pyrazolo[3,4-c]pyridin-6(7H)-yl)ethanone;
1-(1-(4-Fluorobenzyl)-3-(trifluoromethyl)-4,5-dihydro-1H-pyrazolo[3,4-c]pyridin-6(7H)-yl)-2-(1-methyl-2-propylpiperidin-4-yl)ethanone acid;
1-(1-(4-Fluorobenzyl)-3-(trifluoromethyl)-4,5-dihydro-1H-pyrazolo[3,4-c]pyridin-6(7H)-yl)-2-(1-methyl-2-propylpiperidin-4-yl)ethanone acid;
(2R)-4-(2-(1-(4-chloro-2-fluorobenzyl)-3-(trifluoromethyl)-4,5-dihydro-1H-pyrazolo[3,4-c]pyridin-6(7H)-yl)-2-oxoethyl)-1-methylpyrrolidine-2-carboxylic acid;
(2S)-4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)-1-methylpyrrolidine-2-carboxylic acid;
(2S)-4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)-1-isopropylpyrrolidine-2-carboxylic acid;
1-(2-(1-(4-Fluorobenzyl)-3-(trifluoromethyl)-4,5-dihydro-1H-pyrazolo[3,4-c]pyridin-6(7H)-yl)-2-oxoethyl)piperidine-4-carbonitrile;
1-(2-(1-(4-Fluorobenzyl)-3-(trifluoromethyl)-4,5-dihydro-1H-pyrazolo[3,4-c]pyridin-6(7H)-yl)-2-oxoethyl)pyrrolidine-3-carbonitrile;
1-(2-(1-(4-Fluorobenzyl)-3-(trifluoromethyl)-4,5-dihydro-1H-pyrazolo[3,4-c]pyridin-6(7H)-yl)-2-oxoethyl)azetidine-3-carbonitrile;
1-(1-(4-Chloro-2-fluorobenzyl)-3-(trifluoromethyl)-4,5-dihydro-1H-pyrazolo[3,4-c]pyridin-6(7H)-yl)-2-(4-methylpiperidin-1-yl)ethanone;
1-(1-(4-Fluorobenzyl)-3-(trifluoromethyl)-4,5-dihydro-1H-pyrazolo[3,4-c]pyridin-6(7H)-yl)-2-(4-methylpiperidin-1-yl)ethanone;
1-(1-(4-Fluorobenzyl)-3-(trifluoromethyl)-4,5-dihydro-1H-pyrazolo[3,4-c]pyridin-6(7H)-yl)-2-(4-(trifluoromethyl)piperidin-1-yl)ethanone;
Ethyl 1-(2-(1-(4-fluorobenzyl)-3-(trifluoromethyl)-4,5-dihydro-1H-pyrazolo[3,4-c]pyridin-6(7H)-yl)-2-oxoethyl)azepane-4-carboxylate;
Ethyl 1-(2-(1-(4-fluorobenzyl)-3-(trifluoromethyl)-4,5-dihydro-1H-pyrazolo[3,4-c]pyridin-6(7H)-yl)-2-oxoethyl)azepane-4-carboxylate;
Methyl 9-(2-(1-(4-fluorobenzyl)-3-(trifluoromethyl)-4,5-dihydro-1H-pyrazolo[3,4-c]pyridin-6(7H)-yl)-2-oxoethyl)-3-oxa-9-azabicyclo[3.3.1]nonane-7-carboxylate;
Methyl 2-(1-(2-(1-(4-fluorobenzyl)-3-(trifluoromethyl)-4,5-dihydro-1H-pyrazolo[3,4-c]pyridin-6(7H)-yl)-2-oxoethyl)azetidin-3-yl)acetate;
1-(2-(1-(4-Chloro-2-fluorobenzyl)-3-(trifluoromethyl)-4,5-dihydro-1H-pyrazolo[3,4-c]pyridin-6(7H)-yl)-2-oxoethyl)azetidine-3-carboxylic acid;
1-(2-(1-(4-Fluorobenzyl)-3-(trifluoromethyl)-4,5-dihydro-1H-pyrazolo[3,4-c]pyridin-6(7H)-yl)-2-oxoethyl)azetidine-3-carboxylic acid;
1-(2-(1-(4-Fluorobenzyl)-3-(trifluoromethyl)-4,5-dihydro-1H-pyrazolo[3,4-c]pyridin-6(7H)-yl)-2-oxoethyl)azepane-4-carboxylic acid;
1-(2-(1-(4-Chloro-2-fluorobenzyl)-3-(trifluoromethyl)-4,5-dihydro-1H-pyrazolo[3,4-c]pyridin-6(7H)-yl)-2-oxoethyl)azepane-4-carboxylic acid;
2-(2-(1-(4-Chloro-2-fluorobenzyl)-3-(trifluoromethyl)-4,5-dihydro-1H-pyrazolo[3,4-c]pyridin-6(7H)-yl)-2-oxoethyl)-2-azaspiro[3.3]heptane-6-carboxylic acid;
2-(1-(2-(1-(4-Chloro-2-fluorobenzyl)-3-(trifluoromethyl)-4,5-dihydro-1H-pyrazolo[3,4-c]pyridin-6(7H)-yl)-2-oxoethyl)azetidin-3-yl)acetic acid;
2-(1-(2-(1-(4-Fluorobenzyl)-3-(trifluoromethyl)-4,5-dihydro-1H-pyrazolo[3,4-c]pyridin-6(7H)-yl)-2-oxoethyl)azetidin-3-yl)acetic acid;
2-(1-(2-(1-(4-Chloro-2-fluorobenzyl)-3-(trifluoromethyl)-4,5-dihydro-1H-pyrazolo[3,4-c]pyridin-6(7H)-yl)-2-oxoethyl)pyrrolidin-3-yl)acetic acid;
2-(1-(2-(1-(4-Fluorobenzyl)-3-(trifluoromethyl)-4,5-dihydro-1H-pyrazolo[3,4-c]pyridin-6(7H)-yl)-2-oxoethyl)pyrrolidin-3-yl)acetic acid;
9-(2-(1-(4-Fluorobenzyl)-3-(trifluoromethyl)-4,5-dihydro-1H-pyrazolo[3,4-c]pyridin-6(7H)-yl)-2-oxoethyl)-3-oxa-9-azabicyclo[3.3.1]nonane-7-carboxylic acid;
9-(2-(1-(4-Chloro-2-fluorobenzyl)-3-(trifluoromethyl)-4,5-dihydro-1H-pyrazolo[3,4-c]pyridin-6(7H)-yl)-2-oxoethyl)-3-oxa-9-azabicyclo[3.3.1]nonane-7-carboxylic acid;
cis-3-(2-(1-(4-Fluorobenzyl)-3-(trifluoromethyl)-4,5-dihydro-1H-pyrazolo[3,4-c]pyridin-6(7H)-yl)-2-oxoethylamino)cyclobutanecarboxylic acid;
trans-3-(2-(1-(4-Fluorobenzyl)-3-(trifluoromethyl)-4,5-dihydro-1H-pyrazolo[3,4-c]pyridin-6(7H)-yl)-2-oxoethylamino)cyclobutanecarboxylic acid;
cis-4-(2-(1-(4-Fluorobenzyl)-3-(trifluoromethyl)-4,5-dihydro-1H-pyrazolo[3,4-c]pyridin-6(7H)-yl)-2-oxoethylamino)cyclohexanecarboxylic acid;
trans-4-(2-(1-(4-Fluorobenzyl)-3-(trifluoromethyl)-4,5-dihydro-1H-pyrazolo[3,4-c]pyridin-6(7H)-yl)-2-oxoethylamino)cyclohexanecarboxylic acid;
3-(2-(1-(4-Chloro-2-fluorobenzyl)-3-(trifluoromethyl)-4,5-dihydro-1H-pyrazolo[3,4-c]pyridin-6(7H)-yl)-2-oxoethylamino)propanoic acid;
2-(3-(1-(4-Fluorobenzyl)-3-(trifluoromethyl)-4,5,6,7-tetrahydro-1H-pyrazolo[3,4-c]pyridine-6-carbonyl)pyrrolidin-1-yl)acetic acid;
2-(3-(1-(4-Chloro-2-fluorobenzyl)-3-(trifluoromethyl)-4,5,6,7-tetrahydro-1H-pyrazolo[3,4-c]pyridine-6-carbonyl)pyrrolidin-1-yl)acetic acid;
1-(1-(4-Fluorobenzyl)-3-(trifluoromethyl)-4,5-dihydro-1H-pyrazolo[3,4-c]pyridin-6(7H)-yl)-2-(1-(pyridin-2-yl)piperidin-4-yl)ethanone;
1-(1-(4-Fluorobenzyl)-3-(trifluoromethyl)-4,5-dihydro-1H-pyrazolo[3,4-c]pyridin-6(7H)-yl)-2-(1-(pyrimidin-4-yl)piperidin-4-yl)ethanone;
1-(1-(4-Fluorobenzyl)-3-(trifluoromethyl)-4,5-dihydro-1H-pyrazolo[3,4-c]pyridin-6(7H)-yl)-2-(1-(pyridin-4-yl)piperidin-4-yl)ethanone;
trans-4-(2-(1-(4-Fluorobenzyl)-3-(trifluoromethyl)-4,5-dihydro-1H-pyrazolo[3,4-c]pyridin-6(7H)-yl)-2-oxoethyl)-N-(methylsulfonyl)cyclohexanecarboxamide;

trans-4-(2-(1-(4-Fluorobenzyl)-3-(trifluoromethyl)-4,5-dihydro-1H-pyrazolo[3,4-c]pyridin-6(7H)-yl)-2-oxoethyl)-N-(methylsulfonyl)cyclohexanecarboxamide;
cis-4-(2-(1-(4-Fluorobenzyl)-3-(trifluoromethyl)-4,5-dihydro-1H-pyrazolo[3,4-c]pyridin-6(7H)-yl)-2-oxoethyl) cyclohexanecarboxamide;
trans-4-(2-(1-(4-Fluorobenzyl)-3-(trifluoromethyl)-4,5-dihydro-1H-pyrazolo[3,4-c]pyridin-6(7H)-yl)-2-oxoethyl) cyclohexanecarboxamide;
cis-4-(2-(1-(4-Fluorobenzyl)-3-(trifluoromethyl)-4,5-dihydro-1H-pyrazolo[3,4-c]pyridin-6(7H)-yl)-2-oxoethyl) cyclohexanecarbonitrile;
trans-4-(2-(1-(4-Fluorobenzyl)-3-(trifluoromethyl)-4,5-dihydro-1H-pyrazolo[3,4-c]pyridin-6(7H)-yl)-2-oxoethyl) cyclohexanecarbonitrile;
2-(3-(Azetidin-1-yl)cyclobutyl)-1-(1-(4-fluorobenzyl)-3-(trifluoromethyl)-4,5-dihydro-1H-pyrazolo[3,4-c]pyridin-6(7H)-yl)ethanone;
1-(1-(4-Fluorobenzyl)-3-(trifluoromethyl)-4,5-dihydro-1H-pyrazolo[3,4-c]pyridin-6(7H)-yl)-2-(octahydroindolizin-7-yl)ethanone;
1-(1-(4-Fluorobenzyl)-3-(trifluoromethyl)-4,5-dihydro-1H-pyrazolo[3,4-c]pyridin-6 (7H)-yl)-2-(3-(pyrrolidin-1-yl) cyclobutyl)ethanone;
1-(1-(4-Fluorobenzyl)-3-(trifluoromethyl)-4,5-dihydro-1H-pyrazolo[3,4-c]pyridin-6(7H)-yl)-2-(3-(piperidin-1-yl) cyclobutyl)ethanone;
1-(1-(4-Fluorobenzyl)-3-(trifluoromethyl)-4,5-dihydro-1H-pyrazolo[3,4-c]pyridin-6(7H)-yl)-2-(3-morpholinocyclobutyl)ethanone;
2-(4-(Azetidin-1-yl)cyclohexyl)-1-(1-(4-fluorobenzyl)-3-(trifluoromethyl)-4,5-dihydro-1H-pyrazolo[3,4-c]pyridin-6(7H)-yl)ethanone;
2-(cis-4-(3,3-Difluoroazetidin-1-yl)cyclohexyl)-1-(1-(4-fluorobenzyl)-3-(trifluoromethyl)-4,5-dihydro-1H-pyrazolo[3,4-c]pyridin-6(7H)-yl)ethanone;
2-(trans-4-(3,3-difluoroazetidin-1-yl)cyclohexyl)-1-(1-(4-fluorobenzyl)-3-(trifluoromethyl)-4,5-dihydro-1H-pyrazolo[3,4-c]pyridin-6(7H)-yl)ethanone;
1-(1-(4-Fluorobenzyl)-3-(trifluoromethyl)-4,5-dihydro-1H-pyrazolo[3,4-c]pyridin-6(7H)-yl)-2-(4-(pyrrolidin-1-yl) cyclohexyl)ethanone; and
1-(1-(4-Fluorobenzyl)-3-(trifluoromethyl)-4,5-dihydro-1H-pyrazolo[3,4-c]pyridin-6(7H)-yl)-2-(4-morpholinocyclohexyl)ethanone;
or a pharmaceutically acceptable salt thereof.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 6 carbon atoms, or 1 to 4 carbon atoms. In some embodiments, an alkyl comprises from 6 to 20 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, or n-decyl.

"Alkylene" refers to a divalent alkyl group. An alkylene group may be branched or unbranched. Examples of unbranched alkylene groups include methylene, ethylene, propylene, n-butylene, and the like. Examples of branched alkylene groups include —CH(CH$_3$)—, —CH$_2$CH(CH$_3$)—, —CH(CH$_2$CH$_3$)—, —CH$_2$CH(CH$_3$)CH$_2$—, and the like. The alkylene is attached to the rest of the molecule through a single bond and to the radical group through a single bond. The points of attachment of the alkylene to the rest of the molecule and to the radical group can be through one carbon or any two carbons within the carbon chain.

"Alkenyl" refers to an unsaturated hydrocarbon group which may be linear or branched and has at least one carbon-carbon double bond. Alkenyl groups with 2-6 carbon atoms can be preferred. The alkenyl group may contain 1, 2 or 3 carbon-carbon double bonds, or more. Examples of alkenyl groups include ethenyl, n-propenyl, isopropenyl, n-but-2-enyl, n-hex-3-enyl and the like.

"Alkynyl" refers to an unsaturated hydrocarbon group which may be linear or branched and has at least one carbon-carbon triple bond. Alkynyl groups with 2-6 carbon atoms can be preferred. The alkynyl group may contain 1, 2 or 3 carbon-carbon triple bonds, or more. Examples of alkynyl groups include ethynyl, n-propynyl, n-but-2-ynyl, n-hex-3-ynyl and the like.

The number of carbon atoms in a group is specified herein by the prefix "C$_{x-xx}$", wherein x and xx are integers. For example, "C$_{1-4}$alkyl" is an alkyl group which has from 1 to 4 carbon atoms.

"Halogen" or "halo" may be fluoro, chloro, bromo or iodo.

As used herein, the term "haloalkyl" refers to an alkyl, as defined herein, that is substituted by one or more halo groups as defined herein. A haloalkyl can be monohaloalkyl, dihaloalkyl or polyhaloalkyl including perhaloalkyl. A monohaloalkyl can have one iodo, bromo, chloro or fluoro substituent. Dihaloalkyl and polyhaloalkyl groups can be substituted with two or more of the same halo atoms or a combination of different halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms. Preferred haloalkyl groups are trifluoromethyl and difluoromethyl.

As used herein, the term "heterocyclyl" refers to a saturated or unsaturated monocyclic, bicyclic or tricyclic ring system which has from 3- to 15-ring members, or in particular 3- to 12-ring members, at least one of which is a heteroatom, and up to 10 (e.g., 1, 2, 3, or 4) of which may be heteroatoms, wherein the heteroatoms are independently selected from O, S and N, and wherein N and S can be optionally oxidized to various oxidation states. In one embodiment, a heterocyclyl is a 3-7-membered monocyclic. In another embodiment, a heterocyclyl is a 6-12-membered bicyclic. A heterocyclyl includes heteroaryl rings. In a certain embodiments of the invention, the term "heterocyclyl" refers to a saturated or unsaturated, non-aromatic monocyclic, bicyclic or tricyclic ring system which has from 3- to 15-ring members, or in particular 3- to 12-ring members, at least one of which is a heteroatom, and up to 10 (e.g., 1, 2, 3, or 4) of which may be heteroatoms, wherein the heteroatoms are independently selected from O, S and N, and wherein N and S can be optionally oxidized to various oxidation states. In one embodiment, a heterocyclyl is a 3-7-membered monocyclic. In another embodiment, a heterocyclyl is a 6-12-membered bicyclic. In yet another embodiment, a heterocyclycyl is a 7-15-membered tricyclic ring system. The heterocyclyl group can be attached at a heteroatom or a carbon atom. Heterocyclyls include fused, bridged or spiro ring systems. Examples of heterocyclyls include 8 azabicyclo[3.2.1]octanyl, 9-azabicyclo[3.3.1] nonanyl, 3-azabicyclo[3.1.0]hexanyl, azepinyl, azetidinyl, aziridinyl, 3,8-diazabicyclo[3.2.1]octanyl, 3,9 diazabicyclo [3.3.1]nonanyl, 4,7-diazaspiro[2.5]octanyl, benzofuran, benzo[d]oxazolyl, benzothiazolyl, benzothiophenyl, diazepinyl, dihydrofuranyl, dihydropyranyl, dioxanyl, dioxolanyl, dithianyl, dithiolanyl, imidazolidinyl, imidazolinyl, indolyl, morpholinyl, octahydro-1H-pyrido[1,2-a]pyrazinyl, octahydrocyclopenta[c]pyrrolyl, octahydropyrrolo[1,2-a]pyrazinyl, octahydro-1H-pyrido[1,2-a]pyrrolyl, octahydropyrrolo[3,4-c]pyrrolyl, oxapinyl, oxathianyl, oxathiolanyl, oxadiazolyl, oxazepinyl, oxetanyl, oxiranyl, piperazinyl, piperidinyl, pyridinyl, pyrimidinyl, pyrrolidinyl, tetrahydrofuranyl, tetrahydropyranyl, 5,6,7,8 tetrahydroimidazo[1,5-a]pyridinyl and thiomorpholinyl and the like.

As used herein, the term "carbocyclyl" refers to saturated or partially unsaturated monocyclic, bicyclic or tricyclic hydrocarbon groups of 3-15 carbon atoms, preferably 3-12, or more preferably 3-9 carbon atoms. Carbocyclyls include fused, bridged or spiro ring systems. Carbocyclyl groups also include aryl groups. In a certain embodiments of the invention, the term "carbocyclyl" refers to saturated or partially unsaturated (but not aromatic) monocyclic, bicyclic or tricyclic hydrocarbon groups of 3-15 carbon atoms, preferably 3-12, or more preferably 3-9 carbon atoms. Carbocyclyls include fused, bridged or spiro ring systems. The term "carbocyclyl" encompasses cycloalkyl groups. The term "cycloalkyl" refers to completely saturated monocyclic, bicyclic or tricyclic hydrocarbon groups of 3-12 carbon atoms, preferably 3-9, or more preferably 3-8 carbon atoms. Exemplary monocyclic carbocyclyl groups include, but are not limited to, cyclopropyl, cyclobutyl, cyclopentyl, cyclopentenyl, cyclohexyl or cyclohexenyl. Exemplary bicyclic carbocyclyl groups include bornyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bornyl or bicyclo[2.2.2]octyl. Exemplary tricyclic carbocyclyl groups include adamantyl.

The term "fused ring system," as used herein, is a ring system that has a carbocyclyl or heterocyclyl ring wherein two adjacent atoms of the ring are connected and form another ring by one or more (preferably from one to three) atoms selected from C, N, O, or S. A fused ring system can have more than one fused ring within the ring system (e.g., anthracene or 1H-phenalene). A bridged ring system may have from 6-15 ring members, preferably from 7-10 ring members. Examples of fused ring systems include anthracene, 1H-phenalene, naphthalene, quinolone, indole, hexahydro-1H-pyrrolo[2,1-c][1,4]oxazine, benzofuran, benzo[d]oxazolyl, benzothiazolyl, benzothiophenyl, octahydropyrrolo[1,2-a]pyrazine, octahydro-1H-pyrido[1,2-a]pyrazinylor 9H-purine, octahydrocyclopenta[c]pyrrolyl, octahydropyrrolo[1,2-a]pyrazinyl, octahydro-1H-pyrido[1,2-a]pyrrolyl, octahydropyrrolo[3,4-c]pyrrolyl, 5,6,7,8-tetrahydroimidazo[1,5-a]pyridinyl and the like.

The term "bridged ring system," as used herein, is a ring system that has a carbocyclyl or heterocyclyl ring wherein two non-adjacent atoms of the ring are connected (bridged) by one or more (preferably from one to three) atoms selected from C, N, O, or S. A bridged ring system can have more than one bridge within the ring system (e.g., adamantyl). A bridged ring system may have from 6-10 ring members, preferably from 7-10 ring members. Examples of bridged ring systems include adamantyl, 9-azabicyclo[3.3.1]nonan-9-yl, 8-azabicyclo[3.2.1]octanyl, bicyclo[2.2.2]octanyl, 3-azabicyclo[3.1.0]hexanyl, 3-azabicyclo[3.1.1]heptanyl, 3,8-diazabicyclo[3.2.1]octanyl, 3,9-diazabicyclo[3.3.1]nonanyl, bicyclo[2.2.1]heptanyl (also referred to as "bicyclo[2.2.1]heptyl"), (1R,5S)-bicyclo[3.2.1]octanyl, 3-azabicyclo[3.3.1]nonanyl, tricyclo[2.2.1.0$^{2,6}$]heptanyl, bicyclo[2.1.1]hexyl, bicyclo[2.2.1]heptyl, bicyclo[2.2.1]heptenyl, bicyclo[3.2.1]octanyl, bornyl, bicyclo[3.3.1]nonanyl, and bicyclo[3.2.2]nonanyl.

The term "spiro ring system," as used herein, is a ring system that has two rings each of which are independently selected from a carbocyclyl or a heterocyclyl, wherein the two ring structures having one ring atom in common. Spiro ring systems have from 5 to 14 ring members. Example of spiro ring systems include 2-azaspiro[3.3]heptanyl, spiropentanyl, 2-oxa-6-azaspiro[3.3]heptanyl, 2,7-diazaspiro[3.5]nonanyl, 2-oxa-7-azaspiro[3.5]nonanyl, 6-oxa-9-azaspiro[4.5]decanyl, 6-oxa-2-azaspiro[3.4]octanyl, 5-azaspiro[2.3]hexanyl, 2,8-diazaspiro[4.5]decanyl, 4,7-diazaspiro[2.5]octanyl, and spiro[3.3]heptanyl.

As used herein, the term "heteroaryl" refers to a 5-14 membered monocyclic-, bicyclic-, or tricyclic-ring system, having 1 to 10 heteroatoms independently selected from N, O or S, wherein N and S can be optionally oxidized to various oxidation states, and wherein at least one ring in the ring system is aromatic. In one embodiment, the heteroaryl is monocyclic and has 5 or 6 ring members. Examples of monocyclic heteroaryl groups include pyrrolyl, furanyl, thiophenyl, imidazolyl, pyrazolyl, oxazolyl, isoxazolyl, thiazolyl, isothiazolyl, triazolyl, furazanyl, oxadiazolyl, thiadiazolyl, thiadiazolyl, tetrazolyl, pyridinyl, pyranyl, pyrimidinyl, thiopyranyl, diazinyl, oxazinyl, thiazinyl, dioxinyl, dithiinyl, triazinyl, tetrazinyl, thienyl, imidazoyl, oxazolyl, isoxazolyl, and thiazolyl. In another embodiment, the heteroaryl is bicyclic and has from 8 to 10 ring members. Examples of bicyclic heteroaryl groups include indolyl, benzofuranyl, quinolyl, isoquinolyl indazolyl, indolinyl, isoindolyl, indolizinyl, benzamidazolyl, benzo[d]thiazole, quinolinyl, 5,6,7,8-tetrahydroquinoline, octahydrocyclopenta[c]pyrrole, octahydropyrrolo[3,4-b]pyrrole, octahydropyrrolo[3,4-c]pyrrole, octahydropyrrolo[3,2-b]pyrrole, 5,6,7,8-tetrahydroimidazo[1,5-a]pyridine, and 6,7-dihydro-5H-pyrrolo[3,2-d]pyrimidine.

The term "aryl" refers to monocyclic, bicyclic or tricyclic aromatic hydrocarbon groups having from 6 to 14 carbon atoms in the ring portion. In one embodiment, the term aryl refers to monocyclic and bicyclic aromatic hydrocarbon groups having from 6 to 10 carbon atoms. Representative examples of aryl groups include phenyl, naphthyl, fluorenyl, and anthracenyl.

The term "aryl" also refers to a bicyclic or tricyclic group in which at least one ring is aromatic and is fused to one or two non-aromatic hydrocarbon ring(s). Nonlimiting examples include tetrahydronaphthalene, dihydronaphthalenyl and indanyl.

The compounds or pharmaceutically acceptable salts thereof as described herein, can contain one or more asymmetric centers in the molecule. In accordance with the present disclosure any structure that does not designate the stereochemistry is to be understood as embracing all the various optical isomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis, or chromatographic separation using a chiral stationary phase). Unless otherwise indicated, any position occupied by hydrogen is meant to include enrichment by deuterium or tritium above the natural abundance of deuterium or tritium as well. For example, one or more hydrogen atoms are replaced with deuterium at an abundance that is at least 3340 times greater than the natural abundance of deuterium, which is 0.015% (i.e., at least 50.1% incorporation of deuterium), at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In one embodiment, hydrogen is present at all positions at its natural abundance. The compounds or pharmaceutically acceptable salts thereof as described herein, may exist in tautomeric forms and mixtures and separate individual tautomers are contemplated. In addition, some compounds or pharmaceutically acceptable salts thereof as described herein, may exhibit polymorphism.

The compounds or pharmaceutically acceptable salts thereof as described herein, could be an ATX modulator, i.e., it can modulate the activity of ATX.

An "ATX modulating agent" refers a compound or a salt thereof, or composition that is capable of inducing a detectable change in ATX activity in vivo or in vitro (e.g., at least 10% increase or decrease in ATX activity as measured by a given assay such as the assays described in the examples and known in the art. The compound, or salt thereof, can be an ATX modulating agent, i.e., it can modulate the activity of ATX. For example, the compound, or salt thereof, can be an ATX inhibitor. The compound, or salt thereof, can be a selective ATX modulating agent. Being selective can mean that the compound, or salt thereof, binds to ATX preferentially when exposed to a variety of potential binding partners. The compound, or salt thereof, can have a greater affinity for the ATX, by at by at least 100-fold, by at least 50-fold, by at least 10-fold, by at least 5-fold or by at least 2-fold, than for other binding partners. Affinity can be measured, for example, as a dissociation constant ($K_d$), as an inhibition constant (such as $IC_{50}$), or another measure; provided that affinity is measured in a consistent fashion between ATX and the other binding partners it is compared to.

An inhibitor of ATX mediated activity can block interaction of ATX with its native substrate(s), such as LPC. For example, the inhibitor can show an $IC_{50}$ value of less than 1 µM, less than 750 nM, less than 500 nM, less than 250 nM, less than 100 nM, less than 50 nM, less than 25 nM, or less than 10 nM, when measured in a FRET-based assay using FS-3 substrate (see, e.g., Ferguson, C. G., et al., Org Lett. 2006 May 11; 8(10): 2023-2026, which is incorporated by reference in its entirety).

Some substrates and inhibitors of ATX are described in WO 2011/151461, which is incorporated by reference in its entirety.

Another embodiment is a pharmaceutical composition comprising at least one compound described above in the first through thirteenth embodiments and aspects of the first through thirteenth embodiments, or a pharmaceutically acceptable salt thereof, and at least one pharmaceutically acceptable carrier.

Another embodiment is a method of treating, or reducing symptoms of a condition mediated by ATX activity in a mammal including administering to said mammal an effective amount of at least one compound described above in the first through thirteenth embodiments and aspects of the first through thirteenth embodiments, or a pharmaceutically acceptable salt thereof.

In one aspect of this method, the condition is selected from the group consisting of multiple sclerosis, an autoimmune disease, a chronic inflammatory disorder, asthma, an inflammatory neuropathy, arthritis, transplantation rejection, Crohn's disease, ulcerative colitis, lupus erythematosis, psoriasis, an ischemia-reperfusion injury, a solid tumor, a tumor metastasis, a disease associated with angiogenesis, a vascular disease, a pain condition, an acute viral disease, an inflammatory bowel condition, insulin-dependent diabetes, non-insulin dependent diabetes, a fibrosis of the lung, or a malignancy of the lung in a mammal. Alternatively, the condition is multiple sclerosis. Alternatively, the condition is rheumatoid arthritis.

In one aspect of this method, the method further includes the step of administering to the mammal an effective amount of one or more drugs selected from the group consisting of: a corticosteroid, a bronchodilator, an antiasthmatic, an anti-inflammatory, an antirheumatic, an immunosuppressant, an antimetabolite, an immunomodulating agent, an antipsoriatic, and an antidiabetic.

Another embodiment is a method of promoting myelination or remyelination in a mammal in need thereof, including administering to cells an effective amount of at least one compound described above in the first through thirteenth embodiments and aspects of the first through thirteenth embodiments, or a pharmaceutically acceptable salt thereof.

Another embodiment is a method of treating, or reducing chronic pain in a mammal comprising administering to said mammal an effective amount of at least one compound described above in the first through thirteenth embodiments and aspects of the first through thirteenth embodiments, or a pharmaceutically acceptable salt thereof. In one aspect, the chronic pain is inflammatory pain. Alternatively, the chronic pain is neuropathic pain.

Potential uses of an ATX modulating agent include, but are not limited to, treatment of a pathological condition or symptom in a mammal. The pathological disorder can be an inflammatory disorder, an autoimmune disorder, a fibrosis of the lung, or a malignancy of the lung. The pathological disorder can also be an inflammatory disorder, an autoimmune disorder, a fibrosis of the lung, a malignancy of the lung, liver fibrosis, or renal fibrosis. In one embodiment, the pathological disorder is a fibrotic disease, including, for example, a fibrosis of the lung, liver fibrosis, kidney fibrosis, and scleroderma. Treatment of the pathological condition or symptom can include administering to the mammal an effective amount of an ATX modulating agent, e.g., an ATX inhibitor, to prevent, treat or reduce symptoms of the inflammatory disorder, autoimmune disorder, the fibrosis of the lung, or the malignancy of the lung. Treatment of the pathological condition or symptom can also include administering to the mammal an effective amount of an ATX modulating agent, e.g., an ATX inhibitor, to prevent, treat or reduce symptoms of the inflammatory disorder, autoimmune disorder, the fibrosis of the lung, the malignancy of the lung, liver fibrosis, or renal fibrosis. Treatment of the pathological condition or symptom can also include administering to the mammal an effective amount of an ATX modulating agent, e.g., an ATX inhibitor, to prevent, treat or reduce symptoms of the fibrotic disease, including, for example, a fibrosis of the lung, liver fibrosis, kidney fibrosis, and scleroderma. In one embodiment, the inflammatory disorder is rheumatoid arthritis (RA). In another embodiment, the inflammatory disorder is asthma. In another embodiment, the inflammatory disorder is periodontal disease. In another embodiment, the autoimmune disorder is multiple sclerosis (MS). In another embodiment, the autoimmune disorder is scleroderma. A particular example of lung fibrosis is an interstitial lung disease, for instance, pulmonary fibrosis. See, for example, WO 2011/151461, which is incorporated by reference in its entirety. A particular example of lung fibrosis is an interstitial lung disease, for instance, interstitial pneumonia. See, for example, US2013/0109699, which is incorporated by reference in its entirety.

In some embodiments, an ATX inhibitor of the present invention can be used to treat or prevent a demyelinating disease or disorder. Demyelinating diseases or disorders include multiple sclerosis, Guillain-Barre Syndrome, chronic inflammatory demyelinating polyneuropathy (CIDP), transverse myelitis, and optic neuritis, spinal cord injury, stroke or other ischemia, cerebral palsy, Charcot-Marie-Tooth disease (CMT), Sjogren-Larsson syndrome, Refsum disease, Krabbe disease, Canavan disease, Alexander disease, nerve damage due to pernicious anemia, progressive multifocal leukoencephalopathy (PML), Lyme disease, tabes *dorsalis* due to untreated syphilis, demyelination due to exposure to an organophosphates, demyelination due to vitamin B12 deficiency or copper deficiency.

In addition, the compounds or pharmaceutically acceptable salts thereof as described herein, may be useful for inhibition of the multiple substrate lipid kinase (MuLK). MuLK is highly expressed in many human tumor cells and thus its inhibition might slow the growth or spread of tumors.

Neurological Disorders

MS can begin with a relapsing-remitting pattern of neurologic involvement, which then can progress to a chronic phase with increasing neurological damage. MS can be associated with the destruction of myelin, oligodendrocytes or axons localized to chronic lesions. The demyelination observed in MS may not always permanent and remyelination has been documented in early stages of the disease. Remyelination of neurons can require oligodendrocytes.

Axons and dendrites can extend from neurons. The distal tip of an extending axon or neurite can include a specialized region, known as the growth cone. Growth cones can sense the local environment and can guide axonal growth toward a neuron's target cell. Growth cones can respond to environmental cues, for example, surface adhesiveness, growth factors, neurotransmitters and electric fields. The growth cones can advance at a rate of one to two millimeters per day. The growth cone can explore the area ahead of it and on either side, by means of elongations classified as lamellipodia and filopodia. When an elongation contacts an unfavorable surface, it can withdraw. When an elongation contacts a favorable growth surface, it can continue to extend and guides the growth cone in that direction. When the growth cone reaches an appropriate target cell a synaptic connection can be created.

Nerve cell function can be influenced by contact between neurons and other cells in their immediate environment (Rutishauser, et al., 1988, *Physiol. Rev.* 68:819, which is incorporated by reference in its entirety). These cells can include specialized glial cells, oligodendrocytes in the central nervous system (CNS), and Schwann cells in the peripheral nervous system (PNS), which can sheathe the neuronal axon with myelin (Lemke, 1992, in *An Introduction to Molecular Neurobiology*, Z. Hall, Ed., p. 281, Sinauer, each of which is incorporated by reference in its entirety). LPA causes the collapse of the neuron growth cone and tends to inhibit or reverse the morphological differentiation of many neuronal cell lines (see Gendaszewska-Darmach, Acta Biochimica Polonica (2008), 55(2):227-240). Since ATX activity is involved in the generation of LPA, inhibitors of ATX should increase the ability of the nervous system to make synaptic connections. Thus, the compounds or pharmaceutically acceptable salts thereof as described herein, may be useful in treating neurodegenerative disorders such as Alzheimer's disease, Huntington's disease, Parkinson's disease (including Parkinson's dementia), Lewy Body Dementia, amylotrophic lateral sclerosis (ALS), Friedreich's ataxia, spinal muscular atrophy.

CNS neurons can have the inherent potential to regenerate after injury, but they can be inhibited from doing so by inhibitory proteins present in myelin (Brittis et al., 2001, *Neuron* 30:11-14; Jones et al., 2002, *J. Neurosci.* 22:2792-2803; Grimpe et al., 2002, *J. Neurosci.*: 22:3144-3160, each of which is incorporated by reference in its entirety).

Several myelin inhibitory proteins found on oligodendrocytes have been characterized. Known examples of myelin inhibitory proteins can include NogoA (Chen et al., *Nature*, 2000, 403, 434-439; Grandpre et al., *Nature* 2000, 403, 439-444, each of which is incorporated by reference in its entirety), myelin associated glycoprotein (MAG) (McKerracher et al., 1994, *Neuron* 13:805-811; Mukhopadhyay et al., 1994, *Neuron* 13:757-767, each of which is incorporated by reference in its entirety) or oligodendrocyte glycoprotein (OM-gp), Mikol et al., 1988, *J. Cell. Biol.* 106:1273-1279, each of which is incorporated by reference in its entirety). Each of these proteins can be a ligand for the neuronal Nogo receptor-1 (NgR1 (Wang et al., *Nature* 2002, 417, 941-944; Grandpre et al., *Nature* 2000, 403, 439-444; Chen et al., *Nature*, 2000, 403, 434-439; Domeniconi et al., *Neuron* 2002, published online Jun. 28, 2002, each of which is incorporated by reference in its entirety).

Nogo receptor-1 (NgR1) is a GPI-anchored membrane protein that contains 8 leucine rich repeats (Fournier et al., 2001, *Nature* 409:341-346, which is incorporated by reference in its entirety). Upon interaction with inhibitory proteins (e.g., NogoA, MAG and OM-gp), the NgR1 complex can transduce signals that lead to growth cone collapse and inhibition of neurite outgrowth.

There is a need for molecules and methods for inhibiting NgR1-mediated growth cone collapse and the resulting inhibition of neurite outgrowth. Additionally, there is a need for molecules which increase neuronal survival and axon regeneration, particularly for the treatment of disease, disorders or injuries that involve axonal injury, neuronal or oligodendrocyte cell death, demyelination or dymyelination or generally relate to the nervous system.

Such diseases, disorders or injuries can include, but are not limited to, multiple sclerosis (MS), progressive multifocal leukoencephalopathy (PML), encephalomyelitis (EPL), central pontine myelolysis (CPM), adrenoleukodystrophy, Alexander's disease, Pelizaeus Merzbacher disease (PMZ), Globoid cell Leucodystrophy (Krabbe's disease) and Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, AR, Bassen-Komzweig syndrome, Marchiafava-Bignami syndrome, metachromatic leukodystrophy, trigeminal neuralgia, or Bell's palsy. Among these diseases, MS may the most widespread, affecting approximately 2.5 million people worldwide.

Various disease-modifying treatments may be available for MS, including the use of corticosteroids and immunomodulating agents such as interferon beta or Tysabri®. In addition, because of the central role of oligodendrocytes and myelination in MS, there have been efforts to develop therapies to increase oligodendrocyte numbers or enhance myelination. See, e.g., Cohen et al., U.S. Pat. No. 5,574,009; Chang et al., *N. Engl. J. Med.* 346: 165-73 (2002), each of which is incorporated by reference in its entirety. However, there remains an urgent need to devise additional therapies for MS and other demyelination and dismyelination disorders.

The compounds or pharmaceutically acceptable salts thereof as described herein, can promote myelination or remyelination. A method can include administering a compound or a pharmaceutically acceptable salt thereof as described herein, to cells. A method of promoting oligodendrocyte progenitor cell differentiation can include administering a compound or a pharmaceutically acceptable salt thereof as described herein, to cells. A method of treating multiple sclerosis can include administering a compound or a pharmaceutically acceptable salt thereof as described herein, to a subject.

A number of studies have shown that ATX is expressed in non-pathological conditions, throughout development, with high expression levels in the CNS among other tissues. ATX mRNA was identified as highly upregulated during oligodendrocyte differentiation and ATX protein expression is also apparent in maturing ODCs, temporally correlated with the process of myelination. Finally, in the adult brain ATX is expressed in secretory epithelial cells, such as the choroid plexus, ciliary, iris pigment, and retinal pigment epithelial cells, whereas there is evidence for ATX expression in leptomenigneal cells and cells of the CNS vasculature. See, for example, Fuss, B., et al., J Neurosci 17, 9095-9103 (1997); Kawagoe, H., et al. Genomics 30, 380-384 (1995); Lee, H. Y., et al. J Biol Chem 271, 24408-24412 (1996); Narita, M., et al., J Biol Chem 269, 28235-28242 (1994); Bachner, D., et al., Mechanisms of Development 84, 121-125 (1999); Awatramani, R., et al., Nat Genet 35, 70-75 (2003); Li, Y., et al., J Neurol Sci 193, 137-146 (2002); Dugas, J. C., et al., J Neurosci 26, 10967-10983 (2006); Fox, M. A., et al., Molecular and Cellular Neuroscience 27, 140-150 (2004); Hoelzinger, D. B., et al., Neoplasia 7, 7-16 (2005); and Sato, K., et al., J Neurochem 92, 904-914 (2005); each of which is incorporated by reference in its entirety.

Although neurons and astrocytes do not seem to express ATX under physiological conditions, ATX is highly upregulated in astrocytes following brain lesion. Two hallmarks of reactive astrogliosis can be induced by LPA itself: hypertrophy of astrocytes and stress fiber formation. This may indicate an autoregulation loop of astrocytic activation, in which astrocytes upregulate the LPA-generating enzyme ATX and become activated by its metabolite LPA, while increased amounts of the metabolite inhibit the catalytic activity of ATX. See, e.g., Savaskan, N. E., et al., Cell Mol Life Sci 64, 230-243 (2007); Ramakers, G. J, & Moolenaar, W. H., Exp Cell Res 245, 252-262 (1998); and van Meeteren, L. A., et al., J Biol Chem 280, 21155-21161 (2005); each of which is incorporated by reference in its entirety.

ATX expression levels were shown to be elevated in glioblastoma multiform samples, and ATX was shown to augment invasiveness of cells transformed with ras, a key signaling molecule that promotes gliomagenesis. ATX expression was also detected in primary tumor tissues from neuroblastoma patients and retinoic acid induced expression of ATX in N-myc-amplified neuroblastoma cells.

There is significant evidence for ATX signaling in demyelination processes and in other neurodegenerative conditions. As noted above, it has been reported that addition of LPA to dorsal root fibers in ex vivo culture causes demyelination, whereas LPC fails to cause significant demyelination of nerve fibers in ex vivo cultures without further addition of recombinant ATX to the culture. Addition of recombinant ATX caused significant demyelination at equivalent levels to LPA presumable due to conversion of LPC to LPA through the enzymatic activity of ATX. In addition, injury induced demyelination was attenuated by about 50% in atx$^{+/-}$ mice over their wild type counterparts (Nagai, et al., *Molecular Pain* (2010), 6:78).

ATX protein levels were found deregulated in an animal model of MS (experimental autoimmune encephalitis; EAE) at the onset of clinical symptoms. See, e.g., Hoelzinger, D. B., et al. Neoplasia 7, 7-16 (2005); Nam, S. W., et al., Oncogene 19, 241-247 (2000); Kawagoe, H., et al., Cancer Res 57, 2516-2521 (1997); Dufner-Beattie, J., et al., Mol Carcinog 30, 181-189 (2001); Umemura, K., et al., Neuroscience Letters 400, 97-100 (2006); and Fuss, B., et al., J Neurosci 17, 9095-9103 (1997); each of which is incorporated by reference in its entirety. Moreover, significant ATX expression was detected in the cerebrospinal fluid of patients suffering with multiple sclerosis (MS), while completely lacking from the control samples, suggesting a role for ATX in maintenance of cerebrospinal fluid homeostasis during pathological/demyelinating conditions. Hammack, B. N., et al. Proteomic analysis of multiple sclerosis cerebrospinal fluid. Mult Scler 10, 245-260 (2004); and Dennis, J., et al., J Neurosci Res 82, 737-742 (2005); each of which is incorporated by reference in its entirety. Interestingly, ATX mRNA expression was found to be elevated in the frontal cortex of Alzheimer-type dementia patients indicating a potential involvement for ATX signaling in neurodegenerative diseases. LPA receptors are enriched in the CNS and their expression patterns suggest their potential involvement in developmental process including neurogenesis, neuronal migration, axon extension and myelination. Noteworthy, only two receptors have the same spatiotemporal expression as ATX in the CNS (Contos, J. J., et al., Mol Cell Biol 22, 6921-6929 (2002); Jaillard, C, ei al, Edg8/S1P5: an oligodendroglial receptor with dual function on process retraction and cell survival. J Neurosci 25, 1459-1469 (2005); and Saba, J. D. Journal of cellular biochemistry 92, 967-992 (2004); each of which is incorporated by reference in its entirety). LPAi and SIPS are specific for ODCs, and their expression highly correlates with the process of myelination. LPA1 is expressed in restricted fashion within the neuroblasts of the neuroproliferatve Ventricular Zone (VZ) of the developing cortex, in the dorsal olfactory bulb, along the pial cells of neural crest origin, and in developing facial bone tissue. Expression is observed during E11-E18, corresponding to a time period during which neurogenesis occurs. LPA1 expression is undetectable in the VZ after this point, to reappear during the first postnatal week within ODCs. Notably, Schwann cells (the myelinating cells of the Peripheral Nervous System; PNS) express high levels of LPA1 early in development and persistently throughout life, suggesting an influence of LPA on myelinating processes (Weiner. J. A. & Chun, J., Proc Natl Acad Sci USA 96, 5233-5238 (1999), which is incorporated by reference in its entirety).

The above data strongly support a critical role for ATX and LPA signaling in neuronal development, oligodendrocyte differentiation and myelination, as well as possibly in the autoregulation of astrocyte activation. Moreover, the regulation of ATX and thus LPA production at local sites of CNS injury, inflammatory or autoimmune, could contribute to tissue homeostasis through the numerous effects of LPA.

As demyelination and deregulated cerebrospinal fluid homeostasis are the hallmarks of multiple sclerosis, a role of ATX and LPA signaling in the pathophysiology of multiple sclerosis seems very likely.

The compounds or pharmaceutically acceptable salts thereof as described herein can be used to various forms of MS including relapsing-remitting, secondary-progressive, primary-progressive, and progressive-relapsing forms. In addition, compounds or pharmaceutically acceptable salts thereof as described herein, can be used alone or in conjunction with other agents to treat or prevent MS. In some embodiments, compounds or pharmaceutically acceptable salts thereof as described herein, can be used to treat or prevent MS in combination with an immunomodulating therapy such as corticosteroids, beta interferon-1a (such as Avonex® or Rebif®), beta interferon-1b (Betaseron®), natalizumab (Tysabri®), glatiramer, and mitoxantrone.

Promoting myelination, remyelination or oligodendrocyte progenitor cell differentiation can prevent or can treat a pathological condition or symptom in a mammal. A number of diseases or disorders involve demyelination of the central or peripheral nervous system which can occur for a number of reasons such as immune dysfunction in multiple sclerosis, encephalomyelitis, Guillain-Barre Syndrome, chronic inflammatory demyelinating polyneuropathy (CIDP), transverse myelitis, and optic neuritis; demyelination due to injury such as spinal cord injury, traumatic brain injury, stroke, acute ischemic optic neuropathy, or other ischemia, cerebral palsy, neuropathy (e.g. neuropathy due to diabetes, chronic renal failure, hypothyroidism, liver failure, or compression of the nerve), post radiation injury, and central pontine myelolysis (CPM); inherited conditions such as Charcot-Marie-Tooth disease (CMT), Sjogren-Larsson syndrome, Refsum disease, Krabbe disease, Canavan disease, Alexander disease, Friedreich's ataxia, Pelizaeus-Merzbacher disease, Bassen-Kornzweig syndrome, metachromatic leukodystrophy (MLD), adrenoleukodystrophy, and nerve damage due to pernicious anemia; viral infection such as progressive multifocal leukoencephalopathy (PML), Lyme disease, or tabes *dorsalis* due to untreated syphilis; toxic exposure due to chronic alcoholism (which is a possible cause of Marchiafava-Bignami disease), chemotherapy, or exposure to chemicals such as organophosphates; or dietary deficiencies such as vitamin B12 deficiency, vitamin E deficiency, and copper deficiency. Some demyelination disorders can have unknown or multiple causes such as trigeminal neuralgia, Marchiafava-Bignami disease and Bell's palsy. In addition, demyelination can contribute to neuropathic pain. Compounds or pharmaceutically acceptable salts thereof as described herein are expected to be useful in treating demyelination disorders.

Peripheral Nerve Axon Regeneration and Repair

The compounds or pharmaceutically acceptable salts thereof as described herein, can promote peripheral nerve axon regeneration and repair. Inhibition of ATX can redue LPA formation, for treatment of degenerative nerve indications such as Cavernous nerve injury, chemotheraphy-induced peripheral neuropathy, carpal tunnel syndrome, and diabetic neuropathy.

Inflammatory Disorders

Since LPA is a proinflammatory factor reducing the amount of LPA producted by inhibiting ATX is useful for treating inflammatory disorders such as asthma, allergies, arthritis, inflammatory neuropathies, transplantation rejection, Crohn's disease, ulcerative colitis, lupus erythematosis, psoriasis, an inflammatory bowel condition, and diabetes.

Pain Mediation

Pain experienced by mammals can be divided into two main categories: acute pain (or nociceptive) and chronic pain which can be subdivided into chronic inflammatory pain and chronic neuropathic pain. Acute pain is a response to stimulus that causes tissue injury and is a signal to move away from the stimulus to minimize tissue damage. Chronic pain, on the other hand, serves no biological function and develops as a result of inflammation caused by tissue damage (inflammatory pain) or by damage to the nervous system such as demyelination (neuropathic pain). Chronic pain is generally characterized by stimulus-independent, persistent pain or by abnormal pain perception triggered by innocuous stimuli.

LPA has been found to be a mediator of both inflammatory pain and neuropathic pain. The transient receptor potential channel TRPV1 is known to be the originator of inflammatory pain. LPA has been shown to directly activate TRPV1 thereby creating pain stimulus by binding to its intracellular C-terminus (Tigyi, *Nature Chemical Biology* (January 2012), 8:22-23). Thus, compounds which inhibit the formation of LPA by inhibiting the action of ATX would be useful in treating inflammatory pain.

LPA has also been shown to play a role in neuropathic pain. For example, sciatic nerve injury has been shown to induce demyelination, down-regulation of myelin-associated glycoprotein (MAG) and damage to Schwann cell partitioning of C-fiber-containing Remak bundles in the sciatic nerve and dorsal root. However, demyelination, MAG down-regulation and Remak bundle damage in the dorsal root were abolished in $LPA_1$ receptor-deficient ($Lpar1^{-/-}$) mice (Nagai, et al., *Molecular Pain* (2010), 6:78). These results indicate that compounds that inhibit the formation of LPA by inhibiting the action of ATX would decrease dorsal root demyelination following nerve injury and decrease or eliminate neuropathic pain.

Additionally, the pathological disorder can be selected from pain, acute pain, chronic pain, neuropathic pain, visceral pain, nociceptive pain including post-surgical pain, and mixed pain types involving the viscera, gastrointestinal tract, cranial structures, musculoskeletal system, spine, urogenital system, cardiovascular system and CNS, including cancer pain, back and orofacial pain; and pain associated with dysmenorrhea, pelvic pain, cystitis, pancreatitis, migraine, cluster and tension headaches, diabetic neuropathy, peripheral neuropathic pain, sciatica, fibromyalgia, causalgia, and conditions of lower urinary tract dysfunction. (See, for example, WO2013061297, which is incorporated by reference in its entirety).

Thus, the compounds or pharmaceutically acceptable salts thereof as described herein, are useful in treating or preventing chronic pain such as inflammatory pain and neuropathic pain in mammals.

Rheumatoid Arthritis (RA)

Studies in human and animal models of RA suggest that ATX plays a role in the development and progress of the disease. For example, increased ATX mRNA expression was detected in synovial fibroblasts (SFs) from animal models of RA during differential expression profiling, and human RA SFs were shown to express mRNA for both ATX and LPARs (Aidinis, V., et al., PLoS genetics 1, e48 (2005); Zhao, C, et al., Molecular pharmacology 73, 587-600 (2008); each of which is incorporated by reference in its entirety). ATX is overexpressed from activated SFs in arthritic joints, both in animal models and human patients (see WO 2011/151461). ATX expression was shown to be induced from TNF, the major pro-inflammatory factor driving RA.

Disease development was assessed in well established animal models of RA. When ATX expression was conditionally ablated specifically in SFs, the lack of ATX expression in the joints resulted in marked decreased inflammation and synovial hyperplasia. This suggested an active involvement of the ATX-LPA axis in the pathogenesis of the disease. Similar results were also obtained with pharmacologic inhibition of ATX enzymatic activity and LPA signaling. A series of ex vivo experiments on primary SFs revealed that ATX, through LPA production, stimulates rearrangements of the actin cytoskeleton, proliferation and migration to the extracellular matrix (ECM), as well as the secretion of proinflammatory cytokines and matrix metalloproteinases (MMPs). Moreover, the LPA effect was shown to be synergistic with TNF and dependent on the activation of MAPK cellular signaling pathways. See, e.g., Armaka, M., et al., The Journal of experimental medicine 205, 331-337 (2008); which is incorporated by reference in its entirety.

In one embodiment, a method for treating an individual with RA or the individual at risk of suffering thereof comprises administering to said individual an ATX modulating agent of formula (I) in conjunction with an anti-TNF antibody for use in the treatment of RA. Examples of suitable anti-TNF antibodies are adalimumab, etanercept, golimumab, and infliximab (Taylor P C, Feldmann M. Anti-TNF biologic agents: still the therapy of choice for rheumatoid arthritis. Nat Rev Rheumatol. 2009 October; 5(10):578-82).

Asthma

The ATX-LPA pathway appears to have role in the pathogenesis of asthma, for example, see Park, et al., Am J Respir Crit Care Med Vol 188, Iss. 8, pp 928-940, 2013, the entire teachings of which are incorporated herein by reference. Thus the compounds or pharmaceutically acceptable salts thereof as described herein, are useful in preventing, treating, or reducing symptoms of asthma in a mammal in need thereof.

Periodontal Disease

Elevated levels of LPA may contribute to the pathogenesis and progression of periodontal diseases, see Bathena, et al., Journal of Pharmaceutical and Biomedical Analysis 56 (2011) 402-407, the entire teachings of which are incorporated herein by reference. Thus the compounds or pharmaceutically acceptable salts thereof as described herein, are useful in preventing, treating, or reducing symptoms of periodontal disease in a mammal in need thereof.

Pulmonary Fibrosis

Evidence also suggests a role for ATX in pulmonary fibrosis. Mice lacking lysophosphatidic acid (LPA) receptor 1 (LPAR1) were protected from Bleomycin (BLM)-induced pulmonary fibrosis and mortality, suggesting a major role for LPA in disease pathophysiology. The majority of circulating LPA is produced by the phospholipase D activity of Autotaxin (ATX) and the hydrolysis of lysophosphatidylcholine (LPC). Increased ATX expression has been previously reported in the hyperplastic epithelium of fibrotic lungs of human patients and animal models. See, for example, Sakai, et al., Inflammation and Regeneration Vol 33, No. 2 (2013), 78-89; and Budd, et al., Future Med. Chem. (2013) 5(16), 1935-1952, the entire teachings of both are incorporated herein by reference.

Therefore, we hypothesized that genetic or pharmacologic inhibition of ATX activity would reduce local or circulating LPA levels and hence attenuate disease pathogenesis. Thus the compounds or pharmaceutically acceptable salts thereof as described herein, are useful in preventing, treating, or reducing symptoms of pulmonary fibrosis in a mammal in need thereof.

Liver Fibrosis

Subjects with liver fibrosis may exhibit increased ATX and LPA levels in the blood, see, for example, Ikeda, et al., Clinica Chimica Acta 413 (2012) 1817-1821; and Budd, et al., Future Med. Chem. (2013) 5(16), 1935-1952, the entire teachings of both are incorporated herein by reference. Thus the compounds or pharmaceutically acceptable salts thereof as described herein, are useful in preventing, treating, or reducing symptoms of liver fibrosis in a mammal in need thereof.

Renal Fibrosis

Evidence also suggests a role for ATX in renal fibrosis, see for example, Sakai, et al., Inflammation and Regeneration Vol 33, No. 2 (2013), 78-89, and Budd, et al., Future Med. Chem. (2013) 5(16), 1935-1952, the entire teachings of both are incorporated herein by reference. Thus the compounds or pharmaceutically acceptable salts thereof as described herein, are useful in preventing, treating, or reducing symptoms of renal fibrosis in a mammal in need thereof.

Scleroderma

Evidence also suggests a role for ATX in scleroderma/systemic sclerosis, see, for example, Sakai, et al., Inflammation and Regeneration Vol 33, No. 2 (2013), 78-89, the entire teachings of which are incorporated herein by reference. Thus the compounds or pharmaceutically acceptable salts thereof as described herein, are useful in preventing, treating, or reducing symptoms of scleroderma in a mammal in need thereof.

Cancer

Increased ATX expression has been detected in a large number of malignancies, including mammary, thyroid, hepatocellular and renal cell carcinomas, glioblastoma and neuroblastoma, as well as NSCLC. Strikingly, transgenic overexpression of ATX was shown to induce spontaneous mammary carcinogenesis. In accordance, in vitro ATX overexpression in various cell types promotes proliferation and metastasis while inhibiting apoptosis. LPA's actions are concordant with many of the "hallmarks of cancer", indicating a role for LPA in the initiation or progression of malignant disease. Indeed LPA levels are significantly increased in malignant effusions, and its receptors are aberrantly expressed in several human cancers.

LPA has been shown to be involved in wound healing and stimulates the proliferation and migration of endothelial cells promoting processes such as angiogenesis. However, these same processes when deregulated can promote tumor growth and metastasis, and LPA is thought to contribute to the development, progression, and metastasis of several types of cancer including ovarian, prostate, melanoma, breast, head and neck cancers (see Gendaszewska-Darmach, Acta Biochimica Polonica (2008), 55(2):227-240). In addition, since ATX is located outside the cell in circulation, ATX inhibitors are expected to be of most benefit outside the cell. Therefore, ATX inhibitors are expected to be useful in treating cancer, particularly multidrug resistant (MDR) cancers where drug efflux mechanisms are the largest contributor to the drug resistance. Cancer and cancer metastasis include, but are not limited to, lung cancer, mesothelioma, glioma, hepatic carcinoma, gastrointestinal cancers and progression and metastatic aggressiveness thereof.

See, for example: Euer, N., et al., Anticancer Res 22, 733-740 (2002); Liu, S., et al., Cancer Cell 15, 539-550 (2009); Zhang, G., et al., Chin Med J (Engl) 112, 330-332 (1999); Stassar, M. J., et al., Br J Cancer 85. 1372-1382

(2001); Kishi, Y., et al., J Biol Chem 281, 17492-17500 (2006); Kawagoe, H., et al., Cancer Res 57, 2516-2521 (1997); Yang, Y., et al., Am J Respir Cell Mol Biol 21, 216-222 (1999); and Toews, M. L., et al. Biochim Biophys Acta 1582, 240-250 (2002); each of which is incorporated by reference in its entirety.

LPA has been shown to be involved in lymphocyte trafficking and helps promote entry of lymphocytes into secondary lymphoid organs (see Kanda, et al., Nat. Immunology (2008), 9:415-423). Therefore the compounds or pharmaceutically acceptable salts thereof as described herein, are expected to be useful for altering lymphocyte trafficking as a method for prolonging allograft survival, for example transplantation including solid organ transplants, treatment of graft vs. host disease, bone marrow transplantation, and the like.

Urinary Excretion Disorder

Evidence also suggests a role for ATX in urinary excretion disorder, see, for example, US2013/0109699, the entire teachings of which are incorporated herein by reference. Thus the compounds or pharmaceutically acceptable salts thereof as described herein, are useful in preventing, treating, or reducing symptoms of urinary excretion disorder in a mammal in need thereof.

Additional Diseases

Additionally, the pathological disorder can be selected from renal conditions, liver conditions, inflammatory conditions, conditions of the nervous system, conditions of the respiratory system, vascular and cardiovascular conditions, fibrotic diseases, angiogenesis, and tumor metastasis and progression, ocular conditions, metabolic conditions, cholestatic and other forms of chronic pruritus and acute and chronic organ transplant rejection. (See, for example, WO2013186159 and WO2013061297, both of which are incorporated by reference in its entirety).

Renal conditions include, but are not limited to, acute kidney injury and chronic renal disease with and without proteinuria including end-stage renal disease (ESRD). In more detail, this includes decreased creatinine clearance and decreased glomerular filtration rate, microalbuminuria, albuminuria and proteinuria, glomerulosclerosis with expansion of reticulated mesangial matrix with or without significant hypercellularity (particularly diabetic nephropathy and amyloidosis), focal thrombosis of glomerular capillaries (particularly thrombotic microangiopathies), global fibrinoid necrosis, ischemic lesions, malignant nephrosclerosis (such as ischemic retraction, reduced renal blood flow and renal arteriopathy), swelling and proliferation of intracapillary (endothelial and mesangial) and/or extracapillary cells (crescents) like in glomerular nephritis entities, focal segmental glomerular sclerosis, IgA nephropathy, vasculitides/systemic diseases as well as acute and chronic kidney transplant rejection and chronic allograft nephropathy.

Liver conditions include, but are not limited to, liver cirrhosis, hepatic congestion, cholestatic liver disease including pruritus, nonalcoholic steatohepatitis and acute and chronic liver transplant rejection.

Inflammatory conditions include, but are not limited to, arthritis, osteoarthritis, systemic lupus erythematodes, psoriasis, chronic inflammation, inflammatory bowel disease, irritable bowel syndrome, functional bowel disorders, abnormal evacuation disorder and the like as well as inflammatory airways diseases such as idiopathic pulmonary fibrosis (IPF), chronic obstructive pulmonary disease (COPD) or chronic asthma bronchiale.

Conditions of the respiratory system include, but are not limited to, other diffuse parenchymal lung diseases of different etiologies including iatrogenic drug-induced fibrosis, occupational and/or environmental induced fibrosis, systemic diseases and vasculitides, granulomatous diseases (sarcoidosis, hypersensitivity pneumonia), collagen vascular disease, alveolar proteinosis, Langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, silicosis, asbestos induced pulmonary fibrosis or acute respiratory distress syndrome (ARDS).

Conditions of the nervous system include, but are not limited to, schizophrenia, neuro-inflammation (e.g. astrogliosis), peripheral and/or autonomic (diabetic) neuropathies, neuropathies and the like.

Vascular conditions include, but are not limited to, atherosclerosis, thrombotic vascular disease as well as thrombotic micro angiopathies, proliferative arteriopathy (such as swollen myointimal cells surrounded by mucinous extracellular matrix and nodular thickening), decreased vascular compliance (such as stiffness, reduced ventricular compliance and reduced vascular compliance), endothelial dysfunction and the like.

Cardiovascular conditions include, but are not limited to, acute coronary syndrome, coronary heart disease, myocardial infarction, arterial and pulmonary hypertension, thrombosis, stroke and other vascular damage.

Fibrotic diseases include, but are not limited to myocardial and vascular fibrosis, organ fibrosis, renal fibrosis, liver fibrosis, pulmonary fibrosis, skin fibrosis, scleroderma and encapsulating peritonitis. In some embodiments, the fibrotic disease is renal tubulo-interstitial fibrosis or glomerulosclerosis. In another embodiment, the fibrotic disease is idiopathic pulmonary fibrosis. In another embodiment, the fibrotic disease is nonalcoholic liver steatosis, liver fibrosis or liver cirrhosis. Additionally, fibrotic diseases include endomyocardial fibrosis, mediastinal fibrosis, myelofibrosis, retroperitoneal fibrosis, nephrogenic systemic fibrosis, Keloid, atherofibrosis and adhesive capsulitis.

Ocular conditions include, but are not limited to, proliferative and non-proliferative (diabetic) retinopathy, dry and wet age-related macular degeneration (AMD), macular edema, central arterial/venous occlusion, traumatic injury, glaucoma and the like.

Metabolic conditions include, but are not limited to, obesity and diabetes.

The compounds or pharmaceutically acceptable salts thereof as described herein, can be administered as a pharmaceutical composition. Pharmaceutical compositions can include a compound or pharmaceutically acceptable salt thereof as described herein. More particularly, such compounds and salts can be formulated as pharmaceutical compositions using standard pharmaceutically acceptable carriers, fillers, solubilizing agents and stabilizers known to those skilled in the art. For example, a pharmaceutical composition including a compounds or pharmaceutically acceptable salt thereof as described herein, is used to administer the appropriate compound or a pharmaceutically acceptable salt thereof, to a subject.

In cases where a compound as described herein can be sufficiently basic or acidic to form stable nontoxic acid or base salts, preparation and administration of the compounds as pharmaceutically acceptable salts may be appropriate. Examples of pharmaceutically acceptable salts can be organic acid addition salts formed with acids which form a physiological acceptable anion, for example, tosylate, methanesulfonate, acetate, citrate, malonate, tartarate, succinate, benzoate, ascorbate, α-ketoglutarate, or α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases, can include but are not limited to, sodium, potassium, lithium, ammonium, calcium or magnesium salts. Salts derived from organic bases can include, but are not limited to, salts of primary, secondary or tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, or mixed di- and tri-amines where at least two of the substituents on the amine can be different and can be alkyl, substituted alkyl, alkenyl, substituted alkenyl, cycloalkyl, substituted cycloalkyl, cycloalkenyl, substituted cycloalkenyl, aryl, heteroaryl, or heterocyclic and the like. Also included can be amines where the two or three substituents, together with the amino nitrogen, form a heterocyclic or heteroaryl group. Non-limiting examples of amines can include, isopropylamine, trimethyl amine, diethyl amine, tri(iso-propyl) amine, tri(n-propyl) amine, ethanolamine, 2-dimethyl-aminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, or N-ethylpiperidine, and the like. Other carboxylic acid derivatives can be useful, for example, carboxylic acid amides, including carboxamides, lower alkyl carboxamides, or dialkyl carboxamides, and the like.

The compounds or pharmaceutically acceptable salts thereof as described herein, are useful for treating a disease or disorder associated with ATX activity. In one embodiment, a therapeutically effective amount of a compound of formula (I), or a pharmaceutically acceptable salt thereof, is delivered (e.g., administered) to a subject in need thereof. In another embodiment, a pharmaceutical composition comprising a therapeutically effective amount of a compound of formula (I), or a pharmaceutically acceptable salt thereof, and a pharmaceutically-acceptable carrier is administered to a subject in need thereof.

The compounds or pharmaceutically acceptable salts thereof as described herein, can be used in combination with at least one further active ingredient, such as a medicament used in the treatment of multiple sclerosis such as Tysabri®, dimethyl fumarate, an interferon (such as pegylated or non-pegylated interferons, such as interferon β-1a or pegylated interferon β-1a), glatiramer acetate, a compound improving vascular function, an immunomodulating agent (such as Fingolimod, cyclosporins, rapamycins or ascomycins, or their immunosuppressive analogs, e.g. cyclosporine A, cyclosporine G, FK-506, ABT-281, ASM981, rapamycin, 40-O-(2-hydroxy)ethyl-rapamycin etc.); corticosteroids; cyclophosphamide; azathioprine; mitoxanthrone, methotrexate; leflunomide; mizoribine; mycophenolic add; mycophenolate mofetil; 15-deoxyspergualine; diflucortolone valerate; difluprednate; Alclometasone dipropionate; amcinonide; amsacrine; asparaginase; azathioprine; basilixmab; beclometasone dipropionate; betamethasone; betamethasone dipropionate; betamethasone phosphate sodique; betamethasone valerate; budesonide; captopril; chlormethine chlorhydrate; clobetasol propionate; cortisone acetate; cortivazol; cyclophosphamide; cytarabine; daclizumab; dactinomycine; desonide; desoximetasone; dexamethasone; dexamethasone acetate; dexamethasone isonicotinate; dexamethasone metasulfobenzoate sodique; dexamethasonephosphate; dexamethasone tebutate; dichlorisone acetate; doxorubicinee chlorhydrate; epirubicine chlorhydrate; fluclorolone acetonide; fludrocortisone acetate; fludroxycortide; flumetasone pivalate; flunisolide; fluocinolone acetonide; fluocinonide; fluocortolone; fluocortolone hexanoate; fluocortolone pivalate; fluorometholone; fluprednidene acetate; fluticasone propionate; gemcitabine chlorhydrate; halcinonide; hydrocortisone; hydrocortisone acetate; hydrocortisone butyrate; hydrocortisone hemisuccinate; melphalan; meprednisone; mercaptopurine; methylprednisolone; methylprednisolone acetate; methylprednisolone hemisuccinate; misoprostol; muromonab-cd3; mycophenolate mofetil; paramethansone acetate; prednazoline, prednisolone; prednisolone acetate; prednisolone caproate; prednisolone metasulfobenzoate sodique; prednisolone phosphate sodique; prednisone; prednylidene; rifampicine; rifampicine sodique; tacrolimus; teriflunomide; thalidomide; thiotepa; tixocortol pivalate; triamcinolone; triamcinolone acetonide hemisuccinate; triamcinolone benetonide; triamcinolone diacetate; triamcinolone hexacetonide; immunosuppressive monoclonal antibodies, e.g., monoclonal antibodies to leukocyte receptors, e.g., MHC, CD2, CD3, CD4, CD7, CD20 (e.g., rituximab and ocrelizumab), CD25, CD28, B7, CD40, CD45, CD56 (e.g., daclizumab), or CD58 or their ligands; or other immunomodulating agents, e.g. CTLA4Ig, or other adhesion molecule inhibitors, e.g. mAbs or low molecular weight inhibitors including Selectin antagonists and VLA-4 antagonists (such as Tysabri®); remyelinating agents such as BIIB033. The compounds or pharmaceutically acceptable salts thereof as described herein, can also be used in combination with agents which treat the symptoms of multiple sclerosis such as fampridine.

The dose of a compound or pharmaceutically acceptable salt thereof as described herein, or a pharmaceutically acceptable salt thereof, administered to a subject can be 10 g to 500 mg; 25 µg to 100 mg; 50 µg to 100 mg; 0.10 to 100 mg; 0.25 mg to 75 mg; or 0.5 mg to 50 mg per day.

Delivering a compound or pharmaceutically acceptable salt thereof as described herein, to a mammal comprises any delivery method whereby the compound comes in contact with any part of the mammal's body. Delivering a compound or pharmaceutically acceptable salt thereof as described herein, to a mammal includes administering a compound or pharmaceutically acceptable salt thereof as described herein topically, enterally, parenterally, transdermally, transmucosally, via inhalation, intracisternally, epidurally, intravaginally, intravenously, intramuscularly, subcutaneously, intradermally or intravitreally to the mammal. Delivering a compound or pharmaceutically acceptable salt thereof as described herein to a mammal also includes administering topically, enterally, parenterally, transdermally, transmucosally, via inhalation, intracisternally, epidurally, intravaginally, intravenously, intramuscularly, subcutaneously, intradermally or intravitreally to a mammal a compound that metabolizes within or on a surface of the body of the mammal to a compound or pharmaceutically acceptable salt thereof as described herein.

Administering a compound or pharmaceutically acceptable salt thereof as described herein to cells can include cells of an in vitro or in vivo system or model. The cells can be part of a cell line. The cell line can be a primary or secondary cell line. The cell line can be an immortal cell line. The cells can be ruptured and be in the form of a cell lysate. The cells can be part of a living organism, i.e., a subject, for example, a mammal. A mammal can include a rat, a mouse, a gerbil, a hamster, a rabbit or a human. The human can be a subject or a patient.

A method can further include monitoring a property of a sample or a subject. A sample can be removed from a subject. For instance, a sample can include a sample of cells or a tissue from a subject. A sample can include blood, plasma, or neuronal tissue including neurons or glial cells. A sample can also remain in the subject. For example, a sample can be a tissue or cells that are observed within the patient.

A method can further include providing untreated control cells, sample or subject and measuring a property of a sample of the untreated control cells, sample or subject.

A property can include the presence or absence of a molecule, the concentration of a molecule, for example myelin basic protein, myelin associated glycoprotein or myelin oligodendrocyte glycoprotein. In some embodiments, determining the presence of a molecule can include determining the concentration of the molecule, determining the purity of the molecule or determining the quantity of the molecule.

A property can be the conductivity of a tissue or cell. A property can be an emission, for example, electromagnetic radiation.

Monitoring a property can include observing the property of the sample or subject alone. Monitoring a property can include monitoring the property before the sample or subject has been administered a compound or pharmaceutically acceptable salt thereof as described herein. Monitoring a property can include monitoring the property after the sample or subject has been administered a compound or pharmaceutically acceptable salt thereof as described herein. Monitoring a property can include monitoring a property after the sample or subject has been administered a known concentration of a compound or pharmaceutically acceptable salt thereof as described herein.

Monitoring a property of a sample or subject can include observing the property through a microscope. Monitoring a property of the composition can include measuring the property using a microscope. Monitoring a property of the composition can include monitoring the property using still photography or movies. The photography or movies can be on film media or digital form. Monitoring a property can include taking a scan, for example, an MRI or CT scan.

A compound or pharmaceutically acceptable salt thereof as described herein, formulated as a pharmaceutical composition and administered to a mammalian host, such as a human patient in a variety of forms adapted to the chosen route of administration, e.g., orally or parenterally, as eyedrops, by intravenous, intramuscular, topical or subcutaneous routes.

Thus, a compound or pharmaceutically acceptable salt thereof as described herein, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compound or pharmaceutically acceptable salt thereof as described herein may be combined with one or more excipients and used in the form of ingestible tablets, buccal tablets, troches, capsules, elixirs, suspensions, syrups, or wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions can be such that an effective dosage level will be obtained.

The tablets, troches, pills, capsules, and the like can include the following: binders such as gum tragacanth, acacia, corn starch or gelatin; excipients such as dicalcium phosphate; a disintegrating agent such as corn starch, potato starch, alginic acid and the like; a lubricant such as magnesium stearate; or a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl or propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, or nontoxic glyceryl esters, and mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, or thimerosal, and the like. In some cases, isotonic agents, for example, sugars, buffers or sodium chloride will be included. Prolonged absorption of the injectable compositions can be brought about by the use in the compositions of agents delaying absorption, for example, aluminum monostearate or gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation can be vacuum drying and the freeze drying techniques, which can yield a powder of the active ingredient plus any additional desired ingredient present in the previously sterile-filtered solutions.

For topical administration, a compound or pharmaceutically acceptable salt thereof as described herein may be applied in pure form, e.g., when they are liquids. However, it can be generally be desirable to administer them to the skin as compositions or formulations, in combination with a dermatologically acceptable carrier, which may be a solid or a liquid.

Exemplary solid carriers can include finely divided solids such as talc, clay, microcrystalline cellulose, silica, alumina and the like. Useful liquid carriers include water, alcohols or glycols or water-alcohol/glycol blends, in which the compounds or pharmaceutically acceptable salts thereof as described herein can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts or esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver a compound or pharmaceutically acceptable salt thereof as described herein to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), each of which is incorporated by reference in its entirety.

Useful dosages of a compound or pharmaceutically acceptable salt thereof as described herein can be determined by comparing their in vitro activity, and in vivo activity in animal models. Methods for the extrapolation of effective dosages in mice, and other animals, to humans are known to the art; for example, see U.S. Pat. No. 4,938,949, which is incorporated by reference in its entirety.

Generally, the concentration of a compound or pharmaceutically acceptable salt thereof as described herein in a liquid composition, such as a lotion, can be from about 0.1 to about 25 weight percent, such as from about 0.5-10 weight percent. The concentration in a semi-solid or solid composition such as a gel or a powder can be about 0.1-5 wt-%, such as about 0.5-2.5 weight percent based on the total weight of the composition.

The amount of a compound or pharmaceutically acceptable salt thereof as described herein, required for use in treatment can vary not only with the particular salt selected but also with the route of administration, the nature of the condition being treated and the age and condition of the patient and can be ultimately at the discretion of the attendant physician or clinician. In general, however, a dose can be in the range of from about 0.1 to about 10 mg/kg of body weight per day.

The a compound or pharmaceutically acceptable salt thereof as described herein can be conveniently administered in unit dosage form; for example, containing 0.01 to 10 mg, or 0.05 to 1 mg, of active ingredient per unit dosage form. In some embodiments, a dose of 5 mg/kg or less can be suitable.

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations; such as multiple inhalations from an insufflator or by application of a plurality of drops into the eye.

The disclosed method can include a kit comprising a a compound or pharmaceutically acceptable salt thereof as described herein and instructional material which can describe administering a compound or pharmaceutically acceptable salt thereof as described herein or a composition comprising a compound or pharmaceutically acceptable salt thereof as described herein to a cell or a subject. This should be construed to include other embodiments of kits that are known to those skilled in the art, such as a kit comprising a (such as sterile) solvent for dissolving or suspending a compound or pharmaceutically acceptable salt thereof as described herein or composition prior to administering a compound or pharmaceutically acceptable salt thereof as described herein or composition to a cell or a subject. In some embodiments, the subject can be a human.

In accordance with the disclosed methods, as described above or as discussed in the Examples below, there can be employed conventional chemical, cellular, histochemical, biochemical, molecular biology, microbiology, and in vivo techniques which are known to those of skill in the art. Such techniques are explained fully in the literature.

EXAMPLES

Intermediate 1-1 tert-Butyl 1-(4-chloro-2-fluorobenzyl)-3-(trifluoromethyl)-4,5-dihydro-1H-pyrazolo[3,4-c]pyridine-6 (7H)-carboxylate

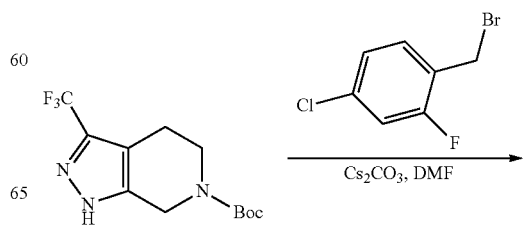

-continued

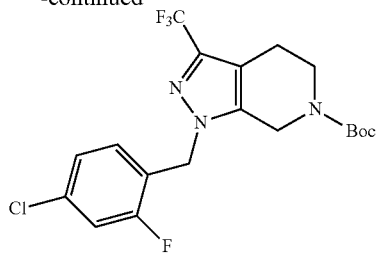

To a solution of tert-butyl 3-(trifluoromethyl)-4,5-dihydro-1H-pyrazolo[3,4-c]pyridine-6(7H)-carboxylate (65 g, 223.16 mmol) in DMF (600 mL) was added Cs$_2$CO$_3$ (91.5 g, 280.83 mmol), and 1-(bromomethyl)-4-chloro-2-fluorobenzene (compound 2) (52.4 g, 234.48 mmol) at 0° C. Then the mixture was warmed to room temperature and stirred for 16 hours. TLC (petroleum ether/EtOAc=3/1) showed the complete consumption of 1-(bromomethyl)-4-chloro-2-fluorobenzene. To the mixture was added brine (1.2 L) and the resulting mixture was extracted with ethyl acetate (1 L). The ethyl acetate phase was washed with brine (500 mL×3), dried over Na$_2$SO$_4$ and concentrated in vacuo to give a pale yellow residue. Petroleum ether was added and the mixture was cooled to 0° C. with stirring and white solid was precipitated out gradually. The solid was collected by filtration, washed with petroleum ether and dried in vacuo to give tert-butyl 1-(4-chloro-2-fluorobenzyl)-3-(trifluoromethyl)-4,5-dihydro-1H-pyrazolo[3,4-c]pyridine-6(7H)-carboxylate as white solid (67 g, yield 69%). $^1$H NMR (400 MHz, Methanol-d4) δ 7.03-7.41 (m, 3H), 5.34 (s, 2H), 4.52 (s, 2H), 3.58-3.65 (m, 2H), 2.58-2.63 (m, 2H), 1.45 (br. s., 9H); LCMS (ESI) m/z 434.3 [M+H]$^+$ Intermediate 1-2 tert-Butyl 1-(4-fluorobenzyl)-3-(trifluoromethyl)-4,5-dihydro-1H-pyrazolo[3,4-c]pyridine-6(7H)-carboxylate

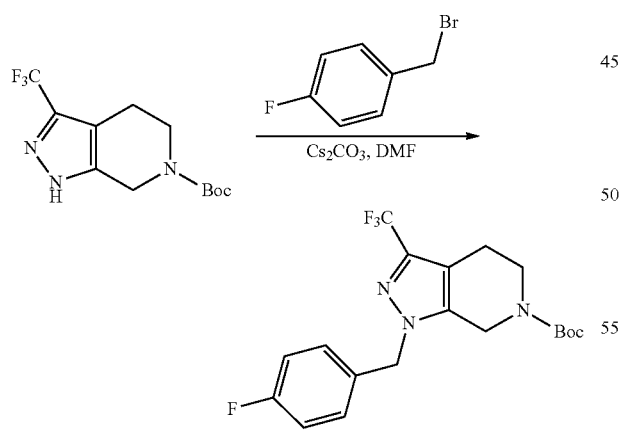

To a mixture of tert-butyl 3-(trifluoromethyl)-4,5-dihydro-1H-pyrazolo[3,4-c]pyridine-6(7H)-carboxylate (0.5 g, 1.7 mmol) and Cs$_2$CO$_3$ (0.67 g, 2.1 mmol) in DMF (10 mL) was added 1-(bromomethyl)-4-fluorobenzene (0.35 g, 1.9 mmol) dropwise. The reaction mixture was stirred at 80° C. overnight. Ethyl acetate (30 mL) was added, and the mixture was washed with brine (20 mL×2). The organic phase was dried over Na$_2$SO$_4$, filtered and concentrated to give the crude, which was purified by prep. HPLC (basic method) followed by SFC to provide tert-butyl 1-(4-fluorobenzyl)-3-(trifluoromethyl)-4,5-dihydro-1H-pyrazolo[3,4-c]pyridine-6(7H)-carboxylate (380 mg, yield 52%) as a colorless oil. $^1$H NMR (400 MHz, Methanol-d4) δ: 7.20-7.17 (m, 2H), 7.06 (t, J=8.0 Hz, 2H), 5.22 (s, 2H), 4.34 (brs, 2H), 3.58 (s, 2H), 2.67 (t, J=5.6 Hz, 2H), 1.45 (s, 9H); LCMS (ESI) m/z 400.1 [M+H]$^+$ Intermediate 1-3 tert-Butyl 1-(4-chloro-2-fluorobenzyl)-4,5-dihydro-1H-pyrazolo[3,4-c]pyridine-6(7H)-carboxylate

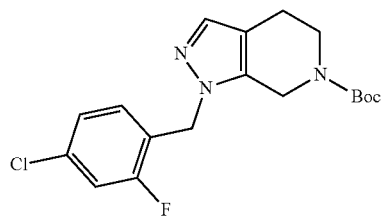 [SMILES: CC(C)(C)OC(=O)N1CCc2cnn(Cc3ccc(Cl)cc3F)c2C1]

The title compound was synthesized according to the procedure described in Intermediate 1-2, using tert-butyl 4,5-dihydro-1H-pyrazolo[3,4-c]pyridine-6(7H)-carboxylate and 1-(bromomethyl)-4-chloro-2-fluorobenzene as starting materials, to obtain a pale oil (yield 20%). $^1$H NMR (400 MHz, Methanol-d4) δ: 7.36 (s, 1H), 7.28 (dd, J 1=10.0 Hz, J2=2 Hz, 1H), 7.22 (d, J=7.6 Hz, 1H), 7.08 (t, J=8.0 Hz, 1H), 5.30 (s, 2H), 4.51 (s, 2H), 3.63 (t, J=5.6 Hz, 2H), 2.60 (t, J=6.0 Hz, 2H), 1.47 (s, 9H); LCMS (ESI) m/z 366.1 [M+H]$^+$ Intermediate 1-4 tert-Butyl 1-(4-fluorobenzyl)-4,5-dihydro-1H-pyrazolo[3,4-c]pyridine-6(7H)-carboxylate

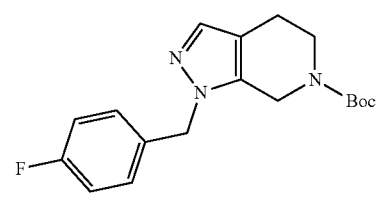 [SMILES: CC(C)(C)OC(=O)N1CCc2cnn(Cc3ccc(F)cc3)c2C1]

The title compound was synthesized according to the procedure described in Intermediate 1-2, using tert-butyl 4,5-dihydro-1H-pyrazolo[3,4-c]pyridine-6(7H)-carboxylate as a starting material, to obtain a pale oil (yield 20%). $^1$H NMR (400 MHz, CDCl$_3$) δ: 7.33 (s, 1H), 7.15-7.12 (m, 2H), 7.02-6.98 (m, 2H), 5.16 (s, 2H), 4.40-4.23 (m, 2H), 2.61-2.54 (m, 2H), 1.48-1.45 (m, 9H); LCMS (ESI) m/z 332.3 [M+H]$^+$

Intermediate 1-5 tert-Butyl 1-(4-chlorobenzyl)-3-(trifluoromethyl)-4,5-dihydro-1H-pyrazolo[3,4-c]pyridine-6(7H)-carboxylate

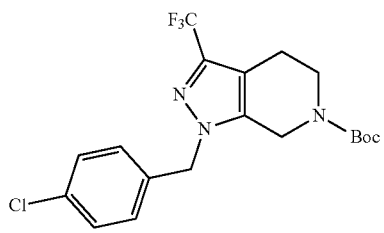 [SMILES: CC(C)(C)OC(=O)N1CCc2c(C(F)(F)F)nn(Cc3ccc(Cl)cc3)c2C1]

The title compound was synthesized according to the procedure described in Intermediate 1-2, using 1-(bromomethyl)-4-chlorobenzene as a starting material, to obtain a colorless gum (yield 39%). $^1$H NMR (400 MHz, Methanol-d4) δ: 7.39 (d, J=8.4 Hz, 2H), 7.21 (d, J=8.0 Hz, 2H), 5.34 (s, 2H), 4.44 (s, 2H), 3.63 (t, J=5.2 Hz, 2H), 2.66 (t, J=5.6 Hz, 2H), 1.44 (d, J=24 Hz, 9H); LCMS (ESI) m/z 416.0 [M+H]$^+$

Intermediate 1-6 tert-Butyl 1-(2,4-dichlorobenzyl)-3-(trifluoromethyl)-4,5-dihydro-1H-pyrazolo[3,4-c]pyridine-6(7H)-carboxylate

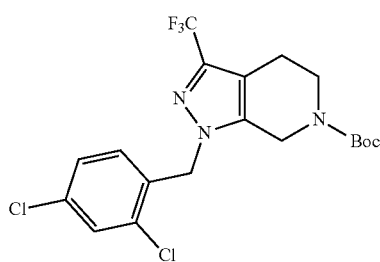 [SMILES: CC(C)(C)OC(=O)N1CCc2c(C(F)(F)F)nn(Cc3ccc(Cl)cc3Cl)c2C1]

The title compound was synthesized according to the procedure described in Intermediate 1-2, using 1-(bromomethyl)-2,4-dichlorobenzene as a starting material, to obtain a colorless gum (yield 36%). $^1$H NMR (400 MHz, Methanol-d4) δ: 7.57 (s, 1H), 7.37 (d, J=8.0 Hz, 1H), 7.00 (brs, 1H), 5.43 (s, 2H), 4.51 (s, 2H), 3.66 (s, 2H), 2.68 (t, J=6.0 Hz, 2H), 1.45 (brs, 9H); LCMS (ESI) m/z 449.9 [M+H]$^+$

Intermediate 1-7 tert-Butyl 3-(trifluoromethyl)-1-(4-(trifluoromethyl)benzyl)-4,5-dihydro-1H-pyrazolo[3,4-c]pyridine-6(7H)-carboxylate

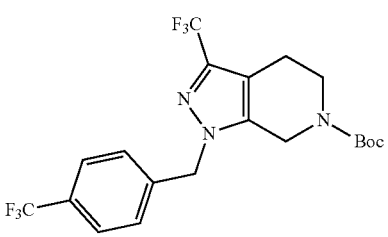 [SMILES: CC(C)(C)OC(=O)N1CCc2c(C(F)(F)F)nn(Cc3ccc(C(F)(F)F)cc3)c2C1]

The title compound was synthesized according to the procedure described in Intermediate 1-2, using 1-(bromoethyl)-4-(trifluoromethyl)benzene as a starting material, to obtain a colorless gum (yield 37%). $^1$H NMR (400 MHz, CDCl$_3$) δ: 7.62 (d, J=8.0 Hz, 2H), 7.29 (d, J=8.0 Hz, 2H), 5.31 (s, 2H), 4.36 (brs, 2H), 3.60 (s, 2H), 2.69 (t, J=5.6 Hz, 2H), 1.46 (s, 9H); LCMS (ESI) m/z 450.0 [M+H]$^+$

Intermediate 1-8 tert-Butyl 1-benzyl-3-(trifluoromethyl)-4,5-dihydro-1H-pyrazolo[3,4-c]pyridine-6(7H)-carboxylate

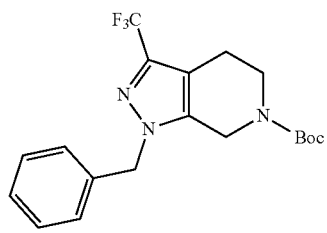 [SMILES: CC(C)(C)OC(=O)N1CCc2c(C(F)(F)F)nn(Cc3ccccc3)c2C1]

The title compound was synthesized according to the procedure described in Intermediate 1-2, using (bromomethyl)benzene as a starting material, to obtain a colorless gum (yield 49%). $^1$H NMR (400 MHz, CDCl$_3$) δ: 7.35-7.33 (m, 3H), 7.20-7.18 (m, 2H), 5.26 (s, 2H), 4.33 (brs, 2H), 3.57 (s, 2H), 2.67 (brs, 2H), 1.45 (s, 9H); LCMS (ESI) m/z 382.0 [M+H]$^+$

Intermediate 1-9 tert-Butyl 1-(cyclohexylmethyl)-3-(trifluoromethyl)-4,5-dihydro-1H-pyrazolo[3,4-c]pyridine-6(7H)-carboxylate

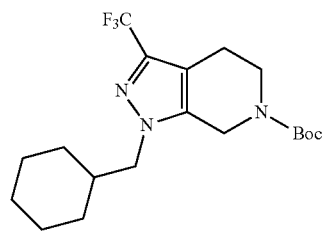 [SMILES: CC(C)(C)OC(=O)N1CCc2c(C(F)(F)F)nn(CC3CCCCC3)c2C1]

The title compound was synthesized according to the procedure described in Intermediate 1-2, using (bromomethyl)cyclohexane as a starting material, to obtain a pale oil (yield 30%). $^1$H NMR (400 MHz, CDCl$_3$) δ: 4.51 (s, 2H), 3.82 (d, J=7.2 Hz, 2H), 3.64 (br, 2H), 2.70-2.69 (m, 2H), 1.98-1.86 (m, 1H), 1.78-1.66 (m, 3H), 1.64-1.58 (m, 2H), 1.51 (s, 9H), 1.30-1.12 (m, 3H), 1.04-0.93 (m, 2H); LCMS (ESI) m/z 388.4 [M+H]$^+$

Intermediate 1-10 tert-Butyl 1-(4-methylbenzyl)-3-(trifluoromethyl)-4,5-dihydro-1H-pyrazolo[3,4-c]pyridine-6(7H)-carboxylate

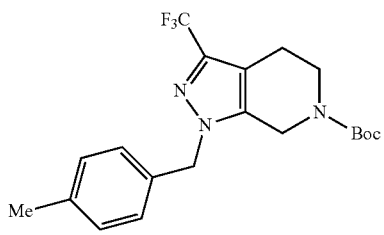 [SMILES: Cc1ccc(Cn2nc(C(F)(F)F)c3c2CN(C(=O)OC(C)(C)C)CC3)cc1]

The title compound was synthesized according to the procedure described in Intermediate 1-2, using 1-(bromomethyl)-4-methylbenzene as a starting material, to obtain a colorless gum (yield 56%). $^1$H NMR (400 MHz, CDCl$_3$) δ: 7.15-7.08 (m, 4H), 5.21 (s, 2H), 4.33-4.26 (m, 2H), 3.56 (s, 2H), 2.65 (s, 2H), 2.32 (s, 3H), 1.45 (s, 9H); LCMS (ESI) m/z 396.0 [M+H]$^+$

Intermediate 1-11 tert-Butyl 1-(4-methoxybenzyl)-3-(trifluoromethyl)-4,5-dihydro-1H-pyrazolo[3,4-c]pyridine-6(7H)-carboxylate

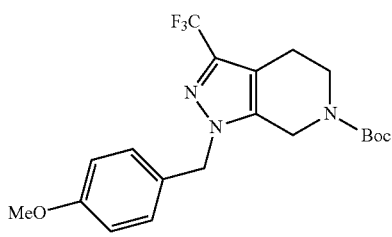 [SMILES: COc1ccc(Cn2nc(C(F)(F)F)c3c2CN(C(=O)OC(C)(C)C)CC3)cc1]

The title compound was synthesized according to the procedure described in Intermediate 1-2, using 1-(bromomethyl)-4-methoxybenzene as a starting material, to obtain a colorless gum (yield 53%). $^1$H NMR (400 MHz, CDCl$_3$) δ: 7.15 (d, J=8.4 Hz, 2H), 7.86 (d, J=8.0 Hz, 2H), 5.19 (s, 2H), 4.33-4.26 (m, 2H), 3.79 (s, 3H), 3.56 (s, 2H), 2.65 (s, 2H), 1.45 (s, 9H); LCMS (ESI) m/z 412.0 [M+H]$^+$

Intermediate 1-12 tert-Butyl 1-((5-chlorothiophen-2-yl)methyl)-3-(trifluoromethyl)-4,5-dihydro-1H-pyrazolo[3,4-c]pyridine-6(7H)-carboxylate

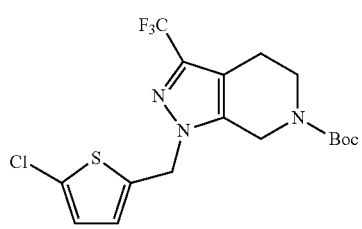 [SMILES: CC(C)(C)OC(=O)N1CCc2c(C(F)(F)F)nn(Cc3ccc(Cl)s3)c2C1]

The title compound was synthesized according to the procedure described in Intermediate 1-2, using 2-(bromomethyl)-5-chlorothiophene as a starting material, to obtain a colorless gum (yield 58%). $^1$H NMR (400 MHz, CDCl$_3$) δ: 6.82-6.78 (m, 2H), 5.29 (s, 2H), 4.46 (brs, 2H), 3.60 (brs, 2H), 2.66 (s, 2H), 1.47 (s, 9H); LCMS (ESI) m/z 421.9 [M+H]$^+$

Intermediate 1-13 tert-Butyl 1-phenethyl-3-(trifluoromethyl)-4,5-dihydro-1H-pyrazolo[3,4-c]pyridine-6(7H)-carboxylate

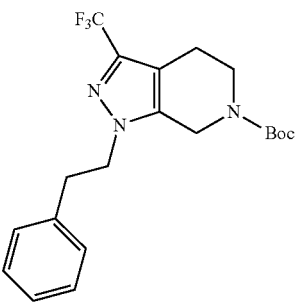 [SMILES: CC(C)(C)OC(=O)N1CCc2c(C(F)(F)F)nn(CCc3ccccc3)c2C1]

The title compound was synthesized according to the procedure described in Intermediate 1-2, using (2-bromoethyl)benzene as a starting material, to obtain a colorless oil (yield 30%). $^1$H NMR (400 MHz, CDCl$_3$) δ: 7.26-7.24 (m, 3H), 6.97 (d, J=6.0 Hz, 2H), 4.18 (t, J=6.8 Hz, 2H), 3.94-3.92 (m, 2H), 3.45 (br, 2H), 3.12 (t, J=6.4 Hz, 2H), 2.61 (br, 2H), 1.45 (s, 9H); LCMS (ESI) m/z 396.0 [M+H]$^+$

Intermediate 1-14 tert-Butyl 1-(3-fluorobenzyl)-3-(trifluoromethyl)-4,5-dihydro-1H-pyrazolo[3,4-c]pyridine-6(7H)-carboxylate

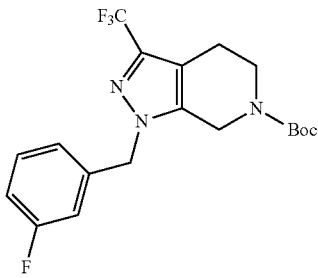 [SMILES: CC(C)(C)OC(=O)N1CCc2c(C(F)(F)F)nn(Cc3cccc(F)c3)c2C1]

The title compound was synthesized according to the procedure described in Intermediate 1-2, using 1-(bromomethyl)-3-fluorobenzene as a starting material, to obtain a colorless oil (yield 56%). $^1$H NMR (400 MHz, CDCl$_3$) δ: 7.32-7.30 (m, 1H), 7.01-6.83 (m, 3H), 5.23 (s, 2H), 4.33 (s, 2H), 3.58 (s, 2H), 2.67 (s, 2H), 1.44 (s, 9H); LCMS (ESI) m/z 399.9 [M+H]$^+$

Intermediate 1-15 tert-Butyl 1-(2-fluorobenzyl)-3-(trifluoromethyl)-4,5-dihydro-1H-pyrazolo[3,4-c]pyridine-6(7H)-carboxylate

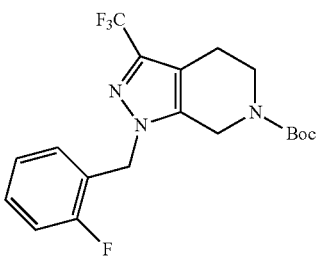 [SMILES: CC(C)(C)OC(=O)N1CCc2c(C(F)(F)F)nn(Cc3ccccc3F)c2C1]

The title compound was synthesized according to the procedure described in Intermediate 1-2, using 1-(bromomethyl)-2-fluorobenzene as a starting material, to obtain a colorless oil (yield 52%). $^1$H NMR (400 MHz, CDCl$_3$) δ: 7.32-7.30 (m, 1H), 7.01-6.83 (m, 3H), 5.23 (s, 2H), 4.33 (s, 2H), 3.58 (s, 2H), 2.67 (s, 2H), 1.44 (s, 9H); LCMS (ESI) m/z 400.0 [M+H]$^+$

Intermediate 1-16 tert-Butyl 1-cyclohexyl-3-(trifluoromethyl)-4,5-dihydro-1H-pyrazolo[3,4-c]pyridine-6(7H)-carboxylate

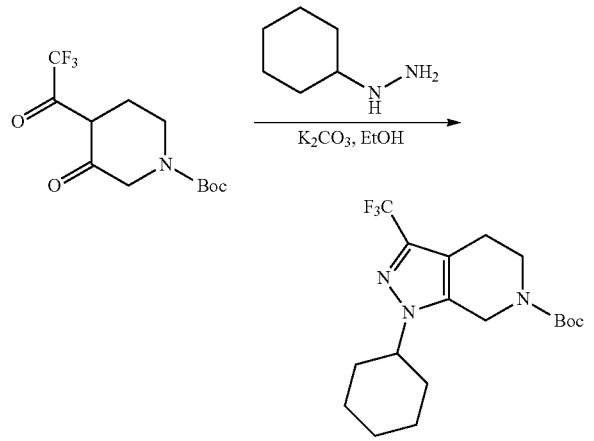

A mixture of tert-butyl 3-oxo-4-(2,2,2-trifluoroacetyl)piperidine-1-carboxylate (200 mg, 0.68 mmol, 1.0 eq), cyclohexylhydrazine (78 mg, 0.68 mmol, 1.0 eq) and K$_2$CO$_3$ in EtOH (5 mL) was stirred at room temperature overnight. TLC (PE/EA=3/1) showed the starting material was consumed completely. The solvent was removed in vacuum and the residue was purified by prep. HPLC (MeCN and H$_2$O with 0.05% NH$_3$H$_2$O as mobile phase) to provide tert-butyl 1-cyclohexyl-3-(trifluoromethyl)-4,5-dihydro-1H-pyrazolo[3,4-c]pyridine-6(7H)-carboxylate (180 mg, yield 65%) as colorless oil. $^1$H NMR (400 MHz, CDCl$_3$) δ: 4.53 (s, 2H), 3.87 (brs, 1H), 3.62 (s, 2H), 2.66 (s, 2H), 2.01-1.89 (m, 6H), 1.72-1.69 (m, 1H), 1.49 (s, 9H), 1.33-1.25 (m, 3H); LCMS (ESI) m/z 374.0 [M+H]$^+$

Intermediate 1-17 tert-Butyl 1-phenyl-3-(trifluoromethyl)-4,5-dihydro-1H-pyrazolo[3,4-c]pyridine-6(7H)-carboxylate

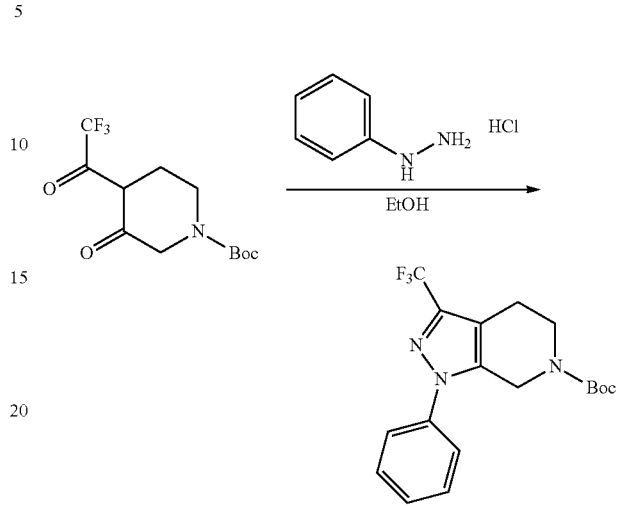

A mixture of tert-butyl 3-oxo-4-(2,2,2-trifluoroacetyl)piperidine-1-carboxylate (400 mg, 1.35 mmol, 1.0 eq), phenylhydrazine hydrochloride (204 mg, 1.42 mmol, 1.05 eq) in EtOH (6 mL) was stirred at room temperature overnight. TLC (PE/EA=3/1) showed the starting material was consumed completely. The solvent was removed in vacuum and the residue was purified by prep. HPLC (MeCN and H$_2$O with 0.225% (v/v) HCOOH as mobile phase) to provide tert-butyl 1-phenyl-3-(trifluoromethyl)-4,5-dihydro-1H-pyrazolo[3,4-c]pyridine-6(7H)-carboxylate (160 mg, yield 32%) as a yellow solid. $^1$H NMR (400 MHz, Methanol-d4) δ: 7.60-7.52 (m, 5H), 4.66-4.63 (m, 2H), 3.75 (t, J=5.6 Hz, 2H), 2.77 (t, J=5.2 Hz, 2H), 1.47 (s, 1H); LCMS (ESI) m/z 368.0 [M+H]$^+$

Intermediate 1-18 tert-Butyl 1-(1-(4-fluorophenyl)ethyl)-3-(trifluoromethyl)-4,5-dihydro-1H-pyrazolo[3,4-c]pyridine-6(7H)-carboxylate

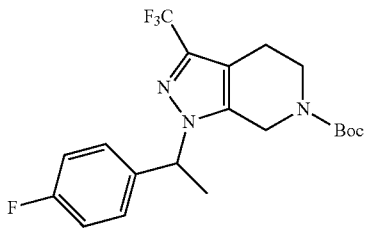 [SMILES: CC(c1ccc(F)cc1)n1nc(C(F)(F)F)c2c1CN(C(=O)OC(C)(C)C)CC2]

Step 1

1-(4-Fluorophenyl)ethyl methanesulfonate

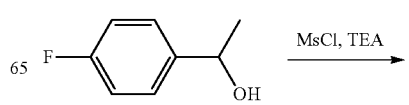

-continued

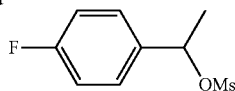

A mixture of 1-(4-fluorophenyl)ethanol (300 mg, 2.14 mmol, 1.0 eq), MsCl (293 mg, 2.57 mmol, 1.2 eq) and TEA (941 mg, 3.2 mmol, 1.5 eq) in DCM (5 mL) was stirred at room temperature overnight. TLC (PE/EA=3/1) showed the starting material was consumed completely. The reaction was quenched with aqueous citric acid solution and then extracted with DCM (5 mL×3). The organic phase was dried over Na$_2$SO$_4$, filtered and concentrated to give 1-(4-fluorophenyl)ethyl methanesulfonate (400 mg, yield 86%), which was used in next step without further purification.

Step 2 tert-Butyl 1-(1-(4-fluorophenyl)ethyl)-3-(trifluoromethyl)-4,5-dihydro-1H-pyrazolo[3,4-c]pyridine-6(7H)-carboxylate

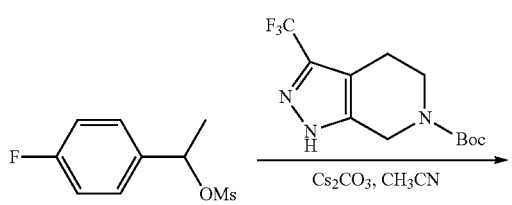

To a mixture of tert-butyl 3-(trifluoromethyl)-4,5-dihydro-1H-pyrazolo[3,4-c]pyridine-6(7H)-carboxylate (0.59 g, 2.0 mmol, 1.1 eq.) and Cs$_2$CO$_3$ (0.89 g, 2.8 mmol, 1.5 eq.) in DMF (10 mL) was added 1-(4-fluorophenyl)ethyl methanesulfonate (0.4 g, 1.8 mmol, 1.0 eq.) dropwise. The reaction mixture was stirred at 80° C. overnight. Ethyl acetate (20 mL) was added and the mixture was washed with brine (10 mL×2). The organic phase was dried over Na$_2$SO$_4$, filtered and concentrated to give the crude, which was purified by prep. HPLC (MeCN and H$_2$O with 0.05% NH$_3$H$_2$O as mobile phase) to provide tert-butyl 1-(1-(4-fluorophenyl)ethyl)-3-(trifluoromethyl)-4,5-dihydro-1H-pyrazolo[3,4-c]pyridine-6(7H)-carboxylate (180 mg, yield 22%) as colorless oil. $^1$H NMR (400 MHz, CDCl$_3$) δ: 7.19-7.09 (m, 2H), 6.96-6.92 (m, 2H), 5.23 (q, J=6.4 Hz, 1H), 4.45-4.01 (m, 2H), 3.66-3.35 (m, 2H), 2.57 (s, 2H), 1.82 (d, J=6.8 Hz, 3H), 1.37 (s, 9H)

Intermediate 1-19 tert-Butyl 1-(2-cyclohexylethyl)-3-(trifluoromethyl)-4,5-dihydro-1H-pyrazolo[3,4-c]pyridine-6(7H)-carboxylate The title compound was synthesized according to the procedure described in Intermediate 1-2, using (2-bromoethyl)cyclohexane as starting material, to obtain a colorless oil (yield 58%). $^1$H NMR (400 MHz, Methanol-d4) δ: 4.57 (s, 2H), 4.09 (t, J=7.6 Hz, 2H), 3.65 (t, J=5.2 Hz, 2H), 2.64 (t, J=4.8 Hz, 2H), 1.77-1.65 (m, 7H), 1.49 (s, 9H), 1.28-1.23 (m, 4H), 1.00-0.97 (m, 2H); LCMS (ESI) m/z 402.1 [M+H]$^+$ Intermediate 1-20

6-tert-Butyl 3-ethyl 1-(4-fluorobenzyl)-4,5-dihydro-1H-pyrazolo[3,4-c]pyridine-3,6(7H)-dicarboxylate

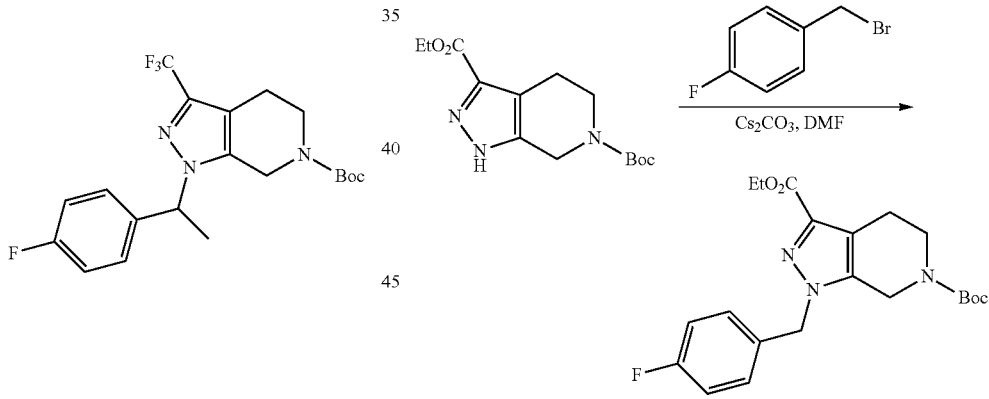

To a mixture of 6-tert-butyl 3-ethyl 4,5-dihydro-1H-pyrazolo[3,4-c]pyridine-3,6(7H)-dicarboxylate (2.0 g, 6.8 mmol, 1.0 eq.) and Cs$_2$CO$_3$ (3.3 g, 10.2 mmol, 1.5 eq.) in DMF (20 mL) was added 1-(bromomethyl)-4-fluorobenzene (1.53 g, 8.1 mmol, 1.2 eq.) dropwise. The reaction mixture was stirred at 25° C. for 12 h. LCMS showed desired product was detected. EtOAc (50 mL) was added and the mixture was washed with brine (20 mL). The organic phase was dried over Na$_2$SO$_4$, filtered and concentrated to give the crude, which was purified column chromatography on silica (PE/EtOAc=10/1~3/1) to provide 6-tert-butyl 3-ethyl 1-(4-fluorobenzyl)-4,5-dihydro-1H-pyrazolo[3,4-c]pyridine-3,6(7H)-dicarboxylate (1.1 g, yield 40%) as a yellow oil. $^1$H NMR (400 MHz, CDCl$_3$) δ: 7.18-7.14 (m, 2H), 7.02-6.98 (m, 2H), 5.26 (s, 2H), 4.38 (q, J=7.2 Hz, 2H), 4.28-4.27 (m, 2H), 3.54 (s, 2H), 2.81-2.79 (m, 2H), 1.43-1.36 (m, 12H) LCMS (ESI) m/z 404.0 [M+H]$^+$

Intermediate 1-21 tert-Butyl 1-(4-fluorobenzyl)-3-(hydroxymethyl)-4,5-dihydro-1H-pyrazolo[3,4-c]pyridine-6(7H)-carboxylate

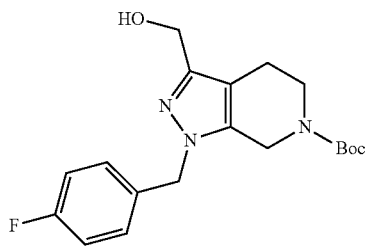 [SMILES: CC(C)(C)OC(=O)N1CCc2c(CO)nn(Cc3ccc(F)cc3)c2C1]

Step 1 tert-Butyl 3-(((tert-butyldiphenylsilyl)oxy)methyl)-4,5-dihydro-1H-pyrazolo[3,4-c]pyridine-6(7H)-carboxylate

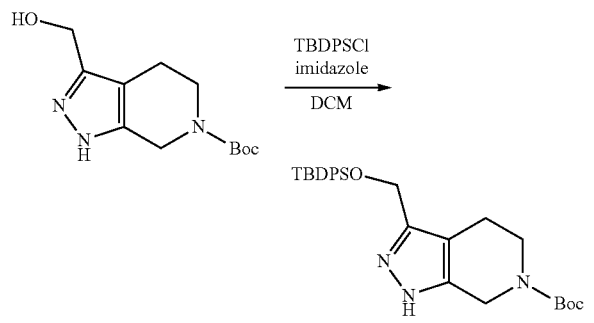

To a solution of tert-butyl 3-(hydroxymethyl)-4,5-dihydro-1H-pyrazolo[3,4-c]pyridine-6(7H)-carboxylate (1.0 g, 3.95 mmol, 1.0 eq) in DCM (10 ml) was added TBDPSCl (3.25 g, 11.48 mmol, 3.0 eq), imidazole (537 mg, 7.89 mmol, 2.0 eq), then the mixture was stirred at 35° C. for 17 hours. TLC (PE/EA=5/1, Rf=0.3) showed the starting material was consumed completely. The solvent was removed in vacuum and the residue was purified by column chromatography (PE/EA=5/1) to provide tert-butyl 3-(((tert-butyldiphenylsilyl)oxy)methyl)-4,5-dihydro-1H-pyrazolo[3,4-c]pyridine-6(7H)-carboxylate (1.5 g, yield 77%) as a yellow oil. $^1$H NMR (400 MHz, Methanol-d4) δ: 7.64-7.62 (m, 4H), 7.44-7.35 (m, 6H), 4.68 (s, 2H), 4.47 (s, 2H), 3.50 (s, 2H), 2.27 (s, 2H), 1.46 (s, 9H), 1.00 (s, 9H).

Step 2 tert-Butyl 3-(((tert-butyldiphenylsilyl)oxy)methyl)-1-(4-fluorobenzyl)-4,5-dihydro-1H-pyrazolo[3,4-c]pyridine-6(7H)-carboxylate

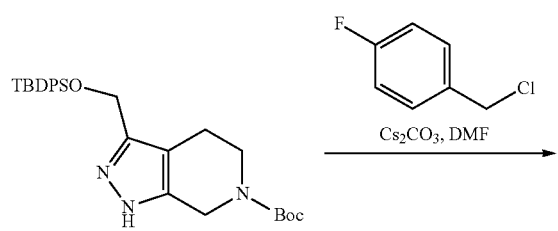

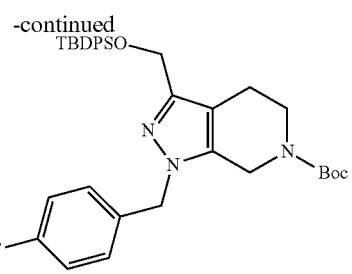

To a mixture of tert-butyl 3-(((tert-butyldiphenylsilyl)oxy)methyl)-4,5-dihydro-1H-pyrazolo[3,4-c]pyridine-6(7H)-carboxylate (1.5 g, 3.05 mmol, 1.0 eq.) in DMF (10 mL) was added Cs$_2$CO$_3$ (1.99 g, 6.10 mmol, 2.0 eq.), 1-(chloromethyl)-4-fluorobenzene (529 mg, 3.66 mmol, 1.2 eq.). The reaction mixture was stirred at 35° C. for 17 hours. The mixture was poured into brine (20 mL) and extracted with EtOAc (20 mL×3). The combined organic phases were dried over Na$_2$SO$_4$, filtered and concentrated to give the crude, which was purified by prep. HPLC (MeCN and H$_2$O with 0.225% FA as mobile phase; from 70-100%) to provide tert-butyl 3-(((tert-butyldiphenylsilyl)oxy)methyl)-1-(4-fluorobenzyl)-4,5-dihydro-1H-pyrazolo[3,4-c]pyridine-6(7H)-carboxylate (900 mg, yield 49%) as a yellow gum. $^1$H NMR (400 MHz, Methanol-d$_4$) δ: 7.65-7.63 (m, 4H), 7.42-7.34 (m, 6H), 7.16-7.03 (m, 4H), 5.12 (s, 2H), 4.70 (s, 2H), 4.36 (s, 2H), 3.50 (s, 2H), 2.46 (s, 2H), 1.46-1.43 (m, 9H), 1.06-0.97 (m, 9H); LCMS (ESI) m/z 600.1 [M+H]$^+$ Step 3 tert-Butyl 1-(4-fluorobenzyl)-3-(hydroxymethyl)-4,5-dihydro-1H-pyrazolo[3,4-c]pyridine-6(7H)-carboxylate

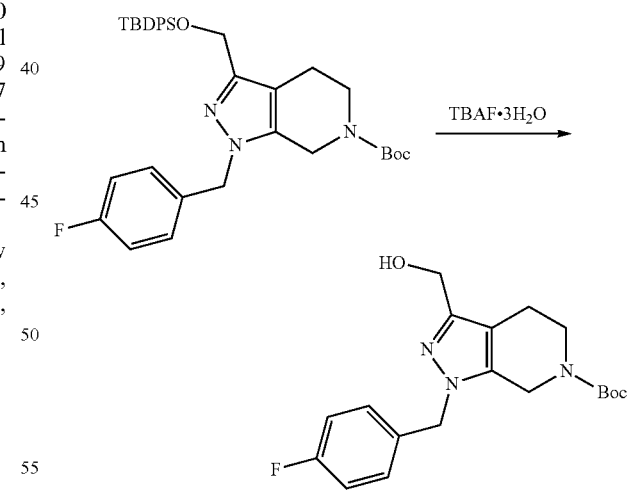

To a solution of tert-butyl 3-(((tert-butyldiphenylsilyl)oxy)methyl)-1-(4-fluorobenzyl)-4,5-dihydro-1H-pyrazolo[3,4-c]pyridine-6(7H)-carboxylate (900 mg, 1.5 mmol, 1.0 eq) in THF (15 ml) was added TBAF.3H$_2$O (2.37 g, 7.5 mmol, 5.0 eq), then the mixture was stirred at 35° C. for 4 hours. The solvent was removed in vacuum and the residue was purified by column chromatography (PE/EA=5/1) to provide tert-butyl 1-(4-fluorobenzyl)-3-(hydroxymethyl)-4,5-dihydro-1H-pyrazolo[3,4-c]pyridine-6(7H)-carboxylate (500 mg, yield 92%) as a yellow oil. $^1$H NMR (400 MHz, Methanol-$d_4$) δ: 7.19-7.16 (m, 2H), 7.07-7.03 (m, 2H), 5.20 (s, 2H), 4.53-4.51 (m, 2H), 4.37 (s, 2H), 3.58 (s, 2H), 2.61-2.59 (m, 2H), 1.44-1.38 (m, 9H); LCMS (ESI) m/z 362.0 [M+H]$^+$ Intermediate 1-22 tert-Butyl 3-ethoxy-1-(4-fluorobenzyl)-4,5-dihydro-1H-pyrazolo[3,4-c]pyridine-6(7H)-carboxylate

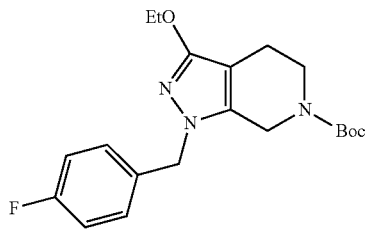

Step 1 tert-Butyl 3-ethoxy-4,5-dihydro-1H-pyrazolo[3,4-c]pyridine-6(7H)-carboxylate

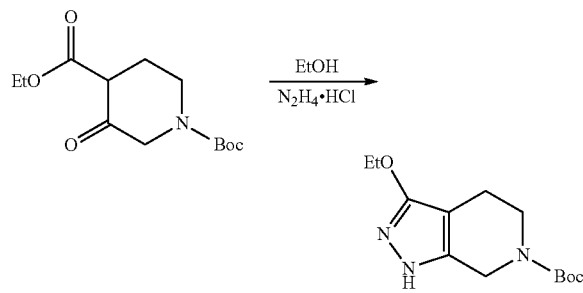

A mixture of 1-tert-butyl 4-ethyl 3-oxopiperidine-1,4-dicarboxylate (500 mg, 1.85 mmol, 1.0 eq) and hydrazine hydrochloride (151 mg, 2.2 mmol, 1.2 eq) in EtOH (10 mL) was stirred at 35° C. overnight. TLC (PE/EA=3/1) showed the starting material was consumed completely. The solvent was removed in vacuum and the residue was purified by prep. HPLC (MeCN and H$_2$O with 0.05% NH$_3$.H$_2$O as mobile phase; from 40-70%) to provide tert-butyl 3-ethoxy-4,5-dihydro-1H-pyrazolo[3,4-c]pyridine-6(7H)-carboxylate (100 mg, yield 22%) as colorless oil. $^1$H NMR (400 MHz, CDCl$_3$) δ: 4.44 (s, 2H), 4.21 (q, J=6.8 Hz, 2H), 3.58 (s, 2H), 2.45 (s, 2H), 1.45 (s, 9H), 1.36 (t, J=6.8 Hz, 3H).

Step 2 tert-Butyl 3-ethoxy-1-(4-fluorobenzyl)-4,5-dihydro-1H-pyrazolo[3,4-c]pyridine-6(7H)-carboxylate

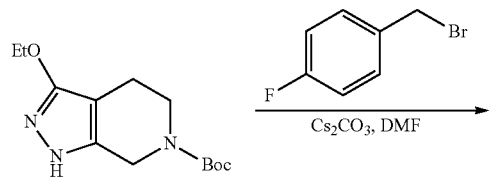

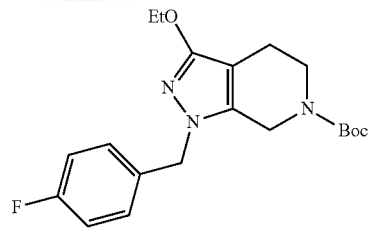 [SMILES: CCOc1nn(Cc2ccc(F)cc2)c2c1CCN(C(=O)OC(C)(C)C)C2]

To a mixture of tert-butyl 3-ethoxy-4,5-dihydro-1H-pyrazolo[3,4-c]pyridine-6(7H)-carboxylate (100 mg, 0.36 mmol, 1.0 eq) and Cs$_2$CO$_3$ (176 mg, 0.54 mmol, 1.5 eq) in DMF (2 mL) was added 1-(bromomethyl)-4-fluorobenzene (68 mg, 0.36 mmol, 1.0 eq). The reaction mixture was stirred at 80° C. overnight. EtOAc (10 mL) was added and the mixture was washed with brine (10 mL×2). The organic phase was dried over Na$_2$SO$_4$, filtered and concentrated to give the crude, which was purified by prep. HPLC (MeCN and H$_2$O with 0.05% NH$_3$.H$_2$O as mobile phase; from 60-90%) to provide tert-butyl 3-ethoxy-1-(4-fluorobenzyl)-4,5-dihydro-1H-pyrazolo[3,4-c]pyridine-6(7H)-carboxylate (60 mg, yield 36%) as colorless oil. $^1$H NMR (400 MHz, CDCl$_3$) δ: 7.11-7.08 (m, 2H), 7.00-6.96 (m, 2H), 4.99 (s, 2H), 4.28-4.20 (m, 4H), 3.53 (s, 2H), 2.44 (s, 2H), 1.44 (s, 9H), 1.37 (t, J=6.8 Hz, 3H); LCMS (ESI) m/z 376.0 [M+H]$^+$ Intermediate 1-23 tert-Butyl-1-(4-fluorobenzyl)-3-iodo-4,5-dihydro-1H-pyrazolo[3,4-c]pyridine-6(7H)-carboxylate Step 1 tert-Butyl 3-iodo-4,5-dihydro-1H-pyrazolo[3,4-c]pyridine-6(7H)-carboxylate

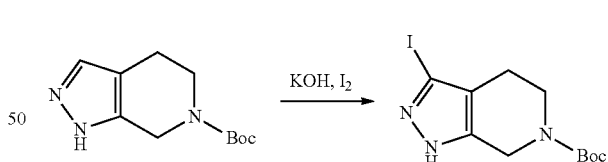

A mixture of tert-butyl 4,5-dihydro-1H-pyrazolo[3,4-c]pyridine-6(7H)-carboxylate (0.67 g, 3 mmol, 1.0 eq), I$_2$ (1.5 g, 6 mmol, 2.0 eq) and KOH (0.67 g, 12 mmol, 4.0 eq) in DMF (5 mL) was stirred at 50° C. for 17 h. LCMS showed desired product was detected. The reaction was quenched with aqueous Na$_2$SO$_3$ solution and extracted with MTBE (10 mL×2). The organic phase was dried over Na$_2$SO$_4$, filtered and concentrated to give the crude, which was purified by column chromatography on silica (PE/EA=3/1) to provide tert-butyl 3-iodo-4,5-dihydro-1H-pyrazolo[3,4-c]pyridine-6(7H)-carboxylate (0.5 g, yield 48%) as a colorless oil. LCMS (ESI) m/z 293.7 [M+H-56]$^+$ Step 2 tert-Butyl-1-(4-fluorobenzyl)-3-iodo-4,5-dihydro-1H-pyrazolo[3,4-c]pyridine-6(7H)-carboxylate

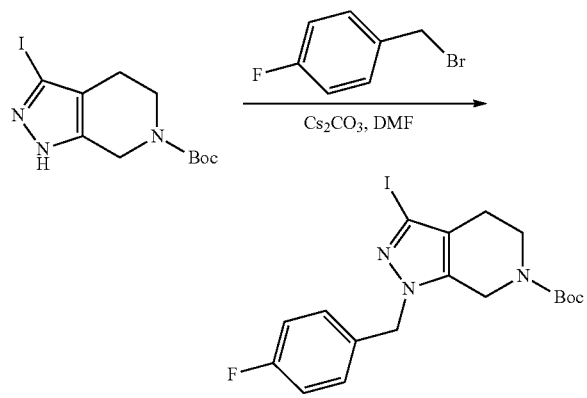

A mixture of tert-butyl 3-iodo-4,5-dihydro-1H-pyrazolo[3,4-c]pyridine-6(7H)-carboxylate (400 mg, 1.15 mmol, 1.0 eq.), 1-(bromomethyl)-4-fluorobenzene (323 mg, 1.72 mmol, 1.5 eq.) and $Cs_2CO_3$ (748 mg, 2.3 mmol, 2.0 eq.) in DMF (5 mL) was stirred at room temperature for 17 h. EA (20 mL) was added and the mixture was washed with brine (10 mL). The organic phase was dried over $Na_2SO_4$, filtered and concentrated to give the crude, which was purified by prep-HPLC (MeCN and $H_2O$ with 0.225% (v/v) FA as mobile phase; from 52-78%) to provide tert-butyl 1-(4-fluorobenzyl)-3-iodo-4,5-dihydro-1H-pyrazolo[3,4-c]pyridine-6(7H)-carboxylate (150 mg, 27.3%) as colorless oil. $^1$H NMR (400 MHz, $CDCl_3$) δ: 7.17-7.14 (m, 2H), 7.02-6.98 (m, 2H), 5.17 (s, 2H), 4.30-4.24 (m, 2H), 3.56 (s, 2H), 2.40 (s, 2H), 1.44 (s, 9H); LCMS (ESI) m/z 457.9 [M+H]$^+$ Intermediate 2-1

1-(4-Chloro-2-fluorobenzyl)-3-(trifluoromethyl)-4,5,6,7-tetrahydro-1H-pyrazolo[3,4-c]pyridine HCl salt

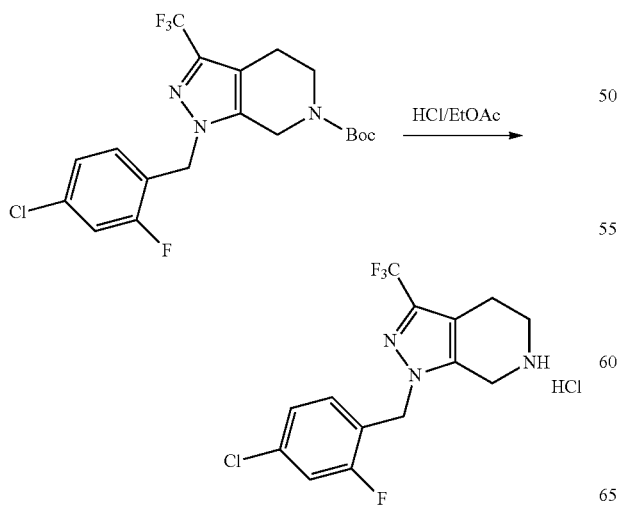

To a mixture of tert-butyl 1-(4-chloro-2-fluorobenzyl)-3-(trifluoromethyl)-4,5-dihydro-1H-pyrazolo[3,4-c]pyridine-6(7H)-carboxylate (67 g, 154.4 mmol) in EtOAc (100 mL) was added HCl/EtOAc (750 mL) at 0° C., then the mixture was warmed to room temperature and stirred for one hour. TLC (petroleum ether/EtOAc=5:1) showed the complete consumption of the starting material. The mixture was concentrated in vacuo to give the product as an off-white solid (55 g, yield 100%). $^1$H NMR (400 MHz, Methanol-d4) δ 7.17-7.36 (m, 3H), 5.40 (s, 2H), 4.45 (s, 2H), 3.49 (t, J=6.15 Hz, 2H), 2.97 (t, J=6.02 Hz, 2H); LCMS (ESI) m/z 334.2 [M+H]$^+$ Intermediate 2-2

1-(4-Fluorobenzyl)-3-(trifluoromethyl)-4,5,6,7-tetrahydro-1H-pyrazolo[3,4-c]pyridine HCl salt

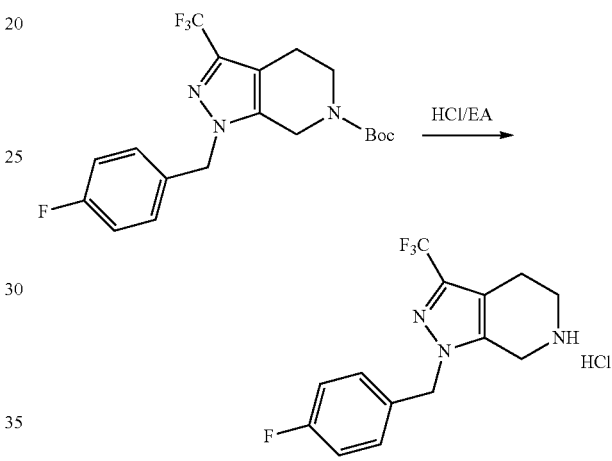

A mixture of tert-butyl 1-(4-fluorobenzyl)-3-(trifluoromethyl)-4,5-dihydro-1H-pyrazolo[3,4-c]pyridine-6(7H)-carboxylate (380 mg, 0.95 mmol) in HCl/Ethyl acetate (5 mL) was stirred at room temperature for 2 h. TLC showed the starting material was consumed completely. The solvent was removed in vacuum to give 1-(4-fluorobenzyl)-3-(trifluoromethyl)-4,5,6,7-tetrahydro-1H-pyrazolo[3,4-c]pyridine hydrochloride (340 mg, yield 100%), which was used in next step without further purification. $^1$H NMR (400 MHz, Methanol-d4) δ: 7.34-7.31 (m, 2H), 7.14 (t, J=8.8 Hz, 2H), 5.40 (s, 2H), 4.36 (s, 2H), 3.49 (t, J=6.4 Hz, 2H), 2.99 (t, J=6.0 Hz, 2H); LCMS (ESI) m/z 299.9 [M+H]$^+$ Intermediate 2-3

1-(4-Chloro-2-fluorobenzyl)-4,5,6,7-tetrahydro-1H-pyrazolo[3,4-c]pyridine HCl salt

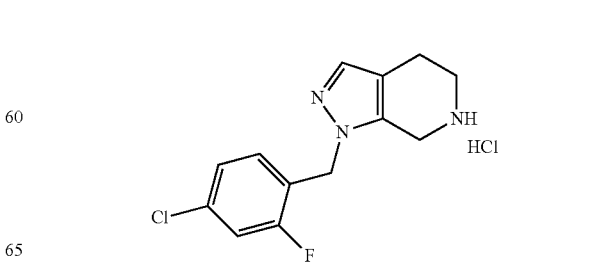

The title compound was synthesized according to the procedure described in Intermediate 2-2, using intermediate 1-3 as a starting material, to obtain a white solid (180 mg, yield 100%). ¹H NMR (400 MHz, Methanol-d4) δ: 7.57 (s, 1H), 7.31-7.21 (m, 3H), 5.40 (s, 2H), 4.45 (s, 2H), 3.49 (t, J=6.0 Hz, 2H), 2.95 (t, J=6.0 Hz, 2H); LCMS m/z 265.8 [M+H]⁺

Intermediate 2-4

1-(4-Fluorobenzyl)-4,5,6,7-tetrahydro-1H-pyrazolo[3,4-c]pyridine HCl salt

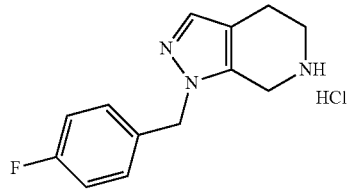 [SMILES: Fc1ccc(Cn2ncc3c2CNCC3)cc1 ; Cl]

The title compound was synthesized according to the procedure described in Intermediate 2-2, using intermediate 1-4 as a starting material, to obtain a white solid (yield 100%).
LCMS m/z 232.2 [M+H]⁺

Intermediate 2-5

1-(4-Chlorobenzyl)-3-(trifluoromethyl)-4,5,6,7-tetrahydro-1H-pyrazolo[3,4-c]pyridine

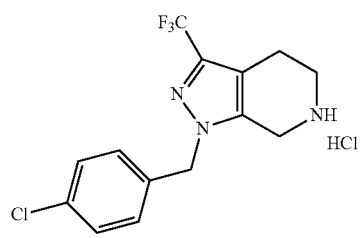 [SMILES: FC(F)(F)c1nn(Cc2ccc(Cl)cc2)c2c1CCNC2 ; Cl]

The title compound was synthesized according to the procedure described in Intermediate 2-2, using intermediate 1-5 as a starting material, to obtain a white solid (yield 71%). ¹H NMR (400 MHz, Methanol-d4) δ: 7.41 (dd, J1=6.8 Hz, J2=2.0 Hz, 2H), 7.27 (d, J=8.8 Hz, 2H), 5.41 (s, 2H), 4.36 (s, 2H), 3.49 (t, J=6.0 Hz, 2H), 3.00 (t, J=6.0 Hz, 2H); LCMS m/z 315.9 [M+H]⁺

Intermediate 2-6

1-(2,4-Dichlorobenzyl)-3-(trifluoromethyl)-4,5,6,7-tetrahydro-1H-pyrazolo[3,4-c]pyridine HCl salt

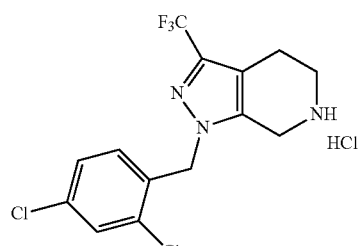

The title compound was synthesized according to the procedure described in Intermediate 2-2, using intermediate 1-6 as a starting material, to obtain a white solid (yield 75%). ¹H NMR (400 MHz, Methanol-d4) δ: 7.72 (d, J=8.0 Hz, 2H), 7.45 (d, J=8.0 Hz, 2H), 5.53 (s, 2H), 4.38 (s, 2H), 3.50 (t, J=6.4 Hz, 2H), 3.01 (t, J=6.0 Hz, 2H); LCMS m/z 349.9 [M+H]⁺

Intermediate 2-7

3-(Trifluoromethyl)-1-(4-(trifluoromethyl)benzyl)-4,5,6,7-tetrahydro-1H-pyrazolo[3,4-c]pyridine HCl salt

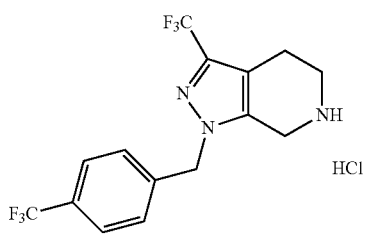 [SMILES: FC(F)(F)c1ccc(Cn2nc(C(F)(F)F)c3c2CNCC3)cc1 ; Cl]

The title compound was synthesized according to the procedure described in Intermediate 2-2, using intermediate 1-7 as a starting material, to obtain a white solid (yield 70%). ¹H NMR (400 MHz, Methanol-d4) δ: 7.72 (d, J=8.0 Hz, 2H), 7.45 (d, J=8.0 Hz, 2H), 5.53 (s, 2H), 4.38 (s, 2H), 3.50 (t, J=6.4 Hz, 2H), 3.01 (t, J=6.0 Hz, 2H); LCMS m/z 349.9 [M+H]⁺

Intermediate 2-8

1-Benzyl-3-(trifluoromethyl)-4,5,6,7-tetrahydro-1H-pyrazolo[3,4-c]pyridine HCl salt

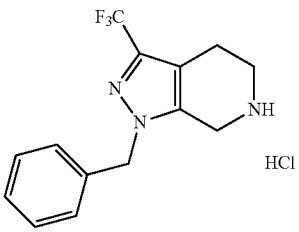 [SMILES: FC(F)(F)c1nn(Cc2ccccc2)c2c1CCNC2 ; Cl]

The title compound was synthesized according to the procedure described in Intermediate 2-2, using intermediate 1-8 as a starting material, to obtain a white solid (yield 100%).
LCMS m/z 282.1 [M+H]⁺

Intermediate 2-9

1-(Cyclohexylmethyl)-3-(trifluoromethyl)-4,5,6,7-tetrahydro-1H-pyrazolo[3,4-c]pyridine HCl salt

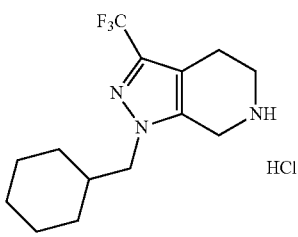 [SMILES: FC(F)(F)c1nn(CC2CCCCC2)c2c1CCNC2 ; Cl]

The title compound was synthesized according to the procedure described in Intermediate 2-2, using intermediate 1-9 as a starting material, to obtain a white solid (yield 100%).
LCMS m/z 288.1 [M+H]$^+$

Intermediate 2-10

1-(4-Methylbenzyl)-3-(trifluoromethyl)-4,5,6,7-tetrahydro-1H-pyrazolo[3,4-c]pyridine HCl salt

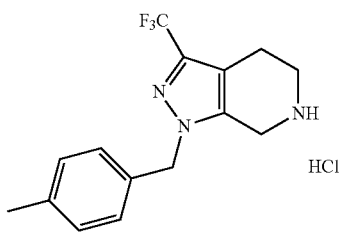 [SMILES: Cc1ccc(Cn2nc(C(F)(F)F)c3c2CNCC3)cc1 ; Cl]

The title compound was synthesized according to the procedure described in Intermediate 2-2, using intermediate 1-10 as a starting material, to obtain a white solid (yield 100%). $^1$H NMR (400 MHz, Methanol-d4) δ: 7.18 (d, J=7.6 Hz, 2H), 7.12 (d, J=7.6 Hz, 2H), 5.34 (s, 2H), 4.26 (s, 2H), 3.43 (t, J=5.6 Hz, 2H), 2.94 (s, 2H), 2.30 (s, 3H); LCMS m/z 295.9 [M+H]$^+$

Intermediate 2-11

1-(4-Methoxybenzyl)-3-(trifluoromethyl)-4,5,6,7-tetrahydro-1H-pyrazolo[3,4-c]pyridine HCl salt

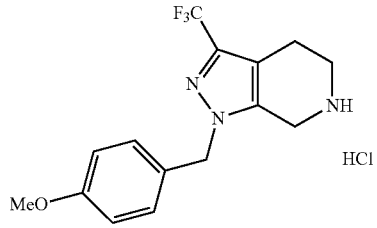 [SMILES: COc1ccc(Cn2nc(C(F)(F)F)c3c2CNCC3)cc1 ; Cl]

The title compound was synthesized according to the procedure described in Intermediate 2-2, using intermediate 1-11 as a starting material, to obtain a white solid (yield 100%). $^1$H NMR (400 MHz, Methanol-d4) δ: 7.19 (d, J=8.4 Hz, 2H), 6.91 (d, J=8.4 Hz, 2H), 5.31 (s, 2H), 4.26 (s, 2H), 3.76 (s, 3H), 3.43 (t, J=6.0 Hz, 2H), 3.94 (t, J=6.0 Hz, 2H); LCMS m/z 311.9 [M+H]$^+$

Intermediate 2-12

1-((5-Chlorothiophen-2-yl)methyl)-3-(trifluoromethyl)-4,5,6,7-tetrahydro-1H-pyrazolo[3,4-c]pyridine HCl salt

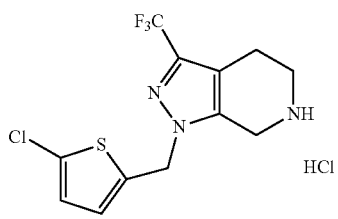 [SMILES: FC(F)(F)c1nn(Cc2ccc(Cl)s2)c2c1CCNC2 ; Cl]

The title compound was synthesized according to the procedure described in Intermediate 2-2, using intermediate 1-12 as a starting material, to obtain a white solid (yield 100%).
LCMS m/z 321.8 [M+H]$^+$

Intermediate 2-13

1-Phenethyl-3-(trifluoromethyl)-4,5,6,7-tetrahydro-1H-pyrazolo[3,4-c]pyridine HCl salt

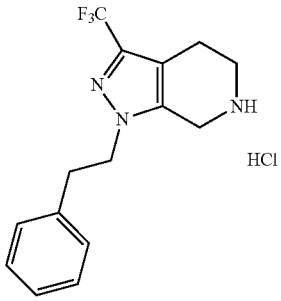 [SMILES: FC(F)(F)c1nn(CCc2ccccc2)c2c1CCNC2 ; Cl]

The title compound was synthesized according to the procedure described in Intermediate 2-2, using intermediate 1-13 as a starting material, to obtain a white solid (yield 100%).
LCMS m/z 295.9 [M+H]$^+$

Intermediate 2-14

1-(3-Fluorobenzyl)-3-(trifluoromethyl)-4,5,6,7-tetrahydro-1H-pyrazolo[3,4-c]pyridine HCl salt

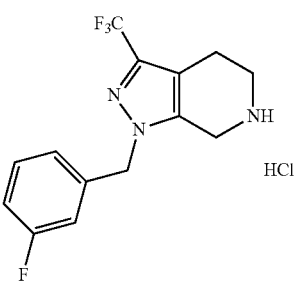 [SMILES: Fc1cccc(Cn2nc(C(F)(F)F)c3c2CNCC3)c1 ; Cl]

The title compound was synthesized according to the procedure described in Intermediate 2-2, using intermediate 1-14 as a starting material, to obtain a white solid (280 mg, yield 100%).

Intermediate 2-15

1-(2-Fluorobenzyl)-3-(trifluoromethyl)-4,5,6,7-tetrahydro-1H-pyrazolo[3,4-c]pyridine HCl salt

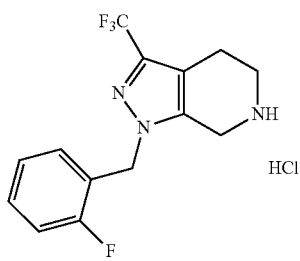 [SMILES: Fc1ccccc1Cn1nc(C(F)(F)F)c2c1CNCC2 ; Cl]

The title compound was synthesized according to the procedure described in Intermediate 2-2, using intermediate 1-15 as a starting material, to obtain a white solid, which is used directly in the next step.

Intermediate 2-16

1-Cyclohexyl-3-(trifluoromethyl)-4,5,6,7-tetrahydro-1H-pyrazolo[3,4-c]pyridine HCl salt

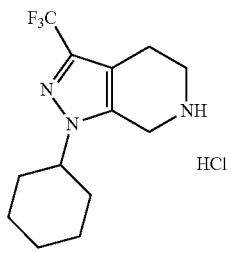 [SMILES: FC(F)(F)c1nn(C2CCCCC2)c2c1CCNC2 ; Cl]

The title compound was synthesized according to the procedure described in Intermediate 2-2, using intermediate 1-16 as a starting material, to obtain a white solid (150 mg, yield 100%).

Intermediate 2-17

1-(1-(4-Fluorophenyl)ethyl)-3-(trifluoromethyl)-4,5,6,7-tetrahydro-1H-pyrazolo[3,4-c]pyridine HCl salt

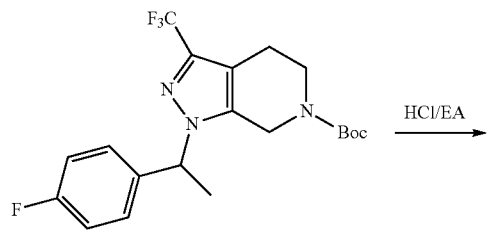

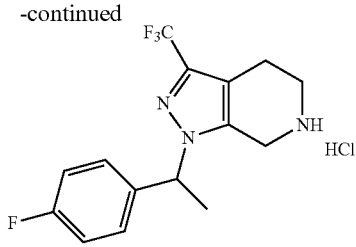

A mixture of tert-butyl 1-(1-(4-fluorophenyl)ethyl)-3-(trifluoromethyl)-4,5-dihydro-1H-pyrazolo[3,4-c]pyridine-6(7H)-carboxylate (180 mg, 0.44 mmol, 1.0 eq.) in HCl/ethyl acetate (3 mL) was stirred at room temperature for 2 h. TLC showed the starting material was consumed completely. The solvent was removed in vacuum to give 1-(1-(4-fluorophenyl)ethyl)-3-(trifluoromethyl)-4,5,6,7-tetrahydro-1H-pyrazolo[3,4-c]pyridine hydrochloride (160 mg, yield 100%), which was used in next step without further purification. LCMS (ESI) m/z 313.9 [M+H]+

Intermediate 2-18

1-(2-Cyclohexylethyl)-3-(trifluoromethyl)-4,5,6,7-tetrahydro-1H-pyrazolo[3,4-c]pyridine HCl salt

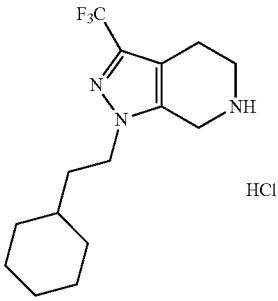 [SMILES: FC(F)(F)c1nn(CCC2CCCCC2)c2c1CCNC2 ; Cl]

The title compound was synthesized according to the procedure described in Intermediate 2-2, using intermediate 1-19 as a starting material, to obtain a white solid (yield 100%). The crude was used in next step directly.

Intermediate 2-19

Ethyl-1-(4-fluorobenzyl)-4,5,6,7-tetrahydro-1H-pyrazolo[3,4-c]pyridine-3-carboxylate hydrochloride

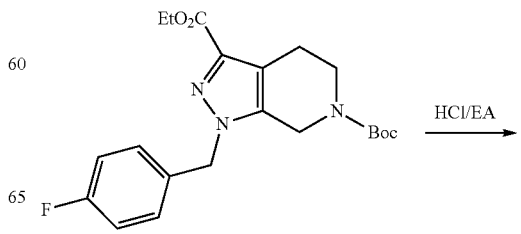

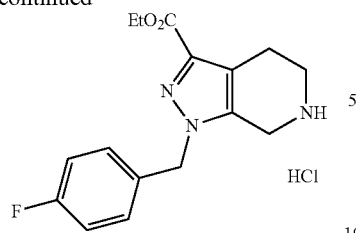

A mixture of 6-tert-butyl 3-ethyl 1-(4-fluorobenzyl)-4,5-dihydro-1H-pyrazolo[3,4-c]pyridine-3,6(7H)-dicarboxylate (Intermediate 1-20) (500 mg, 1.24 mmol, 1.0 eq.) in HCl/EA (5 mL) was stirred at 25° C. for 2 h. LCMS showed desired product was detected. The solvent was removed in vacuum to give ethyl 1-(4-fluorobenzyl)-4,5,6,7-tetrahydro-1H-pyrazolo[3,4-c]pyridine-3-carboxylate hydrochloride (450 mg, 100% crude), which was used in next step without further purification. LCMS (ESI) m/z 303.9 [M+H]$^+$ Intermediate 2-20

(1-(4-Fluorobenzyl)-4,5,6,7-tetrahydro-1H-pyrazolo[3,4-c]pyridin-3-yl)methanol hydrochloride

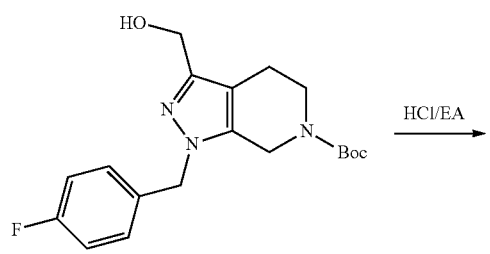

A mixture of tert-butyl 1-(4-fluorobenzyl)-3-(hydroxymethyl)-4,5-dihydro-1H-pyrazolo[3,4-c]pyridine-6(7H)-carboxylate (Intermediate 1-21) (120 mg, 0.33 mmol, 1.0 eq.) in HCl/EA (3 mL) was stirred at 25° C. for 2 h. The solvent was removed in vacuum to give (1-(4-fluorobenzyl)-4,5,6,7-tetrahydro-1H-pyrazolo[3,4-c]pyridin-3-yl)methanol hydrochloride (99 mg, crude), which was used in next step without further purification.

LCMS (ESI) m/z 262.1 [M+H]$^+$

Intermediate 2-21

3-Ethoxy-1-(4-fluorobenzyl)-4,5,6,7-tetrahydro-1H-pyrazolo[3,4-c]pyridine hydrochloride

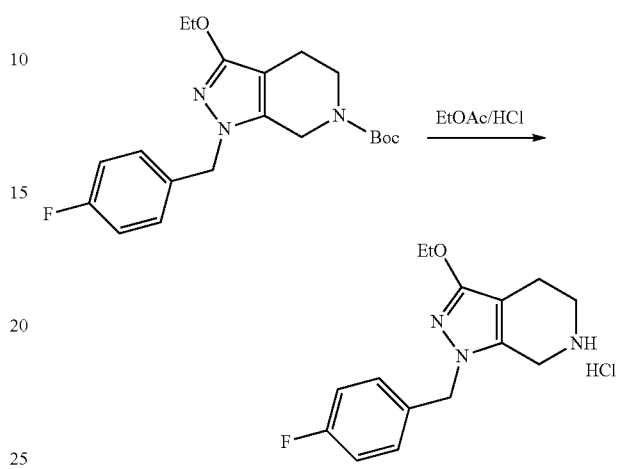

A mixture of tert-butyl 3-ethoxy-1-(4-fluorobenzyl)-4,5-dihydro-1H-pyrazolo[3,4-c]pyridine-6(7H)-carboxylate (Intermediate 1-22) (60 mg, 0.16 mmol, 1.0 eq.) in a mixture of HCl/EtOAc (1 mL/1 mL) was stirred at room temperature for 1 h. TLC showed the starting material was consumed completely. The solvent was removed in vacuum to give 3-ethoxy-1-(4-fluorobenzyl)-4,5,6,7-tetrahydro-1H-pyrazolo[3,4-c]pyridine hydrochloride (50 mg, yield 100%, crude) which was used in next step without further purification. LCMS (ESI) m/z 275.9 [M+H]$^+$

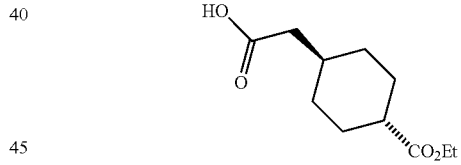

Intermediate 3-1

2-(trans-4-(Ethoxycarbonyl)cyclohexyl)acetic acid

Step 1

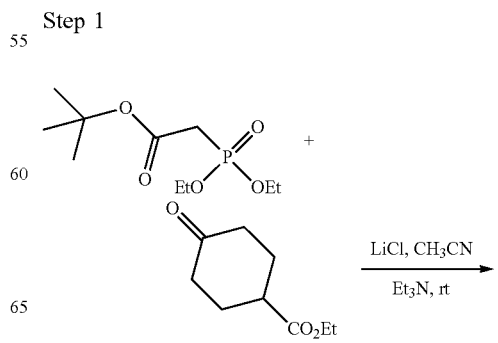

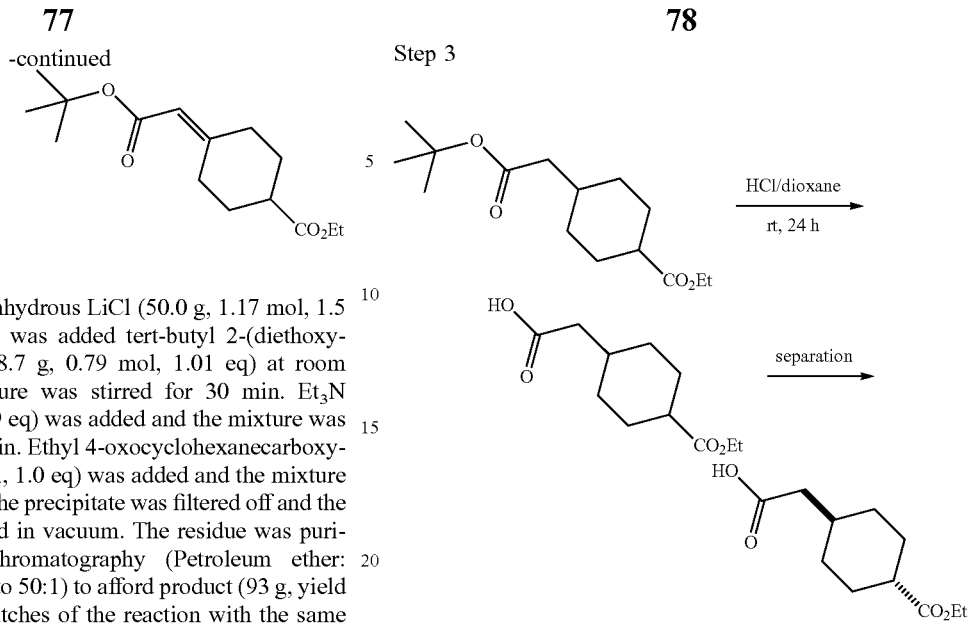

Step 3

To a suspension of anhydrous LiCl (50.0 g, 1.17 mol, 1.5 eq) in CH₃CN (2.9 L) was added tert-butyl 2-(diethoxyphosphoryl)acetate (198.7 g, 0.79 mol, 1.01 eq) at room temperature. The mixture was stirred for 30 min. Et₃N (118.4 g, 45 mmol, 1.49 eq) was added and the mixture was stirred for another 30 min. Ethyl 4-oxocyclohexanecarboxylate (133.3 g, 780 mmol, 1.0 eq) was added and the mixture was stirred overnight. The precipitate was filtered off and the filtrate was concentrated in vacuum. The residue was purified by gel silica chromatography (Petroleum ether: EtOAc=400:1 to 200:1 to 50:1) to afford product (93 g, yield 44%) as an oil. Two batches of the reaction with the same scale were conducted in parallel and 180 g of product was obtained totally. ¹HNMR (400 MHz, CDCl₃) δ: 5.56 (s, 1H), 4.11 (q, J=7.2 Hz, 2H), 3.59 (dt, J=14 Hz, J=4.4 Hz, 1H), 2.49-2.55 (m, 1H), 2.27-2.32 (m, 1H), 2.01-2.17 (m, 4H), 1.61-1.73 (m, 2H), 1.46 (s, 9H), 1.24 (t, J=7.2 Hz, 3H).

Step 2

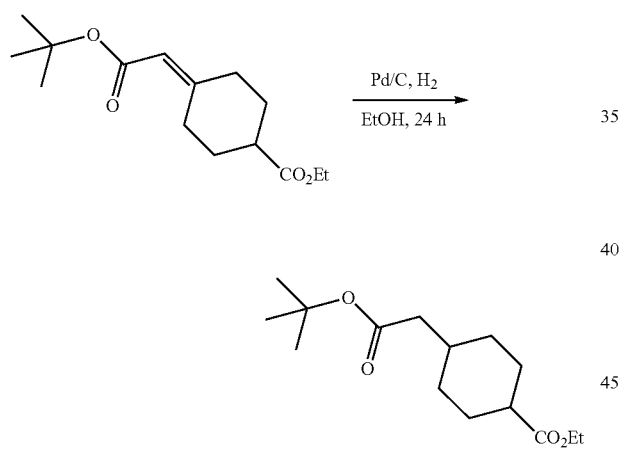

To a solution of ethyl 4-(2-(tert-butoxy)-2-oxoethylidene)cyclohexanecarboxylate (90 g, 335.38 mmol) in ethanol (900 mL) was added 10% of dry Pd/C (20 g), the resulting mixture was hydrogenated under 50 psi of hydrogen pressure at 40° C. for 24 h. The other batch of the reaction was performed with the same scale. TLC (Petroleum ether/EtOAc=3/1) showed the reaction was complete. Two batches of the reaction were combined and filtered through a pad of celite. The filtrate was concentrated in vacuum to give the product as a pale yellow oil (179 g, 98%). ¹HNMR (400 MHz, CDCl₃) δ: 4.07-4.15 (m, 2H), 2.47-2.52 (m, 2H), 2.07-2.22 (m, 3H), 1.72-1.98 (m, 5H), 1.53-1.60 (m, 2H), 1.39-1.49 (m, 10H), 1.21-1.31 (m, 4H), 0.98 (qd, J=13.2 Hz, J=3.6 Hz, 1H)

To a solution of HCl/dioxane (1.0 L) was added ethyl 4-(2-(tert-butoxy)-2-oxoethyl)cyclohexanecarboxylate (90 g, 0.33 mol) at room temperature. The resulting solution was stirred at room temperature for 24 h. The other batch of the reaction was performed with the same scale. TLC (PE/EA=3/1) showed the reaction was complete. Two batches of the reaction were combined and then concentrated in vacuo to give the product as a cis/trans mixture. It was recrystallizated from Petroleum ether/EtOAc to give 25 g of the pure trans product as an off-white solid. The mother liquid was concentrated in vacuum to give the mixture product which was further isolated by prep-HPLC to give another 15 g trans and 61 g of mixture (cis/trans: ~4/1) as a semi-solid.

trans-isomer (Example 3-1): ¹H NMR (400 MHz, CDCl₃) δ: 4.11 (q, J=7.2 Hz, 2H), 2.18-2.28 (m, 3H), 1.86-2.00 (m, 4H), 1.73-1.83 (m, 1H), 1.46 (qd, J=13.2 Hz, J=3.6 Hz, 2H), 1.24 (t, J=7.2 Hz, 3H), 1.03 (qd, J=13.2 Hz, J=3.6 Hz, 2H)

Intermediate 3-2

2-(4-(Ethoxycarbonyl)cyclohexyl)propanoic acid

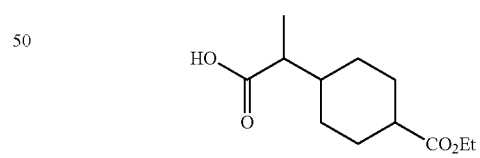

Step 1 tert-Butyl 2-(diethoxyphosphoryl)propanoate

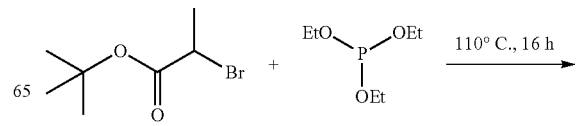

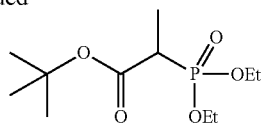

A mixture of tert-butyl 2-bromopropanoate (4.16 g, 20.0 mmol) and triethylphosphite (3.98 g, 24.0 mmol) was stirred at 110° C. for 16 h. Then the mixture was concentrated to give tert-butyl 2-(diethoxyphosphoryl)-propanoate as a colorless oil (5.32 g, yield 100%). $^1$H NMR (400 MHz, Methanol-d4) δ: 4.09-4.20 (m, 4H), 3.99-3.11 (m, 1H), 1.48 (s, 9H), 1.32-1.39 (m, 9H).

Step 2

Ethyl 4-(1-tert-butoxy-1-oxopropan-2-ylidene)cyclohexanecarboxylate

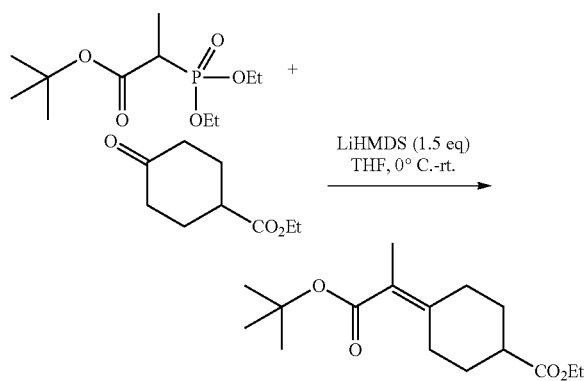

To a solution of tert-butyl 2-(diethoxyphosphoryl)propanoate (5.19 g, 19.51 mmol) in THF (20 mL) with stirring under N$_2$ at 0° C. was added a solution of 1M LiHMDS in THF (19.5 mL, 19.5 mmol). The mixture was stirred at 0° C. for 1 h, then a solution of ethyl 4-oxocyclohexanecarboxylate (2.21 g, 13.0 mmol) in THF (10 mL) was added dropwise into the mixture with stirring at 0° C. The resulting mixture was stirred at rt for 16 h, and quenched with water (50 mL). The mixture was extracted with EtOAc (3×50 mL). The combined organics were dried over Na$_2$SO$_4$, filtered through a silica gel pad and concentrated to afford ethyl 4-(1-tert-butoxy-1-oxopropan-2-ylidene)cyclohexanecarboxylate as a yellow oil (3.6 g, yield 65%). $^1$H NMR (400 MHz, Methanol-d4) δ: 3.91 (q, J=7.2 Hz, 2H), 2.62-2.65 (m, 1H), 2.33-2.42 (m, 2H), 1.74-1.83 (m, 4H), 1.60 (s, 3H), 1.31-1.40 (m, 2H), 1.29 (s, 9H), 1.04 (t, J=7.2 Hz, 3H); LCMS (ESI) m/z 305.2 [M+Na]$^+$ Step 3

Ethyl 4-(1-tert-butoxy-1-oxopropan-2-yl)cyclohexanecarboxylate

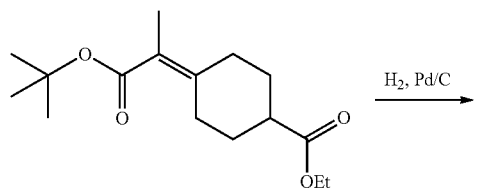

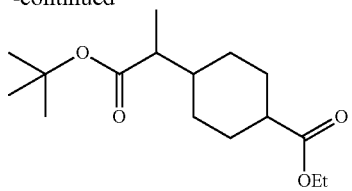

A mixture of ethyl 4-(1-tert-butoxy-1-oxopropan-2-ylidene)cyclohexanecarboxylate (500 mg, 1.77 mmol) and Pd/C (50 mg) in MeOH (10 mL) was hydrogenated under one atmosphere of H$_2$ pressure for 16 h. Then the mixture was filtered and the filtrate was concentrated to give ethyl 4-(1-tert-butoxy-1-oxopropan-2-yl)cyclohexanecarboxylate as a yellow oil (500 mg, yield 100%). LCMS (ESI) m/z 307.1 [M+H]$^+$ Step 4

2-(4-(Ethoxycarbonyl)cyclohexyl)propanoic acid

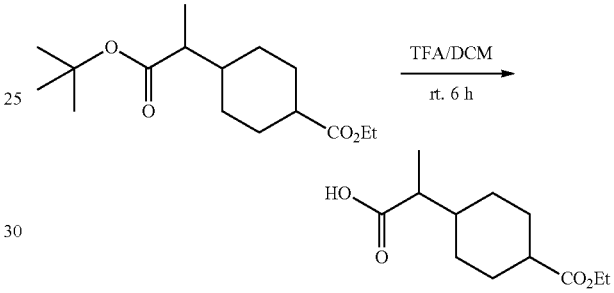

To a mixture of ethyl 4-(1-tert-butoxy-1-oxopropan-2-yl)cyclohexanecarboxylate (450 mg, 1.58 mmol) in DCM (2 mL) was added TFA (1 mL). The mixture was stirred at rt for 6 h and concentrated to afford 2-(4-(ethoxycarbonyl)cyclohexyl)propanoic acid as a yellow oil (350 mg, yield 96%). LCMS (ESI) m/z 229.1 [M+H]$^+$ Intermediate 3-3

2-(3-(Methoxycarbonyl)bicyclo[3.2.1]octan-8-yl)acetic acid

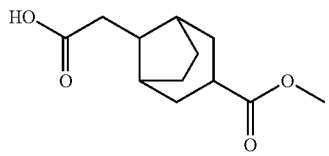 [SMILES: COC(=O)C1CC2CCC(C1)C2CC(=O)O]

Step 1

Methyl 8-(2-tert-butoxy-2-oxoethylidene)bicyclo[3.2.1]octane-3-carboxylate

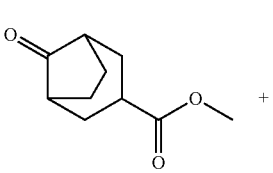

-continued

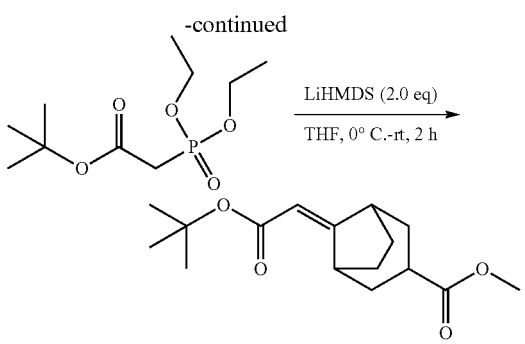

To a solution of tert-butyl 2-(diethoxyphosphoryl)acetate (1.0 g, 4.0 mmol, 2.0 eq) in THF (10 mL) with stirring under $N_2$ at 0° C. was added a solution of 1M LiHMDS (4.0 mL, 4.0 mmol, 2.0 eq) dropwise. The mixture was stirred at 0° C. for 1 h, then a solution of methyl 8-oxobicyclo[3.2.1]octane-3-carboxylate (365 mg, 2.0 mmol, 1.0 eq) in THF (2 mL) was added at 0° C. The resulting mixture was stirred at rt for 2 h and quenched with aq. $NH_4Cl$. The mixture was partitioned between water and EtOAc. The organic layer was dried, filtered and concentrated. The residue was purified by prep-TLC on silica gel (petroleum ether/EtOAc=10:1) to afford methyl 8-(2-tert-butoxy-2-oxoethylidene)bicyclo[3.2.1]octane-3-carboxylate as a yellow oil. (300 mg, yield 50%). $^1$H NMR (400 MHz, $CDCl_3$) δ: 5.57 (s, 1H), 3.65 (s, 3H), 2.87-2.77 (m, 1H), 2.60 (bs, 1H), 1.55-2.02 (m, 9H), 1.48 (s, 9H).

Step 2

Methyl 8-(2-tert-butoxy-2-oxoethyl)bicyclo[3.2.1]octane-3-carboxylate

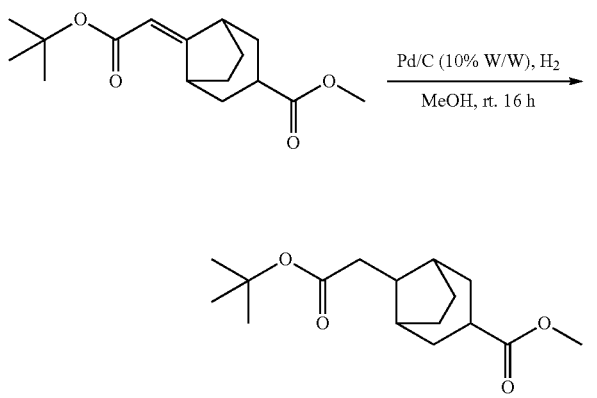

A mixture of methyl 8-(2-tert-butoxy-2-oxoethylidene)bicyclo[3.2.1]octane-3-carboxylate (300 mg, 1.1 mmol, 1.0 eq) and Pd/C (30 mg, 10%, W/W) in MeOH (5 mL) was hydrogenated under one atmosphere of pressure at rt for 16 h. Then the mixture was filtered and the filtrate was concentrated to give methyl 8-(2-tert-butoxy-2-oxoethyl)bicyclo[3.2.1]octane-3-carboxylate as a yellow oil (280 mg, yield 95%). $^1$H NMR (400 MHz, $CDCl_3$) δ: 3.65-3.67 (m, 3H), 2.62-2.66 (m, 1H), 2.48-2.50 (m, 2H), 2.11 (bs, 2H), 1.97-2.02 (m, 1H), 1.64-1.81 (m, 5H), 1.53-1.56 (m, 2H), 1.42-1.45 (m, 10H); LCMS (ESI) m/z 305.1 [M+Na]$^+$ Step 3

2-(3-(Methoxycarbonyl)bicyclo[3.2.1]octan-8-yl)acetic acid

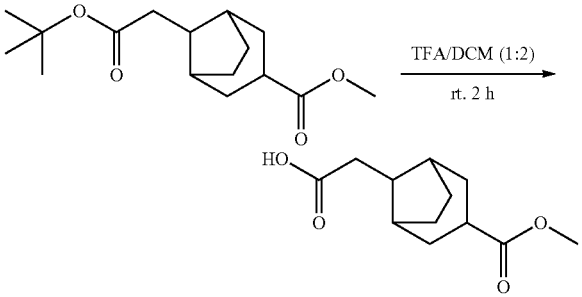

To a mixture of methyl 8-(2-tert-butoxy-2-oxoethyl)bicyclo[3.2.1]octane-3-carboxylate (200 mg, 0.7 mmol, 1.0 eq) in DCM (2 mL) was added TFA (1 mL). The mixture was stirred at rt for 2 h. The mixture was concentrated to afford 2-(3-(methoxycarbonyl)bicyclo[3.2.1]octan-8-yl)acetic acid as a yellow oil (150 mg, yield 95%). LCMS (ESI) m/z 227.1 [M+H]$^+$ Intermediate 3-4

2-(3-(Methoxycarbonyl)cyclopentyl)acetic acid

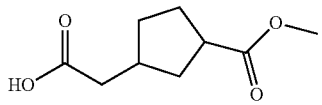

The title compound was synthesized according to the procedure described in Intermediate 3-3, using methyl 3-oxocyclopentanecarboxylate as a starting material, to obtain a yellow oil (700 mg, yield 98% over three steps). LCMS (ESI) m/z 187.1 [M+H]$^+$ Intermediate 3-5

2-(4-(Methoxycarbonyl)-4-methylcyclohexyl)acetic acid

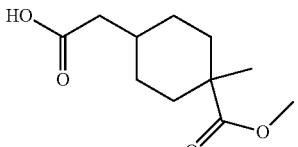

The title compound was synthesized according to the procedure described in Intermediate 3-3, using methyl 1-methyl-4-oxocyclohexanecarboxylate as a starting material, to obtain a yellow oil (yield 95% over three steps). LCMS (ESI) m/z 215.1 [M+H]$^+$ Intermediate 3-6

2-(3-(Methoxycarbonyl)cyclobutyl)acetic acid

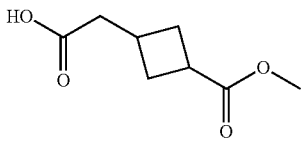

The title compound was synthesized according to the procedure described in Intermediate 3-3, using methyl 3-oxocyclobutanecarboxylate as a starting material, to obtain a yellow oil (yield 97% over three steps). LCMS (ESI) m/z 173.1 [M+H]+

Intermediate 3-7

2-(6-(Methoxycarbonyl)spiro[3.3]heptan-2-yl)acetic acid

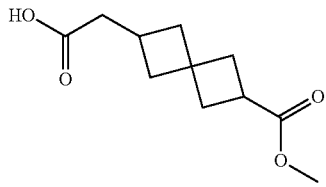

The title compound was synthesized according to the procedure described in Intermediate 3-3, using methyl 6-oxospiro[3.3]heptane-2-carboxylate as a starting material, to obtain a yellow oil (yield 100% over three steps). LCMS (ESI) m/z 213.1 [M+H]+

Intermediate 3-8

2-(3-(Methoxycarbonyl)-2,2-dimethylcyclobutyl) acetic acid

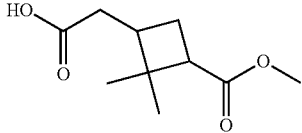

The title compound was synthesized according to the procedure described in Intermediate 3-3, using methyl 2,2-dimethyl-3-oxocyclobutanecarboxylate as a starting material, to obtain a colorless oil (yield 76% over three steps). LCMS (ESI) m/z 201.1 [M+H]+

Intermediate 3-9

2-(3-(Methoxycarbonyl)-2,2-dimethylcyclobutyl) acetic acid

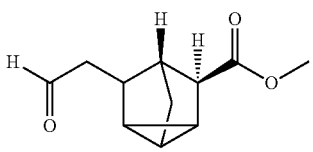

The title compound was synthesized according to the procedure described in Intermediate 3-3, using (+)-(3R,4R)-5-oxotricyclo[2.2.1.02.6]heptane-3-carboxylic acid as a starting material, to obtain a white solid (700 mg, yield 32% over three steps). LCMS (ESI) m/z 211.0 [M+H]+

Intermediate 4-1

2-(8-(tert-Butoxycarbonyl)-8-azabicyclo[3.2.1]octan-3-yl)acetic acid

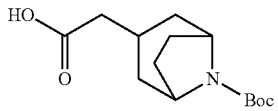 [SMILES: CC(C)(C)OC(=O)N1C2CCC1CC(CC(=O)O)C2]

Step 1 tert-Butyl 3-(2-ethoxy-2-oxoethylidene)-8-azabicyclo[3.2.1]octane-8-carboxylate

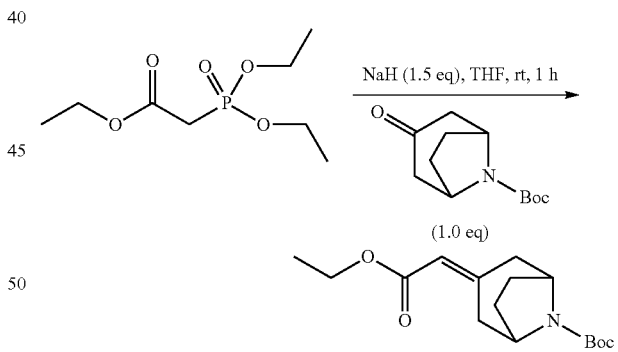

To a solution of triethyl phosphonoacetate (2.24 g, 10.00 mmol) in dry THF (10 mL) with stirring under N2 at 0° C. was added NaH (60% in mineral oil, 0.4 g, 10.00 mmol). The mixture was stirred at 0° C. for 1 h, then a solution of tert-butyl 3-oxo-8-azabicyclo[3.2.1]octane-8-carboxylate (1.5 g, 6.67 mmol) in THF (5 mL) was added dropwise into the mixture with stirring at 0° C. over 45 min. The reaction was stirred at rt for 20 h and quenched with water (50 mL). The mixture was extracted with EtOAc (3×50 mL). The combined organic was dried over Na2SO4, filtered and concentrated to give tert-butyl 3-(2-ethoxy-2-oxoethylidene)-8-azabicyclo[3.2.1]octane-8-carboxylate as a yellow oil (1.2 g, yield 61%). LCMS (ESI) m/z 296.1 [M+H]+

Step 2 tert-Butyl 3-(2-ethoxy-2-oxoethyl)-8-azabicyclo[3.2.1]octane-8-carboxylate

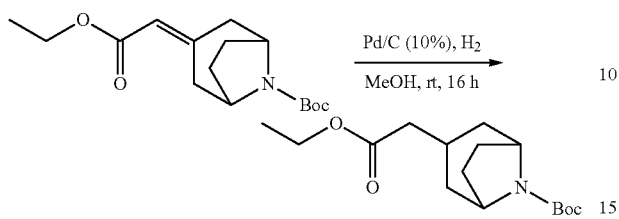

The title compound was synthesized according to the procedure described in Intermediate 3-2, step 3, to obtain a yellow solid (yield 80%). LCMS m/z 298.2 [M+H]⁺

Step 3

2-(8-(tert-Butoxycarbonyl)-8-azabicyclo[3.2.1]octan-3-yl)acetic acid

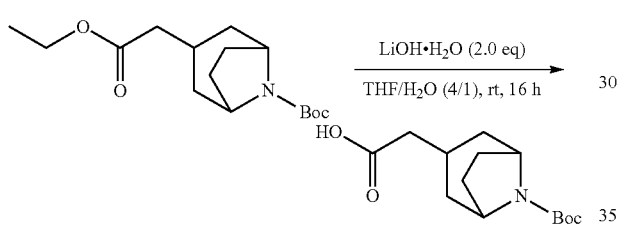

To a solution of tert-butyl 3-(2-ethoxy-2-oxoethyl)-8-azabicyclo[3.2.1]octane-8-carboxylate (800 mg, 2.69 mmol) in THF (4 mL) were added lithium hydroxide monohydrate (226 mg, 5.39 mmol) and H₂O (1 mL). The reaction mixture was stirred at rt for 16 h and acidified to pH=6 with 1N HCl. The mixture was partitioned between ethyl acetate (50 mL) and water (50 mL). The organic phase was washed with brine (2×10 mL), dried over sodium sulfate, filtered and concentrated to give 2-(8-(tert-butoxycarbonyl)-8-azabicyclo[3.2.1]octan-3-yl)acetic acid (600 mg, yield 83%) as a colorless oil. LCMS (ESI) m/z 214.0 [M-55]⁺

Intermediate 4-2

2-(1-(tert-Butoxycarbonyl)-2-methylpiperidin-4-yl)acetic acid

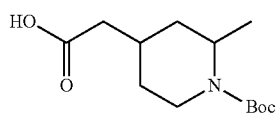 [SMILES: CC1CC(CC(=O)O)CCN1C(=O)OC(C)(C)C]

The title compound was synthesized according to the procedure described in Intermediate 4-1, using tert-butyl 2-methyl-4-oxopiperidine-1-carboxylate as a starting material, to obtain a yellow oil (yield 80% in the final step). LCMS m/z 202.1 [M-55]⁺

Intermediate 4-3

2-(1-(tert-Butoxycarbonyl)-2-(trifluoromethyl)piperidin-4-yl)acetic acid

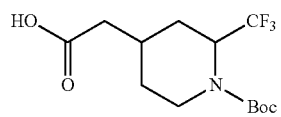

The title compound was synthesized according to the procedure described in Intermediate 4-1, using tert-butyl 2-trifluoromethyl-4-oxopiperidine-1-carboxylate as a starting material, to obtain a yellow solid (yield 85% in the final step). LCMS m/z 334.1 [M+Na]⁺

Intermediate 4-4

2-(1-(tert-Butoxycarbonyl)-2,2-dimethylpiperidin-4-yl)acetic acid

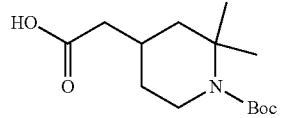

The title compound was synthesized according to the procedure described in Intermediate 4-1, using tert-butyl 2,2-dimethyl-4-oxopiperidine-1-carboxylate as a starting material, to obtain a yellow oil (yield 80% in the final step). LCMS m/z 294.1 [M+Na]⁺

Intermediate 4-5

2-((5S)-1-(tert-Butoxycarbonyl)-5-(methoxycarbonyl)pyrrolidin-3-yl)acetic acid

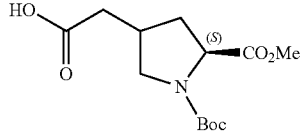

The title compound was synthesized according to the procedure described in Intermediate 4-1, using (S)-1-tert-butyl 2-methyl 4-oxopyrrolidine-1,2-dicarboxylate as a starting material, to obtain a brown oil (700 mg, yield 91% in the final step). LCMS m/z 310.1 [M+Na]⁺

Intermediate 5-1

2-(4-(Methoxycarbonyl)bicyclo[2.2.2]octan-1-yl)acetic acid

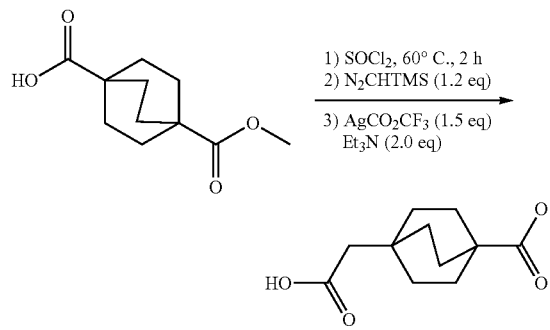

A mixture of 4-(methoxycarbonyl)bicyclo[2.2.2]octane-1-carboxylic acid (500 mg, 2.3 mmol, 1.0 eq) in SOCl$_2$ (2 mL) was stirred at 60° C. for 2 h and concentrated. The residue was dissolved in CH$_3$CN (30 mL) and 2M TMSCHN$_2$ in hexane (1.4 mL, 1.2 eq) was added to the solution. The mixture was stirred at rt for 2 h. To the stirred solution were added AgCO$_2$CF$_3$ (700 mg, 3.4 mmol, 1.5 eq), Et$_3$N (460 mg, 4.6 mmol, 2.0 eq) and H$_2$O (3 mL). The mixture was stirred at rt for 20 h and filtered. The filtrate was concentrated to yield a crude product 2-(4-(methoxycarbonyl)bicyclo[2.2.2]octan-1-yl)acetic acid (320 mg, yield 60%) as a yellow oil, which was used to the next step without further purification. LCMS (ESI) m/z 227.1 [M+H]$^+$ Example 1-1

Ethyl 4-(2-(1-(4-fluorobenzyl)-3-(trifluoromethyl)-4,5-dihydro-1H-pyrazolo[3,4-c]pyridin-6(7H)-yl)-2-oxoethyl)cyclohexanecarboxylate

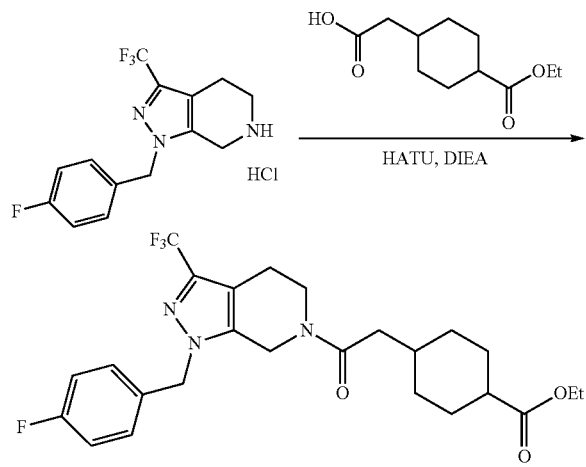

A mixture of 2-(4-(ethoxycarbonyl)cyclohexyl)acetic acid (181 mg, 0.85 mmol), HATU (360 mg, 0.94 mmol), DIEA (500 mg, 4.25 mmol) and 1-(4-fluorobenzyl)-3-(trifluoromethyl)-4,5,6,7-tetrahydro-1H-pyrazolo[3,4-c]pyridine hydrochloride (Intermediate 2-2) (340 mg, 1.0 mmol) in DMF (2 mL) was stirred at room temperature for 17 h. Ethylacetate (10 mL) was added and the mixture was washed with brine (10 mL). The organic phase was dried over Na$_2$SO$_4$, filtered and concentrated to give the crude which was purified by prep. HPLC (MeCN and H$_2$O with 0.05% NH$_3$H$_2$O as mobile phase) to provide ethyl 4-(2-(1-(4-fluorobenzyl)-3-(trifluoromethyl)-4,5-dihydro-1H-pyrazolo[3,4-c]pyridin-6(7H)-yl)-2-oxoethyl)cyclohexanecarboxylate (300 mg, yield 71%) as a colorless oil. $^1$H NMR (400 MHz, Methanol-d4) δ: 7.30-7.27 (m, 2H), 7.17-7.09 (m, 2H), 5.39-5.35 (m, 2H), 4.63-4.55 (m, 2H), 4.15-4.10 (m, 2H), 3.77-3.74 (m, 2H), 2.76-2.55 (m, 2H), 2.43-2.19 (m, 3H), 2.02-0.93 (m, 12H); LCMS (ESI) m/z 496.2 [M+H]$^+$ Example 1-2

1-(1-(4-Chloro-2-fluorobenzyl)-3-(trifluoromethyl)-4,5-dihydro-1H-pyrazolo[3,4-c]pyridin-6(7H)-yl)-2-(1-methylpiperidin-4-yl)ethanone

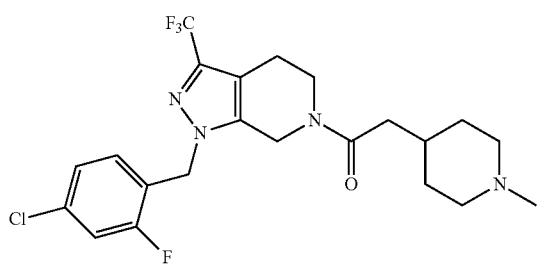 [SMILES: CN1CCC(CC(=O)N2CCc3c(C(F)(F)F)nn(Cc4ccc(Cl)cc4F)c3C2)CC1]

The title compound was synthesized according to the procedure described in Example 1-1, using Intermediate 2-1 and 2-(1-methylpiperidin-4-yl)acetic acid as starting materials, to obtain a colorless gum (yield 52%). $^1$H NMR (400 MHz, Methanol-d4) δ: 7.31-7.21 (m, 3H), 5.43-5.39 (m, 2H), 4.72 (s, 2H), 3.79-3.76 (m, 2H), 3.53-3.50 (m, 2H), 3.10-2.53 (m, 9H), 2.11-2.04 (m, 3H), 1.60-1.54 (m, 2H); LCMS (ESI) m/z 473.8 [M+H]$^+$ Example 1-3

1-(1-(4-Chloro-2-fluorobenzyl)-3-(trifluoromethyl)-4,5-dihydro-1H-pyrazolo[3,4-c]pyridin-6(7H)-yl)-2-phenylethanone

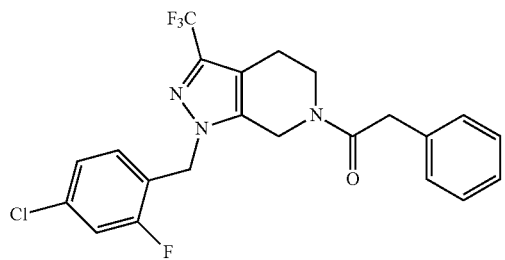 [SMILES: O=C(Cc1ccccc1)N1CCc2c(C(F)(F)F)nn(Cc3ccc(Cl)cc3F)c2C1]

The title compound was synthesized according to the procedure described in Example 1-1, using Intermediate 2-1 and 2-phenylacetic acid as starting materials, to obtain a white solid (yield 33%). $^1$H NMR (400 MHz, Methanol-d4)

δ: 7.34-7.16 (m, 7H), 5.35-5.22 (m, 2H), 4.73-4.59 (m, 2H), 3.89-3.73 (m, 4H), 2.68-2.44 (m, 2H); LCMS (ESI) m/z 452.0 [M+H]+

Example 1-4

Ethyl 4-(2-(1-(4-chloro-2-fluorobenzyl)-4,5-dihydro-1H-pyrazolo[3,4-c]pyridin-6(7H)-yl)-2-oxoethyl)cyclohexanecarboxylate

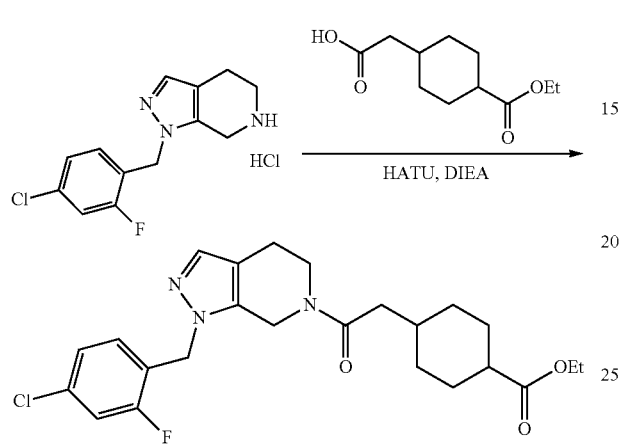

A mixture of 2-(4-(ethoxycarbonyl)cyclohexyl)acetic acid (71 mg, 0.33 mmol, 1.0 eq.), HATU (140 mg, 0.36 mmol, 1.1 eq.), DIEA (426 mg, 3.3 mmol, 10.0 eq.) and 1-(4-chloro-2-fluorobenzyl)-4,5,6,7-tetrahydro-1H-pyrazolo[3,4-c]pyridine hydrochloride (120 mg, 0.4 mmol, 1.2 eq.) in DMF (2 mL) was stirred at room temperature for 17 h. Ethyl acetate (10 mL) was added and the mixture was washed with brine (10 mL). The organic phase was dried over Na₂SO₄, filtered and concentrated to give the crude which was purified by prep. HPLC (MeCN and H₂O with 0.05% NH₃H₂O as mobile phase) to provide ethyl 4-(2-(1-(4-chloro-2-fluorobenzyl)-4,5-dihydro-1H-pyrazolo[3,4-c]pyridin-6(7H)-yl)-2-oxoethyl)cyclohexanecarboxylate (60 mg, yield 33%) as a colorless oil. ¹H NMR (400 MHz, Methanol-d4) δ: 7.38 (s, 1H), 7.29-7.19 (m, 2H), 7.08-7.06 (m, 1H), 5.36-5.32 (m, 2H), 4.69-4.66 (m, 2H), 4.16-4.09 (m, 2H), 3.81-3.74 (m, 2H), 2.70-2.29 (m, 5H), 2.05-1.75 (m, 4H), 1.63-1.62 (m, 2H), 1.46-0.95 (m, 6H)); LCMS (ESI) m/z 462.1 [M+H]+

Example 1-5

1-(1-(4-Chloro-2-fluorobenzyl)-3-(trifluoromethyl)-4,5-dihydro-1H-pyrazolo[3,4-c]pyridin-6(7H)-yl)-2-cyclohexylethanone

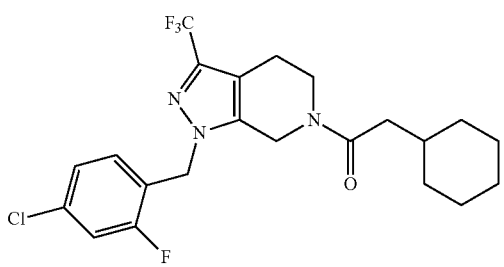 [SMILES: O=C(CC1CCCCC1)N1CCc2c(C(F)(F)F)nn(Cc3ccc(Cl)cc3F)c2C1]

The title compound was synthesized according to the procedure described in Example 1-1, using Intermediate 2-1 and 2-cyclohexylacetic acid as starting materials, to obtain a white solid (yield 40%). ¹H NMR (400 MHz, Methanol-d4) δ: 7.30-7.20 (m, 3H), 5.43-5.38 (m, 2H), 4.72-4.69 (m, 2H), 3.84-3.76 (m, 2H), 2.77-2.66 (m, 2H), 2.40-2.27 (m, 2H), 1.78-1.68 (m, 6H), 1.30-0.94 (m, 5H); LCMS (ESI) m/z 458.1 [M+H]+

Example 1-6

(1-(4-Chloro-2-fluorobenzyl)-3-(trifluoromethyl)-4,5-dihydro-1H-pyrazolo[3,4-c]pyridin-6(7H)-yl) (cyclohexyl)methanone

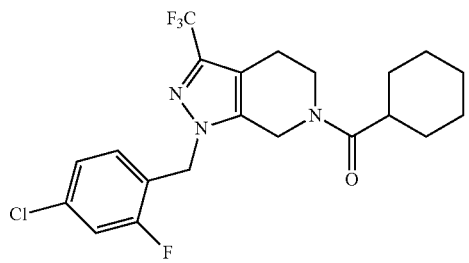 [SMILES: O=C(C1CCCCC1)N1CCc2c(C(F)(F)F)nn(Cc3ccc(Cl)cc3F)c2C1]

The title compound was synthesized according to the procedure described in Example 1-1, using Intermediate 2-1 and 2-cyclohexylacetic acid as starting materials, to obtain a white solid (yield 33%). ¹H NMR (400 MHz, Methanol-d4) δ: 7.34-7.18 (m, 3H), 5.45-5.38 (m, 2H), 4.70 (s, 2H), 3.81 (t, J=5.6 Hz, 2H), 2.78-2.65 (m, 3H), 1.83-1.27 (m, 10H); LCMS (ESI) m/z 444.1 [M+H]+

Example 1-7

1-(1-(4-Chloro-2-fluorobenzyl)-3-(trifluoromethyl)-4,5-dihydro-1H-pyrazolo[3,4-c]pyridin-6(7H)-yl)-2-(pyridin-4-yl)ethanone

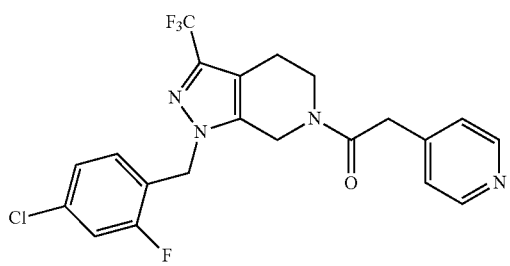 [SMILES: O=C(Cc1ccncc1)N1CCc2c(C(F)(F)F)nn(Cc3ccc(Cl)cc3F)c2C1]

The title compound was synthesized according to the procedure described in Example 1-1, using Intermediate 2-1 and 2-(pyridin-4-yl)acetic acid as starting materials, to obtain a yellow solid (yield 11%). ¹H NMR (400 MHz, Methanol-d4) δ: 8.50-8.46 (m, 2H), 7.39-7.21 (m, 5H), 5.38-5.36 (m, 2H), 4.76-4.71 (m, 2H), 3.99-3.94 (m, 2H), 3.87-3.79 (m, 2H), 2.71-2.69 (m, 2H); LCMS (ESI) m/z 452.9 [M+H]+

Example 1-8

Ethyl 4-(2-(1-(4-chlorobenzyl)-3-(trifluoromethyl)-4,5-dihydro-1H-pyrazolo[3,4-c]pyridin-6(7H)-yl)-2-oxoethyl)cyclohexanecarboxylate

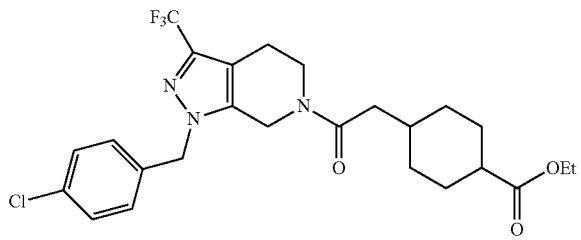 [SMILES: CCOC(=O)C1CCC(CC(=O)N2CCc3c(C(F)(F)F)nn(Cc4ccc(Cl)cc4)c3C2)CC1]

The title compound was synthesized according to the procedure described in Example 1-1, using Intermediate 2-5 as a starting material, to obtain a colorless gum (yield 41%). $^1$H NMR (400 MHz, Methanol-d4) δ: 7.44-7.38 (m, 2H), 7.26-7.21 (m, 2H), 5.40-5.35 (m, 2H), 4.63-4.55 (m, 2H), 4.15-4.10 (m, 2H), 3.77-3.74 (m, 2H), 2.77-2.16 (m, 5H), 2.02-0.90 (m, 12H); LCMS (ESI) m/z 512.2 [M+H]$^+$

Example 1-9

Ethyl 4-(2-(1-(2,4-dichlorobenzyl)-3-(trifluoromethyl)-4,5-dihydro-1H-pyrazolo[3,4-c]pyridin-6(7H)-yl)-2-oxoethyl)cyclohexanecarboxylate

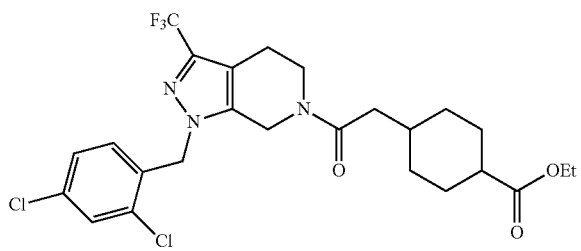 [SMILES: CCOC(=O)C1CCC(CC(=O)N2CCc3c(C(F)(F)F)nn(Cc4ccc(Cl)cc4Cl)c3C2)CC1]

The title compound was synthesized according to the procedure described in Example 1-1, using Intermediate 2-6 as a starting material, to obtain a colorless gum (yield 49%). $^1$H NMR (400 MHz, Methanol-d4) δ: 7.61-7.56 (m, 1H), 7.38-7.34 (m, 1H), 7.03-6.98 (m, 1H), 5.50-5.44 (m, 2H), 4.69-4.64 (m, 2H), 4.16-4.09 (m, 2H), 3.80-3.77 (m, 2H), 2.77-2.26 (m, 5H), 1.95-0.99 (m, 12H); LCMS (ESI) m/z 546.1 [M+H]$^+$

Example 1-10

Ethyl 4-(2-oxo-2-(3-(trifluoromethyl)-1-(4-(trifluoromethyl)benzyl)-4,5-dihydro-1H-pyrazolo[3,4-c]pyridin-6(7H)-yl)ethyl)cyclohexanecarboxylate

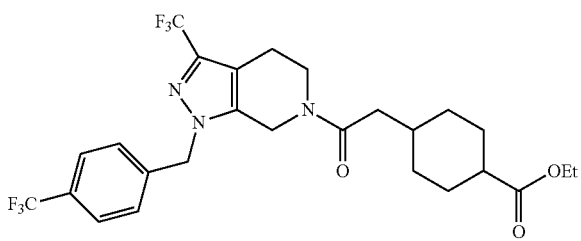 [SMILES: CCOC(=O)C1CCC(CC(=O)N2CCc3c(C(F)(F)F)nn(Cc4ccc(C(F)(F)F)cc4)c3C2)CC1]

The title compound was synthesized according to the procedure described in Example 1-1, using Intermediate 2-7 as a starting material, to obtain a colorless gum (yield 38%). $^1$H NMR (400 MHz, Methanol-d4) δ: 7.74-7.68 (m, 2H), 7.42-7.39 (m, 2H), 5.52-5.47 (m, 2H), 4.65-4.60 (m, 2H), 4.16-4.09 (m, 2H), 3.82-3.76 (m, 2H), 2.78-2.53 (m, 2H), 2.43-2.21 (m, 3H), 2.02-0.87 (m, 12H); LCMS (ESI) m/z 546.2 [M+H]$^+$

Example 1-11

Methyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)benzoate

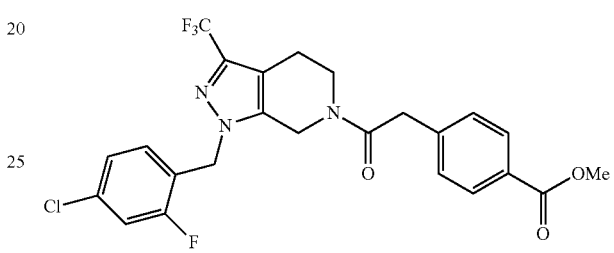

The title compound was synthesized according to the procedure described in Example 1-1, using Intermediate 2-1 and 2-(4-(methoxycarbonyl)phenyl)acetic acid as starting materials, to obtain a white powder after lyophilization (yield 85%). $^1$H NMR (400 MHz, Methanol-d4) δ: 7.83-8.01 (m, 2H), 7.00-7.46 (m, 5H), 5.21-5.42 (m, 2H), 4.56-4.76 (m, 2H), 3.85-4.03 (m, 5H), 3.69-3.85 (m, 2H), 2.51-2.76 (m, 2H); LCMS (ESI) m/z 510.1 [M+H]$^+$

Example 1-12

1-(1-(4-Chloro-2-fluorobenzyl)-3-(trifluoromethyl)-4,5-dihydro-1H-pyrazolo[3,4-c]pyridin-6(7H)-yl)-2-(4-fluorophenyl)ethanone

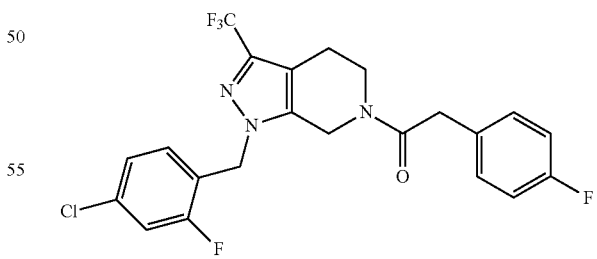

The title compound was synthesized according to the procedure described in Example 1-1, using Intermediate 2-1 and 2-(4-fluorophenyl)acetic acid as starting materials, to obtain a white solid after lyophilization (yield 66%). $^1$H NMR (400 MHz, Methanol-d4) δ: 6.89-7.38 (m, 7H), 5.22-5.42 (m, 2H), 4.56-4.75 (m, 2H), 3.69-3.94 (m, 4H), 2.48-2.70 (m, 2H); LCMS (ESI) m/z 470.1 [M+H]$^+$

Example 1-13

Ethyl 4-(2-(1-benzyl-3-(trifluoromethyl)-4,5-dihydro-1H-pyrazolo[3,4-c]pyridin-6(7H)-yl)-2-oxoethyl)cyclohexanecarboxylate

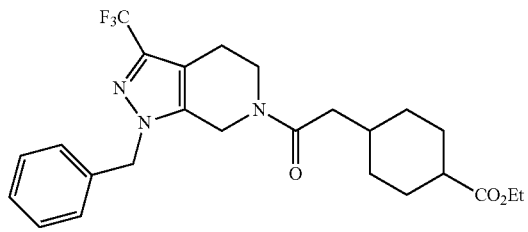 [SMILES: CCOC(=O)C1CCC(CC(=O)N2CCc3c(C(F)(F)F)nn(Cc4ccccc4)c3C2)CC1]

The title compound was synthesized according to the procedure described in Example 1-1, using Intermediate 2-8 as a starting material, to obtain a colorless gum (yield 68%). ¹H NMR (400 MHz, Methanol-d4) δ: 7.38-7.18 (m, 5H), 5.38-5.33 (m, 2H), 4.57-4.46 (m, 2H), 4.13-4.06 (m, 2H), 3.75-3.69 (m, 2H), 2.72-2.62 (m, 2H), 2.54-2.35 (m, 2H), 2.23-2.10 (m, 2H), 1.95-0.82 (m, 11H); LCMS (ESI) m/z 500.2 [M+Na]⁺

Example 1-14

3-(Benzo[d]thiazol-2-yl)-1-(1-(4-fluorobenzyl)-3-(trifluoromethyl)-4,5-dihydro-1H-pyrazolo[3,4-c]pyridin-6(7H)-yl)propan-1-one

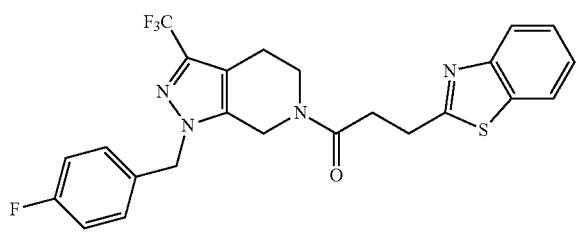 [SMILES: O=C(CCc1nc2ccccc2s1)N1CCc2c(C(F)(F)F)nn(Cc3ccc(F)cc3)c2C1]

The title compound was synthesized according to the procedure described in Example 1-1, using 3-(benzo[d]thiazol-2-yl)propanoic acid as a starting material, to obtain a white powder after lyophilization (yield 92%). ¹H NMR (400 MHz, Methanol-d4) δ: 7.67-7.94 (m, 2H), 7.32-7.49 (m, 2H), 7.17-7.30 (m, 2H), 6.97-7.09 (m, 2H), 5.31 (s, 2H), 4.56-4.66 (m, 2H), 3.78 (t, J=5.65 Hz, 2H), 3.38-3.52 (m, 2H), 2.91-3.16 (m, 2H), 2.56-2.82 (m, 2H); LCMS (ESI) m/z 489.2 [M+H]⁺

Example 1-15

1-(1-(4-Chloro-2-fluorobenzyl)-3-(trifluoromethyl)-4,5-dihydro-1H-pyrazolo[3,4-c]pyridin-6(7H)-yl)-2-(4-hydroxycyclohexyl)ethanone

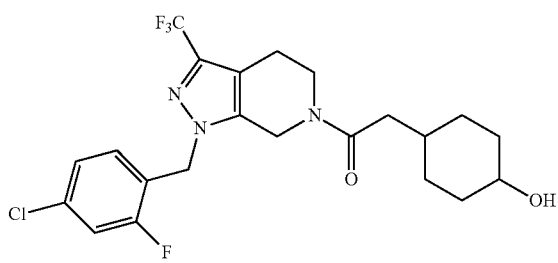 [SMILES: O=C(CC1CCC(O)CC1)N1CCc2c(C(F)(F)F)nn(Cc3ccc(Cl)cc3F)c2C1]

The title compound was synthesized according to the procedure described in Example 1-1, using Intermediate 2-1 and 2-(4-hydroxycyclohexyl)acetic acid as starting materials, to obtain a colorless oil (yield 52%). ¹H NMR (400 MHz, Methanol-d4) δ: 7.32-7.18 (m, 3H), 5.41-5.36 (m, 2H), 4.70-4.67 (m, 2H), 3.82-3.74 (m, 2H), 3.47-3.45 (m, 1H), 2.73-2.64 (m, 2H), 2.39-2.26 (m, 2H), 1.94-1.70 (m, 5H), 1.28-1.00 (m, 4H); LCMS (ESI) m/z 474.0 [M+H]⁺

Example 1-16

Ethyl 4-(2-(1-(cyclohexylmethyl)-3-(trifluoromethyl)-4,5-dihydro-1H-pyrazolo[3,4-c]pyridin-6(7H)-yl)-2-oxoethyl)cyclohexanecarboxylate

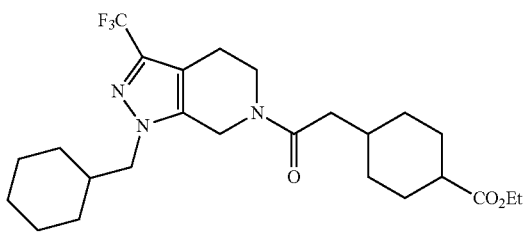 [SMILES: CCOC(=O)C1CCC(CC(=O)N2CCc3c(C(F)(F)F)nn(CC4CCCCC4)c3C2)CC1]

The title compound was synthesized according to the procedure described in Example 1-1, using Intermediate 2-9 as a starting material, to obtain a pale oil (yield 51%). ¹H NMR (400 MHz, CDCl₃) δ: 4.85 (s, 1.7H), 4.48 (s, 0.3H), 4.15-4.06 (m, 2H), 3.81 (d, J=7.2 Hz, 2H), 3.68-3.62 (m, 2H), 2.74-2.67 (m, 2.1H), 2.56-2.28 (m, 2H), 2.25-2.15 (m, 1H), 2.03-1.83 (m, 5H), 1.74-1.42 (m, 8H), 1.30-1.11 (m, 7H), 1.06-0.90 (m, 3H); LCMS (ESI) m/z 484.1 [M+H]⁺

Example 1-17

Ethyl 4-(2-(1-(4-fluorobenzyl)-4,5-dihydro-1H-pyrazolo[3,4-c]pyridin-6(7H)-yl)-2-oxoethyl)cyclohexanecarboxylate

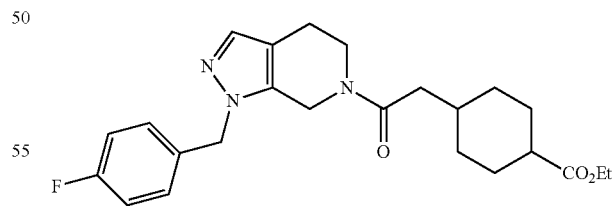

The title compound was synthesized according to the procedure described in Example 1-1, using Intermediate 2-4 as a starting material, to obtain a pale oil (yield 27%). ¹H NMR (400 MHz, CDCl₃) δ: 7.28 (s, 1H), 7.11-7.08 (m, 2H), 7.01-6.92 (m, 2H), 5.17-5.12 (m, 2H), 4.48-4.22 (m, 2H), 4.08-4.02 (m, 2H), 3.69-3.52 (m, 2H), 2.59-2.47 (m, 2H), 2.26-2.09 (m, 2H), 1.95-1.32 (m, 8H), 1.21-1.15 (m, 3H), 0.96-0.90 (m, 1H); LCMS (ESI) m/z 428.1 [M+H]⁺

Example 1-18

Ethyl 4-(2-(1-(3-fluorobenzyl)-3-(trifluoromethyl)-4,
5-dihydro-1H-pyrazolo[3,4-c]pyridin-6(7H)-yl)-2-
oxoethyl)cyclohexanecarboxylate

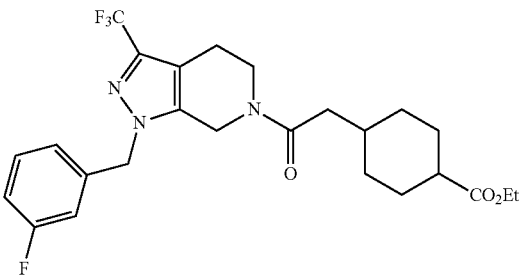 [SMILES: CCOC(=O)C1CCC(CC(=O)N2CCc3c(C(F)(F)F)nn(Cc4cccc(F)c4)c3C2)CC1]

The title compound was synthesized according to the procedure described in Example 1-1, using Intermediate 2-14 as a starting material, to obtain a white solid (yield 50%). $^1$H NMR (400 MHz, Methanol-d4) δ: 7.40-7.35 (m, 1H), 7.09-6.91 (m, 3H), 5.39-5.34 (m, 2H), 4.59-4.53 (m, 2H), 4.11-4.06 (m, 2H), 3.77-3.71 (m, 2H), 2.73-2.63 (m, 2H), 2.52-2.13 (m, 3H), 2.18-0.83 (m, 12H); LCMS (ESI) m/z 496.1 [M+H]$^+$

Example 1-19

Ethyl 4-(2-(1-(2-fluorobenzyl)-3-(trifluoromethyl)-4,
5-dihydro-1H-pyrazolo[3,4-c]pyridin-6(7H)-yl)-2-
oxoethyl)cyclohexanecarboxylate

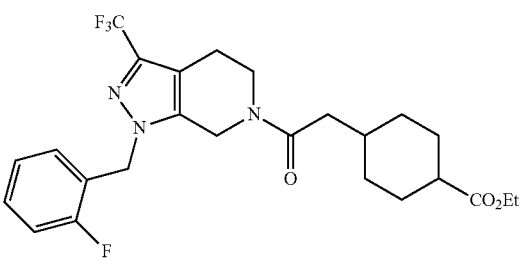 [SMILES: CCOC(=O)C1CCC(CC(=O)N2CCc3c(C(F)(F)F)nn(Cc4ccccc4F)c3C2)CC1]

The title compound was synthesized according to the procedure described in Example 1-1, using Intermediate 2-15 as a starting material, to obtain a white solid (yield 52%). $^1$H NMR (400 MHz, Methanol-d4) δ: 7.38-7.35 (m, 1H), 7.18-7.13 (m, 3H), 5.41-5.36 (m, 2H), 4.67-4.62 (m, 2H), 4.12-4.07 (m, 2H), 3.78-3.72 (m, 2H), 2.72-2.62 (m, 2H), 2.52-2.23 (m, 3H), 1.95-1.75 (m, 4H), 1.59-1.52 (m, 2H), 1.39-0.93 (m, 6H); LCMS (ESI) m/z 496.1 [M+H]$^+$

Example 1-20

(1-(4-Fluorobenzyl)-3-(trifluoromethyl)-4,5-dihydro-
1H-pyrazolo[3,4-c]pyridin-6(7H)-yl)(5,6,7,8-tetrahy-
droimidazo[1,5-a]pyridin-7-yl)methanone

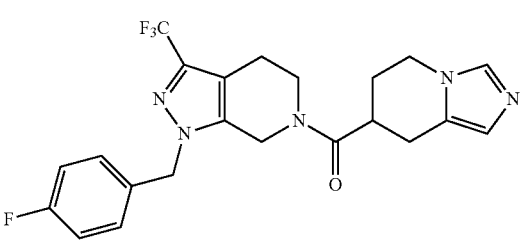 [SMILES: O=C(C1CCn2cncc2C1)N1CCc2c(C(F)(F)F)nn(Cc3ccc(F)cc3)c2C1]

The title compound was synthesized according to the procedure described in Example 1-1, using 5,6,7,8-tetrahydroimidazo[1,5-a]pyridine-7-carboxylic acid as a starting material, to obtain a white powder after lyophilization (45 mg, yield 80%). $^1$H NMR (400 MHz, Methanol-d4) δ: 8.77 (s, 1H), 7.20-7.35 (m, 3H), 6.97-7.16 (m, 2H), 5.27-5.48 (m, 2H), 4.48-4.77 (m, 2H), 4.08-4.44 (m, 2H), 3.71-4.00 (m, 2H), 3.38-3.58 (m, 1H), 2.90-3.13 (m, 2H), 2.61-2.87 (m, 2H), 1.99-2.37 (m, 2H); LCMS (ESI) m/z 448.1 [M+H]$^+$

Example 1-21

1-(1-(4-Chloro-2-fluorobenzyl)-3-(trifluoromethyl)-
4,5-dihydro-1H-pyrazolo[3,4-c]pyridin-6(7H)-yl)-2-
(4-methylcyclohexyl)ethanone

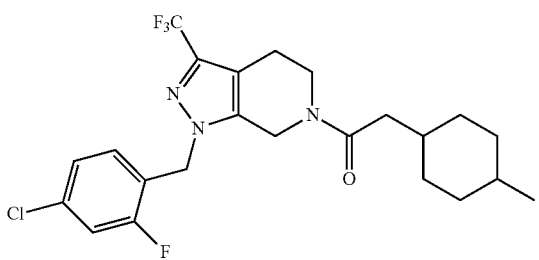 [SMILES: CC1CCC(CC(=O)N2CCc3c(C(F)(F)F)nn(Cc4ccc(Cl)cc4F)c3C2)CC1]

The title compound was synthesized according to the procedure described in Example 1-1, using Intermediate 2-1 and 2-(4-methylcyclohexyl)acetic acid as starting materials, to obtain a yellow gum (yield 90%). $^1$H NMR (400 MHz, Methanol-d4) δ: 7.27-7.16 (m, 3H), 5.40-5.36 (m, 2H), 4.68-4.62 (m, 2H), 3.79-3.75 (m, 2H), 2.72-2.62 (m, 2H), 2.46-2.35 (m, 2H), 2.25-2.24 (m, 0.4H), 1.97 (brs, 0.63H), 1.72-1.27 (m, 8H), 1.02-0.86 (m, 4H); LCMS (ESI) m/z 472.0 [M+H]$^+$

Example 1-22

Methyl 4-(1-(4-fluorobenzyl)-3-(trifluoromethyl)-4,
5,6,7-tetrahydro-1H-pyrazolo[3,4-c]pyridine-6-car-
bonyl)cyclohexanecarboxylate

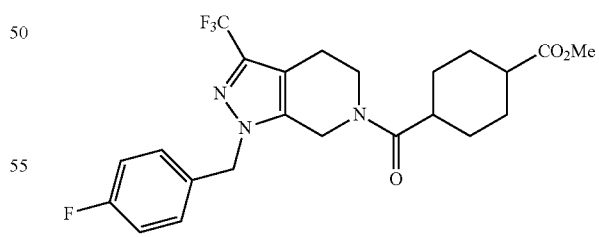

The title compound was synthesized according to the procedure described in Example 1-1, using 4-(methoxycarbonyl)cyclohexanecarboxylic acid as a starting material, to obtain a white solid (yield 88%). $^1$H NMR (400 MHz, Methanol-d4) δ: 2.28-7.25 (m, 2H), 7.11-7.07 (m, 2H), 5.39-5.32 (m, 2H), 4.64-4.55 (m, 2H), 3.77-3.75 (m, 2H), 3.68-3.65 (m, 3H), 2.74-2.62 (m, 3H), 2.46-1.84 (m, 4H), 1.65-1.37 (m, 5H); LCMS (ESI) m/z 468.0 [M+H]$^+$

Example 1-23

Methyl 4-(1-(4-fluorobenzyl)-3-(trifluoromethyl)-4,5,6,7-tetrahydro-1H-pyrazolo[3,4-c]pyridine-6-carbonyl)bicyclo[2.2.2]octane-1-carboxylate

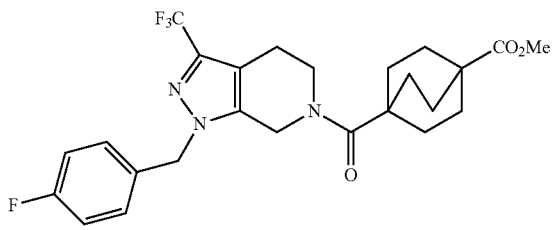 [SMILES: COC(=O)C12CCC(C(=O)N3CCc4c(C(F)(F)F)nn(Cc5ccc(F)cc5)c4C3)(CC1)CC2]

The title compound was synthesized according to the procedure described in Example 1-1, using 4-(methoxycarbonyl)bicyclo[2.2.2]octane-1-carboxylic acid as a starting material, to obtain a white solid (yield 45%). $^1$H NMR (400 MHz, Methanol-d4) δ: 7.31-7.28 (m, 2H), 7.16-7.12 (m, 2H), 5.37 (s, 2H), 4.61 (s, 2H), 3.87 (t, J=5.2 Hz, 2H), 3.66 (s, 3H), 2.71 (t, J=5.2 Hz, 2H), 1.82 (m, 12H); LCMS (ESI) m/z 494.1 [M+H]$^+$

Example 1-24 trans-Ethyl 4-(2-(1-cyclohexyl-3-(trifluoromethyl)-4,5-dihydro-1H-pyrazolo[3,4-c]pyridin-6(7H)-yl)-2-oxoethyl)cyclohexanecarboxylate

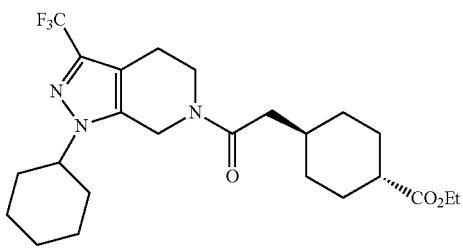 [SMILES: CCOC(=O)[C@H]1CC[C@H](CC(=O)N2CCc3c(C(F)(F)F)nn(C4CCCCC4)c3C2)CC1]

The title compound was synthesized according to the procedure described in Example 1-1, using Intermediate 2-16 and Intermediate 3-1 as starting materials, to obtain a colorless gum (yield 23%). $^1$H NMR (400 MHz, Methanol-d4) δ: 4.73 (s, 2H), 4.10-4.05 (m, 3H), 3.79-3.74 (m, 2H), 2.70-2.58 (m, 2H), 2.41-2.38 (m, 2H), 2.25-2.21 (m, 1H), 1.91-1.71 (m, 12H), 1.46-1.19 (m, 8H), 1.09-1.04 (m, 2H); LCMS (ESI) m/z 470.1 [M+H]$^+$

Example 1-25 trans-Ethyl 4-(2-(1-(4-methylbenzyl)-3-(trifluoromethyl)-4,5-dihydro-1H-pyrazolo[3,4-c]pyridin-6(7H)-yl)-2-oxoethyl)cyclohexanecarboxylate

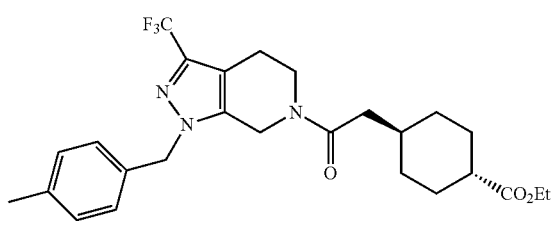 [SMILES: CCOC(=O)[C@H]1CC[C@H](CC(=O)N2CCc3c(C(F)(F)F)nn(Cc4ccc(C)cc4)c3C2)CC1]

The title compound was synthesized according to the procedure described in Example 1-1, using Intermediate 2-10 and Intermediate 3-1 as starting materials, to obtain a white solid (yield 49%). $^1$H NMR (400 MHz, Methanol-d4) δ: 7.21-7.07 (m, 4H), 5.32-5.27 (m, 2H), 4.55-4.47 (m, 2H), 4.08-4.06 (m, 2H), 3.76-3.68 (m, 2H), 2.71-2.61 (m, 2H), 2.36-2.29 (m, 3H), 2.22-2.07 (m, 2H), 1.91-1.78 (m, 4H), 1.58-1.24 (m, 4H), 1.23-1.19 (m, 3H), 1.08-1.05 (m, 1H), 0.86-0.77 (m, 1H); LCMS (ESI) m/z 492.1 [M+H]$^+$

Example 1-26 trans-Ethyl 4-(2-(1-(4-methoxylbenzyl)-3-(trifluoromethyl)-4,5-dihydro-1H-pyrazolo[3,4-c]pyridin-6(7H)-yl)-2-oxoethyl)cyclohexanecarboxylate

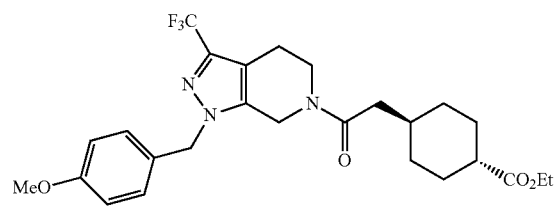 [SMILES: CCOC(=O)[C@H]1CC[C@H](CC(=O)N2CCc3c(C(F)(F)F)nn(Cc4ccc(OC)cc4)c3C2)CC1]

The title compound was synthesized according to the procedure described in Example 1-1, using Intermediate 2-11 and Intermediate 3-1 as starting materials, to obtain a white solid (yield 36%). $^1$H NMR (400 MHz, Methanol-d4) δ: 7.20-7.15 (m, 2H), 6.94-6.87 (m, 2H), 5.29-5.25 (m, 2H), 4.56-4.47 (m, 2H), 4.10-4.06 (m, 2H), 3.77-3.73 (m, 3H), 3.71-3.68 (m, 2H), 2.70-2.61 (m, 2H), 2.36-2.34 (m, 1H), 2.22-2.07 (m. 2H), 1.92-1.79 (m, 3H), 1.58-1.25 (m, 4H), 1.23-1.19 (m, 3H), 1.05-1.01 (m, 1H), 0.82-0.74 (m, 1H); LCMS (ESI) m/z 530.1 [M+Na]$^+$

Example 1-27

Methyl 8-(2-(1-(4-chloro-2-fluorobenzyl)-3-(trifluoromethyl)-4,5-dihydro-1H-pyrazolo[3,4-c]pyridin-6(7H)-yl)-2-oxoethyl)bicyclo[3.2.1]octane-3-carboxylate

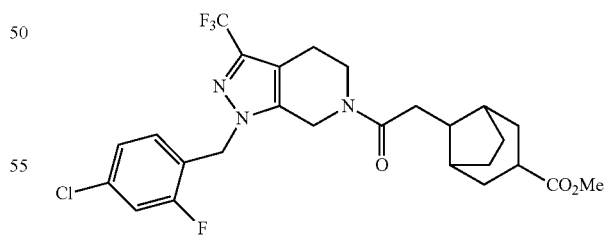

The title compound was synthesized according to the procedure described in Example 1-1, using Intermediate 2-1 and Intermediate 3-3 as starting materials, to obtain a white solid (140 mg, yield 40%). $^1$H NMR (400 MHz, Methanol-d4) δ: 7.07-7.25 (m, 3H), 5.28-5.34 (m, 2H), 4.62-4.65 (m, 2H), 3.72 (t, J=5.6 Hz, 2H), 3.57 (s, 3H), 2.55-2.72 (m, 5H), 1.66-2.04 (m, 7H), 1.40-1.49 (m, 4H); LCMS (ESI) m/z 542.2 [M+H]$^+$

Example 1-28 trans-Ethyl 4-(2-oxo-2-(1-phenethyl-3-(trifluoromethyl)-4,5-dihydro-1H-pyrazolo[3,4-c]pyridin-6(7H)-yl)ethyl)cyclohexanecarboxylate

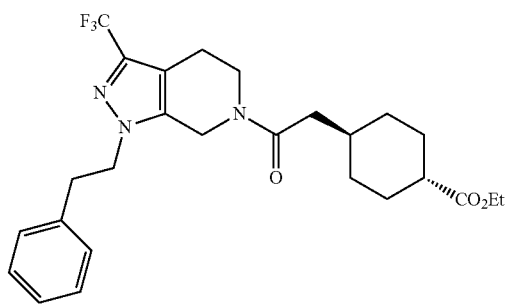 [SMILES: CCOC(=O)[C@H]1CC[C@H](CC(=O)N2CCc3c(C(F)(F)F)nn(CCc4ccccc4)c3C2)CC1]

The title compound was synthesized according to the procedure described in Example 1-1, using Intermediate 2-13 and Intermediate 3-1 as starting materials, to obtain a pale oil (yield 54%). $^1$H NMR (400 MHz, CDCl$_3$) δ: 7.24-7.22 (m, 3H), 6.97 (d, J=6.0 Hz, 2H), 4.21 (t, J=6.8 Hz, 2H), 4.13-4.06 (m, 4H), 3.48 (t, J=5.6 Hz, 2H), 3.12 (t, J=6.8 Hz, 2H), 2.66 (s, 2H), 2.25-2.20 (m, 3H), 1.98 (d, J=12.4 Hz, 2H), 1.84-1.81 (m, 3H), 1.48-1.44 (m, 2H), 1.24 (t, J=6.8 Hz, 3H), 1.01-0.94 (m, 2H); LCMS (ESI) m/z 492.1 [M+H]$^+$

Example 1-29

1-(1-(4-Chloro-2-fluorobenzyl)-3-(trifluoromethyl)-4,5-dihydro-1H-pyrazolo[3,4-c]pyridin-6(7H)-yl)-2-(tetrahydro-2H-pyran-4-yl)ethanone

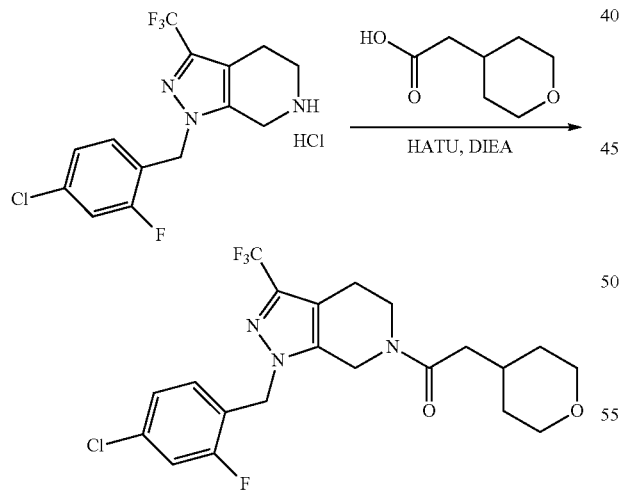

To a solution of 2-(tetrahydro-2H-pyran-4-yl)acetic acid (52 mg, 0.36 mmol, 1.2 eq), 1-(4-chloro-2-fluorobenzyl)-3-(trifluoromethyl)-4,5,6,7-tetrahydro-1H-pyrazolo[3,4-c]pyridine hydrochloride (Intermediate 2-1) (110 mg, 0.30 mmol, 1.0 eq) and HATU (171 mg, 0.45 mmol, 1.5 eq) in DMF (2 mL) was added N,N-diisopropylethylamine (77 mg, 0.60 mmol, 2.0 eq). The mixture was stirred at room temperature for 16 h and diluted with water (100 mL). The mixture was extracted with EtOAc (100 mL×3). The combined organic layers were dried over anhydrous sodium sulfate and concentrated. The residue was purified by prep-HPLC (TFA method) to afford 1-(1-(4-chloro-2-fluorobenzyl)-3-(trifluoromethyl)-4,5-dihydro-1H-pyrazolo[3,4-c]pyridin-6(7H)-yl)-2-(tetrahydro-2H-pyran-4-yl)ethanone as a yellow oil (131 mg, yield 95%). $^1$H NMR (400 MHz, Methanol-d4) δ: 7.31-7.16 (m, 3H), 5.41-5.36 (m, 2H), 4.71-4.70 (m, 2H), 3.92-3.87 (m, 2H), 3.82-3.75 (m, 2H), 3.45-3.35 (m, 2H), 2.76-2.63 (m, 2H), 2.45-2.34 (m, 2H), 2.06-1.92 (m, 1H), 1.68-1.59 (m, 2H), 1.39-1.26 (m, 2H); LCMS (ESI) m/z 459.9 [M+H]$^+$

Example 1-30

1-(1-(4-Fluorobenzyl)-3-(trifluoromethyl)-4,5-dihydro-1H-pyrazolo[3,4-c]pyridin-6(7H)-yl)-2-(tetrahydro-2H-pyran-4-yl)ethanone

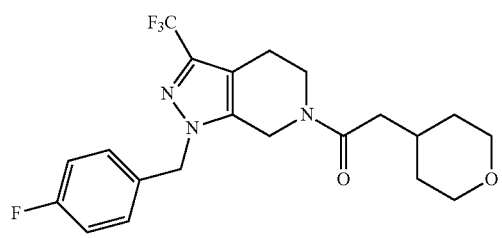 [SMILES: O=C(CC1CCOCC1)N1CCc2c(C(F)(F)F)nn(Cc3ccc(F)cc3)c2C1]

The title compound was synthesized according to the procedure described in Example 1-1, using 2-(tetrahydro-2H-pyran-4-yl)acetic acid as a starting material, to obtain a colorless oil (109 mg, yield 78%). $^1$H NMR (400 MHz, Methanol-d4) δ: 7.31-7.24 (m, 2H), 7.15-7.06 (m, 2H), 5.38-5.32 (m, 2H), 4.61-4.56 (m, 2H), 3.92-3.84 (m, 2H), 3.79-3.73 (m, 2H), 3.44-3.38 (m, 2H), 2.75-2.62 (m, 2H), 2.44-2.23 (m, 2H), 2.04-1.80 (m, 1H), 1.67-1.53 (m, 2H), 1.38-1.26 (m, 2H); LCMS (ESI) m/z 425.9 [M+H]$^+$

Example 1-31

1-(1-(4-Chloro-2-fluorobenzyl)-3-(trifluoromethyl)-4,5-dihydro-1H-pyrazolo[3,4-c]pyridin-6(7H)-yl)-3-(1H-tetrazol-5-yl)propan-1-one

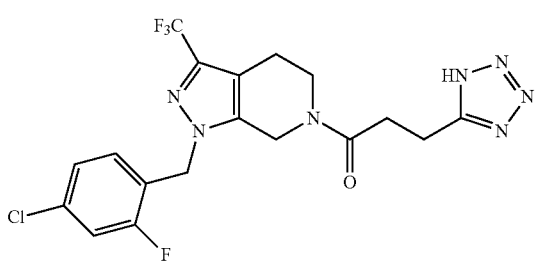 [SMILES: O=C(CCc1nnn[nH]1)N1CCc2c(C(F)(F)F)nn(Cc3ccc(Cl)cc3F)c2C1]

The title compound was synthesized according to the procedure described in Example 1-1, using Intermediate 2-1 and 3-(1H-tetrazol-5-yl)propanoic acid as starting materials, to obtain a white solid (50 mg, yield 21%). $^1$H NMR (400 MHz, Methanol-d4) δ: 7.30-7.14 (m, 3H), 5.41-5.35 (m, 2H), 4.73-4.68 (m, 2H). 3.81-3.76 (m, 2H), 3.27-3.20 (m, 2H), 3.14-3.01 (m, 2H), 2.80-2.63 (m, 2H); LCMS (ESI) m/z 458.0 [M+H]$^+$

Example 1-32

1-(1-(4-Fluorobenzyl)-3-(trifluoromethyl)-4,5-dihydro-1H-pyrazolo[3,4-c]pyridin-6(7H)-yl)-3-(1H-tetrazol-5-yl)propan-1-one

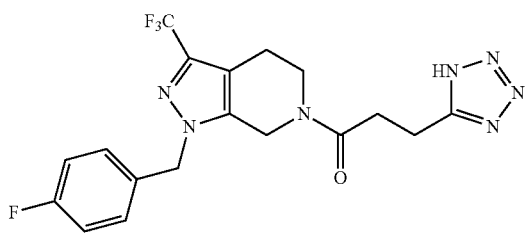 [SMILES: O=C(CCc1nnn[nH]1)N1CCc2c(C(F)(F)F)nn(Cc3ccc(F)cc3)c2C1]

The title compound was synthesized according to the procedure described in Example 1-1, using 3-(1H-tetrazol-5-yl)propanoic acid as a starting material, to obtain a white solid (25 mg, yield 27%). $^1$H NMR (400 MHz, Methanol-d4) δ: 7.31-7.24 (m, 2H), 7.13-7.07 (m, 2H), 5.38-5.32 (m, 2H), 4.62-4.59 (m, 2H). 3.78-3.73 (m, 2H), 3.24-3.18 (m, 2H), 3.09-2.94 (m, 2H), 2.79-2.63 (m, 2H); LCMS (ESI) m/z 424.0 [M+H]$^+$

Example 1-33

1-(1-(4-Chloro-2-fluorobenzyl)-3-(trifluoromethyl)-4,5-dihydro-1H-pyrazolo[3,4-c]pyridin-6(7H)-yl)-2-(octahydroindolizin-7-yl)ethanone TFA salt

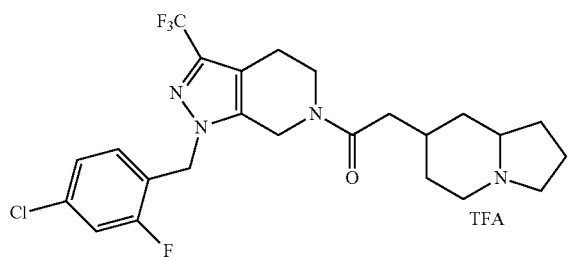 [SMILES: O=C(CC1CCN2CCCC2C1)N1CCc2c(C(F)(F)F)nn(Cc3ccc(Cl)cc3F)c2C1]

Step 1

2-(Octahydroindolizin-7-yl)acetic acid

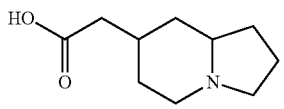 [SMILES: O=C(O)CC1CCN2CCCC2C1]

The title compound was synthesized according to the procedure described in Intermediate 3-3, using hexahydroindolizin-7(1H)-one as a starting material, to obtain a colorless oil (1.4 g, yield 75% over three steps). LCMS (ESI) m/z 206.1 [M+Na]$^+$ Step 2

1-(1-(4-Chloro-2-fluorobenzyl)-3-(trifluoromethyl)-4,5-dihydro-1H-pyrazolo[3,4-c]pyridin-6(7H)-yl)-2-(octahydroindolizin-7-yl)ethanone TFA salt

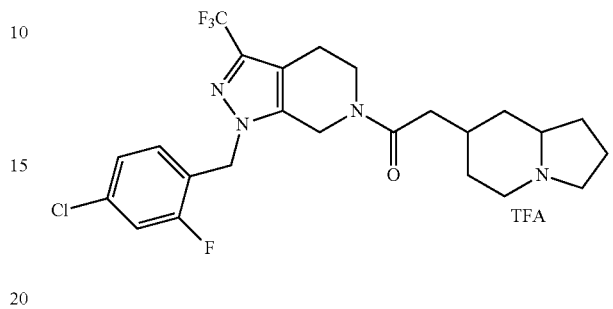

The title compound was synthesized according to the procedure described in Example 1-1, using Intermediate 2-1 and 2-(octahydroindolizin-7-yl)acetic acid as starting materials, followed by Combi-Flash (biotage, 50 g C18 gel, MeCN in H$_2$O with 0.05% TFA) to obtain a white solid (38 mg, yield 23%). $^1$H NMR (400 MHz, Methanol-d4) δ: 7.30-7.17 (m, 3H), 5.41-5.37 (m, 2H), 4.71 (s, 2H), 3.83-3.43 (m, 4H), 3.22-2.95 (m, 3H), 2.77-2.50 (m, 4H), 2.29-2.02 (m, 65H), 1.74-1.32 (m, 3H); LCMS (ESI) m/z 498.9 [M+H]$^+$

Example 1-34

1-(1-(4-Fluorobenzyl)-3-(trifluoromethyl)-4,5-dihydro-1H-pyrazolo[3,4-c]pyridin-6(7H)-yl)-2-(octahydroindolizin-7-yl)ethanone TFA salt

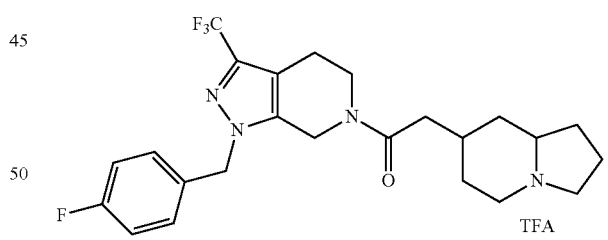

The title compound was synthesized according to the procedure described in Example 1-33, using Intermediate 2-2 and 2-(octahydroindolizin-7-yl)acetic acid as starting materials, to obtain a white solid (56 mg, yield 36%). $^1$H NMR (400 MHz, Methanol-d4) δ: 7.30-7.25 (m, 2H), 7.14-7.07 (m, 2H), 5.38-5.33 (m, 2H), 4.62-4.58 (m, 2H), 3.80-3.40 (m, 4H), 3.20-2.94 (m, 3H), 2.77-2.37 (m, 4H), 2.27-2.01 (m, 5H), 1.70-1.30 (m, 4H); LCMS (ESI) m/z 465.0 [M+H]$^+$

Example 1-35

(1-(4-Fluorobenzyl)-3-(trifluoromethyl)-4,5-dihydro-1H-pyrazolo[3,4-c]pyridin-6(7H)-yl)(quinuclidin-3-yl)methanone TFA salt

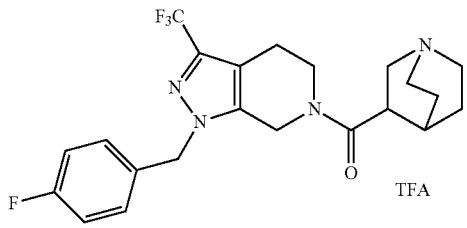 [SMILES: O=C(C1CN2CCC1CC2)N1CCc2c(C(F)(F)F)nn(Cc3ccc(F)cc3)c2C1]

The title compound was synthesized according to the procedure described in Example 1-1, using quinuclidine-3-carboxylic acid as a starting material, to obtain a white solid (110 mg, yield 66%). $^1$H NMR (400 MHz, Methanol-d4) δ: 7.30-7.26 (m, 2H), 7.14-7.08 (m, 2H), 5.41-5.35 (m, 2H), 4.87-4.46 (m, 2H), 4.02-3.87 (m, 2H), 3.72-3.53 (m, 2H), 3.37-3.33 (m, 4H), 3.25-3.20 (m, 1H), 2.82-2.67 (m, 2H), 2.34-1.74 (m, 5H); LCMS (ESI) m/z 437.1 [M+H]$^+$

Example 1-36

(1-(4-Fluorobenzyl)-3-(trifluoromethyl)-4,5-dihydro-1H-pyrazolo[3,4-c]pyridin-6(7H)-yl)(quinuclidin-4-yl)methanone TFA salt

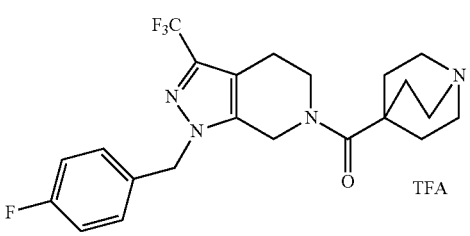 [SMILES: O=C(N1CCc2c(C(F)(F)F)nn(Cc3ccc(F)cc3)c2C1)C12CCN(CC1)CC2]

The title compound was synthesized according to the procedure described in Example 1-1, using quinuclidine-4-carboxylic acid as a starting material, to obtain a yellow solid (43 mg, yield 20%). $^1$H NMR (400 MHz, Methanol-d4) δ: 7.29-7.26 (m, 2H), 7.13-7.09 (m, 2H), 5.36 (s, 2H), 4.63 (s, 2H), 3.95-3.92 (m, 2H), 3.43-3.40 (m, 6H), 2.78-2.75 (m, 2H), 2.26-2.22 (m, 6H); LCMS (ESI) m/z 437.2 [M+H]$^+$

Example 1-37

1-(1-(4-Fluorobenzyl)-3-(trifluoromethyl)-4,5-dihydro-1H-pyrazolo[3,4-c]pyridin-6(7H)-yl)-2-(quinuclidin-3-yl)ethanone TFA salt

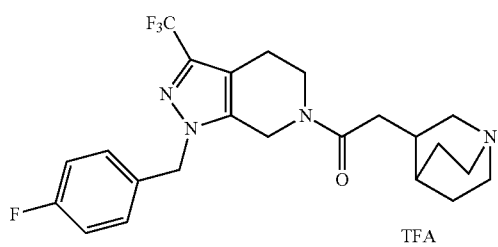 [SMILES: O=C(CC1CN2CCC1CC2)N1CCc2c(C(F)(F)F)nn(Cc3ccc(F)cc3)c2C1]

Step 1

2-(Quinuclidin-3-yl)acetic acid

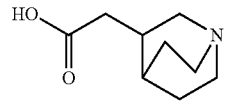 [SMILES: O=C(O)CC1CN2CCC1CC2]

The title compound was synthesized according to the procedure described in Intermediate 3-3, using 1-Azabicyclo[2.2.2]octan-3-one as a starting material, to obtain a yellow oil (0.8 g, yield 100% over three steps). LCMS (ESI) m/z 170.1 [M+H]$^+$ Step 2

1-(1-(4-Fluorobenzyl)-3-(trifluoromethyl)-4,5-dihydro-1H-pyrazolo[3,4-c]pyridin-6(7H)-yl)-2-(quinuclidin-3-yl)ethanone TFA salt

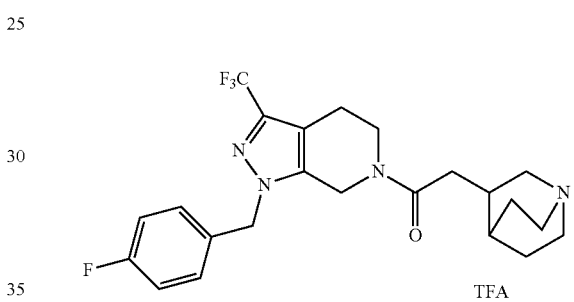

The title compound was synthesized according to the procedure described in Example 1-1, using 2-(quinuclidin-3-yl)acetic acid as a starting material, to obtain a yellow oil (110 mg, yield 18%). $^1$H NMR (400 MHz, Methanol-d4) δ: 7.32-7.26 (m, 2H), 7.17-7.09 (m, 2H), 5.40-5.35 (m, 2H), 4.61-4.57 (m, 2H), 3.81-3.61 (m, 3H), 3.33-3.26 (m, 4H), 2.94-2.54 (m, 6H), 2.13-1.88 (m, 5H); LCMS (ESI) m/z 451.2 [M+H]$^+$

Example 1-38 trans-Ethyl 4-(2-(3-(difluoromethyl)-1-(4-fluorobenzyl)-4,5-dihydro-1H-pyrazolo[3,4-c]pyridin-6(7H)-yl)-2-oxoethyl)cyclohexanecarboxylate

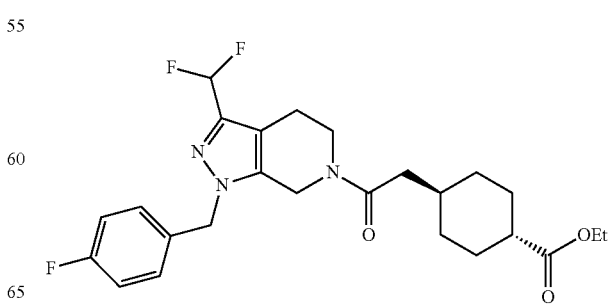

Step 1 tert-Butyl 1-(4-fluorobenzyl)-3-formyl-4,5-dihydro-1H-pyrazolo[3,4-c]pyridine-6(7H)-carboxylate

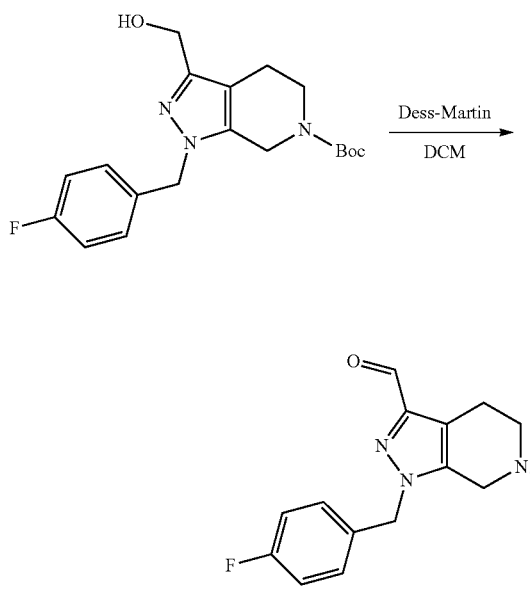

To a solution of tert-butyl 1-(4-fluorobenzyl)-3-(hydroxymethyl)-4,5-dihydro-1H-pyrazolo[3,4-c]pyridine-6(7H)-carboxylate (Intermediate 1-21, 500 mg, 1.4 mmol, 1.0 eq) in DCM (10 ml) was added Dess-Martin (890 mg, 2.1 mmol, 1.5 eq), then the mixture was stirred at 35° C. for 4 hours. The reaction was quenched by addition of 10 mL of sodium sulfite solution, the mixture was extracted with DCM (20 mL×3). The organic layer was dried over $Na_2SO_4$, filtered and concentrated to give the crude which was purified by column chromatography (PE/EA=5/1) to provide tert-butyl 1-(4-fluorobenzyl)-3-formyl-4,5-dihydro-1H-pyrazolo[3,4-c]pyridine-6(7H)-carboxylate (400 mg, yield 79%) as a yellow oil. $^1$H NMR (400 MHz, Methanol-d4) δ: 9.92 (s, 1H), 7.30-7.28 (m, 2H), 7.15-7.09 (m, 2H), 5.40 (s, 2H), 4.45-4.39 (m, 2H), 3.62-3.59 (m, 2H), 2.82-2.79 (m, 2H), 1.50-1.46 (m, 9H).

Step 2 tert-Butyl 3-(difluoromethyl)-1-(4-fluorobenzyl)-4,5-dihydro-1H-pyrazolo[3,4-c]pyridine-6(7H)-carboxylate

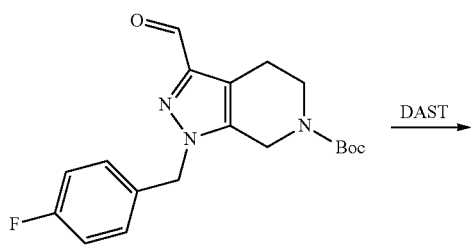

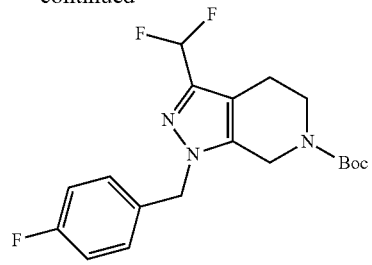

To a solution of tert-butyl 1-(4-fluorobenzyl)-3-formyl-4,5-dihydro-1H-pyrazolo[3,4-c]pyridine-6(7H)-carboxylate (400 mg, 1.11 mmol, 1.0 eq.) in DCM (5 mL) was added DAST (897 mg, 5.55 mmol, 5.0 eq), then the mixture was stirred at 30° C. for 4 h. The solvent was removed in vacuum to give tert-butyl 3-(difluoromethyl)-1-(4-fluorobenzyl)-4,5-dihydro-1H-pyrazolo[3,4-c]pyridine-6(7H)-carboxylate (300 mg, yield 70%) as a yellow oil. $^1$H NMR (400 MHz, Methanol-d4) δ: 7.21-7.20 (m, 2H), 7.11-7.06 (m, 2H), 6.84-6.57 (m, 1H), 5.27 (s, 2H), 4.41 (s, 2H), 3.59 (s, 2H), 2.67-2.65 (m, 2H), 1.47-1.44 (m, 9H); LCMS (ESI) m/z 382.3 [M+H]$^+$

Step 3

3-(Difluoromethyl)-1-(4-fluorobenzyl)-4,5,6,7-tetrahydro-1H-pyrazolo[3,4-c]pyridine hydrochloride A mixture of tert-butyl 3-(difluoromethyl)-1-(4-fluorobenzyl)-4,5-dihydro-1H-pyrazolo[3,4-c]pyridine-6(7H)-carboxylate (300 mg, 0.78 mmol, 1.0 eq.) in HCl/EA (5 mL) was stirred at 30° C. for 2 h. The solvent was removed in vacuum to give 3-(difluoromethyl)-1-(4-fluorobenzyl)-4,5,6,7-tetrahydro-1H-pyrazolo[3,4-c]pyridine hydrochloride (248 mg, yield 100%, crude) which was used in next step without further purification. LCMS (ESI) m/z 281.9 [M+H]$^+$ Step 4 trans-Ethyl 4-(2-(3-(difluoromethyl)-1-(4-fluorobenzyl)-4,5-dihydro-1H-pyrazolo[3,4-c]pyridin-6(7H)-yl)-2-oxoethyl)cyclohexanecarboxylate

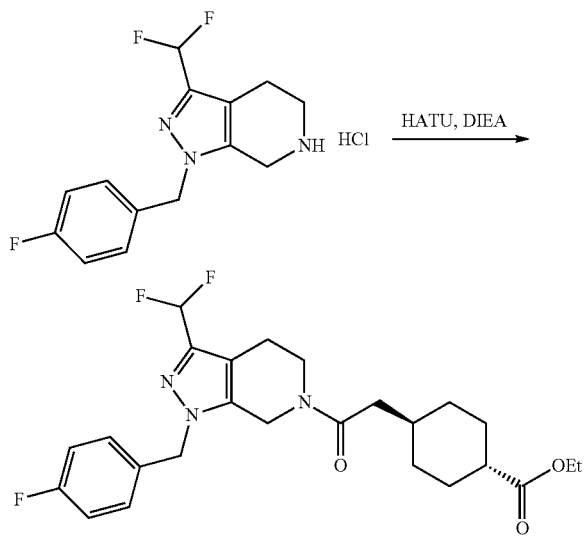

A mixture of 2-(trans-4-(ethoxycarbonyl)cyclohexyl)acetic acid (200 mg, 0.94 mmol, 1.2 eq.), HATU (282 mg, 1.17 mmol, 1.5 eq.), DIEA (504 mg, 3.90 mmol, 5.0 eq.) and 3-(difluoromethyl)-1-(4-fluorobenzyl)-4,5,6,7-tetrahydro-1H-pyrazolo[3,4-c]pyridine hydrochloride (248 mg, 0.78 mmol, 1.0 eq.) in DMF (5 mL) was stirred at 30° C. for 4 h. The mixture was poured into brine (20 mL) and extracted with EA (20 mL×3). The organic phase was dried over $Na_2SO_4$, filtered and concentrated to give the crude, which was purified by prep. HPLC (MeCN and H2O with 0.225% FA as mobile phase; from 39-69%) to provide trans-ethyl 4-(2-(3-(difluoromethyl)-1-(4-fluorobenzyl)-4,5-dihydro-1H-pyrazolo[3,4-c]pyridin-6(7H)-yl)-2-oxoethyl)cyclohexanecarboxylate (200 mg, yield 54%) as a yellow gum. $^1$H NMR (400 MHz, Methanol-d4) δ: 7.27-7.21 (m, 2H), 7.14-7.06 (m, 2H), 6.85-6.58 (m, 1H), 5.33-5.28 (m, 2H), 4.60-4.53 (m, 2H), 4.10-4.06 (m, 2H), 3.77-3.71 (m, 2H), 2.75-2.66 (m, 2H), 2.37-2.16 (m, 3H), 1.96-1.81 (m, 5H), 1.43-1.21 (m, 5H), 1.09-0.85 (m, 2H); LCMS (ESI) m/z 478.1 [M+H]$^+$ Example 1-39 trans-Ethyl 4-(2-(3-cyclopropyl-1-(4-fluorobenzyl)-4,5-dihydro-1H-pyrazolo[3,4-c]pyridin-6(7H)-yl)-2-oxoethyl)cyclohexanecarboxylate

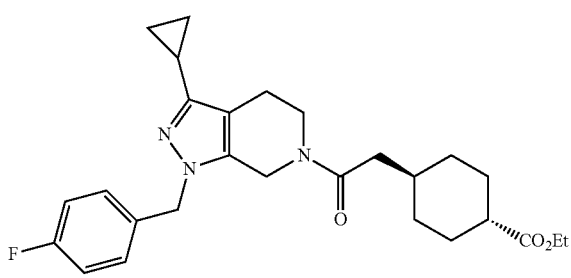 [SMILES: CCOC(=O)[C@H]1CC[C@H](CC(=O)N2CCc3c(C4CC4)nn(Cc4ccc(F)cc4)c3C2)CC1]

Step 1 tert-Butyl 3-cyclopropyl-1-(4-fluorobenzyl)-4,5-dihydro-1H-pyrazolo[3,4-c]pyridine-6(7H)-carboxylate

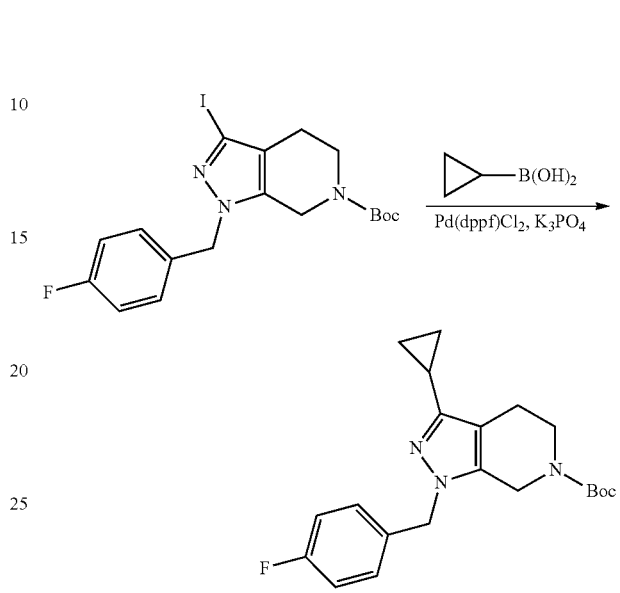

A mixture of tert-butyl 1-(4-fluorobenzyl)-3-iodo-4,5-dihydro-1H-pyrazolo[3,4-c]pyridine-6(7H)-carboxylate (Intermediate 1-23) (100 mg, 0.29 mmol, 1.0 eq.), cyclopropylboronic acid (37 mg, 0.43 mmol, 1.5 eq.), $K_3PO_4$ (184 mg, 0.87 mmol, 3.0 eq.) and Pd(dppf)Cl$_2$ (11 mg, 0.015 mmol, 0.05 eq.) in dioxane (3 mL) was stirred at 80° C. under $N_2$ for 12 h. LCMS showed desired product was detected. The mixture was filtered by silica gel and the filtrate was concentrated to give the crude, which was purified by prep-HPLC (MeCN and $H_2O$ with 0.225% (v/v) FA as mobile phase; from 52-78%) to provide tert-butyl 3-cyclopropyl-1-(4-fluorobenzyl)-4,5-dihydro1H-pyrazolo[3,4-c]pyridine-6(7H)-carboxylate (40 mg, yield 36%) as a yellow gum. $^1$H NMR (400 MHz, CDCl$_3$) δ: 7.08 (br, 2H), 6.97 (br, 2H), 5.07 (s, 2H), 4.26-4.20 (m, 2H), 3.54 (s, 2H), 2.53 (s, 2H), 1.75 (s, 1H), 1.44 (s, 9H), 0.85-0.83 (m, 4H); LCMS (ESI) m/z 372.1 [M+H]$^+$ Step 2

3-Cyclopropyl-1-(4-fluorobenzyl)-4,5,6,7-tetrahydro-1H-pyrazolo[3,4-c]pyridine hydrochloride

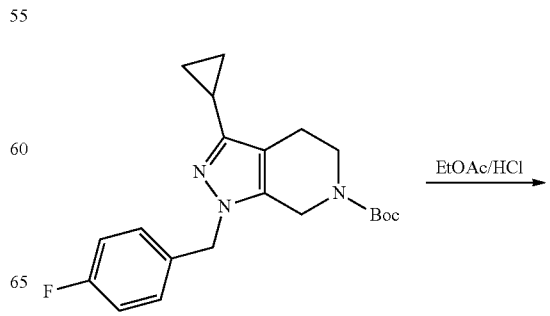

-continued

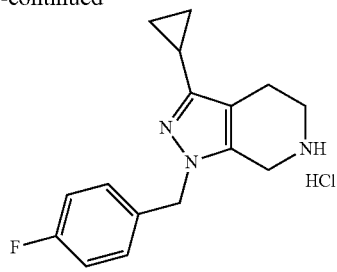

A mixture of tert-butyl 3-cyclopropyl-1-(4-fluorobenzyl)-4,5-dihydro-1H-pyrazolo[3,4-c]pyridine-6(7H)-carboxylate (40 mg, 0.11 mmol, 1.0 eq.) in HCl/EA (2 mL) was stirred at 20° C. for 4 h. LCMS showed the starting material was consumed completely. The solvent was removed in vacuum to give 3-cyclopropyl-1-(4-fluorobenzyl)-4,5,6,7-tetrahydro-1H-pyrazolo[3,4-c]pyridine hydrochloride (31 mg, 100% crude), which was used in next step without further purification. LCMS (ESI) m/z 271.9 [M+H]$^+$
Step 3 trans-Ethyl 4-(2-(3-cyclopropyl-1-(4-fluorobenzyl)-4,5-dihydro-1H-pyrazolo[3,4-c]pyridin-6 (7H)-yl)-2-oxoethyl)cyclohexanecarboxylate

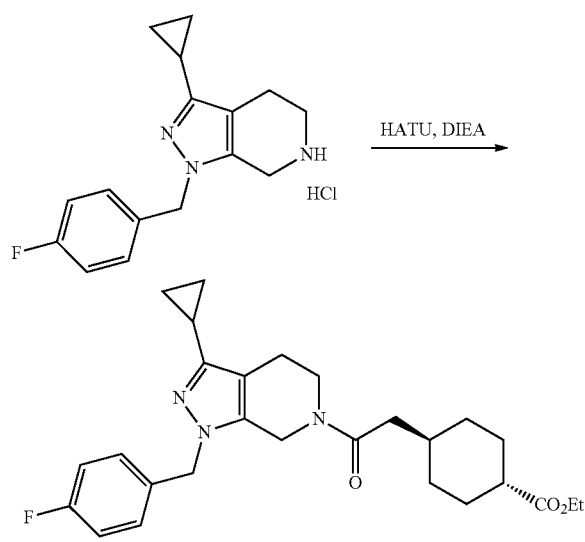

A mixture of 2-(trans-4-(ethoxycarbonyl)cyclohexyl)acetic acid (27 mg, 0.13 mmol, 1.2 eq.), HATU (39 mg, 0.16 mmol, 1.5 eq.), DIEA (69 mg, 0.54 mmol, 5.0 eq.) and 3-cyclopropyl-1-(4-fluorobenzyl)-4,5,6,7-tetrahydro-1H-pyrazolo[3,4-c]pyridine hydrochloride (31 mg, 0.11 mmol, 1.0 eq.) in DMF (2 mL) was stirred at 20° C. for 6 h. EtOAc (10 mL) was added and the mixture was washed with brine (10 mL). The organic phase was dried over Na$_2$SO$_4$, filtered and concentrated to give the crude which was purified by prep-HPLC (MeCN and H$_2$O with 0.225% FA as mobile phase; from 52-67%) to provide trans-ethyl 4-(2-(3-cyclopropyl-1-(4-fluorobenzyl)-4,5-dihydro-1-1H-pyrazolo[3,4-c]pyridin-6(7H)-yl)-2-oxoethyl) cyclohexane carboxylate (30 mg, yield 58%) as a colorless gum. $^1$H NMR (400 MHz, Methanol-d$_4$) δ: 7.15-7.04 (m, 4H), 5.20-5.17 (m, 2H), 4.52-4.44 (m, 2H), 4.07 (t, J=7.2 Hz, 2H), 3.76-3.68 (m, 2H), 2.64-2.37 (m, 2H), 2.35-2.15 (m, 1H), 2.14-2.13 (m, 2H), 1.92-1.79 (m, 6H), 1.40-1.30 (m, 2H), 1.21 (t, J=7.6 Hz, 3H), 0.89-0.87 (m, 2H), 0.82-0.80 (m, 4H); LCMS (ESI) m/z 468.1 [M+H]$^+$ Example 1-40

Ethyl 6-(2-(trans-4-(ethoxycarbonyl)cyclohexyl)acetyl)-1-(4-fluorobenzyl)-4,5,6,7-tetrahydro-1H-pyrazolo[3,4-c]pyridine-3-carboxylate

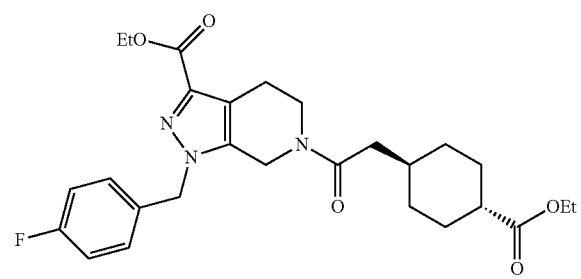 [SMILES: CCOC(=O)c1nn(Cc2ccc(F)cc2)c2c1CCN(C(=O)C[C@H]1CC[C@H](C(=O)OCC)CC1)C2]

The title compound was synthesized according to the procedure described in Example 1-1, using Intermediate 2-19 and 2-(trans-4-(ethoxycarbonyl)cyclohexyl)acetic acid as starting materials, and purified by prep-HPLC (Diamonsil 150×20 mm×5 um; MeCN and H$_2$O with 0.225% FA as mobile phase; from 48-78%; Flow Rate (ml/min): 25) to obtain a colorless gum (380 mg, yield 48%). $^1$H NMR (400 MHz, Methanol-d$_4$) δ: 7.26-7.23 (m, 2H), 7.13-7.05 (m, 2H), 5.37-5.33 (m, 2H), 4.57-4.52 (m, 2H), 4.33 (q, J=7.2 Hz, 2H), 4.07 (q, J=7.2 Hz, 2H), 3.74-3.69 (m, 2H), 2.86-2.85 (m, 2H), 2.37-2.14 (m, 3H), 1.91-1.51 (m, 5H), 1.41-1.34 (m, 5H), 1.21 (t, J=7.2 Hz, 3H), 1.07-0.83 (m, 2H) LCMS (ESI) m/z 522.1 [M+Na]$^+$ Example 1-41 trans-Ethyl-4-(2-(1-(4-fluorobenzyl)-3-(hydroxymethyl)-4,5-dihydro-1H-pyrazolo[3,4-c]pyridin-6(7H)-yl)-2-oxoethyl)cyclohexanecarboxylate

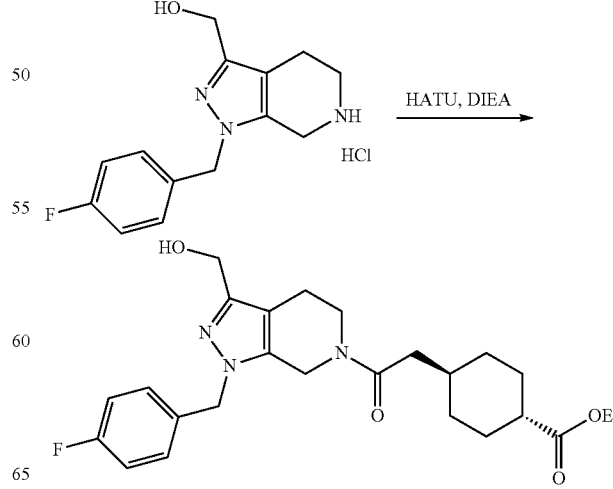

A mixture of 2-(trans-4-(ethoxycarbonyl)cyclohexyl)acetic acid (99 mg, 0.33 mmol, 1.0 eq.), HATU (119 mg, 0.49 mmol, 1.5 eq.), DIEA (213 mg, 1.65 mmol, 5.0 eq.) and (1-(4-fluorobenzyl)-4,5,6,7-tetrahydro-1H-pyrazolo[3,4-c]pyridin-3-yl)methanol hydrochloride (Intermediate 2-20, 85 mg, 0.39 mmol, 1.2 eq.) in DMF (2 mL) was stirred at 25° C. for 4 hours. EtOAc (10 mL) was added and the mixture was washed with brine (10 mL×3). The organic phase was dried over Na$_2$SO$_4$, filtered and concentrated to give the crude which was purified by prep. HPLC (Phenomenex Gemini C18 250×21.2 mm×5 um, MeCN and H$_2$O with 0.05% HCl-MeCN as mobile phase, from 20-40%, Flow Rate (ml/min): 25) to provide trans-ethyl-4-(2-(1-(4-fluorobenzyl)-3-(hydroxymethyl)-4,5-dihydro-1H-pyrazolo[3,4-c]pyridin-6(7H)-yl)-2-oxoethyl)cyclohexanecarboxylate (65 mg, yield 43%) as a white solid. $^1$H NMR (400 MHz, Methanol-d$_4$) δ: 7.22-7.18 (m, 2H), 7.12-7.03 (m, 2H), 5.27-5.23 (m, 2H), 4.58-4.51 (m, 4H), 4.12-4.06 (m, 2H), 3.78-3.71 (m, 2H), 2.72-2.61 (m, 2H), 2.39-2.16 (m, 3H), 1.96-1.81 (m, 5H), 1.43-1.40 (m, 2H), 1.24-1.21 (m, 3H), 1.09-0.90 (m, 2H); LCMS (ESI) m/z 458.1 [M+H]$^+$ Example 1-42 trans-Ethyl 4-(2-(3-carbamoyl-1-(4-fluorobenzyl)-4,5-dihydro-1H-pyrazolo[3,4-c]pyridin-6(7H)-yl)-2-oxoethyl)cyclohexanecarboxylate

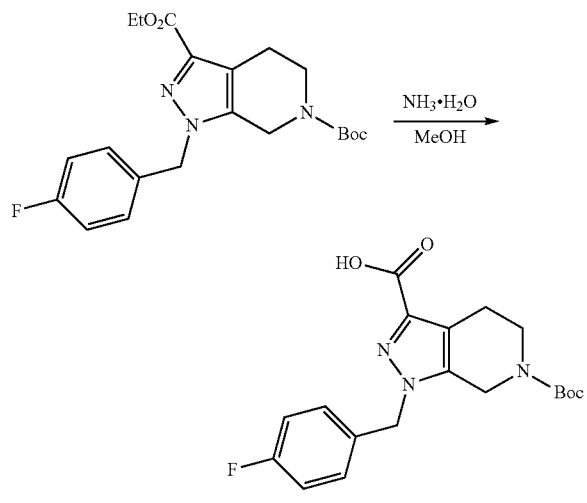

Step 1

6-(tert-Butoxycarbonyl)-1-(4-fluorobenzyl)-4,5,6,7-tetrahydro-1H-pyrazolo[3,4-c]pyridine-3-carboxylic acid

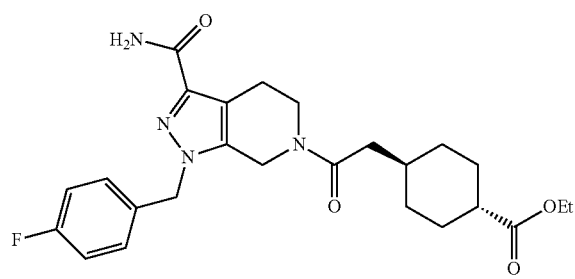

A mixture of 6-tert-butyl 3-ethyl 1-(4-fluorobenzyl)-4,5-dihydro-1H-pyrazolo[3,4-c]pyridine-3,6(7H)-dicarboxylate (Intermediate 1-20, 150 mg, 0.37 mmol, 1.0 eq.) in NH$_3$.H$_2$O (10 mL) and MeOH (1 mL) was stirred at 80° C. for 12 h. LCMS showed the desired product was detected. The solvent was removed in vacuum to give 6-(tert-butoxycarbonyl)-1-(4-fluorobenzyl)-4,5,6,7-tetrahydro-1H-pyrazolo[3,4-c]pyridine-3-carboxylic acid (160 mg, yield 100%, crude), which was used in next step without further purification. LCMS (ESI) m/z 375.9 [M+H]$^+$ Step 2

1-(4-Fluorobenzyl)-4,5,6,7-tetrahydro-1H-pyrazolo[3,4-c]pyridine-3-carboxylic acid hydrochloride

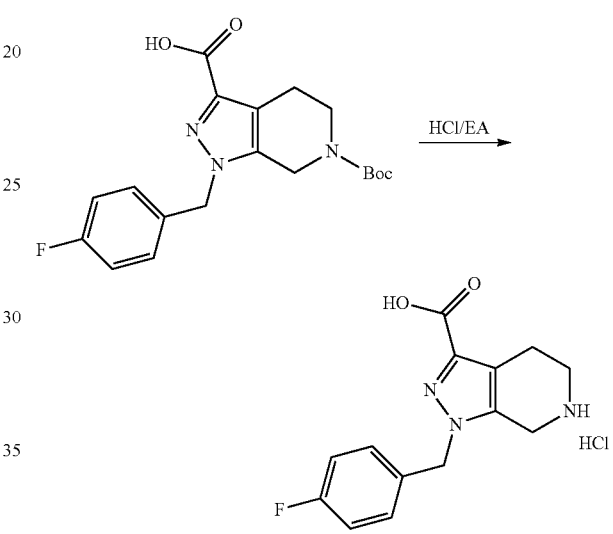

A mixture of 6-(tert-butoxycarbonyl)-1-(4-fluorobenzyl)-4,5,6,7-tetrahydro-1H-pyrazolo[3,4-c]pyridine-3-carboxylic acid (150 mg, 0.4 mmol, 1.0 eq.) in HCl/EA (10 mL) was stirred at 30° C. for 2 h. TLC showed the starting material was consumed completely. The solvent was removed in vacuum to give 1-(4-fluorobenzyl)-4,5,6,7-tetrahydro-1H-pyrazolo[3,4-c]pyridine-3-carboxylic acid hydrochloride (150 mg, yield 100%, crude), which was used in next step without further purification. LCMS (ESI) m/z 276.3 [M+H]$^+$ Step 3

6-(2-(trans-4-(Ethoxycarbonyl)cyclohexyl)acetyl)-1-(4-fluorobenzyl)-4,5,6,7-tetrahydro-1H-pyrazolo[3,4-c]pyridine-3-carboxylic acid

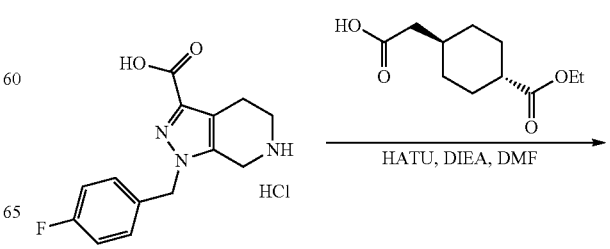

113
-continued

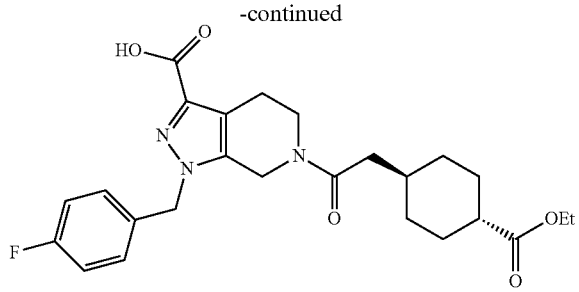

A mixture of 2-(trans-4-(ethoxycarbonyl)cyclohexyl)acetic acid (103 mg, 0.48 mmol, 1.0 eq.), HATU (203 mg, 0.53 mmol, 1.1 eq.), DIEA (310 mg, 2.4 mmol, 5.0 eq.) and 1-(4-fluorobenzyl)-4,5,6,7-tetrahydro-1H-pyrazolo[3,4-c]pyridine-3-carboxylic acid hydrochloride (150 mg, 0.48 mmol, 1.0 eq.) in DMF (3 mL) was stirred at 30° C. for 12 h. EA (10 mL) was added and the mixture was washed with brine (10 mL). The organic phase was dried over $Na_2SO_4$, filtered and concentrated to give the crude which was purified by prep-HPLC (Diamonsil 150×20 mm×5 um; MeCN and $H_2O$ with 0.225% FA as mobile phase; from 37-67%; Flow Rate (ml/min): 25) to provide 6-(2-(trans-4-(ethoxycarbonyl)cyclohexyl)acetyl)-1-(4-fluorobenzyl)-4,5,6,7-tetrahydro-1H-pyrazolo[3,4-c]pyridine-3-carboxylic acid (100 mg, yield 44%) as a white solid. $^1$H NMR (400 MHz, CDCl$_3$) δ: 7.22-7.15 (m, 2H), 7.04-6.99 (m, 2H), 5.27-5.18 (m, 2H), 4.52 (s, 2H), 4.09 (q, J=7.2 Hz, 2H), 3.60-3.58 (m, 2H), 2.93-2.88 (m, 2H), 2.29-2.16 (m, 3H), 1.97-1.82 (m, 5H), 1.46-1.43 (m, 2H), 1.22 (t, J=7.2 Hz, 3H), 1.01-0.98 (m, 2H); LCMS (ESI) m/z 472.1 [M+H]$^+$ Step 4 trans-Ethyl 4-(2-(3-carbamoyl-1-(4-fluorobenzyl)-4,5-dihydro-1H-pyrazolo[3,4-c]pyridin-6(7H)-yl)-2-oxoethyl)cyclohexanecarboxylate

114

A mixture of 6-(2-(trans-4-(ethoxycarbonyl)cyclohexyl)acetyl)-1-(4-fluorobenzyl)-4,5,6,7-tetrahydro-1H-pyrazolo[3,4-c]pyridine-3-carboxylic acid (47 mg, 0.1 mmol, 1.0 eq.), HATU (46 mg, 0.12 mmol, 1.2 eq.), DIEA (39 mg, 0.3 mmol, 3.0 eq.) and NH$_4$Cl (53 mg, 1.0 mmol, 10.0 eq) in DMF (1 mL) was stirred at 30° C. for 4 h. LCMS showed the desired product was detected. EtOAc (10 mL) was added and the mixture was washed with brine (10 mL). The organic phase was dried over $Na_2SO_4$, filtered and concentrated to give the title compound. $^1$H NMR (400 MHz, DMSO-d$_6$) δ: 7.36-7.14 (m, 6H), 5.31-5.28 (m, 2H), 4.49 (s, 2H), 3.99 (q, J=7.2 Hz, 2H), 3.59-3.56 (m, 2H), 2.70-2.59 (m, 2H), 2.26-2.10 (m, 3H), 1.83-1.62 (m, 5H), 1.27-1.21 (m, 2H), 1.12 (t, J=7.2 Hz, 3H), 0.97-0.81 (m, 2H); LCMS (ESI) m/z 493.1 [M+Na]$^+$ Example 1-43 trans-Ethyl 4-(2-(3-cyano-1-(4-fluorobenzyl)-4,5-dihydro-1H-pyrazolo[3,4-c]pyridin-6(7H)-yl)-2-oxoethyl)cyclohexanecarboxylate

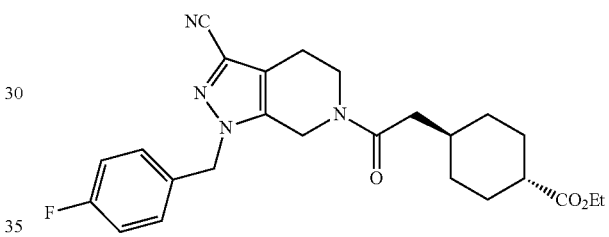

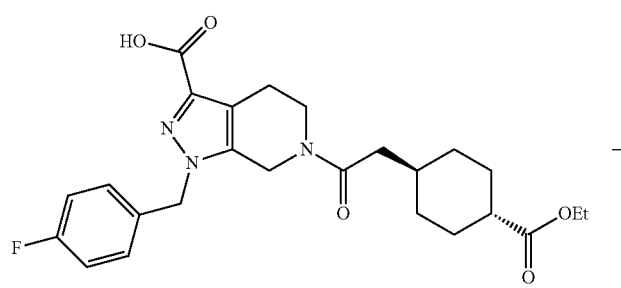

NH$_4$Cl, HATU, DIEA
⟶
DMF

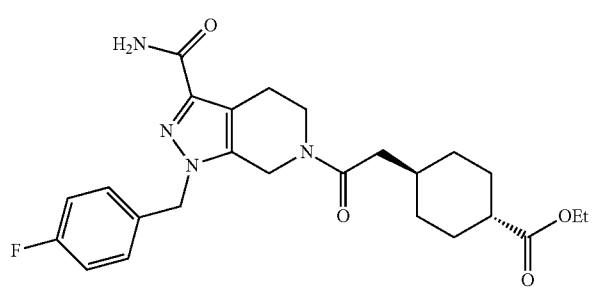 [SMILES: CCOC(=O)[C@H]1CC[C@H](CC(=O)N2CCc3c(C(N)=O)nn(Cc4ccc(F)cc4)c3C2)CC1]

Step 1 tert-Butyl 3-cyano-1-(4-fluorobenzyl)-4,5-dihydro-1H-pyrazolo[3,4-c]pyridine-6(7H)-carboxylate

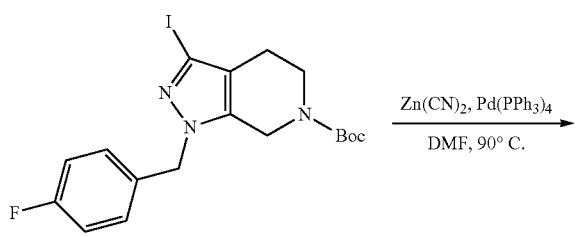

To a solution of tert-butyl 1-(4-fluorobenzyl)-3-iodo-4,5-dihydro-1H-pyrazolo[3,4-c]pyridine-6(7H)-carboxylate (Intermediate 1-23, 150 mg, 0.32 mmol, 1 eq) and dicyanozinc (94 mg, 0.8 mmol, 2.5 eq) in DMF (5 mL) was added Pd(PPh$_3$)$_4$ (40 mg, 0.032 mmol, 0.1 eq) at 35° C. The reaction mixture was stirred at 90° C. under N$_2$ for 18 h. TLC (PE/EtOAc=3:1) showed the starting material has been consumed. The crude product was purified by pre-TLC (PE/EtOAc=3:1) to give tert-butyl 3-cyano-1-(4-fluorobenzyl)-4,5-dihydro-1H-pyrazolo[3,4-c]pyridine-6(7H)-carboxylate (58 mg, yield 51%) as a pale gum. $^1$HNMR (400 MHz, CDCl$_3$) δ: 7.21-7.15 (m, 2H), 7.03 (t, J=8.0 Hz, 2H), 5.19 (s, 2H), 4.41-4.22 (m, 2H), 3.57 (br, 2H), 2.64 (br, 2H), 1.43 (s, 9H).

Step 2

1-(4-Fluorobenzyl)-4,5,6,7-tetrahydro-1H-pyrazolo[3,4-c]pyridine-3-carbonitrile hydrochloride

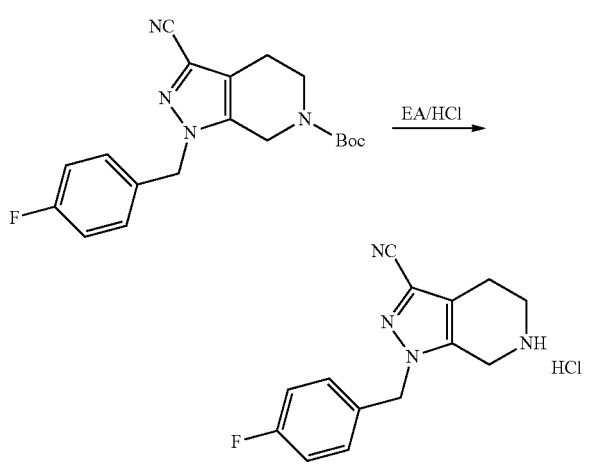

tert-Butyl 3-cyano-1-(4-fluorobenzyl)-4,5-dihydro-1H-pyrazolo[3,4-c]pyridine-6(7H)-carboxylate (58 mg, 0.16 mmol, 1 eq) was added into HCl/EtOAc (6 mL, 4M) at 35° C. The reaction mixture was stirred at 35° C. for 3 h. TLC (PE/EtOAc=3:1) showed the starting material has been consumed. The reaction mixture was concentrated in vacuum to give 1-(4-fluorobenzyl)-4,5,6,7-tetrahydro-1H-pyrazolo[3,4-c]pyridine-3-carbonitrile hydrochloride (47 mg, crude) which was used for the next step without further purification.

Step 3 trans-Ethyl 4-(2-(3-cyano-1-(4-fluorobenzyl)-4,5-dihydro-1H-pyrazolo[3,4-c]pyridin-6(7H)-yl)-2-oxoethyl)cyclohexanecarboxylate

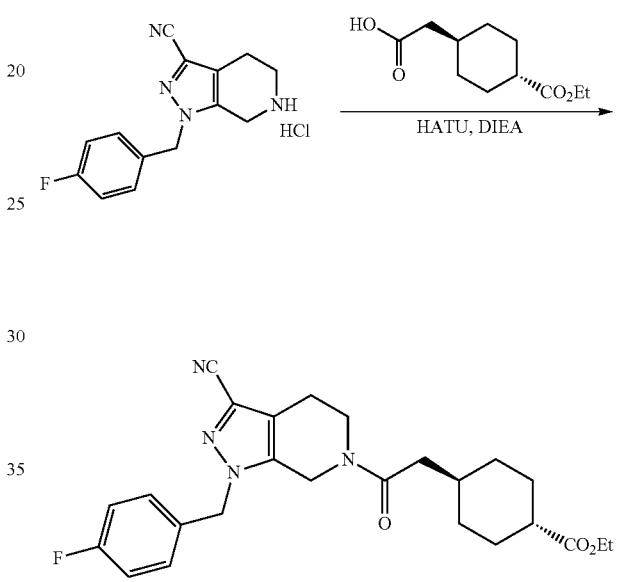

To a solution of 1-(4-fluorobenzyl)-4,5,6,7-tetrahydro-1H-pyrazolo[3,4-c]pyridine-3-carbonitrile hydrochloride (47 mg, crude) and 2-(trans-4-(ethoxycarbonyl) cyclohexyl) acetic acid (70 mg, 0.32 mmol) in DMF (3 mL) was added HATU (160 mg, 0.42 mmol) and DIEA (83 mg, 0.64 mmol) at 35° C. The reaction mixture was stirred at 35° C. for 5 h. LCMS showed the starting material has been consumed. The crude product was purified by pre-HPLC (SYNERGI MAX-RP 150×30 mm, MeCN and H$_2$O with 0.05% (v/v) HCl as mobile phase, from 51-71%, 25 mL/min) to give trans-ethyl 4-(2-(3-cyano-1-(4-fluorobenzyl)-4,5-dihydro-1H-pyrazolo[3,4-c]pyridin-6(7H)-yl)-2-oxoethyl)cyclohexanecarboxylate (40 mg, 56% yield over two steps) as a pale white gum. $^1$H NMR (400 MHz, CDCl$_3$) δ: 7.23-7.16 (m, 2H), 7.03 (t, J=8.4 Hz, 2H), 5.30-5.15 (m, 2H), 4.57-4.24 (m, 2H), 4.09 (q, J=7.2 Hz, 2H), 3.79-3.55 (m, 2H), 2.76-2.64 (m, 2H), 2.31-2.13 (m, 3H), 2.02-1.77 (m, 5H), 1.51-1.38 (m, 2H), 1.22 (t, J=7.2 Hz, 3H), 1.06-0.77 (m, 2H); LCMS (ESI) m/z 453.1[M+H]$^+$

Example 1-44 trans-Ethyl 4-(2-(1-(4-fluorobenzyl)-3-phenyl-4,5-dihydro-1H-pyrazolo[3,4-c]pyridin-6(7H)-yl)-2-oxoethyl)cyclohexanecarboxylate

Step 1 tert-Butyl 1-(4-fluorobenzyl)-3-phenyl-4,5-dihydro-1H-pyrazolo[3,4-c]pyridine-6(7H)-carboxylate

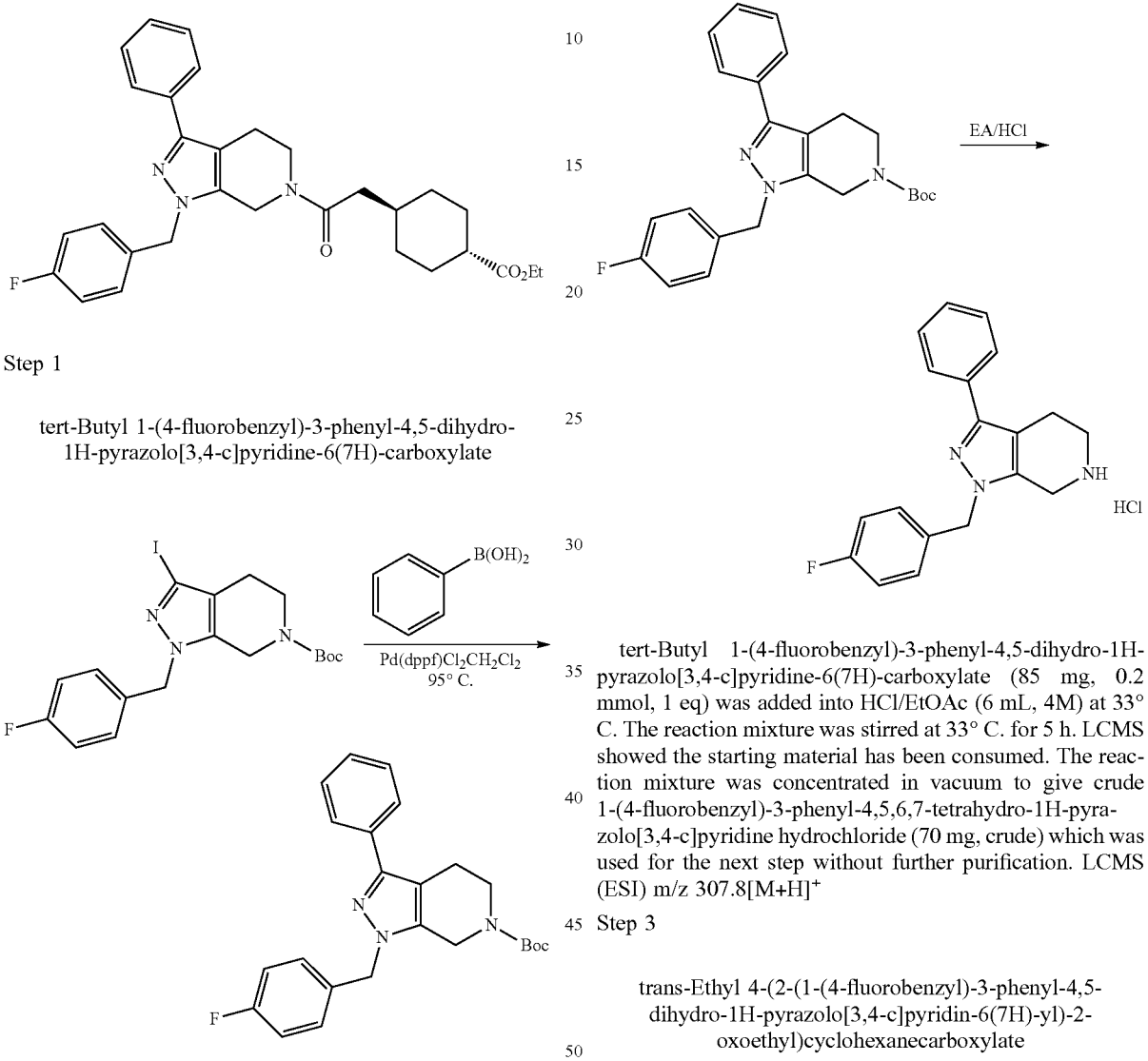

To a solution of tert-butyl 1-(4-fluorobenzyl)-3-iodo-4,5-dihydro-1H-pyrazolo[3,4-c]pyridine-6(7H)-carboxylate (Intermediate 1-23, 150 mg, 0.32 mmol, 1 eq) and phenylboronic acid (78 mg, 0.64 mmol, 2.0 eq) in dioxane (3 mL) was added Pd(dppf)Cl$_2$CH$_2$Cl$_2$ (26 mg, 0.032 mmol, 0.1 eq) and a solution of Na$_2$CO$_3$ (68 mg, 0.64 mmol, 2 eq) in H$_2$O at 28° C. The reaction mixture was stirred at 95° C. under N$_2$ for 18 h. LCMS showed the starting material has been consumed. The crude product was purified by pre-TLC (PE/EtOAc=4:1) to give tert-butyl 1-(4-fluorobenzyl)-3-phenyl-4,5-dihydro-1H-pyrazolo[3,4-c]pyridine-6(7H)-carboxylate (85 mg, yield 65%) as a colorless oil. $^1$H NMR (400 MHz, CDCl$_3$) δ: 7.71 (d, J=7.6 Hz, 2H), 7.40 (t, J=7.6 Hz, 2H), 7.34-7.27 (m, 1H), 7.22-7.15 (m, 2H), 7.00 (t, J=8.4 Hz, 2H), 5.23 (s, 2H), 4.37-4.32 (m, 2H), 3.59 (s, 2H), 2.78 (s, 2H), 1.45 (s, 9H).

Step 2

1-(4-Fluorobenzyl)-3-phenyl-4,5,6,7-tetrahydro-1H-pyrazolo[3,4-c]pyridine hydrochloride tert-Butyl 1-(4-fluorobenzyl)-3-phenyl-4,5-dihydro-1H-pyrazolo[3,4-c]pyridine-6(7H)-carboxylate (85 mg, 0.2 mmol, 1 eq) was added into HCl/EtOAc (6 mL, 4M) at 33° C. The reaction mixture was stirred at 33° C. for 5 h. LCMS showed the starting material has been consumed. The reaction mixture was concentrated in vacuum to give crude 1-(4-fluorobenzyl)-3-phenyl-4,5,6,7-tetrahydro-1H-pyrazolo[3,4-c]pyridine hydrochloride (70 mg, crude) which was used for the next step without further purification. LCMS (ESI) m/z 307.8[M+H]$^+$

Step 3 trans-Ethyl 4-(2-(1-(4-fluorobenzyl)-3-phenyl-4,5-dihydro-1H-pyrazolo[3,4-c]pyridin-6(7H)-yl)-2-oxoethyl)cyclohexanecarboxylate

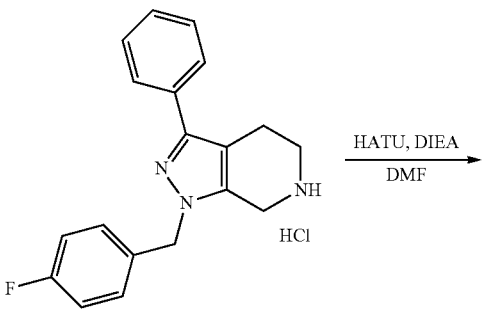

-continued

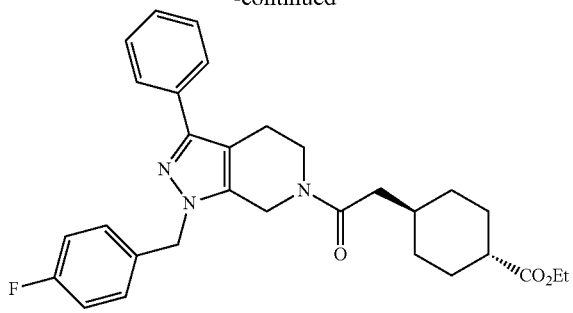

To a solution of 1-(4-fluorobenzyl)-3-phenyl-4,5,6,7-tetrahydro-1H-pyrazolo[3,4-c]pyridine hydrochloride (70 mg, crude) and 2-(trans-4-(ethoxycarbonyl)cyclohexyl)acetic acid (65 mg, 0.3 mmol) in DMF (3 mL) was added HATU (114 mg, 0.3 mmol) and DIEA (65 mg, 0.5 mmol) at 35° C. The reaction mixture was stirred at 35° C. for 5 h. LCMS showed the starting material has been consumed. The crude product was purified by pre-HPLC (SYNERGI MAX-RP 150×30 MM, MeCN and H₂O with 0.05% (v/v) HCl as mobile phase, from 67-87%, 25 mL/min) to give trans-ethyl 4-(2-(1-(4-fluorobenzyl)-3-phenyl-4,5-dihydro-1H-pyrazolo[3,4-c]pyridin-6(7H)-yl)-2-oxoethyl)cyclohexanecarboxylate (67 mg, 67% yield over two steps) as a white gum. $^1$H NMR (400 MHz, CDCl₃) δ: 7.70 (d, J=6.8 Hz, 2H), 7.46-7.38 (m, 2H), 7.36-7.29 (m, 1H), 7.25-7.16 (m, 2H), 7.08-6.97 (m, 2H), 5.33-5.23 (m, 2H), 4.60-4.29 (m, 2H), 4.11 (q, J=7.2 Hz, 2H), 3.83-3.60 (m, 2H), 2.90-2.77 (m, 2H), 2.37-2.13 (m, 3H), 2.05-1.94 (m, 2H), 1.93-1.81 (m, 3H), 1.55-1.36 (m, 2H), 1.24 (t, J=7.2 Hz, 3H), 1.09-0.80 (m, 2H); LCMS (ESI) m/z 504.2[M+H]⁺

Example 1-45 trans-Ethyl-4-(2-oxo-2-(1-(thiophen-3-ylmethyl)-3-(trifluoromethyl)-4,5-dihydro-1H-pyrazolo[3,4-c]pyridin-6(7H)-yl)ethyl)cyclohexanecarboxylate

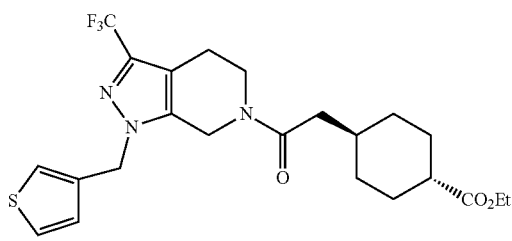 [SMILES: CCOC(=O)[C@H]1CC[C@H](CC(=O)N2CCc3c(C(F)(F)F)nn(Cc4ccsc4)c3C2)CC1]

Step 1 trans-Ethyl 4-(2-oxo-2-(3-(trifluoromethyl)-4,5-dihydro-1H-pyrazolo[3,4-c]pyridin-6(7H)-yl) ethyl)cyclohexanecarboxylate

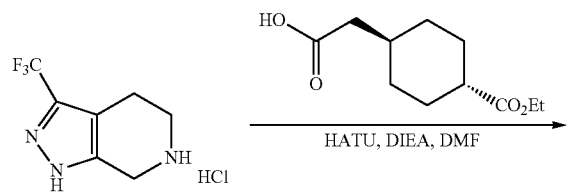

-continued

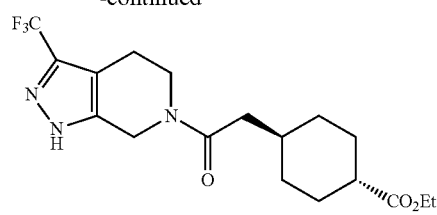

A mixture of 2-(trans-4-(ethoxycarbonyl)cyclohexyl)acetic acid (4.98 g, 23.3 mmol, 1.1 eq.), HATU (8.95 g, 23.3 mmol, 1.1 eq.), DIEA (8.2 g, 63.3 mmol, 3.0 eq.) and 3-(trifluoromethyl)-4,5,6,7-tetrahydro-1H-pyrazolo[3,4-c]pyridine hydrochloride (4.8 g, 21.1 mmol, 1.0 eq.) in DMF (20 mL) was stirred at 25° C. for 12 h. EA (30 mL) was added and the mixture was washed with brine (30 mL). The organic phase was dried over Na₂SO₄, filtered and concentrated to give the crude which was purified by column chromatography on silica (PE/EtOAc=8/1~1/2) to provide trans-ethyl 4-(2-oxo-2-(3-(trifluoromethyl)-4,5-dihydro-1H-pyrazolo[3,4-c]pyridin-6(7H)-yl)ethyl)cyclohexanecarboxylate (3.6 g, yield 38%) as a yellow oil. $^1$H NMR (400 MHz, CDCl₃) δ: 4.78-4.63 (m, 2H), 4.13-4.09 (m, 2H), 3.72-3.69 (m, 2H), 2.81-2.76 (m, 2H), 2.34-2.17 (m, 3H), 1.99-1.85 (m, 4H), 1.48-1.44 (m, 2H), 1.27-1.21 (m, 3H), 1.05-0.95 (m, 2H); 4.78-4.63 (m, 2H), 4.13-4.09 (m, 2H), 3.72-3.69 (m, 2H), 2.81-2.76 (m, 2H), 2.34-2.17 (m, 3H), 1.99-1.85 (m, 4H), 1.48-1.44 (m, 2H), 1.27-1.21 (m, 3H), 1.05-0.95 (m, 2H); LCMS (ESI) m/z 388.0 [M+H]⁺

Step 2

Thiophen-3-ylmethyl methanesulfonate

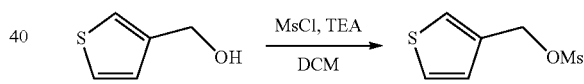

To a mixture of thiophen-3-ylmethanol (500 mg, 4.38 mmol, 1.0 eq.) in DCM (10 mL) was added TEA (885 mg, 8.76 mmol, 2.0 eq.) and MsCl (754 mg, 6.58 mmol, 1.5 eq) dropwise at 0° C. The reaction mixture was stirred at 20° C. for 17 h. TLC showed that the starting material was consumed. The mixture was concentrated to give the crude, which was used for the next step directly.

Step 3 trans-Ethyl-4-(2-oxo-2-(1-(thiophen-3-ylmethyl)-3-(trifluoromethyl)-4,5-dihydro-1H-pyrazolo[3,4-c]pyridin-6(7H)-yl)ethyl)cyclohexanecarboxylate

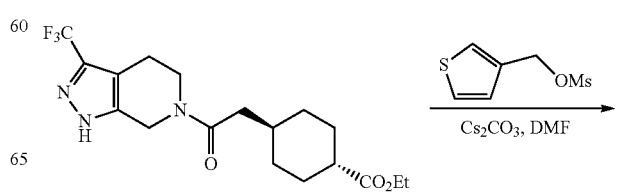

-continued

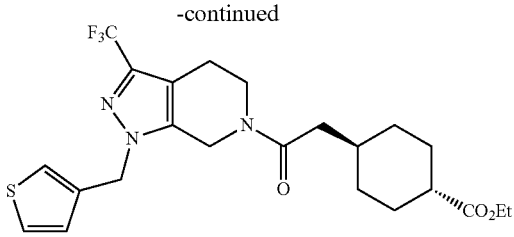

To a mixture of trans-ethyl 4-(2-oxo-2-(3-(trifluoromethyl)-4,5-dihydro-1H-pyrazolo[3,4-c]pyridin-6(7H)-yl)ethyl)cyclohexanecarboxylate (200 mg, 0.52 mmol, 1.0 eq.) and Cs$_2$CO$_3$ (339 mg, 1.04 mmol, 2.0 eq.) in DMF (5 mL) was added thiophen-3-ylmethyl methanesulfonate (119 mg, 0.62 mmol, 1.2 eq.). The reaction mixture was stirred at 20° C. for 17 h. EA (30 mL) was added and the mixture was washed with brine (20 mL×2). The organic phase was dried over Na$_2$SO$_4$, filtered and concentrated to give the crude which was purified by prep. HPLC (Diamonsil 150×20 mm×5 um; MeCN and H$_2$O with 0.225% FA as mobile phase; from 54-74%; Flow Rate (ml/min): 25) to provide trans-ethyl 4-(2-oxo-2-(1-(thiophen-3-ylmethyl)-3-(trifluoromethyl)-4,5-dihydro-1H-pyrazolo[3,4-c]pyridin-6(7H)-yl)ethyl)cyclohexanecarboxylate (100 mg, yield 40%) as a colorless oil. $^1$H NMR (400 MHz, Methanol-d$_4$) δ: 7.39-7.30 (m, 2H), 6.98-6.97 (m, 1H), 5.37-5.32 (m, 2H), 4.67-4.61 (m, 2H), 4.07 (q, J=6.8 Hz, 2H), 3.75-3.69 (m, 2H), 2.70-2.60 (m, 2H), 2.37-2.35 (m, 1H), 2.18-2.17 (m, 2H), 1.91-1.75 (m, 5H), 1.41-1.35 (m, 2H), 1.21 (t, J=6.8 Hz, 3H), 1.19-1.06 (m, 1H), 1.03-0.90 (m, 1H); LCMS (ESI) m/z 484.1 [M+H]$^+$ Example 1-46 trans-Ethyl-4-(2-oxo-2-(1-(thiophen-2-ylmethyl)-3-(trifluoromethyl)-4,5-dihydro-1H-pyrazolo[3,4-c]pyridin-6(7H)-yl)ethyl)cyclohexanecarboxylate

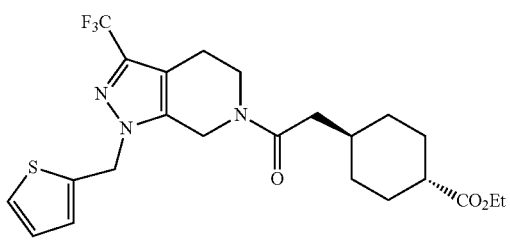 [SMILES: CCOC(=O)[C@H]1CC[C@H](CC(=O)N2CCc3c(C(F)(F)F)nn(Cc4cccs4)c3C2)CC1]

The title compound was synthesized according to the procedure described in Example 1-45, using thiophen-2-ylmethyl methanesulfonate as a starting material. $^1$H NMR (400 MHz, CDCl$_3$) δ: 7.38-7.32 (m, 1H), 7.11-7.08 (m, 1H), 7.03-7.01 (m, 1H), 5.52-5.48 (m, 2H), 4.69-4.44 (m, 2H), 4.16 (q, J=6.8 Hz, 2H), 3.83-3.67 (m, 2H), 2.79-2.76 (m, 2H), 2.36-2.22 (m, 3H), 2.06-1.91 (m, 5H), 1.54-1.50 (m, 2H), 1.29 (t, J=6.8 Hz, 3H), 1.09-0.97 (m, 2H); LCMS (ESI) m/z 484.1 [M+H]$^+$ Example 1-47 trans-Ethyl 4-(2-oxo-2-(1-(thiazol-5-ylmethyl)-3-(trifluoromethyl)-4,5-dihydro-1H-pyrazolo[3,4-c]pyridin-6(7H)-yl)ethyl)cyclohexanecarboxylate

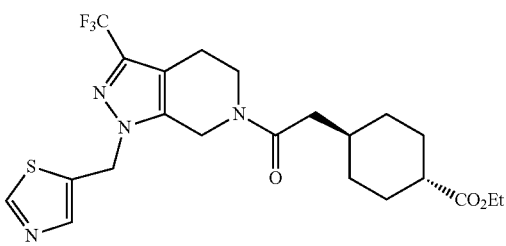 [SMILES: CCOC(=O)[C@H]1CC[C@H](CC(=O)N2CCc3c(C(F)(F)F)nn(Cc4cncs4)c3C2)CC1]

The title compound was synthesized according to the procedure described in Example 1-45, using thiazol-5-ylmethyl methanesulfonate (prepared from thiazol-5-ylmethanol as described in Example 1-45, step 2) as a starting material. $^1$H NMR (400 MHz, CDCl$_3$) δ: 10.00 (s, 1H), 8.63 (s, 1H), 5.93-5.83 (m, 2H), 4.89 (br, 2H), 4.09 (q, J=6.8 Hz, 2H), 3.83-3.70 (m, 2H), 2.73 (br, 2H), 2.51-2.17 (m, 3H), 2.00-1.81 (m, 5H), 1.44-1.41 (m, 2H), 1.23 (t, J=6.8 Hz, 3H), 1.03-0.83 (m, 2H); LCMS (ESI) m/z 485.1 [M+H]$^+$ Example 1-48 trans-Ethyl 4-(2-(1-((4-methylcyclohexyl)methyl)-3-(trifluoromethyl)-4,5-dihydro-1H-pyrazolo[3,4-c]pyridin-6(7H)-yl)-2-oxoethyl) cyclohexanecarboxylate

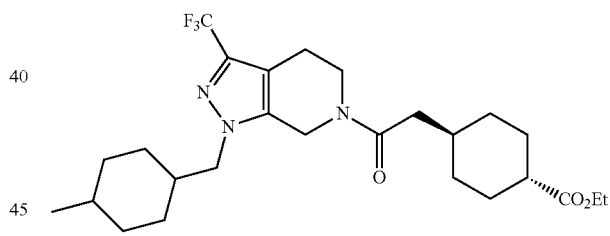

Step 1

(4-Methylcyclohexyl)methyl methanesulfonate

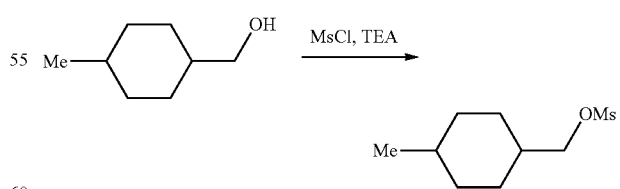

A mixture of (4-methylcyclohexyl)methanol (300 mg, 2.34 mmol, 1.0 eq), MsCl (402 mg, 3.51 mmol, 1.5 eq) and TEA (473 mg, 4.98 mmol, 2.0 eq) in DCM (5 mL) was stirred at room temperature overnight. TLC (PE/EA=3/1) showed the starting material was consumed completely. The reaction was quenched with aqueous citric acid solution and then extracted with DCM (5 mL×3). The organic phase was dried over $Na_2SO_4$, filtered and concentrated to give (4-methylcyclohexyl)methyl methanesulfonate (300 mg, crude) which was used in next step without further purification.

Step 2 tert-Butyl 1-((4-methylcyclohexyl)methyl)-3-(trifluoromethyl)-4,5-dihydro-1H-pyrazolo[3,4-c]pyridine-6(7H)-carboxylate

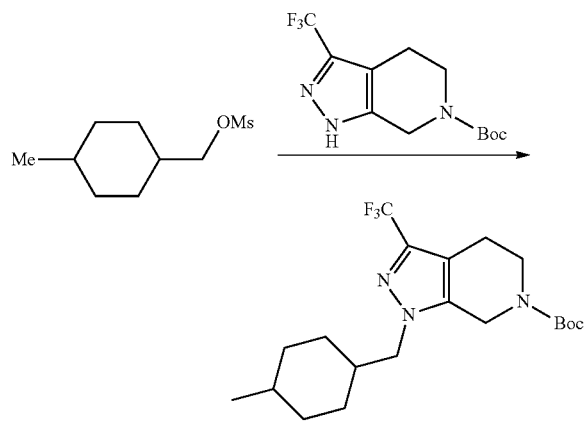

To a mixture of tert-butyl 3-(trifluoromethyl)-4,5-dihydro-1H-pyrazolo[3,4-c]pyridine-6(7H)-carboxylate (508 mg, 1.74 mmol, 1.2 eq.) and $Cs_2CO_3$ (944 mg, 2.90 mmol, 2.0 eq.) in DMF (5 mL) was added (4-methylcyclohexyl) methyl methanesulfonate (300 mg, 1.45 mmol, 1.0 eq.) dropwise. The reaction mixture was stirred at room temperature overnight. EtOAc (20 mL) was added and the mixture was washed with brine (10 mL×2). The organic phase was dried over $Na_2SO_4$, filtered and concentrated to give the crude, which was purified by prep. HPLC (MeCN and $H_2O$ with 0.75% FA as mobile phase; from 63-93%) to provide tert-butyl 1-((4-methylcyclohexyl)methyl)-3-(trifluoromethyl)-4,5-dihydro-1H-pyrazolo[3,4-c]pyridine-6(7H)-carboxylate (350 mg, yield 60%) as a yellow oil. 1H NMR (400 MHz, Methanol-d4) δ: 4.58 (s, 2H), 4.00 (d, J=7.6 Hz, 1H), 3.90 (d, J=7.2 Hz, 1H), 3.65 (s, 2H), 2.65 (t, J=4.8 Hz, 2H), 2.04 (s, 1H), 1.71-1.56 (m, 3H), 1.54-1.49 (m, 9H), 1.43-1.38 (m, 4H), 0.98-0.88 (m, 5H).

Step 3

1-((4-Methylcyclohexyl)methyl)-3-(trifluoromethyl)-4,5,6,7-tetrahydro-1H-pyrazolo[3,4-c]pyridine hydrochloride

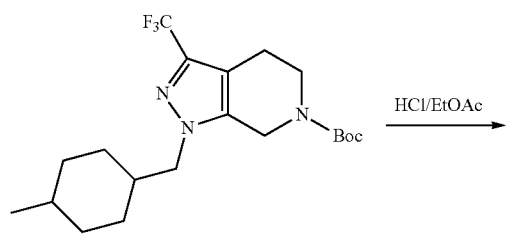

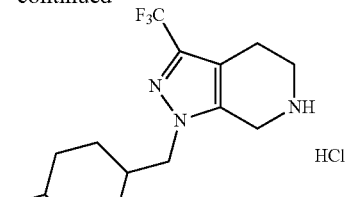

A mixture of tert-butyl 1-((4-methylcyclohexyl)methyl)-3-(trifluoromethyl)-4,5-dihydro-1H-pyrazolo[3,4-c]pyridine-6(7H)-carboxylate (300 mg, 0.75 mmol, 1.0 eq.) in HCl/EtOAc (4 mL) was stirred at room temperature for 2 h. LCMS showed the starting material was consumed completely. The solvent was removed in vacuum to give 1-((4-methylcyclohexyl)methyl)-3-(trifluoromethyl)-4,5,6,7-tetrahydro-1H-pyrazolo[3,4-c]pyridine hydrochloride (250 mg, yield 100%, crude), which was used in next step without further purification. $^1H$ NMR (400 MHz, DMSO-d6) δ: 9.83 (s, 2H), 4.33-4.32 (m, 2H), 4.04-3.92 (m, 2H), 2.79 (s, 2H), 1.95-1.87 (m, 2H), 1.62-1.59 (m, 2H), 1.46-1.23 (m, 5H), 0.90-0.80 (m, 4H). LCMS (ESI) m/z 301.9 [M+H]$^+$ Step 4 trans-Ethyl 4-(2-(1-((4-methylcyclohexyl)methyl)-3-(trifluoromethyl)-4,5-dihydro-1H-pyrazolo[3,4-c] pyridin-6(7H)-yl)-2-oxoethyl) cyclohexanecarboxylate A mixture of 2-trans-4-(ethoxycarbonyl)cyclohexyl)acetic acid (132 mg, 0.62 mmol, 1.0 eq.), HATU (178 mg, 0.74 mmol, 1.2 eq.), DIEA (478 mg, 3.70 mmol, 5.0 eq.) and 1-((4-methylcyclohexyl) methyl)-3-(trifluoromethyl)-4,5,6,7-tetrahydro-1H-pyrazolo[3,4-c]pyridine hydrochloride (250 mg, 0.74 mmol, 1.2 eq.) in DMF (5 mL) was stirred at room temperature overnight. EtOAc (20 mL) was added and the mixture was washed with brine (10 mL×2). The organic phase was dried over $Na_2SO_4$, filtered and concentrated to give the crude, which was purified by prep. HPLC (MeCN and $H_2O$ with 0.75% FA as mobile phase; from 57-87%) to provide trans-ethyl 4-(2-(1-((4-methyl cyclohexyl)methyl)-3-(trifluoromethyl)-4,5-dihydro-1H-pyrazolo[3,4-c]pyridin-6(7H)-yl)-2-oxoethyl) cyclohexanecarboxylate (180 mg, yield 58%) as a colorless oil. $^1H$ NMR (400 MHz, Methanol-d4) δ: 4.74-4.72 (m, 2H), 4.12-3.76 (m, 6H), 2.74-2.65 (m, 2H), 2.41 (d, J=6.8 Hz, 2H), 2.26-2.24 (m, 1H), 2.15-1.95 (m, 3H), 1.90-1.39 (m, 13H), 1.23 (t, J=7.2 Hz, 3H), 1.08-0.90 (m, 6H); LCMS (ESI) m/z 498.2 [M+H]$^+$ Example 1-50 trans-Ethyl 4-(2-(1-(2,4-difluorobenzyl)-3-(trifluoromethyl)-4,5-dihydro-1H-pyrazolo[3,4-c]pyridin-6(7H)-yl)-2-oxoethyl)cyclohexanecarboxylate

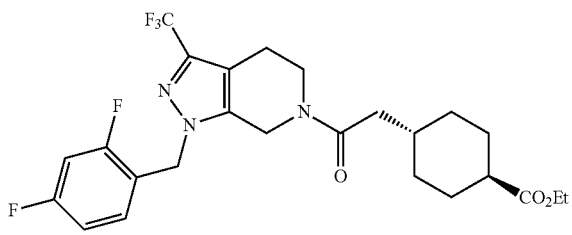 [SMILES: CCOC(=O)[C@H]1CC[C@H](CC(=O)N2CCc3c(C(F)(F)F)nn(Cc4ccc(F)cc4F)c3C2)CC1]

The title compound was synthesized according to the procedure described in Example 1-48, using 1-(bromomethyl)-2,4-difluorobenzene as a starting material. LCMS (ESI) m/z 514.1 [M+H]$^+$ Example 2-1 and 2-2 trans-Ethyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)cyclohexanecarboxylate and cis-Ethyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)cyclohexanecarboxylate To a solution of 2-(4-(ethoxycarbonyl)cyclohexyl)acetic acid (112 mg, 0.525 mmol) and HATU (200 mg, 0.525 mmol) in DMF (2 mL) was added 1-(4-chloro-2-fluorobenzyl)-3-(trifluoromethyl)-4,5,6,7-tetrahydro-1H-pyrazolo[3,4-c]pyridine hydrochloride (185 mg, 0.500 mmol), followed by N,N-diisopropylethylamine (348 µL, 2.00 mmol). The mixture was stirred at room temperature for 15 min. LC-MS shows mainly desired product. The mixture was partitioned between EtOAc and saturated NaHCO$_3$. The organic phase was washed with brine (×3), dried over MgSO$_4$, filtered and concentrated. It was purified by flash chromatography on silica gel column (EtOAc in heptane 20-40%) to collect less polar fractions as cis-ethyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)cyclohexanecarboxylate (68 mg, yield 26%), more polar fractions as trans-ethyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)cyclohexanecarboxylate (86 mg, yield 32%).

trans-isomer (Example 2-1): $^1$H NMR (400 MHz, Methanol-d4) δ 7.10-7.39 (m, 3H), 5.31-5.44 (m, 2H), 4.61-4.74 (m, 2H), 4.09 (q, J=7.19 Hz, 2H), 3.67-3.88 (m, 2H), 2.57-2.81 (m, 2H), 2.15-2.50 (m, 3H), 1.65-2.01 (m, 5H), 1.30-1.53 (m, 2H), 1.23 (t, J=7.03 Hz, 3H), 0.89-1.16 (m, 2H); LCMS (ESI) m/z 530.3 [M+H]$^+$ cis-isomer (Example 2-2): $^1$H NMR (400 MHz, Methanol-d4) δ 7.04-7.36 (m, 3H), 5.30-5.44 (m, 2H), 4.60-4.75 (m, 2H), 4.04-4.22 (m, 2H), 3.69-3.86 (m, 2H), 2.59-2.78 (m, 2H), 2.49-2.59 (m, 1H), 2.27-2.48 (m, 2H), 1.75-2.08 (m, 3H), 1.48-1.70 (m, 4H), 1.19-1.37 (m, 5H); LCMS (ESI) m/z 530.3 [M+H]$^+$

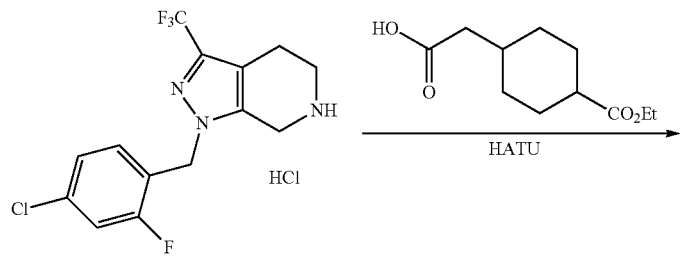

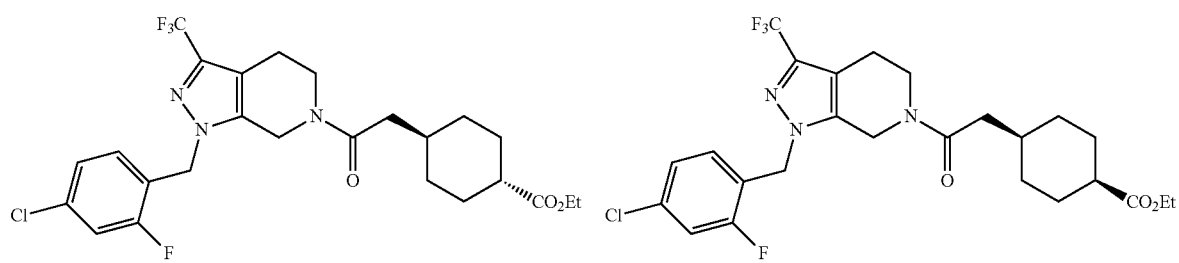

Example 2-3 and 2-4 trans-Ethyl 4-(2-(1-(3-chloro-5-fluorobenzyl)-3-(trifluoromethyl)-4,5-dihydro-1H-pyrazolo[3,4-c]pyridin-6(7H)-yl)-2-oxoethyl)cyclohexanecarboxylate and cis-ethyl 4-(2-(1-(3-chloro-5-fluorobenzyl)-3-(trifluoromethyl)-4,5-dihydro-1H-pyrazolo[3,4-c]pyridin-6(7H)-yl)-2-oxoethyl)cyclohexanecarboxylate

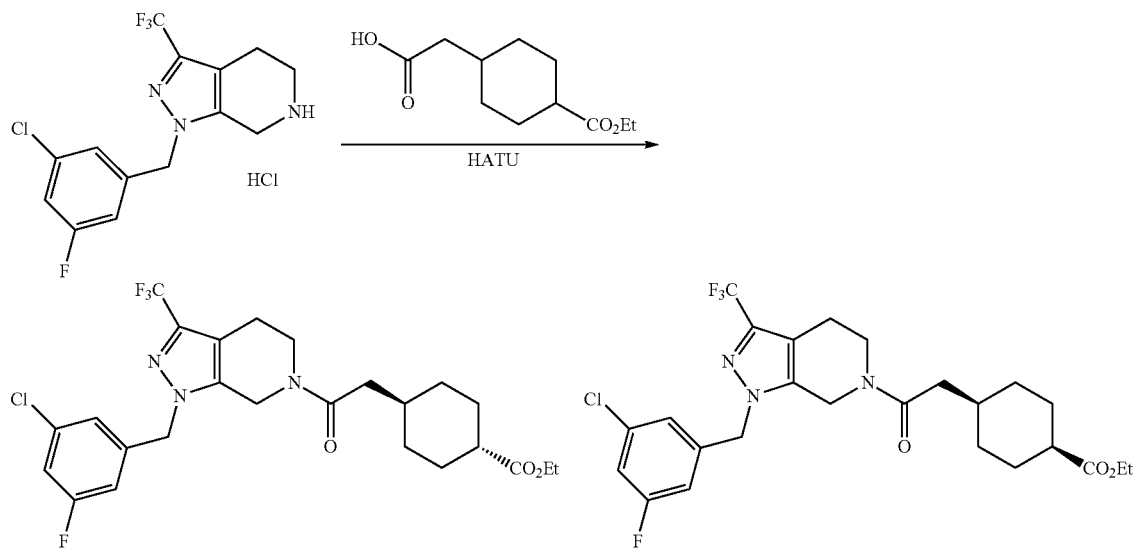

To a solution of HATU (114 mg, 0.300 mmol), 1-(3-chloro-5-fluorobenzyl)-3-(trifluoromethyl)-4,5,6,7-tetrahydro-1H-pyrazolo[3,4-c]pyridine hydrochloride (111 mg, 0.300 mmol), and 4-carboxymethyl-cyclohexanecarboxylic acid ethyl ester (64 mg, 0.30 mmol) in DMF (1.2 mL, 15 mmol) was added N,N-diisopropylethylamine (208 µL, 1.19 mmol). The mixture was stirred at room temperature for 30 min. The solution mixture was filtered and purified by prep HPLC (MeCN and H$_2$O with 0.1% (v/v) TFA as mobile phase) to collect peak 1 (69 mg, trans-isomer, yield 43%) and peak 2 (63 mg, cis-isomer, yield 40%):

trans-isomer (Example 2-3): $^1$H NMR $^1$H NMR (400 MHz, Methanol-d4) δ 7.02-7.26 (m, 2H), 6.84-7.00 (m, 1H), 5.27-5.43 (m, 2H), 4.53-4.67 (m, 2H), 4.00-4.18 (m, 2H), 3.66-3.85 (m, 2H), 2.60-2.85 (m, 2H), 2.08-2.46 (m, 3H), 1.52-2.03 (m, 5H), 1.15-1.49 (m, 5H), 0.81-1.15 (m, 2H); LCMS (ESI) m/z 530.3 [M+H]$^+$ cis-isomer (Example 2-4): $^1$H NMR (400 MHz, Methanol-d4) δ 7.13-7.28 (m, 1H), 6.90-7.11 (m, 1H), 6.79-6.96 (m, 1H), 5.29-5.48 (m, 2H), 4.54-4.70 (m, 2H), 4.01-4.22 (m, 2H), 3.68-3.86 (m, 2H), 2.62-2.82 (m, 2H), 2.47-2.61 (m, 1H), 2.19-2.45 (m, 2H), 1.85-2.12 (m, 3H), 1.47-1.70 (m, 4H), 1.12-1.36 (m, 5H)
LCMS (ESI) m/z 530.3 [M+H]$^+$

Example 3-1 cis-Methyl 4-(1-(4-chloro-2-fluorobenzyl)-3-(trifluoromethyl)-4,5,6,7-tetrahydro-1H-pyrazolo[3,4-c]pyridine-6-carboxamido)cyclohexanecarboxylate

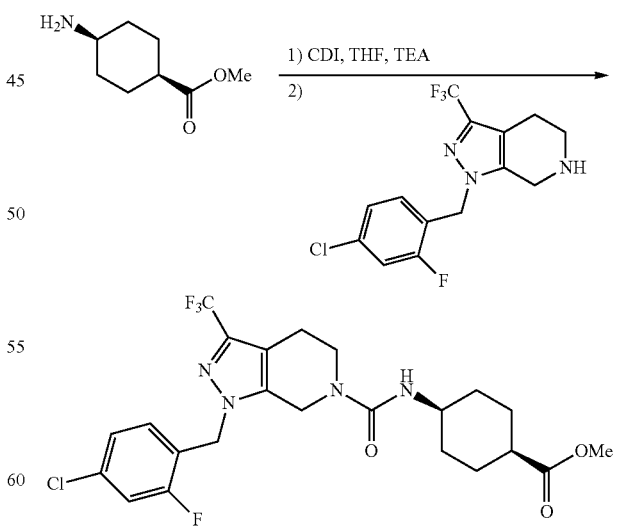

To a stirred mixture of cis-methyl 4-aminocyclohexanecarboxylate (80 mg, 0.51 mmol) and CDI (92 mg, 0.56 mmol) in THF (4 mL) was added TEA (50 mg, 0.51 mmol). The mixture was stirred at room temperature for 2 h.

1-(4-chloro-2-fluorobenzyl)-3-(trifluoromethyl)-4,5,6,7-tetrahydro-1H-pyrazolo[3,4-c]pyridine (282 mg, 0.77 mmol) was added, followed by TEA (50 mg, 0.51 mmol) with stirring at room temperature overnight. The reaction was quenched by brine (20 mL) and the mixture was extracted with EA (20 mL×2). The organic phase was dried over Na$_2$SO$_4$, filtered and concentrated to give the crude which was purified by prep. HPLC (MeCN and H$_2$O with 0.225% (v/v) HCOOH as mobile phase) to provide cis-methyl 4-(1-(4-chloro-2-fluorobenzyl)-3-(trifluoromethyl)-4,5,6,7-tetrahydro-1H-pyrazolo[3,4-c]pyridine-6-carboxamido)cyclohexanecarboxylate (220 mg, yield 85%) as a white solid. $^1$H NMR (400 MHz, Methanol-d4) δ: 7.31-7.23 (m, 2H), 7.15 (t, J=8.4 Hz, 1H), 5.37 (s, 2H), 4.56 (s, 2H), 3.70 (s, 3H), 3.65-3.62 (m, 3H), 2.69-2.61 (m, 3H), 2.08-2.07 (m, 2H), 1.73-1.51 (m, 6H); LCMS (ESI) m/z 539.0 [M+Na]$^+$ Example 3-2 trans-Methyl 4-(1-(4-chloro-2-fluorobenzyl)-3-(trifluoromethyl)-4,5,6,7-tetrahydro-1H-pyrazolo[3,4-c]pyridine-6-carboxamido)cyclohexanecarboxylate

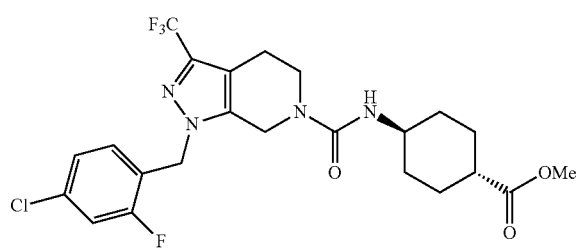 [SMILES: COC(=O)[C@H]1CC[C@H](NC(=O)N2CCc3c(C(F)(F)F)nn(Cc4ccc(Cl)cc4F)c3C2)CC1]

The title compound was synthesized according to the procedure described in Example 3-1, using trans-methyl 4-aminocyclohexanecarboxylate as a starting material, to obtain a white solid (yield 79%). $^1$H NMR (400 MHz, Methanol-d4) δ: 7.31-7.24 (m, 2H), 7.14 (t, J=8.4 Hz, 1H), 5.37 (s, 2H), 4.56 (s, 2H), 3.67 (s, 3H), 3.64 (t, J=5.6 Hz, 2H), 3.55-3.53 (m, 1H), 2.68 (t, J=5.2 Hz, 2H), 2.30-2.28 (m, 1H), 2.00 (t, J=14.4 Hz, 4H), 1.53-1.49 (m, 2H), 1.35-1.26 (m, 2H); LCMS m/z 517.1 [M+H]$^+$ Example 3-3 cis-Methyl 4-(1-(4-chloro-2-fluorobenzyl)-N-methyl-3-(trifluoromethyl)-4,5,6,7-tetrahydro-1H-pyrazolo[3,4-c]pyridine-6-carboxamido)cyclohexanecarboxylate

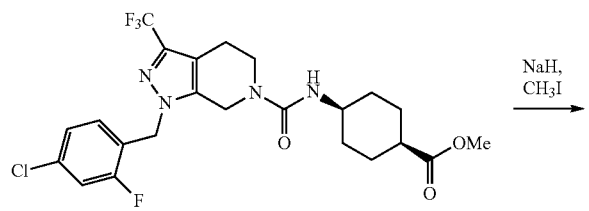

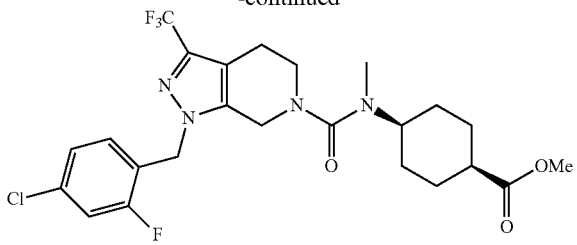

To a mixture of cis-methyl 4-(1-(4-chloro-2-fluorobenzyl)-3-(trifluoromethyl)-4,5,6,7-tetrahydro-1H-pyrazolo[3,4-c]pyridine-6-carboxamido)cyclohexanecarboxylate (206 mg, 0.4 mmol) in THF (5 mL) was added NaH (240 mg, 0.6 mmol) at room temperature and stirred for 15 min. Then MeI (113 mg, 0.8 mmol) was added and stirred for 10 hrs. The reaction was diluted with brine (20 mL) and the mixture was extracted with EA (20 mL×2). The organic phase was dried over Na$_2$SO$_4$, filtered and concentrated to give the crude which was purified by prep. HPLC (MeCN and H$_2$O with 0.225% (v/v) HCOOH as mobile phase) to provide cis-methyl4-(1-(4-chloro-2-fluorobenzyl)-N-methyl-3-(trifluoromethyl)-4,5,6,7-tetrahydro-1H-pyrazolo[3,4-c]pyridine-6-carboxamido)cyclohexanecarboxylate (20 mg, yield 9.4%) as a white solid. $^1$H NMR (400 MHz, Methanol-d4) δ 7.32-7.17 (m, 4H), 5.38 (s, 2H), 4.29 (s, 2H), 3.72 (s, 3H), 3.65-3.63 (m, 1H), 3.45-3.42 (m, 2H), 2.76-2.68 (m, 6H), 2.26-2.23 (m, 2H), 1.74-1.57 (m, 6H). LCMS (ESI) m/z 531.0 [M+H]$^+$ Example 3-4 trans-Methyl 4-(1-(4-chloro-2-fluorobenzyl)-N-methyl-3-(trifluoromethyl)-4,5,6,7-tetrahydro-1H-pyrazolo[3,4-c]pyridine-6-carboxamido)cyclohexanecarboxylate

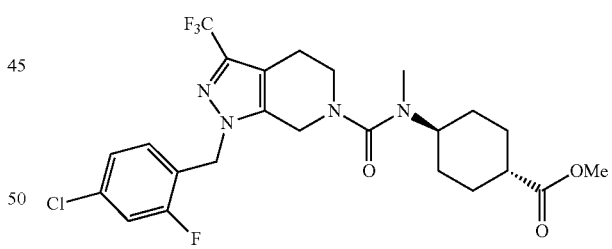

Step 1 trans-Methyl 4-((tert-butoxycarbonyl)amino)cyclohexanecarboxylate

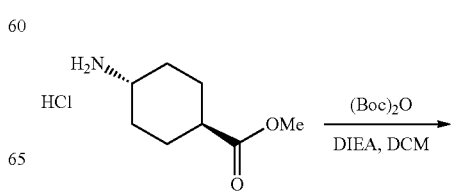

131

-continued

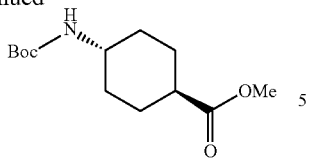

To a suspension of trans-methyl 4-aminocyclohexanecarboxylate hydrochloride (1.5 g, 7.7 mmol) in DCM (80 mL) was added DIEA (4 g, 31 mmol) and (Boc)$_2$O (3 g, 13.9 mmol) at room temperature. The reaction mixture was stirred at room temperature for 1 h. The reaction mixture was concentrated in vacuum to give crude product. The crude product was purified by silica gel chromatography (PE/EtOAc=8:1 to 3:1) to give trans-methyl 4-((tert-butoxycarbonyl)amino)cyclohexanecarboxylate (1.7 g, yield 86%) as a white solid. $^1$H NMR (400 MHz, Methanol-d4) δ 4.38 (br, 1H), 3.66 (s, 3H), 3.47-3.40 (m, 1H), 2.22-2.19 (m, 1H), 2.07-1.98 (m, 4H), 1.56-1.50 (m, 2H), 1.43 (s, 9H), 1.15-1.12 (m, 2H).

Step 2 trans-Methyl 4-((tert-butoxycarbonyl)(methyl)amino)cyclohexanecarboxylate

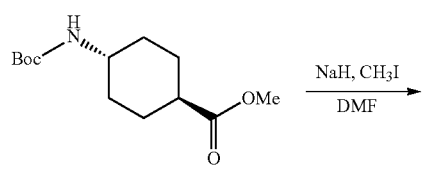

To a solution of trans-methyl 4-((tert-butoxycarbonyl)amino)cyclo hexanecarboxylate (1.7 g, 6.6 mmol) in DMF (50 mL) was added NaH (1.05 g, 26.4 mmol, 60% in mineral) at room temperature. The reaction mixture was stirred at room temperature for 1 h. Iodomethane (9.9 g, 69.7 mmol) was added into the reaction mixture and the reaction mixture was stirred at room temperature for 18 h. TLC (PE/EtOAc=4:1) showed the starting material has been consumed. The mixture was neutralized with HCl (2N) till pH~7. The reaction mixture was added into 100 mL of water. The aqueous was extracted with EtOAc (70 mL×2). The combined organic layers were dried over anhydrous Na$_2$SO$_4$ and concentrated in vacuum to give trans-methyl 4-((tert-butoxycarbonyl)(methyl)amino)cyclo hexanecarboxylate (1.3 g, yield 72%) as a colorless oil.

132

Step 3 trans-Methyl 4-(methylamino)cyclohexanecarboxylate hydrochloride

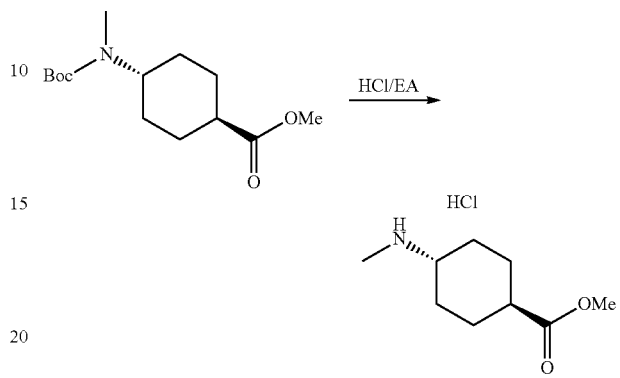

trans-Methyl 4-(methylamino)cyclohexanecarboxylate hydrochloride (1.3 g, 4.7 mmol) was added into a solution of 4N HCl in EtOAc (25 mL) at room temperature. The reaction mixture was stirred at room temperature for 3 h. The suspension was filtered and the filter cake was dried to give trans-methyl 4-(methylam ino)cyclohexanecarboxylate hydrochloride (860 mg, yield 88%) as a white solid. $^1$H NMR (400 MHz, Methanol-d4) δ: 3.65 (s, 3H), 3.06-3.01 (m, 1H), 2.67 (s, 3H), 2.38-2.32 (m, 1H), 2.18-2.09 (m, 4H), 1.54-1.39 (m, 4H)

Step 4 trans-Methyl 4-(1-(4-chloro-2-fluorobenzyl)-N-methyl-3-(trifluoromethyl)-4,5,6,7-tetrahydr o-1H-pyrazolo[3,4-c]pyridine-6-carboxamido)cyclohexanecarboxylate

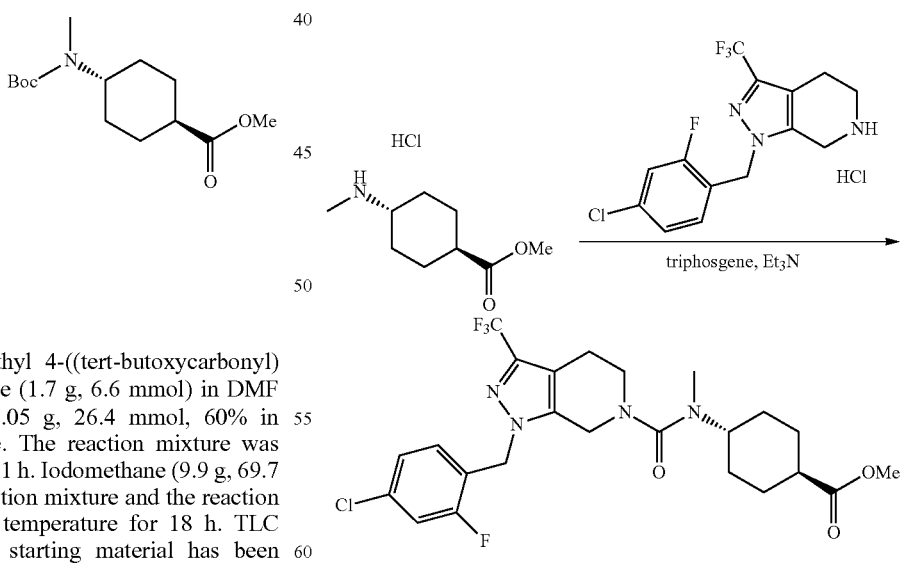

To a solution of triphosgene (33 mg, 0.11 mmol) in DCM (2 mL) was added a solution of Et$_3$N (67 mg, 0.66 mmol) and trans-methyl 4-(methylamino)cyclohexanecar boxylate hydrochloride (68 mg, 0.33 mmol) at 0° C. The reaction mixture was stirred at 0° C. for 2 h. A solution of 1-(4-chloro-2-fluorobenzyl)-3-(trifluo romethyl)-4,5,6,7-tetrahy dro-1H-pyrazolo[3,4-c]pyridine hydrochloride (100 mg, 0.27 mmol) and Et₃N (51 mg, 0.5 mmol) in DCM (3 mL) was added into the reaction mixture. The reaction mixture was allowed to room temperature slowly with stirring for 20 h. LCMS showed the starting material has been consumed. The reaction mixture was concentrated in vacuum to give crude product. The crude product was purified by pre-HPLC (MeCN and H₂O with 0.05% (v/v) HCl as mobile phase) to give trans-methyl 4-(1-(4-chloro-2-fluorobenzyl)-N-methyl-3-(trifluoro methyl)-4,5,6,7-tetrahy dro-1H-pyrazolo[3,4-c] pyridine-6-carboxamido)cyclohexane carboxylate (60 mg, yield 42%) as a white solid. ¹H NMR (400 MHz, CDCl₃) δ 7.20-7.12 (m, 3H), 5.31 (s, 2H), 4.23 (s, 2H), 3.74 (s, 3H), 3.73-3.71 (m, 1H), 3.41 (t, J=5.6 Hz, 2H), 2.82 (s, 5H), 2.29-2.27 (m, 1H), 2.14-2.12 (m, 2H), 1.87-1.86 (m, 2H), 1.67-1.61 (m, 4H); LCMS (ESI) m/z 531.1 [M+H]⁺

Example 4-1

4-(Ethoxycarbonyl)cyclohexyl1-(4-chloro-2-fluorobenzyl)-3-(trifluoromethyl)-4,5-dihydro-1H-pyrazolo[3,4-c]pyridine-6(7H)-carboxylate

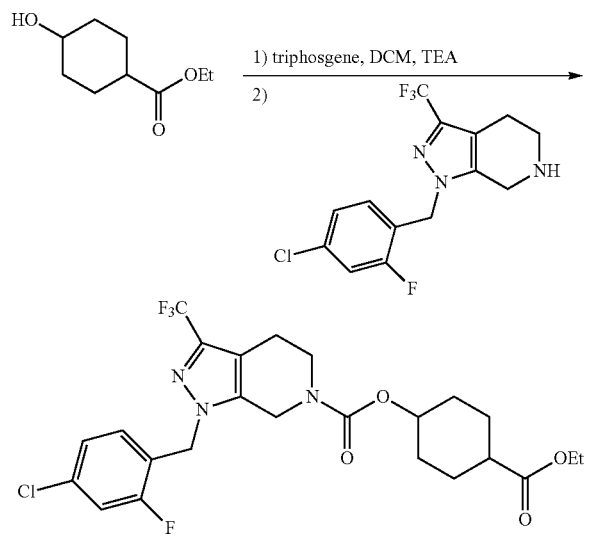

To a stirred mixture of ethyl 4-hydroxycyclohexanecarboxylate (52 mg, 0.3 mmol) and triphosgene (45 mg, 0.15 mmol) in DCM (2 mL) was added TEA (30 mg, 0.3 mmol). The mixture was stirred at room temperature for 3 h. 1-(4-chloro-2-fluorobenzyl)-3-(trifluoromethyl)-4,5,6,7-tetrahydro-1H-pyrazolo[3,4-c]pyridine (110 mg, 0.3 mmol) was added, and followed by TEA (30 mg, 0.3 mmol, 1.0 eq) with stirring at room temperature overnight. The solvent was removed in vacuum and the crude was purified by prep. HPLC (MeCN and H₂O with 0.225% (v/v) HCOOH as mobile phase) to provide 4-(ethoxycarbonyl)cyclohexyl 1-(4-chloro-2-fluorobenzyl)-3-(trifluoromethyl)-4,5-dihydro-1H-pyrazolo[3,4-c]pyridine-6(7H)-carboxylate (90 mg, yield 62%) as a white solid. ¹H NMR (400 MHz, Methanol-d4) δ: 7.30-7.15 (m, 3H), 5.36 (s, 2H), 4.60-4.57 (m, 3H), 4.14-4.08 (m, 2H), 3.69-3.67 (m, 2H), 2.67-2.66 (m, 2H), 2.44-2.34 (m, 1H), 2.00-1.22 (m, 11H); LCMS (ESI) m/z 531.9 [M+H]⁺

Example 5-1 trans-4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)cyclohexanecarboxylic acid

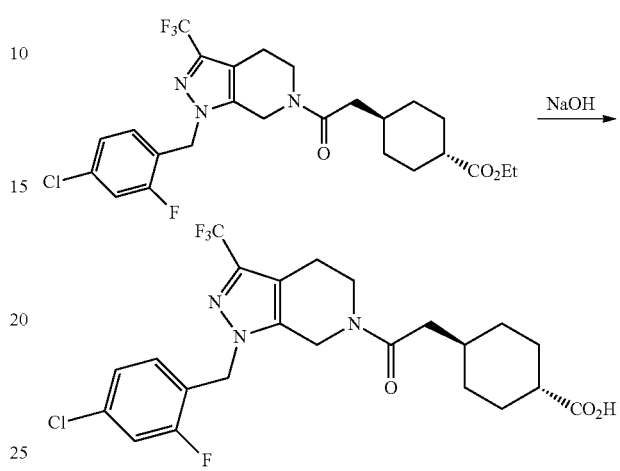

To a solution of trans-ethyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)cyclohexanecarboxylate (85 mg, 0.16 mmol) in THF (1 mL) and MeOH (1 mL) was added 3 M of NaOH (0.2 mL, 0.6 mmol), the mixture was stirred at 50° C. for 1 h. LC-MS shows the reaction was completed. It was acidified by adding 2N HCl, purified by prep HPLC (MeCN and H₂O with 0.1% TFA as mobile phase; from 10-90%) to get trans-4-(2-(1-(4-chloro-2-fluorobenzyl)-3-(trifluoromethyl)-4,5-dihydro-1H-pyrazolo[3,4-c]pyridin-6(7H)-yl)-2-oxoethyl)cyclohexanecarboxylic acid as a white powder after lyophilization (62 mg, yield 77%). ¹H NMR (400 MHz, Methanol-d4) δ 7.03-7.39 (m, 3H), 5.30-5.46 (m, 2H), 4.54-4.77 (m, 2H), 3.66-3.88 (m, 2H), 2.56-2.80 (m, 2H), 2.12-2.44 (m, 3H), 1.59-2.06 (m, 5H), 1.29-1.53 (m, 2H), 0.87-1.20 (m, 2H); LCMS (ESI) m/z 502.3 [M+H]⁺

Example 5-2 cis-4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)cyclohexanecarboxylic acid

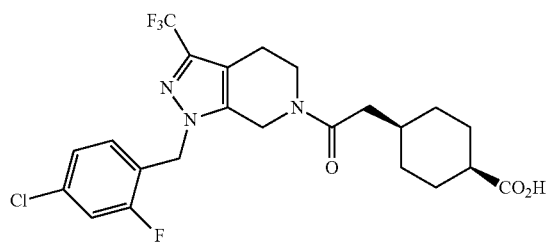 [SMILES: O=C(C[C@H]1CC[C@@H](C(=O)O)CC1)N1CCc2c(C(F)(F)F)nn(Cc3ccc(Cl)cc3F)c2C1]

The title compound was synthesized according to the procedure described in Example 5-1, using Example 2-2 as a starting material, to obtain a white solid (51 mg, yield 80%). ¹H NMR (400 MHz, Methanol-d4) δ: 7.11-7.35 (m, 3H), 5.23-5.45 (m, 2H), 4.63-4.74 (m, 2H), 3.63-3.89 (m, 2H), 2.59-2.81 (m, 2H), 2.49-2.59 (m, 1H), 2.26-2.46 (m, 2H), 1.72-2.10 (m, 3H), 1.49-1.70 (m, 4H), 1.22-1.40 (m, 2H); LCMS m/z 502.3 [M+H]+

Example 5-3 trans-4-(2-(1-(3-chloro-5-fluorobenzyl)-3-(trifluoromethyl)-4,5-dihydro-1H-pyrazolo[3,4-c]pyridin-6(7H)-yl)-2-oxoethyl)cyclohexanecarboxylic acid

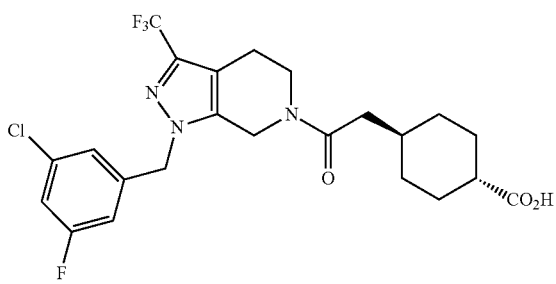 [SMILES: O=C(C[C@H]1CC[C@H](C(=O)O)CC1)N1CCc2c(C(F)(F)F)nn(Cc3cc(F)cc(Cl)c3)c2C1]

The title compound was synthesized according to the procedure described in Example 5-1, using Example 2-3 as a starting material, to obtain a white solid (37 mg, yield 60%). 1H NMR (400 MHz, Methanol-d4) δ: 6.81-7.30 (m, 3H), 5.28-5.44 (m, 2H), 4.51-4.69 (m, 2H), 3.71-3.87 (m, 2H), 2.61-2.80 (m, 2H), 2.08-2.45 (m, 3H), 1.59-2.05 (m, 5H), 1.23-1.51 (m, 2H), 0.83-1.17 (m, 2H); LCMS m/z 502.3 [M+H]+

Example 5-4 cis-4-(2-(1-(3-chloro-5-fluorobenzyl)-3-(trifluoromethyl)-4,5-dihydro-1H-pyrazolo[3,4-c]pyridin-6(7H)-yl)-2-oxoethyl)cyclohexanecarboxylic acid

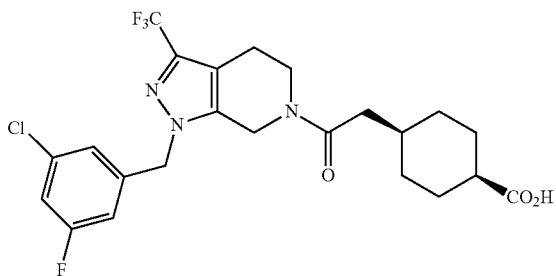 [SMILES: O=C(C[C@H]1CC[C@@H](C(=O)O)CC1)N1CCc2c(C(F)(F)F)nn(Cc3cc(F)cc(Cl)c3)c2C1]

The title compound was synthesized according to the procedure described in Example 5-1, using Example 2-4 as a starting material, to obtain a white solid (27 mg, yield 47%). 1H NMR (400 MHz, Methanol-d4) δ: 6.80-7.26 (m, 3H), 5.25-5.45 (m, 2H), 4.54-4.67 (m, 2H), 3.71-3.85 (m, 2H), 2.60-2.81 (m, 2H), 2.48-2.60 (m, 1H), 2.21-2.46 (m, 2H), 1.72-2.10 (m, 3H), 1.43-1.70 (m, 4H), 1.16-1.37 (m, 2H); LCMS m/z 502.2 [M+H]+

Example 5-5

4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)benzoic acid

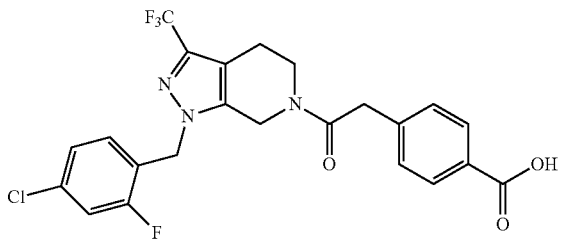 [SMILES: O=C(O)c1ccc(CC(=O)N2CCc3c(C(F)(F)F)nn(Cc4ccc(Cl)cc4F)c3C2)cc1]

The title compound was synthesized according to the procedure described in Example 5-1, using Example 1-11 as a starting material, to obtain a white solid (47 mg, yield 77%). 1H NMR (400 MHz, Methanol-d4) δ: 7.89-8.01 (m, 2H), 6.97-7.43 (m, 5H), 5.20-5.40 (m, 2H), 4.54-4.77 (m, 2H), 3.67-4.02 (m, 4H), 2.51-2.77 (m, 2H); LCMS m/z 496.1 [M+H]+

Example 5-6 cis-4-(1-(4-chloro-2-fluorobenzyl)-3-(trifluoromethyl)-4,5,6,7-tetrahydro-1H-pyrazolo[3,4-c]pyridine-6-carboxamido)cyclohexanecarboxylic acid

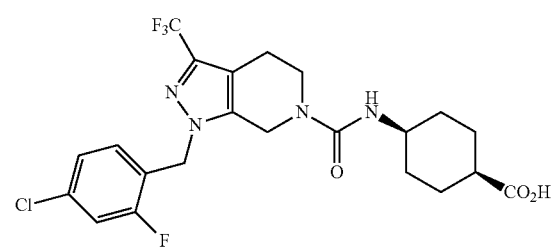 [SMILES: O=C(N[C@H]1CC[C@@H](C(=O)O)CC1)N1CCc2c(C(F)(F)F)nn(Cc3ccc(Cl)cc3F)c2C1]

The title compound was synthesized according to the procedure described in Example 5-1, using Example 3-1 as a starting material, to obtain a white solid (yield 31%). 1H NMR (400 MHz, Methanol-d4) δ: 7.31-7.23 (m, 2H), 7.15 (t, J=8.0 Hz, 1H), 5.37 (s, 2H), 4.56 (s, 2H), 3.65-3.63 (m, 3H), 2.68 (t, J=6.0 Hz, 2H), 2.57-2.56 (m, 1H), 2.11-2.05 (m, 2H), 1.73-1.55 (m, 6H); LCMS m/z 525.0 [M+Na]+

Example 5-7 trans-4-(1-(4-Chloro-2-fluorobenzyl)-3-(trifluoromethyl)-4,5,6,7-tetrahydro-1H-pyrazolo[3,4-c]pyridine-6-carboxamido)cyclohexanecarboxylic acid

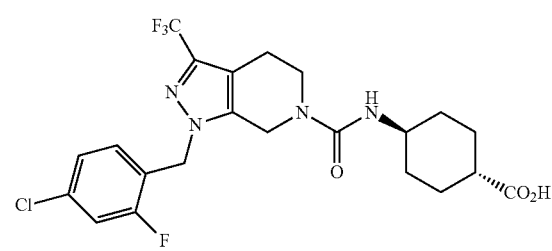 [SMILES: O=C(N[C@H]1CC[C@H](C(=O)O)CC1)N1CCc2c(C(F)(F)F)nn(Cc3ccc(Cl)cc3F)c2C1]

The title compound was synthesized according to the procedure described in Example 5-1, using Example 3-2 as a starting material, to obtain a white solid (yield 35%). ¹H NMR (400 MHz, Methanol-d4) δ: 7.31-7.24 (m, 2H), 7.14 (t, J=8.0 Hz, 1H), 6.47-6.45 (m, 0.3H), 5.37 (s, 2H), 4.57 (s, 2H), 3.64 (t, J=5.6 Hz, 2H), 3.55-3.54 (m, 1H), 2.68 (t, J=5.6 Hz, 2H), 2.24-2.23 (m, 1H), 2.05-1.97 (m, 4H), 1.53-1.50 (m, 2H), 1.33-1.29 (m, 2H); LCMS m/z 503.0 [M+H]⁺

Example 5-8

4-(1-(4-Chloro-2-fluorobenzyl)-3-(trifluoromethyl)-4,5,6,7-tetrahydro-1H-pyrazolo[3,4-c]pyridine-6-carboxamido)bicyclo[2.2.2]octane-1-carboxylic acid

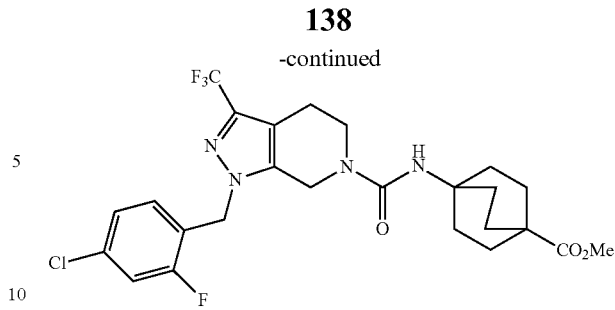

To a suspension of methyl 4-aminobicyclo[2.2.2]octane-1-carboxylate hydrochloride (70 mg, 0.31 mmol, 1 eq) in DCM (6 mL) was added DIEA (160 mg, 1.24 mmol, 4 eq) and CDI (51 mg, 0.31 mmol, 1 eq) at room temperature. The reaction mixture was stirred at 40° C. for 5 h. Compound 1-(4-chloro-2-fluorobenzyl)-3-(trifluoromethyl)-4,5,6,7-tetrahydro-1H-pyrazolo[3,4-c]pyridine hydrochloride (114 mg, 0.31 mmol, 1 eq) was added into the reaction mixture. The reaction mixture was stirred at 40° C. for 12 h. The reaction mixture was concentrated in vacuum to give crude product. The crude product was purified by pre-HPLC (MeCN and H₂O with 0.05% NH₃H₂O as mobile phase) to give methyl 4-(1-(4-chloro-2-fluorobenzyl)-3-(trifluoromethyl)-4,5,6,7-tetrahydro-1H-pyrazolo[3,4-c]pyridine-6-carboxamido)bicyclo[2.2.2]octane-1-carboxylate (29 mg, yield 17%) as a white solid. LCMS (ESI) m/z 543.0 [M+H]⁺

Step 1

Methyl 4-(1-(4-chloro-2-fluorobenzyl)-3-(trifluoromethyl)-4,5,6,7-tetrahydro-1H-pyrazolo[3,4-c]pyridine-6-carboxamido)bicyclo[2.2.2]octane-1-carboxylate

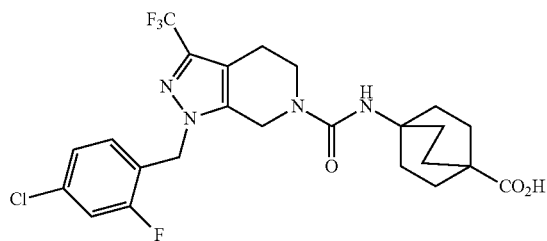 [SMILES: O=C(NC12CCC(C(=O)O)(CC1)CC2)N1CCc2c(C(F)(F)F)nn(Cc3ccc(Cl)cc3F)c2C1]

Step 2

4-(1-(4-chloro-2-fluorobenzyl)-3-(trifluoromethyl)-4,5,6,7-tetrahydro-1H-pyrazolo[3,4-c]pyridine-6-carboxamido)bicyclo[2.2.2]octane-1-carboxylic acid

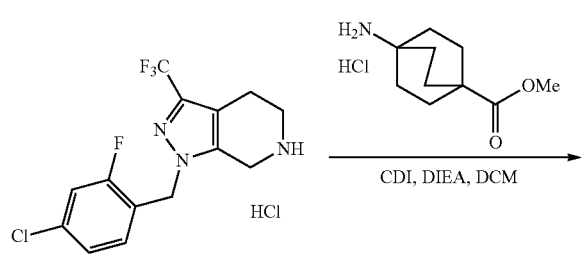

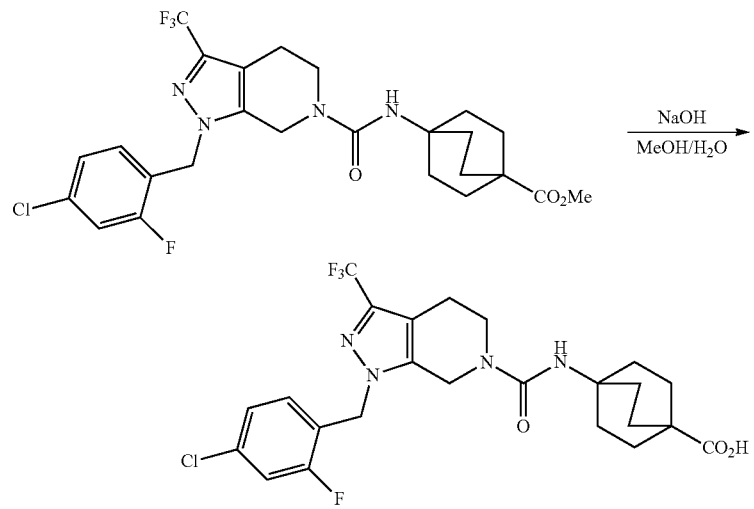

To a solution of compound 4-(1-(4-chloro-2-fluorobenzyl)-3-(trifluoromethyl)-4,5,6,7-tetrahydro-1H-pyrazolo[3,4-c]pyridine-6-carboxamido)bicyclo[2.2.2]octane-1-carboxylate (25 mg, 0.046 mmol, 1 eq) in methanol (2 mL) was added a solution of NaOH (19 mg, 0.46 mmol, 10 eq) in water (0.2 mL) at room temperature. The reaction mixture was stirred at room temperature for 12 h. LCMS showed the starting material has been consumed. The reaction mixture was neutralized with 2N HCl till pH ~7 and concentrated in vacuum to give crude product. The crude product was purified by pre-HPLC (MeCN and H$_2$O with 0.05% NH$_3$H$_2$O as mobile phase) to give 4-(1-(4-chloro-2-fluorobenzyl)-3-(trifluoromethyl)-4,5,6,7-tetrahydro-1H-pyrazolo[3,4-c]pyridine-6-carboxamido)bicyclo[2.2.2]octane-1-carboxylic acid as a white solid (14 mg, yield 58%). $^1$H NMR (400 MHz, Methanol-d4) δ: 7.26 (d, J=5.6 Hz, 1H), 7.21 (d, J=8.4 Hz, 1H), 7.09 (t, J=8.4 Hz, 1H), 5.33 (s, 2H), 4.45 (s, 2H), 3.55 (br, 2H), 2.63 (br, 2.0H), 1.88 (br, 12H). LCMS (ESI) m/z 529.1 [M+H]$^+$ Example 5-9 cis-4-(1-(4-Chloro-2-fluorobenzyl)-N-methyl-3-(trifluoromethyl)-4,5,6,7-tetrahydro-1H-pyrazolo[3,4-c]pyridine-6-carboxamido)cyclohexanecarboxylic acid

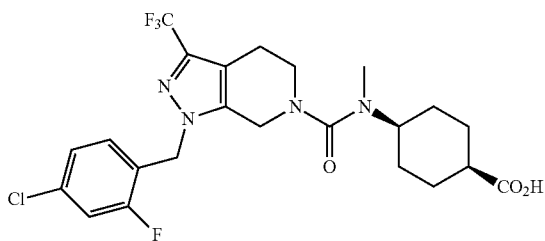 [SMILES: CN(C(=O)N1CCc2c(C(F)(F)F)nn(Cc3ccc(Cl)cc3F)c2C1)[C@H]1CC[C@@H](C(=O)O)CC1]

The title compound was synthesized according to the procedure described in Example 5-1, using Example 3-3 as a starting material, to obtain a white solid (yield 59%). $^1$H NMR (400 MHz, Methanol-d4) δ: 7.29-7.15 (m, 3H), 5.36 (s, 2H), 4.28 (s, 2H), 3.61-3.58 (m, 2H), 3.41-3.01 (m, 2H), 2.78-2.62 (m, 6H), 2.24-2.15 (m, 2H), 1.17-1.55 (m, 6H); LCMS m/z 539.0 [M+Na]$^+$ Example 5-10 trans-4-(1-(4-Chloro-2-fluorobenzyl)-N-methyl-3-(trifluoromethyl)-4,5,6,7-tetrahydro-1H-pyrazolo[3,4-c]pyridine-6-carboxamido)cyclohexanecarboxylic acid

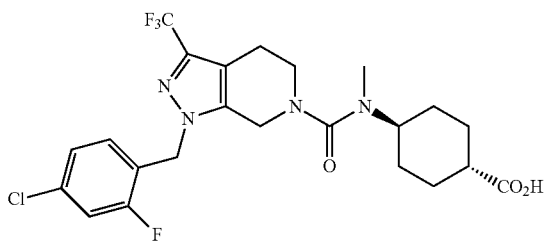 [SMILES: CN(C(=O)N1CCc2c(C(F)(F)F)nn(Cc3ccc(Cl)cc3F)c2C1)[C@H]1CC[C@H](C(=O)O)CC1]

The title compound was synthesized according to the procedure described in Example 5-1, using Example 3-4 as a starting material, to obtain a white solid (yield 77%). $^1$H NMR (400 MHz, Methanol-d4) δ: 7.27 (dd, J=9.6 Hz, J=1.6 Hz, 1H), 7.22 (d, J=8.4 Hz, 1H), 7.15 (t, J=8.4 Hz, 1H), 5.34 (s, 2H), 4.26 (s, 2H), 3.59-3.53 (m, 1H), 3.40 (t, J=5.6 Hz, 2H), 2.77 (s, 3H), 2.72 (br, 2H), 2.24-2.21 (m, 1H), 2.07-2.02 (m, 2H), 1.74-1.72 (m, 2H), 1.63-1.57 (m, 2H), 1.53-1.48 (m, 2H); LCMS m/z 517.1 [M+H]$^+$ Example 5-11

4-(1-(4-Fluorobenzyl)-3-(trifluoromethyl)-4,5,6,7-tetrahydro-1H-pyrazolo[3,4-c]pyridine-6-carbonyl)bicyclo[2.2.2]octane-1-carboxylic acid

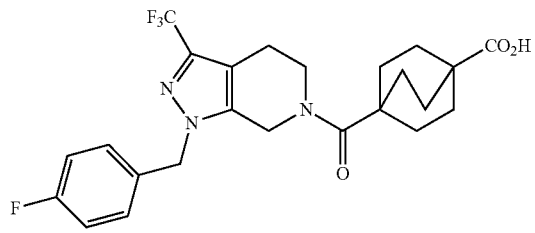 [SMILES: O=C(O)C12CCC(C(=O)N3CCc4c(C(F)(F)F)nn(Cc5ccc(F)cc5)c4C3)(CC1)CC2]

The title compound was synthesized according to the procedure described in Example 5-1, using Example 1-23 as a starting material, to obtain a white solid (yield 83%). $^1$H NMR (400 MHz, Methanol-d4) δ: 7.27-7.24 (m, 2H), 7.12-7.08 (m, 2H), 5.33 (s, 2H), 4.57 (s, 2H), 3.93 (s, 2H), 2.68 (s, 2H), 1.79 (m, 12H); LCMS m/z 480.0 [M+H]$^+$ Example 5-12

4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)bicyclo[2.2.2]octane-1-carboxylic acid

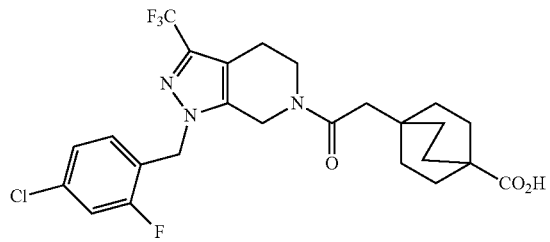 [SMILES: O=C(CC12CCC(C(=O)O)(CC1)CC2)N1CCc2c(C(F)(F)F)nn(Cc3ccc(Cl)cc3F)c2C1]

Step 1

Methyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)bicyclo[2.2.2]octane-1-carboxylate

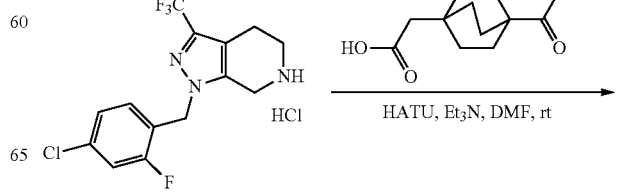

-continued

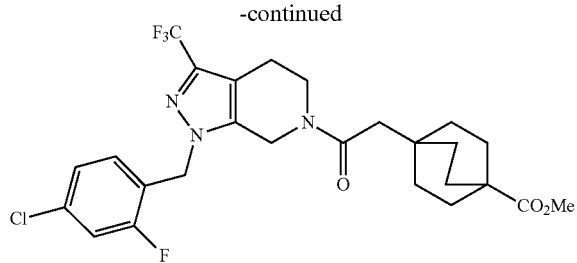

Into a stirred solution of 1-(4-chloro-2-fluorobenzyl)-3-(trifluoromethyl)-4,5,6,7-tetrahydro-1H-pyrazolo[3,4-c]pyridine hydrochloride (100 mg, 0.3 mmol, 1.0 eq), 2-(4-(methoxycarbonyl)bicyclo[2.2.2]octan-1-yl)acetic acid (Intermediate 5-1, 136 mg, 0.6 mmol, 2.0 eq) and HATU (172 mg, 0.45 mmol, 1.5 eq) in DMF (3 mL) was added Et$_3$N (95 mg, 0.9 mmol, 3.0 eq). The mixture was stirred at rt for 2 h and then directly purified by reverse phase HPLC (MeCN and H$_2$O with 0.05% TFA as mobile phase) to give 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)bicyclo[2.2.2]octane-1-carboxylate (118 mg, yield 73%) as a yellow solid. LCMS (ESI) m/z 542.2 [M+H]$^+$ Step 2

4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)bicyclo[2.2.2]octane-1-carboxylic acid

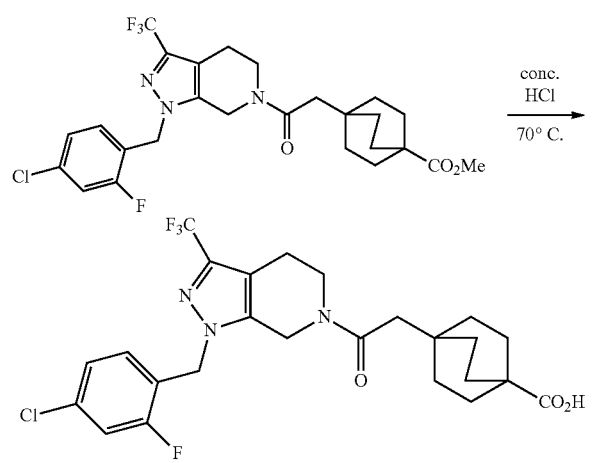

A mixture of methyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)bicyclo[2.2.2]octane-1-carboxylate (118 mg, 0.2 mmol, 1.0 eq) and con. HCl (2 mL) was stirred at 70° C. for 20 h and concentrated. The residue was purified by reverse phase HPLC (MeCN and H$_2$O with 0.05% TFA as mobile phase) to give 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)bicyclo[2.2.2]octane-1-carboxylic acid (57 mg, yield 50%) as white solid. $^1$H NMR (400 MHz, Methanol-d4) δ: 7.27-7.07 (m, 3H), 5.33-5.27 (m, 2H), 4.60-4.56 (m, 2H), 3.72-3.67 (m, 2H), 2.64-2.53 (m, 2H), 2.24-2.11 (m, 2H), 1.72-1.51 (m, 10H), 1.36-1.32 (m, 2H); LCMS (ESI) m/z 528.2 [M+H]$^+$ Example 5-13

4-(2-(1-(4-Fluorobenzyl)-3-(trifluoromethyl)-4,5-dihydro-1H-pyrazolo[3,4-c]pyridin-6(7H)-yl)-2-oxoethyl)bicyclo[2.2.2]octane-1-carboxylic acid

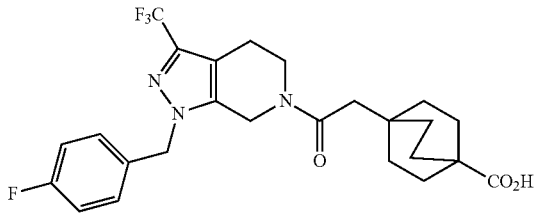 [SMILES: O=C(CC12CCC(C(=O)O)(CC1)CC2)N1CCc2c(C(F)(F)F)nn(Cc3ccc(F)cc3)c2C1]

The title compound was synthesized according to the procedure described in Example 5-12, using Intermediate 2-2 as a starting material, to obtain a white solid (yield 45%). $^1$H NMR (400 MHz, Methanol-d4) δ: 7.35-7.26 (m, 2H), 7.20-7.08 (m, 2H), 5.38-5.33 (m, 2H), 4.61-4.55 (m, 2H), 3.79-3.75 (m, 2H), 2.74-2.63 (m, 2H), 2.33-2.12 (m, 2H), 1.81-1.59 (m, 10H), 1.37-1.32 (m, 2H); LCMS m/z 494.1 [M+H]$^+$ Example 5-14 trans-4-(2-(1-(4-Methylbenzyl)-3-(trifluoromethyl)-4,5-dihydro-1H-pyrazolo[3,4-c]pyridin-6(7H)-yl)-2-oxoethyl)cyclohexanecarboxylic acid

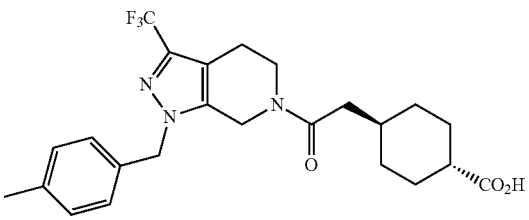 [SMILES: Cc1ccc(Cn2nc(C(F)(F)F)c3c2CN(C(=O)C[C@H]2CC[C@H](C(=O)O)CC2)CC3)cc1]

The title compound was synthesized according to the procedure described in Example 5-1, using Example 1-25 as a starting material, to obtain a white solid (yield 38%). $^1$H NMR (400 MHz, Methanol-d4) δ: 7.21-7.07 (m, 4H), 5.32-5.28 (m, 2H), 4.55-4.47 (m, 2H), 3.76-3.69 (m, 2H), 2.71-2.61 (m, 2H), 2.36-2.30 (m, 3H), 2.23-2.12 (m, 1H), 2.09-1.94 (m, 2H), 1.84-1.75 (m, 3H), 1.60-1.27 (m, 4H), 1.07-1.04 (m, 1H), 0.83-0.80 (m, 1H); LCMS m/z 464.2 [M+H]$^+$ Example 5-15 trans-4-(2-(1-(4-Methoxylbenzyl)-3-(trifluoromethyl)-4,5-dihydro-1H-pyrazolo[3,4-c]pyridin-6(7H)-yl)-2-oxoethyl)cyclohexanecarboxylic acid

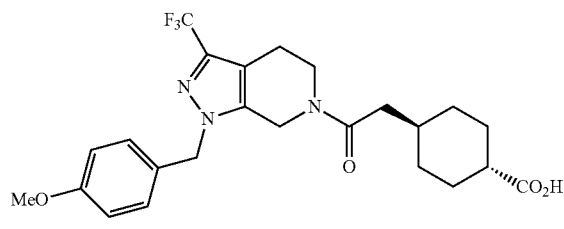 [SMILES: COc1ccc(Cn2nc(C(F)(F)F)c3c2CN(C(=O)C[C@H]2CC[C@H](C(=O)O)CC2)CC3)cc1]

The title compound was synthesized according to the procedure described in Example 5-1, using Example 1-26 as a starting material, to obtain a white solid (yield 30%). ¹H NMR (400 MHz, Methanol-d4) δ: 7.20-7.15 (m, 2H), 6.95-6.88 (m, 2H), 5.29-5.25 (m, 2H), 4.56-4.47 (m, 2H), 3.77-3.68 (m, 5H), 2.70-2.61 (m, 2H), 2.36-2.35 (m, 1H), 2.19-2.11 (m. 1H), 2.09-2.08 (m, 1H), 1.95-1.78 (m, 3H), 1.75-1.45 (m, 2H), 1.42-1.27 (m, 2H), 1.09-1.04 (m, 2H), 0.81-0.78 (m, 1H); LCMS m/z 480.2 [M+H]⁺

Example 5-16 trans-4-(2-Oxo-2-(1-phenethyl-3-(trifluoromethyl)-4,5-dihydro-1H-pyrazolo[3,4-c]pyridin-6(7H)-yl)ethyl)cyclohexanecarboxylic acid

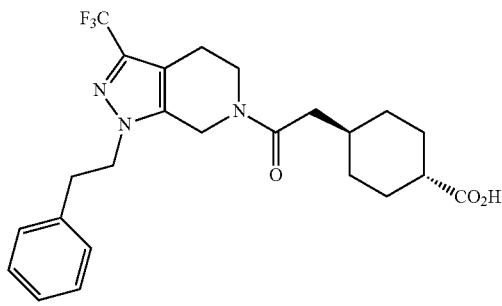 [SMILES: O=C(C[C@H]1CC[C@H](C(=O)O)CC1)N1CCc2c(C(F)(F)F)nn(CCc3ccccc3)c2C1]

The title compound was synthesized according to the procedure described in Example 5-1, using Example 1-28 as a starting material, to obtain a white solid (yield 65%). ¹H NMR (400 MHz, CDCl₃) δ: 7.27-7.15 (m, 3H), 6.95 (d, J=6.0 Hz, 2H), 4.33-4.23 (m, 2H), 4.00-3.90 (m, 2H), 3.61-3.52 (m, 2H), 3.09 (q, J=6.8 Hz, 2H), 2.62-2.53 (m, 2H), 2.30 (d, J=7.2 Hz, 1H), 2.24-2.15 (m, 1H), 2.03 (d, J=6.8 Hz, 1H), 1.95 (d, J=12.8 Hz, 2H), 1.82-1.64 (m, 3H), 1.39 (q, J=13.2 Hz, 2H), 1.09-0.95 (m, 2H); LCMS m/z 464.0 [M+H]⁺

Example 5-17 trans-4-(2-(1-((5-chlorothiophen-2-yl)methyl)-3-(trifluoromethyl)-4,5-dihydro-1H-pyrazolo[3,4-c]pyridin-6(7H)-yl)-2-oxoethyl)cyclohexanecarboxylic acid

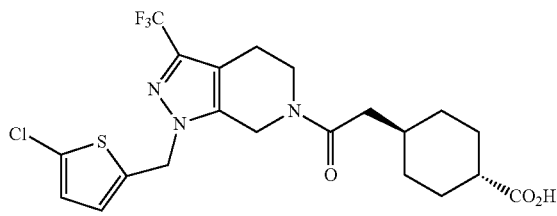 [SMILES: O=C(C[C@H]1CC[C@H](C(=O)O)CC1)N1CCc2c(C(F)(F)F)nn(Cc3ccc(Cl)s3)c2C1]

The title compound was synthesized according to the procedure described in Example 5-1, using Intermediate 2-12 as a starting material, to obtain a white solid (yield 63% over two steps). ¹H NMR (400 MHz, Methanol-d4) δ: 6.97-6.83 (m, 2H), 5.48-5.43 (m, 2H), 4.69-4.65 (m, 2H), 3.78-3.71 (m, 2H), 2.71-2.62 (m, 2H), 2.38-2.20 (m, 3H), 1.97-1.59 (m, 5H), 1.42-1.36 (m, 2H), 1.07-0.91 (m, 2H); LCMS m/z 490.0 [M+H]⁺

Example 5-18

(2S)-1-(tert-Butoxycarbonyl)-4-(2-(1-(4-chloro-2-fluorobenzyl)-3-(trifluoromethyl)-4,5-dihydro-1H-pyrazolo[3,4-c]pyridin-6(7H)-yl)-2-oxoethyl)pyrrolidine-2-carboxylic acid

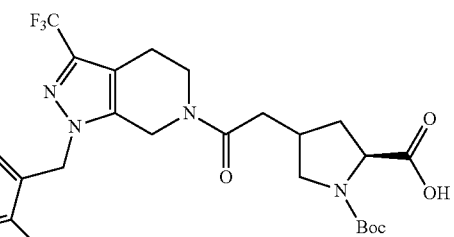

Step 1

(2S)-1-tert-Butyl 2-methyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)pyrrolidine-1,2-dicarboxylate

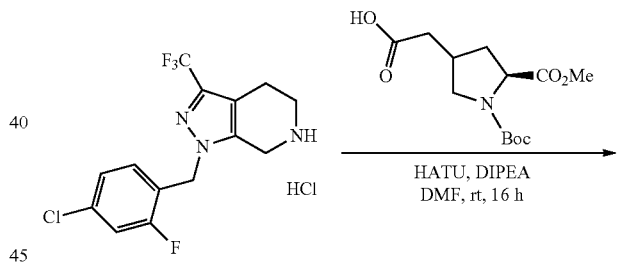

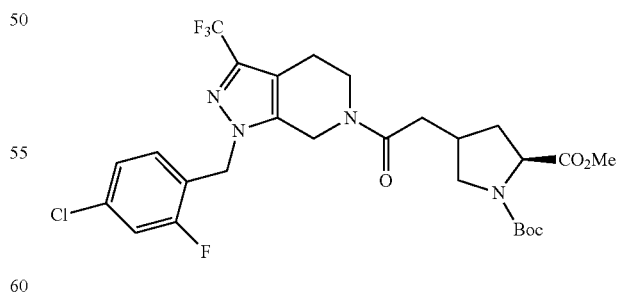

The title compound was synthesized according to the procedure described in Example 1-1, using 2-((5S)-1-(tert-butoxycarbonyl)-5-(methoxycarbonyl)pyrrolidin-3-yl)acetic acid (Intermediate 4-5) as a starting material, to obtain a brown oil (530 mg, yield 75%).

LCMS (ESI) m/z 625.2 [M+Na]⁺

Step 2

(2S)-1-(tert-Butoxycarbonyl)-4-(2-(1-(4-chloro-2-fluorobenzyl)-3-(trifluoromethyl)-4,5-dihydro-1H-pyrazolo[3,4-c]pyridin-6(7H)-yl)-2-oxoethyl)pyrrolidine-2-carboxylic acid

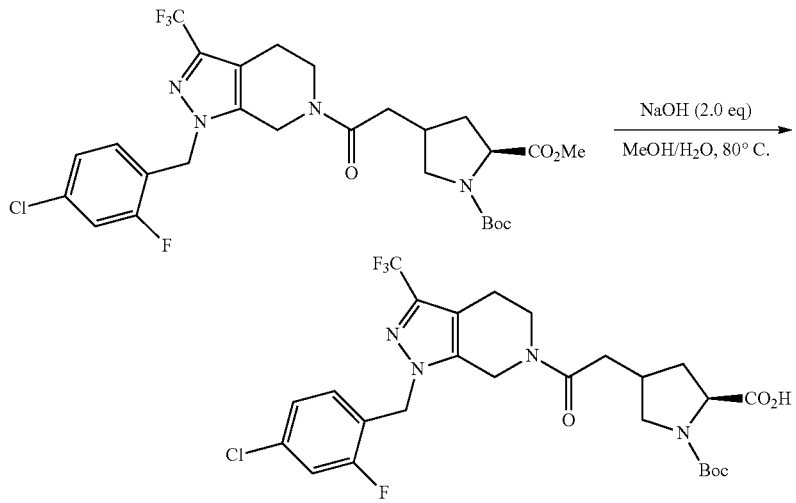

The title compound was synthesized according to the procedure described in Example 5-1, using (2S)-1-tert-butyl 2-methyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)pyrrolidine-1,2-dicarboxylate as a starting material, to obtain a white solid (450 mg, yield 87%). $^1$H NMR (400 MHz, Methanol-d4) δ: 7.17-7.32 (m, 3H), 5.37-5.40 (m, 2H), 4.66-4.70 (m, 2H), 4.18-4.24 (m, 1H), 3.72-3.83 (m, 3H), 3.03-3.09 (m, 1H), 2.55-2.76 (m, 6H), 1.64-1.70 (m, 1H), 1.42-1.45 (m, 9H); LCMS (ESI) m/z 533.2 [M-55]$^+$ Example 5-19 trans-4-(2-(1-(1-(4-Fluorophenyl)ethyl)-3-(trifluoromethyl)-4,5-dihydro-1H-pyrazolo[3,4-c]pyridin-6(7H)-yl)-2-oxoethyl)cyclohexanecarboxylic acid Step 1 trans-Ethyl 4-(2-(1-(1-(4-fluorophenyl)ethyl)-3-(trifluoromethyl)-4,5-dihydro-1H-pyrazolo[3,4-c]pyridin-6(7H)-yl)-2-oxoethyl)cyclohexanecarboxylate and cis-ethyl 4-(2-(1-(1-(4-fluorophenyl)ethyl)-3-(trifluoromethyl)-4,5-dihydro-1H-pyrazolo[3,4-c]pyridin-6(7H)-yl)-2-oxoethyl)cyclohexanecarboxylate

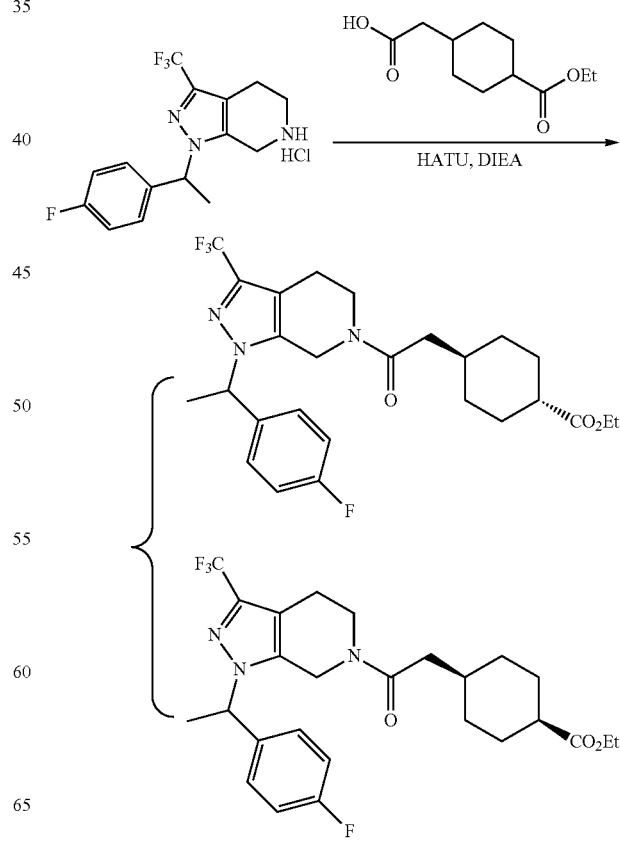

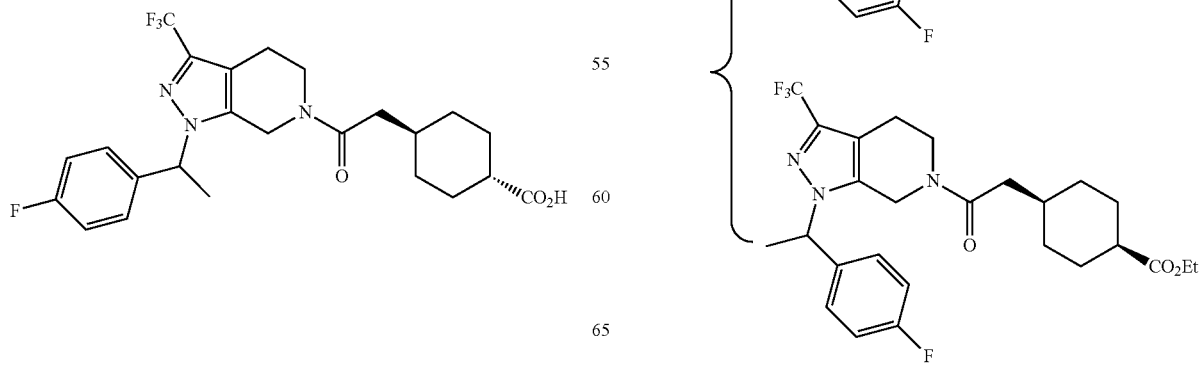

A mixture of 2-(4-(ethoxycarbonyl)cyclohexyl)acetic acid (108 mg, 0.50 mmol, 1.1 eq.), HATU (192 mg, 0.5 mmol, 1.1 eq.), DIEA (362 mg, 2.8 mmol, 3.0 eq.) and 1-(1-(4-fluorophenyl)ethyl)-3-(trifluoromethyl)-4,5,6,7-tetrahydro-1H-pyrazolo[3,4-c]pyridine hydrochloride (160 mg, 0.46 mmol, 1.0 eq.) in DMF (5 mL) was stirred at room temperature overnight. EA (20 mL) was added and the mixture was washed with brine (10 mL×2). The organic phase was dried over Na$_2$SO$_4$, filtered and concentrated to give the crude which was purified by prep. HPLC (MeCN and H$_2$O with 0.05% NH$_3$H$_2$O as mobile phase; from 66-96%) to provide trans-ethyl 4-(2-(1-(1-(4-fluorophenyl)ethyl)-3-(trifluoromethyl)-4,5-dihydro-1H-pyrazolo[3,4-c]pyridin-6(7H)-yl)-2-oxoethyl)cyclohexanecarboxylate (50 mg, yield 21%) and cis-ethyl 4-(2-(1-(1-(4-fluorophenyl)ethyl)-3-(trifluoromethyl)-4,5-dihydro-1H-pyrazolo[3,4-c]pyridin-6(7H)-yl)-2-oxoethyl)cyclohexanecarboxylate (32 mg, yield 14%) as a colorless gum.

trans-isomer: $^1$H NMR (400 MHz, Methanol-d4) δ: 7.31-7.27 (m, 2H), 7.14-7.09 (m, 2H), 5.63-5.56 (m, 1H), 4.79-4.64 (m, 1H), 4.41-4.37 (m, 1H), 4.11 (q, J=6.8 Hz, 2H), 3.70-3.68 (m, 2H), 2.75-2.66 (m, 2H), 2.39-2.12 (m, 3H), 1.95-1.51 (m, 8H), 1.49-1.23 (m, 5H), 1.10-0.76 (m, 2H). LCMS (ESI) m/z 532.0 [M+Na]$^+$ cis-isomer: $^1$H NMR (400 MHz, Methanol-d4) δ: 7.32-7.27 (m, 2H), 7.13-7.07 (m, 2H), 5.64-5.56 (m, 1H), 4.74-4.64 (m, 1H), 4.40-4.36 (m, 1H), 4.17-4.12 (m, 1H), 3.78-3.67 (m, 2H), 2.75-2.52 (m, 3H), 2.41-2.13 (m, 2H), 2.06-1.88 (m, 5H), 1.63-1.17 (m, 9H), 0.98-0.94 (m, 1H). LCMS (ESI) m/z 532.0 [M+Na]$^+$ Step 2 trans-4-(2-(1-(1-(4-Fluorophenyl)ethyl)-3-(trifluoromethyl)-4,5-dihydro-1H-pyrazolo[3,4-c]pyridin-6(7H)-yl)-2-oxoethyl)cyclohexanecarboxylic acid

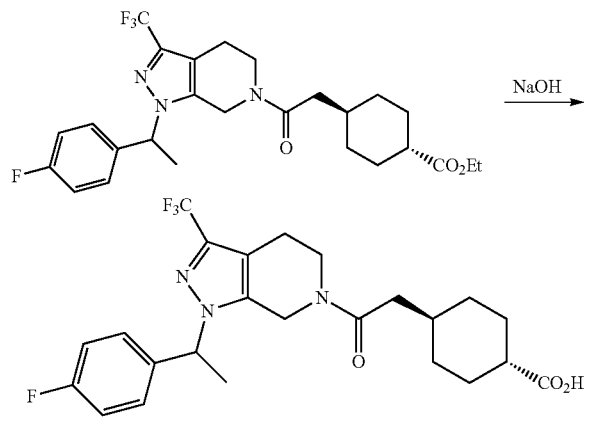

A mixture of trans-ethyl 4-(2-(1-(1-(4-fluorophenyl)ethyl)-3-(trifluoromethyl)-4,5-dihydro-1H-pyrazolo[3,4-c]pyridin-6(7H)-yl)-2-oxoethyl)cyclohexanecarboxylate (50 mg, 0.098 mmol, 1.0 eq.) and NaOH (8 mg, 0.2 mmol, 2.0 eq.) in MeOH/H$_2$O (2 mL) was stirred at room temperature overnight. TLC (PE/EA=1/1) showed the starting material was consumed completely. The solvent was removed in vacuum and the residue was dissolved in water. The aqueous phase was adjusted to about pH=2, then the solvent was removed in vacuum to give the crude which was purified by prep. HPLC (MeCN and H$_2$O with 0.225% FA as mobile phase; from 45-70%) to provide trans-4-(2-(1-(1-(4-fluorophenyl) ethyl)-3-(trifluoromethyl)-4,5-dihydro-1H-pyrazolo[3,4-c]pyridin-6(7H)-yl)-2-oxoethyl)cyclohexanecarboxylic acid (36 mg, yield 75%) as a white solid. $^1$H NMR (400 MHz, Methanol-d4) δ: 7.28-7.25 (m, 2H), 7.14-7.05 (m, 2H), 5.61-5.54 (m, 1H), 4.77-4.62 (m, 1H), 4.38-4.34 (m, 1H), 3.75-3.68 (m, 2H), 2.71-2.62 (m, 2H), 2.37-2.10 (m, 3H), 1.98-1.28 (m, 10H), 1.10-0.78 (m, 2H). LCMS (ESI) m/z 482.1 [M+H]$^+$ Example 5-20 cis-4-(2-(1-(1-(4-Fluorophenyl)ethyl)-3-(trifluoromethyl)-4,5-dihydro-1H-pyrazolo[3,4-c]pyridin-6(7H)-yl)-2-oxoethyl)cyclohexanecarboxylic acid

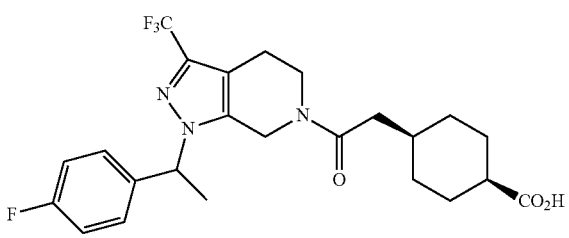 [SMILES: CC(c1ccc(F)cc1)n1nc(C(F)(F)F)c2c1CN(C(=O)C[C@H]1CC[C@@H](C(=O)O)CC1)CC2]

The title compound was synthesized according to the procedure described in Example 5-19, using cis-ethyl 4-(2-(1-(1-(4-fluorophenyl)ethyl)-3-(trifluoromethyl)-4,5-dihydro-1H-pyrazolo[3,4-c]pyridine-6(7H)-yl)-2-oxoethyl)cyclohexanecarboxylate as a starting material, the product was obtained as a white solid (yield 53%). $^1$H NMR (400 MHz, Methanol-d4) δ: 7.28-7.25 (m, 2H), 7.13-7.05 (m, 2H), 5.62-5.52 (m, 1H), 4.77-4.68 (m, 1H), 4.38-4.32 (m, 1H), 3.77-3.68 (m, 2H), 2.71-2.53 (m, 3H), 2.39-2.14 (m, 2H), 2.01-1.86 (m, 5H), 1.65-1.50 (m, 5H), 1.31-1.28 (m, 2H). LCMS (ESI) m/z 504.1 [M+Na]$^+$ Example 5-21 cis-4-(2-Oxo-2-(1-phenyl-3-(trifluoromethyl)-4,5-dihydro-1H-pyrazolo[3,4-c]pyridin-6(7H)-yl)ethyl) cyclohexanecarboxylic acid

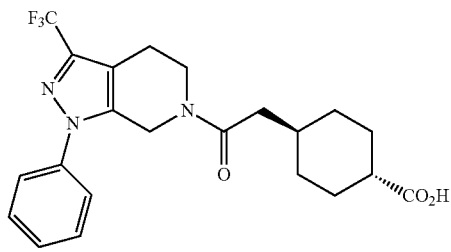 [SMILES: O=C(C[C@H]1CC[C@H](C(=O)O)CC1)N1CCc2c(C(F)(F)F)nn(-c3ccccc3)c2C1]

The title compound was synthesized according to the procedure described in Example 5-19, using Intermediate 1-17 as a starting material, the product was obtained as a white solid (18 mg, yield 16% over three steps). $^1$H NMR (400 MHz, Methanol-d4) δ: 7.58-7.49 (m, 5H), 4.78-4.75 (m, 2H), 3.90-3.83 (m, 2H), 2.81-2.73 (m, 2H), 2.40-2.27 (m, 2H), 2.26-2.20 (m, 1H), 1.97-1.50 (m, 5H), 1.42-1.27 (m, 2H), 1.20-0.96 (m, 1H); LCMS (ESI) m/z 436.0 [M+H]$^+$

Example 5-22 trans-4-(2-Oxo-2-(1-(pyridin-3-ylmethyl)-3-(trifluoromethyl)-4,5-dihydro-1H-pyrazolo[3,4-c]pyridin-6(7H)-yl)ethyl)cyclohexanecarboxylic acid

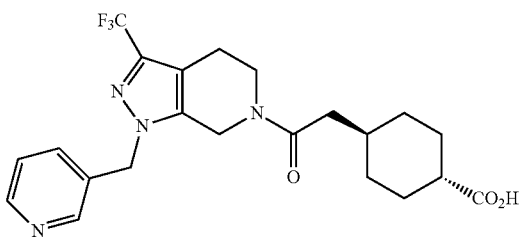 [SMILES: O=C(C[C@H]1CC[C@H](C(=O)O)CC1)N1CCc2c(C(F)(F)F)nn(Cc3cccnc3)c2C1]

Step 1 trans-Ethyl 4-(2-oxo-2-(1-(pyridin-3-ylmethyl)-3-(trifluoromethyl)-4,5-dihydro-1H-pyrazolo[3,4-c]pyridin-6(7H)-yl)ethyl)cyclohexanecarboxylate

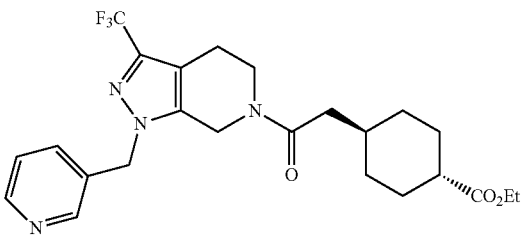 [SMILES: CCOC(=O)[C@H]1CC[C@H](CC(=O)N2CCc3c(C(F)(F)F)nn(Cc4cccnc4)c3C2)CC1]

The title compound was synthesized according to the procedure described in Example 1-48, using 3-(chloromethyl)pyridine hydrochloride as a starting material. LCMS (ESI) m/z 479.1 [M+H]+

Step 2 trans-4-(2-Oxo-2-(1-(pyridin-3-ylmethyl)-3-(trifluoromethyl)-4,5-dihydro-1H-pyrazolo[3,4-c]pyridin-6(7H)-yl)ethyl)cyclohexanecarboxylic acid

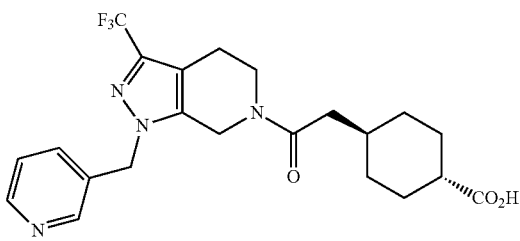 [SMILES: O=C(C[C@H]1CC[C@H](C(=O)O)CC1)N1CCc2c(C(F)(F)F)nn(Cc3cccnc3)c2C1]

The title compound was synthesized according to the procedure described in Example 5-1, using trans-ethyl 4-(2-oxo-2-(1-(pyridin-3-ylmethyl)-3-(trifluoromethyl)-4,5-dihydro-1H-pyrazolo[3,4-c]pyridin-6(7H)-yl)ethyl)cyclohexanecarboxylate as a starting material. $^1$H NMR (400 MHz, Methanol-d4) δ: 8.56-8.52 (m, 2H), 7.82-7.77 (m, 1H), 7.54-7.51 (m, 1H), 5.47-5.44 (m, 2H), 4.70-4.68 (m, 2H), 3.80-3.75 (m, 2H), 2.75-2.73 (m, 2H), 2.40-2.28 (m, 2H), 2.23-2.13 (m, 1H), 1.98-1.65 (m, 5H), 1.44-1.40 (m, 2H), 1.09-0.94 (m, 2H); LCMS (ESI) m/z 451.1 [M+H]+

Example 5-23 trans-4-(2-Oxo-2-(1-(pyridin-2-ylmethyl)-3-(trifluoromethyl)-4,5-dihydro-1H-pyrazolo[3,4-c]pyridin-6(7H)-yl)ethyl)cyclohexanecarboxylic acid

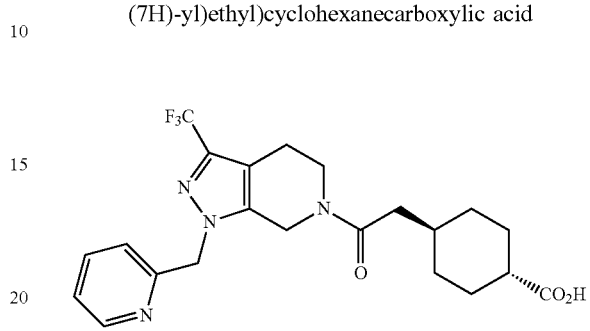

The title compound was synthesized according to the procedure described in Example 5-22, using 2-(chloromethyl)pyridine hydrochloride as a starting material, to obtain a white solid (95 mg, yield 73% in the final step). $^1$H NMR (400 MHz, Methanol-d4) δ: 8.56-8.52 (m, 2H), 7.82-7.77 (m, 1H), 7.54-7.51 (m, 1H), 5.47-5.44 (m, 2H), 4.70-4.68 (m, 2H), 3.80-3.75 (m, 2H), 2.75-2.73 (m, 2H), 2.40-2.28 (m, 2H), 2.23-2.13 (m, 1H), 1.98-1.65 (m, 5H), 1.44-1.40 (m, 2H), 1.09-0.94 (m, 2H); LCMS (ESI) m/z 451.1 [M+H]+

Example 5-24 trans-4-(2-Oxo-2-(1-(pyridin-4-ylmethyl)-3-(trifluoromethyl)-4,5-dihydro-1H-pyrazolo[3,4-c]pyridin-6(7H)-yl)ethyl)cyclohexanecarboxylic acid

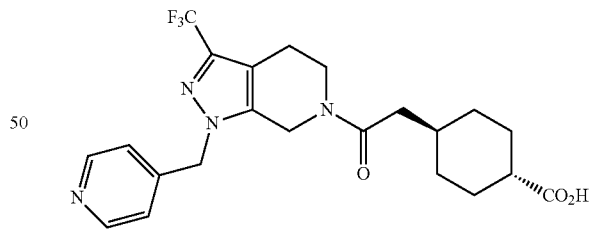

The title compound was synthesized according to the procedure described in Example 5-22, using 4-(chloromethyl)pyridine hydrochloride as a starting material. $^1$H NMR (400 MHz, Methanol-d4) δ: 8.61 (d, J=5.2 Hz, 1H), 7.37 (t, J=6.0 Hz, 1H), 5.55-5.54 (m, 2H), 4.64 (s, 2H), 3.81-3.76 (m, 2H), 2.76-2.67 (m, 2H), 2.39-2.37 (m, 2H), 2.27-2.17 (m, 1H), 1.97-1.75 (m, 5H), 1.42-1.36 (m, 2H), 1.08-0.93 (m, 2H); LCMS (ESI) m/z 451.0 [M+H]+

Example 5-25 cis-4-(2-(1-((5-Chlorothiophen-2-yl)methyl)-3-(trifluoromethyl)-4,5-dihydro-1H-pyrazolo[3,4-c]pyridin-6(7H)-yl)-2-oxoethyl)cyclohexanecarboxylic acid

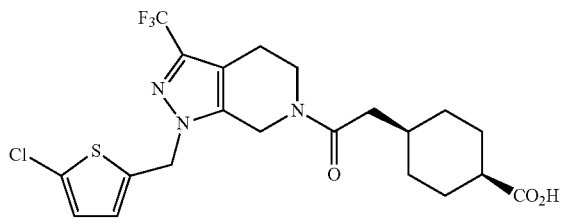 [SMILES: O=C(C[C@H]1CC[C@@H](C(=O)O)CC1)N1CCc2c(C(F)(F)F)nn(Cc3ccc(Cl)s3)c2C1]

The title compound was synthesized according to the procedure described in Example 5-22, using 2-chloro-5-(chloromethyl)thiophene and 2-(cis-4-ethoxycarbonyl)cyclohexyl) acetic acid as starting materials. $^1$H NMR (400 MHz, Methanol-d$_4$) δ: 6.97-6.94 (m, 1H), 6.91-6.86 (m, 1H), 5.49-5.44 (m, 2H), 4.70-4.66 (m, 2H), 3.80-3.63 (m, 2H), 2.72-2.54 (m, 3H), 2.43-2.30 (m, 2H), 2.03-1.93 (m, 3H), 1.61-1.55 (m, 4H), 1.33-1.30 (m, 2H); LCMS (ESI) m/z 489.9 [M+H]$^+$

Example 5-26 trans-4-(2-Oxo-2-(1-(thiophen-2-ylmethyl)-3-(trifluoromethyl)-4,5-dihydro-1H-pyrazolo[3,4-c]pyridin-6(7H)-yl)ethyl)cyclohexanecarboxylic acid

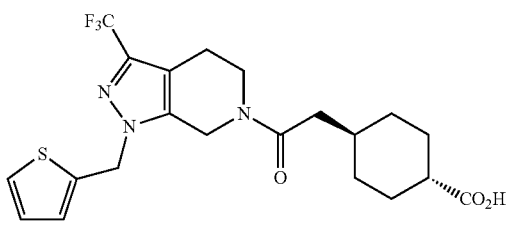 [SMILES: O=C(C[C@H]1CC[C@H](C(=O)O)CC1)N1CCc2c(C(F)(F)F)nn(Cc3cccs3)c2C1]

The title compound was synthesized according to the procedure described in Example 5-1, using Example 1-46 as a starting material. $^1$H NMR (400 MHz, Methanol-d$_4$) δ: 7.46-7.38 (m, 1H), 7.15-7.11 (m, 1H), 7.03-6.99 (m, 1H), 5.58-5.53 (m, 2H), 4.69-4.63 (m, 2H), 3.78-3.73 (m, 2H), 2.72-2.63 (m, 2H), 2.40-2.23 (m, 3H), 1.99-1.70 (m, 5H), 1.44-1.37 (m, 2H), 1.09-0.95 (m, 2H) LCMS (ESI) m/z 456.0 [M+H]$^+$

Example 5-27 trans-4-(2-Oxo-2-(1-(thiophen-3-ylmethyl)-3-(trifluoromethyl)-4,5-dihydro-1H-pyrazolo[3,4-c]pyridin-6(7H)-yl)ethyl)cyclohexanecarboxylic acid

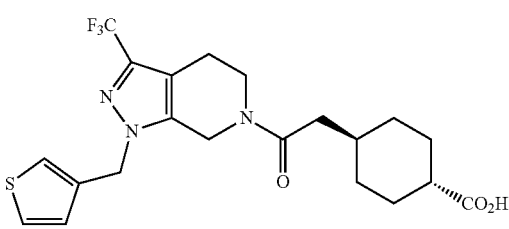 [SMILES: O=C(C[C@H]1CC[C@H](C(=O)O)CC1)N1CCc2c(C(F)(F)F)nn(Cc3ccsc3)c2C1]

The title compound was synthesized according to the procedure described in Example 5-1, using Example 1-45 as a starting material, to obtain a white solid (40 mg, yield 44%) $^1$H NMR (400 MHz, Methanol-d$_4$) δ: 7.41-7.31 (m, 2H), 6.99-6.97 (m, 1H), 5.45-5.26 (m, 2H), 4.67-4.61 (m, 2H), 3.82-3.70 (m, 2H), 2.71-2.61 (m, 2H), 2.38-2.36 (m, 1H), 2.19-2.17 (m, 2H), 1.97-1.68 (m, 5H), 1.43-1.39 (m, 2H), 1.08-1.04 (m, 1H), 0.92-0.80 (m, 1H); LCMS (ESI) m/z 456.0 [M+H]$^+$

Example 5-28 trans-4-(2-Oxo-2-(1-(thiazol-5-ylmethyl)-3-(trifluoromethyl)-4,5-dihydro-1H-pyrazolo[3,4-c]pyridin-6(7H)-yl)ethyl)cyclohexanecarboxylic acid

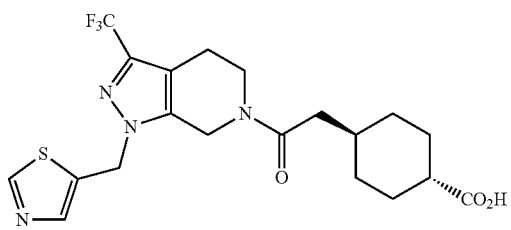 [SMILES: O=C(C[C@H]1CC[C@H](C(=O)O)CC1)N1CCc2c(C(F)(F)F)nn(Cc3cncs3)c2C1]

The title compound was synthesized according to the procedure described in Example 5-1, using Example 1-47 as a starting material. $^1$H NMR (400 MHz, Methanol-d4) δ: 9.69-9.60 (m, 1H), 8.26-8.24 (m, 1H), 5.72-5.69 (m, 2H), 4.77 (s, 2H), 3.80-3.74 (m, 2H), 2.72-2.62 (m, 2H), 2.40-2.36 (m, 2H), 2.26-2.21 (m, 1H), 1.98-1.95 (m, 2H), 1.84-1.71 (m, 3H), 1.43-1.34 (m, 2H), 1.09-1.02 (m, 2H). LCMS (ESI) m/z 479.0 [M+Na]$^+$

Example 5-29 trans-4-(2-Oxo-2-(1-(pyrimidin-5-ylmethyl)-3-(trifluoromethyl)-4,5-dihydro-1H-pyrazolo[3,4-c]pyridin-6(7H)-yl)ethyl)cyclohexanecarboxylic acid

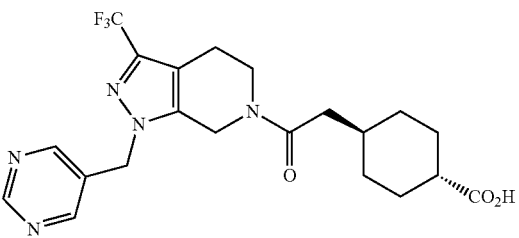

The title compound was synthesized according to the procedure described in Example 5-22, using 5-(chloromethyl)pyrimidine as a starting material. $^1$H NMR (400 MHz, CDCl$_3$) δ: 9.22 (s, 1H), 8.69 (s, 2H), 5.31 (s, 2H), 4.68 (s, 2H), 3.70-3.67 (m, 2H), 2.77 (s, 2H), 2.35-2.25 (m, 3H), 2.07-2.04 (m, 2H), 1.91-1.88 (m, 2H), 1.55-1.46 (m, 2H), 1.10-1.01 (m, 2H) LCMS (ESI) m/z 474.1 [M+Na]$^+$

Example 5-30 trans-4-(2-(1-(2,4-Difluorobenzyl)-3-(trifluoromethyl)-4,5-dihydro-1H-pyrazolo[3,4-c]pyridin-6(7H)-yl)-2-oxoethyl)cyclohexanecarboxylic acid

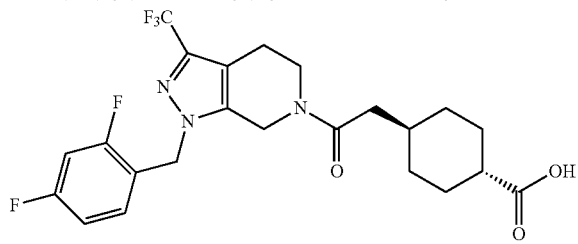

The title compound was synthesized according to the procedure described in Example 5-22, using 1-(bromomethyl)-2,4-difluorobenzene as a starting material. $^1$H NMR (400 MHz, Methanol-d4) δ: 7.28-7.25 (m, 1H), 7.03-6.94 (m, 2H), 5.38-5.33 (m, 2H), 4.69-4.61 (m, 2H), 3.79-3.72 (m, 2H), 2.71-2.65 (m, 2H), 2.39-2.30 (m, 2H), 2.28-2.17 (m, 1H), 1.98-1.75 (m, 5H), 1.52-1.25 (m, 2H), 1.08-1.05 (m, 2H); LCMS (ESI) m/z 486.1 [M+H]$^+$

Example 5-31 trans-4-(2-(1-(3,4-Difluorobenzyl)-3-(trifluoromethyl)-4,5-dihydro-1H-pyrazolo[3,4-c]pyridin-6(7H)-yl)-2-oxoethyl)cyclohexanecarboxylic acid

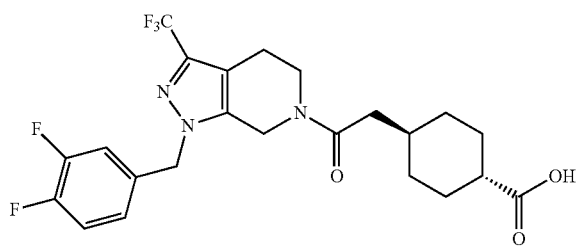 [SMILES: O=C(C[C@H]1CC[C@H](C(=O)O)CC1)N1CCc2c(C(F)(F)F)nn(Cc3ccc(F)c(F)c3)c2C1]

The title compound was synthesized according to the procedure described in Example 5-22, using 1-(bromomethyl)-3,4-difluorobenzene as a starting material. $^1$H NMR (400 MHz, Methanol-d4) δ: 7.27-7.04 (m, 3H), 5.36-5.32 (m, 2H), 4.63-4.59 (m, 2H), 3.79-3.73 (m, 2H), 2.75-2.64 (m, 2H), 2.39-2.22 (m, 3H), 1.98-1.62 (m, 5H), 1.43-1.40 (m, 2H), 1.09-0.91 (m, 2H); LCMS (ESI) m/z 486.1 [M+H]$^+$

Example 5-32 trans-4-(2-(1-(2,4,5-Trifluorobenzyl)-3-(trifluoromethyl)-4,5-dihydro-1H-pyrazolo[3,4-c]pyridin-6(7H)-yl)-2-oxoethyl)cyclohexanecarboxylic acid

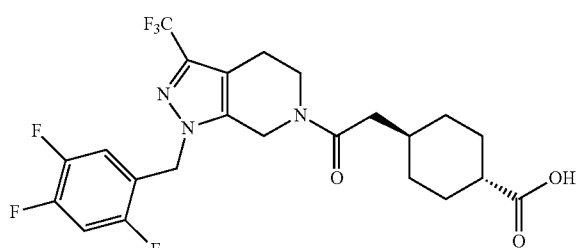

The title compound was synthesized according to the procedure described in Example 5-22, using 1-(bromomethyl)-2,4,5-trifluorobenzene as a starting material. $^1$H NMR (400 MHz, Methanol-d4) δ: 7.29-7.17 (m, 2H), 5.38-5.34 (m, 2H), 4.73 (s, 2H), 3.83-3.76 (m, 2H), 3.75-3.73 (m, 2H), 2.41-2.36 (m, 2H), 2.34-2.23 (m, 1H), 2.00-1.83 (m, 5H), 1.46-1.42 (m, 2H), 1.11-1.07 (m, 2H); LCMS (ESI) m/z 504.1 [M+H]$^+$

Example 5-33 trans-4-(2-(1-(3,4,5-Trifluorobenzyl)-3-(trifluoromethyl)-4,5-dihydro-1H-pyrazolo[3,4-c]pyridin-6(7H)-yl)-2-oxoethyl)cyclohexanecarboxylic acid

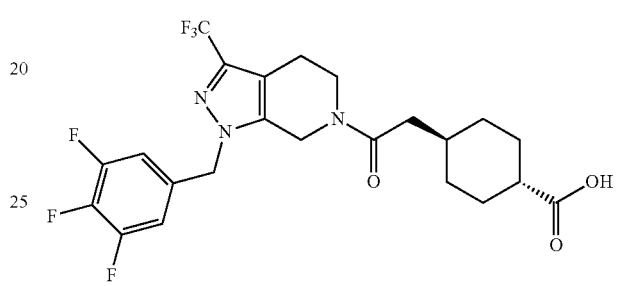

The title compound was synthesized according to the procedure described in Example 5-22, using 1-(bromomethyl)-3,4,5-trifluorobenzene as a starting material. $^1$H NMR (400 MHz, Methanol-d4) δ: 7.06-7.00 (m, 2H), 5.38-5.35 (m, 2H), 4.67 (s, 2H), 3.83-3.77 (m, 2H), 2.78-2.76 (m, 2H), 2.42-2.33 (m, 2H), 2.31-2.15 (m, 1H), 2.01-1.79 (m, 5H), 1.47-1.43 (m, 2H), 1.12-1.08 (m, 2H); LCMS (ESI) m/z 504.1 [M+H]$^+$

Example 5-34 cis-4-(2-(1-(2,4-Difluorobenzyl)-3-(trifluoromethyl)-4,5-dihydro-1H-pyrazolo[3,4-c]pyridin-6(7H)-yl)-2-oxoethyl)cyclohexanecarboxylic acid

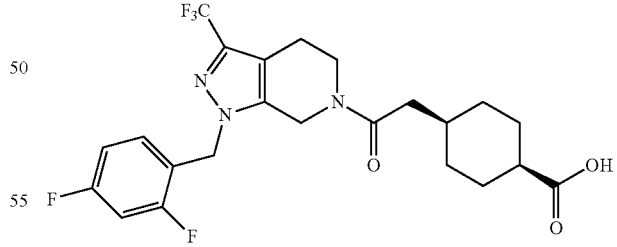

The title compound was synthesized according to the procedure described in Example 5-22, using 1-(bromomethyl)-2,4-difluorobenzene and 2-(cis-4-(ethoxycarbonyl)cyclohexyl)acetic acid as starting materials. $^1$H NMR (400 MHz, Methanol-d4) δ: 7.30-7.24 (m, 1H), 7.04-6.94 (m, 2H), 5.37-5.33 (m, 2H), 4.68-4.61 (m, 2H), 3.80-3.72 (m, 2H), 2.71-2.70 (m, 1H), 2.62-2.53 (m, 2H), 2.41-2.31 (m, 2H), 2.02-1.91 (m, 4H), 1.59-1.55 (m, 3H), 1.35-1.29 (m, 2H); LCMS (ESI) m/z 486.1 [M+H]$^+$

Example 5-35 cis-4-(2-(1-(4-Cyanobenzyl)-3-(trifluoromethyl)-4,5-dihydro-1H-pyrazolo[3,4-c]pyridin-6(7H)-yl)-2-oxoethyl)cyclohexanecarboxylic acid

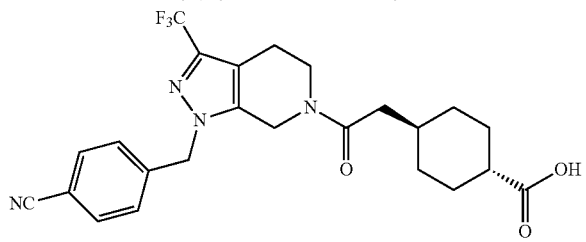 [SMILES: N#Cc1ccc(Cn2nc(C(F)(F)F)c3c2CN(C(=O)C[C@H]2CC[C@H](C(=O)O)CC2)CC3)cc1]

The title compound was synthesized according to the procedure described in Example 5-22, using 4-(bromomethyl)benzonitrile as a starting material, to obtain a white solid (90 mg, yield 64%). $^1$H NMR (400 MHz, Methanol-$d_4$) δ: 7.77-7.72 (m, 2H), 7.38-7.34 (m, 2H), 5.49-5.45 (m, 2H), 4.62-4.59 (m, 2H), 3.80-3.74 (m, 2H), 2.74-2.65 (m, 2H), 2.39-2.21 (m, 3H), 1.98-1.71 (m, 5H), 1.43-1.37 (m, 2H), 1.09-0.95 (m, 2H); LCMS (ESI) m/z 475.0 [M+H]$^+$

Example 5-37 trans-4-(2-(1-((4-Methylcyclohexyl)methyl)-3-(trifluoromethyl)-4,5-dihydro-1H-pyrazolo[3,4-c]pyridin-6(7H)-yl)-2-oxoethyl)cyclohexanecarboxylic acid

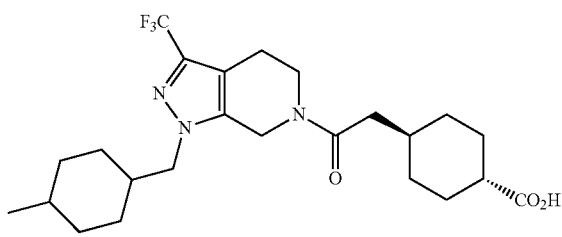 [SMILES: CC1CCC(Cn2nc(C(F)(F)F)c3c2CN(C(=O)C[C@H]2CC[C@H](C(=O)O)CC2)CC3)CC1]

The title compound was synthesized according to the procedure described in Example 5-1, using Example 1-48 as a starting material. $^1$H NMR (400 MHz, Methanol-d4) δ: 11.99 (brs, 1H), 4.63-4.61 (m, 2H), 4.02-3.87 (m, 2H), 3.645-3.64 (m, 2H), 2.60 (s, 1H), 2.52-2.48 (m, 2H), 2.29-2.27 (m, 2H), 2.20-1.98 (m, 1H), 1.95-1.87 (m, 1H), 1.84-1.81 (m, 2H), 1.69-1.29 (m, 7H), 1.24-1.17 (m, 5H), 0.99-0.80 (m, 6H); LCMS (ESI) m/z 470.1 [M+H]$^+$

Example 5-38 trans-4-(2-(3-Cyclopropyl-1-(4-fluorobenzyl)-4,5-dihydro-1H-pyrazolo[3,4-c]pyridin-6(7H)-yl)-2-oxoethyl)cyclohexanecarboxylic acid

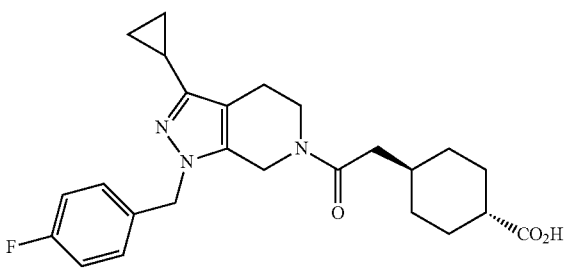 [SMILES: O=C(C[C@H]1CC[C@H](C(=O)O)CC1)N1CCc2c(C3CC3)nn(Cc3ccc(F)cc3)c2C1]

The title compound was synthesized according to the procedure described in Example 5-1, using Example 1-39 as a starting material, to obtain a white solid (10 mg, yield 38%). $^1$H NMR (400 MHz, Methanol-d4) δ: 7.14-6.99 (m, 4H), 5.19-5.15 (m, 2H), 4.50-4.43 (m, 2H), 3.76-3.68 (m, 2H), 2.63-2.61 (m, 2H), 2.37-2.35 (m, 1H), 2.14-2.12 (m, 2H), 1.97-1.39 (m, 8H), 0.87-0.85 (m, 1H), 0.79-0.78 (m, 4H); LCMS (ESI) m/z 440.1 [M+H]$^+$

Example 5-39 trans-4-(2-(1-(4-Fluorobenzyl)-3-phenyl-4,5-dihydro-1H-pyrazolo[3,4-c]pyridin-6(7H)-yl)-2-oxoethyl)cyclohexanecarboxylic acid

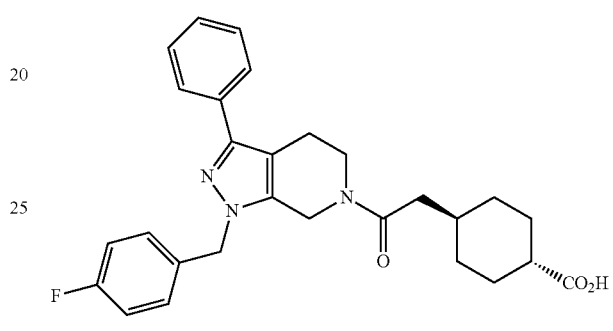

The title compound was synthesized according to the procedure described in Example 5-1, using Example 1-44 as a starting material, to obtain a white solid (36 mg, yield 61%). $^1$H NMR (400 MHz, Methanol-$d_4$) δ: 7.66 (d, J=7.6 Hz, 2H), 7.41 (t, J=7.6 Hz, 2H), 7.36-7.21 (m, 3H), 7.15-7.03 (m, 2H), 5.41-5.27 (m, 2H), 4.65-4.53 (m, 2H), 3.82-3.72 (m, 2H), 2.89-2.73 (m, 2H), 2.40 (d, J=6.8 Hz, 1H), 2.26-2.09 (m, 2H), 2.01-1.76 (m, 3H), 1.75-1.54 (m, 2H), 1.49-1.26 (m, 2H), 1.12-0.84 (m, 2H); LCMS (ESI) m/z 476.1[M+H]$^+$

Example 5-40 trans-4-(2-(1-(4-Fluorobenzyl)-3-(pyridin-3-yl)-4,5-dihydro-1H-pyrazolo[3,4-c]pyridin-6(7H)-yl)-2-oxoethyl)cyclohexanecarboxylic acid

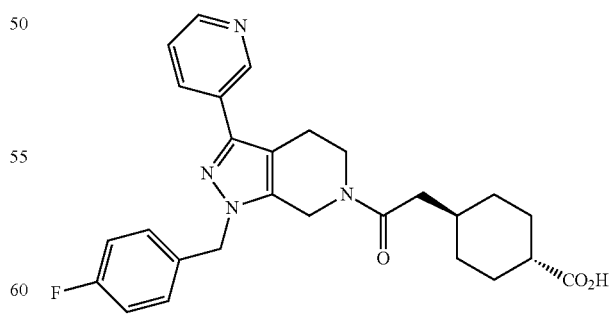

The title compound was synthesized according to the procedure described in Example 5-39, using pyridin-3-ylboronic acid as a starting material. $^1$H NMR (400 MHz, Methanol-$d_4$) δ: 9.03 (br, 1H), 8.81 (d, J=5.2 Hz, 1H), 8.67 (d, J=7.6 Hz, 1H), 8.01 (t, J=7.2 Hz, 1H), 7.40-7.31 (m, 2H), 7.26-7.17 (m, 2H), 5.47-5.38 (m, 2H), 4.65 (br, 2H), 3.71 (d, J=5.2 Hz, 2H), 2.91-2.75 (m, 2H), 2.34 (d, J=6.0 Hz, 1H), 2.23-2.03 (m, 2H), 1.91-1.56 (m, 5H), 1.36-1.18 (m, 2H), 1.06-0.84 (m, 2H). LCMS (ESI) m/z 477.1[M+H]$^+$ Example 5-41 trans-4-(2-(1-(4-Fluorobenzyl)-3-(pyridin-3-yl)-4,5-dihydro-1H-pyrazolo[3,4-c]pyridin-6(7H)-yl)-2-oxoethyl)cyclohexanecarboxylic acid

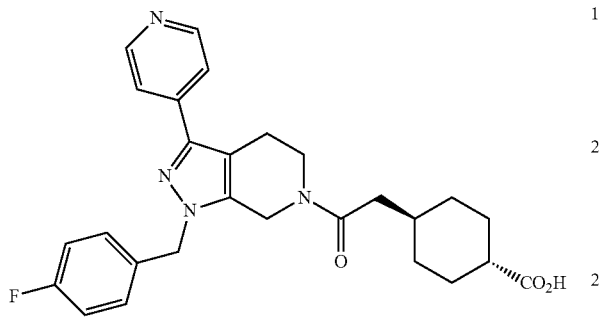

The title compound was synthesized according to the procedure described in Example 5-39, using pyridin-4-ylboronic acid as a starting material. $^1$H NMR (400 MHz, Methanol-d$_4$) δ: 8.83 (t, J=6.4 Hz, 2H), 8.18 (d, J=5.6 Hz, 2H), 7.37-7.27 (m, 2H), 7.23-7.14 (m, 2H), 5.48-5.40 (m, 2H), 4.62 (br, 2H), 3.68 (br, 2H), 2.95-2.78 (m, 2H), 2.30 (d, J=6.4 Hz, 1H), 2.21-2.01 (m, 2H), 1.89-1.51 (m, 5H), 1.30-1.16 (m, 2H), 1.02-0.81 (m, 2H); LCMS (ESI) m/z 477.1 [M+H]$^+$ Example 5-42 trans-4-(2-(3-Ethoxy-1-(4-fluorobenzyl)-4,5-dihydro-1H-pyrazolo[3,4-c]pyridin-6(7H)-yl)-2-oxoethyl)cyclohexanecarboxylic acid

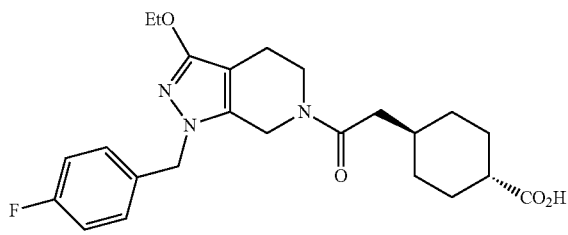 [SMILES: CCOc1nn(Cc2ccc(F)cc2)c2c1CCN(C(=O)C[C@H]1CC[C@H](C(=O)O)CC1)C2]

The title compound was synthesized according to the procedure described in Example 5-12, using Intermediate 2-21 and 2-((trans-4-(ethoxycarbonyl)cyclohexyl)acetic acid as starting materials, to obtain a white solid (23 mg, yield 64%). $^1$H NMR (400 MHz, CDCl$_3$) δ: 7.12-7.09 (m, 2H), 7.04-6.95 (m, 2H), 5.04-5.00 (m, 2H), 4.46 (s, 2H), 4.22 (q, J=7.2 Hz, 2H), 3.73-3.55 (m, 2H), 2.50-2.44 (m, 2H), 2.28-2.14 (m, 3H), 2.01-1.65 (m, 5H), 1.44-1.37 (m, 2H), 1.36 (t, J=7.2 Hz, 3H), 1.02-0.81 (m, 2H); LCMS (ESI) m/z 444.0 [M+H]$^+$ Example 5-43 trans-4-(2-(3-(Dimethylamino)-1-(4-fluorobenzyl)-4,5-dihydro-1H-pyrazolo[3,4-c]pyridin-6 (7H)-yl)-2-oxoethyl)cyclohexanecarboxylic acid

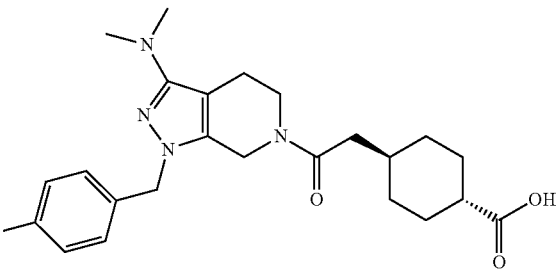

Step 1 tert-Butyl 3-(1,3-dioxoisoindolin-2-yl)-4,5-dihydro-1H-pyrazolo[3,4-c]pyridine-6(7H)-carboxylate

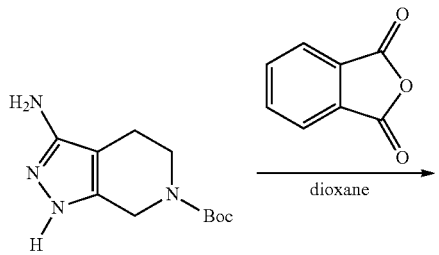

To a mixture of tert-butyl 3-amino-4,5-dihydro-1H-pyrazolo[3,4-c]pyridine-6(7H)-carboxylate (1.0 g, 4.2 mmol, 1.0 eq.) in dioxane (20 mL) was added isobenzofuran-1,3-dione (1.86 g, 12.6 mmol, 3.0 eq.). The reaction mixture was stirred at 120° C. for 17 hours. The mixture was concentrated to give the crude, which was purified by column chromatography (PE/EtOAc=3:1) to provide tert-butyl 3-(1,3-dioxoisoindolin-2-yl)-4,5-dihydro-1H-pyrazolo[3,4-c]pyridine-6(7H)-carboxylate (1.25 g, yield 80%) as a yellow gum. $^1$H NMR (400 MHz, Methanol-d$_4$) δ: 7.96-7.95 (m, 1H), 7.89-7.87 (m, 1H), 7.73-7.59 (m, 1H), 7.58-7.57 (m, 1H), 4.61 (s, 1H), 3.65 (s, 1H), 2.48 (t, J=4.8 Hz, 1H), 1.49 (s, 9H).

Step 2 tert-Butyl 3-(1,3-dioxoisoindolin-2-yl)-1-(4-fluorobenzyl)-4,5-dihydro-1H-pyrazolo[3,4-c]pyridine-6(7H)-carboxylate

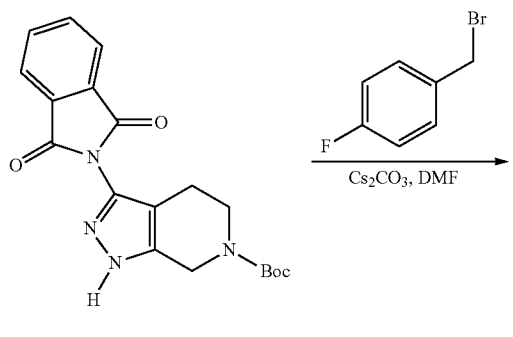

To a solution of tert-butyl 3-(1,3-dioxoisoindolin-2-yl)-4,5-dihydro-1H-pyrazolo[3,4-c]pyridine-6(7H)-carboxylate (1.0 g, 2.7 mmol, 1.0 eq.) in DMF (20 mL) was added Cs$_2$CO$_3$ (1.76 g, 5.4 mmol, 2.0 eq.), 1-(bromomethyl)-4-fluorobenzene (0.62 mg, 3.26 mmol, 1.2 eq.). The reaction mixture was stirred at 25° C. for 17 hours. The mixture was filtered and the filtrate was poured into water (40 mL) and extracted with EtOAc (40 mL×3). The organic phase was dried over Na$_2$SO$_4$, filtered and concentrated to give the crude, which was purified by prep. HPLC (MeCN and H$_2$O with 0.225% FA as mobile phase; from 47-73%) to afford the compound (600 mg) was further separated by SFC (Mobile phase: 40% methanol (0.05% DEA); Column: Chiralpak AS-H 250×4.6 mm I.D; Detection wavelength: 220 nm) to provide tert-butyl 3-(1,3-dioxoisoindolin-2-yl)-1-(4-fluorobenzyl)-4,5-dihydro-1H-pyrazolo[3,4-c]pyridine-6(7H)-carboxylate (90 mg, yield 7%) as a white solid. $^1$H NMR (400 MHz, DMSO-d$_6$) δ: 7.95-7.88 (m, 4H), 7.29-7.21 (m, 2H), 7.19-7.17 (m, 2H), 5.28 (s, 2H), 4.45 (s, 2H), 3.47 (t, J=5.2 Hz, 2H), 2.33 (s, 2H), 1.36 (s, 9H); LCMS (ESI) m/z 477.0 [M+H]$^+$ Step 3 tert-Butyl-3-amino-1-(4-fluorobenzyl)-4,5-dihydro-1H-pyrazolo[3,4-c]pyridine-6(7H)-carboxylate

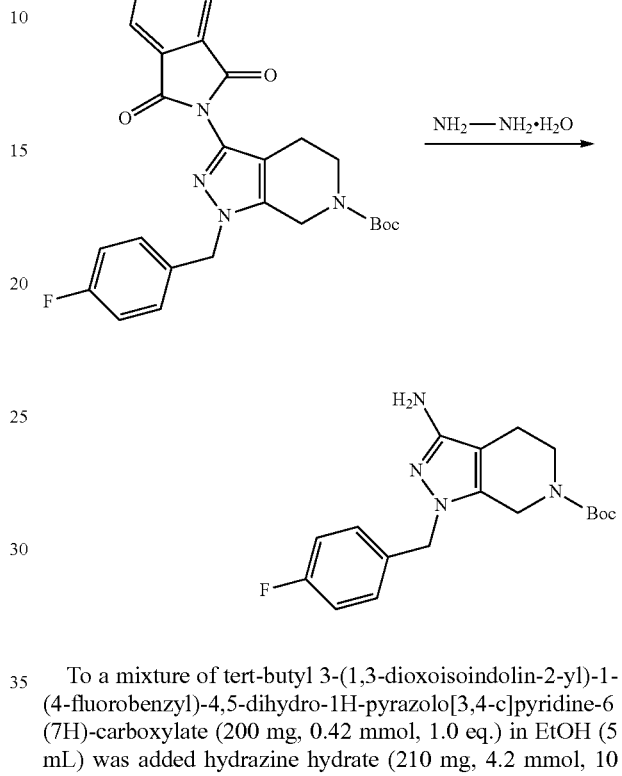

To a mixture of tert-butyl 3-(1,3-dioxoisoindolin-2-yl)-1-(4-fluorobenzyl)-4,5-dihydro-1H-pyrazolo[3,4-c]pyridine-6(7H)-carboxylate (200 mg, 0.42 mmol, 1.0 eq.) in EtOH (5 mL) was added hydrazine hydrate (210 mg, 4.2 mmol, 10 eq.). The reaction mixture was stirred at 28° C. for 4 hours. The mixture was filtered and the filtrate was concentrated to give the crude, which was purified by prep. HPLC (10 mmol/L NH$_4$HCO$_3$ as mobile phase; from 31-61%) to provide tert-butyl 3-amino-1-(4-fluorobenzyl)-4,5-dihydro-1H-pyrazolo[3,4-c]pyridine-6(7H)-carboxylate (80 mg, purity 55%) as white solid. $^1$H NMR (400 MHz, Methanol-d4) δ: 7.14-7.11 (m, 2H), 7.05-7.01 (m, 2H), 4.99 (s, 2H), 4.32 (s, 2H), 2.39 (t, J=5.2 Hz, 2H), 1.45-1.38 (m, 9H); LCMS (ESI) m/z 347.0 [M+H]$^+$ Step 4 tert-Butyl 3-(dimethylamino)-1-(4-fluorobenzyl)-4,5-dihydro-1H-pyrazolo[3,4-c]pyridine-6(7H)-carboxylate

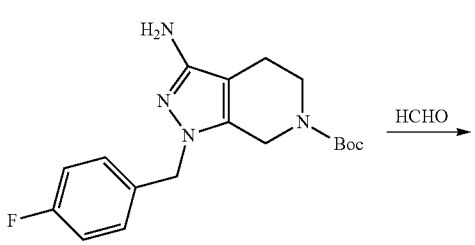

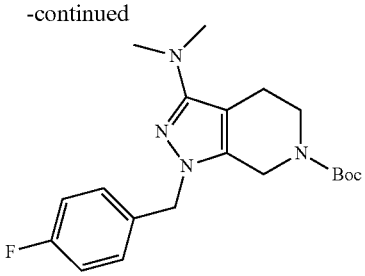

To a solution of tert-butyl 3-amino-1-(4-fluorobenzyl)-4,5-dihydro-1H-pyrazolo[3,4-c]pyridine-6(7H)-carboxylate (80 mg, 0.16 mmol, 1.0 eq) and DIEA (30 mg, 0.23 mmol, 1.0 eq) in THF (2 mL) was added Ti(iPrO)$_4$ (131 mg, 0.46 mmol, 2.0 eq) followed by formaldehyde (35 mg, 1.15 mmol, 5.0 eq). Then the mixture was microwaved at 80° C. for 1 h. NaBH$_3$CN (29 mg, 0.46 mmol, 2.0 eq) was added and the mixture was stirred at 28° C. for 2 h. The reaction was filtered and the filtrate was concentrated to give the crude which was purified by prep. HPLC (MeCN and H$_2$O with 0.225% FA as mobile phase; from 39-69%) to provide tert-butyl 3-(dimethylamino)-1-(4-fluorobenzyl)-4,5-dihydro-1H-pyrazolo[3,4-c]pyridine-6(7H)-carboxylate (28 mg, yield 33%) as a yellow gum. $^1$H NMR (400 MHz, Methanol-d$_4$) δ: 7.15-7.03 (m, 2H), 5.08 (s, 2H), 4.31 (s, 2H), 3.56 (s, 2H), 2.80 (s, 6H), 2.58 (t, J=5.2 Hz, 2H), 1.44-1.40 (m, 9H); LCMS (ESI) m/z 375.1 [M+H]$^+$ Step 5

1-(4-Fluorobenzyl)-N,N-dimethyl-4,5,6,7-tetrahydro-1H-pyrazolo[3,4-c]pyridin-3-amine hydrochloride

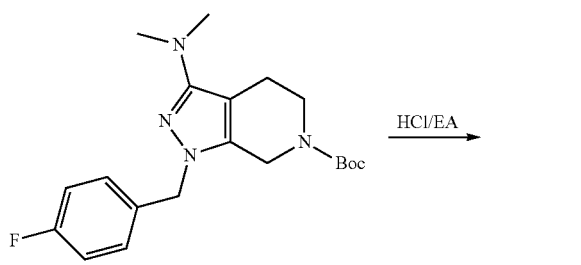

A mixture of tert-butyl 3-(dimethylamino)-1-(4-fluorobenzyl)-4,5-dihydro-1H-pyrazolo[3,4-c]pyridine-6(7H)-carboxylate (20 mg, 0.05 mmol, 1.0 eq.) in HCl/EtOAc (2 mL) was stirred at 30° C. for 2 h. TLC showed the starting material was consumed completely. The solvent was removed in vacuum to give 1-(4-fluorobenzyl)-N,N-dimethyl-4,5,6,7-tetrahydro-1H-pyrazolo[3,4-c]pyridin-3-amine hydrochloride (16 mg, yield 100%, crude) which was used in next step without further purification. LCMS (ESI) m/z 274.9 [M+H]$^+$ Step 6 trans-Ethyl 4-(2-(3-(dimethylamino)-1-(4-fluorobenzyl)-4,5-dihydro-1H-pyrazolo[3,4-c]pyridin-6(7H)-yl)-2-oxoethyl)cyclohexanecarboxylate

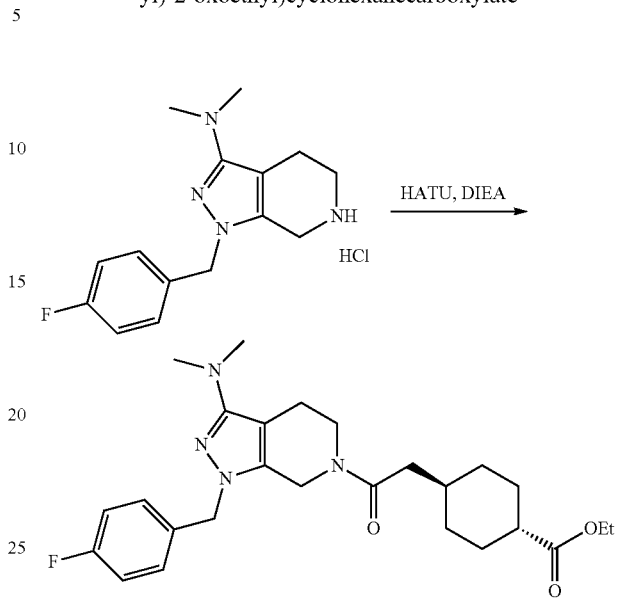

A mixture of 2-(trans-4-(ethoxycarbonyl)cyclohexyl)acetic acid (13 mg, 0.06 mmol, 1.2 eq), HATU (19 mg, 0.08 mmol, 1.5 eq.), DIEA (32 mg, 0.25 mmol, 5.0 eq) and 1-(4-fluorobenzyl)-N,N-dimethyl-4,5,6,7-tetrahydro-1H-pyrazolo[3,4-c]pyridin-3-amine hydrochloride (16 mg, 0.05 mmol, 1.0 eq.) in DMF (1 mL) was stirred at 30° C. for 4 hours. The mixture was poured into brine (10 mL) and extracted with EtOAc (10 mL×3). The combined organic phases were dried over Na$_2$SO$_4$, filtered and concentrated to give a yellow gum (23 mg, yield 100%, crude), which was used in next step without further purification. LCMS (ESI) m/z 471.1 [M+H]$^+$ Step 7 trans-4-(2-(3-(Dimethylamino)-1-(4-fluorobenzyl)-4,5-dihydro-1H-pyrazolo[3,4-c]pyridin-6(7H)-yl)-2-oxoethyl)cyclohexanecarboxylic acid

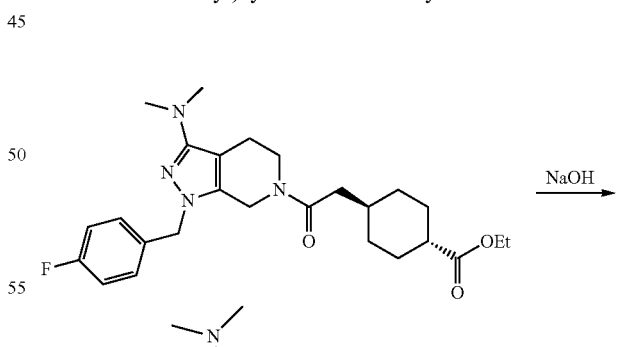

A mixture of trans-ethyl 4-(2-(3-(dimethylamino)-1-(4-fluorobenzyl)-4,5-dihydro-1H-pyrazolo[3,4-c]pyridin-6(7H)-yl)-2-oxoethyl)cyclohexanecarboxylate (23 mg, 0.05 mmol, 1.0 eq) and NaOH (10 mg, 0.25 mmol, 5.0 eq) in MeOH (2.0 mL)/H₂O (0.5 mL) was stirred at 30° C. for 17 hours. LCMS showed the starting material was consumed completely. The solvent was removed in vacuum and the residue was dissolved in water. The aqueous phase was adjusted to pH~2, then the solvent was removed in vacuum to give the crude, which was purified by prep. HPLC (MeCN and H₂O with 0.05% HCl as mobile phase; from 26-46%) to provide trans-4-(2-(3-(dimethylamino)-1-(4-fluorobenzyl)-4,5-dihydro-1H-pyrazolo[3,4-c]pyridin-6(7H)-yl)-2-oxoethyl) cyclohexanecarboxylic acid (23 mg, yield 88%) as a white solid. ¹H NMR (400 MHz, Methanol-d₄) δ: 7.31-7.27 (m, 2H), 7.16-7.09 (m, 2H), 5.34-5.25 (m, 2H), 4.66-4.61 (m, 2H), 3.80-3.78 (m, 2H), 3.24-3.22 (m, 6H), 2.83-2.73 (m, 2H), 2.40-2.21 (m, 3H), 1.99-1.70 (m, 5H), 1.44-1.37 (m, 2H), 1.10-0.95 (m, 2H); LCMS (ESI) m/z 443.1 [M+H]⁺

Example 5-44 trans-4-(2-(3-(Difluoromethyl)-1-(4-fluorobenzyl)-4,5-dihydro-1H-pyrazolo[3,4-c]pyridin-6(7H)-yl)-2-oxoethyl)cyclohexanecarboxylic acid

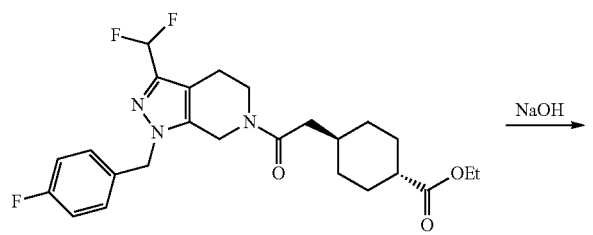

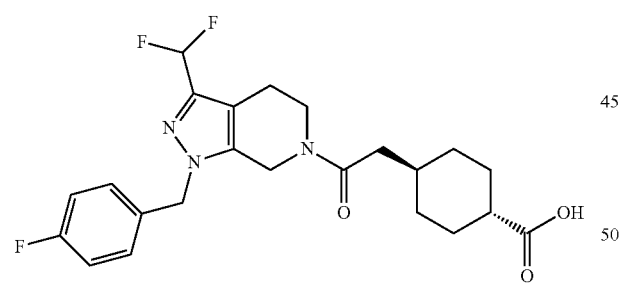

A mixture of trans-ethyl 4-(2-(3-(difluoromethyl)-1-(4-fluorobenzyl)-4,5-dihydro-1H-pyrazolo[3,4-c]pyridin-6(7H)-yl)-2-oxoethyl)cyclohexanecarboxylate (Example 1-38, 200 mg, 0.42 mmol, 1.0 eq.) and NaOH (84 mg, 2.09 mmol, 5.0 eq.) in MeOH/H₂O (3 mL/1 mL) was stirred at 28° C. for 2 h. LCMS showed the starting material was consumed completely. The solvent was removed in vacuum and the residue was dissolved in water. The aqueous phase was adjusted to about pH~2, the solvent was removed in vacuum to give the crude which was purified by prep. HPLC (MeCN and H₂O with 0.05% HCl as mobile phase; from 42-62%) to provide trans-4-(2-(3-(difluoromethyl)-1-(4-fluorobenzyl)-4,5-dihydro-1H-pyrazolo[3,4-c]pyridin-6(7H)-yl)-2-oxoethyl)cyclohexanecarboxylic acid (138 mg, yield 73%) as a white solid. ¹H NMR (400 MHz, Methanol-d₄) δ: 7.24-7.21 (m, 2H), 7.11-7.05 (m, 2H), 6.71-6.57 (m, 1H), 5.32-5.28 (m, 2H), 4.59-4.52 (m, 2H), 3.78-3.71 (m, 2H), 2.76-2.65 (m, 2H), 2.38-2.16 (m, 3H), 1.98-1.80 (m, 5H), 1.43-1.40 (m, 2H), 1.08-0.90 (m, 2H); LCMS (ESI) m/z 450.0 [M+H]⁺

Example 5-45 trans-4-(2-(1-(4-Fluorobenzyl)-3-(hydroxymethyl)-4,5-dihydro-1H-pyrazolo[3,4-c]pyridin-6(7H)-yl)-2-oxoethyl)cyclohexanecarboxylic acid

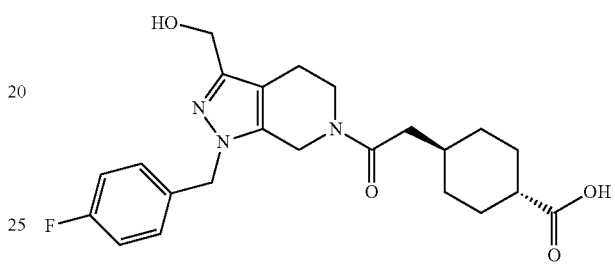

The title compound was synthesized according to the procedure described in Example 5-1, using Example 1-41 as a starting material, to obtain a white solid (23 mg, yield 45%). ¹H NMR (400 MHz, Methanol-d₄) δ: 7.29-7.26 (m, 2H), 7.16-7.09 (m, 2H), 5.42-5.40 (m, 2H), 4.70-4.62 (m, 4H), 3.77-3.75 (m, 2H), 2.71-2.61 (m, 2H), 2.39-2.21 (m, 3H), 2.20-2.11 (m, 5H), 1.45-1.32 (m, 2H), 1.11-0.90 (m, 2H); LCMS (ESI) m/z 430.1 [M+H]⁺

Example 5-46 trans-4-(2-(3-Cyano-1-(4-fluorobenzyl)-4,5-dihydro-1H-pyrazolo[3,4-c]pyridin-6(7H)-yl)-2-oxoethyl)cyclohexanecarboxylic acid

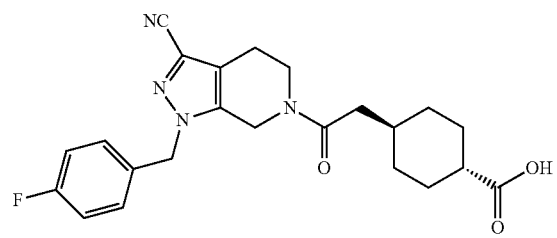 [SMILES: N#Cc1nn(Cc2ccc(F)cc2)c2c1CCN(C(=O)C[C@H]1CC[C@H](C(=O)O)CC1)C2]

The title compound was synthesized according to the procedure described in Example 5-1, using Example 1-43 as a starting material, to obtain a white solid (7 mg, yield 21%). ¹H NMR (400 MHz, Methanol-d₄) δ: 7.32-7.24 (m, 2H), 7.15-7.05 (m, 2H), 5.39-5.31 (m, 2H), 4.64-4.52 (m, 2H), 3.79-3.71 (m, 2H), 2.74-2.59 (m, 2H), 2.36 (d, J=6.4 Hz, 1H), 2.24-2.10 (m, 2H), 2.00-1.55 (m, 5H), 1.45-1.27 (m, 2H), 1.11-0.83 (m, 2H); LCMS (ESI) m/z 425.1[M+H]⁺

Example 5-47 trans-4-(2-(3-Carbamoyl-1-(4-fluorobenzyl)-4,5-dihydro-1H-pyrazolo[3,4-c]pyridin-6(7H)-yl)-2-oxoethyl)cyclohexanecarboxylic acid

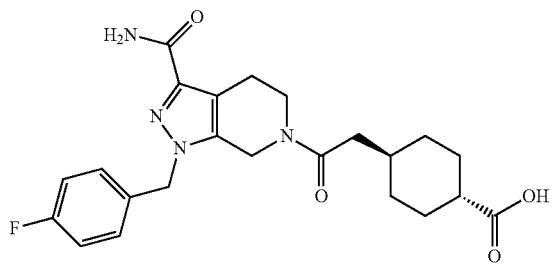 [SMILES: NC(=O)c1nn(Cc2ccc(F)cc2)c2c1CCN(C(=O)C[C@H]1CC[C@H](C(=O)O)CC1)C2]

The title compound was synthesized according to the procedure described in Example 5-1, using Example 1-42 as a starting material, to obtain a white solid (20 mg, yield 52%). $^1$H NMR (400 MHz, DMSO-$d_6$) δ: 12.00 (brs, 1H), 7.33-7.15 (m, 6H), 5.31-5.29 (m, 2H), 4.49 (s, 2H), 3.59-3.54 (m, 2H), 2.70-2.60 (m, 2H), 2.26-2.10 (m, 3H), 1.83-1.62 (m, 5H), 1.25-1.22 (m, 2H), 0.95-0.81 (m, 2H) LCMS (ESI) m/z 465.2 [M+Na]$^+$

Example 5-48

2-(trans-4-(2-(1-(4-Fluorobenzyl)-3-(trifluoromethyl)-4,5-dihydro-1H-pyrazolo[3,4-c]pyridin-6(7H)-yl)-2-oxoethyl)cyclohexyl)acetic acid

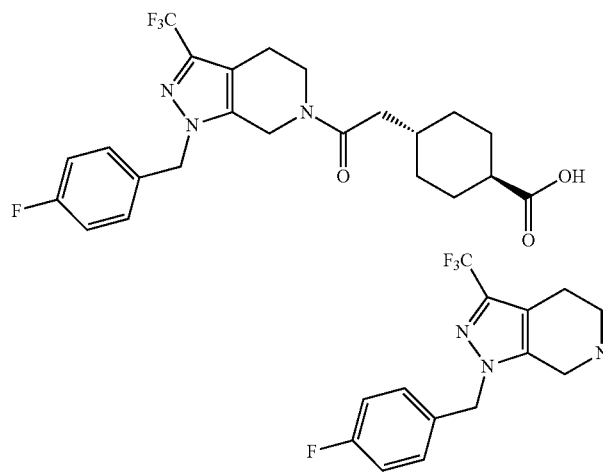

1) SOCl$_2$ (5.0 eq), DCM, reflux
2) TMSCHN$_2$ (3.0 eq), CH$_3$CN, rt
3) CF$_3$COOAg (1.5 eq), H$_2$O, 80° C.

To a solution of Example 7-1 (190 mg, 0.41 mmol) in DCM (5 mL) were added SOCl$_2$ (242 mg, 2.03 mmol). The reaction mixture was stirred at reflux for 3 h, and concentrated in vacuum. CH$_3$CN (5 mL) was added to the residue, followed by adding 2 M of trimethylsilyldiazomethane in THF (0.62 mL, 1.23 mmol) at 0° C. The mixture was stirred at rt for 16 h, then H$_2$O (5 mL) and CF$_3$COOAg (136 mg, 0.62 mmol) was added. After the reaction was stirred at 80° C. for 2 h, the mixture was filtered and the filtrate was concentrated, and purified by reverse phase HPLC (NH$_4$HCO$_3$ method) to give 2-(trans-4-(2-(1-(4-fluorobenzyl)-3-(trifluoromethyl)-4,5-dihydro-1H-pyrazolo[3,4-c]pyridin-6(7H)-yl)-2-oxoethyl)cyclohexyl)acetic acid (50 mg, yield 25%). $^1$H NMR (400 MHz, Methanol-d4) δ: 7.31-7.26 (m, 2H), 7.17-7.08 (m, 2H), 5.38-5.34 (m, 2H), 4.62-4.56 (m, 2H), 3.80-3.73 (m, 2H), 2.75-2.72 (m, 2H), 2.39-2.37 (m, 1H), 2.19-1.13 (m, 3H), 1.80-1.63 (m, 6H), 1.10-0.91 (m, 4H); LCMS (ESI) m/z 482.2 [M+H]$^+$

Example 5-49

2-(cis-4-(2-(1-(4-Fluorobenzyl)-3-(trifluoromethyl)-4,5-dihydro1H-pyrazolo[3,4-c]pyridin-6(7H)-yl)-2-oxoethyl)cyclohexyl)acetic acid

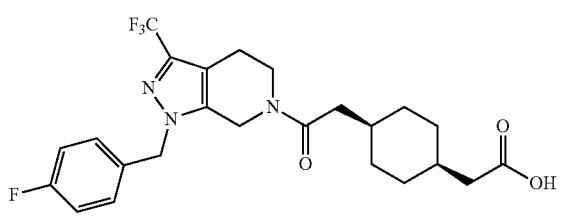 [SMILES: O=C(O)C[C@H]1CC[C@@H](CC(=O)N2CCc3c(C(F)(F)F)nn(Cc4ccc(F)cc4)c3C2)CC1]

The title compound was synthesized according to the procedure described in Example 5-48, using Example 7-2 as a starting material, to obtain a white solid (56 mg, yield 27%). $^1$H NMR (400 MHz, Methanol-d4) δ: 7.30-7.26 (m, 2H), 7.17-7.08 (m, 2H), 5.39-5.34 (m, 2H), 4.62-4.56 (m, 2H), 3.80-3.74 (m, 2H), 3.31-3.29 (m, 1H), 2.76-2.63 (m, 2H), 2.48-2.47 (m, 1H), 2.31-2.27 (m, 2H), 2.01-1.77 (m, 2H), 1.59-1.26 (m, 8H); LCMS (ESI) m/z 482.0 [M+H]$^+$

Example 5-50

4-(1-(4-Fluorobenzyl)-3-(trifluoromethyl)-4,5,6,7-tetrahydro-1H-pyrazolo[3,4-c]pyridine-6-carbonyl)bicyclo[2.2.1]heptane-1-carboxylic acid

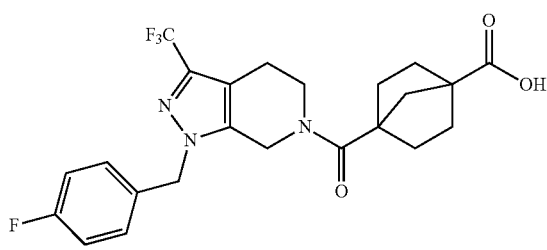 [SMILES: O=C(O)C12CCC(C(=O)N3CCc4c(C(F)(F)F)nn(Cc5ccc(F)cc5)c4C3)(CC1)C2]

Step 1

Methyl 4-(1-(4-fluorobenzyl)-3-(trifluoromethyl)-4,5,6,7-tetrahydro-1H-pyrazolo[3,4-c]pyridine-6-carbonyl)bicyclo[2.2.1]heptane-1-carboxylate

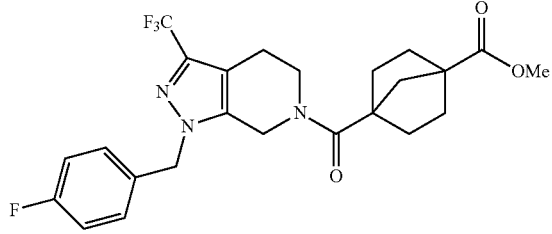 [SMILES: COC(=O)C12CCC(C(=O)N3CCc4c(C(F)(F)F)nn(Cc5ccc(F)cc5)c4C3)(CC1)C2]

The title compound was synthesized according to the procedure described in Example 1-1, using 4-(methoxycarbonyl)bicyclo[2.2.1]heptane-1-carboxylic acid as a starting material, to obtain a white solid (170 mg, yield 74%). LCMS (ESI) m/z 480.2 [M+H]+

Step 2

4-(1-(4-Fluorobenzyl)-3-(trifluoromethyl)-4,5,6,7-tetrahydro-1H-pyrazolo[3,4-c]pyridine-6-carbonyl)bicyclo[2.2.1]heptane-1-carboxylic acid

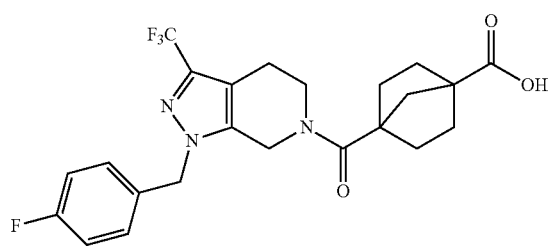 [SMILES: O=C(O)C12CCC(C(=O)N3CCc4c(C(F)(F)F)nn(Cc5ccc(F)cc5)c4C3)(CC1)C2]

The title compound was synthesized according to the procedure described in Example 5-1, using methyl 4-(1-(4-fluorobenzyl)-3-(trifluoromethyl)-4,5,6,7-tetrahydro-1H-pyrazolo[3,4-c]pyridine-6-carbonyl)bicyclo[2.2.1]heptane-1-carboxylate as a starting material, to obtain a white solid (100 mg, yield 60%). ¹H NMR (400 MHz, Methanol-d4) δ: 7.30-7.28 (m, 2H), 7.15-7.10 (m, 2H), 5.36 (s, 2H), 4.57 (s, 2H), 3.80 (br s, 2H), 2.69 (br s, 2H), 2.06-1.99 (m, 10H); LCMS (ESI) m/z 466.1 [M+H]+

Example 5-51

4-(1-(4-Fluorobenzyl)-3-(trifluoromethyl)-4,5,6,7-tetrahydro-1H-pyrazolo[3,4-c]pyridine-6-carbonyl)bicyclo[2.2.1]heptane-1-carboxylic acid

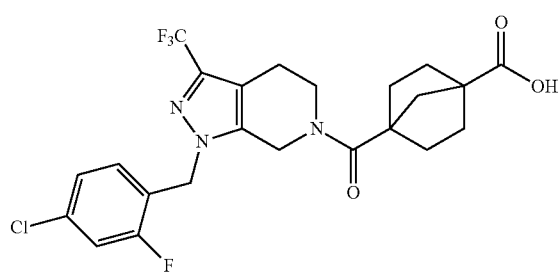 [SMILES: O=C(O)C12CCC(C(=O)N3CCc4c(C(F)(F)F)nn(Cc5ccc(Cl)cc5F)c4C3)(CC1)C2]

The title compound was synthesized according to the procedure described in Example 5-50, using Intermediate 2-1 as a starting material, to obtain a white solid (53 mg, yield 49% over two steps). ¹H NMR (400 MHz, Methanol-d4) δ: 7.32-7.21 (m, 3H), 5.39 (s, 2H), 4.67 (s, 2H), 3.83 (br s, 2H), 2.70 (br s, 2H), 2.09-1.75 (m, 10H); LCMS (ESI) m/z 500.1 [M+H]+

Example 5-52

4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)bicyclo[2.2.1]heptane-1-carboxylic acid

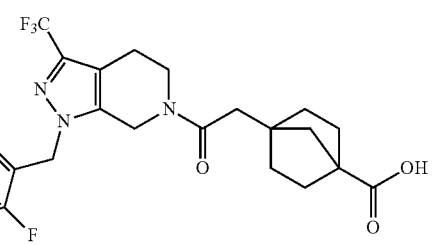

Step 1

2-(4-(Methoxycarbonyl)bicyclo[2.2.1]heptan-1-yl)acetic acid

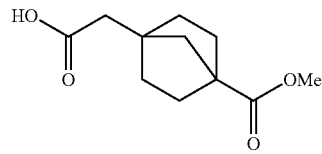 [SMILES: COC(=O)C12CCC(CC(=O)O)(CC1)C2]

The title compound was synthesized according to the procedure described in Intermediate 5-1, using 4-(methoxycarbonyl)bicyclo[2.2.1]heptane-1-carboxylic acid as a starting material, to obtain a yellow oil (200 mg, yield 75%). LCMS (ESI) m/z 213.1 [M+H]+

Step 2

4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)bicyclo[2.2.1]heptane-1-carboxylic acid

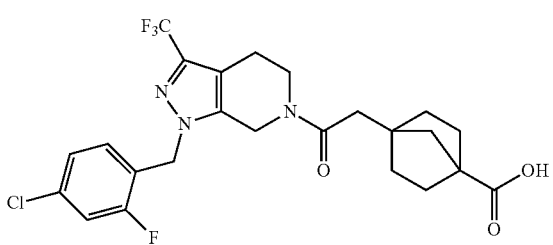 [SMILES: O=C(CC12CCC(C(=O)O)(CC1)C2)N1CCc2c(C(F)(F)F)nn(Cc3ccc(Cl)cc3F)c2C1]

The title compound was synthesized according to the procedure described in Example 5-50, using Intermediate 2-1 and 2-(4-(methoxycarbonyl)bicyclo[2.2.1]heptan-1-yl) acetic acid as starting materials, to obtain a white solid (16 mg, yield 7% over two steps). ¹H NMR (400 MHz, Methanol-d4) δ: 7.35-7.16 (m, 3H), 5.43-5.38 (m, 2H), 4.71-4.67 (m, 2H), 3.83-3.78 (m, 2H), 2.74-2.63 (m, 4H), 2.14-1.40 (m, 10H); LCMS (ESI) m/z 514.1 [M+H]⁺

Example 5-53

4-(2-(1-(4-Fluorobenzyl)-3-(trifluoromethyl)-4,5-dihydro-1H-pyrazolo[3,4-c]pyridin-6(7H)-yl)-2-oxoethyl)bicyclo[2.2.1]heptane-1-carboxylic acid

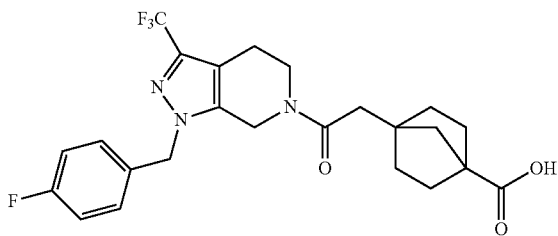 [SMILES: O=C(CC12CCC(C(=O)O)(CC1)C2)N1CCc2c(C(F)(F)F)nn(Cc3ccc(F)cc3)c2C1]

The title compound was synthesized according to the procedure described in Example 5-52, using Intermediate 2-2 as a starting material, to obtain a white solid (15 mg, yield 8% over two steps). ¹H NMR (400 MHz, Methanol-d4) δ: 7.34-7.26 (m, 2H), 7.17-7.09 (m, 2H), 5.38-5.34 (m, 2H), 4.62-4.57 (m, 2H), 3.81-3.76 (m, 2H), 2.76-2.53 (m, 4H), 2.04-1.84 (m, 2H), 1.70-1.30 (m, 8H); LCMS (ESI) m/z 480.2 [M+H]⁺

Example 5-54

4-(2-(1-(4-Chloro-2-fluorobenzyl)-3-(trifluoromethyl)-4,5-dihydro-1H-pyrazolo[3,4-c]pyridin-6(7H)-yl)-2-oxoethyl) adamantancarboxylic acid

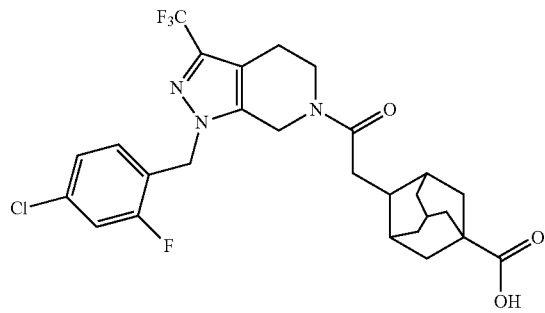 [SMILES: O=C(CC1C2CC3CC1CC(C(=O)O)(C3)C2)N1CCc2c(C(F)(F)F)nn(Cc3ccc(Cl)cc3F)c2C1]

Step 1

5-Carbomethoxyadamantan-2-one

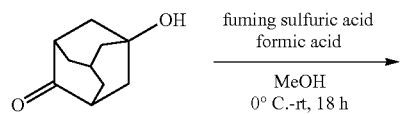

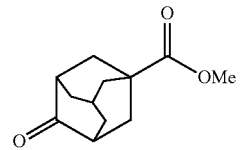

To fuming sulfuric acid (38 mL) was added a solution of 5-hydroxy-2-adamantanone (1.5 g, 9.0 mmol, 1.0 eq) in formic acid (8 mL) at 60° C. After the addition was completed, formic acid (9 mL) was added dropwise. The resulting mixture was stirred for 1 h at 60° C. and then 16 h at rt. The mixture was added dropwise to MeOH (100 mL) with stirring at 0° C. After addition, the mixture was stirred at rt for 2 h. Then the mixture was poured into ice-water, extracted with dichloromethane (3×100 mL). The combined organic layers were dried over Na₂SO₄, concentrated to afford 5-carbomethoxyadamantan-2-one as yellow oil (1.02 g, yield 54%). LCMS (ESI) m/z 209.0 [M+H]⁺

Step 2

2-(4-(Methoxycarbonyl)adamantan)acetic acid

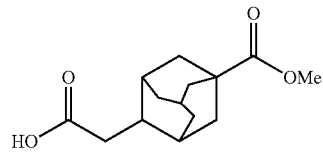 [SMILES: COC(=O)C12CC3CC(C1)C(CC(=O)O)C(C3)C2]

The title compound was synthesized according to the procedure described in Intermediate 3-3, using 5-carbomethoxyadamantan-2-one as a starting material, to obtain a yellow oil (1.7 g, yield 100% over three steps). LCMS (ESI) m/z 253.0 [M+H]⁺

Step 3

4-(2-(1-(4-Chloro-2-fluorobenzyl)-3-(trifluoromethyl)-4,5-dihydro-1H-pyrazolo[3,4-c]pyridin-6(7H)-yl)-2-oxoethyl) adamantancarboxylic acid

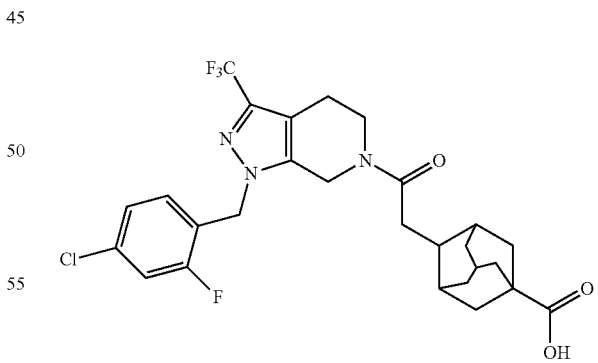

The title compound was synthesized according to the procedure described in Example 1-50, using Intermediate 2-1 and 2-(4-(methoxycarbonyl)adamantan)acetic acid as starting materials, to obtain a white solid (50 mg, yield 19% over two steps). ¹H NMR (400 MHz, Methanol-d4) δ: 7.22-7.07 (m, 3H), 5.33-5.27 (m, 2H), 4.61 (s, 2H), 3.71-3.68 (m, 2H), 2.67-2.42 (m, 4H), 2.13-1.35 (m, 14H); LCMS (ESI) m/z 553.9 [M+H]⁺

Example 5-55

1-(1-(4-Fluorobenzyl)-3-(trifluoromethyl)-4,5-dihydro-1H-pyrazolo[3,4-c]pyridin-6(7H)-yl)-2-(2-azaspiro[3.3]heptan-6-yl)adamantane carboxylic acid

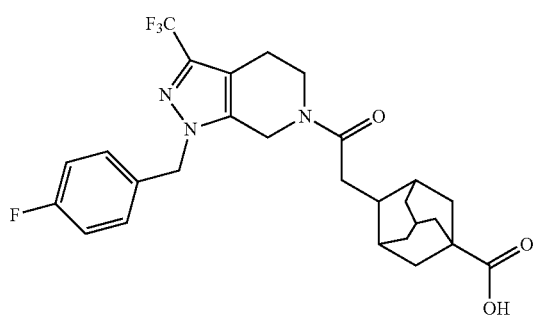 [SMILES: O=C(CC1C2CC3CC1CC(C(=O)O)(C3)C2)N1CCc2c(C(F)(F)F)nn(Cc3ccc(F)cc3)c2C1]

The title compound was synthesized according to the procedure described in Example 5-54, using Intermediate 2-2 as a starting material, to obtain a white solid (40 mg, yield 56% for the final step). $^1$H NMR (400 MHz, Methanol-d4) δ: 7.21-7.15 (m, 2H), 7.05-6.98 (m, 2H), 5.30-5.23 (m, 2H), 4.51-4.48 (m, 2H), 3.69-3.67 (m, 2H), 2.67-2.31 (m, 4H), 2.11-1.35 (m, 14H); LCMS (ESI) m/z 520.0 [M+H]$^+$

Example 5-56

(2R)-1-(tert-Butoxycarbonyl)-4-(2-(1-(4-chloro-2-fluorobenzyl)-3-(trifluoromethyl)-4,5-dihydro-1H-pyrazolo[3,4-c]pyridin-6(7H)-yl)-2-oxoethyl)pyrrolidine-2-carboxylic acid

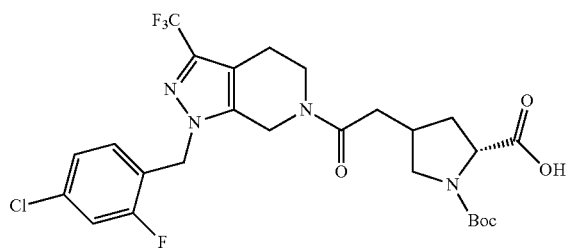 [SMILES: CC(C)(C)OC(=O)N1CC(CC(=O)N2CCc3c(C(F)(F)F)nn(Cc4ccc(Cl)cc4F)c3C2)C[C@@H]1C(=O)O]

The title compound was synthesized according to the procedure described in Example 5-18, using 2-((5R)-1-(tert-butoxycarbonyl)-5-(methoxycarbonyl)pyrrolidin-3-yl)acetic acid as a starting material, to obtain a white solid (350 mg, yield 93% over two steps). $^1$H NMR (400 MHz, Methanol-d4) δ: 7.22-7.06 (m, 3H), 5.30-5.27 (m, 2H), 4.60-4.58 (m, 2H), 4.12-4.08 (m, 1H), 3.72-3.62 (m, 3H), 2.99-2.95 (m, 1H), 2.66-2.45 (m, 6H), 1.60-1.57 (m, 1H), 1.35-1.19 (m, 9H); LCMS (ESI) m/z 489.2 [M-Boc+H]$^+$

Example 6-1

4-(2-(1-(3-Fluorobenzyl)-3-(trifluoromethyl)-4,5-dihydro-1H-pyrazolo[3,4-c]pyridin-6(7H)-yl)-2-oxoethyl)cyclohexanecarboxylic acid

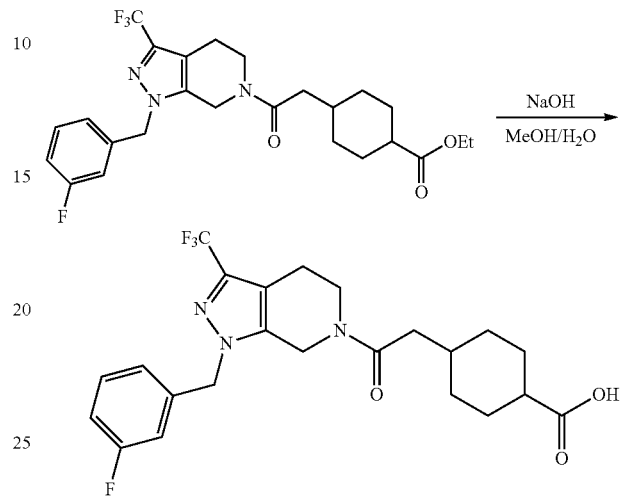

A mixture of ethyl 4-(2-(1-(3-fluorobenzyl)-3-(trifluoromethyl)-4,5-dihydro-1H-pyrazolo[3,4-c]pyridin-6(7H)-yl)-2-oxoethyl)cyclohexanecarboxylate (125 mg, 0.25 mmol) and NaOH (20 mg, 0.51 mmol) in MeOH/H$_2$O (3 mL) was stirred at room temperature overnight. TLC (PE/EA=1/1) showed the starting material was consumed completely. The solvent was removed in vacuum and the residue was dissolved in water. The aqueous phase was adjusted to about pH~2, then the solvent was removed in vacuum to give the crude which was purified by prep. HPLC (MeCN and H$_2$O with 0.225% (v/v) HCOOH as mobile phase) to provide 4-(2-(1-(3-fluorobenzyl)-3-(trifluoromethyl)-4,5-dihydro-1H-pyrazolo[3,4-c]pyridin-6(7H)-yl)-2-oxoethyl)cyclohexanecarboxylic acid (78 mg, yield 67%) as a mixture of cis and trans isomers. $^1$H NMR (400 MHz, Methanol-d4) δ: 7.40-7.33 (m, 1H), 7.05-6.91 (m, 3H), 5.39-5.34 (m, 2H), 4.60-4.53 (m, 2H), 3.77-3.71 (m, 2H), 2.73-2.63 (m, 2H), 2.52 (brs, 0.53H), 2.39-2.17 (m, 2H), 2.16-2.09 (m, 0.4H), 1.97-0.83 (m, 9H); LCMS (ESI) m/z 468.0 [M+H]$^+$

Example 6-2

4-(2-Oxo-2-(3-(trifluoromethyl)-1-(4-(trifluoromethyl)benzyl)-4,5-dihydro-1H-pyrazolo[3,4-c]pyridin-6(7H)-yl)ethyl)cyclohexanecarboxylic acid

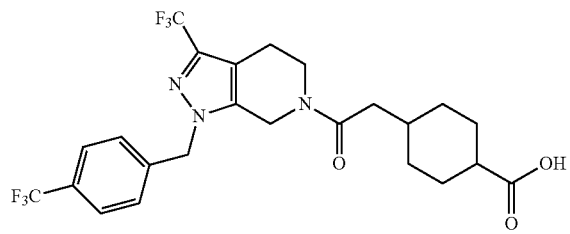 [SMILES: O=C(O)C1CCC(CC(=O)N2CCc3c(C(F)(F)F)nn(Cc4ccc(C(F)(F)F)cc4)c3C2)CC1]

The title compound was synthesized according to the procedure described in Example 6-1 as a mixture of isomers, using Example 1-10 as a starting material, to obtain a white solid (yield 42%). $^1$H NMR (400 MHz, Methanol-d4) δ: 7.74-7.68 (m, 2H), 7.43-7.39 (m, 2H), 5.52-5.47 (m, 2H), 4.65-4.61 (m, 2H), 3.82-3.76 (m, 2H), 2.77-2.68 (m, 2H), 2.55-2.21 (m, 3H), 2.01-1.72 (m, 4H), 1.64-1.35 (m, 4H), 1.11-0.90 (m, 1H); LCMS m/z 518.2 [M+H]$^+$ Example 6-3

4-(2-(1-(2-Fluorobenzyl)-3-(trifluoromethyl)-4,5-dihydro-1H-pyrazolo[3,4-c]pyridin-6(7H)-yl)-2-oxoethyl)cyclohexanecarboxylic acid

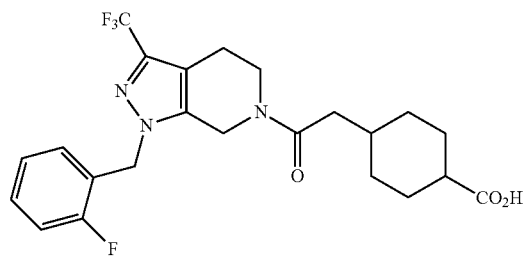 [SMILES: O=C(O)C1CCC(CC(=O)N2CCc3c(C(F)(F)F)nn(Cc4ccccc4F)c3C2)CC1]

The title compound was synthesized according to the procedure described in Example 6-1 as a mixture of isomers, using Example 1-19 as a starting material, to obtain a colorless gum (yield 63%). $^1$H NMR (400 MHz, Methanol-d4) δ: 7.38-7.33 (m, 1H), 7.18-7.12 (m, 3H), 5.41-5.36 (m, 2H), 4.67-4.62 (m, 2H), 3.78-3.72 (m, 2H), 2.71-2.62 (m, 2H), 2.52-2.24 (m, 3H), 1.97-1.75 (m, 4H), 1.59-1.53 (m, 2H), 1.39-1.20 (m, 2H), 1.07-0.93 (m, 1H); LCMS m/z 468.0 [M+H]$^+$ Example 6-4

4-(1-(1-(4-Chloro-2-fluorobenzyl)-3-(trifluoromethyl)-4,5-dihydro-1H-pyrazolo[3,4-c]pyridin-6(7H)-yl)-1-oxopropan-2-yl)cyclohexanecarboxylic acid

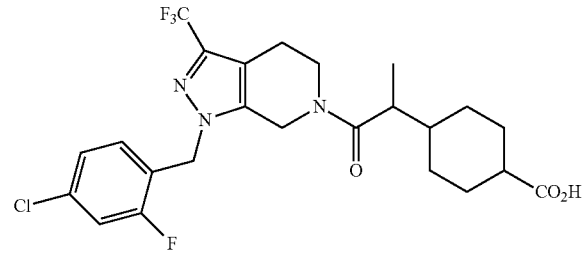 [SMILES: CC(C(=O)N1CCc2c(C(F)(F)F)nn(Cc3ccc(Cl)cc3F)c2C1)C1CCC(C(=O)O)CC1]

Step 1

Ethyl 4-(1-(1-(4-chloro-2-fluorobenzyl)-3-(trifluoromethyl)-4,5-dihydro-1H-pyrazolo[3,4-c]pyridin-6(7H)-yl)-1-oxopropan-2-yl)cyclohexanecarboxylate

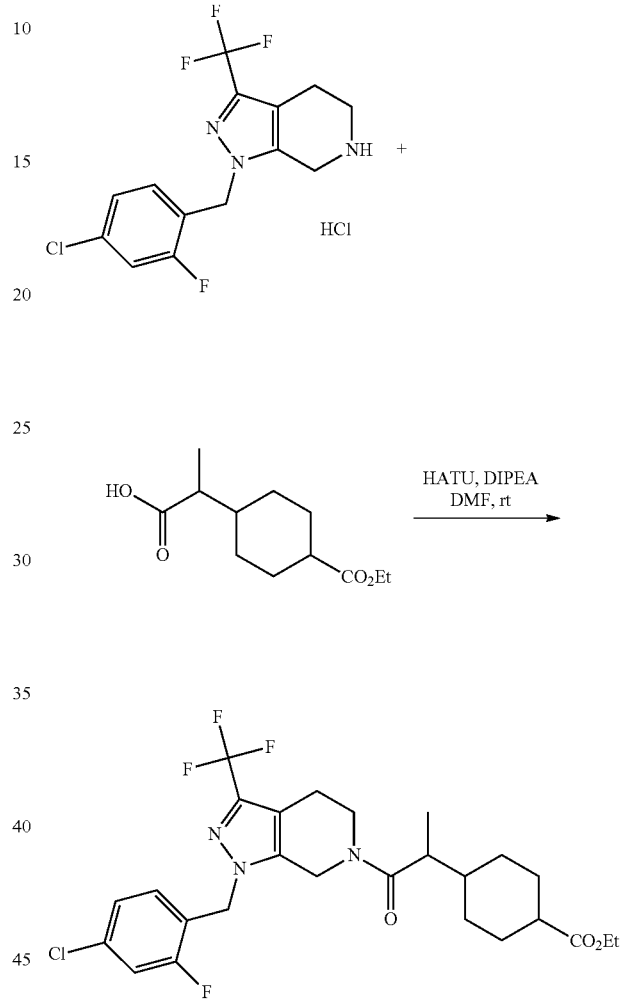

To a solution of 2-(4-(ethoxycarbonyl)cyclohexyl)propanoic acid (Intermediate 3-2, 111 mg, 0.487 mmol) and HATU (186 mg, 0.487 mmol) in DMF (2 mL) was added 1-(4-chloro-2-fluorobenzyl)-3-(trifluoromethyl)-4,5,6,7-tetrahydro-1H-pyrazolo[3,4-c]pyridine hydrochloride (120 mg, 0.325 mmol), followed by N,N-diisopropylethylamine (84 mg, 0.650 mmol). The mixture was stirred at rt for 16 h. The mixture was directly purified by prep HPLC (MeCN and H$_2$O with 0.05% TFA as mobile phase) to afford ethyl 4-(1-(1-(4-chloro-2-fluorobenzyl)-3-(trifluoromethyl)-4,5-dihydro-1H-pyrazolo[3,4-c]pyridin-6(7H)-yl)-1-oxopropan-2-yl)cyclohexanecarboxylate as a white solid after lyophilization (150 mg, yield 85%). LCMS (ESI) m/z 544.2 [M+H]$^+$ Step 2

4-(1-(1-(4-Chloro-2-fluorobenzyl)-3-(trifluoromethyl)-4,5-dihydro-1H-pyrazolo[3,4-c]pyridin-6(7H)-yl)-1-oxopropan-2-yl)cyclohexanecarboxylic acid

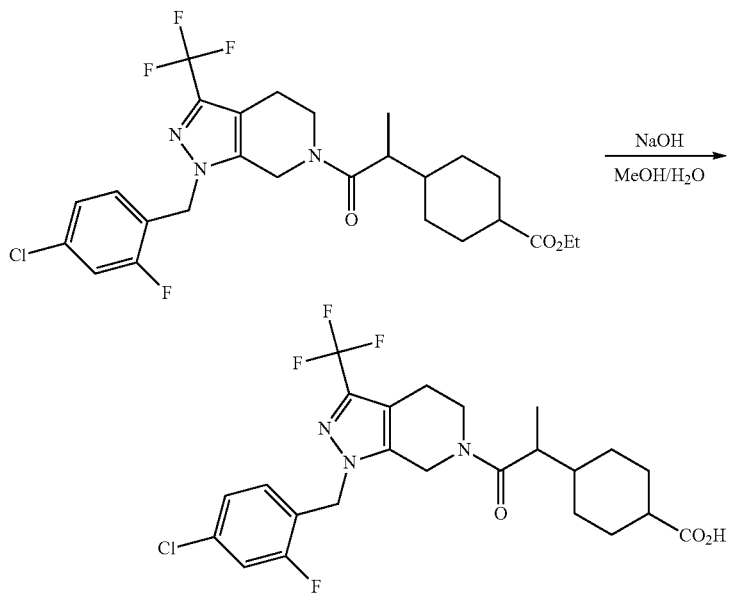

To a solution of ethyl 4-(1-(1-(4-chloro-2-fluorobenzyl)-3-(trifluoromethyl)-4,5-dihydro-1H-pyrazolo[3,4-c]pyridin-6(7H)-yl)-1-oxopropan-2-yl)cyclohexanecarboxylate (150 mg, 0.275 mmol) in MeOH (5 mL) and H$_2$O (5 mL) was added NaOH (33 mg, 0.825 mmol). The mixture was stirred at rt for 6 h. Then the organic solvent was removed under reduced pressure and the residue was acidified to pH=4 with 1N HCl. The mixture was purified by prep HPLC (MeCN and H$_2$O with 0.05% TFA as mobile phase) to afford 4-(1-(1-(4-chloro-2-fluorobenzyl)-3-(trifluoromethyl)-4,5-dihydro-1H-pyrazolo[3,4-c]-pyridin-6(7H)-yl)-1-oxopropan-2-yl)cyclohexanecarboxylic acid as a white solid after lyophilization (78 mg, yield 54%). $^1$H NMR (400 MHz, Methanol-d4) δ: 7.11-7.21 (m, 3H), 5.29-5.34 (m, 2H), 4.64-4.68 (m, 2H), 3.73-3.76 (m, 2H), 2.57-2.68 (m, 3H), 0.91-2.12 (m, 13 H); LCMS (ESI) m/z 516.2 [M+H]$^+$ Example 6-5

4-(2-(1-(4-chloro-2-fluorobenzyl)-3-(trifluoromethyl)-4,5-dihydro-1H-pyrazolo[3,4-c]pyridin-6(7H)-yl)-2-oxoethyl)-1-methylcyclohexanecarboxylic acid

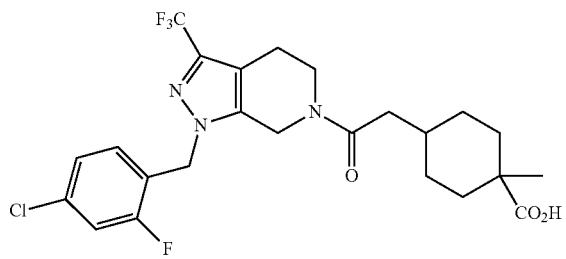 [SMILES: CC1(C(=O)O)CCC(CC(=O)N2CCc3c(C(F)(F)F)nn(Cc4ccc(Cl)cc4F)c3C2)CC1]

The title compound was synthesized according to the procedure described in Example 6-4 as a mixture of isomers, using Intermediate 3-5 as a starting material, to obtain a white solid (yield 33% over two steps). $^1$H NMR (400 MHz, Methanol-d4) δ: 7.33-7.17 (m, 3H), 5.42-5.37 (m, 2H), 4.70-4.67 (m, 2H), 3.82-3.74 (m, 2H), 2.76-2.63 (m, 2H), 2.46-2.26 (m, 2H), 2.19-2.15 (m, 1H), 1.79-1.61 (m, 4H), 1.36-1.10 (m, 7H); LCMS m/z 516.2 [M+H]$^+$ Example 6-6

3-(2-(1-(4-Chloro-2-fluorobenzyl)-3-(trifluoromethyl)-4,5-dihydro-1H-pyrazolo[3,4-c]pyridin-6(7H)-yl)-2-oxoethyl)cyclopentanecarboxylic acid

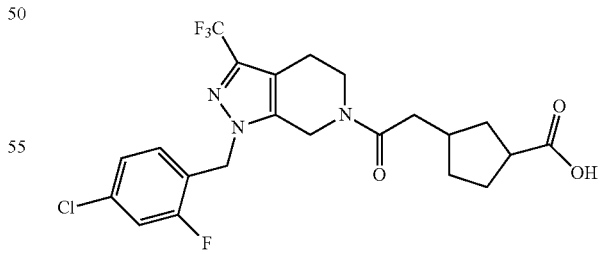

The title compound was synthesized according to the procedure described in Example 6-4 as a mixture of isomers, using Intermediate 3-4 as a starting material, to obtain a white solid (yield 25% over two steps). $^1$H NMR (400 MHz, Methanol-d4) δ: 7.24-7.08 (m, 3H), 5.33-5.28 (m, 2H), 4.61 (s, 2H), 3.74-3.67 (m, 2H), 2.74-1.78 (m, 10H), 1.42-1.18 (m, 2H); LCMS m/z 488.1 [M+H]$^+$

Example 6-7

3-(2-(1-(4-Fluorobenzyl)-3-(trifluoromethyl)-4,5-dihydro-1H-pyrazolo[3,4-c]pyridin-6(7H)-yl)-2-oxoethyl)cyclopentanecarboxylic acid

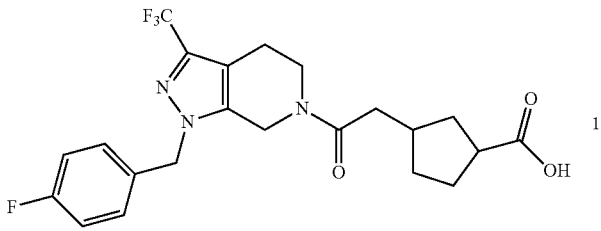

The title compound was synthesized according to the procedure described in Example 6-4 as a mixture of isomers, using Intermediate 2-2 and Intermediate 3-4 as starting materials, to obtain a white solid (yield 64% over two steps). $^1$H NMR (400 MHz, Methanol-d4) δ: 7.21-7.15 (m, 2H), 7.05-6.98 (m, 2H), 5.28-5.23 (m, 2H), 4.51-4.46 (m, 2H), 3.69-3.63 (m, 2H), 2.80-2.23 (m, 4H), 2.08-1.76 (m, 6H), 1.51-1.12 (m, 2H); LCMS m/z 454.2 [M+H]$^+$

Example 6-8

3-(2-(1-(4-Chloro-2-fluorobenzyl)-3-(trifluoromethyl)-4,5-dihydro-1H-pyrazolo[3,4-c]pyridin-6(7H)-yl)-2-oxoethyl)cyclobutanecarboxylic acid

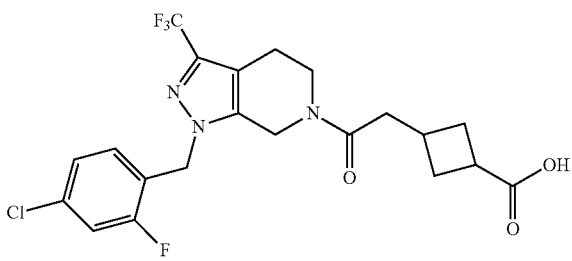 [SMILES: O=C(O)C1CC(CC(=O)N2CCc3c(C(F)(F)F)nn(Cc4ccc(Cl)cc4F)c3C2)C1]

The title compound was synthesized according to the procedure described in Example 6-4 as a mixture of isomers, using Intermediate 3-6 as a starting material, to obtain a white solid (yield 62% over two steps). $^1$H NMR (400 MHz, Methanol-d4) δ: 7.33-7.16 (m, 3H), 5.42-5.37 (m, 2H), 4.69-4.68 (m, 2H), 3.80-3.73 (m, 2H), 3.14-2.92 (m, 1H), 2.76-2.71 (m, 2H), 2.66-2.53 (m, 3H), 2.47-2.32 (m, 2H), 2.04-1.88 (m, 2H); LCMS m/z 474.0 [M+H]$^+$

Example 6-9

3-(2-(1-(4-Fluorobenzyl)-3-(trifluoromethyl)-4,5-dihydro-1H-pyrazolo[3,4-c]pyridin-6(7H)-yl)-2-oxoethyl)cyclobutanecarboxylic acid

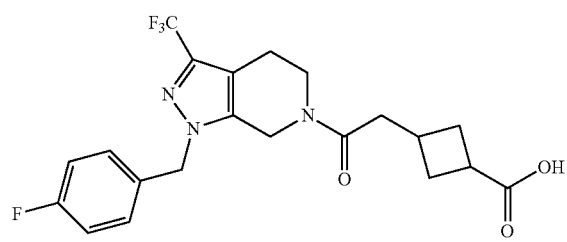 [SMILES: O=C(O)C1CC(CC(=O)N2CCc3c(C(F)(F)F)nn(Cc4ccc(F)cc4)c3C2)C1]

The titled compound was synthesized according to the procedure described in Example 6-4 as a mixture of isomers, using Intermediate 2-2 and Intermediate 3-6 as starting materials, to obtain a white solid (yield 52% over two steps). $^1$H NMR (400 MHz, Methanol-d4) δ: 7.32-7.25 (m, 2H), 7.16-7.08 (m, 2H), 5.39-5.33 (m, 2H), 4.59-4.56 (m, 2H), 3.77-3.71 (m, 2H), 3.14-2.91 (m, 1H), 2.76-2.62 (m, 4H), 2.51-2.29 (m, 3H), 2.03-1.84 (m, 2H); LCMS m/z 440.2 [M+H]$^+$

Example 6-10

8-(2-(1-(4-Chloro-2-fluorobenzyl)-3-(trifluoromethyl)-4,5-dihydro-1H-pyrazolo[3,4-c]pyridin-6(7H)-yl)-2-oxoethyl)bicyclo[3.2.1]octane-3-carboxylic acid

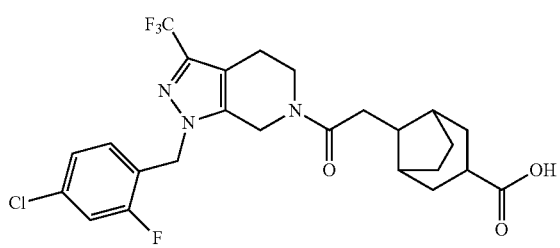 [SMILES: O=C(O)C1CC2CCC(C1)C2CC(=O)N1CCc2c(C(F)(F)F)nn(Cc3ccc(Cl)cc3F)c2C1]

The titled compound was synthesized according to the procedure described in Example 6-4 as a mixture of isomers, using Intermediate 3-3 as a starting material, to obtain a white solid (yield 70% over two steps). $^1$H NMR (400 MHz, Methanol-d4) δ: 7.07-7.25 (m, 3H), 5.28-5.33 (m, 2H), 4.62-4.66 (m, 2H), 3.70-3.74 (m, 2H), 2.48-2.71 (m, 5H), 1.84-2.04 (m, 3H), 1.66-1.76 (m, 4H), 1.42-1.55 (m, 4H); LCMS m/z 528.1 [M+H]$^+$

Example 6-11

4-(2-(1-(4-Fluorobenzyl)-3-(trifluoromethyl)-4,5-dihydro-1H-pyrazolo[3,4-c]pyridin-6(7H)-yl)-2-oxoethyl)-1-methylcyclohexanecarboxylic acid

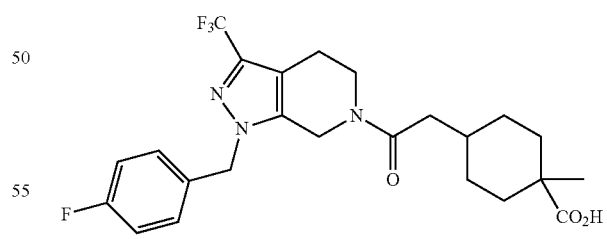

The title compound was synthesized according to the procedure described in Example 6-4 as a mixture of isomers, using Intermediate 2-2 and Intermediate 3-5 as starting materials, to obtain a white solid (yield 31% over two steps). $^1$H NMR (400 MHz, Methanol-d4) δ: 7.31-7.26 (m, 2H), 7.16-7.08 (m, 2H), 5.39-5.36 (m, 2H), 4.61-4.53 (m, 2H), 3.79-3.72 (m, 2H), 2.76-2.64 (m, 2H), 2.45-2.35 (m, 1H), 2.24-2.12 (m, 2H), 1.78-1.08 (m, 11H); LCMS m/z 482.1 [M+H]$^+$

Example 6-12

6-(2-(1-(4-Chloro-2-fluorobenzyl)-3-(trifluoromethyl)-4,5-dihydro-1H-pyrazolo[3,4-c]pyridin-6(7H)-yl)-2-oxoethyl)spiro[3.3]heptane-2-carboxylic acid

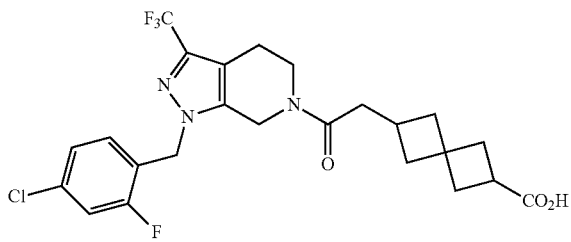 [SMILES: O=C(O)C1CC2(CC(CC(=O)N3CCc4c(C(F)(F)F)nn(Cc5ccc(Cl)cc5F)c4C3)C2)C1]

The title compound was synthesized according to the procedure described in Example 6-4 as a mixture of isomers, using Intermediate 3-7 as a starting material, to obtain a white solid (yield 76% over two steps). $^1$H NMR (400 MHz, Methanol-d4) δ: 12.01 (br s, 1H), 7.54-7.51 (m, 1H), 7.36-7.27 (m, 2H), 5.46-5.42 (m, 2H), 4.66-4.65 (m, 2H), 3.68-3.63 (m, 2H), 2.92-2.88 (m, 1H), 2.66-2.64 (m, 2H), 2.50-2.42 (m, 2H), 2.24-2.02 (m, 7H), 1.91-1.82 (m, 2H); LCMS m/z 514.1 [M+H]$^+$

Example 6-13

6-(2-(1-(4-Fluorobenzyl)-3-(trifluoromethyl)-4,5-dihydro-1H-pyrazolo[3,4-c]pyridin-6(7H)-yl)-2-oxoethyl)spiro[3.3]heptane-2-carboxylic acid

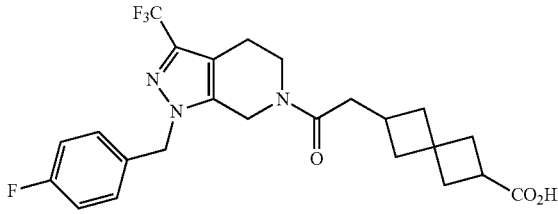 [SMILES: O=C(O)C1CC2(CC(CC(=O)N3CCc4c(C(F)(F)F)nn(Cc5ccc(F)cc5)c4C3)C2)C1]

The title compound was synthesized according to the procedure described in Example 6-4 as a mixture of isomers, using Intermediate 2-2 and Intermediate 3-7 as starting materials, to obtain a white solid (yield 60% over two steps). $^1$H NMR (400 MHz, Methanol-d4) δ: 7.21-7.15 (m, 2H), 7.06-6.98 (m, 2H), 5.27-5.22 (m, 2H), 4.48-4.41 (m, 2H), 3.66-3.59 (m, 2H), 2.89-2.85 (m, 1H), 2.64-2.62 (m, 2H), 2.48-2.42 (m, 2H), 2.27-1.90 (m, 7H), 1.70-1.42 (m, 2H); LCMS m/z 480.2 [M+H]$^+$

Example 6-14

3-(2-(1-(4-Chloro-2-fluorobenzyl)-3-(trifluoromethyl)-4,5-dihydro-1H-pyrazolo[3,4-c]pyridin-6(7H)-yl)-2-oxoethyl)-2,2-dimethylcyclobutanecarboxylic acid

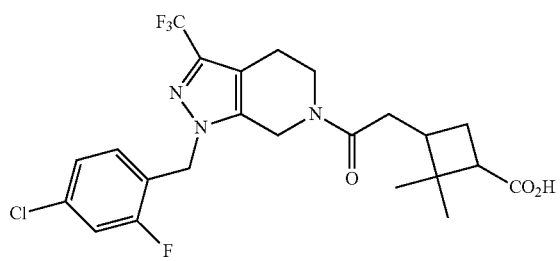 [SMILES: CC1(C)C(CC(=O)N2CCc3c(C(F)(F)F)nn(Cc4ccc(Cl)cc4F)c3C2)CC1C(=O)O]

The title compound was synthesized according to the procedure described in Example 6-4 as a mixture of isomers, using Intermediate 3-8 as a starting material, to obtain a white solid (37 mg, yield 22% over two steps). $^1$H NMR (400 MHz, Methanol-d4) δ: 7.06-7.23 (m, 3H), 5.27-5.32 (m, 2H), 4.57-4.60 (m, 2H), 3.64-3.70 (m, 2H), 2.66-2.68 (m, 2H), 2.24-2.56 (m, 4H), 1.78-1.99 (m, 2H), 0.86-1.15 (m, 6H); LCMS m/z 502.0 [M+H]$^+$

Example 6-15

3-(2-(1-(4-Fluorobenzyl)-3-(trifluoromethyl)-4,5-dihydro-1H-pyrazolo[3,4-c]pyridin-6(7H)-yl)-2-oxoethyl)-2,2-dimethylcyclobutanecarboxylic acid

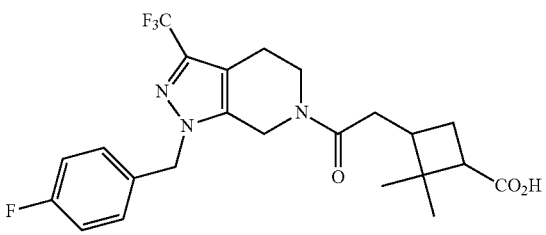 [SMILES: CC1(C)C(CC(=O)N2CCc3c(C(F)(F)F)nn(Cc4ccc(F)cc4)c3C2)CC1C(=O)O]

The title compound was synthesized according to the procedure described in Example 6-4 as a mixture of isomers, using Intermediate 2-2 and Intermediate 3-8 as starting materials, to obtain a white solid (36 mg, yield 26% over two steps). $^1$H NMR (400 MHz, Methanol-d4) δ: 7.25-7.31 (m, 2H), 7.08-7.16 (m, 2H), 5.33-5.39 (m, 2H), 4.56-4.58 (m, 2H), 3.70-3.78 (m, 2H), 2.27-2.80 (m, 6H), 1.80-2.10 (m, 2H), 0.92-1.24 (m, 6H); LCMS m/z 468.2 [M+H]$^+$

Example 6-16

(3R,4R)-5-(2-(1-(4-Chloro-2-fluorobenzyl)-3-(trifluoromethyl)-4,5-dihydro-1H-pyrazolo[3,4-c]pyridin-6(7H)-yl)-2-oxoethyl)tricyclo[2.2.1.0$^{2,6}$]heptane-3-carboxylic acid

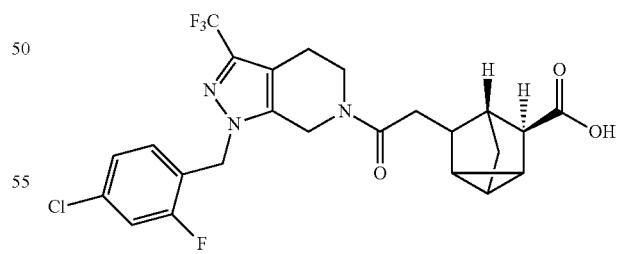

The title compound was synthesized according to the procedure described in Example 6-4 as a mixture of isomers, using Intermediate 3-9 as starting a material, to obtain a white solid (20 mg, yield 31% over two steps). $^1$H NMR (400 MHz, Methanol-d4) δ: 7.30-7.18 (m, 3H), 5.42-5.37 (m, 2H), 4.73-4.68 (m, 2H), 3.86-3.73 (m, 2H), 2.77-2.30 (m, 5H), 2.11-1.97 (m, 2H), 1.58-1.20 (m, 5H); LCMS m/z 512.2 [M+H]$^+$

Example 6-17

(3R,4R)-5-(2-(1-(4-Fluorobenzyl)-3-(trifluoromethyl)-4,5-dihydro-1H-pyrazolo[3,4-c]pyridin-6(7H)-yl)-2-oxoethyl)tricyclo[2.2.1.0²,⁶]heptane-3-carboxylic acid

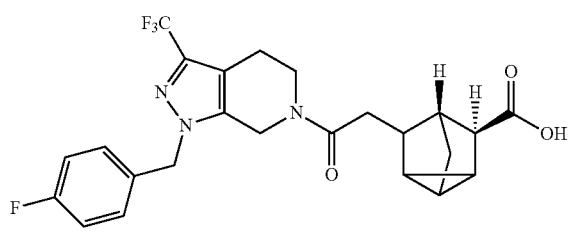 [SMILES: O=C(O)[C@H]1C2C3C[C@@H]1C(CC(=O)N1CCc4c(C(F)(F)F)nn(Cc5ccc(F)cc5)c4C1)C32]

The title compound was synthesized according to the procedure described in Example 6-4 as a mixture of isomers, using Intermediate 2-2 and Intermediate 3-9 as starting materials, to obtain a white solid (45 mg, yield 12% over two steps). $^1$H NMR (400 MHz, Methanol-d4) δ: 7.29-7.25 (m, 2H), 7.15-7.08 (m, 2H), 5.38-5.34 (m, 2H), 4.64-4.55 (m, 2H), 3.82-3.73 (m, 2H), 2.76-2.38 (m, 5H), 2.30-1.87 (m, 2H), 1.54-1.09 (m, 5H); LCMS m/z 478.2 [M+H]$^+$

Example 6-18

3-(2-(1-(4-Chloro-2-fluorobenzyl)-3-(trifluoromethyl)-4,5-dihydro-1H-pyrazolo[3,4-c]pyridin-6(7H)-yl)-2-oxoethyl)-1-methylcyclobutanecarboxylic acid

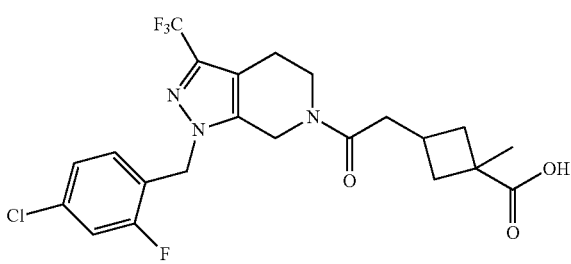 [SMILES: CC1(C(=O)O)CC(CC(=O)N2CCc3c(C(F)(F)F)nn(Cc4ccc(Cl)cc4F)c3C2)C1]

Step 1

2-(3-(Methoxycarbonyl)-3-methylcyclobutyl)acetic acid

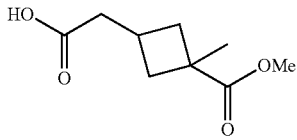

The title compound was synthesized according to the procedure described in Intermediate 3-3, using methyl 1-methyl-3-oxocyclobutanecarboxylate as a starting material, to obtain a yellow oil (220 mg, yield 36% over three steps). LCMS (ESI) m/z 187.1 [M+H]$^+$

Step 2

3-(2-(1-(4-Chloro-2-fluorobenzyl)-3-(trifluoromethyl)-4,5-dihydro-1H-pyrazolo[3,4-c]pyridin-6(7H)-yl)-2-oxoethyl)-1-methylcyclobutanecarboxylic acid The title compound was synthesized according to the procedure described in Example 5-50, using Intermediate 2-1 and 2-(3-(methoxycarbonyl)-3-methylcyclobutyl)acetic acid as starting materials, followed by Combi-Flash (biotage, 50 g C18 gel, MeCN in H$_2$O with 0.05% TFA) to obtain a yellow solid (70 mg, contain 1 eq. TFA, yield 55%). $^1$H NMR (400 MHz, Methanol-d4) δ: 7.33-7.16 (m, 3H), 5.42-5.37 (m, 2H), 4.68 (s, 2H), 3.80-3.73 (m, 2H), 2.75-2.57 (m, 6H), 2.20-1.68 (m, 3H), 1.43-1.33 (m, 3H); LCMS (ESI) m/z 488.1 [M+H]$^+$

Example 7-1 and 7-2 trans-4-(2-(1-(4-Fluorobenzyl)-3-(trifluoromethyl)-4,5-dihydro-1H-pyrazolo[3,4-c]pyridin-6(7H)-yl)-2-oxoethyl)cyclohexanecarboxylic acid and cis-4-(2-(1-(4-fluorobenzyl)-3-(trifluoro methyl)-4,5-dihydro-1H-pyrazolo[3,4-c]pyridin-6(7H)-yl)-2-oxoethyl)cyclohexanecarboxylic acid

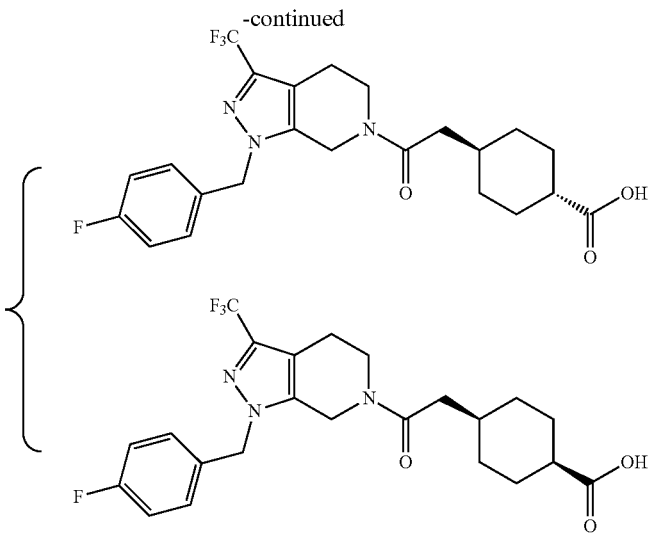

A mixture of ethyl 4-(2-(1-(4-fluorobenzyl)-3-(trifluoromethyl)-4,5-dihydro-1H-pyrazolo[3,4-c]pyridin-6(7H)-yl)-2-oxoethyl)cyclohexanecarboxylate (Example 1-1) (300 mg, 0.61 mmol) and NaOH (50 mg, 1.22 mmol) in MeOH/H$_2$O (4 mL) was stirred at room temperature overnight. TLC (PE/EA=1/1) showed the starting material was consumed completely. The solvent was removed in vacuum and the residue was dissolved in water. The pH of aqueous phase was adjusted to about 2. Then the solvent was removed in vacuum to give the crude which was purified by prep. HPLC (MeCN and H$_2$O with 0.225% (v/v) HCOOH as mobile phase) to provide trans-4-(2-(1-(4-fluorobenzyl)-3-(trifluoromethyl)-4,5-dihydro-1H-pyrazolo[3,4-c]pyridin-6(7H)-yl)-2-oxoethyl)cyclohexanecarboxylic acid (127 mg, yield 45%) and cis-4-(2-(1-(4-fluorobenzyl)-3-(trifluoromethyl)-4,5-dihydro-1H-pyrazolo[3,4-c]pyridin-6(7H)-yl)-2-oxoethyl)cyclohexanecarboxylic acid (92 mg, yield 33%) as a white solid.

trans-isomer (Example 7-1; peak-1): $^1$H NMR (400 MHz, Methanol-d4) δ: 7.26-7.23 (m, 2H), 7.14-7.06 (m, 2H), 5.36-5.31 (m, 2H), 4.59-4.53 (m, 2H), 3.76-3.70 (m, 2H), 2.71-2.62 (m, 2H), 2.37-2.35 (m, 1H), 2.20-2.15 (m, 2H), 1.97-1.55 (m, 5H), 1.42-1.35 (m, 2H), 1.07-0.90 (m, 2H); LCMS (ESI) m/z 468.0 [M+H]$^+$ cis-isomer (Example 7-2; peak-2): $^1$H NMR (400 MHz, Methanol-d4) δ: 7.26-7.23 (m, 2H), 7.13-7.05 (m, 2H), 5.35-5.31 (m, 2H), 4.59-4.52 (m, 2H), 3.77-3.70 (m, 2H), 2.71-2.62 (m, 2H), 2.53-2.51 (m, 1H), 2.40-2.38 (m, 1H), 2.21-2.19 (m, 1H), 1.97-1.92 (m, 3H), 1.72-1.52 (m, 4H), 1.31-1.21 (m, 2H); LCMS (ESI) m/z 468.0 [M+H]$^+$ Example 7-3 and 7-4 trans-4-(2-(1-(4-Chloro-2-fluorobenzyl)-4,5-dihydro-1H-pyrazolo[3,4-c]pyridin-6(7H)-yl)-2-oxoethyl)cyclohexanecarboxylic acid and cis-4-(2-(1-(4-chloro-2-fluorobenzyl)-4,5-dihydro-1H-pyrazolo[3,4-c]pyridin-6(7H)-yl)-2-oxoethyl)cyclohexanecarboxylic acid

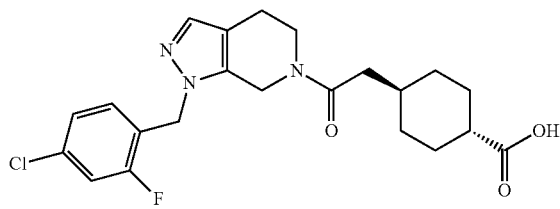

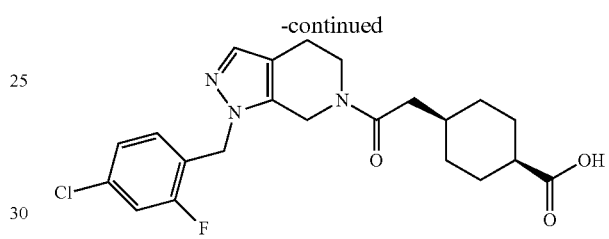

The title compounds were synthesized according to the procedure described in Example 7-1 and 7-2, using Example 1-4 as a starting material, to obtain:

trans-isomer (Example 7-3, peak-1, white solid, yield 23%): $^1$H NMR (400 MHz, Methanol-d4) δ: 7.38 (s, 1H), 7.28-7.04 (m, 3H), 5.36-5.32 (m, 2H), 4.69-4.66 (m, 2H), 3.82-3.74 (m, 2H), 2.71-2.61 (m, 2H), 2.42-1.65 (m, 8H), 1.47-1.33 (m, 2H), 1.12-0.97 (m, 2H); LCMS (ESI) m/z 434.1 [M+H]$^+$ cis-isomer (Example 7-4, peak-2, white solid, yield 23%): $^1$H NMR (400 MHz, Methanol-d4) δ: 7.38 (s, 1H), 7.37-7.05 (m, 3H), 5.36-5.32 (m, 2H), 4.69-4.67 (m, 2H), 3.82-3.74 (m, 2H), 2.71-2.60 (m, 3H), 2.45-2.33 (m, 2H), 2.05-1.82 (m, 3H), 1.65-1.57 (m, 4H), 1.38-1.34 (m, 2H); LCMS (ESI) m/z 434.1 [M+H]$^+$ Example 7-5 and 7-6 trans-4-(2-(1-(4-CXhlorobenzyl)-3-(trifluoromethyl)-4,5-dihydro-1H-pyrazolo[3,4-c]pyridin-6(7H)-yl)-2-oxoethyl)cyclohexanecarboxylic acid and cis-4-(2-(1-(4-chlorobenzyl)-3-(trifluoromethyl)-4,5-dihydro-1H-pyrazolo[3,4-c]pyridin-6(7H)-yl)-2-oxoethyl)cyclohexanecarboxylic acid

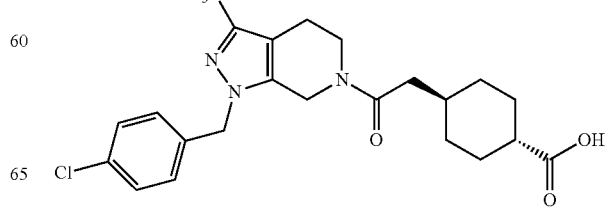

185

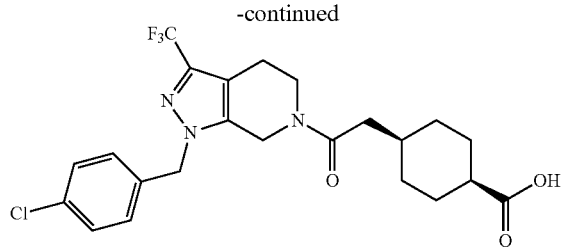

The title compounds were synthesized according to the procedure described in Example 7-1 and 7-2, using Example 1-8 as a starting material, to obtain:

trans-isomer (Example 7-5, peak-1, white solid, yield 35%): ¹H NMR (400 MHz, Methanol-d4) δ: 7.44-7.38 (m, 2H), 7.26-7.21 (m, 2H), 5.40-5.36 (m, 2H), 4.63-4.55 (m, 2H), 3.80-3.75 (m, 2H), 2.77-2.66 (m, 2H), 2.41-2.16 (m, 3H), 2.02-1.52 (m, 5H), 1.46-1.42 (m, 2H), 1.11-0.92 (m, 2H); LCMS (ESI) m/z 484.1 [M+H]⁺ cis-isomer (Example 7-6, peak-2, white solid, yield 38%): ¹H NMR (400 MHz, Methanol-d4) δ: 7.44-7.38 (m, 2H), 7.26-7.21 (m, 2H), 5.40-5.36 (m, 2H), 4.63-4.55 (m, 2H), 3.80-3.75 (m, 2H), 2.77-2.66 (m, 2H), 2.55-2.53 (m, 1H), 2.44-2.22 (m, 2H), 2.01-1.72 (m, 3H), 1.64-1.55 (m, 4H), 1.35-1.25 (m, 2H); LCMS (ESI) m/z 505.9 [M+Na]⁺

Example 7-7 and 7-8 trans-4-(2-(1-(2,4-Dichlorobenzyl)-3-(trifluoromethyl)-4,5-dihydro-1H-pyrazolo[3,4-c]pyridin-6(7H)-yl)-2-oxoethyl)cyclohexanecarboxylic acid and cis-4-(2-(1-(2,4-dichlorobenzyl)-3-(trifluoromethyl)-4,5-dihydro-1H-pyrazolo[3,4-c]pyridin-6(7H)-yl)-2-oxoethyl)cyclohexanecarboxylic acid

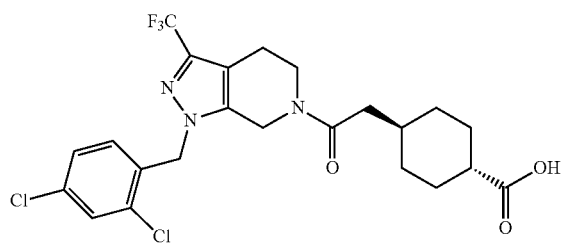

186

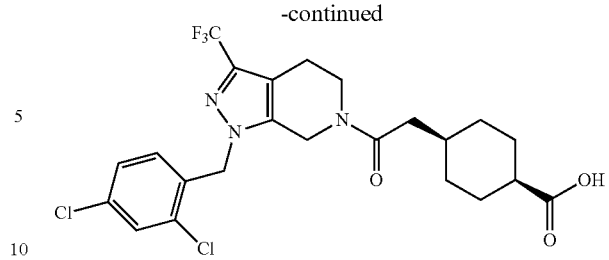

The title compounds were synthesized according to the procedure described in Example 7-1 and 7-2, using Example 1-9 as a starting material, to obtain:

trans-isomer (Example 7-7, peak-1, white solid, yield 33%): ¹H NMR (400 MHz, Methanol-d4) δ: 7.61-7.57 (m, 1H), 7.40-7.35 (m, 1H), 7.03-6.98 (m, 1H), 5.50-5.44 (m, 2H), 4.69-4.64 (m, 2H), 3.83-3.78 (m, 2H), 2.79-2.69 (m, 2H), 2.42-2.16 (m, 3H), 2.01-1.98 (m, 2H), 1.88-1.66 (m, 3H), 1.46-1.35 (m, 2H), 1.12-0.96 (m, 2H); LCMS (ESI) m/z 518.1 [M+H]⁺ cis-isomer (Example 7-8, peak-2, white solid, yield 34%): ¹H NMR (400 MHz, Methanol-d4) δ: 7.60-7.56 (m, 1H), 7.37-7.35 (m, 1H), 7.05-6.98 (m, 1H), 5.50-5.44 (m, 2H), 4.69-4.64 (m, 2H), 3.84-3.78 (m, 2H), 2.79-2.68 (m, 2H), 2.56-2.54 (m, 1H), 2.45-2.30 (m, 2H), 2.05-1.82 (m, 3H), 1.65-1.57 (m, 4H), 1.36-1.34 (m, 2H); LCMS (ESI) m/z 539.9 [M+Na]⁺

Example 7-9 and 7-10 cis-4-((1-(4-Chloro-2-fluorobenzyl)-3-(trifluoromethyl)-4,5,6,7-tetrahydro-1H-pyrazolo[3,4-c]pyridine-6-carbonyl)oxy)cyclohexanecarboxylic acid and trans-4-((1-(4-chloro-2-fluorobenzyl)-3-(trifluoromethyl)-4,5,6,7-tetrahydro-1H-pyrazolo[3,4-c]pyridine-6-carbonyl)oxy)cyclohexanecarboxylic acid

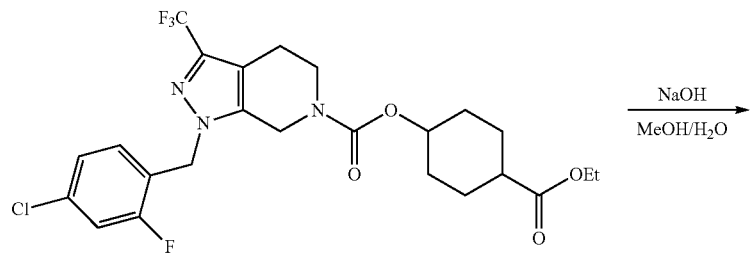

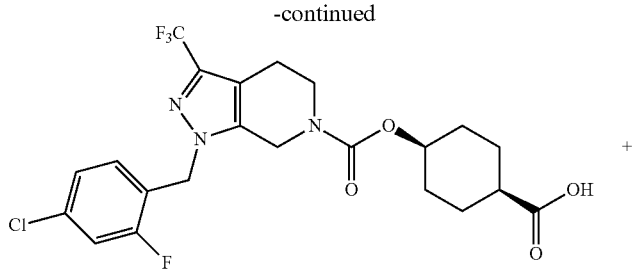

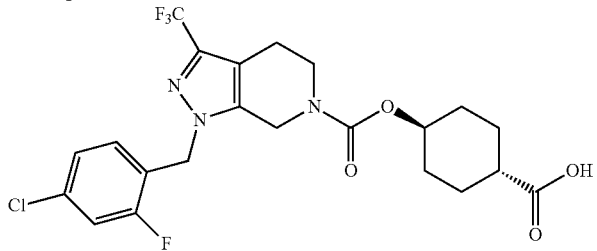

A mixture of 4-(ethoxycarbonyl)cyclohexyl1-(4-chloro-2-fluorobenzyl)-3-(trifluoromethyl)-4,5-dihydro-1H-pyrazolo[3,4-c]pyridine-6(7H)-carboxylate (Example 4-1, 280 mg, 0.53 mmol, 1.0 eq.) and NaOH (43 mg, 1.05 mmol, 2.0 eq.) in MeOH/H$_2$O (5 mL) was stirred at room temperature overnight. TLC (PE/EA=1/1) showed the starting material was consumed completely. The solvent was removed in vacuum and the residue was dissolved in water. The aqueous phase was adjusted to about pH=2. Then the solvent was removed in vacuum to give the crude which was purified by prep. HPLC (MeCN and H$_2$O with 0.225% (v/v) HCOOH as mobile phase) to provide cis-4-((1-(4-chloro-2-fluorobenzyl)-3-(trifluoromethyl)-4,5,6,7-tetrahydro-1H-pyrazolo[3,4-c]pyridine-6-carbonyl)oxy)cyclohexanecarboxylic acid (65 mg, yield 24%) and trans-4-((1-(4-chloro-2-fluorobenzyl)-3-(trifluoromethyl)-4,5,6,7-tetrahydro-1H-pyrazolo[3,4-c]pyridine-6-carbonyl)oxy)cyclohexanecarboxylic acid (55 mg, yield 20%) as a white solid.

cis isomer (Example 7-9, peak-1): $^1$H NMR (400 MHz, Methanol-d4) δ: 7.28-7.23 (m, 3H), 5.36 (s, 2H), 4.61 (s, 2H), 3.72-3.68 (m, 2H), 3.31-3.30 (m, 1H), 2.68 (s, 2H), 2.41-2.39 (m, 1H), 1.86-1.66 (m, 8H); LCMS (ESI) m/z 504.0 [M+H]$^+$ trans isomer (Example 7-10, peak-2): $^1$H NMR (400 MHz, Methanol-d4) δ: 7.27-7.13 (m, 3H), 5.34 (s, 2H), 4.55 (brs, 2H), 3.65 (s, 2H), 3.33-3.30 (m, 1H), 2.64 (s, 2H), 2.29 (t, J=11.2 Hz, 1H), 2.00 (brs, 4H), 1.57-1.36 (m, 4H); LCMS (ESI) m/z 504.0 [M+H]$^+$ Example 7-11 and 7-12 trans-4-(2-(1-Benzyl-3-(trifluoromethyl)-4,5-dihydro-1H-pyrazolo[3,4-c]pyridin-6(7H)-yl)-2-oxoethyl)cyclohexanecarboxylic acid and cis-4-(2-(1-benzyl-3-(trifluoromethyl)-4,5-dihydro-1H-pyrazolo[3,4-c]pyridin-6(7H)-yl)-2-oxoethyl)cyclohexanecarboxylic acid

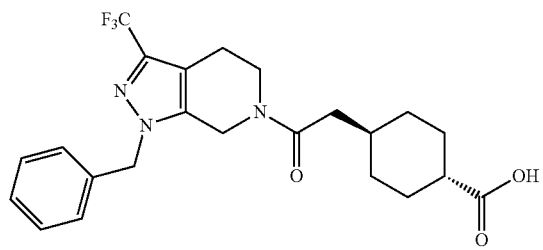

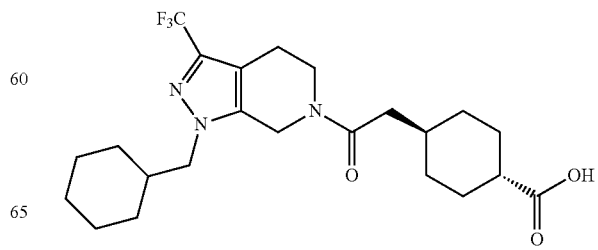

The title compounds were synthesized according to the procedure described in Example 7-1 and 7-2, using Example 1-13 as a starting material, to obtain:

trans-isomer (Example 7-11, peak-1, white solid, yield 10%): $^1$H NMR (400 MHz, Methanol-d4) δ: 7.40-7.20 (m, 5H), 5.39-5.35 (m, 2H), 4.59-4.51 (m, 2H), 3.79-3.71 (m, 2H), 2.73-2.64 (m, 2H), 2.38-2.37 (m, 1H), 2.21-2.12 (m, 2H), 1.99-1.28 (m, 7H), 1.09-0.87 (m, 2H); LCMS (ESI) m/z 450.0 [M+H]$^+$ cis-isomer (Example 7-12, peak-2, white solid, yield 30%): $^1$H NMR (400 MHz, Methanol-d4) δ: 7.40-7.20 (m, 5H), 5.39-5.34 (m, 2H), 4.58-4.47 (m, 2H), 3.78-3.71 (m, 2H), 2.73-2.63 (m, 2H), 2.53-2.48 (m, 1H), 2.41-2.39 (m, 1H), 2.12-2.10 (m, 1H), 2.01-1.72 (m, 3H), 1.61-1.51 (m, 4H), 1.32-1.20 (m, 2H); LCMS (ESI) m/z 450.2 [M+H]$^+$ Example 7-13 and 7-14 trans and cis-4 4-(2-(1-(cyclohexylmethyl)-3-(trifluoromethyl)-4,5-dihydro-1H-pyrazolo[3,4-c]pyridin-6(7H)-yl)-2-oxoethyl)cyclohexanecarboxylic acids -continued

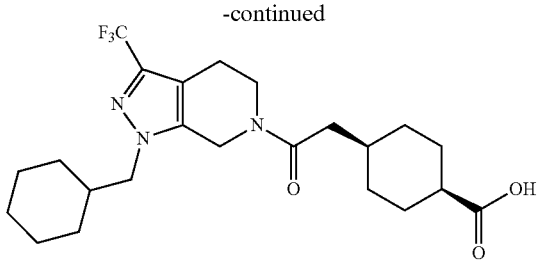

The title compounds were synthesized according to the procedure described in Example 7-1 and 7-2, using Example 1-16 as a starting material, to obtain:

Isomer-1 (Example 7-13, peak-1, white solid, yield 14%): $^1$H NMR (400 MHz, Methanol-d4) δ: 4.70 (s, 2H), 3.96-3.86 (m, 2H), 3.82-3.76 (m, 2H), 2.76-2.62 (m, 2H), 2.56-2.50 (m, 1H), 2.46-2.38 (m, 2H), 2.06-1.52 (m, 13H), 1.37-1.16 (m, 5H), 1.09-0.96 (m, 2H); LCMS (ESI) m/z 456.2 [M+H]$^+$ Isomer-2 (Example 7-14, peak-2, white solid, yield 14%): $^1$H NMR (400 MHz, Methanol-d4) δ: 4.70 (s, 2H), 3.96-3.86 (m, 2H), 3.83-3.71 (m, 2H), 2.77-2.62 (m, 2H), 2.42-2.35 (m, 2H), 2.26-2.15 (m, 1H), 2.01-1.63 (m, 9H), 1.60-1.52 (m, 2H), 1.46-1.37 (m, 2H), 1.30-1.17 (m, 3H), 1.13-0.96 (m, 4H); LCMS (ESI) m/z 456.2 [M+H]$^+$ Example 7-15 and 7-16 trans and cis-4-(2-(1-(4-Fluorobenzyl)-4,5-dihydro-1H-pyrazolo[3,4-c]pyridin-6(7H)-yl)-2-oxoethyl)cyclohexanecarboxylic acids

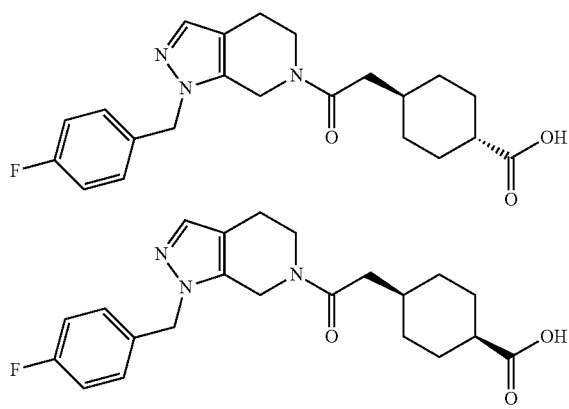

The title compounds were synthesized according to the procedure described in Example 7-1 and 7-2, using Example 1-17 as a starting material, to obtain:

Isomer-1 (Example 7-15, peak-1, white solid, yield 15%): $^1$H NMR (400 MHz, Methanol-d4) δ: 7.34 (s, 1H), 7.22-7.14 (m, 2H), 7.11-7.02 (m, 2H), 5.29-5.24 (m, 2H), 4.57-4.51 (m, 2H), 3.74-3.69 (m, 2H), 2.68-2.54 (m, 2H), 2.36 (d, J=6.4 Hz, 1H), 2.24-2.10 (m, 2H), 1.99-1.63 (m, 5H), 1.47-1.26 (m, 2H), 1.13-0.82 (m, 2H); LCMS (ESI) m/z 400.0 [M+H]$^+$ Isomer-2 (Example 7-16, peak-2, white solid, yield 15%): $^1$H NMR (400 MHz, Methanol-d4) δ: 7.34 (s, 1H), 7.23-7.12 (m, 2H), 7.11-7.01 (m, 2H), 5.28-5.24 (m, 2H), 4.57-4.50 (m, 2H), 3.73-3.69 (m, 2H), 2.69-2.62 (m, 1.3H), 2.58-2.47 (m, 1.8H), 2.39 (d, J=7.2 Hz, 1H), 2.20 (d, J=7.2 Hz, 1H), 2.04-1.88 (m, 3H), 1.64-1.45 (m, 4H), 1.35-1.18 (m, 2H); LCMS (ESI) m/z 400.0 [M+H]$^+$ Example 7-17 and 7-18 trans-4-(1-(4-Fluorobenzyl)-3-(trifluoromethyl)-4,5,6,7-tetrahydro-1H-pyrazolo[3,4-c]pyridine-6-carbonyl)cyclohexanecarboxylic acid and cis-4-(1-(4-fluorobenzyl)-3-(trifluoromethyl)-4,5,6,7-tetrahydro-1H-pyrazolo[3,4-c]pyridine-6-carbonyl)cyclohexanecarboxylic acid

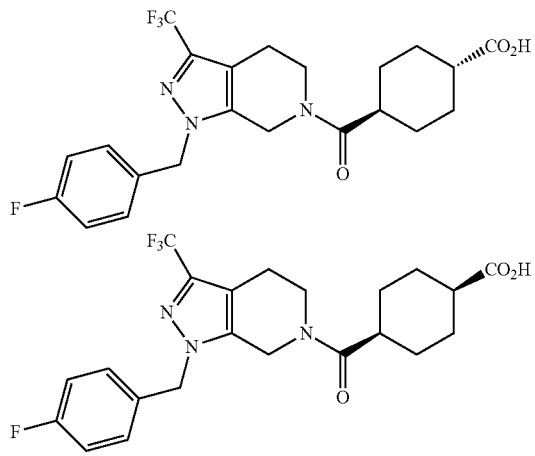

The title compounds were synthesized according to the procedure described in Example 7-1 and 7-2, using Example 1-22 as a starting material, to obtain:

trans-isomer (Example 7-17, peak-1, white solid, yield 5%): $^1$H NMR (400 MHz, Methanol-d4) δ: 7.25-7.23 (m, 2H), 7.13-7.06 (m, 2H), 5.38-5.31 (m, 2H), 4.57 (s, 2H), 3.76 (s, 2H), 2.74-2.61 (m, 2H), 2.42-2.66 (m, 2H), 2.02-1.81 (m, 3H), 1.55-1.36 (m, 5H); LCMS (ESI) m/z 453.9 [M+H]$^+$ cis-isomer (Example 7-18, peak-2, white solid, yield 18%): $^1$H NMR (400 MHz, Methanol-d4) δ: 7.26-7.05 (m, 4H), 5.37-5.30 (m, 2H), 4.56-4.54 (m, 2H), 3.74 (s, 2H), 2.77-2.44 (m, 4H), 2.16-2.08 (m, 2H), 1.69-1.37 (m, 6H); LCMS (ESI) m/z 454.0 [M+H]$^+$ Example 7-19 and 7-20 trans-4-(2-(1-cyclohexyl-3-(trifluoromethyl)-4,5-dihydro-1H-pyrazolo[3,4-c]pyridin-6(7H)-yl)-2-oxoethyl)cyclohexanecarboxylic acid and cis-4-(2-(1-cyclohexyl-3-(trifluoromethyl)-4,5-dihydro-1H-pyrazolo[3,4-c]pyridin-6(7H)-yl)-2-oxoethyl)cyclohexanecarboxylic acid

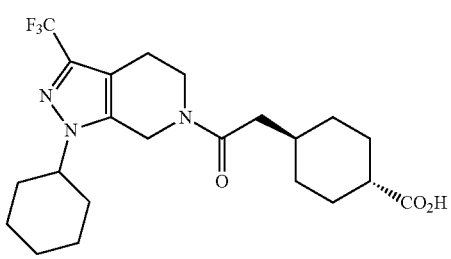

-continued

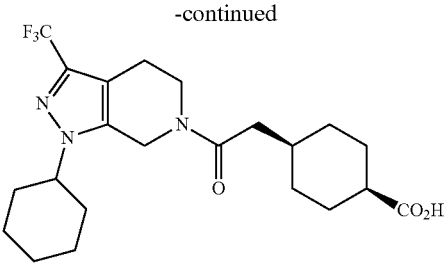

The title compounds were synthesized according to the procedure described in Example 7-1 and 7-2, using Intermediate 2-16 as a starting material, to obtain:

trans-isomer (Example 7-19, peak-1, white solid, yield 46% in the final separation step): $^1$H NMR (400 MHz, Methanol-d4) δ: 4.73 (s, 2H), 4.07-4.01 (m, 1H), 3.81-3.74 (m, 2H), 2.70-2.58 (m, 2H), 2.42-2.39 (m, 2H), 2.24-2.20 (m, 1H), 1.98-1.72 (m, 11H), 1.48-1.25 (m, 6H), 1.09-1.06 (m, 2H); LCMS (ESI) m/z 442.1 [M+H]$^+$ cis-isomer (Example 7-20, peak-2, white solid, yield 38% in the final separation step): $^1$H NMR (400 MHz, Methanol-d4) δ: 4.73 (s, 2H), 4.07-4.01 (m, 1H), 3.80-3.74 (m, 2H), 2.70-2.61 (m, 2H), 2.40-2.39 (m, 2H), 2.22-2.18 (m, 1H), 1.98-1.71 (m, 11H), 1.47-1.25 (m, 6H), 1.09-1.06 (m, 2H); LCMS (ESI) m/z 442.1 [M+H]$^+$ Example 7-21 and 7-22 cis-4-(2-(1-(2-Cyclohexylethyl)-3-(trifluoromethyl)-4,5-dihydro-1H-pyrazolo[3,4-c]pyridin-6(7H)-yl)-2-oxoethyl)cyclohexanecarboxylic acid and trans-4-(2-(1-(2-cyclohexylethyl)-3-(trifluoromethyl)-4,5-dihydro-1H-pyrazolo[3,4-c]pyridin-6(7H)-yl)-2-oxoethyl)cyclohexanecarboxylic acid

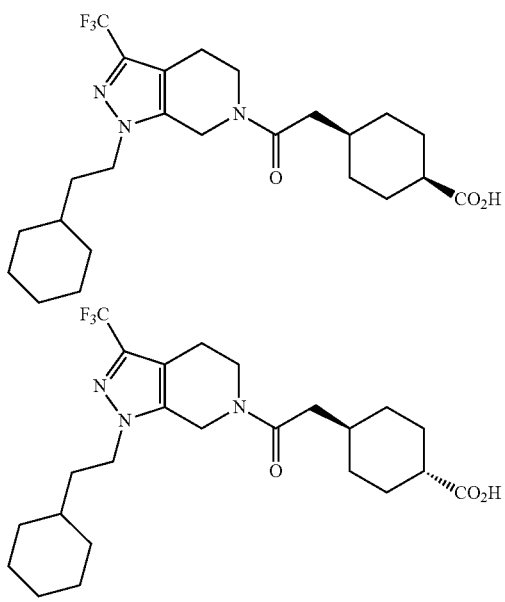

The title compounds were synthesized according to the procedure described in Example 7-1 and 7-2, using Intermediate 2-18 as a starting material, to obtain:

cis-isomer (Example 7-21, peak-1, white solid, yield 30% in the final separation step): $^1$H NMR (400 MHz, Methanol-d4) δ: 4.78-4.60 (m, 2H), 4.10-4.07 (m, 2H), 3.80-3.77 (m, 2H), 2.73-2.65 (m, 2H), 2.60-2.55 (m, 1H), 2.13-2.12 (m, 2H), 1.85-1.67 (m, 11H), 1.65-1.45 (m, 2H), 1.30-1.21 (m, 7H), 1.15-0.90 (m, 2H); LCMS (ESI) m/z 470.1 [M+H]$^+$ trans-isomer (Example 7-22, peak-2, white solid, yield 28% in the final separation step): $^1$H NMR (400 MHz, Methanol-d4) δ: 4.71-4.65 (m, 2H), 4.11-4.07 (m, 2H), 3.78-3.75 (m, 2H), 2.71-2.60 (m, 2H), 2.45-2.38 (m, 3H), 2.05-1.85 (m, 3H), 1.80-1.55 (m, 10H), 1.50-1.20 (m, 7H), 1.10-0.85 (m, 2H); LCMS (ESI) m/z 470.1 [M+H]$^+$ Example 7-23 and Example 7-24 cis-3-(2-(1-(4-Fluorobenzyl)-3-(trifluoromethyl)-4,5-dihydro-1H-pyrazolo[3,4-c]pyridin-6(7H)-yl)-2-oxoethyl)-1-methylcyclobutanecarboxylic acid and trans-3-(2-(1-(4-fluorobenzyl)-3-(trifluoromethyl)-4,5-dihydro-1H-pyrazolo[3,4-c]pyridin-6(7H)-yl)-2-oxoethyl)-1-methylcyclobutanecarboxylic acid

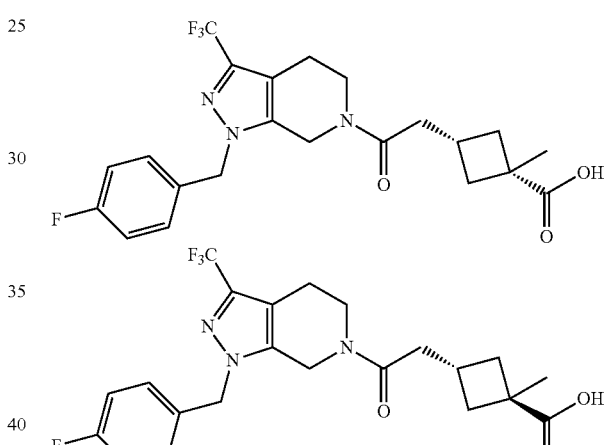

Step 1

Methyl 3-(2-(1-(4-fluorobenzyl)-3-(trifluoromethyl)-4,5-dihydro-1H-pyrazolo[3,4-c]pyridin-6(7H)-yl)-2-oxoethyl)-1-methylcyclobutanecarboxylate

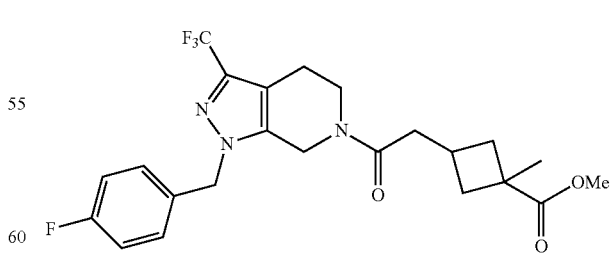

The title compound was synthesized according to the procedure described in Example 1-1, using 2-(3-(methoxycarbonyl)-3-methylcyclobutyl)acetic acid (Example 6-18, step 1) as a starting material, to obtain a yellow oil (150 mg, yield 50%). LCMS (ESI) m/z 467.9 [M+H]$^+$ Step 2 cis-3-(2-(1-(4-Fluorobenzyl)-3-(trifluoromethyl)-4,5-dihydro-1H-pyrazolo[3,4-c]pyridin-6(7H)-yl)-2-oxoethyl)-1-methylcyclobutanecarboxylic acid and trans-3-(2-(1-(4-fluorobenzyl)-3-(trifluoromethyl)-4,5-dihydro-1H-pyrazolo[3,4-c]pyridin-6(7H)-yl)-2-oxoethyl)-1-methylcyclobutanecarboxylic acid

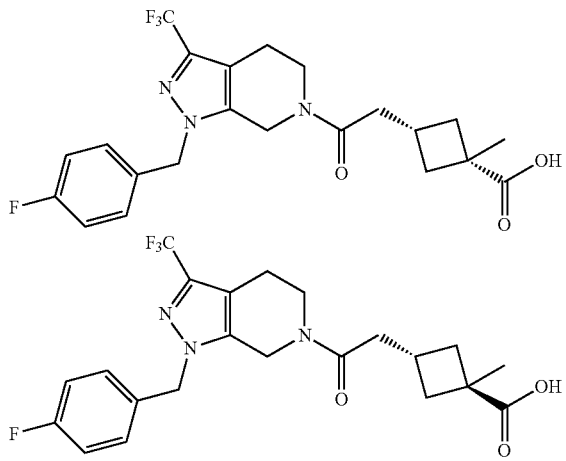

The title compound was synthesized according to the procedure described in Example 7-1 and 7-2, using methyl 3-(2-(1-(4-fluorobenzyl)-3-(trifluoromethyl)-4,5-dihydro-1H-pyrazolo[3,4-c]pyridin-6(7H)-yl)-2-oxoethyl)-1-methylcyclobutanecarboxylate as a starting material, to obtain:

cis-isomer (Example 7-23, 28 mg, yield 25%, white solid) a yellow solid (70 mg, contain 1 eq. TFA, yield 55%). $^1$H NMR (400 MHz, Methanol-d4) δ: 7.33-7.24 (m, 2H), 7.16-7.08 (m, 2H), 5.41-5.33 (m, 2H), 4.59 (bs, 2H), 3.91-3.71 (m, 2H), 2.76-2.53 (m, 5H), 2.11-1.94 (m, 4H), 1.37-1.35 (m, 3H); LCMS (ESI) m/z 454.1 [M+H]$^+$ trans-isomer (Example 7-24, 17 mg, yield 15%, white solid) a yellow solid (70 mg, contain 1 eq. TFA, yield 55%). $^1$H NMR (400 MHz, Methanol-d4) δ: 7.31-7.25 (m, 2H), 7.17-7.08 (m, 2H), 5.38-5.33 (m, 2H), 4.58-4.53 (m, 2H), 3.77-3.70 (m, 2H), 2.76-2.43 (m, 7H), 1.68-1.58 (m, 2H), 1.34-1.31 (m, 3H); LCMS (ESI) m/z 454.1 [M+H]$^+$ Example 7-25 and Example 7-26 cis-4-(2-(1-(4-fluorobenzyl)-3-(trifluoromethyl)-4,5-dihydro-1H-pyrazolo[3,4-c]pyridin-6(7H)-yl)-2-oxoethyl)-1-methylcyclohexanecarboxylic acid and trans-4-(2-(1-(4-fluorobenzyl)-3-(trifluoromethyl)-4,5-dihydro-1H-pyrazolo[3,4-c]pyridin-6(7H)-yl)-2-oxoethyl)-1-methylcyclohexanecarboxylic acid

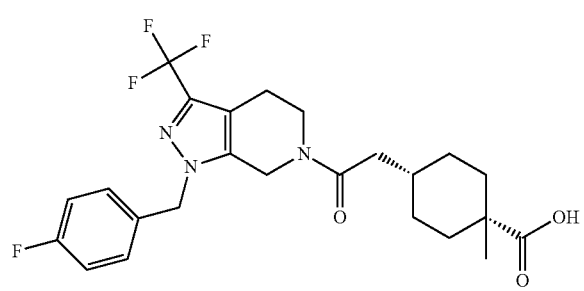

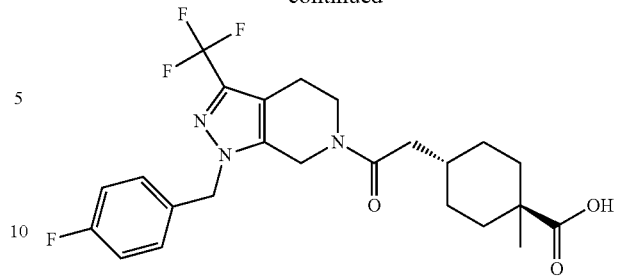

The title compound was synthesized according to the procedure described in Example 7-1 and 7-2, using Example 6-11 as a starting material, to obtain:

cis-isomer (Example 7-25). $^1$H NMR (400 MHz, Methanol-d4) δ: 7.21-7.16 (m, 2H), 7.06-6.98 (m, 2H), 5.29-5.24 (m, 2H), 4.52-4.46 (m, 2H), 3.71-3.63 (m, 2H), 2.66-2.55 (m, 2H), 2.35-2.13 (m, 2H), 1.69-1.43 (m, 7H), 1.24-1.06 (m, 5H); LCMS (ESI) m/z 482.0 [M+H]$^+$ trans-isomer (Example 7-26). $^1$H NMR (400 MHz, Methanol-d4) δ: 7.31-7.25 (m, 2H), 7.16-7.08 (m, 2H), 5.37-5.33 (m, 2H), 4.61-4.53 (m, 2H), 3.79-3.72 (m, 2H), 2.74-2.63 (m, 2H), 2.36-2.12 (m, 4H), 1.76-1.55 (m, 3H), 1.23-1.04 (m, 7H); LCMS (ESI) m/z 482.0 [M+H]$^+$ Example 8-1 tert-Butyl 3-(2-(1-(4-chloro-2-fluorobenzyl)-3-(trifluoromethyl)-4,5-dihydro-1H-pyrazolo[3,4-c]pyridin-6(7H)-yl)-2-oxoethyl)-8-azabicyclo[3.2.1]octane-8-carboxylate

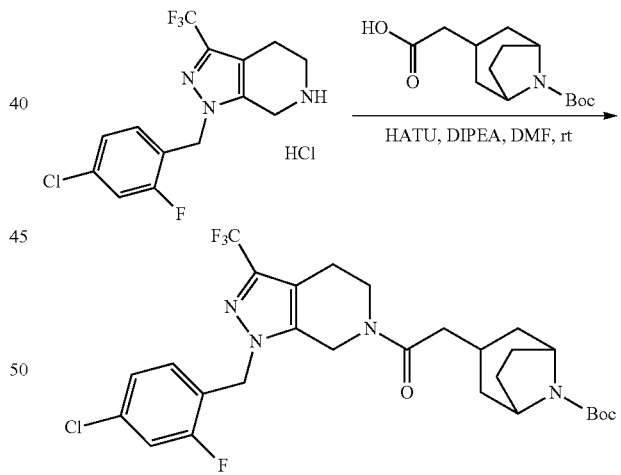

To a solution of 1-(4-chloro-2-fluorobenzyl)-3-(trifluoromethyl)-4,5,6,7-tetrahydro-1H-pyrazolo[3,4-c]pyridine hydrochloride (500 mg, 1.35 mmol) in DMF (5 mL) was added 2-(8-(tert-butoxycarbonyl)-8-azabicyclo[3.2.1]octan-3-yl)acetic acid (Intermediate 4-1, 364 mg, 1.35 mmol), HATU (513 mg, 1.35 mmol) and DIPEA (351 mg, 2.70 mmol, 2.0 eq). The mixture was stirred at rt for 3 h and directly purified by reversed phase HPLC (CH$_3$CN/H$_2$O with 0.05% TFA as mobile phase; from 0% to 95%) to give tert-butyl 3-(2-(1-(4-chloro-2-fluorobenzyl)-3-(trifluoromethyl)-4,5-dihydro-1H-pyrazolo[3,4-c]pyridin-6(7H)-yl)-2-oxoethyl)-8-azabicyclo[3.2.1]octane-8-carboxylate as a white solid (480 mg, yield 55%). $^1$H NMR (400 MHz, Methanol-d4) δ: 7.30-7.17 (m, 3H), 5.41-5.37 (m, 2H), 4.70-4.65 (m, 2H), 4.17 (br s, 2H), 3.81-3.74 (m, 2H), 2.74-1.62 (m, 11H), 1.47 (s, 9H), 1.45-1.31 (m, 2H); ESI-MS m/z 607.3 [M+Na]$^+$ Example 8-2 tert-Butyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)piperidine-1-carboxylate

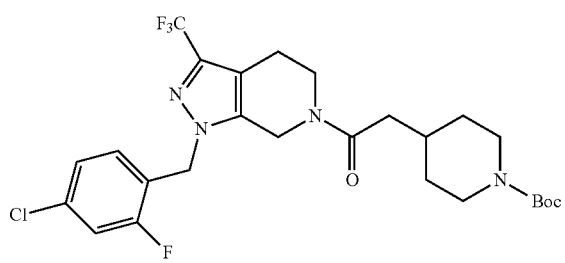 [SMILES: CC(C)(C)OC(=O)N1CCC(CC(=O)N2CCc3c(C(F)(F)F)nn(Cc4ccc(Cl)cc4F)c3C2)CC1]

The title compound was synthesized according to the procedure described in Example 8-1, using 2-(1-(tert-butoxycarbonyl)piperidin-4-yl)acetic acid as a starting material. $^1$H NMR (400 MHz, Methanol-d4) δ: 7.31-7.21 (m, 3H), 5.43-5.39 (m, 2H), 4.72-4.69 (m, 2H), 4.09-4.06 (m, 2H), 3.93-3.76 (m, 2H), 2.77-2.67 (m, 4H), 2.47-2.34 (m, 2H), 2.06-1.73 (m, 3H), 1.47 (s, 9H), 1.20-1.13 (m, 2H); LCMS (ESI) m/z 581.0 [M+Na]$^+$ Example 8-3 tert-Butyl 3-(2-(1-(4-chloro-2-fluorobenzyl)-3-(trifluoromethyl)-4,5-dihydro-1H-pyrazolo[3,4-c]pyridin-6(7H)-yl)-2-oxoethyl)azetidine-1-carboxylate

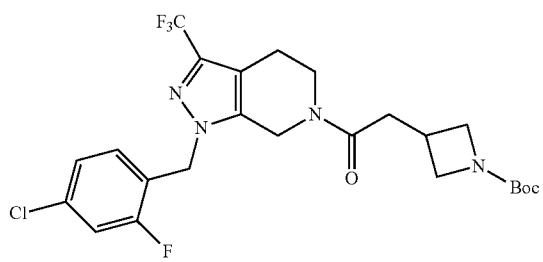 [SMILES: CC(C)(C)OC(=O)N1CC(CC(=O)N2CCc3c(C(F)(F)F)nn(Cc4ccc(Cl)cc4F)c3C2)C1]

The title compound was synthesized according to the procedure described in Example 8-1, using 2-(1-(tert-butoxycarbonyl)azetidin-3-yl)acetic acid as a starting material, to obtain a white solid (264 mg, yield 99%). $^1$H NMR (400 MHz, Methanol-d4) δ: 7.07-7.36 (m, 3H), 5.29-5.44 (m, 2H), 4.66 (s, 2H), 4.07 (t, J=7.91 Hz, 2H), 3.68-3.85 (m, 2H), 3.59 (d, J=5.27 Hz, 2H), 2.55-2.94 (m, 5H), 1.42 (s, 9H); LCMS (ESI) m/z 531.2 [M+H]$^+$ Example 8-4 tert-Butyl 3-(2-(1-(4-fluorobenzyl)-3-(trifluoromethyl)-4,5-dihydro-1H-pyrazolo[3,4-c]pyridin-6(7H)-yl)-2-oxoethyl)piperidine-1-carboxylate

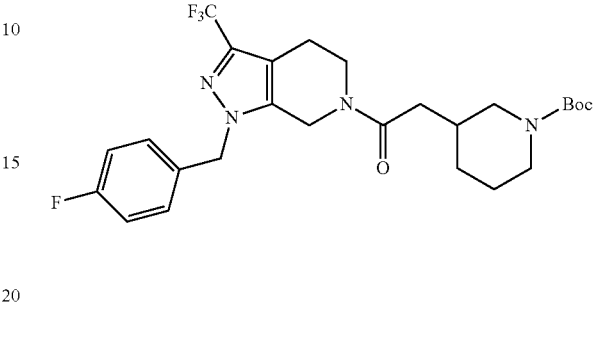

The title compound was synthesized according to the procedure described in Example 8-1, using 2-(1-(tert-butoxycarbonyl)piperidin-3-yl)acetic acid as a starting material, to obtain a white solid (yield 74%). $^1$H NMR (400 MHz, Methanol-d4) δ: 7.27-7.24 (m, 2H), 7.13-7.06 (m, 2H), 5.36-5.31 (m, 2H), 4.60-4.54 (m, 2H), 3.78-3.70 (m, 4H), 2.90-2.64 (m, 4H), 2.64-2.19 (m, 2H), 1.92-1.62 (m, 4H), 1.37 (s, 9H), 1.25-1.22 (m, 1H); LCMS (ESI) m/z 547.1 [M+Na]$^+$ Example 8-5 tert-Butyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)-2-methylpiperidine-1-carboxylate

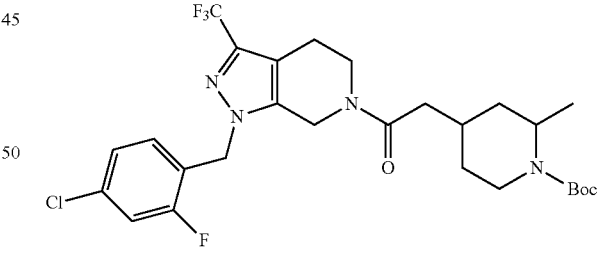

The title compound was synthesized according to the procedure described in Example 8-1, using Intermediate 4-2 as a starting material, to obtain a white solid (yield 64%). $^1$H NMR (400 MHz, Methanol-d4) δ: 7.22-7.07 (m, 3H), 5.32-5.27 (m, 2H), 4.62-4.59 (m, 2H), 4.28-3.56 (m, 4H), 3.22-2.75 (m, 1H), 2.64-2.55 (m, 2H), 2.42-2.05 (m, 2H), 1.96-1.48 (m, 3H), 1.36 (s, 9H), 1.30-1.03 (m, 5H); LCMS (ESI) m/z 595.2 [M+Na]$^+$

Example 8-6 tert-Butyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)-2,2-dimethylpiperidine-1-carboxylate

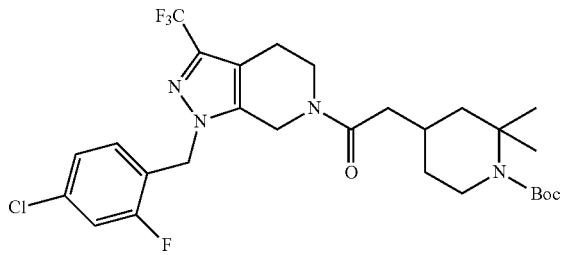 [SMILES: CC(C)(C)OC(=O)N1CCC(CC(=O)N2CCc3c(C(F)(F)F)nn(Cc4ccc(Cl)cc4F)c3C2)CC1(C)C]

The title compound was synthesized according to the procedure described in Example 8-1, using Intermediate 4-4 as a starting material, to obtain a white solid (yield 35%). $^1$H NMR (400 MHz, Methanol-d4) δ: 7.33-7.18 (m, 3H), 5.42-5.38 (m, 2H), 4.76-4.67 (m, 2H), 3.90-3.68 (m, 3H), 3.36-3.08 (m, 2H), 2.77-2.64 (m, 2H), 2.51-1.77 (m, 3H), 1.58-1.08 (m, 18H); LCMS (ESI) m/z 609.2 [M+Na]$^+$

Example 8-7 tert-Butyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)-2-(trifluoromethyl)piperidine-1-carboxylate

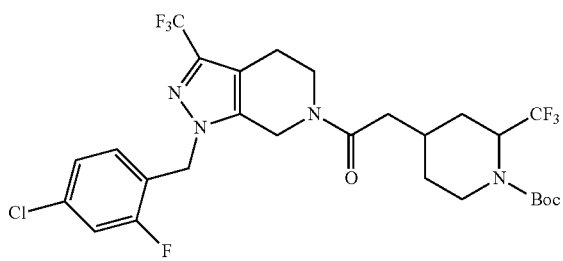 [SMILES: CC(C)(C)OC(=O)N1CCC(CC(=O)N2CCc3c(C(F)(F)F)nn(Cc4ccc(Cl)cc4F)c3C2)CC1C(F)(F)F]

The title compound was synthesized according to the procedure described in Example 8-1, using Intermediate 4-3 as a starting material, to obtain a white solid (yield 50%). $^1$H NMR (400 MHz, Methanol-d4) δ: 7.22-7.08 (m, 3H), 5.31-5.28 (m, 2H), 4.71-4.52 (m, 3H), 4.08-3.65 (m, 3H), 3.02-2.34 (m, 5H), 2.27-1.68 (m, 3H), 1.53-1.44 (m, 1H), 1.43 (s, 9H), 1.15-0.97 (m, 1H); LCMS (ESI) m/z 649.1 [M+Na]$^+$

Example 8-8 tert-Butyl 2-ethyl-4-(2-(1-(4-fluorobenzyl)-3-(trifluoromethyl)-4,5-dihydro-1H-pyrazolo[3,4-c]pyridin-6(7H)-yl)-2-oxoethyl)piperidine-1-carboxylate

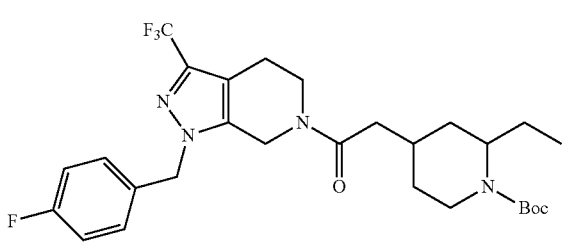 [SMILES: CCC1CC(CC(=O)N2CCc3c(C(F)(F)F)nn(Cc4ccc(F)cc4)c3C2)CCN1C(=O)OC(C)(C)C]

Step 1

2-(1-(tert-Butoxycarbonyl)-2-ethylpiperidin-4-yl)acetic acid

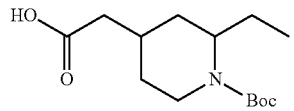

The title compound was synthesized according to the procedure described in Intermediate 4-1, using tert-butyl 2-ethyl-4-oxopiperidine-1-carboxylate as a starting material, to obtain a yellow solid (300 mg, yield 49% over two steps). LCMS (ESI) m/z 294.2 [M+Na]$^+$ Step 2 tert-Butyl 2-ethyl-4-(2-(1-(4-fluorobenzyl)-3-(trifluoromethyl)-4,5-dihydro-1H-pyrazolo[3,4-c]pyridin-6(7H)-yl)-2-oxoethyl)piperidine-1-carboxylate

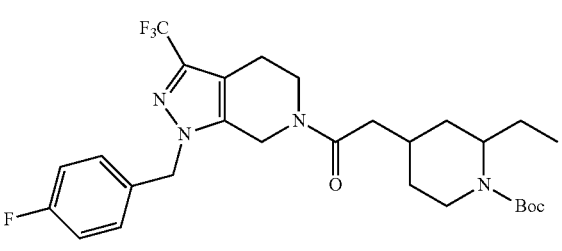 [SMILES: CCC1CC(CC(=O)N2CCc3c(C(F)(F)F)nn(Cc4ccc(F)cc4)c3C2)CCN1C(=O)OC(C)(C)C]

The title compound was synthesized according to the procedure described in Example 8-1, using 2-(1-(tert-butoxycarbonyl)-2-ethylpiperidin-4-yl)acetic acid and Intermediate 2-2 as starting materials, to obtain a yellow solid (300 mg, yield 55%). $^1$H NMR (400 MHz, Methanol-d4) δ: 7.23-7.16 (m, 2H), 7.07-6.99 (m, 2H), 5.28-5.24 (m, 2H), 4.58-4.47 (m, 2H), 4.08-3.60 (m, 4H), 2.96-2.54 (m, 3H), 2.41-2.02 (m, 2H), 1.91-1.74 (m, 1H), 1.63-1.38 (m, 3H), 1.36 (s, 9H), 1.21-0.98 (m, 3H), 0.81-0.69 (m, 3H); LCMS (ESI) m/z 575.2 [M+Na]$^+$

Example 8-9 tert-Butyl 4-(2-(1-(4-fluorobenzyl)-3-(trifluoromethyl)-4,5-dihydro-1H-pyrazolo[3,4-c]pyridin-6(7H)-yl)-2-oxoethyl)-2-propylpiperidine-1-carboxylate

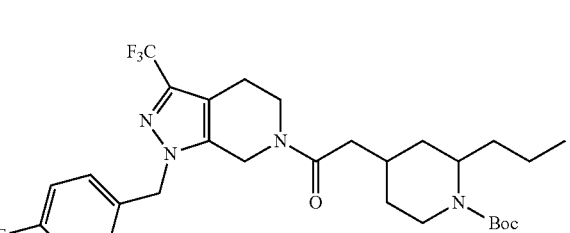

The title compound was synthesized according to the procedure described in Example 8-8, using 2-(1-(tert-butoxycarbonyl)-2-propylpiperidin-4-yl)acetic acid (prepared as Intermediate 4-1, using tert-butyl 2-propyl-4-oxopiperidine-1-carboxylate) as a starting material, to obtain a white solid (450 mg, yield 75% for the final step). $^1$H NMR (400 MHz, Methanol-d4) δ: 7.31-7.26 (m, 2H), 7.15-7.08 (m, 2H), 5.38-5.33 (m, 2H), 4.64-4.57 (m, 2H), 4.25-3.68 (m, 4H), 3.10-2.65 (m, 3H), 2.50-1.61 (m, 6H), 1.45 (s, 9H), 1.34-1.01 (m, 5H), 0.93 (t, J=7.2 Hz, 3H); LCMS (ESI) m/z 589.0 [M+Na]$^+$ Example 8-10 tert-Butyl 4-(1-(4-fluorobenzyl)-3-(trifluoromethyl)-4,5,6,7-tetrahydro-1H-pyrazolo[3,4-c]pyridine-6-carbonyl)bicyclo[2.2.2]octan-1-ylcarbamate

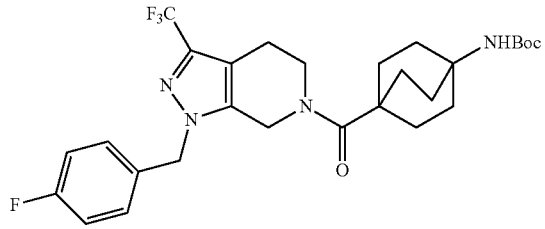 [SMILES: CC(C)(C)OC(=O)NC12CCC(C(=O)N3CCc4c(C(F)(F)F)nn(Cc5ccc(F)cc5)c4C3)(CC1)CC2]

The title compound was synthesized according to the procedure described in Example 8-1, using 4-(tert-butoxycarbonylamino)bicyclo[2.2.2]octane-1-carboxylic acid as a starting material, to obtain a white solid (720 mg, yield 45%). $^1$H NMR (400 MHz, Methanol-d4) δ: 7.30-7.27 (m, 2H), 7.16-7.12 (m, 2H), 5.35 (s, 2H), 4.59 (s, 2H), 3.84 (t, J=5.6 Hz, 2H), 2.69 (t, J=5.2 Hz, 2H), 1.90-1.80 (m, 12H), 1.43 (s, 9H); LCMS (ESI) m/z 551.2 [M+H]$^+$ Example 9-1

2-(8-Aza-bicyclo[3.2.1]octan-3-yl)-1-(1-(4-chloro-2-fluorobenzyl)-3-(trifluoromethyl)-4,5-dihydro-1H-pyrazolo[3,4-c]pyridin-6(7H)-yl)ethanone TFA salt

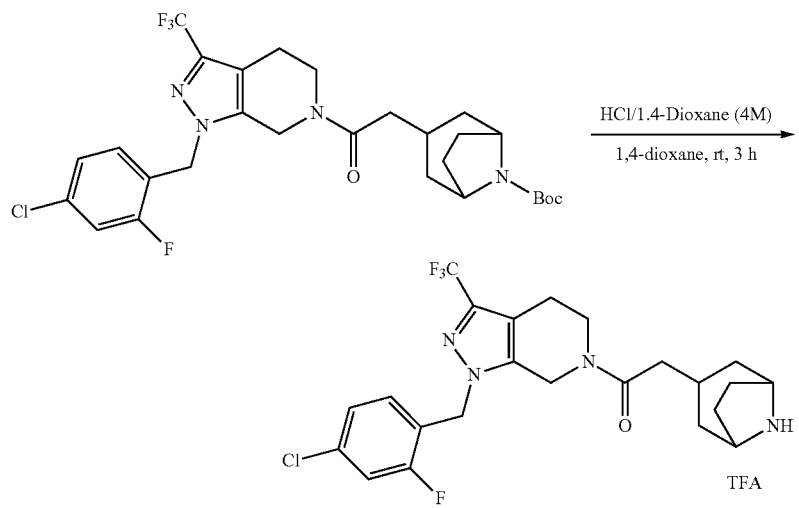

tert-Butyl 3-(2-(1-(4-chloro-2-fluorobenzyl)-3-(trifluoromethyl)-4,5-dihydro-1H-pyrazolo[3,4-c]pyridin-6(7H)-yl)-2-oxoethyl)-8-azabicyclo[3.2.1]octane-8-carboxylate (Example 8-1, 400 mg, 0.68 mmol) was added to a solution of HCl in 1,4-dioxane (4M, 10 mL). The mixture was stirred at rt for 3 h. LC-MS showed the reaction was completed. The mixture was concentrated and the residue was purified by reversed phase HPLC (CH$_3$CN/H$_2$O with 0.05% TFA as mobile phase; from 0% to 95%) to give 2-(8-aza-bicyclo[3.2.1]octan-3-yl)-1-(1-(4-chloro-2-fluorobenzyl)-3-(trifluoromethyl)-4,5-dihydro-1H-pyrazolo[3,4-c]pyridin-6(7H)-yl)ethanone TFA salt as a white solid (250 mg, yield 75%). $^1$H NMR (400 MHz, Methanol-d4) δ 7.31-7.18 (m, 3H), 5.43-5.37 (m, 2H), 4.71-4.69 (m, 2H), 4.01 (br s, 2H), 3.83-3.74 (m, 2H), 2.79-2.66 (m, 2H), 2.48-1.91 (m, 9H), 1.77-1.54 (m, 2H); ESI-MS m/z 485.2 [M+H]$^+$ Example 9-2

1-(1-(4-Chloro-2-fluorobenzyl)-3-(trifluoromethyl)-4,5-dihydro-1H-pyrazolo[3,4-c]pyridin-6(7H)-yl)-2-(piperidin-4-yl)ethanone HCl salt

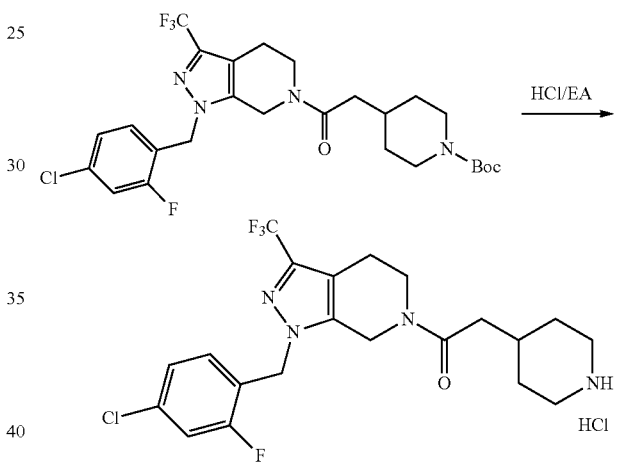

A mixture of tert-butyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)piperidine-1-carboxylate (Example 8-2, 50 mg, 0.09 mmol, 1.0 eq.) in HCl/EtOAc (3 mL) was stirred at room temperature for 2 h. TLC (PE/EA=2/1) showed the starting material was consumed completely. The solvent was removed in vacuum and the crude was purified by prep. HPLC (MeCN and H₂O with 0.05% (v/v) HCl as mobile phase) to give 1-(1-(4-chloro-2-fluorobenzyl)-3-(trifluoromethyl)-4,5-dihydro-1H-pyrazolo[3,4-c]pyridin-6(7H)-yl)-2-(piperidin-4-yl)ethanone hydrochloride (20 mg, 53% yield) as a white solid. ¹H NMR (400 MHz, Methanol-d4) δ: 7.31-7.22 (m, 3H), 5.44-5.39 (m, 2H), 4.73 (s, 2H), 3.79-3.77 (m, 2H), 3.41-3.38 (m, 2H), 3.03 (t, J=8.8 Hz, 2H), 2.79-2.65 (m, 2H), 2.55-2.46 (m, 2H), 2.15-2.00 (m, 3H), 1.54-1.48 (m, 2H); LCMS (ESI) m/z 459.1 [M+H]⁺

Example 9-3

2-(Azetidin-3-yl)-1-(1-(4-chloro-2-fluorobenzyl)-3-(trifluoromethyl)-4,5-dihydro-1H-pyrazolo[3,4-c]pyridin-6(7H)-yl)ethanone TFA salt

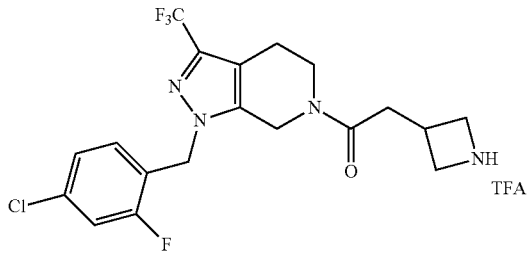 [SMILES: O=C(CC1CNC1)N1CCc2c(C(F)(F)F)nn(Cc3ccc(Cl)cc3F)c2C1]

The title compound was synthesized according to the procedure described in Example 9-1, using Example 8-3 as a starting material, to obtain a white solid (66 mg, yield 25%). ¹H NMR (400 MHz, Methanol-d4) δ: 7.09-7.38 (m, 3H), 5.26-5.43 (m, 2H), 4.60-4.72 (m, 2H), 4.16 (t, J=10.04 Hz, 2H), 3.85-3.96 (m, 2H), 3.68-3.83 (m, 2H), 3.19-3.27 (m, 1H), 2.82-2.98 (m, 2H), 2.60-2.82 (m, 2H); LCMS (ESI) m/z 431.1 [M+H]⁺

Example 9-4

1-(1-(4-Fluorobenzyl)-3-(trifluoromethyl)-4,5-dihydro-1H-pyrazolo[3,4-c]pyridin-6(7H)-yl)-2-(piperidin-3-yl)ethanone HCl salt

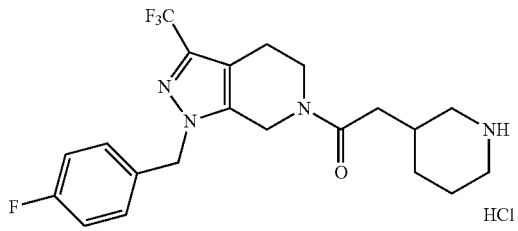 [SMILES: O=C(CC1CCCNC1)N1CCc2c(C(F)(F)F)nn(Cc3ccc(F)cc3)c2C1 ; Cl]

The title compound was synthesized according to the procedure described in Example 9-2, using Example 8-4 as a starting material, to obtain a white solid (600 mg, yield 100%). ¹H NMR (400 MHz, Methanol-d4) δ: 7.27-7.23 (m, 2H), 7.14-7.06 (m, 2H), 5.36-5.32 (m, 2H), 4.59-4.54 (m, 2H), 3.73-3.68 (m, 2H), 3.41-3.33 (m, 2H), 2.87-2.86 (m, 1H), 2.73-2.24 (m, 6H), 1.92-1.71 (m, 3H), 1.32-1.22 (m, 1H); LCMS (ESI) m/z 425.1 [M+H]⁺

Example 9-5

1-(1-(4-Chloro-2-fluorobenzyl)-3-(trifluoromethyl)-4,5-dihydro-1H-pyrazolo[3,4-c]pyridin-6(7H)-yl)-2-(2-methylpiperidin-4-yl)ethanone TFA salt

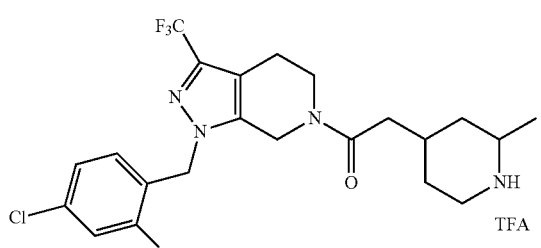

The title compound was synthesized according to the procedure described in Example 9-1, using Example 8-5 as a starting material, to obtain a white solid (yield 81%). ¹H NMR (400 MHz, Methanol-d4) δ: 7.32-7.18 (m, 3H), 5.43-5.37 (m, 2H), 4.71 (s, 2H), 3.84-3.75 (m, 2H), 3.57-3.38 (m, 1H), 3.25-3.19 (m, 1H), 3.07-3.00 (m, 1H), 2.76-2.43 (m, 4H), 2.05-1.98 (m, 3H), 1.78-1.65 (m, 1H), 1.34-1.30 (m, 4H); LCMS (ESI) m/z 473.1 [M+H]⁺

Example 9-6

1-(1-(4-Chloro-2-fluorobenzyl)-3-(trifluoromethyl)-4,5-dihydro-1H-pyrazolo[3,4-c]pyridin-6(7H)-yl)-2-(2,2-dimethylpiperidin-4-yl)ethanone TFA salt

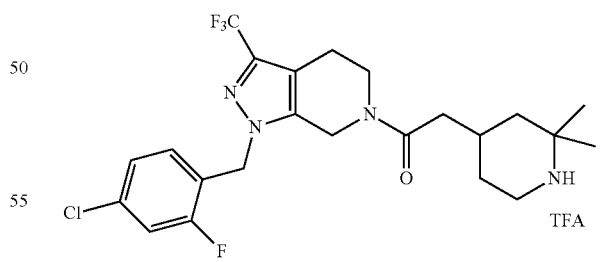

The title compound was synthesized according to the procedure described in Example 9-1, using Example 8-6 as a starting material, to obtain a white solid (yield 80%). ¹H NMR (400 MHz, Methanol-d4) δ: 7.33-7.21 (m, 3H), 5.41-5.38 (m, 2H), 4.75-4.65 (m, 2H), 3.89-3.67 (m, 2H), 3.36-3.21 (m, 3H), 2.77-2.54 (m, 2H), 2.50-2.28 (m, 4H), 2.02-1.83 (m, 1H), 1.41-1.26 (m, 7H); LCMS (ESI) m/z 487.1 [M+H]⁺

Example 9-7

1-(1-(4-Chloro-2-fluorobenzyl)-3-(trifluoromethyl)-4,5-dihydro-1H-pyrazolo[3,4-c]pyridin-6(7H)-yl)-2-(2-(trifluoromethyl)piperidin-4-yl)ethanone TFA salt

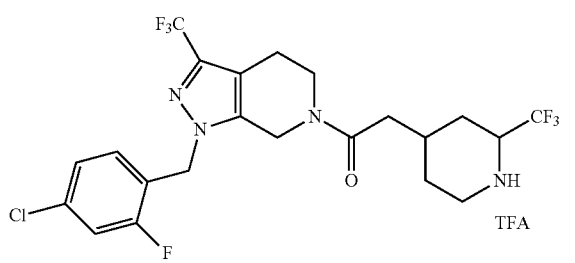 [SMILES: O=C(CC1CCNC(C(F)(F)F)C1)N1CCc2c(C(F)(F)F)nn(Cc3ccc(Cl)cc3F)c2C1 ; "TFA"]

The title compound was synthesized according to the procedure described in Example 9-1, using Example 8-7 as a starting material, to obtain a white solid (yield 60%). $^1$H NMR (400 MHz, Methanol-d4) δ: 7.32-7.18 (m, 3H), 5.43-5.38 (m, 2H), 4.77-4.68 (m, 2H), 4.44-4.19 (m, 1H), 3.85-3.74 (m, 2H), 3.56-3.35 (m, 1H), 3.27-3.10 (m, 1H), 2.77-1.82 (m, 8H), 2.53-1.45 (m, 1H); LCMS (ESI) m/z 527.1 [M+H]$^+$

Example 9-8

(2s)-4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)pyrrolidine-2-carboxylic acid TFA salt

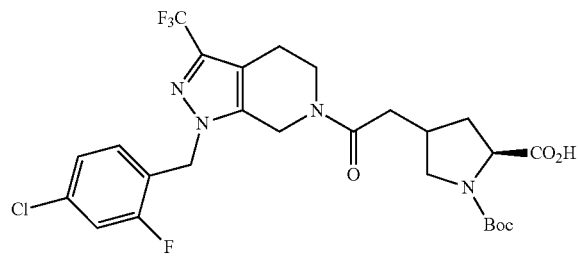

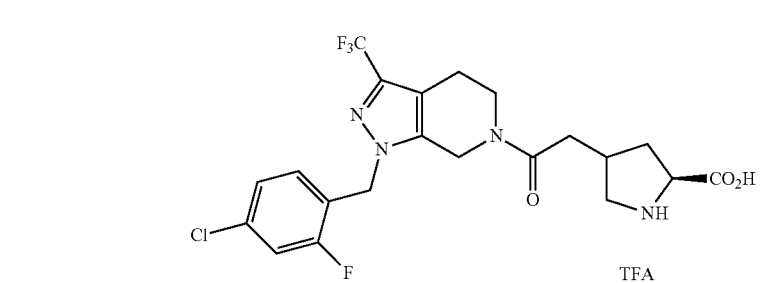

To a solution of (2s)-1-(tert-butoxycarbonyl)-4-(2-(1-(4-chloro-2-fluorobenzyl)-3-(trifluoromethyl)-4,5-dihydro-1H-pyrazolo[3,4-c]pyridin-6(7H)-yl)-2-oxoethyl)pyrrolidine-2-carboxylic acid (Example 5-18, 350 mg, 0.59 mmol, 1.0 eq) in dioxane (5 mL) was added conc. HCl (2 mL). The mixture was stirred at rt for 2 h and concentrated. The residue was purified by prep HPLC (MeCN and H$_2$O with 0.05% TFA as mobile phase) to afford (2S)-4-(2-(1-(4-chloro-2-fluorobenzyl)-3-(trifluoromethyl)-4,5-dihydro-1H-pyrazolo[3,4-c]pyridin-6(7H)-yl)-2-oxoethyl)pyrrolidine-2-carboxylic acid trifluoroacetate salt as white solid (290 mg, yield 100%). $^1$H NMR (400 MHz, Methanol-d4) δ: 7.18-7.32 (m, 3H), 5.37-5.40 (m, 2H), 4.66-4.70 (m, 2H), 4.34-4.39 (m, 1H), 3.62-3.86 (m, 3H), 3.01-3.07 (m, 1H), 2.60-2.88 (m, 6H), 1.79-1.87 (m, 1H); LCMS (ESI) m/z 489.1 [M+H]$^+$

Example 9-9

(4-Aminobicyclo[2.2.2]octan-1-yl)(1-(4-fluorobenzyl)-3-(trifluoromethyl)-4,5-dihydro-1H-pyrazolo[3,4-c]pyridin-6(7H)-yl)methanone TFA salt

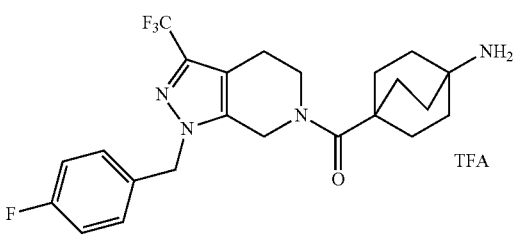 [SMILES: NC12CCC(C(=O)N3CCc4c(C(F)(F)F)nn(Cc5ccc(F)cc5)c4C3)(CC1)CC2 ; "TFA"]

The title compound was synthesized according to the procedure described in Example 9-1, using Example 8-10 as a starting material, to obtain a white solid (350 mg, yield 85%). $^1$H NMR (400 MHz, Methanol-d4) δ: 7.29-7.25 (m, 2H), 7.15-7.10 (m, 2H), 5.35 (s, 2H), 4.58 (s, 2H), 3.86 (t, J=5.6 Hz, 2H), 2.72 (t, J=4.8 Hz, 2H), 2.03-1.99 (m, 6H), 1.83-1.79 (m, 6H); LCMS (ESI) m/z 451.0 [M+H]$^+$

Example 9-10

2-(4-Aminobicyclo[2.2.2]octan-1-yl)-1-(1-(4-fluorobenzyl)-3-(trifluoromethyl)-4,5-dihydro-1H-pyrazolo[3,4-c]pyridin-6(7H)-yl)ethanone TFA salt

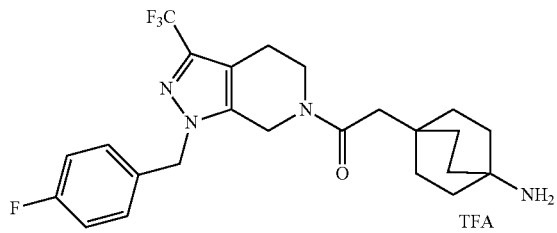 [SMILES: NC12CCC(CC(=O)N3CCc4c(C(F)(F)F)nn(Cc5ccc(F)cc5)c4C3)(CC1)CC2 ; "TFA"]

Step 1 tert-Butyl 4-(2-(1-(4-fluorobenzyl)-3-(trifluoromethyl)-4,5-dihydro-1H-pyrazolo[3,4-c]pyridin-6(7H)-yl)-2-oxoethyl)bicyclo[2.2.2]octan-1-ylcarbamate

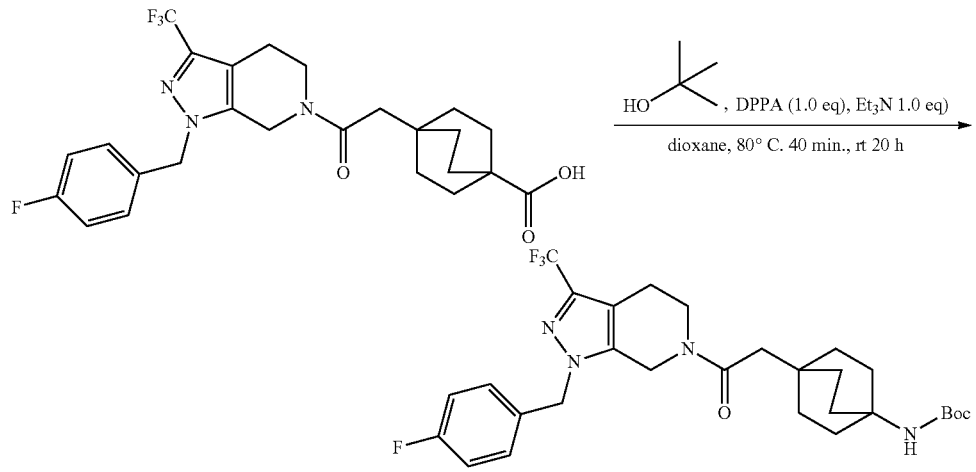

A mixture of 4-(2-(1-(4-fluorobenzyl)-3-(trifluoromethyl)-4,5-dihydro-1H-pyrazolo[3,4-c]pyridin-6(7H)-yl)-2-oxoethyl)bicyclo[2.2.2]octane-1-carboxylic acid (Example 5-13, 150 mg, 0.30 mmol, 1.0 eq), 2-methylpropan-2-ol (45 mg, 0.60 mmol, 2.0 eq), DPPA (82 mg, 0.3 mmol, 1.0 eq) and Et$_3$N (30 mg, 0.3 mmol, 1.0 eq) in dioxane (10 mL) was heated at 80° C. for 40 min and then at rt for 20 h. The mixture was concentrated and the residue was purified by prep HPLC (CH$_3$CN/H$_2$O with 0.05% ammonia as mobile phase) to afford tert-butyl 4-(2-(1-(4-fluorobenzyl)-3-(trifluoromethyl)-4,5-dihydro-1H-pyrazolo[3,4-c]pyridin-6(7H)-yl)-2-oxoethyl)bicyclo[2.2.2]octan-1-ylcarbamate as a brown solid (140 mg, yield 81%). LCMS (ESI) m/z 509.2 [M-55]$^+$

Step 2

2-(4-Aminobicyclo[2.2.2]octan-1-yl)-1-(1-(4-fluorobenzyl)-3-(trifluoromethyl)-4,5-dihydro-1H-pyrazolo[3,4-c]pyridin-6(7H)-yl)ethanone TFA salt

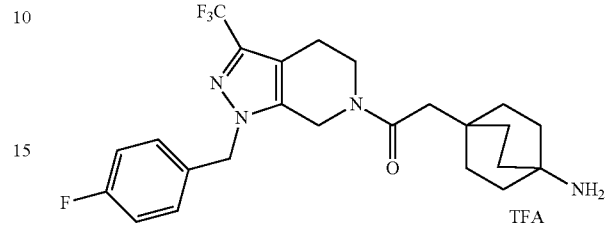

The title compound was synthesized according to the procedure described in Example 9-1, using tert-butyl 4-(2-(1-(4-fluorobenzyl)-3-(trifluoromethyl)-4,5-dihydro-1H-pyrazolo[3,4-c]pyridin-6(7H)-yl)-2-oxoethyl)bicyclo[2.2.2]octan-1-ylcarbamate as a starting material, to obtain a

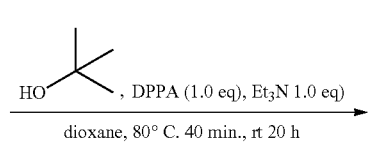

yellow oil (90 mg, yield 69%). $^1$H NMR (400 MHz, Methanol-d4) δ: 7.33-7.25 (m, 2H), 7.19-7.08 (m, 2H), 5.38-5.33 (m, 2H), 4.59-4.54 (m, 2H), 3.78-3.73 (m, 2H), 2.74-2.64 (m, 2H), 2.36-2.16 (m, 2H), 1.77-1.50 (m, 12H); LCMS (ESI) m/z 465.2 [M+H]$^+$

Example 9-11

2-(2-Ethylpiperidin-4-yl)-1-(1-(4-fluorobenzyl)-3-(trifluoromethyl)-4,5-dihydro-1H-pyrazolo[3,4-c]pyridin-6(7H)-yl)ethanone TFA salt

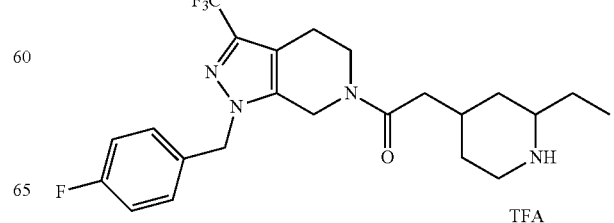

The title compound was synthesized according to the procedure described in Example 9-1, using Example 8-8 as a starting material, to obtain a yellow solid (170 mg, yield 60%). $^1$H NMR (400 MHz, Methanol-d4) δ: 7.31-7.26 (m, 2H), 7.17-7.09 (m, 2H), 5.39-5.34 (m, 2H), 4.67-4.56 (m, 2H), 3.82-3.71 (m, 2H), 3.40-3.00 (m, 4H), 2.77-2.59 (m, 3H), 2.55-1.92 (m, 3H), 1.80-1.57 (m, 4H), 1.04-1.00 (m, 3H); LCMS (ESI) m/z 453.2 [M+H]$^+$ Example 9-12

1-(1-(4-Fluorobenzyl)-3-(trifluoromethyl)-4,5-dihydro-1H-pyrazolo[3,4-c]pyridin-6(7H)-yl)-2-(2-propylpiperidin-4-yl)ethanone acid TFA salt

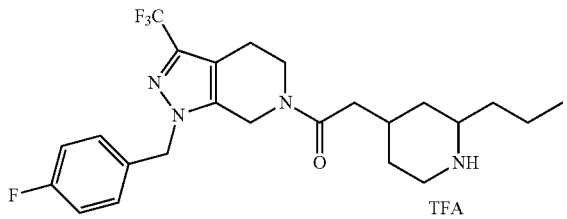 [SMILES: CCCC1CC(CC(=O)N2CCc3c(C(F)(F)F)nn(Cc4ccc(F)cc4)c3C2)CCN1 ; "TFA"]

The title compound was synthesized according to the procedure described in Example 9-1, using Example 8-9 as a starting material, to obtain a yellow solid (220 mg, yield 90%). $^1$H NMR (400 MHz, Methanol-d4) δ: 7.29-7.25 (m, 2H), 7.08-7.15 (m, 2H), 5.38-5.34 (m, 2H), 4.62-4.57 (m, 2H), 3.81-3.72 (m, 2H), 3.36-3.32 (m, 1H), 3.23-2.97 (m, 2H), 2.75-1.08 (m, 13H), 0.97 (t, J=7.2 Hz, 3H); LCMS (ESI) m/z 467.0 [M+H]$^+$ Example 9-13

1-(1-(4-Fluorobenzyl)-3-(trifluoromethyl)-4,5-dihydro-1H-pyrazolo[3,4-c]pyridin-6(7H)-yl)-2-(2-(trifluoromethyl)piperidin-4-yl)ethanone TFA salt

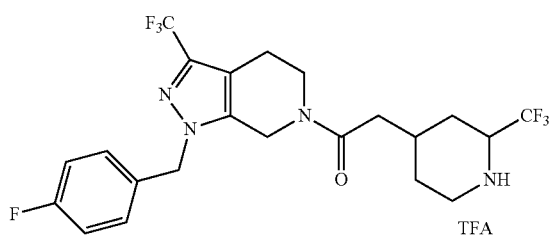 [SMILES: O=C(CC1CCNC(C(F)(F)F)C1)N1CCc2c(C(F)(F)F)nn(Cc3ccc(F)cc3)c2C1 ; "TFA"]

The title compound was synthesized according to the procedure described in Example 9-7, using Intermediate 2-2 as a starting material, to obtain a white solid (220 mg, yield 85%). $^1$H NMR (400 MHz, Methanol-d4) δ: 7.31-7.26 (m, 2H), 7.16-7.08 (m, 2H), 5.39-5.34 (m, 2H), 4.62-4.56 (m, 2H), 4.38-4.20 (m, 1H), 3.81-3.72 (m, 2H), 3.55-3.35 (m, 1H), 3.22-3.16 (m, 1H), 2.78-2.40 (m, 4H), 2.31-1.80 (m, 4H), 1.51-1.44 (m, 1H); LCMS (ESI) m/z 493.0 [M+H]$^+$ Example 9-14

(2R)-4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)pyrrolidine-2-carboxylic acid TFA salt

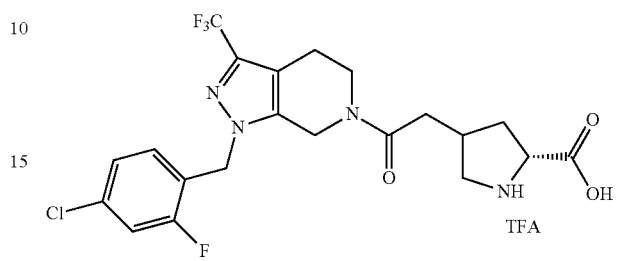

The title compound was synthesized according to the procedure described in Example 9-8, using Example 5-56 as a starting material, to obtain a white solid (230 mg, yield 79%). $^1$H NMR (400 MHz, Methanol-d4) δ: 7.30-7.16 (m, 3H), 5.42-5.37 (m, 2H), 4.69 (s, 2H), 3.80-3.73 (m, 2H), 3.64-3.60 (m, 1H), 3.14-3.09 (m, 1H), 2.86-2.41 (m, 7H), 1.59-1.56 (m, 1H); LCMS (ESI) m/z 489.2 [M+H]$^+$ Example 9-15

1-(1-(4-Chloro-2-fluorobenzyl)-3-(trifluoromethyl)-4,5-dihydro-1H-pyrazolo[3,4-c]pyridin-6(7H)-yl)-2-(morpholin-2-yl)ethanone TFA salt

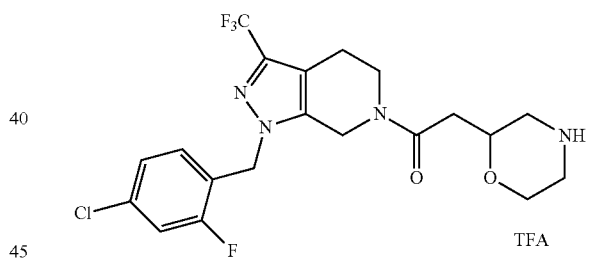

Step 1 tert-Butyl 2-(2-(1-(4-chloro-2-fluorobenzyl)-3-(trifluoromethyl)-4,5-dihydro-1H-pyrazolo[3,4-c]pyridin-6(7H)-yl)-2-oxoethyl)morpholine-4-carboxylate

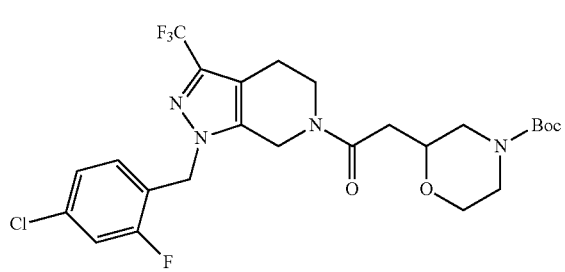 [SMILES: CC(C)(C)OC(=O)N1CCOC(CC(=O)N2CCc3c(C(F)(F)F)nn(Cc4ccc(Cl)cc4F)c3C2)C1]

The titled compound was synthesized according to the procedure described in Example 8-1, using 2-(4-(tert-butoxycarbonyl)morpholin-2-yl)acetic acid as a starting material, to obtain a yellow oil (160 mg, yield 95%). LCMS (ESI) m/z 50.1 [M-55]⁺

Step 2

1-(1-(4-Chloro-2-fluorobenzyl)-3-(trifluoromethyl)-4,5-dihydro-1H-pyrazolo[3,4-c]pyridin-6(7H)-yl)-2-(morpholin-2-yl)ethanone TFA salt

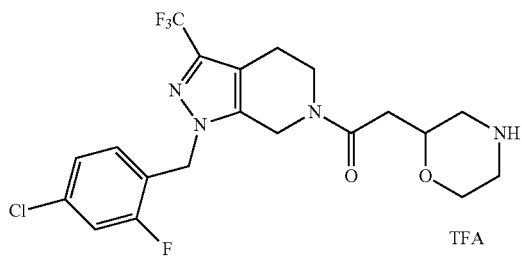 [SMILES: O=C(CC1CNCCO1)N1CCc2c(C(F)(F)F)nn(Cc3ccc(Cl)cc3F)c2C1 ; "TFA"]

The title compound was synthesized according to the procedure described in Example 9-1, using tert-butyl 2-(2-(1-(4-chloro-2-fluorobenzyl)-3-(trifluoromethyl)-4,5-dihydro-1H-pyrazolo[3,4-c]pyridin-6(7H)-yl)-2-oxoethyl)morpholine-4-carboxylate as a starting material, to obtain a yellow oil (144 mg, yield 88%). ¹H NMR (400 MHz, Methanol-d4) δ: 7.32-7.18 (m, 3H), 5.39-5.37 (m, 2H), 4.77-4.66 (m, 2H), 4.18-4.02 (m, 2H), 3.84-3.74 (m, 3H), 3.45-3.42 (m, 1H), 3.27-2.65 (m, 7H); LCMS (ESI) m/z 460.9 [M+H]⁺

Example 9-16

1-(1-(4-Fluorobenzyl)-3-(trifluoromethyl)-4,5-dihydro-1H-pyrazolo[3,4-c]pyridin-6(7H)-yl)-2-(morpholin-2-yl)ethanone TFA salt

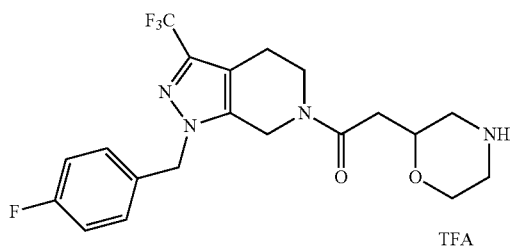 [SMILES: O=C(CC1CNCCO1)N1CCc2c(C(F)(F)F)nn(Cc3ccc(F)cc3)c2C1 ; "TFA"]

The title compound was synthesized according to the procedure described in Example 9-15, using Intermediate 2-2 as a starting material, to obtain a white solid (140 mg, yield 80%). ¹H NMR (400 MHz, Methanol-d4) δ: 7.30-7.25 (m, 2H), 7.15-7.08 (m, 2H), 5.36-5.33 (m, 2H), 4.64-4.56 (m, 2H), 4.06-3.72 (m, 5H), 3.43-3.40 (m, 1H), 3.13-2.63 (m, 7H); LCMS (ESI) m/z 427.0 [M+H]⁺

Example 9-17

2-(cis-4-Aminocyclohexyl)-1-(1-(4-chloro-2-fluorobenzyl)-3-(trifluoromethyl)-4,5-dihydro-1H-pyrazolo[3,4-c]pyridin-6(7H)-yl)ethanone TFA salt

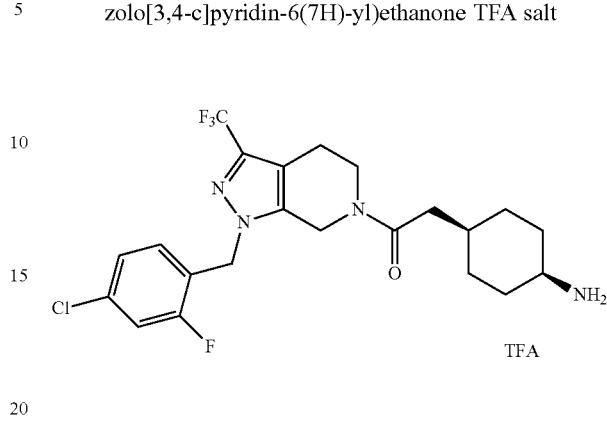

The title compound was synthesized according to the procedure described in Example 9-15, using 2-((cis-4-((tert-butoxycarbonyl)amino)cyclohexyl)acetic acid as a starting material, to obtain a colorless oil (34 mg, yield 22% over two steps). ¹H NMR (400 MHz, Methanol-d4) δ: 7.32-7.19 (m, 3H), 5.42-5.38 (m, 2H), 4.72-4.69 (m, 2H), 3.84-3.76 (m, 2H), 3.30-3.26 (m, 1H), 2.78-2.65 (m, 2H), 2.53-2.43 (m, 2H), 2.11-1.91 (m, 1H), 1.86-1.65 (m, 6H), 1.55-1.49 (m, 2H); LCMS (ESI) m/z 472.9 [M+H]⁺

Example 9-18

2-(cis-4-Aminocyclohexyl)-1-(1-(4-fluorobenzyl)-3-(trifluoromethyl)-4,5-dihydro-1H-pyrazolo[3,4-c]pyridin-6(7H)-yl)ethanone TFA salt

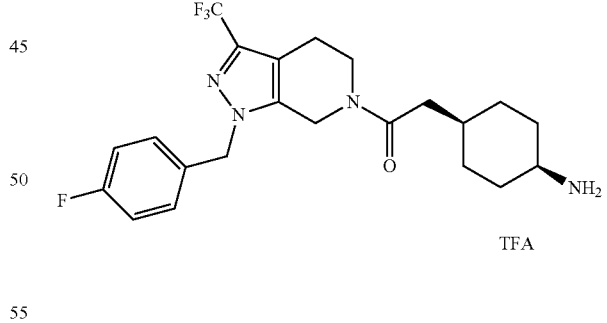

The title compound was synthesized according to the procedure described in Example 9-15, using Intermediate 2-2 and 2-((cis-4-((tert-butoxycarbonyl)amino)cyclohexyl)acetic acid as starting materials, to obtain a colorless oil (34 mg, yield 22% over two steps). ¹H NMR (400 MHz, Methanol-d4) δ: 7.30-7.26 (m, 2H), 7.17-7.09 (m, 2H), 5.39-5.34 (m, 2H), 4.63-4.55 (m, 2H), 3.81-3.74 (m, 2H), 3.30-3.26 (m, 1H), 2.77-2.66 (m, 2H), 2.52-2.32 (m, 2H), 2.09-1.39 (m, 9H); LCMS (ESI) m/z 439.0 [M+H]⁺

211

Example 9-19

2-(trans-4-aminocyclohexyl)-1-(1-(4-chloro-2-fluorobenzyl)-3-(trifluoromethyl)-4,5-dihydro-1H-pyrazolo[3,4-c]pyridin-6(7H)-yl)ethanone TFA salt

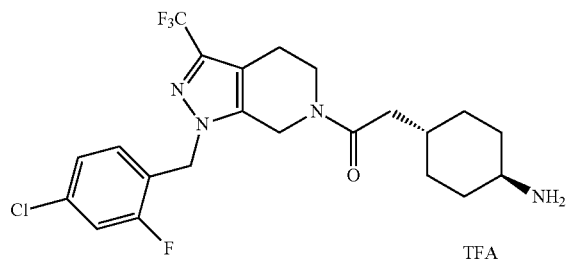 [SMILES: N[C@H]1CC[C@H](CC(=O)N2CCc3c(C(F)(F)F)nn(Cc4ccc(Cl)cc4F)c3C2)CC1]

The title compound was synthesized according to the procedure described in Example 9-15, using 2-((trans-4-((tert-butoxycarbonyl)amino)cyclohexyl)acetic acid as a starting material, to obtain a colorless oil (120 mg, yield 69% over two steps). $^1$H NMR (400 MHz, Methanol-d4) δ: 7.33-7.18 (m, 3H), 5.41-5.37 (m, 2H), 4.71-4.68 (m, 2H), 3.83-3.74 (m, 2H), 3.05-3.01 (m, 1H), 2.75-2.64 (m, 2H), 2.44-2.31 (m, 2H), 2.04-1.80 (m, 5H), 1.43-1.36 (m, 2H), 1.21-1.06 (m, 2H); LCMS (ESI) m/z 472.9 [M+H]$^+$

Example 9-20

2-(trans-4-Aminocyclohexyl)-1-(1-(4-fluorobenzyl)-3-(trifluoromethyl)-4,5-dihydro-1H-pyrazolo[3,4-c]pyridin-6(7H)-yl)ethanone TFA salt

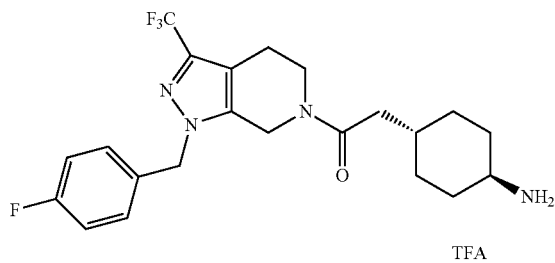 [SMILES: N[C@H]1CC[C@H](CC(=O)N2CCc3c(C(F)(F)F)nn(Cc4ccc(F)cc4)c3C2)CC1]

The title compound was synthesized according to the procedure described in Example 9-15, using Intermediate 2-2 and 2-((tras-4-((tert-butoxycarbonyl)amino)cyclohexyl)acetic acid as starting materials, to obtain a white solid (112 mg, yield 62% over two steps). $^1$H NMR (400 MHz, Methanol-d4) δ: 7.31-7.25 (m, 2H), 7.17-7.08 (m, 2H), 5.38-5.34 (m, 2H), 4.62-4.55 (m, 2H), 3.80-3.72 (m, 2H), 3.05-3.01 (m, 1H), 2.75-2.63 (m, 2H), 2.42-2.20 (m, 2H), 2.04-1.76 (m, 5H), 1.42-1.33 (m, 2H), 1.20-0.97 (m, 2H); LCMS (ESI) m/z 439.0 [M+H]$^+$

212

Example 9-21

1-(1-(4-Chloro-2-fluorobenzyl)-3-(trifluoromethyl)-4,5-dihydro-1H-pyrazolo[3,4-c]pyridin-6(7H)-yl)-2-(octahydrocyclopenta[c]pyrrol-5-yl)ethanone TFA salt

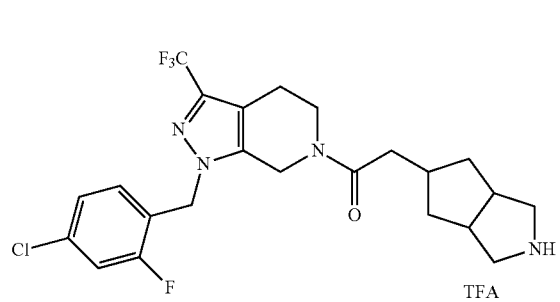 [SMILES: O=C(CC1CC2CNCC2C1)N1CCc2c(C(F)(F)F)nn(Cc3ccc(Cl)cc3F)c2C1]

The title compound was synthesized according to the procedure described in Example 9-15, using 2-(2-(tert-butoxycarbonyl)octahydrocyclopenta[c]pyrrol-5-yl)acetic acid (as prepared from tert-butyl 5-oxohexahydrocyclopenta[c]pyrrole-2(1H)-carboxylate using the procedure described in intermediate 3-1) as starting materials, to obtain a white solid (70 mg, yield 44% over two steps). $^1$H NMR (400 MHz, Methanol-d4) δ: 7.30-7.20 (m, 3H), 5.41-5.37 (m, 2H), 4.70-4.69 (m, 2H), 3.82-3.74 (m, 2H), 3.28-3.26 (m, 2H), 3.18-3.15 (m, 2H), 2.90 (bs, 2H), 2.75-2.66 (m, 2H), 2.60-2.51 (m, 2H), 2.31-2.20 (m, 3H), 1.09-1.07 (m, 2H); LCMS (ESI) m/z 484.9 [M+H]$^+$

Example 9-22

(1-(4-Fluorobenzyl)-3-(trifluoromethyl)-4,5-dihydro-1H-pyrazolo[3,4-c]pyridin-6(7H)-yl)(4-(methylamino)bicyclo[2.2.2]octan-1-yl)methanone TFA salt

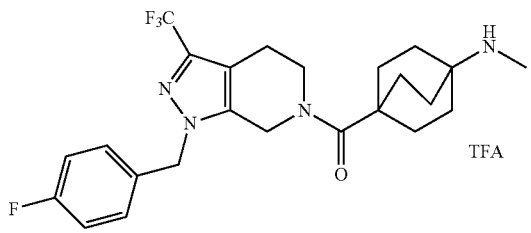 [SMILES: CNC12CCC(C(=O)N3CCc4c(C(F)(F)F)nn(Cc5ccc(F)cc5)c4C3)(CC1)CC2]

Step 1 tert-Butyl 4-(1-(4-fluorobenzyl)-3-(trifluoromethyl)-4,5,6,7-tetrahydro-1H-pyrazolo[3,4-c]pyridine-6-carbonyl)bicyclo[2.2.2]octan-1-yl(methyl)carbamate

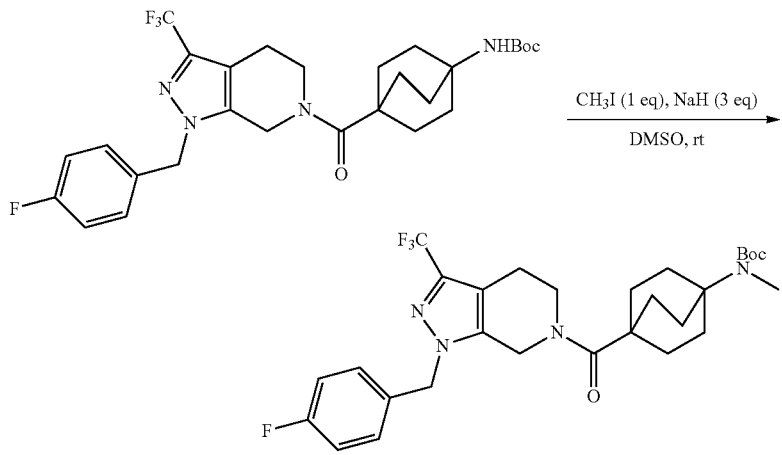

To a stirred solution of Example 8-10 (150 mg, 0.3 mmol, 1.0 eq) in DMSO (2 mL) was added NaH (40 mg, 0.9 mmol, 3.0 eq), followed by CH₃I (40 mg, 0.3 mmol, 1.0 eq). The mixture was stirred at rt for 4 h and quenched with MeOH (0.5 mL). The crude product was purified by prep HPLC (MeCN and H₂O with 0.05% ammonia as mobile phase) to give tert-butyl 4-(1-(4-fluorobenzyl)-3-(trifluoromethyl)-4,5,6,7-tetrahydro-1H-pyrazolo[3,4-c]pyridine-6-carbonyl)bicyclo[2.2.2]octan-1-yl(methyl)carbamate (140 mg, yield 91%); LCMS (ESI) m/z 565.3 [M+H]⁺

Step 2

(1-(4-Fluorobenzyl)-3-(trifluoromethyl)-4,5-dihydro-1H-pyrazolo[3,4-c]pyridin-6(7H)-yl)(4-(methylamino)bicyclo[2.2.2]octan-1-yl)methanone TFA salt

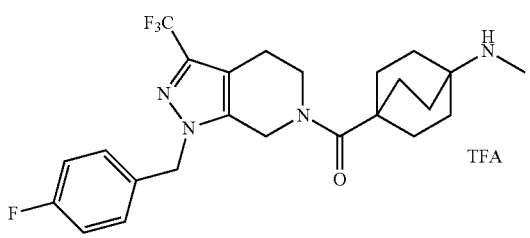 [SMILES: CNC12CCC(C(=O)N3CCc4c(C(F)(F)F)nn(Cc5ccc(F)cc5)c4C3)(CC1)CC2]

The title compound was synthesized according to the procedure described in Example 9-1, using tert-butyl 4-(1-(4-fluorobenzyl)-3-(trifluoromethyl)-4,5,6,7-tetrahydro-1H-pyrazolo[3,4-c]pyridine-6-carbonyl)bicyclo[2.2.2]octan-1-yl(methyl)carbamate as a starting material, to obtain (1-(4-fluorobenzyl)-3-(trifluoromethyl)-4,5-dihydro-1H-pyrazolo[3,4-c]pyridin-6(7H)-yl) (4-(methylamino)bicyclo[2.2.2]octan-1-yl)methanone TFA salt (90 mg, yield 78%). ¹H NMR (400 MHz, Methanol-d4) δ: 7.29-7.26 (m, 2H), 7.15-7.11 (m, 2H), 5.35 (s, 2H), 4.58 (s, 2H), 3.86 (t, J=5.6 Hz, 2H), 2.72 (t, J=5.2 Hz, 2H), 2.58 (s, 3H), 2.03-1.99 (m, 6H), 1.83-1.80 (m, 6H); LCMS (ESI) m/z 465.2 [M+H]⁺

Example 9-23

1-(1-(4-Fluorobenzyl)-3-(trifluoromethyl)-4,5-dihydro-1H-pyrazolo[3,4-c]pyridin-6(7H)-yl)-2-(pyrrolidin-3-yl)ethanone hydrochloride

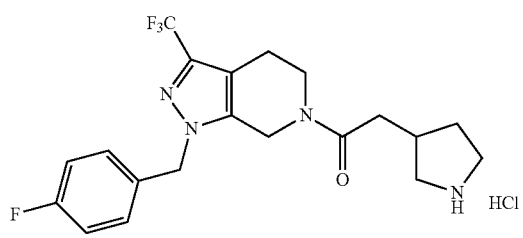 [SMILES: O=C(CC1CCNC1)N1CCc2c(C(F)(F)F)nn(Cc3ccc(F)cc3)c2C1 ; Cl]

Step 1 tert-Butyl 3-(2-(1-(4-fluorobenzyl)-3-(trifluoromethyl)-4,5-dihydro-1H-pyrazolo[3,4-c]pyridin-6(7H)-yl)-2-oxoethyl)pyrrolidine-1-carboxylate

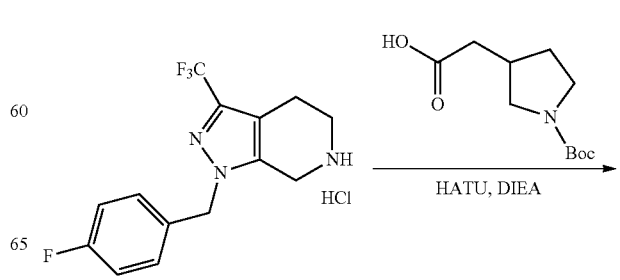

-continued

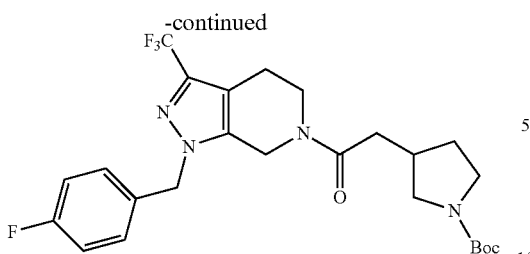

A mixture of 2-(1-(tert-butoxycarbonyl)pyrrolidin-3-yl) acetic acid (421 mg, 1.84 mmol, 1.1 eq.), HATU (604 mg, 2.5 mmol, 1.5 eq.), DIEA (1.08 g, 8.35 mmol, 5.0 eq.) and 1-(4-fluorobenzyl)-3-(trifluoromethyl)-4,5,6,7-tetrahydro-1H-pyrazolo[3,4-c]pyridinehydro chloride (Intermediate 2-2) (500 mg, 1.67 mmol, 1.0 eq.) in DMF (10 mL) was stirred at 20° C. for 17 h. The mixture was poured into brine (20 mL) and extracted with EtOAc (20 mL×3). The organic phase was dried over $Na_2SO_4$, filtered and concentrated to give tert-butyl 3-(2-(1-(4-fluorobenzyl)-3-(trifluoromethyl)-4,5-dihydro-1H-pyrazolo[3,4-c]pyridin-6(7H)-yl)-2-oxo-ethyl)pyrrolidine-1-carboxylate (400 mg, crude), which was used in next step without further purification.

Step 2

1-(1-(4-Fluorobenzyl)-3-(trifluoromethyl)-4,5-dihydro-1H-pyrazolo[3,4-c]pyridin-6(7H)-yl)-2-(pyrrolidin-3-yl)ethanone hydrochloride

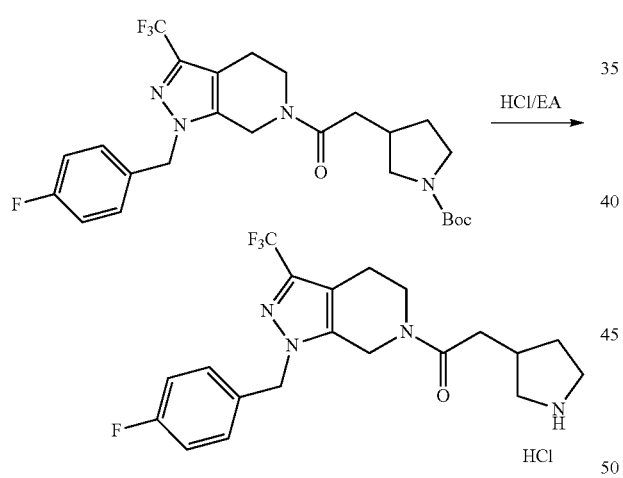

A mixture of tert-butyl 3-(2-(1-(4-fluorobenzyl)-3-(trifluoromethyl)-4,5-dihydro-1H-pyrazolo[3,4-c]pyridin-6(7H)-yl)-2-oxoethyl)pyrrolidine-1-carboxylate (400 mg, 0.78 mmol, 1.0 eq.) in HCl/EtOAc (8 mL) was stirred at 20° C. for 2 h. LCMS showed the starting material was consumed completely. The solvent was removed in vacuum to give the crude, which was purified by prep-HPLC (MeCN and $H_2O$ with 0.225% FA as mobile phase; from 10-40%) to provide 1-(1-(4-fluorobenzyl)-3-(trifluoromethyl)-4,5-dihydro-1H-pyrazolo[3,4-c]pyridin-6(7H)-yl)-2-(pyrrolidin-3-yl) ethanone hydrochloride (200 mg, yield 62%) as a white solid. $^1$HNMR (400 MHz, Methanol-$d_4$) δ: 7.29-7.23 (m, 2H), 7.13-7.06 (m, 2H), 5.37-5.31 (m, 2H), 4.59-4.55 (m, 2H), 3.76-3.71 (m, 2H), 3.70-3.68 (m, 1H), 3.53-3.52 (m, 1H), 3.21-3.15 (m, 1H), 2.88-2.62 (m, 6H), 2.25-2.23 (m, 1H), 1.71-1.66 (m, 1H); LCMS (ESI) m/z 411.1 [M+H]$^+$ Example 10-1

1-(1-(4-Chloro-2-fluorobenzyl)-3-(trifluoromethyl)-4,5-dihydro-1H-pyrazolo[3,4-c]pyridin-6(7H)-yl)-2-(8-methyl-8-aza-bicyclo[3.2.1]octan-3-yl)ethanone TFA salt

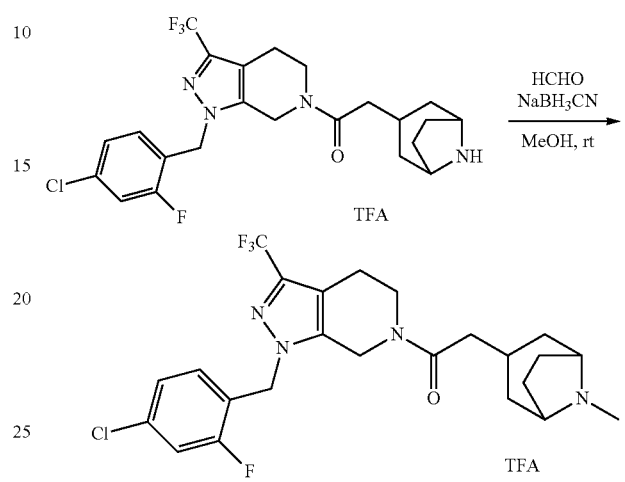

To a solution of 2-(8-azabicyclo[3.2.1]octan-3-yl)-1-(1-(4-chloro-2-fluorobenzyl)-3-(trifluoromethyl)-4,5-dihydro-1H-pyrazolo[3,4-c]pyridin-6(7H)-yl)ethanone TFA salt (Example 9-1, 150 mg, 0.31 mmol) in MeOH (3 mL) was added formaldehyde aqueous solution (0.1 mL, 30%) and NaBH$_3$CN (94 mg, 1.55 mmol). The reaction mixture was stirred at rt for 3 h and diluted with water (50 mL). The mixture was extracted with EtOAc (3×50 mL). The combined organic layer was dried over $Na_2SO_4$, filtered and concentrated. The residue was purified by prep HPLC (CH$_3$CN/H$_2$O with 0.05% TFA as mobile phase; from 0% to 95%) to give 1-(1-(4-chloro-2-fluorobenzyl)-3-(trifluoromethyl)-4,5-dihydro-1H-pyrazolo[3,4-c]pyridin-6(7H)-yl)-2-(8-methyl-8-aza-bicyclo[3.2.1]octan-3-yl)ethanone as a white solid (60 mg, yield 39%). $^1$H NMR (400 MHz, Methanol-d4) 7.31-7.18 (m, 3H), 5.43-5.37 (m, 2H), 4.71-4.69 (m, 2H), 3.88-3.73 (m, 4H), 2.83-2.65 (m, 5H), 2.49-2.30 (m, 5H), 2.21-1.62 (m, 6H); LCMS (ESI) m/z 499.2 [M+H]$^+$ Example 10-2

1-(1-(4-Chloro-2-fluorobenzyl)-3-(trifluoromethyl)-4,5-dihydro-1H-pyrazolo[3,4-c]pyridin-6(7H)-yl)-2-(1,2-dimethylpiperidin-4-yl)ethanone TFA salt

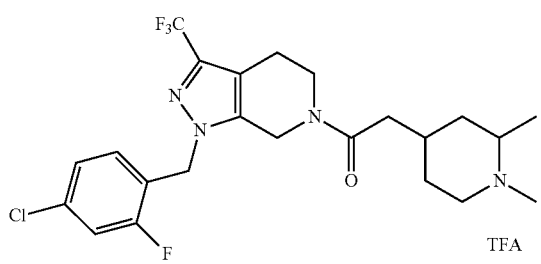 [SMILES: CC1CC(CC(=O)N2CCc3c(C(F)(F)F)nn(Cc4ccc(Cl)cc4F)c3C2)CCN1C]

The title compound was synthesized according to the procedure described in Example 10-1, using Example 9-5 as a starting material, to obtain a white solid (yield 80%). ¹H NMR (400 MHz, Methanol-d4) δ: 7.31-7.18 (m, 3H), 5.43-5.37 (m, 2H), 4.71-4.69 (m, 2H), 3.83-3.74 (m, 2H), 3.53-3.38 (m, 1H), 3.24-3.05 (m, 2H), 2.92-2.63 (m, 6H), 2.52-2.21 (m, 2H), 2.20-1.49 (m, 4H), 1.29-1.38 (m, 3H); LCMS (ESI) m/z 487.2 [M+H]⁺

Example 10-3

1-(1-(4-Chloro-2-fluorobenzyl)-3-(trifluoromethyl)-4,5-dihydro-1H-pyrazolo[3,4-c]pyridin-6(7H)-yl)-2-(1,2,2-trimethylpiperidin-4-yl)ethanone TFA salt

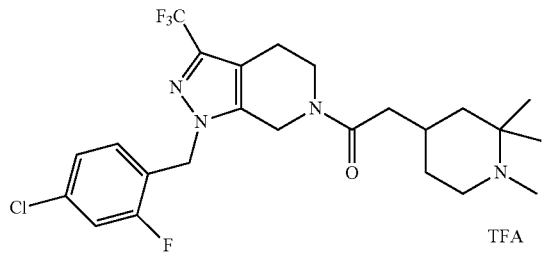 [SMILES: CN1CCC(CC(=O)N2CCc3c(C(F)(F)F)nn(Cc4ccc(Cl)cc4F)c3C2)CC1(C)C]

The title compound was synthesized according to the procedure described in Example 10-1, using Example 9-6 as a starting material, to obtain a white solid (yield 80%). ¹H NMR (400 MHz, Methanol-d4) δ: 7.34-7.19 (m, 3H), 5.41-5.38 (m, 2H), 4.71-4.68 (m, 2H), 3.86-3.74 (m, 2H), 3.29-3.22 (m, 2H), 2.78-2.65 (m, 5H), 2.49-2.32 (m, 3H), 2.05-1.95 (m, 2H), 1.49-1.39 (m, 8H); LCMS (ESI) m/z 501.1 [M+H]⁺

Example 10-4

1-(1-(4-Chloro-2-fluorobenzyl)-3-(trifluoromethyl)-4,5-dihydro-1H-pyrazolo[3,4-c]pyridin-6(7H)-yl)-2-(1-methyl-2-(trifluoromethyl)piperidin-4-yl)ethanone TFA salt

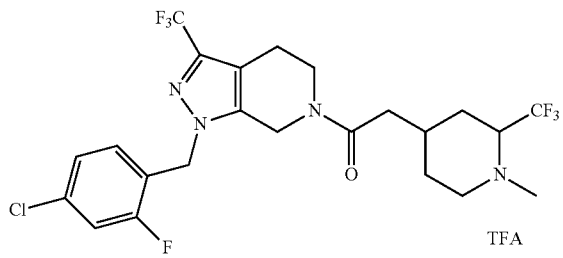 [SMILES: CN1CCC(CC(=O)N2CCc3c(C(F)(F)F)nn(Cc4ccc(Cl)cc4F)c3C2)CC1C(F)(F)F]

The titled compound was synthesized according to the procedure described in Example 10-1, using Example 9-7 as a starting material, to obtain a white solid (yield 50%). ¹H NMR (400 MHz, Methanol-d4) δ: 7.32-7.19 (m, 3H), 5.41-5.38 (m, 2H), 4.76-4.68 (m, 2H), 4.33-4.20 (m, 1H), 3.87-3.74 (m, 2H), 3.61-3.27 (m, 2H), 3.02-2.96 (m, 3H), 2.78-2.57 (m, 4H), 2.50-1.99 (m, 4H), 1.78-1.58 (m, 1H); LCMS (ESI) m/z 541.1 [M+H]⁺

Example 10-5

1-(1-(4-Fluorobenzyl)-3-(trifluoromethyl)-4,5-dihydro-1H-pyrazolo[3,4-c]pyridin-6(7H)-yl)-2-(1-methylpyrrolidin-3-yl)ethanone

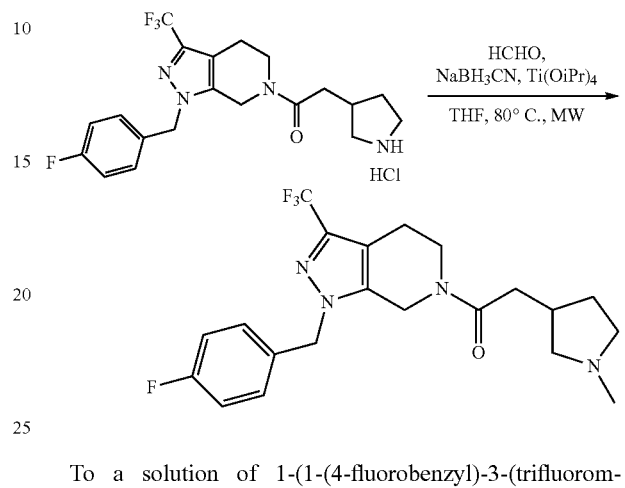

To a solution of 1-(1-(4-fluorobenzyl)-3-(trifluoromethyl)-4,5-dihydro-1H-pyrazolo[3,4-c]pyridin-6(7H)-yl)-2-(pyrrolidin-3-yl)ethanone hydrochloride (Example 9-23) (40 mg, 0.1 mmol, 1.0 eq) and DIEA (13 mg, 0.1 mmol, 1.0 eq) in THF (2 mL) was added Ti(iPrO)₄ (57 mg, 0.2 mmol, 2.0 eq) followed by formaldehyde (6.0 mg, 0.2 mmol, 2 eq). Then the mixture was stirred at 80° C. for 1 h under microwave. NaBH₃CN (12 mg, 0.2 mmol, 2.0 eq) was added and the mixture was stirred at room temperature for 4 h. The reaction was diluted with brine (10 mL) and was extracted with EA (10 mL×2). The organic phase was dried over Na₂SO₄, filtered and concentrated to give the crude, which was purified by prep. HPLC (MeCN and H₂O with 0.225% FA as mobile phase; from 11-41%) to provide 1-(1-(4-fluorobenzyl)-3-(trifluoromethyl)-4,5-dihydro-1H-pyrazolo[3,4-c]pyridin-6(7H)-yl)-2-(1-methylpyrrolidin-3-yl)ethanone (20 mg, yield 47%) as a colorless gum. ¹H NMR (400 MHz, Methanol-d4) δ: 8.50 (s, 1H), 7.26-7.23 (m, 2H), 7.13-7.05 (m, 2H), 5.36-5.31 (m, 2H), 4.58-4.53 (m, 2H), 3.76-3.70 (m, 2H), 3.68-3.67 (m, 1H), 3.53-3.52 (m, 1H), 3.03-3.01 (m, 1H), 2.86 (s, 3H), 2.80-2.63 (m, 6H), 2.30-2.29 (m, 1H), 1.78-1.75 (m, 1H); LCMS (ESI) m/z 425.1 [M+H]⁺

Example 10-6

1-(1-(4-Fluorobenzyl)-3-(trifluoromethyl)-4,5-dihydro-1H-pyrazolo[3,4-c]pyridin-6(7H)-yl)-2-(1-isopropylpyrrolidin-3-yl)ethanone

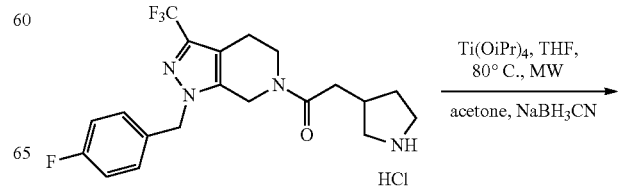

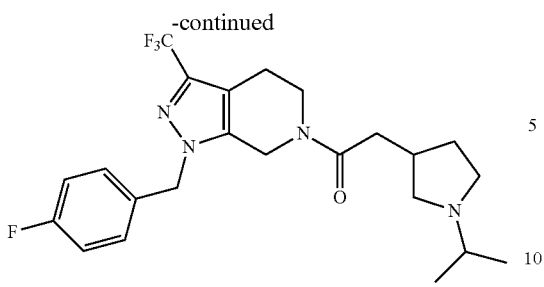

To a solution of 1-(1-(4-fluorobenzyl)-3-(trifluoromethyl)-4,5-dihydro-1H-pyrazolo[3,4-c]pyridin-6(7H)-yl)-2-(pyrrolidin-3-yl)ethanone hydrochloride (Example 9-23) (40 mg, 0.1 mmol, 1.0 eq) and DIEA (13 mg, 0.1 mmol, 1.0 eq) in THF (2 mL) was added Ti(iPrO)$_4$ (57 mg, 0.2 mmol, 2.0 eq) followed by acetone (12 mg, 0.2 mmol, 2 eq). Then the mixture was was stirred at 80° C. for 1 h under microwave. NaBH$_3$CN (12 mg, 0.2 mmol, 2.0 eq) was added and the mixture was stirred at room temperature for 4 h. The reaction was diluted with brine (10 mL) and the mixture was extracted with EA (10 mL×2). The organic phase was dried over Na$_2$SO$_4$, filtered and concentrated to give the crude which was purified by prep. HPLC (MeCN and H$_2$O with 0.225% FA as mobile phase; from 22-52%) to provide 1-(1-(4-fluorobenzyl)-3-(trifluoromethyl)-4,5-dihydro-1H-pyrazolo[3,4-c]pyridin-6(7H)-yl)-2-(1-isopropylpyrrolidin-3-yl)ethanone (15 mg, yield 36%) as a colorless gum. $^1$H NMR (400 MHz, Methanol-d4) δ: 8.52 (s, 1H), 7.26-7.23 (m, 2H), 7.11-7.05 (m, 2H), 5.36-5.31 (m, 2H), 4.58-4.53 (m, 2H), 3.76-3.70 (m, 2H), 3.69-3.68 (m, 1H), 3.35-3.32 (m, 3H), 2.77-2.74 (m, 1H), 2.69-2.62 (m, 5H), 2.27-2.26 (m, 1H), 1.72-1.69 (m, 1H), 1.32 (d, J=6.4 Hz, 6H); LCMS (ESI) m/z 453.1 [M+H]$^+$ Example 10-7

2-(2-Ethyl-1-methylpiperidin-4-yl)-1-(1-(4-fluorobenzyl)-3-(trifluoromethyl)-4,5-dihydro-1H-pyrazolo[3,4-c]pyridin-6(7H)-yl)ethanone TFA salt

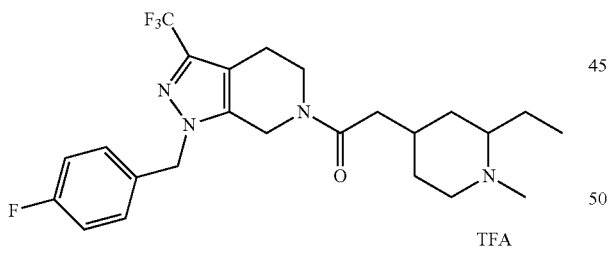

The title compound was synthesized according to the procedure described in Example 10-1, using Example 9-11 as a starting material, to obtain a yellow oil (70 mg, yield 60%). $^1$H NMR (400 MHz, Methanol-d4) δ: 7.30-7.25 (m, 2H), 7.16-7.07 (m, 2H), 5.39-5.33 (m, 2H), 4.66-4.57 (m, 2H), 3.87-3.69 (m, 2H), 3.53-3.49 (m, 1H), 3.36-3.03 (m, 2H), 2.94-2.34 (m, 7H), 2.31-1.77 (m, 5H), 1.76-1.40 (m, 2H), 1.04-0.89 (m, 3H); LCMS (ESI) m/z 467.2 [M+H]$^+$ Example 10-8

1-(1-(4-Fluorobenzyl)-3-(trifluoromethyl)-4,5-dihydro-1H-pyrazolo[3,4-c]pyridin-6(7H)-yl)-2-(1-methyl-2-propylpiperidin-4-yl)ethanone acid TFA salt

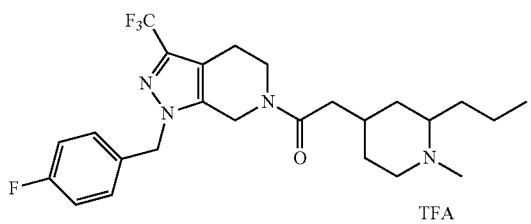 [SMILES: CCCC1CC(CC(=O)N2CCc3c(C(F)(F)F)nn(Cc4ccc(F)cc4)c3C2)CCN1C]

The title compound was synthesized according to the procedure described in Example 10-1, using Example 9-12 as a starting material, to obtain a yellow solid (60 mg, yield 58%). $^1$H NMR (400 MHz, Methanol-d4) δ: 7.31-7.26 (m, 2H), 7.16-7.08 (m, 2H), 5.38-5.34 (m, 2H), 4.62-4.57 (m, 2H), 3.77-3.72 (m, 2H), 3.53-3.50 (m, 1H), 3.30-3.09 (m, 2H), 2.95-2.66 (m, 5H), 2.51-1.20 (m, 11H), 0.98 (t, J=7.2 Hz, 3H); LCMS (ESI) m/z 481.0 [M+H]$^+$ Example 10-9

(4-(dimethylamino)bicyclo[2.2.2]octan-1-yl)(1-(4-fluorobenzyl)-3-(trifluoromethyl)-4,5-dihydro-1H-pyrazolo[3,4-c]pyridin-6(7H)-yl)methanone trifluoroacetate salt TFA salt

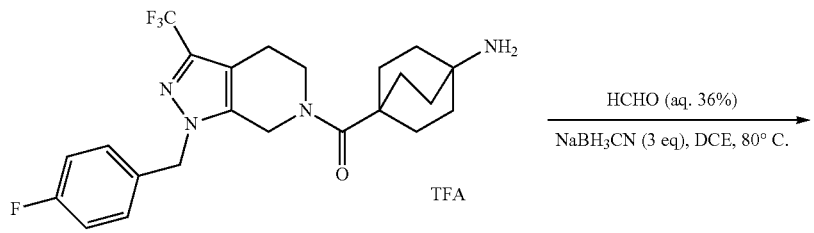

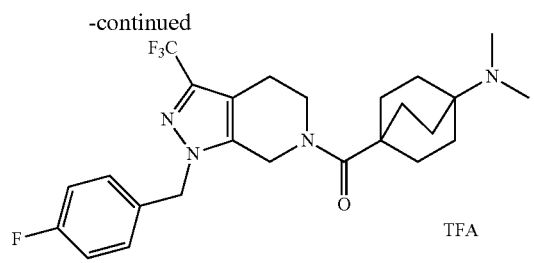

A mixture of Example 9-9 (120 mg, 0.26 mmol, 1.0 eq), HCHO (1 mL, 36% aqueous solution) and NaBH$_3$CN (50 mg, 0.78 mmol, 3.0 eq) in DCE (5 mL) was stirred at 80° C. for 20 h. The mixture was diluted with DCM (100 mL), washed with water (200 mL×2), brine (100 mL), dried and concentrated. The residue was purified by prep HPLC (MeCN and H$_2$O with 0.05% TFA as mobile phase) to give (4-(dimethylamino)bicyclo[2.2.2]octan-1-yl)(1-(4-fluorobenzyl)-3-(trifluoromethyl)-4,5-dihydro-1H-pyrazolo[3,4-c]pyridin-6(7H)-yl)methanone TFA salt as a white solid (100 mg, yield 79%) a yellow solid (60 mg, yield 58%). $^1$H NMR (400 MHz, Methanol-d4) δ: 7.30-7.26 (m, 2H), 7.15-7.11 (m, 2H), 5.35 (s, 2H), 4.58 (s, 2H), 3.86 (t, J=5.6 Hz, 2H), 2.79 (s, 6 H), 2.72 (t, J=5.2 Hz, 2H), 2.01-2.00 (m, 6H), 1.91-1.87 (m, 6H); LCMS (ESI) m/z 479.0 [M+H]$^+$ Example 10-10

(2R)-4-(2-(1-(4-chloro-2-fluorobenzyl)-3-(trifluoromethyl)-4,5-dihydro-1H-pyrazolo[3,4-c]pyridin-6(7H)-yl)-2-oxoethyl)-1-methylpyrrolidine-2-carboxylic acid TFA salt

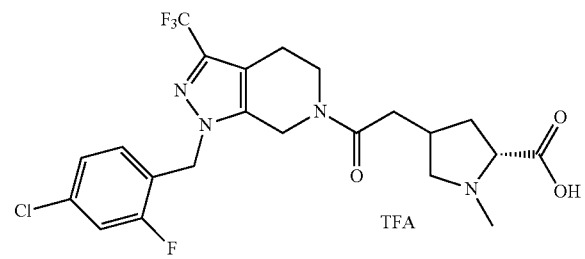 [SMILES: CN1CC(CC(=O)N2CCc3c(C(F)(F)F)nn(Cc4ccc(Cl)cc4F)c3C2)C[C@@H]1C(=O)O]

The titled compound was synthesized according to the procedure described in Example 10-1, using Example 9-14 as a starting material, to obtain a yellow oil (60 mg, yield 53%). $^1$H NMR (400 MHz, Methanol-d4) δ: 7.29-7.17 (m, 3H), 5.40-5.38 (m, 2H), 4.70-4.66 (m, 2H), 4.44-4.24 (m, 1H), 3.98-3.50 (m, 4H), 3.00-2.66 (m, 9H), 1.93-1.90 (m, 1H); LCMS (ESI) m/z 502.9 [M+H]$^+$ Example 10-11

(2S)-4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)-1-methylpyrrolidine-2-carboxylic acid TFA salt

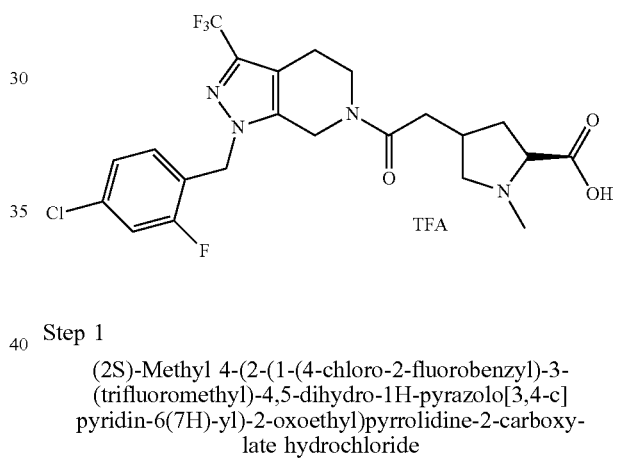

Step 1

(2S)-Methyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)pyrrolidine-2-carboxylate hydrochloride

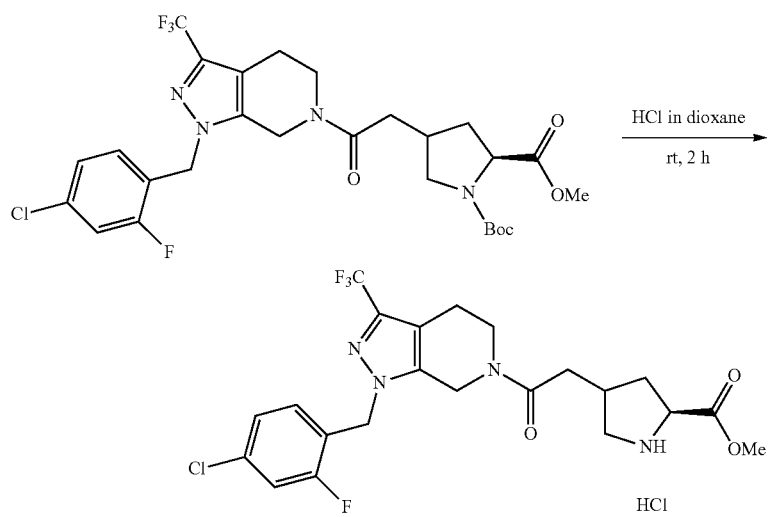

The title compound was synthesized according to the procedure described in Example 9-1, using (2S)-1-tert-butyl 2-methyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)pyrrolidine-1,2-dicarboxylate (from Example 5-18, step 1) as a starting material, to obtain a crude product as a yellow oil (166 mg, yield 100%). LCMS (ESI) m/z 503.1 [M+H]$^+$ Step 2

(2S)-Methyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)-1-methylpyrrolidine-2-carboxylate TFA salt

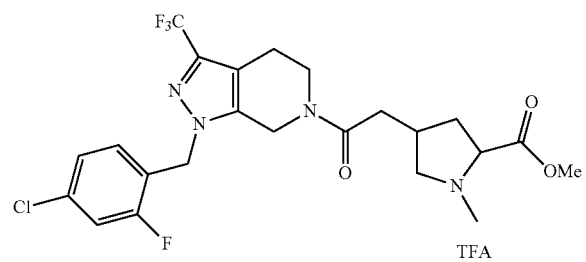 [SMILES: COC(=O)C1CC(CC(=O)N2CCc3c(C(F)(F)F)nn(Cc4ccc(Cl)cc4F)c3C2)CN1C]

The title compound was synthesized according to the procedure described in Example 10-1, using (2S)-methyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)pyrrolidine-2-carboxylate hydrochloride as a starting material, to obtain a yellow oil (25 mg, yield 27%). LCMS (ESI) m/z 517.2 [M+H]$^+$ Step 3

(2S)-4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)-1-methylpyrrolidine-2-carboxylic acid TFA salt

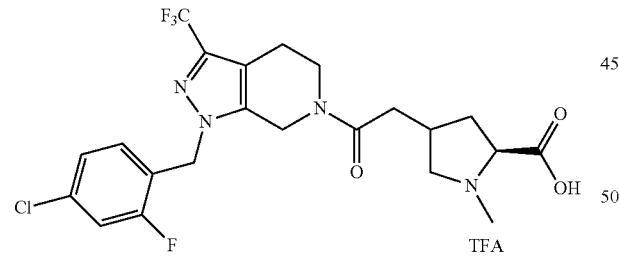

The title compound was synthesized according to the procedure described in Example 5-1, using (2S)-methyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)-1-methylpyrrolidine-2-carboxylate TFA salt as a starting material, to obtain a yellow oil (25 mg, yield 27%), to obtain a white solid (10 mg, yield 62%). $^1$H NMR (400 MHz, Methanol-d4) δ: 7.18-7.31 (m, 3H), 5.36-5.40 (m, 2H), 4.66-4.71 (m, 2H), 4.28-4.32 (m, 1H), 3.70-3.83 (m, 2H), 3.50-3.53 (m, 2H), 3.00 (s, 3H), 2.97-3.00 (m, 1H), 2.65-2.88 (m, 5H), 1.88-1.96 (m, 1H); LCMS (ESI) m/z 502.9 [M+H]$^+$ Example 10-12

(2S)-4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)-1-isopropylpyrrolidine-2-carboxylic acid TFA salt

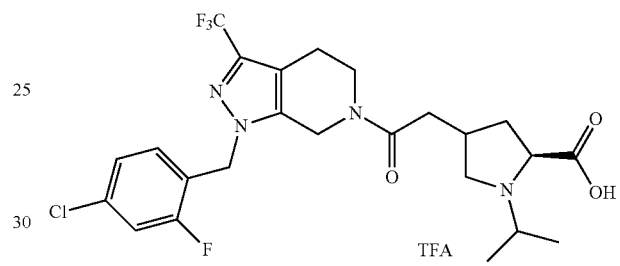

The titled compound was synthesized according to the procedure described in Example 10-11, using acetone as a starting material, to obtain a white solid (30 mg, yield 52%). $^1$H NMR (400 MHz, Methanol-d4) δ: 7.19-7.28 (m, 3H), 5.37-5.40 (m, 2H), 5.00-5.04 (m, 2H), 4.45-4.50 (m, 1H), 3.66-3.82 (m, 4H), 3.33-3.35 (m, 1H), 2.65-2.87 (m, 6H), 1.91-1.94 (m, 1H), 1.36 (d, J=6.8 Hz, 6H); LCMS (ESI) m/z 530.9 [M+H]$^+$ Example 11-1

1-(1-(4-Fluorobenzyl)-3-(trifluoromethyl)-4,5-dihydro-1H-pyrazolo[3,4-c]pyridin-6(7H)-yl)-2-(1-methylpiperidin-3-yl)ethanone formate

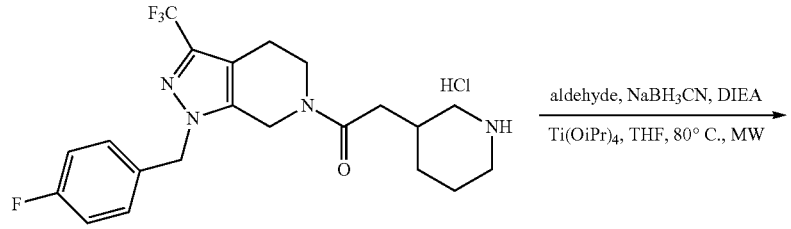

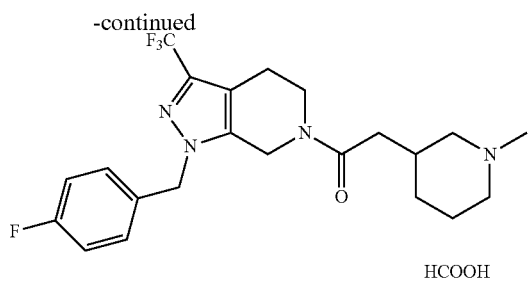

HCOOH

To a solution of 1-(1-(4-fluorobenzyl)-3-(trifluoromethyl)-4,5-dihydro-1H-pyrazolo[3,4-c]pyridin-6(7H)-yl)-2-(piperidin-3-yl)ethanone hydrochloride (Example 9-4, 50 mg, 0.12 mmol, 1.0 eq) and DIEA (19 mg, 0.14 mmol, 1.2 eq) in THF (2 mL) was added Ti($^i$PrO)$_4$ (68 mg, 0.24 mmol, 2.0 eq) followed by formaldehyde (6 mg, 0.18 mmol, 1.5 eq). Then the mixture was microwaved at 80° C. for 1 h. NaBH$_3$CN (15 mg, 0.24 mmol, 2.0 eq) was added and the mixture was stirred at room temperature for 2 h. The reaction was diluted with brine (10 mL) and the mixture was extracted with EA (10 mL×2). The organic phase was dried over Na$_2$SO$_4$, filtered and concentrated to give the crude which was purified by prep. HPLC (MeCN and H$_2$O with 0.225% (v/v) HCOOH as mobile phase) to provide 1-(1-(4-fluorobenzyl)-3-(trifluoromethyl)-4,5-dihydro-1H-pyrazolo[3,4-c]pyridin-6(7H)-yl)-2-(1-methylpiperidin-3-yl)ethanone (20 mg, yield 38%) as a colorless gum. $^1$H NMR (400 MHz, Methanol-d4) δ: 8.47 (s, 1H), 7.27-7.23 (m, 2H), 7.14-7.06 (m, 2H), 5.35-5.31 (m, 2H), 4.63-4.52 (m, 2H), 3.74-3.69 (m, 2H), 3.45-3.37 (m, 2H), 2.77-2.73 (m, 5H), 2.63-2.26 (m, 5H), 1.90-1.77 (m, 3H), 1.29-1.21 (m, 1H); LCMS (ESI) m/z 439.1 [M+H]$^+$

Example 11-2

1-(1-(4-Chloro-2-fluorobenzyl)-3-(trifluoromethyl)-4,5-dihydro-1H-pyrazolo[3,4-c]pyridin-6(7H)-yl)-2-(1-isopropylpiperidin-4-yl)ethanone HCl salt

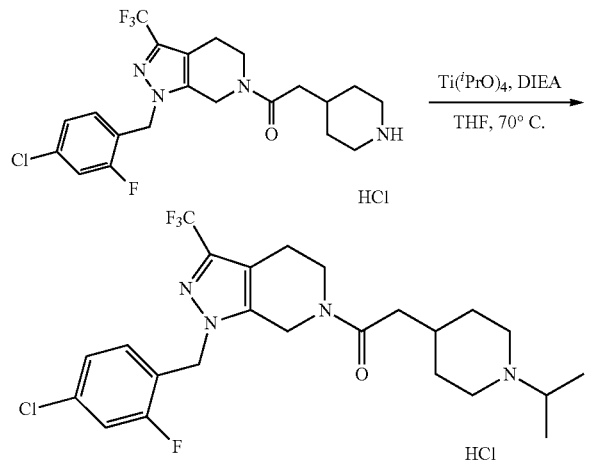

To a solution of 1-(1-(4-chloro-2-fluorobenzyl)-3-(trifluoromethyl)-4,5-dihydro-1H-pyrazolo[3,4-c]pyridin-6(7H)-yl)-2-(piperidin-4-yl)ethanone hydrochloride (Example 9-2, 150 mg, 0.31 mmol, 1.0 eq) and DIEA (72 mg, 0.46 mmol, 1.5 eq) in THF (5 mL) was added Ti($^i$PrO)$_4$ (264 mg, 0.93 mmol, 3.0 eq) followed by acetone (27 mg, 0.46 mmol, 1.5 eq). Then the mixture was stirred at 70° C. overnight. NaBH$_3$CN (39 mg, 0.62 mmol, 2.0 eq) was added and the mixture was stirred at room temperature for 2 h. The mixture was diluted with water (3 mL) and CH$_3$OH (3 mL), filtered and the filtrate was concentrated to give the crude which was purified by prep. HPLC (MeCN and H$_2$O with 0.05% (v/v) HCl as mobile phase) to provide 1-(1-(4-chloro-2-fluorobenzyl)-3-(trifluoromethyl)-4,5-dihydro-1H-pyrazolo[3,4-c]pyridin-6(7H)-yl)-2-(1-isopropylpiperidin-4-yl)ethanone hydrochloride (15 mg, yield 12%) as a yellow solid. $^1$H NMR (400 MHz, Methanol-d4) δ: 7.29-7.16 (m, 3H), 5.40-5.35 (m, 2H), 4.69 (s, 2H), 3.80-3.74 (m, 2H), 3.48-3.41 (m, 3H), 3.06-3.00 (m, 2H), 2.74-2.63 (m, 2H), 2.51-2.43 (m, 2H), 2.08-2.04 (m, 3H), 1.56-1.50 (m, 2H), 1.34 (d, J=6.4 Hz, 6H); LCMS (ESI) m/z 501.1 [M+H]$^+$

Example 11-3

1-(1-(4-Chloro-2-fluorobenzyl)-3-(trifluoromethyl)-4,5-dihydro-1H-pyrazolo[3,4-c]pyridin-6(7H)-yl)-2-(1-ethylpiperidin-4-yl)ethanone HCl salt

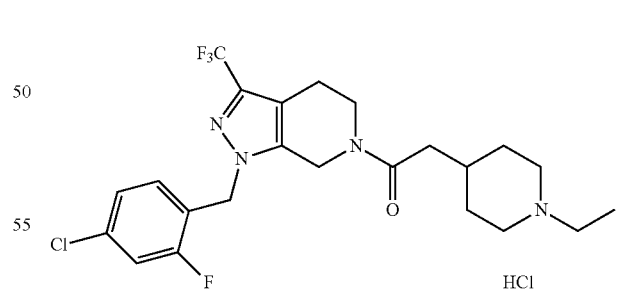

The title compound was synthesized according to the procedure described in Example 11-2, using acetaldehyde as a starting material, to obtain a white solid (yield 19%). $^1$H NMR (400 MHz, Methanol-d4) δ: 7.27-7.20 (m, 3H), 5.39-5.35 (m, 2H), 4.69 (s, 2H), 3.80-3.73 (m, 2H), 3.56-3.53 (m, 2H), 3.16-3.13 (m, 2H), 2.96-2.90 (m, 2H), 2.73-2.64 (m, 2H), 2.51-2.44 (m, 2H), 2.07-2.03 (m, 3H), 1.49-1.46 (m, 2H), 1.32 (t, J=7.2 Hz, 3H); LCMS (ESI) m/z 487.0 [M+H]$^+$

Example 11-4

1-(1-(4-Fluorobenzyl)-3-(trifluoromethyl)-4,5-di-hydro-1H-pyrazolo[3,4-c]pyridin-6(7H)-yl)-2-(1-isopropylpiperidin-3-yl)ethanone formate

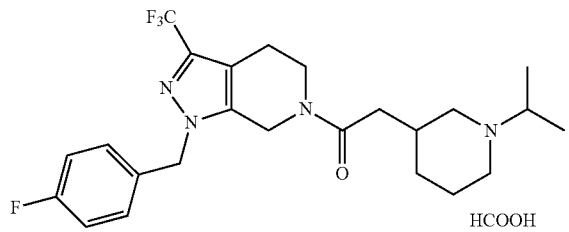 [SMILES: CC(C)N1CCCC(CC(=O)N2CCc3c(C(F)(F)F)nn(Cc4ccc(F)cc4)c3C2)C1 ; "HCOOH"]

The title compound was synthesized according to the procedure described in Example 11-1, using acetone as a starting material, to obtain a colorless gum (yield 27%). $^1$H NMR (400 MHz, Methanol-d4) δ: 8.48 (s, 1H), 7.27-7.23 (m, 2H), 7.14-7.06 (m, 2H), 5.36-5.32 (m, 2H), 4.60-4.52 (m, 2H), 3.73-3.69 (m, 2H), 3.46-3.36 (m, 3H), 2.75-2.74 (m, 1H), 2.65-2.28 (m, 6H), 1.96-1.80 (m, 3H), 1.32-1.18 (m, 7H); LCMS (ESI) m/z 467.1 [M+H]$^+$

Example 12-1

Methyl 1-(2-(1-(4-fluorobenzyl)-3-(trifluoromethyl)-4,5-dihydro-1H-pyrazolo[3,4-c]pyridin-6(7H)-yl)-2-oxoethyl)piperidine-4-carboxylate

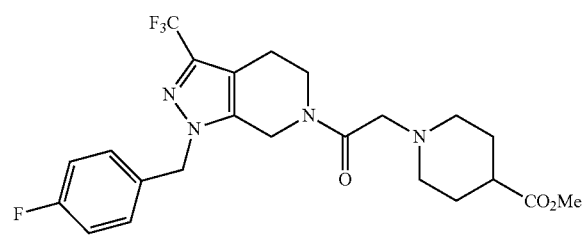 [SMILES: COC(=O)C1CCN(CC(=O)N2CCc3c(C(F)(F)F)nn(Cc4ccc(F)cc4)c3C2)CC1]

Step 1

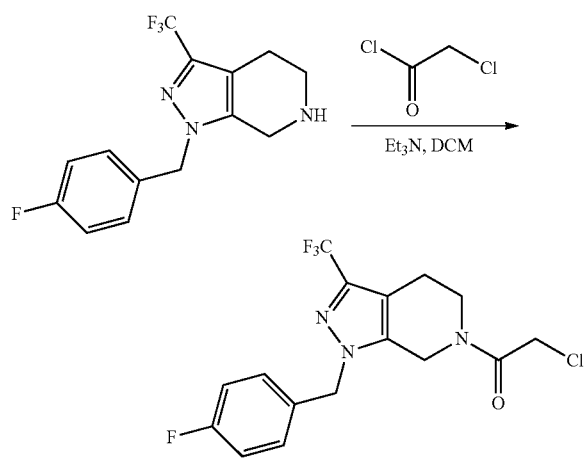

To a solution of compound 1-(4-fluorobenzyl)-3-(trifluoromethyl)-4,5,6,7-tetrahydro-1H-pyrazolo[3,4-c]pyridine (137.4 mg, 0.41 mmol) in DCM (10 mL) was added 2-chloroacetyl chloride (92 mg, 0.82 mmol) followed by TEA (83 mg, 0.82 mmol). Then the mixture was stirred at room temperature for 3 h. TLC (PE/EA=1/1) showed the starting material was consumed completely. The reaction was diluted with water (20 mL), extracted with DCM (10 mL×2). The organic phase was dried over Na$_2$SO$_4$, filtered and concentrated to give the crude 2-chloro-1-(1-(4-fluorobenzyl)-3-(trifluoromethyl)-4,5-dihydro-1H-pyrazolo[3,4-c]pyridin-6(7H)-yl)ethanone (180 mg), which was used in next step without further purification.

Step 2

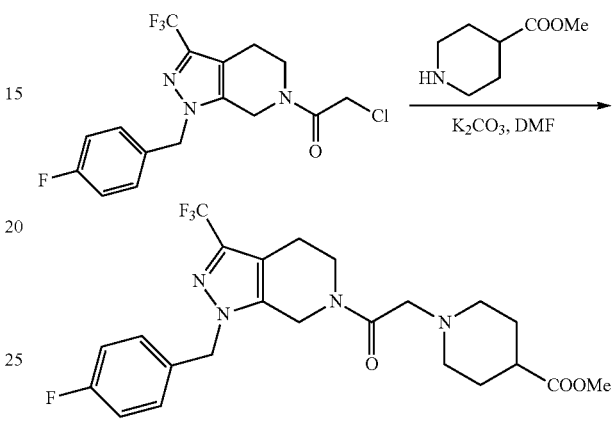

To a mixture of 2-chloro-1-(1-(4-fluorobenzyl)-3-(trifluoromethyl)-4,5-dihydro-1H-pyrazolo[3,4-c]pyridin-6(7H)-yl)ethanone (150 mg, 0.37 mmol) and K$_2$CO$_3$ (103 mg, 0.74 mmol) in DMF (5 mL) was added methyl piperidine-4-carboxylate (79 mg, 0.55 mmol). Then the mixture was stirred at room temperature overnight. TLC (PE/EA=1/1) showed the starting material was consumed completely. The reaction was diluted with brine (20 mL) and the mixture was extracted with EA (20 mL×2). The organic phase was dried over Na$_2$SO$_4$, filtered and concentrated to give the crude which was purified by prep-HPLC (MeCN and H$_2$O with 0.225% (v/v) HCOOH as mobile phase) to provide methyl 1-(2-(1-(4-fluorobenzyl)-3-(trifluoromethyl)-4,5-dihydro-1H-pyrazolo[3,4-c]pyridin-6(7H)-yl)-2-oxoethyl)piperidine-4-carboxylate as a white solid (50 mg, yield 25%). $^1$H NMR (400 MHz, Methanol-d4) δ 7.27-7.25 (m, 2H), 7.10-7.06 (m, 2H), 5.37-5.33 (m, 2H), 4.65-4.52 (m, 2H), 4.35-4.30 (m, 2H), 3.82-3.60 (m, 7H), 3.16-3.06 (m, 2H), 2.87-2.69 (m, 3H), 2.22-1.95 (m, 4H). LCMS (ESI) m/z 483.0 [M+H]$^+$

Example 12-2

1-(1-(4-Chloro-2-fluorobenzyl)-3-(trifluoromethyl)-4,5-dihydro-1H-pyrazolo[3,4-c]pyridin-6(7H)-yl)-2-(piperidin-1-yl)ethanone

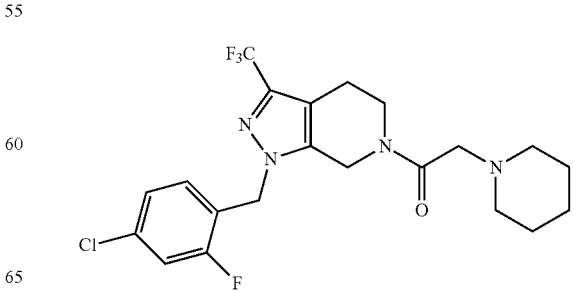

The title compound was synthesized according to the procedure described in Example 12-1, using Intermediate 2-1 and piperidine as starting materials, to obtain a white solid (yield 52% over two steps). $^1$H NMR (400 MHz, Methanol-d4) δ: 7.29-7.21 (m, 3H), 5.40-5.36 (m, 2H), 4.75-4.62 (m, 2H), 4.32-4.29 (m, 2H), 3.87-3.84 (m, 1H), 3.65-3.55 (m, 3H), 3.03-3.00 (m, 2H), 2.79-2.69 (m, 2H), 1.91-1.83 (m, 5H), 1.55 (brs, 1H); LCMS (ESI) m/z 459.0 [M+H]$^+$ Example 12-3

Ethyl 1-(2-(1-(4-chloro-2-fluorobenzyl)-3-(trifluoromethyl)-4,5-dihydro-1H-pyrazolo[3,4-c]pyridin-6(7H)-yl)-2-oxoethyl)piperidine-3-carboxylate

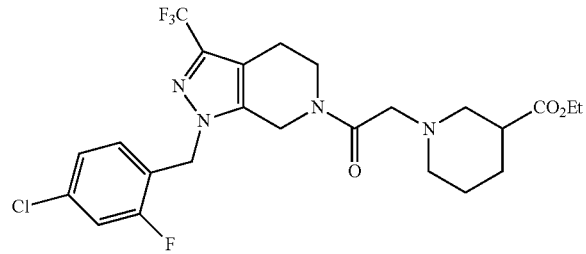 [SMILES: CCOC(=O)C1CCCN(CC(=O)N2CCc3c(C(F)(F)F)nn(Cc4ccc(Cl)cc4F)c3C2)C1]

The title compound was synthesized according to the procedure described in Example 12-1, using Intermediate 2-1 and ethyl piperidine-3-carboxylate as starting materials, to obtain a white solid (yield 70% over two steps). $^1$H NMR (400 MHz, Methanol-d4) δ: 7.34-7.22 (m, 3H), 5.43-5.41 (m, 2H), 4.79-4.65 (m, 2H), 4.42-4.21 (m, 4H), 3.91-3.66 (m, 4H), 3.14-2.74 (m, 4H), 2.23-1.96 (m, 4H), 1.65 (brs, 1H), 1.20 (s, 3H); LCMS (ESI) m/z 531.0 [M+H]$^+$ Example 12-4

Methyl 8-(2-(1-(4-chloro-2-fluorobenzyl)-3-(trifluoromethyl)-4,5-dihydro-1H-pyrazolo[3,4-c]pyridin-6(7H)-yl)-2-oxoethyl)-8-azabicyclo[3.2.1]octane-3-carboxylate

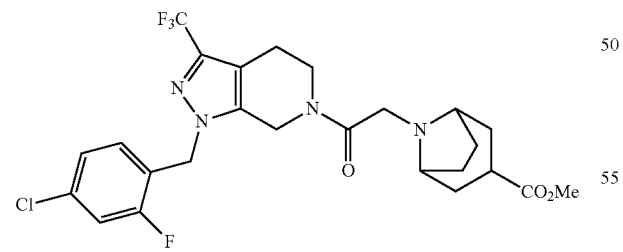

The title compound was synthesized according to the procedure described in Example 12-1, using Intermediate 2-1 and methyl 8-azabicyclo[3.2.1]octane-3-carboxylate as starting materials, to obtain a white solid (yield 75% over two steps). $^1$H NMR (400 MHz, Methanol-d4) δ: 7.28-7.21 (m, 3H), 5.41-5.37 (m, 2H), 4.75-4.64 (m, 2H), 4.23 (s, 2H), 4.07 (s, 2H), 3.86-3.42 (m, 5H), 3.01 (brs, 1H), 2.79-2.78 (m, 2H), 2.36-2.04 (m, 8H); LCMS (ESI) m/z 543.0 [M+H]$^+$ Example 12-5

Ethyl 1-(2-(1-(4-fluorobenzyl)-3-(trifluoromethyl)-4,5-dihydro-1H-pyrazolo[3,4-c]pyridin-6(7H)-yl)-2-oxoethyl)piperidine-3-carboxylate

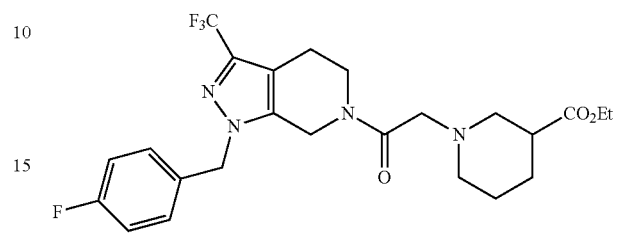

The title compound was synthesized according to the procedure described in Example 12-1, using ethyl piperidine-3-carboxylate as a starting material, to obtain a white solid (yield 76% over two steps). $^1$H NMR (400 MHz, DMSO-d6) δ: 9.91 (brs, 1H), 7.33-7.18 (m, 4H), 5.41 (s, 2H), 4.67-4.63 (m, 2H), 4.45 (s, 2H), 4.10-4.05 (m, 2H), 3.75-3.56 (m, 3H), 3.05-2.73 (m, 3H), 2.60-2.48 (m, 2H), 2.03-1.47 (m, 5 H), 1.19-1.15 (m, H); LCMS (ESI) m/z 497.1 [M+H]$^+$ Example 12-6

Ethyl 1-(1-(1-(4-chloro-2-fluorobenzyl)-3-(trifluoromethyl)-4,5-dihydro-1H-pyrazolo[3,4-c]pyridin-6(7H)-yl)-1-oxopropan-2-yl)piperidine-4-carboxylate

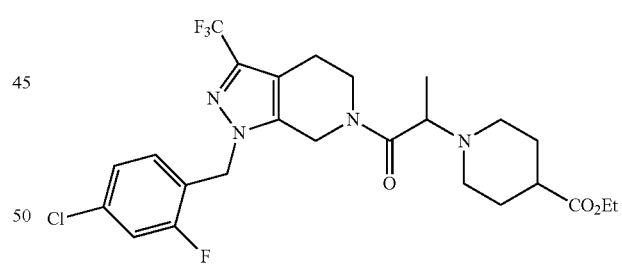

The title compound was synthesized according to the procedure described in Example 12-1, using Intermediate 2-1 and 2-bromopropanoyl chloride as starting materials, to obtain a white solid (90 mg, yield 41% over two steps). $^1$H NMR (400 MHz, Methanol-d4) δ: 7.33-7.18 (m, 3H), 5.43-5.37 (m, 2H), 4.71-4.54 (m, 2H), 4.20-4.15 (m, 2H), 4.00-3.48 (m, 4H), 3.27-2.64 (m, 6H), 2.31-1.85 (m, 4H), 1.63-1.50 (m, 3H), 1.27 (t, J=6.8 Hz, 3H); LCMS (ESI) m/z 545.2 [M+H]$^+$

Example 12-7

Methyl 1-(2-(1-(4-fluorobenzyl)-3-(trifluoromethyl)-4,5-dihydro-1H-pyrazolo[3,4-c]pyridin-6(7H)-yl)-2-oxoethyl)pyrrolidine-3-carboxylate

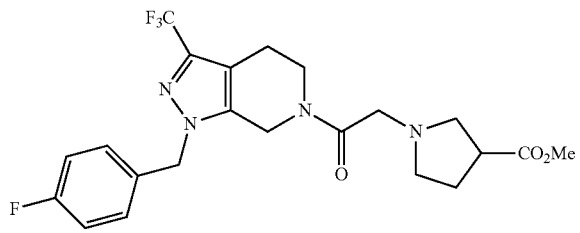 [SMILES: COC(=O)C1CCN(CC(=O)N2CCc3c(C(F)(F)F)nn(Cc4ccc(F)cc4)c3C2)C1]

The title compound was synthesized according to the procedure described in Example 12-1, using methyl pyrrolidine-3-carboxylate as a starting material, to obtain a white solid (yield 53% over two steps). $^1$H NMR (400 MHz, Methanol-d4) δ: 7.27-7.23 (m, 2H), 7.13-7.06 (m, 2H), 5.31 (s, 2H), 4.73-4.57 (m, 2H), 3.72-3.61 (m, 4H), 3.47-3.44 (m, 1H), 3.30-3.22 (m, 2H), 3.05-2.63 (m, 7H), 2.07-1.98 (m, 2H); LCMS (ESI) m/z 491.0 [M+Na]$^+$

Example 12-8

1-(1-(4-Chloro-2-fluorobenzyl)-3-(trifluoromethyl)-4,5-dihydro-1H-pyrazolo[3,4-c]pyridin-6(7H)-yl)-2-(4-(trifluoromethyl)piperidin-1-yl)ethanone

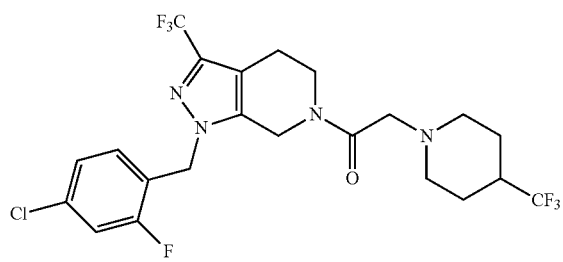 [SMILES: O=C(CN1CCC(C(F)(F)F)CC1)N1CCc2c(C(F)(F)F)nn(Cc3ccc(Cl)cc3F)c2C1]

The title compound was synthesized according to the procedure described in Example 12-1, using Intermediate 2-2 and 4-(trifluoromethyl)piperidine as starting materials, to obtain a white solid (50 mg, yield 30% over two steps). $^1$H NMR (400 MHz, Methanol-d4) δ: 7.33-7.18 (m, 3H), 5.41-5.38 (m, 2H), 4.80-4.70 (m, 2H), 3.82-3.79 (m, 2H), 3.35-3.26 (m, 2H), 3.01-2.66 (m, 4H), 2.17-2.03 (m, 3H), 1.88-1.79 (m, 2H), 1.66-1.40 (m, 2H); LCMS (ESI) m/z 527.2 [M+H]$^+$

Example 12-9

Ethyl 3-(2-(1-(4-fluorobenzyl)-3-(trifluoromethyl)-4,5-dihydro-1H-pyrazolo[3,4-c]pyridin-6(7H)-yl)-2-oxoethylamino)propanoate

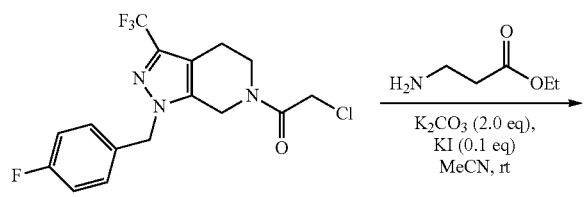

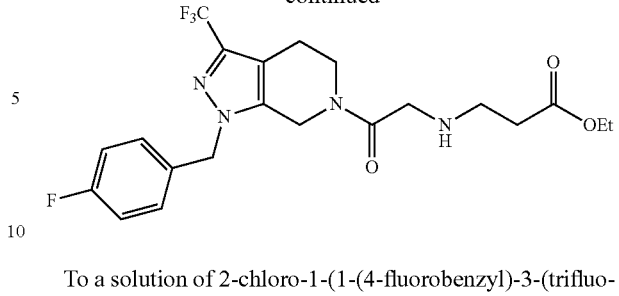

To a solution of 2-chloro-1-(1-(4-fluorobenzyl)-3-(trifluoromethyl)-4,5-dihydro-1H-pyrazolo[3,4-c]pyridin-6(7H)-yl)ethanone (150 mg, 0.36 mmol, 1.0 eq) in MeCN (5 mL) were added ethyl 3-aminopropanoate (86 mg, 0.73 mmol, 2.0 eq), Cs$_2$CO$_3$ (239 mg, 0.73 mmol, 2.0 eq) and KI (6 mg, 0.04 mmol, 0.1 eq). The mixture was stirred at rt for 16 h and diluted with EtOAc (100 mL). The organic layer was washed with water (100 mL), brine (100 mL), dried and concentrated. The residue was purified by prep HPLC (MeCN and H$_2$O with NH$_4$HCO$_3$ as mobile phase) to give ethyl 3-(2-(1-(4-fluorobenzyl)-3-(trifluoromethyl)-4,5-dihydro-1H-pyrazolo[3,4-c]pyridin-6(7H)-yl)-2-oxoethylamino)propanoate as a yellow oil (100 mg, yield 60%). $^1$H NMR (400 MHz, Methanol-d4) δ: 7.30-7.26 (m, 2H), 7.15-7.08 (m, 2H), 5.37-5.35 (m, 2H), 4.66-4.55 (m, 2H), 4.18 (q, J=7.2 Hz, 2H), 4.03-3.90 (m, 2H), 3.83-3.63 (m, 2H), 3.22-3.14 (m, 2H), 2.80-2.70 (m, 4H), 1.29-1.25 (m, 3H); LCMS (ESI) m/z 457.2 [M+H]$^+$

Example 12-10

1-(2-(1-(4-Fluorobenzyl)-3-(trifluoromethyl)-4,5-dihydro-1H-pyrazolo[3,4-c]pyridin-6(7H)-yl)-2-oxoethyl)piperidine-4-carbonitrile TFA salt

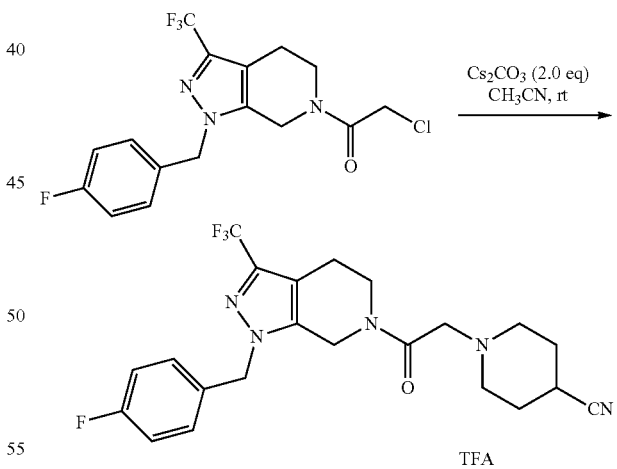

To a solution of 2-chloro-1-(1-(4-fluorobenzyl)-3-(trifluoromethyl)-4,5-dihydro-1H-pyrazolo[3,4-c]pyridin-6(7H)-yl)ethanone (Example 12-1, step 1) (100 mg, 0.267 mmol) and piperidine-4-carbonitrile hydrochloride (78 mg, 0.533 mmol) in CH$_3$CN (8 mL) was added Cs$_2$CO$_3$ (174 mg, 0.533 mmol). The mixture was stirred at rt for 16 h. The reaction mixture was filtered and the filtrate was concentrated. The residue was purified by reverse phase HPLC (MeCN and H$_2$O with 0.05% TFA as mobile phase) to give 1-(2-(1-(4-fluorobenzyl)-3-(trifluoromethyl)-4,5-dihydro-1H-pyrazolo

[3,4-c]pyridin-6(7H)-yl)-2-oxoethyl)piperidine-4-carbonitrie trifluoroacetate salt as a yellow solid (60 mg, yield 50%). ¹H NMR (400 MHz, Methanol-d4) δ: 7.32-7.26 (m, 2H), 7.15-7.08 (m, 2H), 5.37-5.36 (m, 2H), 4.67-4.52 (m, 2H), 4.40-4.32 (m, 2H), 3.87-3.61 (m, 4H), 3.52-3.35 (m, 1H), 3.24-2.91 (m, 2H), 2.83-2.71 (m, 2H), 2.29-2.20 (m, 4H); LCMS (ESI) m/z 450.0 [M+H]⁺

Example 12-11

1-(2-(1-(4-Fluorobenzyl)-3-(trifluoromethyl)-4,5-dihydro-1H-pyrazolo[3,4-c]pyridin-6(7H)-yl)-2-oxoethyl)pyrrolidine-3-carbonitrile TFA salt

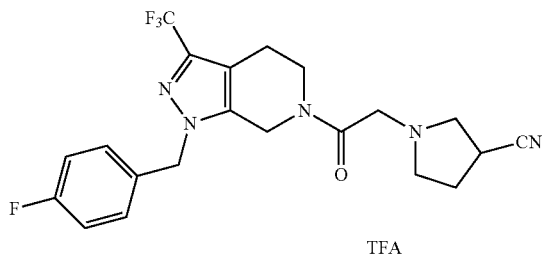 [SMILES: N#CC1CCN(CC(=O)N2CCc3c(C(F)(F)F)nn(Cc4ccc(F)cc4)c3C2)C1]

TFA

The titled compound was synthesized according to the procedure described in Example 12-10, using pyrrolidine-3-carbonitrile hydrochloride as a starting material, to obtain a white solid (120 mg, yield 65%). ¹H NMR (400 MHz, Methanol-d4) δ: 7.31-7.26 (m, 2H), 7.16-7.08 (m, 2H), 5.36-5.34 (m, 2H), 4.69-4.61 (m, 2H), 3.82-3.72 (m, 2H), 3.52-3.36 (m, 2H), 3.23-3.09 (m, 1H), 2.95-2.49 (m, 6H), 2.33-1.96 (m, 2H); LCMS (ESI) m/z 436.0 [M+H]⁺

Example 12-12

1-(2-(1-(4-Fluorobenzyl)-3-(trifluoromethyl)-4,5-dihydro-1H-pyrazolo[3,4-c]pyridin-6(7H)-yl)-2-oxoethyl)azetidine-3-carbonitrile TFA salt

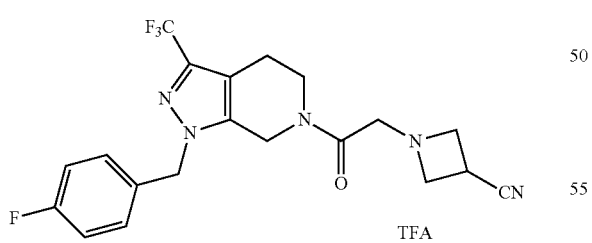

TFA

The titled compound was synthesized according to the procedure described in Example 12-10, using azetidine-2-carbonitrile hydrochloride as a starting material, to obtain a yellow solid (76 mg, yield 68%). ¹H NMR (400 MHz, Methanol-d4) δ: 7.31-7.26 (m, 2H), 7.16-7.08 (m, 2H), 5.37-5.35 (m, 2H), 4.63-4.44 (m, 8H), 4.04-4.00 (m, 1H), 3.83-3.58 (m, 2H), 2.82-2.69 (m, 2H); LCMS (ESI) m/z 422.0 [M+H]⁺

Example 12-13

1-(1-(4-Chloro-2-fluorobenzyl)-3-(trifluoromethyl)-4,5-dihydro-1H-pyrazolo[3,4-c]pyridin-6(7H)-yl)-2-(4-methylpiperidin-1-yl)ethanone

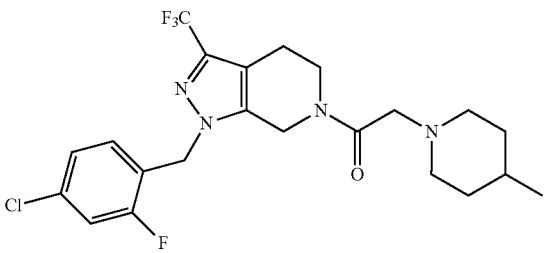 [SMILES: CC1CCN(CC(=O)N2CCc3c(C(F)(F)F)nn(Cc4ccc(Cl)cc4F)c3C2)CC1]

The titled compound was synthesized according to the procedure described in Example 12-1, using Intermediate 2-1 and 4-methylpiperidine as starting materials, to obtain a yellow solid (70 mg, yield 50%). ¹H NMR (400 MHz, Methanol-d4) δ: 7.31-7.19 (m, 3H), 5.40-5.37 (m, 2H), 4.82-4.70 (m, 2H), 3.82-3.78 (m, 2H), 3.32 (s, 2H), 2.89-2.66 (m, 4H), 2.10-1.98 (m, 2H), 1.65-1.56 (m, 2H), 1.37-1.01 (m, 3H), 0.94-0.90 (m, 3H); LCMS (ESI) m/z 473.2 [M+H]⁺

Example 12-14

1-(1-(4-Fluorobenzyl)-3-(trifluoromethyl)-4,5-dihydro-1H-pyrazolo[3,4-c]pyridin-6(7H)-yl)-2-(4-methylpiperidin-1-yl)ethanone

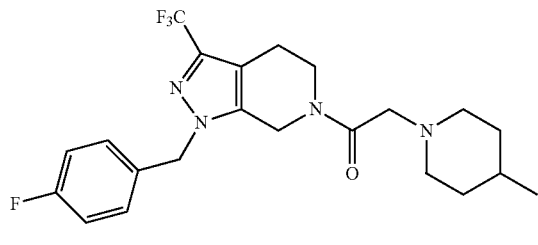 [SMILES: CC1CCN(CC(=O)N2CCc3c(C(F)(F)F)nn(Cc4ccc(F)cc4)c3C2)CC1]

The titled compound was synthesized according to the procedure described in Example 12-1, using 4-methylpiperidine as a starting material, to obtain a yellow solid (51 mg, yield 30%). ¹H NMR (400 MHz, Methanol-d4) δ: 7.29-7.26 (m, 2H), 7.15-7.09 (m, 2H), 5.37-5.34 (m, 2H), 4.72-4.60 (m, 2H), 3.79-3.77 (m, 2H), 3.34-3.16 (m, 2H), 2.91-2.65 (m, 4H), 2.13-1.97 (m, 2H), 1.66-1.55 (m, 2H), 1.39-1.00 (m, 3H), 0.95-0.90 (m, 3H); LCMS (ESI) m/z 439.2 [M+H]⁺

Example 12-15

1-(1-(4-Fluorobenzyl)-3-(trifluoromethyl)-4,5-dihydro-1H-pyrazolo[3,4-c]pyridin-6(7H)-yl)-2-(4-(trifluoromethyl)piperidin-1-yl)ethanone

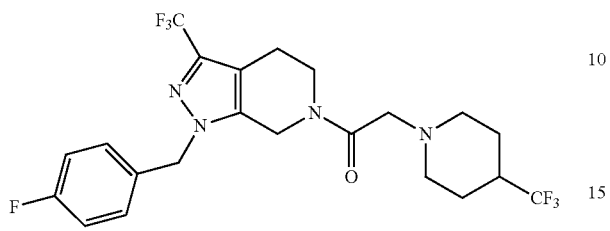

The titled compound was synthesized according to the procedure described in Example 12-1, using 4-(trifluoromethyl)piperidine as a starting material, to obtain a yellow solid (58 mg, yield 30%). $^1$H NMR (400 MHz, Methanol-d4) δ: 7.30-7.26 (m, 2H), 7.15-7.08 (m, 2H), 5.37-5.34 (m, 2H), 4.67-4.61 (m, 2H), 3.80-3.65 (m, 2H), 3.34-3.18 (m, 2H), 3.00-2.66 (m, 4H), 2.18-2.00 (m, 3H), 1.86-1.78 (m, 2H), 1.66-1.28 (m, 2H); LCMS (ESI) m/z 493.2 [M+H]$^+$

Example 12-16

Ethyl 1-(2-(1-(4-fluorobenzyl)-3-(trifluoromethyl)-4,5-dihydro-1H-pyrazolo[3,4-c]pyridin-6(7H)-yl)-2-oxoethyl)azepane-4-carboxylate TFA salt

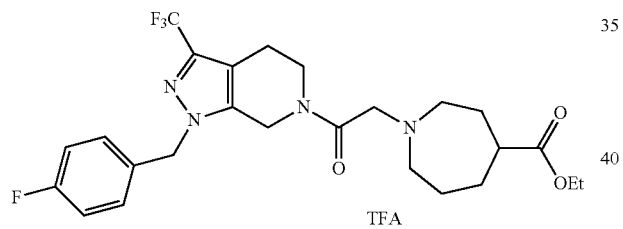

The titled compound was synthesized according to the procedure described in Example 12-10, using ethyl azepane-4-carboxylate hydrochloride as a starting material, to obtain a yellow oil (100 mg, yield 49%). $^1$H NMR (400 MHz, Methanol-d4) δ: 7.32-7.26 (m, 2H), 7.15-7.08 (m, 2H), 5.41-5.39 (m, 2H), 4.77-4.62 (m, 2H), 4.40-4.34 (m, 2H), 4.17 (q, J=7.2 Hz, 2H), 3.86-3.44 (m, 5H), 3.31-3.17 (m, 1H), 2.83-2.72 (m, 3H), 2.25-1.91 (m, 6H), 1.29 (t, J=7.2 Hz, 3H); LCMS (ESI) m/z 511.2 [M+H]$^+$

Example 12-17

Ethyl 1-(2-(1-(4-fluorobenzyl)-3-(trifluoromethyl)-4,5-dihydro-1H-pyrazolo[3,4-c]pyridin-6(7H)-yl)-2-oxoethyl)azepane-4-carboxylate TFA salt

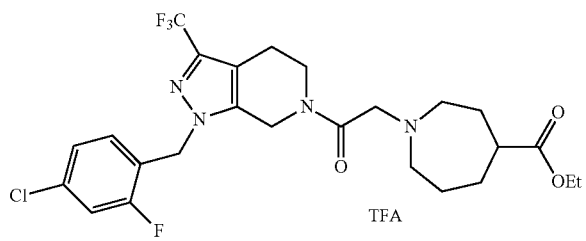 [SMILES: CCOC(=O)C1CCCN(CC(=O)N2CCc3c(C(F)(F)F)nn(Cc4ccc(Cl)cc4F)c3C2)CC1]

The titled compound was synthesized according to the procedure described in Example 12-1, using ethyl azepane-4-carboxylate hydrochloride and Intermediate 2-1 as a starting materials, to obtain a colorless oil (110 mg, yield 55%). $^1$H NMR (400 MHz, Methanol-d4) δ: 7.33-7.21 (m, 3H), 5.41-5.39 (m, 2H), 4.77-4.62 (m, 2H), 4.40-4.34 (m, 2H), 4.17 (q, J=7.2 Hz, 2H), 3.89-3.44 (m, 5H), 3.31-3.17 (m, 1H), 2.83-2.71 (m, 3H), 2.25-1.91 (m, 6H), 1.29 (q, J=7.2 Hz, 3H); LCMS (ESI) m/z 545.2 [M+H]$^+$

Example 12-18

Methyl 9-(2-(1-(4-fluorobenzyl)-3-(trifluoromethyl)-4,5-dihydro-1H-pyrazolo[3,4-c]pyridin-6(7H)-yl)-2-oxoethyl)-3-oxa-9-azabicyclo[3.3.1]nonane-7-carboxylate

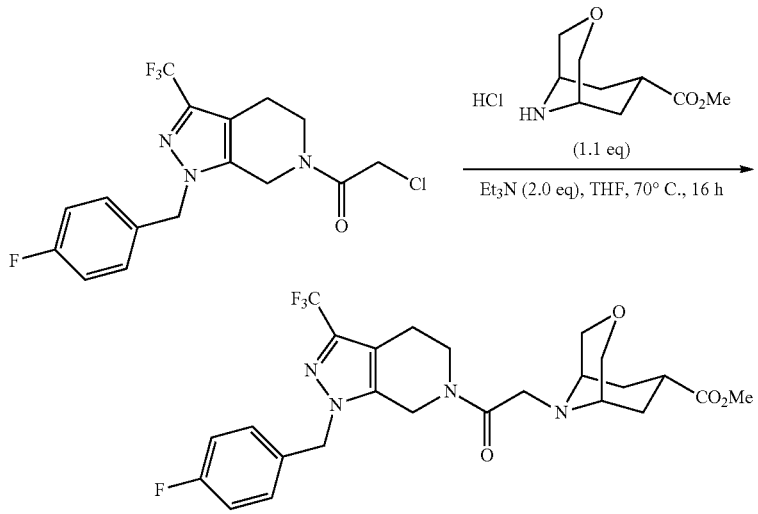

The title compound was synthesized according to the procedure described in Example 12-1, using methyl 3-oxa-9-azabicyclo[3.3.1]nonane-7-carboxylate hydrochloride as a starting material, to obtain a colorless oil (80 mg, yield 51%). LCMS (ESI) m/z 525.2 [M+H]+

Example 12-19

Methyl 2-(1-(2-(1-(4-fluorobenzyl)-3-(trifluoromethyl)-4,5-dihydro-1H-pyrazolo[3,4-c]pyridin-6(7H)-yl)-2-oxoethyl)azetidin-3-yl)acetate TFA salt

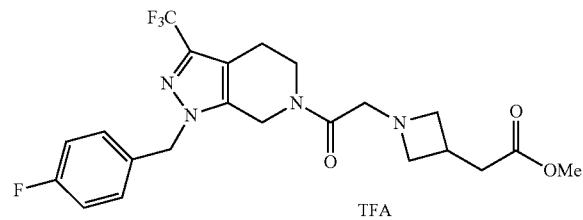 [SMILES: COC(=O)CC1CN(CC(=O)N2CCc3c(C(F)(F)F)nn(Cc4ccc(F)cc4)c3C2)C1]

The title compound was synthesized according to the procedure described in Example 12-10, using methyl 2-(azetidin-3-yl)acetate as a starting material, to obtain a colorless oil (90 mg, yield 48%). $^1$H NMR (400 MHz, Methanol-d4) δ: 7.32-7.08 (m, 4H), 5.38-5.35 (m, 2H), 4.63-3.80 (m, 8H), 3.72-3.60 (m, 5H), 3.31-2.23 (m, 1H), 2.81-2.69 (m, 4H); LCMS (ESI) m/z 468.9 [M+H]+

Example 13-1

1-(2-(1-(4-Fluorobenzyl)-3-(trifluoromethyl)-4,5-dihydro-1H-pyrazolo[3,4-c]pyridin-6(7H)-yl)-2-oxoethyl)piperidine-4-carboxylic acid

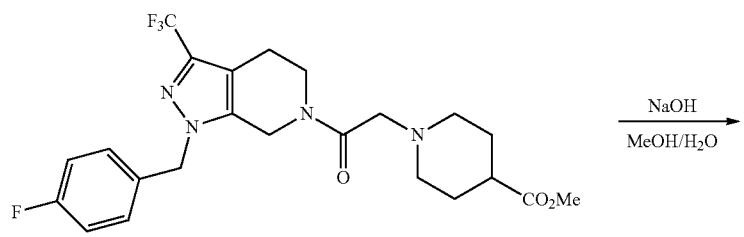

A mixture of methyl 1-(2-(1-(4-fluorobenzyl)-3-(trifluoromethyl)-4,5-dihydro-1H-pyrazolo[3,4-c]pyridin-6(7H)-yl)-2-oxoethyl)piperidine-4-carboxylate (Example 12-1, 50 mg, 0.10 mmol) and NaOH (8 mg, 0.19 mmol) in MeOH/H$_2$O (2 mL) was stirred at room temperature overnight. TLC (PE/EA=1/1) showed the starting material was consumed completely. The solvent was removed in vacuum and the residue was dissolved in water. The pH of aqueous phase was adjusted to about 2. Then the solvent was removed in vacuum to give the crude, which was purified by prep.-HPLC (MeCN and H$_2$O with 0.225% (v/v) HCOOH as mobile phase) to provide 1-(2-(1-(4-fluorobenzyl)-3-(trifluoromethyl)-4,5-dihydro-1H-pyrazolo[3,4-c]pyridin-6(7H)-yl)-2-oxoethyl)piperidine-4-carboxylic acid (30 mg, yield 59%) as a white solid. $^1$H NMR (400 MHz, Methanol-d4) δ 7.31-7.27 (m, 2H), 7.17-7.10 (m, 2H), 5.39-5.37 (m, 2H), 4.67-4.12 (m, 2H), 4.09-3.83 (m, 4H), 3.33-3.25 (m, 2H), 2.93-2.71 (m, 4H), 2.51 (brs, 1H), 2.12-1.96 (m, 4H); LCMS (ESI) m/z 469.0 [M+H]+

Example 13-2

1-(2-(1-(4-Chloro-2-fluorobenzyl)-3-(trifluoromethyl)-4,5-dihydro-1H-pyrazolo[3,4-c]pyridin-6(7H)-yl)-2-oxoethyl)piperidine-4-carboxylic acid

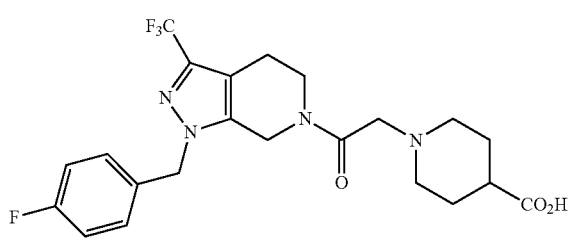

The title compound was synthesized according to the procedure described in Example 13-1, using Intermediate 2-1 as a starting material, to obtain a colorless oil (yield 59% in the final step). ¹H NMR (400 MHz, Methanol-d4) δ: 8.39 (s, 1H), 7.33-7.21 (m, 3H), 5.42-5.39 (m, 2H), 4.76-4.72 (m, 2H), 4.09-3.92 (m, 2H), 3.86-3.70 (m, 2H), 3.37-3.25 (m, 2H), 2.93-2.71 (m, 4H), 2.50-2.47 (m, 1H), 2.12-1.97 (m, 4H); LCMS (ESI) m/z 503.1 [M+H]⁺

Example 13-3

1-(2-(1-(4-Chloro-2-fluorobenzyl)-3-(trifluoromethyl)-4,5-dihydro-1H-pyrazolo[3,4-c]pyridin-6(7H)-yl)-2-oxoethyl)piperidine-3-carboxylic acid

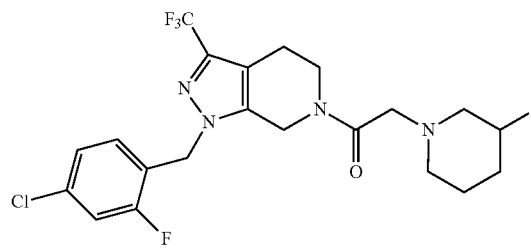

The title compound was synthesized according to the procedure described in Example 13-1, using Example 12-3 as a starting material, to obtain a white solid (yield 50%). ¹H NMR (400 MHz, DMSO-d6) δ: 9.82 (brs, 1.4H), 9.42 (brs, 0.6H), 7.49-7.47 (m, 1H), 7.30-7.26 (m, 2H), 5.42 (s, 2H), 4.74-4.63 (m, 2H), 4.43-4.39 (m, 2H), 3.75 (s, 1H), 3.34-2.47 (m, 7H), 2.03-1.83 (m, 4H), 1.43 (s, 1H); LCMS (ESI) m/z 503.1 [M+H]⁺

Example 13-4

8-(2-(1-(4-Chloro-2-fluorobenzyl)-3-(trifluoromethyl)-4,5-dihydro-1H-pyrazolo[3,4-c]pyridin-6(7H)-yl)-2-oxoethyl)-8-azabicyclo[3.2.1]octane-3-carboxylic acid

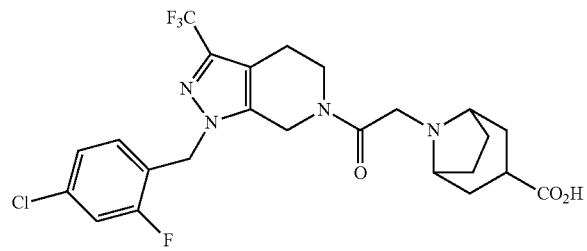 [SMILES: O=C(O)C1CC2CCC(C1)N2CC(=O)N1CCc2c(C(F)(F)F)nn(Cc3ccc(Cl)cc3F)c2C1]

The title compound was synthesized according to the procedure described in Example 13-1, using Example 12-4 as a starting material, to obtain a white solid (yield 55%). ¹H NMR (400 MHz, Methanol-d4) δ: 7.28-7.21 (m, 3H), 5.41-5.37 (m, 2H), 4.75-4.63 (m, 2H), 4.22-4.20 (m, 2H), 4.07 (s, 2H), 3.88-3.62 (m, 2H), 2.96-2.94 (m, 1H), 2.94-2.79 (m, 2H), 2.35-2.06 (m, 8H); LCMS (ESI) m/z 529.0 [M+H]⁺

Example 13-5

8-(2-(1-(4-Fluorobenzyl)-3-(trifluoromethyl)-4,5-dihydro-1H-pyrazolo[3,4-c]pyridin-6(7H)-yl)-2-oxoethyl)-8-azabicyclo[3.2.1]octane-3-carboxylic acid

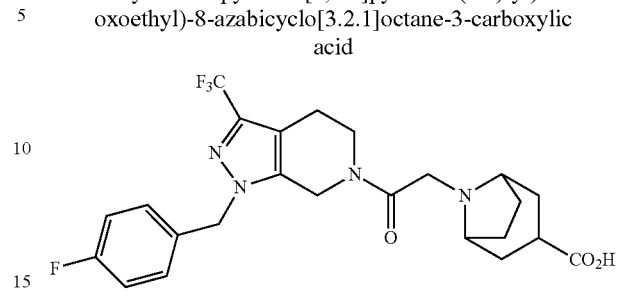

The title compound was synthesized according to the procedure described in Example 13-1, using methyl 8-azabicyclo[3.2.1]octane-3-carboxylate as a starting material, to obtain a white solid (yield 75% in the final step). ¹H NMR (400 MHz, Methanol-d4) δ: 7.34-7.28 (m, 2H), 7.16-7.10 (m, 2H), 5.42-5.37 (m, 2H), 4.69-4.58 (m, 2H), 4.24-4.20 (m, 2H), 4.10 (s, 2H), 3.87-3.64 (m, 2H), 3.00-2.73 (m, 3H), 2.38-2.09 (m, 8H); LCMS (ESI) m/z 495.1 [M+H]⁺

Example 13-6

9-(2-(1-(4-Fluorobenzyl)-3-(trifluoromethyl)-4,5-dihydro-1H-pyrazolo[3,4-c]pyridin-6(7H)-yl)-2-oxoethyl)-9-azabicyclo[3.3.1]nonane-3-carboxylic acid

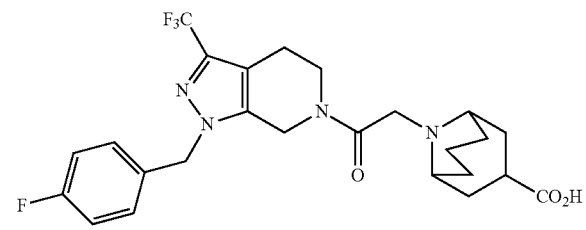 [SMILES: O=C(O)C1CC2CCCC(C1)N2CC(=O)N1CCc2c(C(F)(F)F)nn(Cc3ccc(F)cc3)c2C1]

The title compound was synthesized according to the procedure described in Example 13-1, using methyl 9-azabicyclo[3.3.1]nonane-3-carboxylate as a starting material, to obtain a white solid (yield 74% in the final step). ¹H NMR (400 MHz, Methanol-d4) δ: 7.33-7.11 (m, 4H), 5.43-5.36 (m, 2H), 4.68-4.40 (m, 4H), 3.86-3.72 (m, 4H), 3.39 (brs, 1H), 2.83-2.72 (m, 2H), 2.33-1.76 (m, 10H); LCMS (ESI) m/z 509.1 [M+H]⁺

Example 13-7

1-(2-(1-(4-Fluorobenzyl)-3-(trifluoromethyl)-4,5-dihydro-1H-pyrazolo[3,4-c]pyridin-6(7H)-yl)-2-oxoethyl)piperidine-3-carboxylic acid

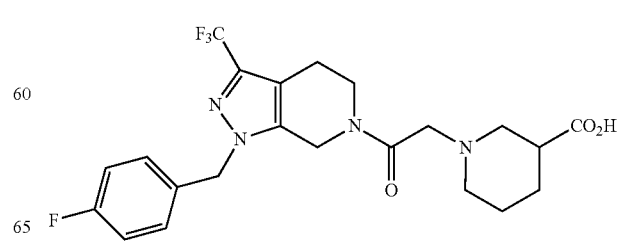

The title compound was synthesized according to the procedure described in Example 13-1, using Example 12-5 as a starting material, to obtain a white solid (yield 52%). $^1$H NMR (400 MHz, DMSO-d6) δ: 9.73 (s, 1H), 7.32-7.18 (m, 4H), 5.41-5.38 (m, 2H), 4.72-4.61 (m, 2H), 4.42-4.39 (m, 2H), 3.77-3.56 (m, 3H), 3.15-2.61 (m, 6H), 2.48-1.41 (m, 5H); LCMS (ESI) m/z 469.0 [M+H]$^+$ Example 13-8

1-(1-(1-(4-Chloro-2-fluorobenzyl)-3-(trifluoromethyl)-4,5-dihydro-1H-pyrazolo[3,4-c]pyridin-6(7H)-yl)-1-oxopropan-2-yl)piperidine-4-carboxylic acid

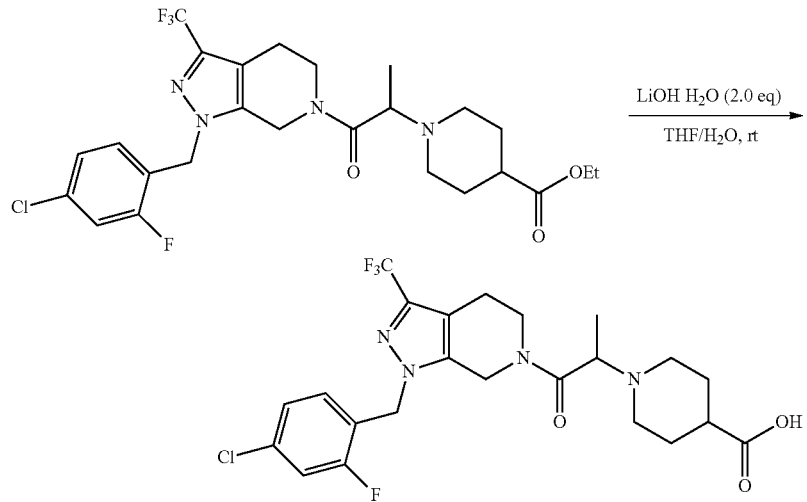

To a solution of ethyl 1-(1-(1-(4-chloro-2-fluorobenzyl)-3-(trifluoromethyl)-4,5-dihydro-1H-pyrazolo[3,4-c]pyridin-6(7H)-yl)-1-oxopropan-2-yl)piperidine-4-carboxylate (Example 12-6, 80 mg, 0.15 mmol, 1.0 eq) in THF (4 mL) were added lithium hydroxide monohydrate (12 mg, 0.29 mmol, 2.0 eq) and H$_2$O (1 mL). The reaction mixture was stirred at rt for 16 h and was adjusted to pH~6 with 1N HCl. The resulted solution was purified by prep HPLC (MeCN/H$_2$O with 10 mM NH$_4$HCO$_3$ as mobile phase) to afford 1-(1-(1-(4-Chloro-2-fluorobenzyl)-3-(trifluoromethyl)-4,5-dihydro-1H-pyrazolo[3,4-c]pyridin-6(7H)-yl)-1-oxopropan-2-yl)piperidine-4-carboxylic acid (17 mg, yield 22%) as white solid. $^1$H NMR (400 MHz, Methanol-d4) δ: 7.33-7.20 (m, 3H), 5.42-5.38 (m, 2H), 4.78-4.54 (m, 1H), 4.10-3.71 (m, 3H), 3.10-1.50 (m, 12H), 1.34-1.20 (m, 3H); LCMS (ESI) m/z 517.1 [M+H]$^+$ Example 13-9

2-(2-(1-(4-Chloro-2-fluorobenzyl)-3-(trifluoromethyl)-4,5-dihydro-1H-pyrazolo[3,4-c]pyridin-6(7H)-yl)-2-oxoethyl)octahydrocyclopenta[c]pyrrole-5-carboxylic acid TFA salt

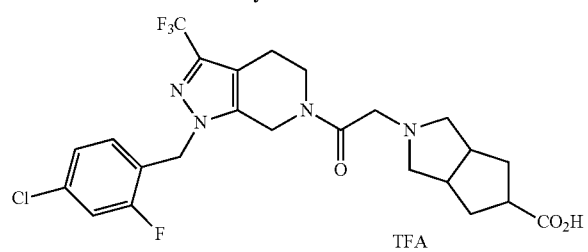

Step 1

2-chloro-1-(1-(4-chloro-2-fluorobenzyl)-3-(trifluoromethyl)-4,5-dihydro-1H-pyrazolo[3,4-c]pyridin-6(7H)-yl)ethanone To a mixture of 1-(4-chloro-2-fluorobenzyl)-3-(trifluoromethyl)-4,5,6,7-tetrahydro-1H-pyrazolo[3,4-c]pyridine hydrochloride (100 mg, 0.3 mmol, 1.0 eq) and Et$_3$N (46 mg, 0.45 mmol, 1.5 eq) in DCM (5 mL) was added 2-chloroacetyl chloride (51 mg, 0.45 mmol, 1.5 eq). The reaction mixture was stirred at rt for 2 h and concentrated to yield 2-chloro-1-(1-(4-chloro-2-fluorobenzyl)-3-(trifluoromethyl)-4,5-dihydro-1H-pyrazolo[3,4-c]pyridin-6(7H)-yl)ethanone as a crude product, which was used to the next step without further purification. LCMS (ESI) m/z 410.1 [M+H]+

Step 2

Methyl 2-(2-(1-(4-chloro-2-fluorobenzyl)-3-(trifluoromethyl)-4,5-dihydro-1H-pyrazolo[3,4-c]pyridin-6(7H)-yl)-2-oxoethyl)octahydrocyclopenta[c]pyrrole-5-carboxylate TFA salt

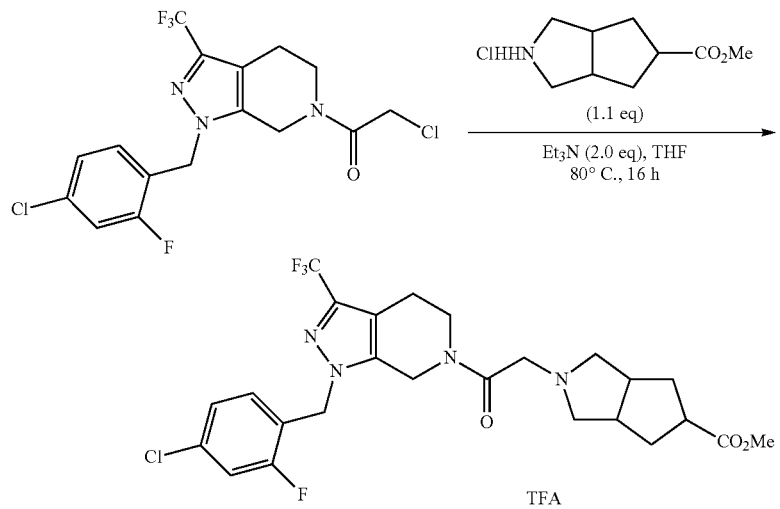

To a mixture of 2-chloro-1-(1-(4-chloro-2-fluorobenzyl)-3-(trifluoromethyl)-4,5-dihydro-1H-pyrazolo[3,4-c]pyridin-6(7H)-yl)ethanone (110 mg, 0.27 mmol, 1.0 eq) and Et₃N (55 mg, 0.54 mmol, 2.0 eq) in THF (5 mL) was added methyl octahydrocyclopenta[c]pyrrole-5-carboxylate hydrochloride (55 mg, 0.32 mmol, 1.2 eq). The reaction mixture was stirred at 80° C. for 16 h. After cooling to rt, the mixture was concentrated and purified by reversed phase HPLC (MeCN and H₂O with 0.05% TFA as mobile phase) to give Methyl 2-(2-(1-(4-chloro-2-fluorobenzyl)-3-(trifluoromethyl)-4,5-dihydro-1H-pyrazolo[3,4-c]pyridin-6(7H)-yl)-2-oxoethyl)octahydrocyclopenta[c]pyrrole-5-carboxylate trifluoroacetate salt as white solid (60 mg, yield 41% over two steps). LCMS (ESI) m/z 543.2 [M+H]+

Step 3

2-(2-(1-(4-Chloro-2-fluorobenzyl)-3-(trifluoromethyl)-4,5-dihydro-1H-pyrazolo[3,4-c]pyridin-6(7H)-yl)-2-oxoethyl)octahydrocyclopenta[c]pyrrole-5-carboxylic acid TFA salt

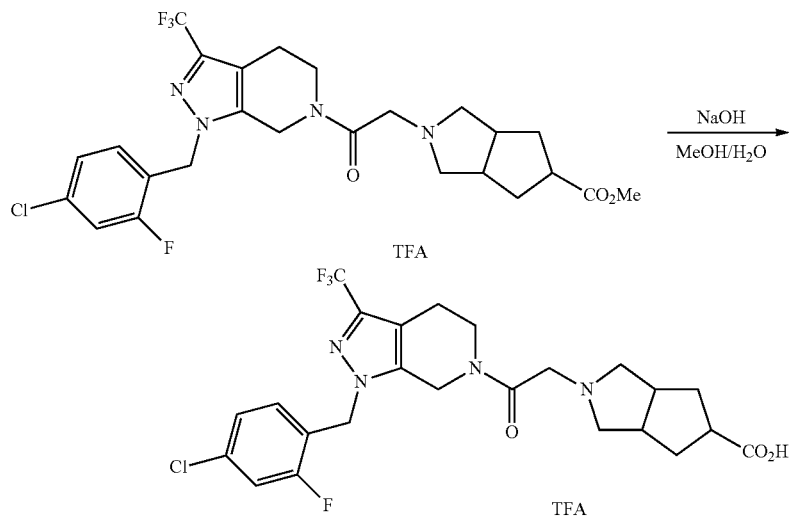

A mixture of methyl 2-(2-(1-(4-chloro-2-fluorobenzyl)-3-(trifluoromethyl)-4,5-dihydro-1H-pyrazolo[3,4-c]pyridin-6(7H)-yl)-2-oxoethyl)octahydrocyclopenta[c]pyrrole-5-carboxylate trifluoroacetate salt (60 mg, 0.11 mmol, 1.0 eq) in MeOH (3 mL) and H$_2$O (0.5 mL) was added NaOH (9 mg, 0.22 mmol, 2.0 eq). The reaction mixture was stirred at rt for 2 h. The reaction mixture was concentrated and acidified to pH=5 with 1N HCl. The mixture was purified by reverse phase HPLC (MeCN and H$_2$O with 0.05% TFA as mobile phase) to give 2-(2-(1-(4-chloro-2-fluorobenzyl)-3-(trifluoromethyl)-4,5-dihydro-1H-pyrazolo[3,4-c]pyridin-6(7H)-yl)-2-oxoethyl)octahydrocyclopenta[c]pyrrole-5-carboxylic acid trifluoroacetate salt (40 mg, yield 61%) as a white solid. $^1$H NMR (400 MHz, Methanol-d4) δ: 7.32-7.21 (m, 3H), 5.39 (s, 2H), 4.76-4.20 (m, 2H), 4.44-4.39 (m, 2H), 3.96-3.42 (m, 4H), 3.27-2.70 (m, 7H), 2.32-1.81 (m, 4H); LCMS (ESI) m/z 529.1 [M+H]$^+$ Example 13-10

2-(2-(1-(4-Fluorobenzyl)-3-(trifluoromethyl)-4,5-dihydro-1H-pyrazolo[3,4-c]pyridin-6(7H)-yl)-2-oxoethyl)octahydrocyclopenta[c]pyrrole-5-carboxylic acid TFA salt

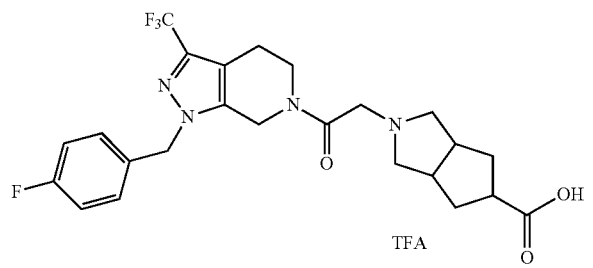 [SMILES: O=C(O)C1CC2CN(CC(=O)N3CCc4c(C(F)(F)F)nn(Cc5ccc(F)cc5)c4C3)CC2C1]

The title compound was synthesized according to the procedure described in Example 13-9, using Intermediate 2-2 as a starting material, to obtain a white solid (yield 52% in the final step). $^1$H NMR (400 MHz, Methanol-d4) δ: 7.30-7.26 (m, 2H), 7.16-7.09 (m, 2H), 5.35 (s, 2H), 4.66-4.49 (m, 2H), 4.42-4.32 (m, 2H), 3.95-3.33 (m, 4H), 3.06-2.70 (m, 7H), 2.34-2.25 (m, 1H), 2.02-1.81 (m, 3H); LCMS (ESI) m/z 495.1 [M+H]$^+$ Example 13-11

3-((2-(1-(4-Chloro-2-fluorobenzyl)-3-(trifluoromethyl)-4,5-dihydro-1H-pyrazolo[3,4-c]pyridin-6(7H)-yl)-2-oxoethyl)amino)-2,2-dimethylcyclobutanecarboxylic acid TFA salt

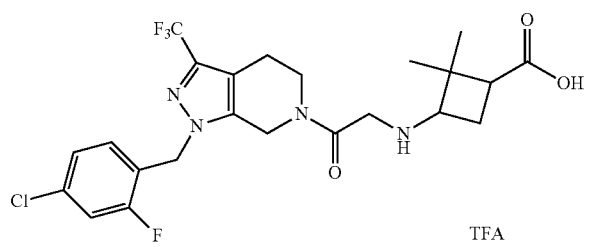 [SMILES: CC1(C)C(NCC(=O)N2CCc3c(C(F)(F)F)nn(Cc4ccc(Cl)cc4F)c3C2)CC1C(=O)O]

The title compound was synthesized according to the procedure described in Example 13-9, using methyl 3-amino-2,2-dimethylcyclobutanecarboxylate as a starting material, to obtain a white solid (yield 33% in the final step). $^1$H NMR (400 MHz, Methanol-d4) δ: 7.32-7.22 (m, 3H), 5.41-5.39 (m, 2H), 4.77-4.65 (m, 2H), 4.19-4.08 (m, 2H), 3.89-3.66 (m, 2H), 3.52-3.48 (m, 1H), 2.82-2.72 (m, 3H), 2.41-2.34 (m, 2H), 1.38 (s, 3H), 1.23 (s, 3H); LCMS (ESI) m/z 517.1 [M+H]$^+$ Example 13-12

1-(2-(1-(4-Fluorobenzyl)-3-(trifluoromethyl)-4,5-dihydro-1H-pyrazolo[3,4-c]pyridin-6(7H)-yl)-2-oxoethyl)pyrrolidine-3-carboxylic acid

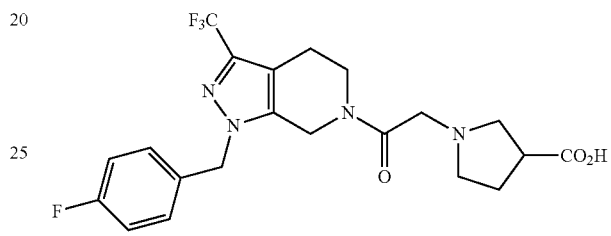

The title compound was synthesized according to the procedure described in Example 13-1, using Example 12-7 as a starting material, to obtain a colorless gum (yield 9%). $^1$H NMR (400 MHz, Methanol-d4) δ: 7.24-7.21 (m, 2H), 7.10-7.02 (m, 2H), 5.32-5.29 (m, 2H), 4.60-4.51 (m, 2H), 4.32-4.16 (m, 2H), 3.60-3.57 (m, 2H), 3.45-3.26 (m, 4H), 3.02-3.00 (m, 1H), 2.75-2.65 (m, 2H), 2.24-2.18 (m, 2H); LCMS (ESI) m/z 455.0 [M+H]$^+$ Example 13-13

2-(1-(2-(1-(4-Chloro-2-fluorobenzyl)-3-(trifluoromethyl)-4,5-dihydro-1H-pyrazolo[3,4-c]pyridin-6(7H)-yl)-2-oxoethyl)piperidin-4-yl)acetic acid TFA salt

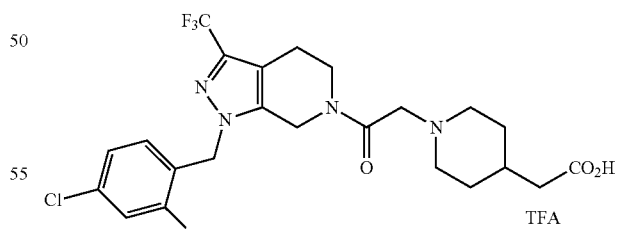

The title compound was synthesized according to the procedure described in Example 13-9, using methyl 2-(piperidin-4-yl)acetate hydrochloride as a starting material, to obtain a white solid (yield 36% over three steps). $^1$H NMR (400 MHz, Methanol-d4) δ: 7.30-7.22 (m, 3H), 5.40-5.39 (m, 2H), 4.77-4.61 (m, 2H), 4.40-4.29 (m, 2H), 3.90-3.63 (m, 4H), 3.10-3.05 (m, 2H), 2.83-2.71 (m, 2H), 2.44-2.04 (m, 5H), 2.68-1.59 (m, 2H); LCMS (ESI) m/z 517.2 [M+H]$^+$

Example 13-14

3-((2-(1-(4-Fluorobenzyl)-3-(trifluoromethyl)-4,5-dihydro-1H-pyrazolo[3,4-c]pyridin-6(7H)-yl)-2-oxoethyl)amino)-2,2-dimethylcyclobutanecarboxylic acid TFA salt

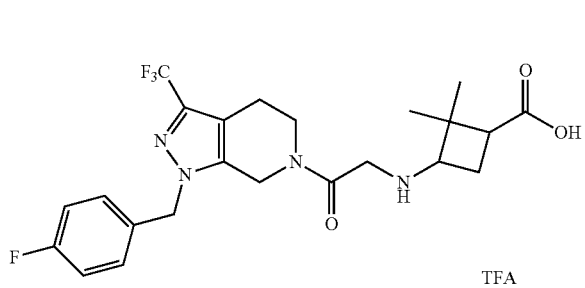 [SMILES: CC1(C)C(NCC(=O)N2CCc3c(C(F)(F)F)nn(Cc4ccc(F)cc4)c3C2)CC1C(=O)O]

TFA

The title compound was synthesized according to the procedure described in Example 13-9, using Intermediate 2-2 and methyl 3-amino-2,2-dimethylcyclobutanecarboxylate as starting materials, to obtain a white solid (yield 22% over three steps). $^1$H NMR (400 MHz, Methanol-d4) δ: 7.31-7.26 (m, 2H), 7.16-7.08 (m, 2H), 5.37-5.35 (m, 2H), 4.66-4.53 (m, 2H), 3.97-3.64 (m, 4H), 3.20-3.09 (m, 1H), 2.80-2.68 (m, 2H), 2.56-2.53 (m, 1H), 2.38-2.31 (m, 1H), 2.13-2.05 (m, 1H), 1.33-1.31 (m, 3H), 1.13-1.11 (m, 3H); LCMS (ESI) m/z 483.2 [M+H]$^+$

Example 13-15

2-(1-(2-(1-(4-Fluorobenzyl)-3-(trifluoromethyl)-4,5-dihydro-1H-pyrazolo[3,4-c]pyridin-6(7H)-yl)-2-oxoethyl)piperidin-4-yl)acetic acid TFA salt

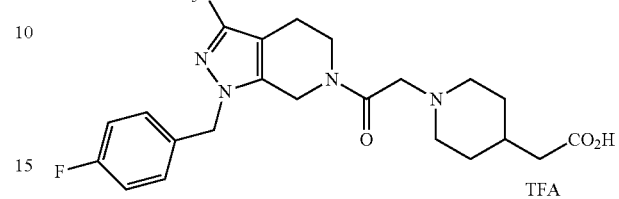

TFA

The title compound was synthesized according to the procedure described in Example 13-9, using Intermediate 2-2 and methyl 2-(piperidin-4-yl)acetate hydrochloride as starting materials, to obtain a white solid (50 mg, yield 37% over three steps). $^1$H NMR (400 MHz, Methanol-d4) δ: 7.30-7.23 (m, 2H), 7.13-7.08 (m, 2H), 5.36 (s, 2H), 4.67-4.50 (m, 2H), 4.32-4.24 (m, 2H), 3.85-3.60 (m, 4H), 3.09-3.02 (m, 2H), 3.82-2.70 (m, 2H), 2.34-2.32 (m, 2H), 2.06-2.03 (m, 3H), 1.64-1.60 (m, 2H); LCMS (ESI) m/z 483.2 [M+H]$^+$

Example 13-16

3-(2-(1-(4-Fluorobenzyl)-3-(trifluoromethyl)-4,5-dihydro-1H-pyrazolo[3,4-c]pyridin-6(7H)-yl)-2-oxoethylamino)propanoic acid TFA salt

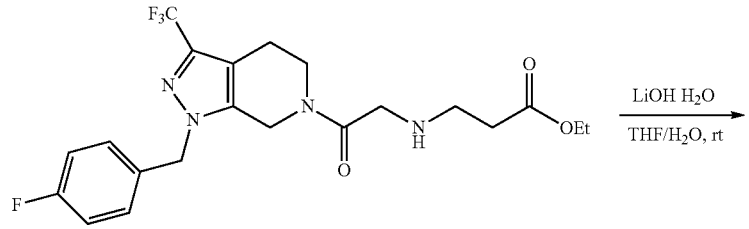

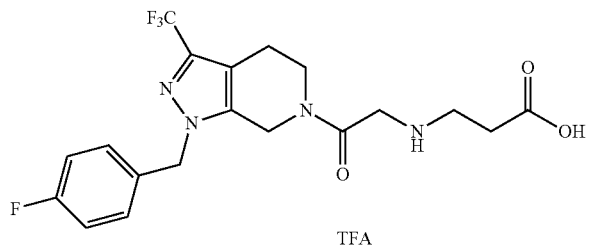

TFA

To a solution of ethyl 3-(2-(1-(4-fluorobenzyl)-3-(trifluoromethyl)-4,5-dihydro-1H-pyrazolo[3,4-c]pyridin-6(7H)-yl)-2-oxoethylamino)propanoate (90 mg, 0.20 mmol, 1.0 eq) in THF/H₂O (5 mL, 4/1) was added LiOH.H₂O (17 mg, 0.39 mmol, 2.0 eq). The mixture was stirred at rt for 16 h and acidified to pH=5 with 1 N HCl. The mixture was purified by prep HPLC (MeCN and H₂O with 0.05% TFA as mobile phase) to give 3-(2-(1-(4-fluorobenzyl)-3-(trifluoromethyl)-4,5-dihydro-1H-pyrazolo[3,4-c]pyridin-6(7H)-yl)-2-oxoethylamino)propanoic acid trifluoroacetate salt as yellow oil (39 mg, yield 46%). ¹H NMR (400 MHz, Methanol-d4) δ: 7.32-7.26 (m, 2H), 7.15-7.08 (m, 2H), 5.37-5.35 (m, 2H), 4.67-4.54 (m, 2H), 4.23-4.16 (m, 2H), 3.86-3.63 (m, 2H), 3.35-3.32 (m, 2H), 2.82-2.71 (m, 4H); LCMS (ESI) m/z 429.2 [M+H]⁺

Example 13-17

1-(2-(1-(4-Chloro-2-fluorobenzyl)-3-(trifluoromethyl)-4,5-dihydro-1H-pyrazolo[3,4-c]pyridin-6(7H)-yl)-2-oxoethyl)azetidine-3-carboxylic acid TFA salt

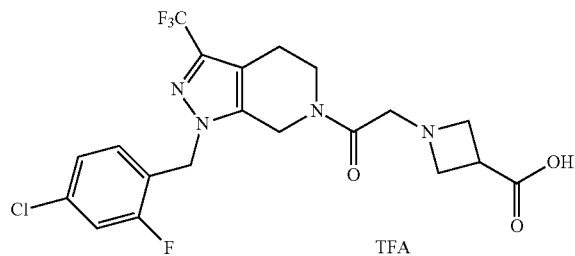 [SMILES: O=C(O)C1CN(CC(=O)N2CCc3c(C(F)(F)F)nn(Cc4ccc(Cl)cc4F)c3C2)C1]

The title compound was synthesized according to the procedure described in Example 13-9, using methyl azetidine-3-carboxylate as a starting material, to obtain a yellow solid (20 mg, yield 60%). ¹H NMR (400 MHz, Methanol-d4) δ: 7.35-7.21 (m, 3H), 5.41-5.38 (m, 2H), 4.77-4.36 (m, 8H), 3.86-3.62 (m, 3H), 2.82-2.68 (m, 2H); LCMS (ESI) m/z 475.1 [M+H]⁺

Example 13-18

1-(2-(1-(4-Fluorobenzyl)-3-(trifluoromethyl)-4,5-dihydro-1H-pyrazolo[3,4-c]pyridin-6(7H)-yl)-2-oxoethyl)azetidine-3-carboxylic acid TFA salt

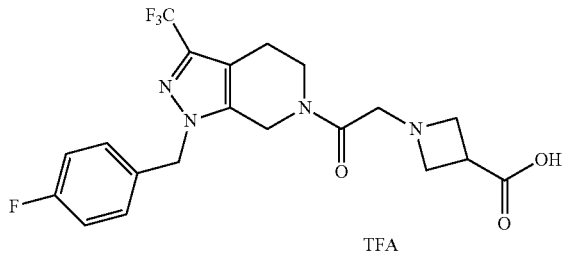 [SMILES: O=C(O)C1CN(CC(=O)N2CCc3c(C(F)(F)F)nn(Cc4ccc(F)cc4)c3C2)C1]

The title compound was synthesized according to the procedure described in Example 13-9, using Intermediate 2-2 and methyl azetidine-3-carboxylate as starting materials, to obtain a yellow oil (6 mg, yield 15% in the final step). ¹H NMR (400 MHz, Methanol-d4) δ: 7.33-7.26 (m, 2H), 7.16-7.08 (m, 2H), 5.39-5.35 (m, 2H), 4.67-4.52 (m, 3H), 4.48-4.33 (m, 3H), 3.86-3.59 (m, 4H), 2.81-2.69 (m, 2H), 2.16-2.01 (m, 1H); LCMS (ESI) m/z 441.1 [M+H]⁺

Example 13-19

1-(2-(1-(4-Fluorobenzyl)-3-(trifluoromethyl)-4,5-dihydro-1H-pyrazolo[3,4-c]pyridin-6(7H)-yl)-2-oxoethyl)azepane-4-carboxylic acid TFA salt

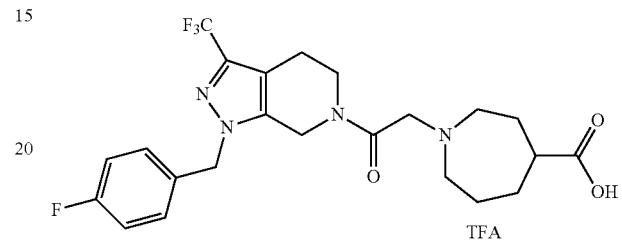

The title compound was synthesized according to the procedure described in Example 13-9, using Intermediate 2-2 and ethyl azepane-4-carboxylate hydrochloride as starting materials, to obtain a white solid (43 mg, yield 51% in the final step). ¹H NMR (400 MHz, Methanol-d4) δ: 7.20-7.17 (m, 2H), 7.06-6.99 (m, 2H), 5.29-5.25 (m, 2H), 4.59-4.50 (m, 2H), 4.03-3.92 (m, 2H), 3.76-3.57 (m, 2H), 3.18-2.85 (m, 4H), 2.72-2.47 (m, 3H), 2.06-1.58 (m, 6H); LCMS (ESI) m/z 483.2 [M+H]⁺

Example 13-20

1-(2-(1-(4-Chloro-2-fluorobenzyl)-3-(trifluoromethyl)-4,5-dihydro-1H-pyrazolo[3,4-c]pyridin-6(7H)-yl)-2-oxoethyl)azepane-4-carboxylic acid TFA salt

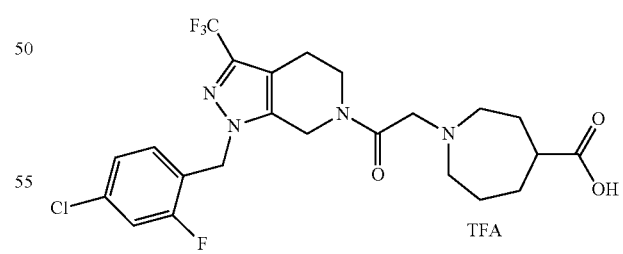

The title compound was synthesized according to the procedure described in Example 13-9, using ethyl azepane-4-carboxylate hydrochloride as a starting material, to obtain a white solid (70 mg, yield 74% in the final step). ¹H NMR (400 MHz, Methanol-d4) δ: 7.33-7.18 (m, 3H), 5.42-5.39 (m, 2H), 4.79-4.70 (m, 2H), 4.23-3.67 (m, 4H), 3.31-3.05 (m, 4H), 2.82-2.62 (m, 3H), 2.18-1.78 (m, 6H); LCMS (ESI) m/z 516.9 [M+H]⁺

Example 13-21

2-(2-(1-(4-Chloro-2-fluorobenzyl)-3-(trifluoromethyl)-4,5-dihydro-1H-pyrazolo[3,4-c]pyridin-6(7H)-yl)-2-oxoethyl)-2-azaspiro[3.3]heptane-6-carboxylic acid TFA salt

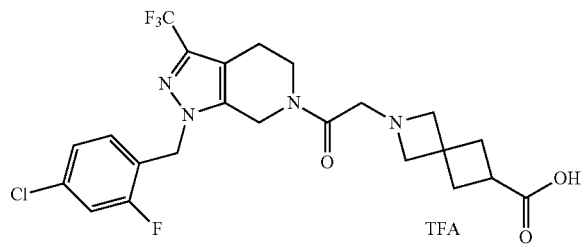 [SMILES: O=C(O)C1CC2(C1)CN(CC(=O)N1CCc3c(C(F)(F)F)nn(Cc4ccc(Cl)cc4F)c3C1)C2]

The title compound was synthesized according to the procedure described in Example 13-9, using methyl 2-azaspiro[3.3]heptane-6-carboxylate as a starting material, to obtain a white solid (14 mg, yield 60% in the final step). $^1$H NMR (400 MHz, Methanol-d4) δ: 7.31-7.19 (m, 3H), 5.39-5.37 (m, 2H), 4.72-4.57 (m, 2H), 4.42-4.34 (m, 4H), 4.14-4.11 (m, 2H), 3.84-3.59 (m, 2H), 3.04-3.00 (m, 1H), 2.81-2.46 (m, 6H); LCMS (ESI) m/z 515.1 [M+H]$^+$

Example 13-22

2-(1-(2-(1-(4-Chloro-2-fluorobenzyl)-3-(trifluoromethyl)-4,5-dihydro-1H-pyrazolo[3,4-c]pyridin-6(7H)-yl)-2-oxoethyl)azetidin-3-yl)acetic acid TFA salt

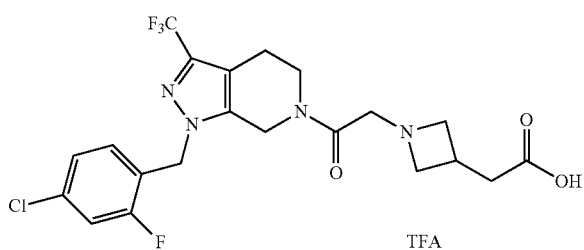 [SMILES: O=C(O)CC1CN(CC(=O)N2CCc3c(C(F)(F)F)nn(Cc4ccc(Cl)cc4F)c3C2)C1]

The title compound was synthesized according to the procedure described in Example 13-9, using methyl 2-(azetidin-3-yl)acetate as a starting material, to obtain a colorless oil (12 mg, yield 15% in the final step). $^1$H NMR (400 MHz, Methanol-d4) δ: 7.32-7.17 (m, 3H), 5.40-5.38 (m, 2H), 4.72-4.41 (m, 3H), 4.15-3.51 (m, 6H), 2.80-2.63 (m, 5H), 2.49-2.33 (m, 1H); LCMS (ESI) m/z 488.9 [M+H]$^+$

Example 13-23

2-(1-(2-(1-(4-Fluorobenzyl)-3-(trifluoromethyl)-4,5-dihydro-1H-pyrazolo[3,4-c]pyridin-6(7H)-yl)-2-oxoethyl)azetidin-3-yl)acetic acid TFA salt

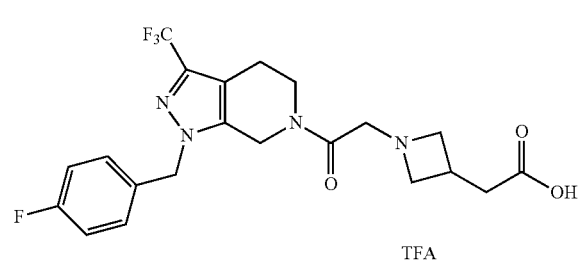 [SMILES: O=C(O)CC1CN(CC(=O)N2CCc3c(C(F)(F)F)nn(Cc4ccc(F)cc4)c3C2)C1]

The title compound was synthesized according to the procedure described in Example 13-9, using Intermediate 2-2 and methyl 2-(azetidin-3-yl)acetate as starting materials, to obtain a white solid (21 mg, yield 27% in the final step). $^1$H NMR (400 MHz, Methanol-d4) δ: 7.31-7.26 (m, 2H), 7.15-7.08 (m, 2H), 5.37-5.34 (m, 2H), 4.66-4.55 (m, 2H), 4.47-4.39 (m, 1H), 4.14-4.03 (m, 1H), 3.82-3.65 (m, 2H), 3.58-3.42 (m, 2H), 2.79-2.62 (m, 6H), 2.40-2.18 (m, 1H); LCMS (ESI) m/z 454.9 [M+H]$^+$

Example 13-24

2-(1-(2-(1-(4-Chloro-2-fluorobenzyl)-3-(trifluoromethyl)-4,5-dihydro-1H-pyrazolo[3,4-c]pyridin-6(7H)-yl)-2-oxoethyl)pyrrolidin-3-yl)acetic acid TFA salt

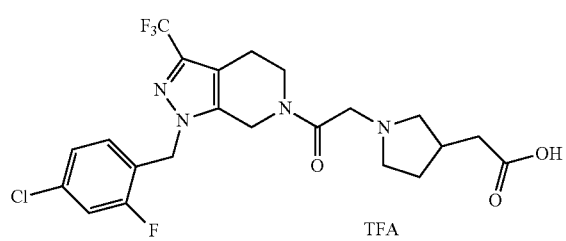 [SMILES: O=C(O)CC1CCN(CC(=O)N2CCc3c(C(F)(F)F)nn(Cc4ccc(Cl)cc4F)c3C2)C1]

The title compound was synthesized according to the procedure described in Example 13-9, using ethyl 2-(pyrrolidin-3-yl)acetate as a starting material, to obtain a white solid (59 mg, yield 57% in the final step). $^1$H NMR (400 MHz, Methanol-d4) δ: 7.33-7.19 (m, 3H), 5.40-5.38 (m, 2H), 4.73-4.70 (m, 2H), 4.07-3.68 (m, 4H), 3.37-3.33 (m, 1H), 3.24-3.04 (m, 2H), 2.89-2.63 (m, 4H), 2.40-2.17 (m, 3H), 1.72-1.65 (m, 1H); LCMS (ESI) m/z 503.1 [M+H]$^+$

Example 13-25

2-(1-(2-(1-(4-Fluorobenzyl)-3-(trifluoromethyl)-4,5-dihydro-1H-pyrazolo[3,4-c]pyridin-6(7H)-yl)-2-oxoethyl)pyrrolidin-3-yl)acetic acid TFA salt

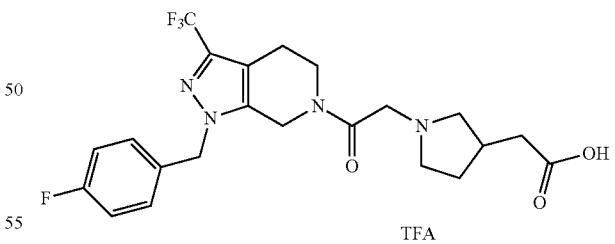

The title compound was synthesized according to the procedure described in Example 13-9, using Intermediate 2-2 and ethyl 2-(pyrrolidin-3-yl)acetate as starting materials, to obtain a white solid (47 mg, yield 63% in the final step). $^1$H NMR (400 MHz, Methanol-d4) δ: 7.31-7.27 (m, 2H), 7.16-7.09 (m, 2H), 5.37-5.35 (m, 2H), 4.65-4.55 (m, 2H), 4.28-4.10 (m, 2H), 3.84-3.62 (m, 2H), 3.50-3.39 (m, 2H), 3.30-3.24 (m, 1H), 3.30-3.16 (m, 1H), 2.82-2.67 (m, 3H), 2.45-2.22 (m, 3H), 1.81-1.71 (m, 1H); LCMS (ESI) m/z 469.0 [M+H]$^+$

Example 13-26

9-(2-(1-(4-Fluorobenzyl)-3-(trifluoromethyl)-4,5-dihydro-1H-pyrazolo[3,4-c]pyridin-6(7H)-yl)-2-oxoethyl)-3-oxa-9-azabicyclo[3.3.1]nonane-7-carboxylic acid TFA salt

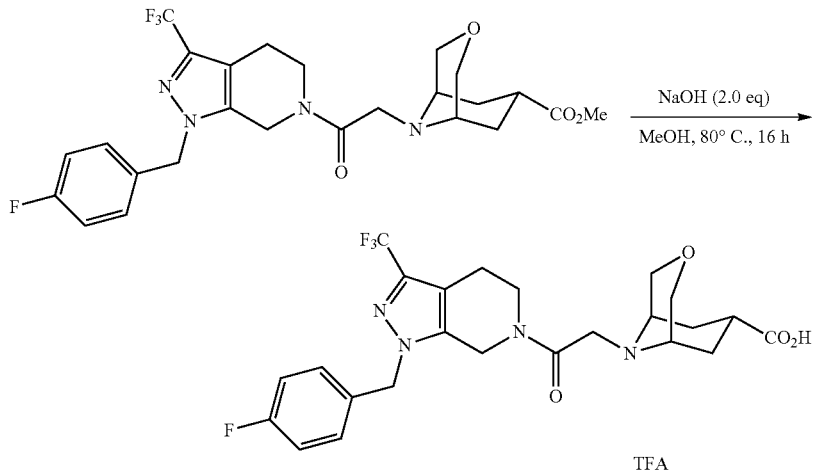

The title compound was synthesized according to the procedure described in Example 13-9, using Example 12-18 as a starting material, to obtain a white solid (29 mg, yield 52%). $^1$H NMR (400 MHz, Methanol-d4) δ: 7.33-7.26 (m, 2H), 7.16-7.08 (m, 2H), 5.39-5.36 (m, 2H), 4.68-4.55 (m, 4H), 4.23-4.09 (m, 4H), 3.89-3.63 (m, 5H), 2.85-2.72 (m, 2H), 2.41 (br, 4H); LCMS (ESI) m/z 511.2 [M+H]$^+$

Example 13-27

9-(2-(1-(4-Chloro-2-fluorobenzyl)-3-(trifluoromethyl)-4,5-dihydro-1H-pyrazolo[3,4-c]pyridin-6(7H)-yl)-2-oxoethyl)-3-oxa-9-azabicyclo[3.3.1]nonane-7-carboxylic acid TFA salt

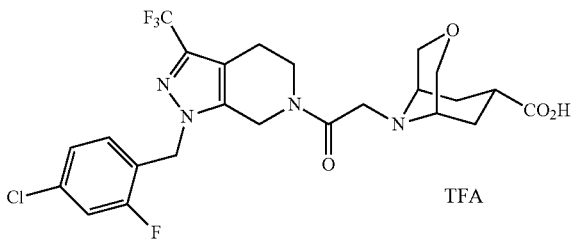 [SMILES: O=C(O)C1CC2COCC(C1)N2CC(=O)N1CCc2c(C(F)(F)F)nn(Cc3ccc(Cl)cc3F)c2C1]

The title compound was synthesized according to the procedure described in Example 13-26, using Intermediate 2-1 as a starting material, to obtain a white solid (13 mg, yield 17%). $^1$H NMR (400 MHz, Methanol-d4) δ: 7.33-7.20 (m, 3H), 5.43-5.37 (m, 2H), 4.84-4.70 (m, 2H), 4.00-3.98 (m, 1H), 3.86-3.73 (m, 7H), 3.62-3.58 (m, 1H), 2.88-2.65 (m, 4H), 2.24-2.11 (m, 2H), 1.90-1.81 (m, 2H); LCMS (ESI) m/z 545.1 [M+H]$^+$

Example 13-28 cis-3-(2-(1-(4-Fluorobenzyl)-3-(trifluoromethyl)-4,5-dihydro-1H-pyrazolo[3,4-c]pyridin-6(7H)-yl)-2-oxoethylamino)cyclobutanecarboxylic acid TFA salt

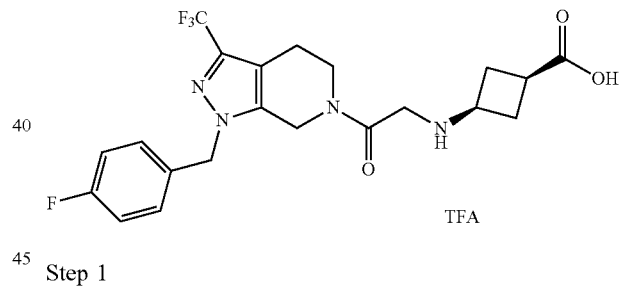

Step 1 cis-Ethyl 3-(2-(1-(4-fluorobenzyl)-3-(trifluoromethyl)-4,5-dihydro-1H-pyrazolo[3,4-c]pyridin-6(7H)-yl)-2-oxoethylamino)cyclobutanecarboxylatepropanoate TFA salt

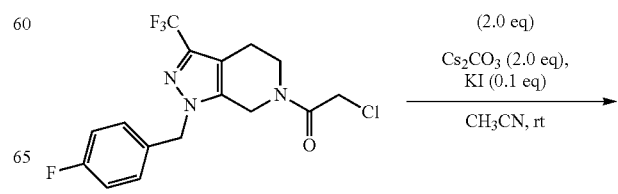

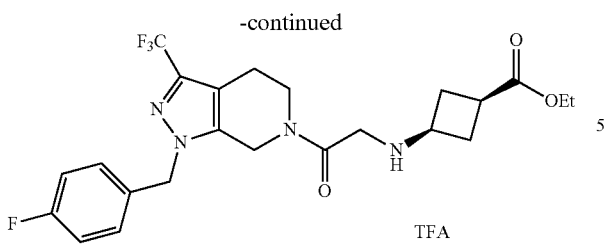

To a solution of 2-chloro-1-(1-(4-fluorobenzyl)-3-(trifluoromethyl)-4,5-dihydro-1H-pyrazolo[3,4-c]pyridin-6(7H)-yl)ethanone (Example 12-1, Step 1) (150 mg, 0.400 mmol) and cis-ethyl 3-aminocyclobutanecarboxylate (114 mg, 0.800 mmol) in CH$_3$CN (8 mL) were added Cs$_2$CO$_3$ (358 mg, 1.097 mmol) and KI (6 mg, 0.036 mmol). The mixture was stirred at rt for 16 h. The reaction mixture was filtered and the filtrate was concentrated and purified by prep HPLC (MeCN and H$_2$O with 0.05% TFA as mobile phase) to give cis-ethyl 3-(2-(1-(4-fluorobenzyl)-3-(trifluoromethyl)-4,5-dihydro-1H-pyrazolo[3,4-c]pyridin-6(7H)-yl)-2-oxoethylamino)cyclobutanecarboxylatepropanoate TFA salt as a white solid (120 mg, yield 66%); LCMS (ESI) m/z 483.2 [M+H]$^+$ Step 2 cis-3-(2-(1-(4-Fluorobenzyl)-3-(trifluoromethyl)-4,5-dihydro-1H-pyrazolo[3,4-c]pyridin-6(7H)-yl)-2-oxoethylamino)cyclobutanecarboxylic acid TFA salt

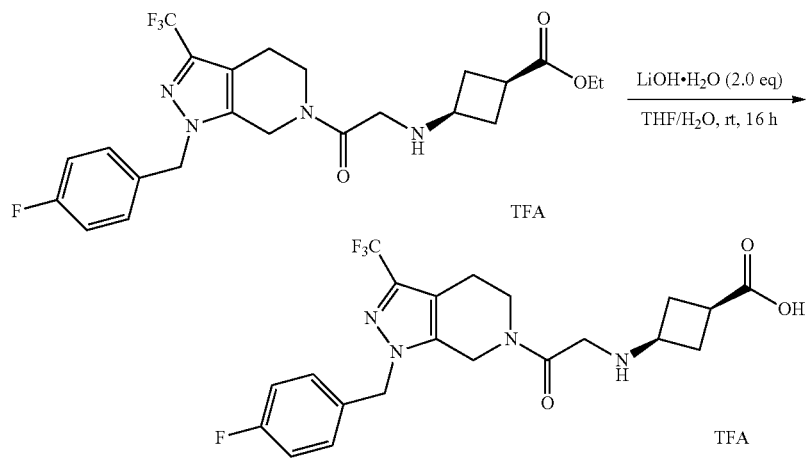

To a mixture of cis-ethyl 3-(2-(1-(4-fluorobenzyl)-3-(trifluoromethyl)-4,5-dihydro-1H-pyrazolo[3,4-c]pyridin-6(7H)-yl)-2-oxoethylamino)cyclobutanecarboxylatepropanoate (120 mg, 0.249 mmol) in THF (4 mL) and H$_2$O (1 mL) was added LiOH.H$_2$O (21 mg, 0.498 mmol). The reaction mixture was stirred at rt for 16 h. The mixture was concentrated and acidified to pH-5 with 1N HCl. The mixture was purified by prep HPLC (MeCN and H$_2$O with 0.05% TFA as mobile phase) to give cis-3-(2-(1-(4-fluorobenzyl)-3-(trifluoromethyl)-4,5-dihydro-1H-pyrazolo[3,4-c]pyridin-6(7H)-yl)-2-oxoethylamino)cyclobutanecarboxylic acid TFA salt as a white solid (62 mg, yield 55%). $^1$H NMR (400 MHz, Methanol-d4) δ: 7.34-7.19 (m, 4H), 5.39-5.37 (m, 2H), 4.62-4.61 (m, 2H), 3.70-3.60 (m, 2H), 3.41-3.33 (m, 2H), 3.10-3.04 (m, 1H), 2.66-2.55 (m, 3H), 2.32-2.25 (m, 2H), 1.84-1.77 (m, 2H); LCMS (ESI) m/z 454.9 [M+H]$^+$ Example 13-29 trans-3-(2-(1-(4-Fluorobenzyl)-3-(trifluoromethyl)-4,5-dihydro-1H-pyrazolo[3,4-c]pyridin-6(7H)-yl)-2-oxoethylamino)cyclobutanecarboxylic acid TFA salt

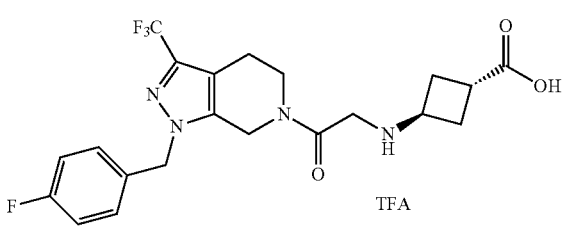 [SMILES: O=C(CN[C@H]1C[C@H](C(=O)O)C1)N1CCc2c(C(F)(F)F)nn(Cc3ccc(F)cc3)c2C1]

The title compound was synthesized according to the procedure described in Example 13-28, using trans-ethyl 3-aminocyclobutanecarboxylate as a starting material, to obtain a white solid (26 mg, yield 21% in the final step). $^1$H NMR (400 MHz, Methanol-d4) δ: 7.31-7.26 (m, 2H), 7.15-7.08 (m, 2H), 5.37-5.35 (m, 2H), 4.65-4.54 (m, 2H), 3.94-3.63 (m, 5H), 3.06-2.94 (m, 1H), 2.80-2.69 (m, 2H), 2.55-2.49 (m, 2H), 2.35-2.27 (m, 2H); LCMS (ESI) m/z 454.9 [M+H]$^+$ Example 13-30 cis-4-(2-(1-(4-Fluorobenzyl)-3-(trifluoromethyl)-4,5-dihydro-1H-pyrazolo[3,4-c]pyridin-6(7H)-yl)-2-oxoethylamino)cyclohexanecarboxylic acid TFA salt

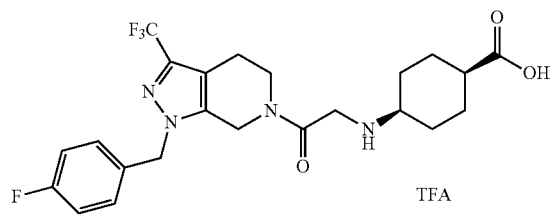 [SMILES: O=C(CN[C@H]1CC[C@@H](C(=O)O)CC1)N1CCc2c(C(F)(F)F)nn(Cc3ccc(F)cc3)c2C1]

The title compound was synthesized according to the procedure described in Example 13-28, using cis-methyl 4-aminocyclohexanecarboxylate as a starting material, to obtain a white solid (59 mg, yield 55% in the final step). $^1$H NMR (400 MHz, Methanol-d4) δ: 7.24-7.17 (m, 2H), 7.07-7.00 (m, 2H), 5.30-5.27 (m, 2H), 4.57-4.47 (m, 2H), 3.99-3.87 (m, 2H), 3.77-3.57 (m, 2H), 2.94-2.87 (m, 1H), 3.73-2.60 (m, 2H), 2.33 (br, 1H), 2.13-2.10 (m, 2H), 1.79-1.44 (m, 6H); LCMS (ESI) m/z 483.0 [M+H]$^+$

Example 13-31 trans-4-(2-(1-(4-Fluorobenzyl)-3-(trifluoromethyl)-4,5-dihydro-1H-pyrazolo[3,4-c]pyridin-6(7H)-yl)-2-oxoethylamino)cyclohexanecarboxylic acid TFA salt

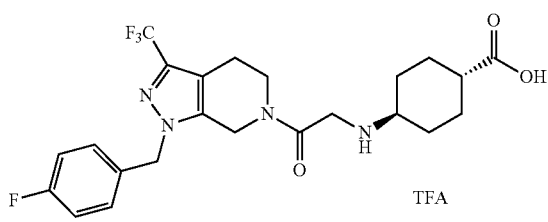 [SMILES: O=C(CN[C@H]1CC[C@H](C(=O)O)CC1)N1CCc2c(C(F)(F)F)nn(Cc3ccc(F)cc3)c2C1]

The title compound was synthesized according to the procedure described in Example 13-28, using trans-methyl 4-aminocyclohexanecarboxylate as a starting material, to obtain a white solid (59 mg, yield 55% in the final step). $^1$H NMR (400 MHz, Methanol-d4) δ: 7.31-7.25 (m, 2H), 7.13-7.08 (m, 2H), 5.38-5.35 (m, 2H), 4.66-4.54 (m, 2H), 4.07-3.94 (m, 2H), 3.85-3.65 (m, 2H), 3.98-2.69 (m, 3H), 2.15-2.04 (m, 5H), 1.52-1.35 (m, 4H); LCMS (ESI) m/z 483.0 [M+H]$^+$

Example 13-32

3-(2-(1-(4-Chloro-2-fluorobenzyl)-3-(trifluoromethyl)-4,5-dihydro-1H-pyrazolo[3,4-c]pyridin-6(7H)-yl)-2-oxoethylamino)propanoic acid TFA salt

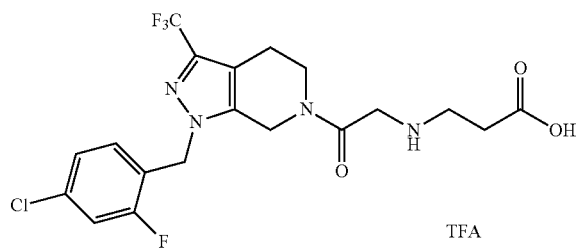 [SMILES: O=C(O)CCNCC(=O)N1CCc2c(C(F)(F)F)nn(Cc3ccc(Cl)cc3F)c2C1]

The title compound was synthesized according to the procedure described in Example 13-28, using ethyl 3-aminopropanoate as a starting material, to obtain a yellow oil (56 mg, yield 60% in the final step). $^1$H NMR (400 MHz, Methanol-d4) δ: 7.32-7.19 (m, 3H), 5.41-5.39 (m, 2H), 4.76-4.65 (m, 2H), 4.15-4.08 (m, 2H), 3.88-3.66 (m, 2H), 3.21-3.18 (m, 2H), 2.82-2.69 (m, 2H), 2.53 (t, J=6.4 Hz, 2H); LCMS (ESI) m/z 463.2 [M+H]$^+$

Example 14-1

6-(1-(4-Chloro-2-fluorobenzyl)-3-(trifluoromethyl)-4,5-dihydro-1H-pyrazolo[3,4-c]pyridin-6(7H)-yl)-6-oxohexanoic acid

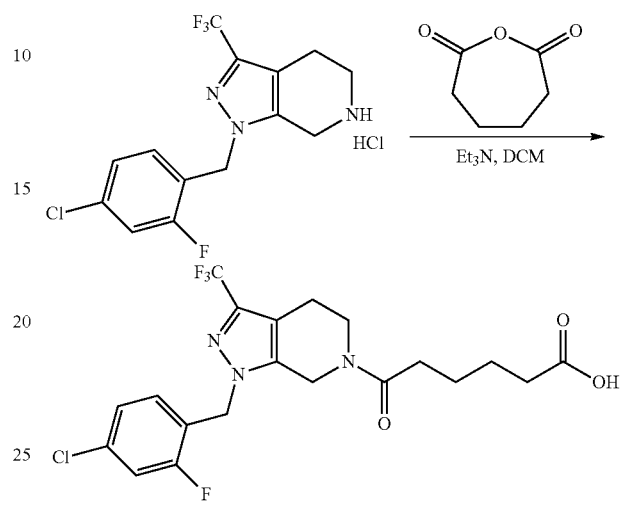

To a solution of 1-(4-chloro-2-fluorobenzyl)-3-(trifluoromethyl)-4,5,6,7-tetrahydro-1H-pyrazolo[3,4-c]pyridine hydrochloride (50 mg, 0.135 mmol) in DCM (2 mL) was added oxepane-2,7-dione (25.9 mg, 0.203 mmol) followed by TEA (27.3 mg, 0.27 mmol). Then the mixture was stirred at room temperature for 3 h. TLC (DCM/MeOH=10/1) showed the starting material was consumed completely. The reaction was diluted with water (5 mL), extracted with DCM (10 mL×2). The organic phase was dried over Na$_2$SO$_4$, filtered and concentrated to give the crude product, which was purified by prep-HPLC (MeCN and H$_2$O with 0.225% (v/v) HCOOH as mobile phase) to provide 6-(1-(4-chloro-2-fluorobenzyl)-3-(trifluoromethyl)-4,5-dihy dro-1H-pyrazolo[3,4-c]pyridin-6(7H)-yl)-6-oxohexanoic acid (17 mg, yield 27%) a yellow solid. $^1$H NMR (400 MHz, Methanol-d4) δ: 7.27-7.15 (m, 3H), 5.39-5.34 (m, 2H), 4.67 (s, 2H), 3.78-3.72 (m, 2H), 2.73 (br, 2H), 2.67 (br, 1H), 2.51-2.42 (m, 2H), 2.31 (br, 2H), 1.65-1.60 (m, 3H). LCMS (ESI) m/z 462.0 [M+H]$^+$

Example 14-2

5-(1-(4-Chloro-2-fluorobenzyl)-3-(trifluoromethyl)-4,5-dihydro-1H-pyrazolo[3,4-c]pyridin-6(7H)-yl)-5-oxopentanoic acid

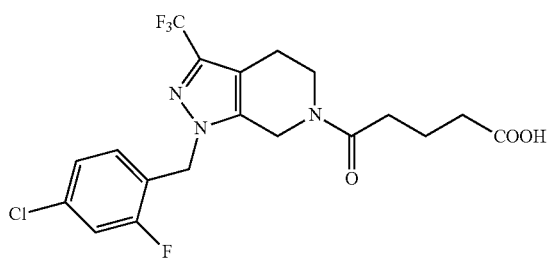 [SMILES: O=C(O)CCCC(=O)N1CCc2c(C(F)(F)F)nn(Cc3ccc(Cl)cc3F)c2C1]

The title compound was synthesized according to the procedure described in Example 14-1, using dihydro-2H-pyran-2,6(3H)-dione as a starting material, to obtain a white solid (yield 50%). $^1$H NMR (400 MHz, Methanol-d4) δ: 7.27-7.16 (m, 3H), 5.39-5.35 (m, 2H), 4.71-4.68 (m, 2H), 3.78-3.72 (m, 2H), 2.63-2.33 (m, 6H), 1.91-1.87 (m, 2H); LCMS (ESI) m/z 448.0 [M+H]$^+$ Example 14-3

4-(1-(4-Chloro-2-fluorobenzyl)-3-(trifluoromethyl)-4,5-dihydro-1H-pyrazolo[3,4-c]pyridin-6(7H)-yl)-4-oxobutanoic acid

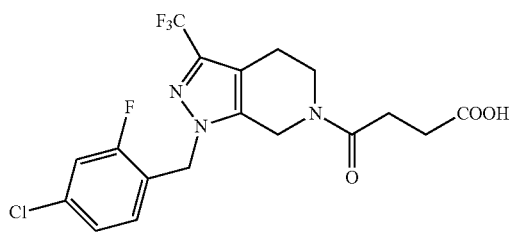 [SMILES: O=C(O)CCC(=O)N1CCc2c(C(F)(F)F)nn(Cc3ccc(Cl)cc3F)c2C1]

The title compound was synthesized according to the procedure described in Example 14-1, using dihydrofuran-2,5-dione as a starting material, to obtain a white solid (yield 26%). $^1$H NMR (400 MHz, Methanol-d4) δ: 7.27-7.15 (m, 3H), 5.38-5.34 (m, 2H), 4.72-4.67 (m, 2H), 3.77-3.74 (m, 2H), 2.75-2.54 (m, 6H); LCMS (ESI) m/z 433.9 [M+H]$^+$ Example 15-1

2-(4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)piperidin-1-yl)acetic acid

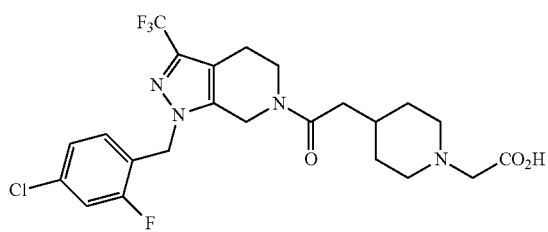 [SMILES: O=C(O)CN1CCC(CC(=O)N2CCc3c(C(F)(F)F)nn(Cc4ccc(Cl)cc4F)c3C2)CC1]

Step 1

Methyl 2-(4-(2-(1-(4-chloro-2-fluorobenzyl)-3-(trifluoromethyl)-4,5-dihydro-1H-pyrazolo[3,4-c]pyridin-6(7H)-yl)-2-oxoethyl)piperidin-1-yl)acetate

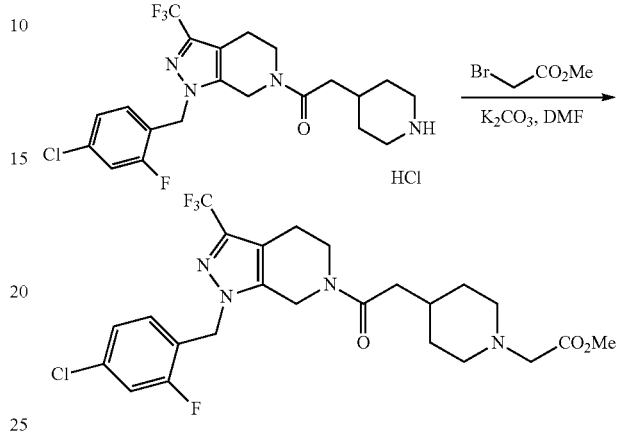

To a solution of 1-(1-(4-chloro-2-fluorobenzyl)-3-(trifluoromethyl)-4,5-dihydro-1H-pyrazolo[3,4-c]pyridin-6(7H)-yl)-2-(piperidin-4-yl)ethanone hydrochloride (Example 9-2, 200 mg, 0.44 mmol) in DMF (5 mL) was added methyl 2-bromoacetate (81 mg, 0.53 mmol) followed by K$_2$CO$_3$ (121 mg, 0.88 mmol). Then the mixture was stirred at room temperature overnight. TLC (PE/EA=1/1) showed the starting material was consumed completely. The reaction was diluted with water (20 mL) and the mixture was extracted with EA (10 mL×2). The organic phase was dried over Na$_2$SO$_4$, filtered and concentrated to give the crude which was purified by prep. HPLC (MeCN and H$_2$O with 0.225% (v/v) HCOOH as mobile phase) to provide methyl 2-(4-(2-(1-(4-chloro-2-fluorobenzyl)-3-(trifluoromethyl)-4,5-dihydro-1H-pyrazolo[3,4-c]pyridin-6(7H)-yl)-2-oxoethyl)piperidin-1-yl) acetate (145 mg, yield 63%) as colorless oil. LCMS (ESI) m/z 531.2 [M+H]$^+$ Step 2

2-(4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)piperidin-1-yl)acetic acid

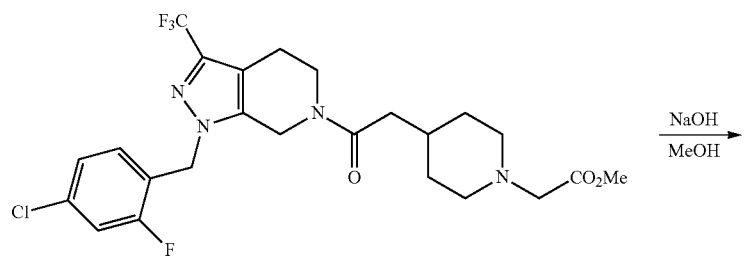

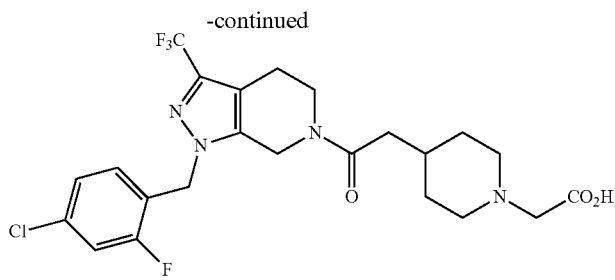

A mixture of methyl 2-(4-(2-(1-(4-chloro-2-fluorobenzyl)-3-(trifluoromethyl)-4,5-dihydro-1H-pyrazolo[3,4-c]pyridin-6(7H)-yl)-2-oxoethyl)piperidin-1-yl)acetate (140 mg, 0.26 mmol, 1.0 eq.) and NaOH (22 mg, 0.53 mmol, 2.0 eq.) in MeOH/H₂O (2 mL) was stirred at room temperature overnight. TLC (PE/EA=1/1) showed the starting material was consumed completely. The pH of the mixture was adjusted to about 2. Then the solvent was removed in vacuum to give the crude, which was purified by prep. HPLC (MeCN and H₂O with 0.225% (v/v) HCOOH as mobile phase) to provide 2-(4-(2-(1-(4-chloro-2-fluorobenzyl)-3-(trifluoromethyl)-4,5-dihydro-1H-pyrazolo[3,4-c]pyridin-6(7H)-yl)-2-oxoethyl)piperidin-1-yl)acetic acid (38 mg, yield 29%) as colorless oil. ¹H NMR (400 MHz, Methanol-d4) δ: 7.31-7.20 (m, 3H), 5.39-5.35 (m, 2H), 4.68 (s, 2H), 3.79-3.74 (m, 2H), 3.61 (s, 4H), 3.02 (brs, 2H), 2.74-2.64 (m, 2H), 2.51-2.42 (m, 2H), 2.09-1.97 (m, 3H), 1.60-1.57 (m, 2H); LCMS (ESI) m/z 517.1 [M+H]⁺

Example 15-2

3-(3-(1-(4-Fluorobenzyl)-3-(trifluoromethyl)-4,5,6,7-tetrahydro-1H-pyrazolo[3,4-c]pyridine-6-carbonyl)pyrrolidin-1-yl)propanoic acid TFA salt

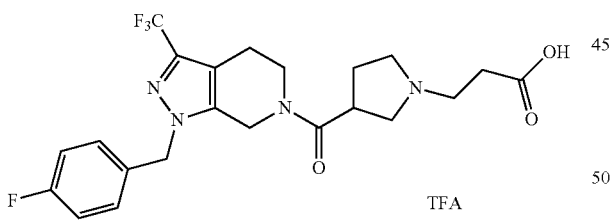

The title compound was synthesized according to the procedure described in Example 15-1, using (1-(4-fluorobenzyl)-3-(trifluoromethyl)-4,5-dihydro-1H-pyrazolo[3,4-c]pyridin-6(7H)-yl)(pyrrolidin-3-yl)methanone hydrochloride (Intermediate 2-2) and ethyl 3-bromopropanoate as starting materials, to obtain a white solid (30 mg, yield 26% over last two steps). ¹H NMR (400 MHz, Methanol-d4) δ: 7.29-7.26 (m, 2H), 7.16-7.08 (m, 2H), 5.40-5.34 (m, 2H), 4.73-4.54 (m, 2H), 4.01-3.70 (m, 5H), 3.53-3.10 (m, 4H), 2.86-2.01 (m, 6H); LCMS (ESI) m/z 469.2 [M+H]⁺

Example 15-3

3-(3-(1-(4-chloro-2-fluorobenzyl)-3-(trifluoromethyl)-4,5,6,7-tetrahydro-1H-pyrazolo[3,4-c]pyridine-6-carbonyl)pyrrolidin-1-yl)propanoic acid

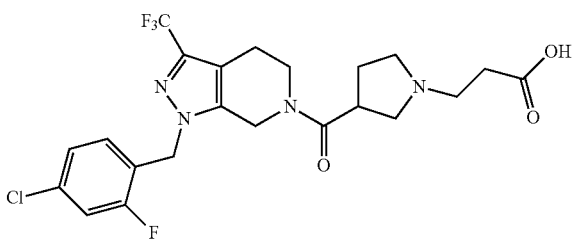 [SMILES: O=C(O)CCN1CCC(C(=O)N2CCc3c(C(F)(F)F)nn(Cc4ccc(Cl)cc4F)c3C2)C1]

The title compound was synthesized according to the procedure described in Example 15-1, using (1-(4-fluorobenzyl)-3-(trifluoromethyl)-4,5-dihydro-1H-pyrazolo[3,4-c]pyridin-6(7H)-yl)(pyrrolidin-3-yl)methanone hydrochloride and ethyl 3-bromopropanoate as a starting material, and purified by prep HPLC (MeCN and H₂O with 10 mM NH₄HCO₃ as mobile phase) to obtain a white solid (27 mg, yield 14% over last two steps). ¹H NMR (400 MHz, Methanol-d4) δ: 7.33-7.19 (m, 3H), 5.43-5.38 (m, 2H), 4.87-4.63 (m, 2H), 3.91-3.71 (m, 4H), 3.50-3.34 (m, 5H), 2.85-2.68 (m, 2H), 2.58-2.49 (m, 3H), 2.20-2.02 (m, 1H); LCMS (ESI) m/z 503.2 [M+H]⁺

Example 15-4

2-(3-(1-(4-Fluorobenzyl)-3-(trifluoromethyl)-4,5,6,7-tetrahydro-1H-pyrazolo[3,4-c]pyridine-6-carbonyl)pyrrolidin-1-yl)acetic acid TFA salt

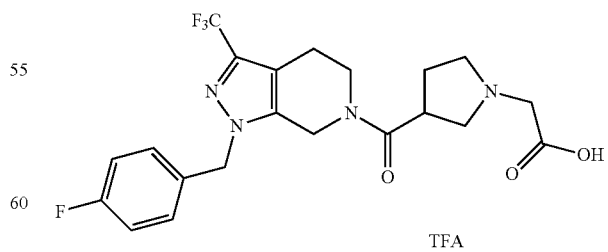

The title compound was synthesized according to the procedure described in Example 15-2, using ethyl 2-bromoacetate as a starting material, to obtain a yellow solid (20 mg, yield 19% in the final step). ¹H NMR (400 MHz, Methanol-d4) δ: 7.30-7.26 (m, 2H), 7.16-7.08 (m, 2H), 5.40-5.34 (m, 2H), 4.73-4.55 (m, 2H), 4.29-4.17 (m, 2H), 3.93-3.74 (m, 6H), 2.79-1.98 (m, 5H); LCMS (ESI) m/z 455.1 [M+H]+

Example 15-5

2-(3-(1-(4-Chloro-2-fluorobenzyl)-3-(trifluoromethyl)-4,5,6,7-tetrahydro-1H-pyrazolo[3,4-c]pyridine-6-carbonyl)pyrrolidin-1-yl)acetic acid TFA salt

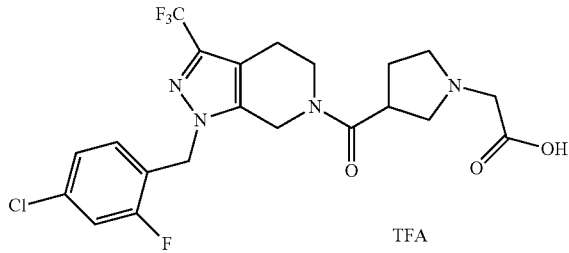 [SMILES: O=C(O)CN1CCC(C(=O)N2CCc3c(C(F)(F)F)nn(Cc4ccc(Cl)cc4F)c3C2)C1]

The title compound was synthesized according to the procedure described in Example 15-2, using Intermediate 2-1 and ethyl 2-bromoacetate as starting materials, to obtain a white solid (62 mg, yield 81% in the final step). ¹H NMR (400 MHz, Methanol-d4) δ: 7.33-7.19 (m, 3H), 5.43-5.38 (m, 2H), 4.87-4.65 (m, 2H), 3.92-3.73 (m, 6H), 3.60-3.46 (m, 3H), 2.83-2.66 (m, 2H), 2.51-2.05 (m, 2H); LCMS (ESI) m/z 489.1 [M+H]+

Example 16-1

Methyl 3-(2-(1-(4-fluorobenzyl)-3-(trifluoromethyl)-4,5-dihydro-1H-pyrazolo[3,4-c]pyridin-6(7H)-yl)-2-oxoethyl)piperidine-1-carboxylate

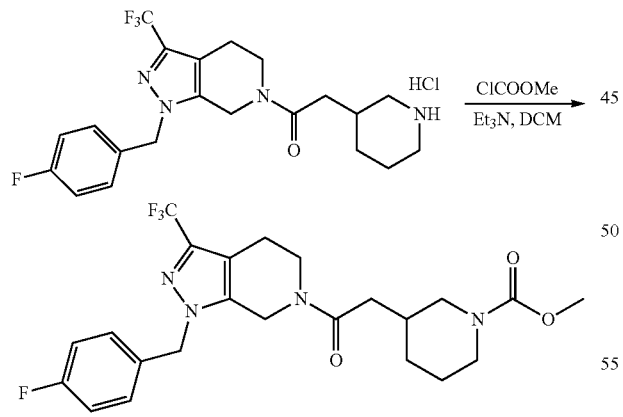

To a solution of 1-(1-(4-fluorobenzyl)-3-(trifluoromethyl)-4,5-dihydro-1H-pyrazolo[3,4-c]pyridin-6(7H)-yl)-2-(piperidin-3-yl)ethanone hydrochloride (Example 9-4, 180 mg, 0.44 mmol) in DCM (3 mL) was added methyl carbonochloridate (50 mg, 0.53 mmol) followed by TEA (134 mg, 1.32 mmol). Then the mixture was stirred at room temperature overnight. TLC (PE/EA=1/2) showed the starting material was consumed completely. The reaction was diluted with water (5 mL) and the mixture was extracted with DCM (10 mL×2). The organic phase was dried over anhydrous Na₂SO₄, filtered and concentrated to give the crude which was purified by prep. HPLC (and H₂O with 0.05% NH₃H₂O as mobile phase) to provide methyl 3-(2-(1-(4-fluorobenzyl)-3-(trifluoromethyl)-4,5-dihydro-1H-pyrazolo[3,4-c]pyridin-6(7H)-yl)-2-oxoethyl)piperidine-1-carboxylate (30 mg, yield 14%) as a white solid. ¹H NMR (400 MHz, Methanol-d4) δ: 7.26-7.24 (m, 2H), 7.13-7.06 (m, 2H), 5.36-5.32 (m, 2H), 4.60-4.53 (m, 2H), 3.95-3.83 (m, 2H), 3.79-3.61 (m, 4H), 2.85 (brs, 1H), 2.72-2.63 (m, 2H), 2.51-2.38 (m, 2H), 2.20 (brs, 1H), 1.95-1.11 (m, 6H); LCMS (ESI) m/z 505.0 [M+Na]+

Example 17-1

Methyl 3-(2-(1-(4-fluorobenzyl)-3-(trifluoromethyl)-4,5-dihydro-1H-pyrazolo[3,4-c]pyridin-6(7H)-yl)-2-oxoethyl)piperidine-1-carboxylate

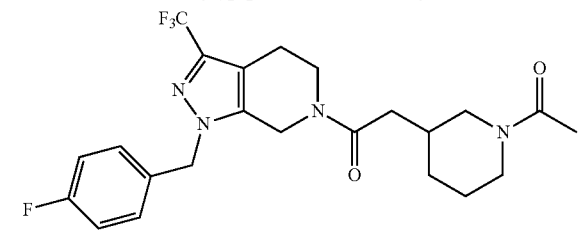 [SMILES: CC(=O)N1CCCC(CC(=O)N2CCc3c(C(F)(F)F)nn(Cc4ccc(F)cc4)c3C2)C1]

The title compound was synthesized according to the procedure described in Example 16-1 as a colorless gum (yield 26%). ¹H NMR (400 MHz, Methanol-d4) δ: 7.31-7.27 (m, 2H), 7.18-7.10 (m, 2H), 5.40-5.35 (m, 2H), 4.58-4.56 (m, 2H), 4.29-4.26 (m, 1H), 3.85-3.75 (m, 3H), 3.18-3.08 (m, 1H), 2.86-2.15 (m, 6H), 2.11-2.04 (m, 3H), 1.91-1.34 (m, 4H); LCMS m/z 489.0 [M+Na]+

Example 18-1

1-(1-(4-Fluorobenzyl)-3-(trifluoromethyl)-4,5-dihydro-1H-pyrazolo[3,4-c]pyridin-6(7H)-yl)-2-(1-(pyrimidin-2-yl)piperidin-4-yl)ethanone TFA salt

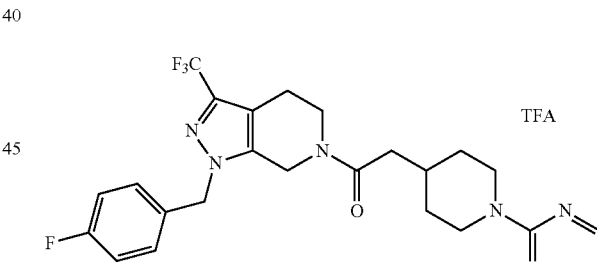

Step 1 tert-Butyl 4-(2-(1-(4-fluorobenzyl)-3-(trifluoromethyl)-4,5-dihydro-1H-pyrazolo[3,4-c]pyridin-6(7H)-yl)-2-oxoethyl)piperidine-1-carboxylate

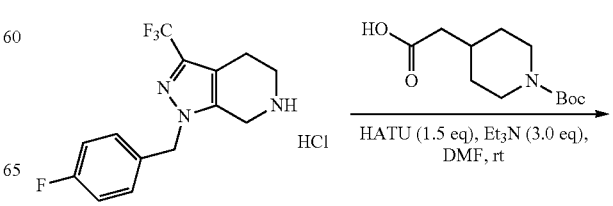

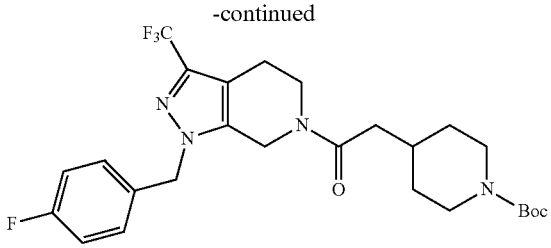

To a stirred solution of 1-(4-fluorobenzyl)-3-(trifluoromethyl)-4,5,6,7-tetrahydro-1H-pyrazolo[3,4-c]pyridine hydrochloride (200 mg, 0.6 mmol, 1.0 eq), 2-(1-(tert-butoxycarbonyl)piperidin-4-yl)acetic acid (150 mg, 0.6 mmol, 1.0 eq) and HATU (340 mg, 0.9 mmol, 1.5 eq) in DMF was added Et₃N (180 mg, 1.8 mmol, 3.0 eq). The mixture was stirred at rt for 2 h. The reaction mixture was purified by prep HPLC (MeCN and H₂O with 0.05% ammonia as mobile phase) to give tert-butyl 4-(2-(1-(4-fluorobenzyl)-3-(trifluoromethyl)-4,5-dihydro-1H-pyrazolo[3,4-c]pyridin-6(7H)-yl)-2-oxoethyl)piperidine-1-carboxylate as a colorless oil (190 mg, yield 55%). LCMS (ESI) m/z 469.2 [M-55]⁺

Step 2

1-(1-(4-Fluorobenzyl)-3-(trifluoromethyl)-4,5-dihydro-1H-pyrazolo[3,4-c]pyridin-6(7H)-yl)-2-(piperidin-4-yl)ethanone HCl salt

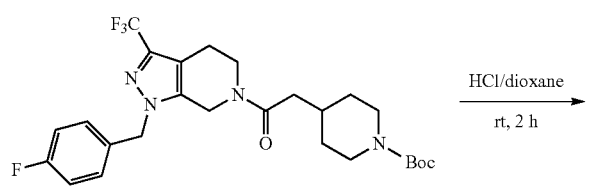

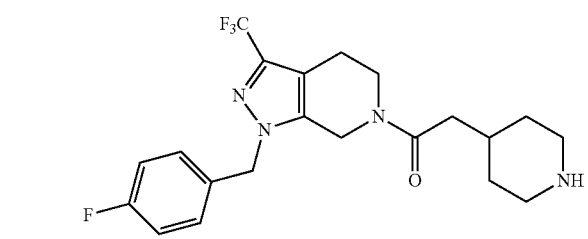

tert-Butyl 4-(2-(1-(4-fluorobenzyl)-3-(trifluoromethyl)-4,5-dihydro-1H-pyrazolo[3,4-c]pyridin-6(7H)-yl)-2-oxoethyl)piperidine-1-carboxylate (190 mg, 0.36 mmol, 1.0 eq) was added to a solution of 4M HCl in 1,4-dioxane (5 mL). The mixture was stirred at rt for 2 h and concentrated to give 1-(1-(4-fluorobenzyl)-3-(trifluoromethyl)-4,5-dihydro-1H-pyrazolo[3,4-c]pyridin-6(7H)-yl)-2-(piperidin-4-yl)ethanone hydrochloride as colorless oil (120 mg, yield 78%). LCMS (ESI) m/z 425.1 [M+1]⁺

Step 3

1-(1-(4-Fluorobenzyl)-3-(trifluoromethyl)-4,5-dihydro-1H-pyrazolo[3,4-c]pyridin-6(7H)-yl)-2-(1-(pyrimidin-2-yl)piperidin-4-yl)ethanone TFA salt

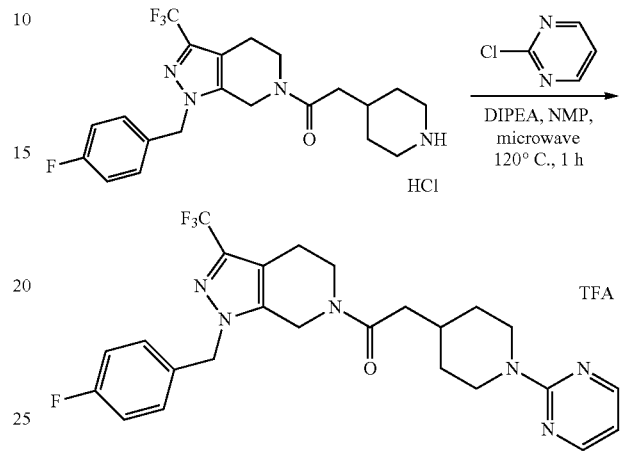

A mixture of 1-(1-(4-fluorobenzyl)-3-(trifluoromethyl)-4,5-dihydro-1H-pyrazolo[3,4-c]pyridin-6(7H)-yl)-2-(piperidin-4-yl)ethanone hydrochloride (120 mg, 0.26 mmol, 1.0 eq), 2-chloropyrimidine (30 mg, 0.26 mmol, 1.0 eq) and DIPEA (100 mg, 0.78 mmol, 3.0 eq) in NMP (2 mL) was stirred under microwave condition at 120° C. for 1 h. The mixture was cooled to rt and purified by prep HPLC (MeCN and H₂O with 0.05% TFA as mobile phase) to give 1-(1-(4-fluorobenzyl)-3-(trifluoromethyl)-4,5-dihydro-1H-pyrazolo[3,4-c]pyridin-6(7H)-yl)-2-(1-(pyrimidin-2-yl)piperidin-4-yl)ethanone TFA salt as a white solid (30 mg, yield 24%). ¹H NMR (400 MHz, Methanol-d₄) δ: 8.44 (d, J=4.8 Hz, 2H), 7.29-7.27 (m, 2H), 7.14-7.10 (m, 2H), 6.76 (t, J=5.2 Hz, 1H), 5.37-5.34 (m, 2H), 4.63-4.57 (m, 4H), 3.81-3.73 (m, 2H), 3.13-3.07 (m, 2H), 2.76-2.66 (m, 2H), 2.49-2.27 (m, 2H), 2.20-1.76 (m, 3H), 1.32-1.10 (m, 2H); LCMS (ESI) m/z 503.2 [M+H]⁺

Example 18-2

1-(1-(4-Fluorobenzyl)-3-(trifluoromethyl)-4,5-dihydro-1H-pyrazolo[3,4-c]pyridin-6(7H)-yl)-2-(1-(pyridin-2-yl)piperidin-4-yl)ethanone TFA salt

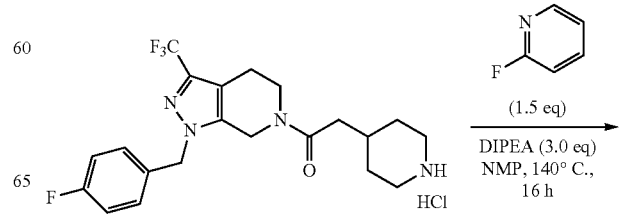

-continued

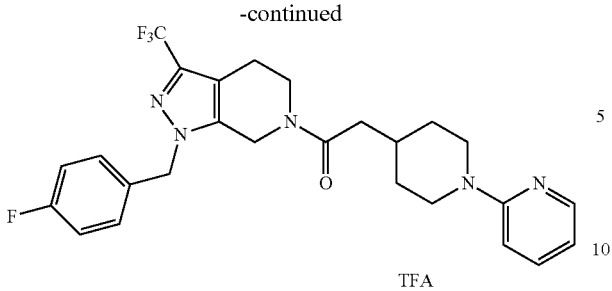

TFA

A mixture of 1-(1-(4-fluorobenzyl)-3-(trifluoromethyl)-4,5-dihydro-1H-pyrazolo[3,4-c]pyridin-6(7H)-yl)-2-(piperidin-4-yl)ethanone hydrochloride (from Example 18-1, step 2, 200 mg, 0.37 mmol), 2-fluoropyridine (108 mg, 1.114 mmol) and DIPEA (144 mg, 1.114 mmol) in NMP (5 mL) was heated at 140° C. with stirring for 16 h. The mixture was purified by prep HPLC (MeCN/H₂O with 0.05% TFA as mobile phase; from 0% to 50%) to afford 1-(1-(4-fluorobenzyl)-3-(trifluoromethyl)-4,5-dihydro-1H-pyrazolo[3,4-c]pyridin-6(7H)-yl)-2-(1-(pyridin-2-yl)piperidin-4-yl)ethanone TFA salt as a white solid after lyophilization (36 mg, yield 17%). ¹H NMR (400 MHz, Methanol-d4) δ: 8.04-8.03 (m, 1H), 7.54-7.50 (m, 1H), 7.29-7.26 (m, 2H), 7.12-7.07 (m, 2H), 6.82-6.79 (m, 1H), 6.63-6.60 (m, 1H), 5.37-5.34 (m, 2H), 4.63-4.57 (m, 2H), 4.24-4.16 (m, 2H), 3.81-3.73 (m, 2H), 2.88-2.65 (m, 4H), 2.46-2.25 (m, 2H), 2.08-1.84 (m, 1H), 1.82-1.68 (m, 2H), 1.32-1.28 (m, 2H); LCMS (ESI) m/z 501.9 [M+H]⁺

Example 18-3

1-(1-(4-Fluorobenzyl)-3-(trifluoromethyl)-4,5-dihydro-1H-pyrazolo[3,4-c]pyridin-6(7H)-yl)-2-(1-(pyrimidin-4-yl)piperidin-4-yl)ethanone TFA salt

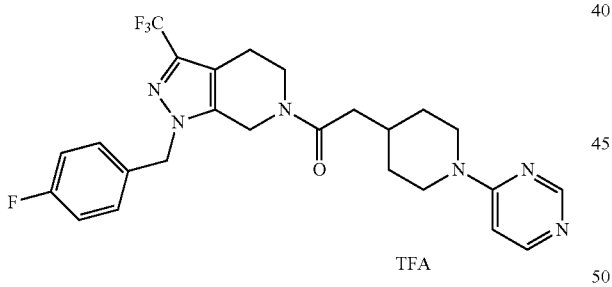

TFA

The title compound was synthesized according to the procedure described in Example 18-2, using 4-chloropyrimidine as a starting material, to obtain a yellow solid (59 mg, yield 24% in the final step). ¹H NMR (400 MHz, Methanol-d4) δ: 8.65-8.63 (m, 1H), 8.14-8.10 (m, 1H), 7.30-7.26 (m, 2H), 7.13-7.08 (m, 3H), 5.37-5.34 (m, 2H), 5.15-5.12 (m, 1H), 4.63-4.57 (m, 2H), 4.24-4.21 (m, 1H), 3.82-3.73 (m, 2H), 3.31 (m, 1H), 3.11-3.07 (m, 1H), 2.76-2.64 (m, 2H), 2.50-2.02 (m, 3H), 2.00-1.85 (m, 2H), 1.36-1.07 (m, 2H); LCMS (ESI) m/z 503.0 [M+H]⁺

Example 18-4

1-(1-(4-Fluorobenzyl)-3-(trifluoromethyl)-4,5-dihydro-1H-pyrazolo[3,4-c]pyridin-6(7H)-yl)-2-(1-(pyridin-4-yl)piperidin-4-yl)ethanone TFA salt

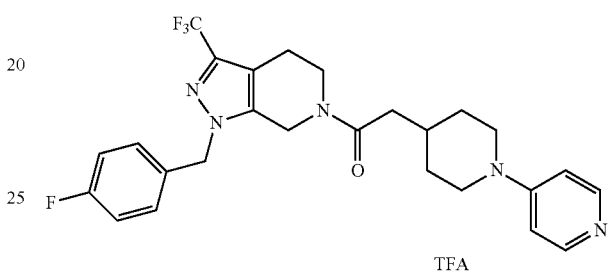

TFA

The title compound was synthesized according to the procedure described in Example 18-2, using 4-chloropyridine as a starting material, to obtain a yellow solid (35 mg, yield 37% in the final step). ¹H NMR (400 MHz, Methanol-d4) δ: 8.08-8.06 (m, 2H), 7.29-7.26 (m, 2H), 7.12-7.07 (m, 2H), 6.89-6.87 (m, 2H), 5.37-5.34 (m, 2H), 4.63-4.56 (m, 2H), 4.07-3.99 (m, 2H), 3.81-3.73 (m, 2H), 3.02-2.91 (m, 2H), 2.76-2.64 (m, 2H), 2.47-2.25 (m, 2H), 2.04-1.90 (m, 1H), 1.87-1.73 (m, 2H), 1.36-1.16 (m, 2H); LCMS (ESI) m/z 502.2 [M+H]⁺

Example 19-1 trans-4-(2-(1-(4-Fluorobenzyl)-3-(trifluoromethyl)-4,5-dihydro-1H-pyrazolo[3,4-c]pyridin-6(7H)-yl)-2-oxoethyl)-N-(methylsulfonyl)cyclohexanecarboxamide

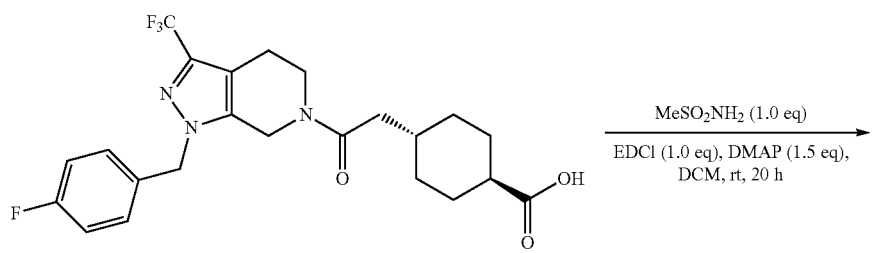

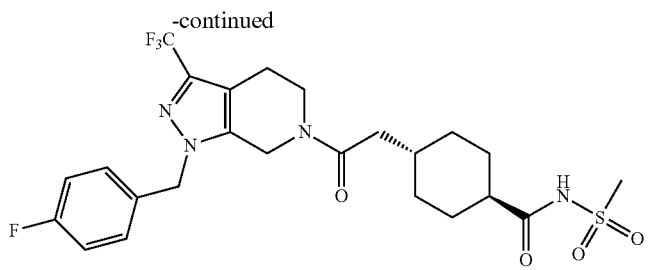

To a stirred solution of trans-4-(2-(1-(4-fluorobenzyl)-3-(trifluoromethyl)-4,5-dihydro-1H-pyrazolo[3,4-c]pyridin-6(7H)-yl)-2-oxoethyl)cyclohexanecarboxylic acid (Example 7-1, 100 mg, 0.2 mmol, 1.0 eq), methanesulfonamide (20 mg, 0.2 mmol, 1.0 eq) and EDCI (38 mg, 0.2 mmol, 1.0 eq) in DCM (10 mL) was added DMAP (36 mg, 0.3 mmol, 1.5 eq). The mixture was stirred at rt for 20 h and then concentrated. The residue was purified by reverse phase HPLC (MeCN and H₂O with 0.05% ammonia as mobile phase) to give trans-4-(2-(1-(4-fluorobenzyl)-3-(trifluoromethyl)-4,5-dihydro-1H-pyrazolo[3,4-c]pyridin-6(7H)-yl)-2-oxoethyl)-N-(methylsulfonyl)cyclohexanecarboxamide as a white solid (60 mg, yield 52%). ¹H NMR (400 MHz, Methanol-d₄) δ: 7.20-7.15 (m, 2H), 7.06-6.97 (m, 2H), 5.27-5.23 (m, 2H), 4.51-4.44 (m, 2H), 3.69-3.62 (m, 2H), 3.06 (s, 3H), 2.64-2.52 (m, 2H), 2.29-2.05 (m, 2H), 1.79-1.32 (m, 7H), 1.48-1.42 (m, 2H), 0.99-0.96 (m, 2H); LCMS (ESI) m/z 545.2 [M+H]⁺

Example 19-2 trans-4-(2-(1-(4-Fluorobenzyl)-3-(trifluoromethyl)-4,5-dihydro-1H-pyrazolo[3,4-c]pyridin-6(7H)-yl)-2-oxoethyl)-N-(methylsulfonyl)cyclohexanecarboxamide A solution of cis-4-(2-(1-(4-fluorobenzyl)-3-(trifluoromethyl)-4,5-dihydro-1H-pyrazolo[3,4-c]pyridin-6(7H)-yl)-2-oxoethyl)cyclohexanecarboxylic acid (Example 7-2, 90 mg, 0.2 mmol, 1.0 eq) in SOCl₂ (2 mL) was heated to 60° C. for 2 h, and then concentrated. The residue was dissolved in DCM (2 mL). To the acid chloride solution was added methanesulfonamide (38 mg, 0.4 mmol, 2.0 eq) and K₂CO₃ (56 mg, 0.4 mmol, 2.0 eq). The reaction was stirred at rt for 2 h and filtered. The filtrate was concentrated and the residue was purified by prep HPLC MeCN and H₂O with 0.05% ammonia as mobile phase) to give cis-4-(2-(1-(4-fluorobenzyl)-3-(trifluoromethyl)-4,5-dihydro-1H-pyrazolo[3,4-c]pyridin-6(7H)-yl)-2-oxoethyl)-N-(methylsulfonyl)cyclohexane carboxamide as a yellow solid (20 mg, yield 20%). ¹H NMR (400 MHz, Methanol-d4) δ: 7.19-7.15 (m, 2H), 7.07-6.98 (m, 2H), 5.34-5.23 (m, 2H), 4.63-4.47 (m, 3H), 3.74-3.65 (m, 2H), 3.14-3.12 (m, 3H), 2.93-2.87 (m, 1H), 2.67-2.46 (m, 2H), 2.38-2.19 (m, 2H), 2.09-1.76 (m, 3H), 1.62-1.34 (m, 5H); LCMS (ESI) m/z 545.1 [M+H]⁺

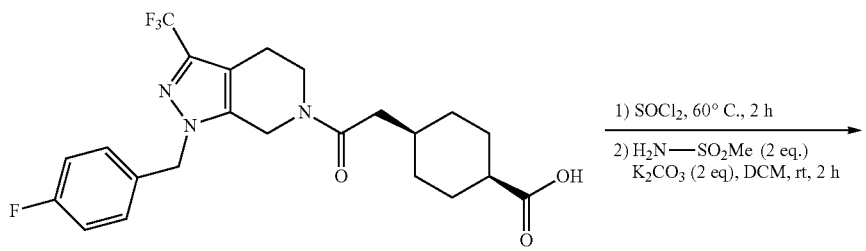

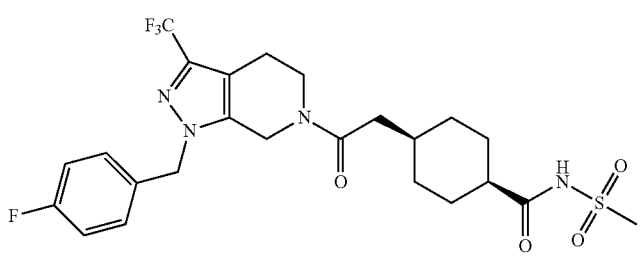

Example 20-1 cis-4-(2-(1-(4-Fluorobenzyl)-3-(trifluoromethyl)-4,5-dihydro-1H-pyrazolo[3,4-c]pyridin-6(7H)-yl)-2-oxoethyl)cyclohexanecarboxamide

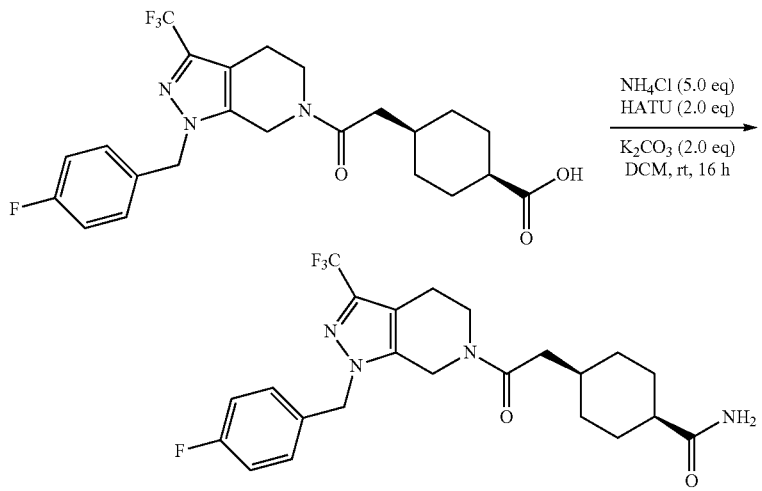

To a solution of cis-4-(2-(1-(4-fluorobenzyl)-3-(trifluoromethyl)-4,5-dihydro-1H-pyrazolo[3,4-c]pyridin-6(7H)-yl)-2-oxoethyl)cyclohexanecarboxylic acid (Example 7-2, 270 mg, 0.6 mmol, 1.0 eq) in DCM (3 mL) was added NH$_4$Cl (160 mg, 3.0 mmol, 5.0 eq), HATU (460 mg, 1.2 mmol, 2.0 eq) and K$_2$CO$_3$ (170 mg, 1.2 mmol, 2.0 eq). The mixture was stirred at rt for 16 h and filtered. The filtrate was purified by prep HPLC (MeCN and H$_2$O with 0.05% ammonia as mobile phase) to give cis-4-(2-(1-(4-fluorobenzyl)-3-(trifluoromethyl)-4,5-dihydro-1H-pyrazolo[3,4-c]pyridin-6(7H)-yl)-2-oxoethyl)cyclohexanecarboxamide as a white solid (180 mg, yield 60%). $^1$H NMR (400 MHz, Methanol-d4) δ: 7.32-7.26 (m, 2H), 7.16-7.09 (m, 2H), 5.40-5.34 (m, 2H), 4.62-4.60 (m, 2H), 3.80-3.74 (m, 2H), 2.77-2.63 (m, 2H), 2.53-2.34 (m, 3H), 2.11-1.76 (m, 3H), 1.64-1.43 (m, 6H); LCMS (ESI) m/z 467.2 [M+H]$^+$

Example 20-2 trans-4-(2-(1-(4-Fluorobenzyl)-3-(trifluoromethyl)-4,5-dihydro-1H-pyrazolo[3,4-c]pyridin-6(7H)-yl)-2-oxoethyl)cyclohexanecarboxamide

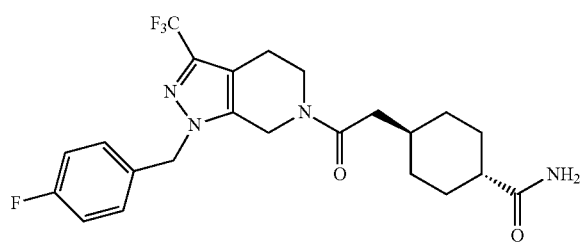 [SMILES: NC(=O)[C@H]1CC[C@H](CC(=O)N2CCc3c(C(F)(F)F)nn(Cc4ccc(F)cc4)c3C2)CC1]

The title compound was synthesized according to the procedure described in Example 20-1, using Example 7-1 as a starting material, to obtain a white solid (245 mg, yield 82%). $^1$H NMR (400 MHz, Methanol-d4) δ: 7.19-7.15 (m, 2H), 7.05-6.98 (m, 2H), 5.28-5.23 (m, 2H), 5.52-4.45 (m, 2H), 3.68-3.63 (m, 2H), 2.65-2.53 (m, 2H), 2.30-2.07 (m, 3H), 1.94-1.70 (m, 4H), 1.40-0.82 (m, 5H); LCMS (ESI) m/z 467.2 [M+H]$^+$

Example 21-1 cis-4-(2-(1-(4-Fluorobenzyl)-3-(trifluoromethyl)-4,5-dihydro-1H-pyrazolo[3,4-c]pyridin-6(7H)-yl)-2-oxoethyl)cyclohexanecarbonitrile

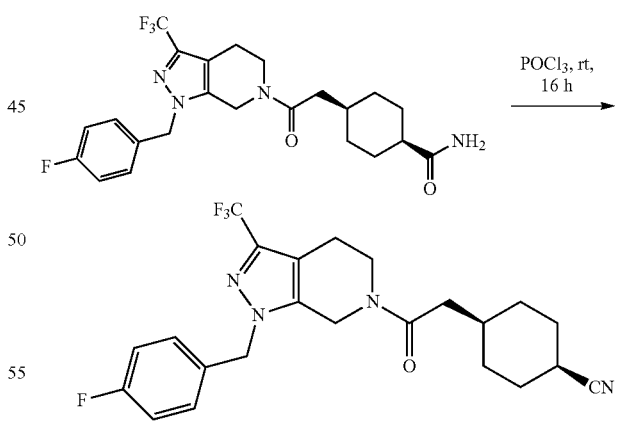

A solution of cis-4-(2-(1-(4-fluorobenzyl)-3-(trifluoromethyl)-4,5-dihydro-1H-pyrazolo[3,4-c]pyridin-6(7H)-yl)-2-oxoethyl)cyclohexanecarboxamide (Example 20-1, 150 mg, 0.3 mmol, 1.0 eq) in POCl$_3$ (2 mL) was stirred at room temperature for 16 h and concentrated. The residue was purified by prep HPLC (MeCN and H$_2$O with 0.05% TFA as mobile phase) to obtain cis-4-(2-(1-(4-fluorobenzyl)-3-(trifluoromethyl)-4,5-dihydro-1H-pyrazolo[3,4-c]pyridin-6(7H)-yl)-2-oxoethyl)cyclohexanecarbonitrile as a white solid (80 mg, yield 60%). ¹H NMR (400 MHz, Methanol-d4) δ: 7.32-7.26 (m, 2H), 7.11-7.08 (m, 2H), 5.39-5.34 (m, 2H), 4.65-4.57 (m, 2H), 3.81-3.75 (m, 2H), 3.04 (br s, 1H), 2.76-2.64 (m, 2H), 2.46-2.06 (m, 2H), 1.76-1.57 (m, 7H), 1.41-1.24 (m, 2H); LCMS (ESI) m/z 449.2 [M+H]⁺

Example 21-2 trans-4-(2-(1-(4-Fluorobenzyl)-3-(trifluoromethyl)-4,5-dihydro-1H-pyrazolo[3,4-c]pyridin-6(7H)-yl)-2-oxoethyl)cyclohexanecarbonitrile

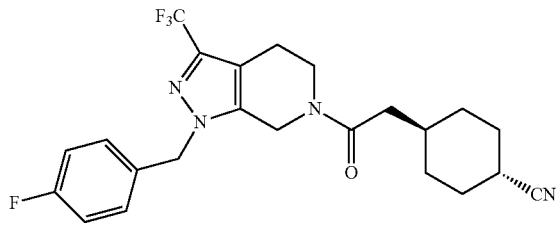 [SMILES: N#C[C@H]1CC[C@H](CC(=O)N2CCc3c(C(F)(F)F)nn(Cc4ccc(F)cc4)c3C2)CC1]

The title compound was synthesized according to the procedure described in Example 21-1, using Example 20-2 as a starting material, to obtain a white solid (55 mg, yield 57%). ¹H NMR (400 MHz, Methanol-d4) δ: 7.29-7.18 (m, 4H), 5.39-5.37 (m, 2H), 4.59 (s, 2H), 3.67-3.62 (m, 2H), 3.16 (s, 1H), 2.63-2.58 (m, 2H), 2.30-2.19 (m, 2H), 1.98-1.95 (m, 2H), 1.72-1.63 (m, 3H), 1.48-1.42 (m, 2H), 0.99-0.93 (m, 2H); LCMS (ESI) m/z 449.0 [M+H]⁺

Example 22-1

2-(3-(Azetidin-1-yl)cyclobutyl)-1-(1-(4-fluorobenzyl)-3-(trifluoromethyl)-4,5-dihydro-1H-pyrazolo[3,4-c]pyridin-6(7H)-yl)ethanone TFA salt

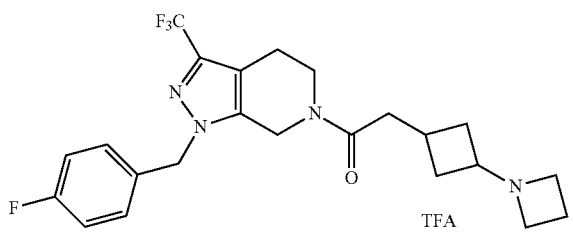 [SMILES: O=C(CC1CC(N2CCC2)C1)N1CCc2c(C(F)(F)F)nn(Cc3ccc(F)cc3)c2C1]

Step 1

Methyl 2-(3-(azetidin-1-yl)cyclobutyl)acetate

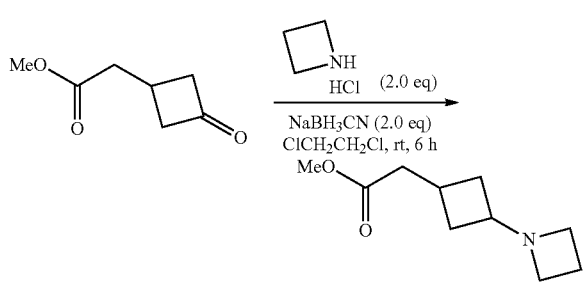

To a solution of methyl 2-(3-oxocyclobutyl)acetate (200 mg, 1.41 mmol) in dichloroethane (6 mL) was added azetidine hydrochloride (262 mg, 2.82 mmol) and NaBH₃CN (177 mg, 2.82 mmol). The mixture was stirred at rt for 16 h, then water (50 mL) was added. The mixture was extracted with DCM (50 mL×3). The combined organic layers were dried and concentrated to give a yellow oil which was used to the next step without further purification; LCMS (ESI) m/z 184.1 [M+H]⁺

Step 2

2-(3-(Azetidin-1-yl)cyclobutyl)acetic acid

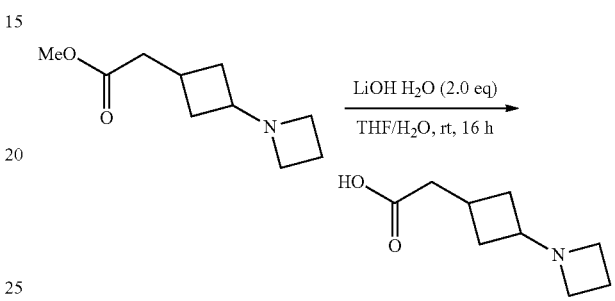

To a solution of methyl 2-(3-(azetidin-1-yl)cyclobutyl)acetate (crude from previous step) in THF (8 mL) were added lithium hydroxide monohydrate (118 mg, 2.82 mmol) and H₂O (2 mL). The reaction mixture was stirred at rt for 16 h then acidified to pH~5 with 1N HCl. The mixture was concentrated to give methyl 2-(3-(azetidin-1-yl)cyclobutyl)acetic acid which was used to the next step without further purification; LCMS (ESI) m/z 170.1 [M+H]⁺

Step 3

2-(3-(Azetidin-1-yl)cyclobutyl)-1-(1-(4-fluorobenzyl)-3-(trifluoromethyl)-4,5-dihydro-1H-pyrazolo[3,4-c]pyridin-6(7H)-yl)ethanone TFA salt

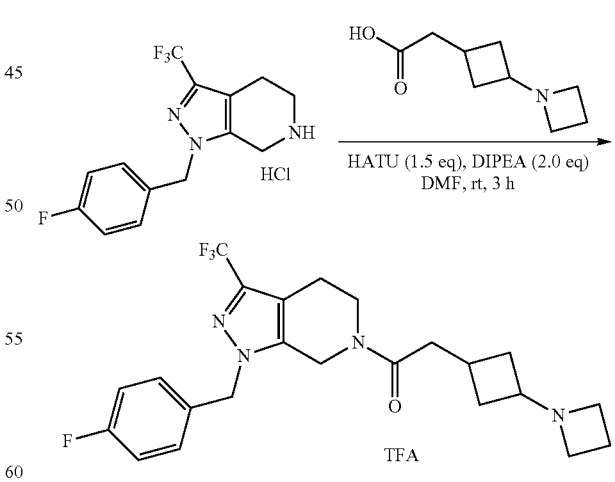

To a solution of 1-(4-fluorobenzyl)-3-(trifluoromethyl)-4,5,6,7-tetrahydro-1H-pyrazolo[3,4-c]pyridine hydrochloride (Intermediate 2-2, 150 mg, 0.45 mmol) in DMF (4 mL) was added 2-(3-(azetidin-1-yl)cyclobutyl)acetic acid (crude from previous step), HATU (185 mg, 0.67 mmol) and DIPEA (115 mg, 0.90 mmol). The mixture was stirred at rt for 3 h and directly purified by reverse phase HPLC (MeCN and H₂O with 0.05% TFA as mobile phase) to give 2-(3-(azetidin-1-yl)cyclobutyl)-1-(1-(4-fluorobenzyl)-3-(trifluorometh-yl)-4,5-dihydro-1H-pyrazolo[3,4-c]pyridin-6(7H)-yl)ethanone TFA salt as a colourless oil (65 mg, yield 32%). ¹H NMR (400 MHz, Methanol-d4) δ: 7.34-7.24 (m, 2H), 7.14-7.07 (m, 2H), 5.37-5.33 (m, 2H), 4.59-4.54 (m, 2H), 4.25-4.13 (m, 2H), 4.08-3.83 (m, 3H), 3.76-3.70 (m, 2H), 2.75-2.37 (m, 8H), 2.27-2.09 (m, 2H), 1.82-1.75 (m, 1H); LCMS (ESI) m/z 451.0 [M+H]⁺

Example 22-2

1-(1-(4-Fluorobenzyl)-3-(trifluoromethyl)-4,5-dihydro-1H-pyrazolo[3,4-c]pyridin-6(7H)-yl)-2-(octahydroindolizin-7-yl)ethanone TFA salt

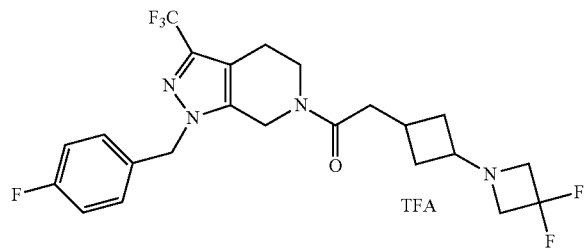 [SMILES: O=C(CC1CC(N2CC(F)(F)C2)C1)N1CCc2c(C(F)(F)F)nn(Cc3ccc(F)cc3)c2C1]

The title compound was synthesized according to the procedure described in Example 22-1, using 3,3-difluoroazetidine hydrochloride as a starting material, to obtain a colorless oil (40 mg, yield 18% in the final step). ¹H NMR (400 MHz, Methanol-d4) δ: 7.30-7.24 (m, 2H), 7.15-7.07 (m, 2H), 5.37-5.33 (m, 2H), 4.75-4.69 (m, 4H), 4.59-4.54 (m, 2H), 4.17-3.96 (m, 1H), 3.77-3.64 (m, 2H), 2.81-2.71 (m, 4H), 2.65-2.47 (m, 2H), 2.44-2.32 (m, 1H), 2.24-1.87 (m, 2H); LCMS (ESI) m/z 486.9 [M+H]⁺

Example 22-3

1-(1-(4-Fluorobenzyl)-3-(trifluoromethyl)-4,5-dihydro-1H-pyrazolo[3,4-c]pyridin-6(7H)-yl)-2-(3-(pyrrolidin-1-yl)cyclobutyl)ethanone TFA salt

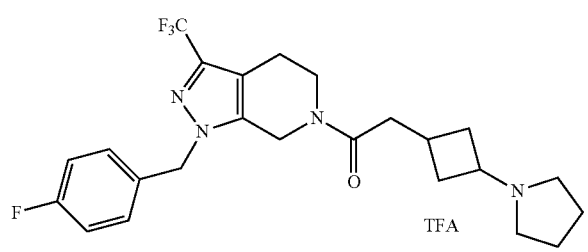 [SMILES: O=C(CC1CC(N2CCCC2)C1)N1CCc2c(C(F)(F)F)nn(Cc3ccc(F)cc3)c2C1]

The title compound was synthesized according to the procedure described in Example 22-1, using pyrrolidine in Step 1 as a starting material, to obtain a white solid (34 mg, yield 16% in the final step). ¹H NMR (400 MHz, Methanol-d4) δ: 7.33-7.25 (m, 2H), 7.15-7.08 (m, 2H), 5.37-5.33 (m, 2H), 4.59-4.54 (m, 2H), 3.90-3.63 (m, 3H), 3.53-3.49 (m, 2H), 3.04-3.93 (m, 2H), 2.77-2.75 (m, 2H), 2.71-2.34 (m, 5H), 2.23-1.84 (m, 6H); LCMS (ESI) m/z 465.0 [M+H]⁺

Example 22-4

1-(1-(4-Fluorobenzyl)-3-(trifluoromethyl)-4,5-dihydro-1H-pyrazolo[3,4-c]pyridin-6(7H)-yl)-2-(3-(piperidin-1-yl)cyclobutyl)ethanone TFA salt

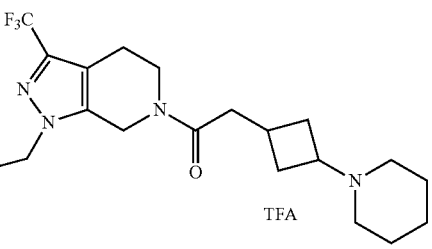

The title compound was synthesized according to the procedure described in Example 22-1, using piperidine in Step 1 as a starting material, to obtain a yellow oil (69 mg, yield 32% in the final step). ¹H NMR (400 MHz, Methanol-d4) δ: 7.31-7.25 (m, 2H), 7.15-7.08 (m, 2H), 5.39-5.33 (m, 2H), 4.59-4.55 (m, 2H), 3.78-3.69 (m, 2H), 3.55-3.48 (m, 1H), 3.44-3.41 (m, 2H), 2.79-2.43 (m, 9H), 1.96-1.44 (m, 8H); LCMS (ESI) m/z 479.0 [M+H]⁺

Example 22-5

1-(1-(4-Fluorobenzyl)-3-(trifluoromethyl)-4,5-dihydro-1H-pyrazolo[3,4-c]pyridin-6(7H)-yl)-2-(3-morpholinocyclobutyl)ethanone TFA salt The title compound was synthesized according to the procedure described in Example 22-1, using morpholine in Step 1 as a starting material, to obtain a yellow oil (74 mg, yield 31% in the final step). ¹H NMR (400 MHz, Methanol-d4) δ: 7.28-7.24 (m, 2H), 7.16-7.07 (m, 2H), 5.38-5.33 (m, 2H), 4.59-4.55 (m, 2H), 4.07-4.04 (m, 2H), 3.85-3.54 (m, 5H), 3.41-3.37 (m, 2H), 3.00-2.92 (m, 2H), 2.78-2.38 (m, 6H), 2.16-1.96 (m, 2H); LCMS (ESI) m/z 481.2 [M+H]⁺

Example 22-6

2-(4-(Azetidin-1-yl)cyclohexyl)-1-(1-(4-fluorobenzyl)-3-(trifluoromethyl)-4,5-dihydro-1H-pyrazolo[3,4-c]pyridin-6(7H)-yl)ethanone TFA salt

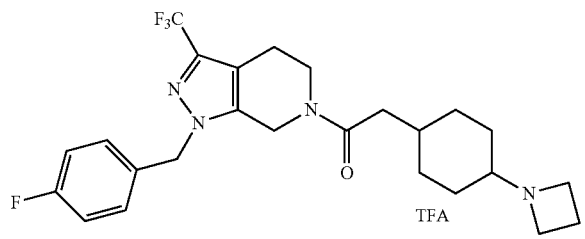 [SMILES: O=C(CC1CCC(N2CCC2)CC1)N1CCc2c(C(F)(F)F)nn(Cc3ccc(F)cc3)c2C1]

Step 1

4-(2-(1-(4-Fluorobenzyl)-3-(trifluoromethyl)-4,5-dihydro-1H-pyrazolo[3,4-c]pyridin-6(7H)-yl)-2-oxoethyl)cyclohexanone

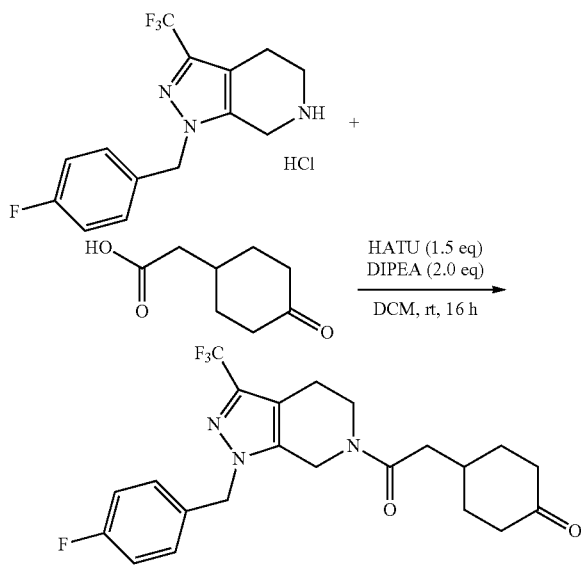

The title compound was synthesized according to the procedure described in Example 1-1, using 2-(4-oxocyclohexyl)acetic acid as a starting material, to obtain a yellow oil (960 mg, yield 70%). LCMS (ESI) m/z 438.1 [M+H]+

Step 2

2-(4-(Azetidin-1-yl)cyclohexyl)-1-(1-(4-fluorobenzyl)-3-(trifluoromethyl)-4,5-dihydro-1H-pyrazolo[3,4-c]pyridin-6(7H)-yl)ethanone TFA salt

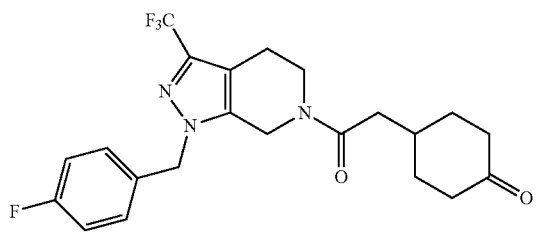

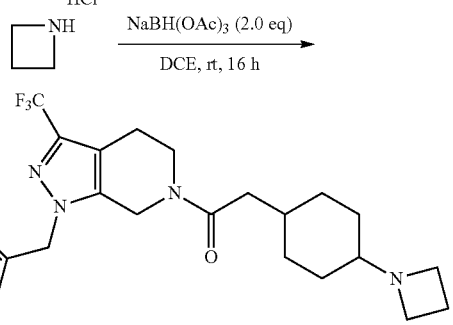

To a solution of 4-(2-(1-(4-fluorobenzyl)-3-(trifluoromethyl)-4,5-dihydro-1H-pyrazolo[3,4-c]pyridin-6(7H)-yl)-2-oxoethyl)cyclohexanone (170 mg, 0.38 mmol, 1.0 eq) in DCE (3 mL) was added azetidine hydrochloride (56 mg, 0.58 mmol, 1.5 eq). After stirring for 30 min at rt, NaBH(OAc)$_3$ (161 mg, 0.76 mmol) was added to the mixture and the mixture was stirred at rt for 16 h. The mixture was quenched with water (1 mL) and concentrated. The residue was purified by prep HPLC (MeCN/H$_2$O with 0.05% TFA as mobile phase) to give 2-(4-(azetidin-1-yl)cyclohexyl)-1-(1-(4-fluorobenzyl)-3-(trifluoromethyl)-4,5-dihydro-1H-pyrazolo[3,4-c]pyridin-6(7H)-yl)ethanone TFA salt as a yellow oil (100 mg, yield 53%). $^1$H NMR (400 MHz, Methanol-d4) δ: 7.29-7.24 (m, 2H), 7.14-7.07 (m, 2H), 5.39-5.32 (m, 2H), 4.61-4.55 (m, 2H), 4.16-4.10 (m, 4H), 3.77-3.71 (m, 2H), 3.32-3.05 (m, 1H), 2.74-2.21 (m, 6H), 2.04-1.63 (m, 7H), 1.19-1.12 (m, 2H); LCMS (ESI) m/z 479.0 [M+H]+

Example 22-7 and Example 22-8

2-(cis-4-(3,3-Difluoroazetidin-1-yl)cyclohexyl)-1-(1-(4-fluorobenzyl)-3-(trifluoromethyl)-4,5-dihydro-1H-pyrazolo[3,4-c]pyridin-6(7H)-yl)ethanone TFA salt and 2-(trans-4-(3,3-difluoroazetidin-1-yl)cyclohexyl)-1-(1-(4-fluorobenzyl)-3-(trifluoromethyl)-4,5-dihydro-1H-pyrazolo[3,4-c]pyridin-6(7H)-yl)ethanone TFA salt

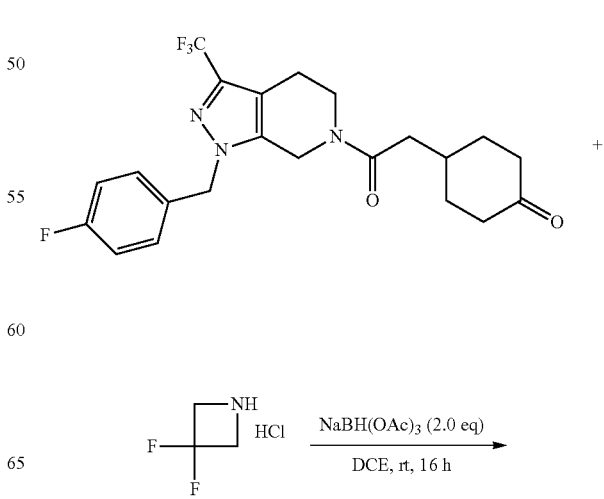

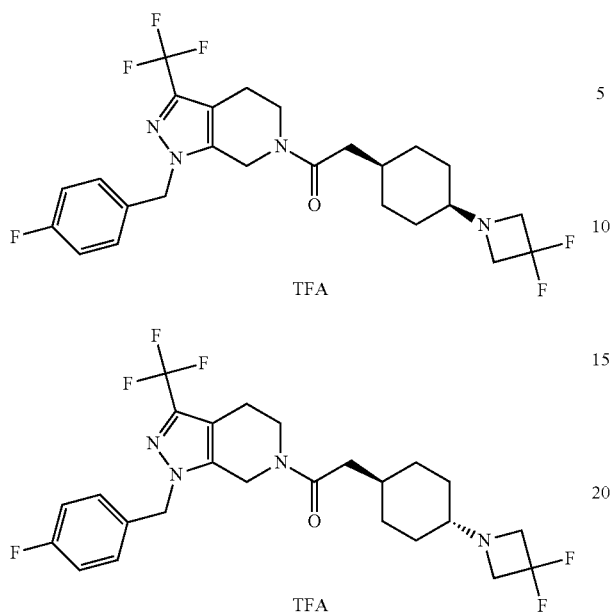

TFA

TFA

The title compound was synthesized according to the procedure described in Example 22-6, using 3,3-difluoro-azetidine hydrochloride as a starting material, to obtain:

cis-isomer (Example 22-7, yellow oil, 30 mg): ¹H NMR (400 MHz, Methanol-d4) δ: 7.29-7.25 (m, 2H), 7.15-7.08 (m, 2H), 5.39-5.33 (m, 2H), 4.82-4.75 (m, 4H), 4.61-4.57 (m, 2H), 3.78-3.73 (m, 2H), 3.40-3.39 (m, 1H), 2.76-2.65 (m, 2H), 2.51-2.33 (m, 2H), 2.16 (br s, 1H), 1.86-1.51 (m, 8H); LCMS (ESI) m/z 515.0 [M+H]⁺ trans-isomer (Example 22-8, yellow soilid, 50 mg): ¹H NMR (400 MHz, Methanol-d4) δ: 7.21-7.14 (m, 2H), 7.06-6.96 (m, 2H), 5.26-5.22 (m, 2H), 4.50-4.43 (m, 2H), 3.68-3.60 (m, 2H), 3.52-3.45 (m, 4H), 2.63-2.51 (m, 2H), 2.28-1.93 (m, 3H), 1.71-1.52 (m, 5H), 0.98-0.73 (m, 4H); LCMS (ESI) m/z 515.0 [M+H]⁺

Example 22-9

1-(1-(4-Fluorobenzyl)-3-(trifluoromethyl)-4,5-di-hydro-1H-pyrazolo[3,4-c]pyridin-6(7H)-yl)-2-(4-(pyrrolidin-1-yl)cyclohexyl)ethanone TFA salt

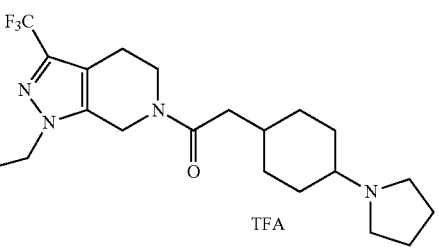

TFA

The title compound was synthesized according to the procedure described in Example 22-6, using pyrrolidine as a starting material, to obtain a yellow oil (100 mg, yield 52% in the final step). ¹H NMR (400 MHz, Methanol-d4) δ: 7.29-7.25 (m, 2H), 7.14-7.07 (m, 2H), 5.38-5.33 (m, 2H), 4.62-4.65 (m, 2H), 3.78-3.60 (m, 4H), 3.14-3.07 (m, 3H), 2.75-2.64 (m, 2H), 2.55-1.47 (m, 14H), 1.17-1.13 (m, 1H); LCMS (ESI) m/z 493.0 [M+H]⁺

Example 22-10

1-(1-(4-Fluorobenzyl)-3-(trifluoromethyl)-4,5-di-hydro-1H-pyrazolo[3,4-c]pyridin-6(7H)-yl)-2-(4-morpholinocyclohexyl)ethanone TFA salt

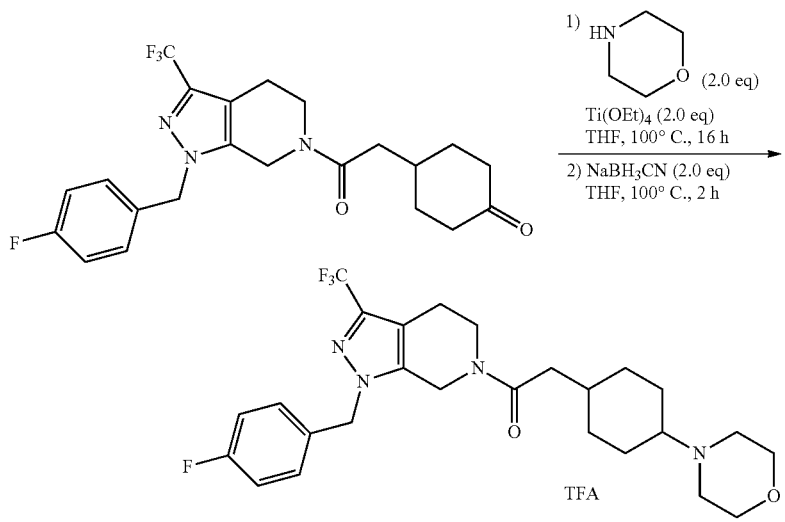

A solution of 4-(2-(1-(4-fluorobenzyl)-3-(trifluoromethyl)-4,5-dihydro-1H-pyrazolo[3,4-c]pyridin-6(7H)-yl)-2-oxoethyl)cyclohexanone (Step 22-6, Step 1) (87 mg, 0.2 mmol, 1.0 eq), morpholine (35 mg, 0.4 mmol, 2.0 eq) and Ti(OEt)₄ (120 mg, 0.4 mmol, 2.0 eq) in THF (1 mL) was heated at 100° C. for 16 h in sealed tube. The mixture was cooled to rt and NaBH₃CN (28 mg, 0.4 mmol, 2.0 eq) was added. The tube was sealed and the mixture was heated at 100° C. for 2 h. The mixture was diluted with EtOAc (100 mL), washed with water (100 mL×2), dried and concentrated. The residue was purified by prep HPLC (MeCN and H₂O with 0.05% TFA as mobile phase) to give 1-(1-(4-fluorobenzyl)-3-(trifluoromethyl)-4,5-dihydro-1H-pyrazolo[3,4-c]pyridin-6(7H)-yl)-2-(4-morpholinocyclohexyl)ethanone TFA salt as a yellow oil (50 mg, yield 40%). $^1$H NMR (400 MHz, Methonol-d4) δ: 7.33-7.27 (m, 2H), 7.19-7.08 (m, 2H), 5.41-5.34 (m, 2H), 4.62-4.56 (m, 2H), 4.10-4.06 (m, 2H), 3.85-3.73 (m, 4H), 3.54-3.44 (m, 2H), 3.21-3.12 (m, 3H), 2.76-2.57 (m, 3H), 2.45-2.42 (m, 1H), 2.27-2.13 (m, 2H), 2.00-1.68 (m, 5H), 1.59-1.44 (m, 1H), 1.20-1.01 (m, 1H); LCMS (ESI) m/z 509.2 [M+H]$^+$ Example 23

Activity Measurements

ATX (Autotaxin) is a 125 KDa glycoprotein with lysophospholipase D (LPLD) activity that generates the bioactive lipid lysophosphatidic acid (LPA) from lysophosphatidylcholine (LPC). The ATX biochemical assay utilizes a FRET (fluorescence resonance energy transfer) technology platform. The fluorescence signal of FRET substrate FS-3 is quenched due to intra-molecular FRET of a fluorophore to a non-fluorescing quencher (Ferguson, C. G., et al., Org Lett. 2006 May 11; 8(10): 2023-2026, which is incorporated by reference in its entirety). ATX catalyzes the hydrolysis of the substrate which separates the dabsyl quencher from the fluorescein reporter, which becomes fluorescent. The reaction is monitored by a SpectraMax M5 (Molecular Devices, Sunnyvale, Calif.) with at excitation wavelength 485 nm and emission wavelength 535 nm.

Reagents

Fatty acid free-BSA (Sigma A8806): 10 mg/mL in H₂O, stored at 4° C.

2×ATX assay buffer: 100 mM Tris, 280 mM NaCl, 10 mM KCl, 2 mM CaCl₂, 2 mM MgCl₂, pH 7.4.

Human ATX protein: expressed and purified in house. Stored at −80° C.

Substrate FS-3 (Echelon, L-2000): 100 μg in 77.74 μL H₂O (1 mM stock), stored at −20° C.

384-well flat bottom plates—Corning #3575.

Assay

Compound dilution—All compounds were provided at 10 mM in 100% DMSO. In the first well, 2 μL of 10 mM compound was added to 78 μL of DMSO (1:40 dilution). In subsequent wells 3-fold dilution (total 10 dilutions) were performed.

1×ATX assay buffer was made up with a final concentration of 1 mg/mL fatty acid free-BSA using 2×ATX assay buffer, 10 mg/ml fatty acid free-BSA and ddH₂O.

ATX protein was diluted with 1×ATX assay buffer to a concentration of 1.32 μg/mL (1.32×). 38 μL was added per well to the assay plate. The final concentration of ATX in the reaction as 1.0 μg/mL.

2 μL per well of compounds was transferred to provide the desired concentration. The plate was centrifuged, then incubated at room temperature for 30 minutes on the shaker.

FS-3 was diluted with 1×ATX assay buffer to a concentration of FS-3 of 10 μM (5×). Then, 10 μL was added per well to the assay plate. The final concentration of FS-3 in the reaction was 2 μM. The plate was centrifuged. The plate was kept shaking at room temperature for 2 hours. Because FS-3 substrate is light sensitive, plates were kept covered and protected from light.

Fluorescence was measured using SpectraMax M5 (excitation at 485 nm/emission at 538 nm, top read).

The compounds of examples 1-1, 1-2, 1-3, 1-4, 1-5, 1-8, 1-9, 1-10, 1-11, 1-12, 1-13, 1-14, 1-15, 1-16, 1-17, 1-18, 1-19, 1-21, 1-25, 1-26, 1-27, 2-1, 2-2, 2-3, 2-4, 3-1, 4-1, 5-1, 5-2, 5-3, 5-4, 5-5, 5-6, 5-7, 5-8, 5-9, 5-10, 5-11, 5-12, 5-13, 5-14, 5-15, 5-17, 5-18, 5-19, 5-20, 6-1, 6-2, 6-3, 6-4, 6-5, 6-6, 6-7, 6-8, 6-9, 6-10, 6-11, 6-12, 6-13, 6-14, 6-15, 6-16, 6-17, 7-1, 7-2, 7-3, 7-4, 7-5, 7-6, 7-7, 7-8, 7-9, 7-10, 7-11, 7-12, 7-13, 7-14, 7-15, 7-16, 7-17, 7-18, 7-21, 7-22, 8-1, 8-2, 8-3, 8-4, 8-5, 8-6, 8-7, 9-1, 9-3, 9-4, 9-5, 9-6, 9-7, 9-8, 10-1, 10-2, 10-3, 10-4, 11-1, 11-2, 11-3, 11-4, 12-1, 12-2, 12-3, 12-4, 12-5, 12-6, 12-7, 12-8, 13-1, 13-10, 13-11, 13-12, 13-13, 13-14, 13-15, 13-16, 13-2, 13-3, 13-4, 13-5, 13-6, 13-7, 13-8, 13-9, 14-1, 14-2, 14-3, 15-1, 16-1, 17-1, 18-1, 1-29, 1-30, 1-31, 1-32, 1-33, 1-34, 1-37, 1-38, 1-39, 1-43, 1-44, 1-45, 1-46, 1-47, 1-48, 1-50, 5-22, 5-24, 5-25, 5-26, 5-27, 5-28, 5-30, 5-31, 5-32, 5-33, 5-34, 5-35, 5-37, 5-38, 5-39, 5-40, 5-41, 5-42, 5-43, 5-44, 5-45, 5-46, 5-48, 5-49, 5-50, 5-51, 5-52, 5-53, 5-54, 5-55, 5-56, 6-18, 7-23, 7-24, 7-25, 7-26, 8-8, 8-9, 8-10, 9-11, 9-12, 9-13, 9-14, 9-15, 9-16, 9-17, 9-18, 9-19, 9-20, 9-21, 9-23, 10-6, 10-7, 10-8, 10-10, 10-11, 10-12, 12-10, 12-11, 12-12, 12-13, 12-14, 12-15, 12-16, 12-17, 12-18, 12-19, 13-17, 13-18, 13-19, 13-20, 13-21, 13-22, 13-23, 13-24, 13-25, 13-26, 13-27, 13-28, 13-29, 13-30, 13-31, 13-32, 15-4, 15-5, 18-2, 18-3, 18-4, 19-1, 19-2, 20-1, 20-2, 21-1, 21-2, 22-1, 22-2, 22-3, 22-4, 22-5, 22-6, 22-7, 22-8, 22-9, and 22-10, had an IC$_{50}$ of no greater than 100 nM.

The compounds of examples 1-28, 3-2, 3-4, 5-16, 15-2, 1-35, 5-23, 9-9, 9-10, and 10-5 had an IC$_{50}$ of greater than 100 nM but no greater than 250 nM.

The compounds of examples 1-24, 1-36, 1-41, 5-47, 9-22, and 10-9 had an IC50 of greater than 250 nM but no greater than 500 nM.

The compounds of examples 3-3, 5-21, 7-19, 7-20 1-40, 1-42, and 5-29 had an IC$_{50}$ of greater than 500 nM and but no greater than 10 μM.

The compounds of examples 1-6, 1-7, 1-20, 1-22, 12-9, and 15-3 had an IC50 of greater than 10 μM.

LPA Plasma Assay and IC$_{50}$ Assay by LC-MS/MS

20:4 LPA (Lysophosphatidic acid) and 18:1 LPA were purchased from Avanti Polar Lipids, INC at a concentration of 10 mg/mL in chloroform, respectively. Stock solutions for 20:4 LPA and 18:1 LPA were separately prepared at 1.00 mg/mL in Methanol and were stored in a −20° C. freezer. 18:3 LPA, the internal standard, was purchased from Eschelon Bioscience, Inc. as 1 mg in powder form. A stock solution was prepared at 1 mg/mL in chloroform and then diluted to 100 μg/mL in Methanol and was stored in a −20° C. freezer. The internal standard solution of 125 ng/mL in acetonitrile was prepared and stored in a 4° C. refrigerator.

Plasma LPA Assays

2% BSA (Bovine serum albumin) was used as a surrogate matrix for preparation of standards and QC samples due to the presence of endogenous LPAs in rat plasma samples. 20:4 LPA and 18:1 LPA calibration standards were prepared fresh with each batch at concentrations ranging from 0.5 ng/mL to 1000 ng/mL in 2% BSA. 20:4 LPA and 18:1 LPA QC samples were prepared fresh with each batch at concentrations of 1, 5, 20, 50, 250, and 1000 ng/mL in 2% BSA. Study samples were thawed on ice and processed within 2 hours on ice. The protein precipitation method was applied for sample preparation. The injection plate was loaded onto a CTC PAL autosampler for injection to determine the concentration of 20:4 LPA and 18:1 LPA by LC/MS/MS. Reverse phase HPLC using a C8 column was used for the separation.

IC$_{50}$ Assay

The stock solution (10 mM) for each compound was made in DMSO. For each compound, the stock solution (10 mM in DMSO) was diluted in 60% DMSO to make ten intermediate stock solutions. The ten intermediate stocks were then diluted in rat $K_2$ EDTA plasma to make ten samples at concentrations ranging from 30 μM to 0.00152 μM. One control sample was made by spiking DMSO into rat $K_2$ EDTA plasma. All eleven samples were placed in 37° C. incubator for 18 hours, extracted right after 18 hr incubation and transferred to an autosampler tray for injection onto the LC-MS/MS system. The quantitation of $IC_{50}$ assay was performed by determining the peak area ratio of 20:4 LPA (or 18:1 LPA) over internal standard (18:3 LPA). The $IC_{50}$ value for each compound was calculated by using GraphPad Prism software.

The compounds of examples 1-14, 5-1, 5-2, 5-3, 5-4, 5-5, 5-6, 5-7, 5-11, 5-13, 5-14, 5-15, 5-17, 6-1, 6-2, 6-3, 6-7, 6-9, 6-10, 6-11, 6-13, 7-1, 7-2, 7-5, 7-6, 7-7, 7-8, 7-10, 7-11, 7-12, 7-13, 7-14, 9-7, 13-1, 13-6, 13-10, 13-11, 13-12, 13-2, 13-3, 13-4, 13-5, 14-1, 14-2, 15-1, 16-1, -17-1, 10-12, 10-8, 12-10, 1-29, 13-17, 13-20, 13-26, 13-27, 13-30, 13-31, 18-2, 19-1, 19-2, 20-2, 21-1, 21-2, 5-22, 5-30, 5-31, 5-32, 5-33, 5-37, 5-38, 5-42, 5-44, 5-48, 5-50, 9-11, 9-14, and 9-15 had an $IC_{50}$ of no greater than 100 nM. The compounds of examples 6-4, 7-3, 7-4, 7-9, 7-15, 7-16, 9-1, 10-2, 10-4, 11-3, 12-2, 13-8, 14-3, 10-11 and 12-15 had an $IC_{50}$ of greater than 100 nM but no greater than 250 nM. The compounds of examples 1-2 and 7-18 had an $IC_{50}$ of greater than 250 nM but no greater than 500 nM.

OPC Differentiation Assay

Enriched populations of oligodendrocytes are grown from post-natal day 2 (P2) female Sprague Dawley rats. The forebrain is dissected out and placed in Hank's buffered saline solution (HBSS; Invitrogen, Grand Island, N.Y.). The tissue is cut into 1 mm fragments and incubated at 37° C. for 15 minutes in 0.01% trypsin and 10 μg/mL DNase. Dissociated cells are plated on poly-L-lysine-coated T75 tissue culture flasks and grown at 37° C. for 10 days in Dulbecco's modified Eagle's medium (DMEM) with 20% fetal calf serum (Invitrogen). A2B5+ OPCs are collected by shaking the flask overnight at 200 rpm and 37° C., resulting in a 95% pure population.

For the differentiation assay, 2 μM and 20 μM antagonist or the same concentrations of vehicle (DMSO) are applied to OPCs cultured in CNTF/T3 containing media. After a 3-day incubation, cells are lysed in 80 μL lysis buffer (50 mM HEPES [4-(2-hydroxyethyl)-1-piperazineethanesulfonic acid], pH 7.5, 150 mM NaCl, 1.5 mM $MgCl_2$, 1 mM ethylene glycol tetraacetic acid [EGTA], 1% Triton X-100 and 10% glycerol) for 30 minutes at 4° C. After centrifugation at 14,000 g for 15 minutes, the supernatants are boiled in Laemmli sample buffer, subjected to 4-20% SDS-PAGE, and analyzed by Western blotting with anti-MBP, anti-myelin-associated glycoprotein (MAG), or anti-beta actin antibodies. The secondary antibodies used are anti-mouse IgG-HRP (horseradish peroxidase) and anti-rabbit IgG-HRP respectively.

DRG-OPC Myelination Assay

Embryonic neocortical neurons are dissected from embryonic day 18 (E18) Sprague Dawley rats, and then plated on poly-D-lysine (100 μg/mL)-coated cover slips and grown in neurobasal medium supplemented with B27 (Invitrogen) for one week. A2B5+ OPCs are prepared as described above and then added into the cultured neocortical neurons. One day later, different concentrations of an ATX inhibitor and control reagents are applied into the co-cultures. Fresh media containing the different concentrations of an ATX inhibitor or control compounds are supplied every three days. After ten days, co-cultures are subjected to sodium dodecyl sulfate polyacrylamide gel electrophoresis (SDS-PAGE)/Western blot analyses to quantify MAG, MBP, and MOG.

Remyelination Assay in Brain Slice Culture

Approximately three to four consecutive 300 μm slices are taken from the junction of the corpus callosum to the hippocampus in post-natal, day 17 Sprague Dawley rats (Charles River, Willmington, Mass.). Slices are cultured in basal DMEM supplemented with 25% horse serum for three days, before being treated with 6 mg/mL LPC (Sigma L-4129) for a further three days. The medium is then changed, and slices incubated with medium containing an ATX inhibitor or vehicle control for a final period of three days, after which myelination is visualized by black gold staining (Millipore, Bedford, Mass.) following the manufacture's protocol. Images are acquired using a Leica M420 microscope (Bannockburn, Ill.) and the staining intensity of corpus callosum is analyzed using Metamorph software (Molecular Devices, Downingtown, Pa.). Three or four brain slices are used for each treatment group.

Lysolecithin Demyelination Model

Adult Sprague Dawley rats (220-260 g) are anesthetized by intraperitoneal injection of a cocktail, consisting of Ketamine (35 mg/kg), Xylazine (6 mg/kg) and Acepromazine (1 mg/kg). The back of the animal is shaved from the lower thoracic to the lumbar region, subsequently sanitized with 70% isopropanol, Betadine Scrub solution, and 70% isopropanol again. The animal is then placed onto stereotaxic frame.

After ensuring an adequate anesthetic level, the skin is incised along the midline over the thoracic region. The dorsal fascia is incised and the paraspinal muscles separated from the spinous processes of the thoracic vertebrae T-9 through T-11. The T-10 vertebra is demolished, and the lamina removed with micro-rongeurs. Once the dorsal spinal cord region is exposed, a microcapillary glass needle is inserted into the dorsal column to a depth of 0.6 mm. The demyelinating reagent, 1.5 μL of 1% Lysolecithin (LPC, Sigma#L1381) in saline is injected with the infusion rate of 2 nL/sec controlled by a micro-pump (World Precision Instrument #micro4). Once the injection is completed, the needle is placed for additional 1 min before removal. The paraspinal muscles and the lumbar fascia are closed with suture (#5, silk). The skin incision is closed with wound clips. Animals are allowed to recover from the anesthesia and are observed in the humidified incubator.

Buprenorphine (0.05 mg/kg) is administered subcutaneously (s.c.) twice a day for additional two days following operation.

Three days following the primary surgery, treatments with an ATX inhibitor (30 pmol), LPA (30 pmol) or control (0.1% DMSO in saline) are injected at the primary injection region in a volume of 1.5 μL with the same infusion speed as indicated above. Nine days following the primary surgery, the animals are anesthetized and perfused trans-cardially with heparin (10 iu/mL) in saline followed by 4% PFA in PBS. The spinal cords are removed and post fixed in PFA overnight. Then the cords are cut into 100 μM thickness longitudinally and then 1% loxuol fast blue is stained and histological evaluation for remyelination and repair is assessed under microscope.

For systemic treatment, the animals are administered once daily intraperitoneally with either an ATX inhibitor (10 mg/kg) or control (15% HPCD (hydroxypropyl-β-cyclodextrin)) 2 days following the primary surgery. Nine days after the primary surgery, animals are sacrificed and the spinal cords were processed as indicated above.

CFA Inflammatory Pain Model

In the CFA (complete Freund's adjuvant) model, adult male SD (250-300 g) rats are anesthetized with isoflurane inhalation (4.5% induction/2.0% maintenance). Heat-killed M. Tuberculosis H37 RA (non-viable) suspended at a concentration of 1.0 mg/ml in incomplete Freund's adjuvant is used (Chondrex Inc., catalog#7008). At day 0, intradermal injection (i.d.) of 100 µl of CFA (1:1 oil/saline) is slowly perfused into the right footpad of the rats. At day 1, baseline tactile allodynia test are conducted: rats that develop sensitive painful response are enrolled to the study. At day 2, rats are orally dosed once with either vehicle or ATX inhibitor, then at 2 hrs, 4 hrs, 6 hrs and 24 hrs after dosage, all rats are tested for mechanical allodynia response.

Tactile allodynia is tested as follows. A rat is placed in an elevated Plexiglas observation chamber (approximately 4"×6"×10") having a wire grid (1 cm² spacing) mesh floor under polycarbonate cages. The rat is left to acclimate to the experimental conditions for 20 minutes before testing begins. After the rat is calm, tactile allodynia is assessed using a series of von Frey filaments ranging from 2.04-28.84 g (Stoelting, Wood Dale, Ill.). Graded pressure is presented to a localized area on the plantar surface of the paw via the use of Von Frey hairs (monofilaments which are calibrated to bend at a known pressure). A response to the VonFrey hair is recorded as the rat withdrawing the tested paw and is usually followed by lifting and licking. A series of filaments are used to determine the threshold response using the established "Up-Down" method. Each paw is tested 4-6 times repeatedly with 1-2 seconds (modified from Seltzer et al., 1991) in between each probe to accurately assess the behavior. A sharp lifting of the paw is scored as a positive response.

Rat Model of Neuropathic Pain

Chronic Constriction Injury (CCI) Surgery: In the CCI model (Bennett and Xie, Pain, 1989, which is incorporated by reference in its entirety), adult male SD (250-275 g) rats are anesthetized with isoflurane inhalation (4.5% induction/2.0% maintenance). The surgery is performed under aseptic conditions and involves exposing the sciatic nerve at the mid-thigh level. Ocular lubricant is used as needed to prevent corneal drying. After shaving and disinfecting the skin (betadine followed by 70% ethanol), a small incision is made just caudal to the biceps femoris. Care is taken to not disturb the sciatic nerve. The nerve is slightly elevated, and 4 loose ligatures of 4-0 chromic gut suture are inserted under the nerve, and then are loosely tied around it. The sutures constrict the nerve but do not strangle it. Prior to inserting the chromic gut, it is rinsed twice in sterile saline. The incision is closed with wound clips, and rats are allowed to recover from anesthesia on a circulating water heating pad before being returned to their home cages. In the sham controls the skin is opened, and the sciatic nerve is identified and elevated, but no sutures are tied around the nerve. All rats are screened for pain response around post-surgery day 7 and only rats with sensitive pain response are enrolled to the study.

Animals are orally dosed twice/day for 3 times/week with either vehicle or ATX inhibitor post-surgery at days 10, 12, 14, 17, 19 and 21, and animals are also tested at the same schedule for three types of neuropathic pain: thermal hyperalgesia, tactile allodynia and incapacitance.

(1) Plantar thermal hyperalgesia: Rats are tested for hyperalgesia using a plantar device (Ugo Basile Inc., Cat. #37370). After acclimation to the testing room, rats are placed on an elevated glass floor beneath inverted clear plastic cages, and a radiant heat source beneath the glass is aimed at the mid-plantar surface of the hindpaw after they have ceased all exploratory behavior. The onset of light activates a timer, which is terminated by a hindpaw withdrawal response. A cutoff time of 30 seconds is used to avoid tissue damage in the absence of a response. The average withdrawal latency value of three trials from the ipsilateral hindpaw is measured with at least 5-10 minutes between each trial to avoid any tissue damage.

(2) Tactile allodynia is tested as described above.

(3) Incapacitance: The incapacitance test measures the weight the rat places on each of its hindpaws. The rat is placed in a small, clear Plexiglas box (6" long×3" wide×4" tall). The box is tilted up and opens in the front. The rat is placed in the box so that its hindpaws are at the back (lower) portion of the box, and the forepaws are at the front (raised) part of the box. The rat's head is at the opening in the front of the box. The box is placed on a divided scale such that each of the rat's hindpaws is on one of the two weighing pans of the scale. The weight that the rat placed on each hindpaw is then measured. The procedure is rapid (about 10 sec) and does not cause the animal any pain.

Sciatic Nerve Crush Mouse Model

The sciatic nerve crush (as described, for example, in *Reproducible Mouse Sciatic Nerve Crush and Subsequent Assesment of Regeneration by Whole Mount Muscle Analysis*, Bauder, A. R., and Ferguson, T. A., *J. Vis. Exp.* (60), e3606, DOI: 10.3791/3606 (2012)) damages nerves of the sciatic nerve and is a useful mouse model system for studying sciatic nerve injury. Methods used to evaluate the efficacy of a treatment on a sciatic nerve injury are similar to those described for human patients, and include, e.g. evaluating changes in temperature threshold or changes in nerve potential.

Other embodiments are within the scope of the following claims.

What is claimed is:
1. A compound of Formula (I):

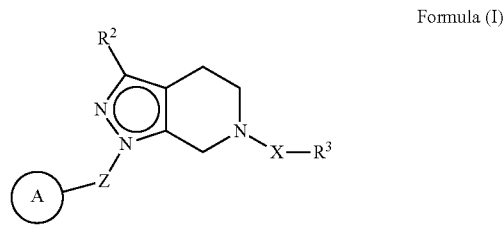

Formula (I)

or a pharmaceutically acceptable salt thereof, wherein:
X is selected from —C(O)—, —C(O)$_2$—, and —C(O)NR$^X$—;
Z is a bond or C$_{1-5}$alkylene;
Ring A is selected from cyclohexyl, phenyl, and 5- or 6-membered heteroaryl, wherein Ring A is optionally substituted with one to three R$^1$;
R$^1$ is selected from C$_{1-4}$alkyl, halo, —CN, —OR$^{1a}$, —S(O)$_2$R$^{1a}$, —C(O)$_2$R$^{1a}$, —NO$_2$, —N(R$^{1a}$)C(O)$_2$R$^{1a}$, —N(R$^{1a}$)S(O)$_2$R$^{1a}$, and —SR$^{1a}$, wherein said C$_{1-4}$alkyl is optionally substituted with one to three R$^{10}$;
R$^{1a}$ in each occurrence is independently selected from H and C$_{1-4}$alkyl;
R$^{10}$ in each occurrence is independently selected from halo, —OR$^{10a}$, and —N(R$^{10a}$); and
R$^{10a}$ in each occurrence is independently selected from H and C$_{1-4}$alkyl;

$R^L$ is selected from H and $C_{1-3}$alkyl;

$R^X$ is selected from H and $C_{1-3}$alkyl;

$R^2$ is H, halo or $C_{1-4}$alkyl optionally substituted with 1 to 3 halo;

$R^3$ is selected from:
  i. —[CHR$^{3a}$]$_z$—R$^4$;
  ii. —[CHR$^{3a}$]$_x$-L-[CHR$^{3a}$]$_y$—R$^4$;
  iii. —[CHR$^{3a}$]$_z$-(L)$_m$-R$^5$;
  iv. —[CHR$^{3a}$]$_x$-L-[CHR$^{3a}$]$_y$—R$^5$; and
  v. R$^5$, m is 0 or 1;

L is selected from —N(R$^L$)— and —O—;

$R^{3a}$ is hydrogen or $C_{1-3}$alkyl;

x and y are each independently selected from 1, 2, or 3;

z is 1, 2, 3, 4, 5, or 6;

$R^4$ is selected from —C(O)$_2$R$^{4a}$, —C(O)N(R$^{4a}$)$_2$, —OR$^{4a}$, —N(R$^{4a}$)$_2$, CN, —S(O)$_2$N(R$^{4a}$)$_2$, —S(O)$_2$N(R$^{4a}$)C(O)R$^{4a}$, —SR$^{4a}$, —S(O)R$^{4a}$, —S(O)$_2$R$^{4a}$, —S(O)$_2$OR$^{4a}$, —C(O)N(R$^{4a}$)S(O)$_2$R$^{4a}$, —C(O)N(R$^{4a}$)S(O)$_2$R$^{4a}$, —C(O)N(R$^{4a}$)OR$^{4a}$, —C(O)N(R$^{4a}$)CN, —CR$^{4a}$(CF$_3$)OR$^{4a}$, —C(CF$_3$)$_2$OR$^{4a}$, —P(O)(OR$^{4a}$)$_2$, and —B(OR$^{4a}$)$_2$;

$R^{4a}$ in each occurrence is independently selected from H and $C_{1-6}$alkyl;

$R^5$ is selected from 3- to 12-membered carbocyclyl and 3- to 12-membered heterocyclyl, wherein R$^5$ is optionally substituted with one or more R$^{30}$;

$R^{30}$ in each occurrence is independently selected from 3- to 6-membered monocyclic carbocyclyl, 3- to 6-membered monocyclic heterocyclyl, $C_{1-6}$alkyl, halo, CN, —S(O)$_2$OR$^{30a}$, —S(O)$_2$N(R$^{30a}$)$_2$, —S(O)$_2$N(R$^{30a}$)C(O)R$^{30a}$, —C(O)N(R$^{30a}$)S(O)$_2$R$^{30a}$, —C(O)N(R$^{30a}$)S(O)$_2$R$^{30a}$, —C(O)N(R$^{30a}$)OR$^{30a}$, —C(O)N(R$^{30a}$)CN, —CH(CF$_3$)OR$^{30a}$, —C(CF$_3$)$_2$OR$^{30a}$, —P(O)(OR$^{30a}$)$_2$, —B(OR$^{30a}$)$_2$, —C(O)$_2$R$^{30a}$, —C(O)N(R$^{30a}$)$_2$, —OR$^{30a}$, —N(R$^{30a}$)$_2$, and —C(O)R$^{30a}$, wherein said 3- to 6-membered monocyclic carbocyclyl, 3- to 6-membered monocyclic heterocyclyl, and $C_{1-6}$alkyl in each occurrence are optionally and independently substituted with one or more R$^{35}$; and $R^{30a}$ in each occurrence is independently selected from H, $C_{1-6}$alkyl, 3- to 6-membered monocyclic carbocyclyl, and 3- to 6-membered monocyclic heterocyclyl;

$R^{35}$ in each occurrence is independently selected from halo, —OR$^{35a}$, —C(O)$_2$R$^{35a}$, —C(O)N(R$^{35a}$)$_2$, —S(O)$_2$R$^{30a}$, and —N(R$^{35a}$)$_2$; and $R^{35a}$ in each occurrence is independently selected from H and $C_{1-6}$alkyl.

2. The compound of claim 1, wherein the compound is represented by the following formula:

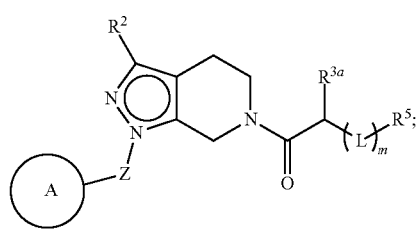

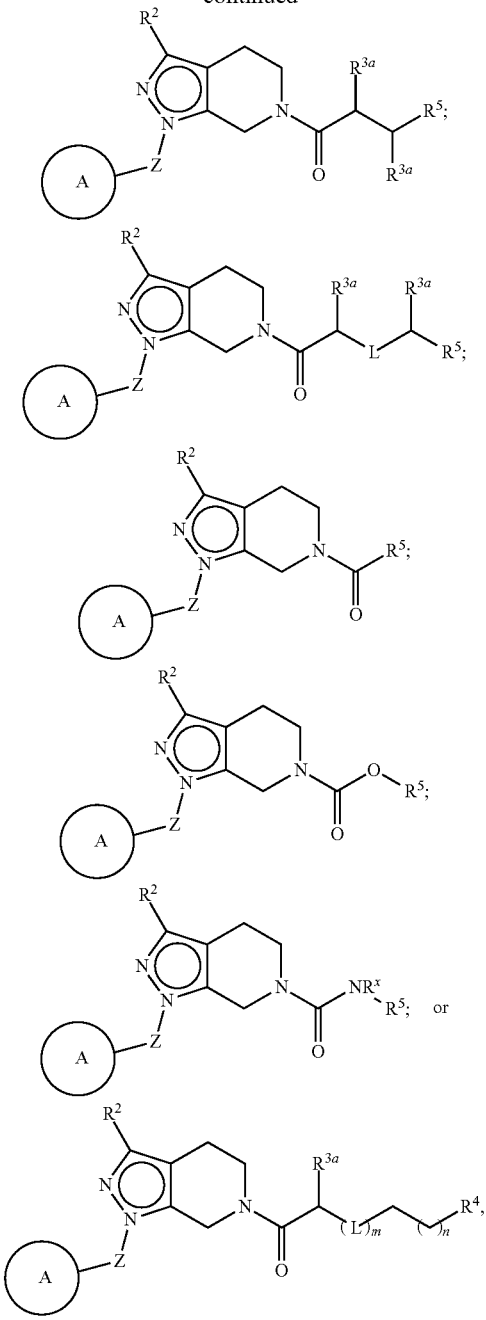

or a pharmaceutically acceptable salt thereof, wherein R$^x$ is hydrogen or methyl; n is 0, 1, or 2.

3. The compound of claim 2, wherein Ring A is either unsubstituted or substituted with 1, 2 or 3 groups independently selected from methyl, ethyl, propyl, isopropyl, butyl, tert-butyl, isobutyl, sec-butyl, fluoro, chloro, methyoxy, ethoxy, and trifluoromethyl.

4. The compound of claim 2, wherein Z is a bond, —CH$_2$—, —CH(CH$_3$)—, or —CH$_2$CH$_2$—; and R$^2$ is H, halo, or $C_{1-4}$alkyl optionally substituted with 1 to 3 halo.

5. The compound of claim 2, wherein:

R$^5$ is a cyclobutyl, cyclopentyl, cyclohexyl, spiro[3.3]heptanyl, tricyclo[2.2.1.0$^{2,6}$]heptanyl, phenyl, bicyclo[2.1.1]hexyl, bicyclo[2.2.1]heptyl, bicyclo[2.2.1]heptenyl, bicyclo[2.2.2]octanyl, bicyclo[3.2.1]octanyl, bicyclo[3.3.1]nonanyl, bicyclo[3.2.2]nonanyl, 8-azabicyclo[3.2.1]octanyl, 9-azabicyclo[3.3.1]nonanyl, 3-azabicyclo[3.1.0]hexanyl, azetidinyl, 3,8-diazabicyclo[3.2.1]octanyl, 3,9-diazabicyclo[3.3.1]nonanyl, 4,7-diazaspiro[2.5]octanyl, benzofuran, benzo[d]oxazolyl, benzothiazolyl, benzothiophenyl, diazepinyl, morpholinyl, octahydro-1H-pyrido[1,2-a]pyrazinyl, octahydrocyclopenta[c]pyrrolyl, octahydropyrrolo[1,2-a]pyrazinyl, piperazinyl, piperidinyl, pyridinyl, pyrimidinyl, pyrrolidinyl, and 5,6,7,8-tetrahydroimidazo[1,5-a]pyridinyl, wherein $R^5$ is substituted with 1, 2 or 3 groups selected from $R^{30}$;

$R^{30}$ in each occurrence is independently selected from 5- or 6-membered heteroaryl, $C_{1-4}$alkyl, halo, CN, —S(O)$_2$OR$^{30a}$, —C(O)N(R$^{30a}$)S(O)$_2$R$^{30a}$, —C(O)N(R$^{30a}$)S(O)$_2$R$^{30a}$, —P(O)(OR$^{30a}$)$_2$, —C(O)$_2$R$^{30a}$, —OR$^{30a}$, and —C(O)R$^{30a}$, wherein said 5- or 6-membered heteroaryl and $C_{1-4}$alkyl in each occurrence are optionally and independently substituted with 1, 2, or 3 $R^{35}$, and the 5- or 6-membered heteroaryl is selected from pyrrolyl, imidazolyl, pyrazolyl, triazolyl, pyridinyl, pyranyl, and pyrimidinyl, and $R^{30a}$ in each occurrence is independently selected from H and methyl, ethyl, propyl, isopropyl, butyl, tert-butyl, isobutyl, sec-butyl;

$R^{35}$ in each occurrence is independently selected from halo, $C_{1-4}$alkyl, and —C(O)$_2$R$^{35a}$; and $R^{35a}$ in each occurrence is independently selected from H and methyl, ethyl, propyl, isopropyl, butyl, tert-butyl, isobutyl, sec-butyl.

6. The compound of claim 2, wherein m is 1 and L is —NH—, —N(CH$_3$)— or —O—; and $R^4$ is —C(O)$_2$R$^{4a}$, —CN, —SO$_3$R$^{4a}$, S(O)$_2$R$^{4a}$, —CR$^{4a}$(CF$_3$)OR$^{4a}$, or —C(CF$_3$)$_2$OR$^{4a}$; and $R^{4a}$ in each occurrence is independently selected from H and $C_{1-4}$alkyl.

7. The compound of claim 6, wherein $R^4$ is —CO$_2$H, —CO$_2$—CH$_3$, or —CO$_2$—CH$_2$CH$_3$.

8. The compound of claim 1, wherein the compound is represented by the following formula:

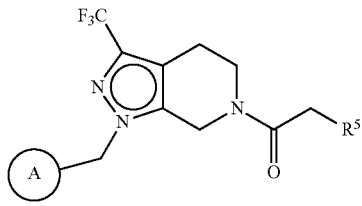

or a pharmaceutically acceptable salt thereof, wherein
Ring A is phenyl, optionally substituted with one or more halo;
$R^5$ is selected from 4- to 10-membered carbocyclyl and 4- to 10-membered heterocyclyl, wherein $R^5$ optionally substituted with one or more $R^{30}$;
$R^{30}$ in each occurrence is independently selected from $C_{1-4}$alkyl optionally substituted with 1, 2, or 3 halo and —C(O)$_2$R$^{30a}$; and
$R^{30a}$ in each occurrence is independently selected from H and $C_{1-4}$alkyl.

9. The compound of claim 8, wherein
Ring A is phenyl, optionally substituted with one or two halo;
$R^5$ is selected from 9-azabicyclo[3.3.1]nonanyl, piperidinyl, and cyclohexyl, each of which is optionally substituted with 1, 2, or 3 groups independently selected from methyl, —CO$_2$H, and —CF$_3$.

10. The compound of claim 1, wherein the compound is represented by the following formula:

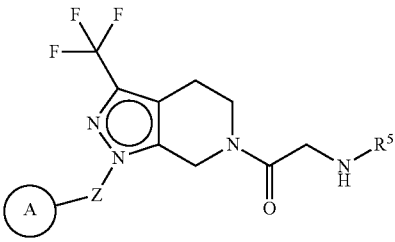

or a pharmaceutically acceptable salt thereof, Ring A is phenyl, optionally substituted with one or more halo;
$R^5$ is selected from 4- to 10-membered carbocyclyl and 4- to 10-membered heterocyclyl, wherein $R^5$ optionally substituted with one or more $R^{30}$;
$R^{30}$ in each occurrence is independently selected from $C_{1-4}$alkyl optionally substituted with 1, 2, or 3 halo, and —C(O)$_2$R$^{30a}$; and
$R^{30a}$ in each occurrence is independently selected from H and $C_{1-4}$alkyl.

11. The compound of claim 10, wherein
Ring A is phenyl, optionally substituted with one or two halo;
$R^5$ is cyclobutyl optionally substituted with 1, 2, or 3 groups independently selected from methyl or —CO$_2$H.

12. The compound of claim 1, wherein the compound is represented by the following formula:

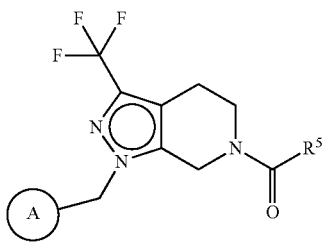

or a pharmaceutically acceptable salt thereof, Ring A is phenyl, optionally substituted with one or more halo;
$R^5$ is selected from 4- to 10-membered carbocyclyl and 4- to 10-membered heterocyclyl, wherein $R^5$ optionally substituted with one or more $R^{30}$;
$R^{30}$ in each occurrence is independently selected from $C_{1-4}$alkyl optionally substituted with 1, 2, or 3 halo, and —C(O)$_2$R$^{30a}$; and
$R^{30a}$ in each occurrence is independently selected from H and $C_{1-4}$alkyl.

13. The compound of claim 12, wherein
Ring A is phenyl, optionally substituted with one or two halo;
$R^5$ is selected from 9-azabicyclo[3.3.1]nonanyl, piperidinyl, pyrrolidinyl, tetrahydroimidazo[1,5-a]pyridinyl, bicyclo[2.2.2]octanyl, cyclobutyl, and cyclohexyl, each of which is optionally substituted with 1, 2, or 3 groups independently selected from methyl, —CO$_2$H, —CO$_2$CH$_3$, —CH$_2$CH$_2$CO$_2$H, and —CF$_3$.

14. The compound of claim 1, wherein the compound is represented by the following formula:

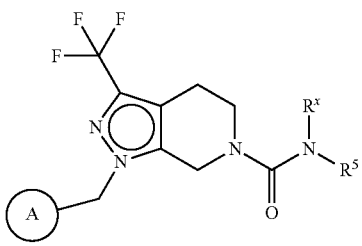

or a pharmaceutically acceptable salt thereof, Ring A is phenyl, optionally substituted with one or more halo;
$R^5$ is selected from 4- to 10-membered carbocyclyl and 4- to 10-membered heterocyclyl, wherein $R^5$ optionally substituted with one or more $R^{30}$;
$R^{30}$ in each occurrence is independently selected from $C_{1-4}$alkyl optionally substituted with 1, 2, or 3 halo and —C(O)$_2$R$^{30a}$; and
$R^{30a}$ in each occurrence is independently selected from H and $C_{1-4}$alkyl.

15. The compound of claim 14, wherein
Ring A is phenyl, optionally substituted with one or two halo;
$R^5$ is selected from 9-azabicyclo[3.3.1]nonanyl, piperidinyl, bicyclo[2.2.2]octanyl, cyclobutyl, and cyclohexyl, each of which is optionally substituted with 1, 2, or 3 groups independently selected from methyl, —CO$_2$H, —CO$_2$CH$_3$, and —CF$_3$.

16. The compound of claim 1, wherein the compound is represented by the following formula:

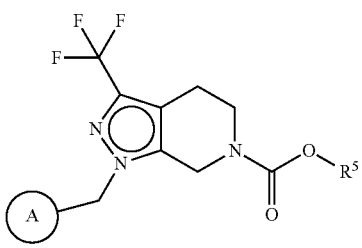

or a pharmaceutically acceptable salt thereof, Ring A is phenyl, optionally substituted with one or more halo;
$R^5$ is selected from 4- to 10-membered carbocyclyl and 4- to 10-membered heterocyclyl, wherein $R^5$ optionally substituted with one or more $R^{30}$;
$R^{30}$ in each occurrence is independently selected from $C_{1-4}$alkyl optionally substituted with 1, 2, or 3 halo, and —C(O)$_2$R$^{30a}$; and
$R^{30a}$ in each occurrence is independently selected from H and $C_{1-4}$alkyl.

17. The compound of claim 16, wherein
Ring A is phenyl, optionally substituted with one or two halo;
$R^5$ is selected from 9-azabicyclo[3.3.1]nonanyl, piperidinyl, bicyclo[2.2.2]octanyl, cyclobutyl, and cyclohexyl, each of which is optionally substituted with 1, 2, or 3 groups independently selected from methyl, —CO$_2$H, —CO$_2$CH$_3$, and —CF$_3$.

18. A pharmaceutical composition comprising at least one compound of claim 1, or a pharmaceutically acceptable salt thereof, and at least one pharmaceutically acceptable carrier.

19. The compound of claim 2, wherein $R^5$ is cyclohexyl, cyclopentyl, cyclobutyl, bicyclo[2.2.2]octanyl, bicyclo[3.2.1]octanyl, spiro[3.3]heptanyl, tricyclo[2.2.1.0$^{2,6}$]heptanyl, phenyl, piperidinyl, pyridinyl, pyrrolidinyl, azetidinyl, 8-azabicyclo[3.2.1]octanyl, 9-azabicyclo[3.3.1]nonanyl, octahydrocyclopenta[c]pyrrolyl, 5,6,7,8-tetrahydroimidazo[1,5-a]pyridinyl, or benzothiazolyl, each of which is optionally substituted with 1 to 3 groups selected from —CO—CH$_3$, —CO$_2$H, —CH$_2$—CO$_2$H, —CH$_2$—CH$_2$—CO$_2$H, —CO$_2$—(C$_{1-4}$alkyl), —CO$_2$—(C$_{1-4}$alkyl), C$_{1-4}$alkyl optionally substituted with 1, 2, or 4 halo, halo, hydroxyl, and pyrimidinyl.

20. The compound of claim 1, wherein the compound is selected from:
Ethyl 4-(2-(1-(4-fluorobenzyl)-3-(trifluoromethyl)-4,5-dihydro-1H-pyrazolo[3,4-c]pyridin-6(7H)-yl)-2-oxoethyl)cyclohexanecarboxylate,
1-(1-(4-Chloro-2-fluorobenzyl)-3-(trifluoromethyl)-4,5-dihydro-1H-pyrazolo[3,4-c]pyridin-6(7H)-yl)-2-(1-methylpiperidin-4-yl)ethanone,
1-(1-(4-Chloro-2-fluorobenzyl)-3-(trifluoromethyl)-4,5-dihydro-1H-pyrazolo[3,4-c]pyridin-6(7H)-yl)-2-phenylethanone,
Ethyl 4-(2-(1-(4-chloro-2-fluorobenzyl)-4,5-dihydro-1H-pyrazolo[3,4-c]pyridin-6(7H)-yl)-2-oxoethyl)cyclohexanecarboxylate,
1-(1-(4-Chloro-2-fluorobenzyl)-3-(trifluoromethyl)-4,5-dihydro-1H-pyrazolo[3,4-c]pyridin-6(7H)-yl)-2-cyclohexylethanone,
(1-(4-Chloro-2-fluorobenzyl)-3-(trifluoromethyl)-4,5-dihydro-1H-pyrazolo[3,4-c]pyridin-6(7H)-yl)(cyclohexyl)methanone,
1-(1-(4-Chloro-2-fluorobenzyl)-3-(trifluoromethyl)-4,5-dihydro-1H-pyrazolo[3,4-c]pyridin-6(7H)-yl)-2-(pyridin-4-yl)ethanone,
Ethyl 4-(2-(1-(4-chlorobenzyl)-3-(trifluoromethyl)-4,5-dihydro-1H-pyrazolo[3,4-c]pyridin-6(7H)-yl)-2-oxoethyl)cyclohexanecarboxylate,
Ethyl 4-(2-(1-(2,4-dichlorobenzyl)-3-(trifluoromethyl)-4,5-dihydro-1H-pyrazolo[3,4-c]pyridin-6(7H)-yl)-2-oxoethyl)cyclohexanecarboxylate,
Ethyl 4-(2-oxo-2-(3-(trifluoromethyl)-1-(4-(trifluoromethyl)benzyl)-4,5-dihydro-1H-pyrazolo[3,4-c]pyridin-6(7H)-yl)ethyl)cyclohexanecarboxylate,
Methyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)benzoate,
1-(1-(4-Chloro-2-fluorobenzyl)-3-(trifluoromethyl)-4,5-dihydro-1H-pyrazolo[3,4-c]pyridin-6(7H)-yl)-2-(4-fluorophenyl)ethanone,
Ethyl 4-(2-(1-benzyl-3-(trifluoromethyl)-4,5-dihydro-1H-pyrazolo[3,4-c]pyridin-6(7H)-yl)-2-oxoethyl)cyclohexanecarboxylate,
3-(Benzo[d]thiazol-2-yl)-1-(1-(4-fluorobenzyl)-3-(trifluoromethyl)-4,5-dihydro-1H-pyrazolo[3,4-c]pyridin-6(7H)-yl)propan-1-one,
1-(1-(4-Chloro-2-fluorobenzyl)-3-(trifluoromethyl)-4,5-dihydro-1H-pyrazolo[3,4-c]pyridin-6(7H)-yl)-2-(4-hydroxycyclohexyl)ethanone,
Ethyl 4-(2-(1-(cyclohexylmethyl)-3-(trifluoromethyl)-4,5-dihydro-1H-pyrazolo[3,4-c]pyridin-6(7H)-yl)-2-oxoethyl)cyclohexanecarboxylate,
Ethyl 4-(2-(1-(4-fluorobenzyl)-4,5-dihydro-1H-pyrazolo[3,4-c]pyridin-6(7H)-yl)-2-oxoethyl)cyclohexanecarboxylate, Ethyl 4-(2-(1-(3-fluorobenzyl)-3-(trifluoromethyl)-4,5-dihydro-1H-pyrazolo[3,4-c]pyridin-6(7H)-yl)-2-oxoethyl)cyclohexanecarboxylate,
Ethyl 4-(2-(1-(2-fluorobenzyl)-3-(trifluoromethyl)-4,5-dihydro-1H-pyrazolo[3,4-c]pyridin-6(7H)-yl)-2-oxoethyl)cyclohexanecarboxylate,
(1-(4-Fluorobenzyl)-3-(trifluoromethyl)-4,5-dihydro-1H-pyrazolo[3,4-c]pyridin-6(7H)-yl)(5,6,7,8-tetrahydroimidazo[1,5-a]pyridin-7-yl)methanone,
1-(1-(4-Chloro-2-fluorobenzyl)-3-(trifluoromethyl)-4,5-dihydro-1H-pyrazolo[3,4-c]pyridin-6(7H)-yl)-2-(4-methylcyclohexyl)ethanone,
Methyl 4-(1-(4-fluorobenzyl)-3-(trifluoromethyl)-4,5,6,7-tetrahydro-1H-pyrazolo[3,4-c]pyridine-6-carbonyl)cyclohexanecarboxylate,
Methyl 4-(1-(4-fluorobenzyl)-3-(trifluoromethyl)-4,5,6,7-tetrahydro-1H-pyrazolo[3,4-c]pyridine-6-carbonyl)bicyclo[2.2.2]octane-1-carboxylate,
trans-Ethyl 4-(2-(1-cyclohexyl-3-(trifluoromethyl)-4,5-dihydro-1H-pyrazolo[3,4-c]pyridin-6(7H)-yl)-2-oxoethyl)cyclohexanecarboxylate,
trans-Ethyl 4-(2-(1-(4-methylbenzyl)-3-(trifluoromethyl)-4,5-dihydro-1H-pyrazolo[3,4-c]pyridin-6(7H)-yl)-2-oxoethyl)cyclohexanecarboxylate,
trans-Ethyl 4-(2-(1-(4-methoxylbenzyl)-3-(trifluoromethyl)-4,5-dihydro-1H-pyrazolo[3,4-c]pyridin-6(7H)-yl)-2-oxoethyl)cyclohexanecarboxylate,
Methyl 8-(2-(1-(4-chloro-2-fluorobenzyl)-3-(trifluoromethyl)-4,5-dihydro-1H-pyrazolo[3,4-c]pyridin-6(7H)-yl)-2-oxoethyl)bicyclo[3.2.1]octane-3-carboxylate,
trans-Ethyl 4-(2-oxo-2-(1-phenethyl-3-(trifluoromethyl)-4,5-dihydro-1H-pyrazolo[3,4-c]pyridin-6(7H)-yl)ethyl)cyclohexanecarboxylate,
trans-Ethyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)cyclohexanecarboxylate,
cis-Ethyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)cyclohexanecarboxylate,
trans-Ethyl 4-(2-(1-(3-chloro-5-fluorobenzyl)-3-(trifluoromethyl)-4,5-dihydro-1H-pyrazolo[3,4-c]pyridin-6(7H)-yl)-2-oxoethyl)cyclohexanecarboxylate,
cis-ethyl 4-(2-(1-(3-chloro-5-fluorobenzyl)-3-(trifluoromethyl)-4,5-dihydro-1H-pyrazolo[3,4-c]pyridin-6(7H)-yl)-2-oxoethyl)cyclohexanecarboxylate,
cis-Methyl 4-(1-(4-chloro-2-fluorobenzyl)-3-(trifluoromethyl)-4,5,6,7-tetrahydro-1H-pyrazolo[3,4-c]pyridine-6-carboxamido)cyclohexanecarboxylate,
trans-Methyl 4-(1-(4-chloro-2-fluorobenzyl)-3-(trifluoromethyl)-4,5,6,7-tetrahydro-1H-pyrazolo[3,4-c]pyridine-6-carboxamido)cyclohexanecarboxylate,
cis-Methyl 4-(1-(4-chloro-2-fluorobenzyl)-N-methyl-3-(trifluoromethyl)-4,5,6,7-tetrahydro-1H-pyrazolo[3,4-c]pyridine-6-carboxamido)cyclohexanecarboxylate,
trans-Methyl 4-(1-(4-chloro-2-fluorobenzyl)-N-methyl-3-(trifluoromethyl)-4,5,6,7-tetrahydro-1H-pyrazolo[3,4-c]pyridine-6-carboxamido)cyclohexanecarboxylate,
4-(Ethoxycarbonyl)cyclohexyl1-(4-chloro-2-fluorobenzyl)-3-(trifluoromethyl)-4,5-dihydro-1H-pyrazolo[3,4-c]pyridine-6(7H)-carboxylate,
trans-4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)cyclohexanecarboxylic acid,
cis-4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)cyclohexanecarboxylic acid,
trans-4-(2-(1-(3-chloro-5-fluorobenzyl)-3-(trifluoromethyl)-4,5-dihydro-1H-pyrazolo[3,4-c]pyridin-6(7H)-yl)-2-oxoethyl)cyclohexanecarboxylic acid,
cis-4-(2-(1-(3-chloro-5-fluorobenzyl)-3-(trifluoromethyl)-4,5-dihydro-1H-pyrazolo[3,4-c]pyridin-6(7H)-yl)-2-oxoethyl)cyclohexanecarboxylic acid,
4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)benzoic acid,
cis-4-(1-(4-chloro-2-fluorobenzyl)-3-(trifluoromethyl)-4,5,6,7-tetrahydro-1H-pyrazolo[3,4-c]pyridine-6-carboxamido)cyclohexanecarboxylic acid,
trans-4-(1-(4-Chloro-2-fluorobenzyl)-3-(trifluoromethyl)-4,5,6,7-tetrahydro-1H-pyrazolo[3,4-c]pyridine-6-carboxamido)cyclohexanecarboxylic acid,
4-(1-(4-Chloro-2-fluorobenzyl)-3-(trifluoromethyl)-4,5,6,7-tetrahydro-1H-pyrazolo[3,4-c]pyridine-6-carboxamido)bicyclo[2.2.2]octane-1-carboxylic acid,
cis-4-(1-(4-Chloro-2-fluorobenzyl)-N-methyl-3-(trifluoromethyl)-4,5,6,7-tetrahydro-1H-pyrazolo[3,4-c]pyridine-6-carboxamido)cyclohexanecarboxylic acid,
trans-4-(1-(4-Chloro-2-fluorobenzyl)-N-methyl-3-(trifluoromethyl)-4,5,6,7-tetrahydro-1H-pyrazolo[3,4-c]pyridine-6-carboxamido)cyclohexanecarboxylic acid,
4-(1-(4-Fluorobenzyl)-3-(trifluoromethyl)-4,5,6,7-tetrahydro-1H-pyrazolo[3,4-c]pyridine-6-carbonyl)bicyclo[2.2.2]octane-1-carboxylic acid,
4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)bicyclo[2.2.2]octane-1-carboxylic acid,
4-(2-(1-(4-Fluorobenzyl)-3-(trifluoromethyl)-4,5-dihydro-1H-pyrazolo[3,4-c]pyridin-6(7H)-yl)-2-oxoethyl)bicyclo[2.2.2]octane-1-carboxylic acid,
trans-4-(2-(1-(4-Methylbenzyl)-3-(trifluoromethyl)-4,5-dihydro-1H-pyrazolo[3,4-c]pyridin-6(7H)-yl)-2-oxoethyl)cyclohexanecarboxylic acid,
trans-4-(2-(1-(4-Methoxylbenzyl)-3-(trifluoromethyl)-4,5-dihydro-1H-pyrazolo[3,4-c]pyridin-6(7H)-yl)-2-oxoethyl)cyclohexanecarboxylic acid,
trans-4-(2-Oxo-2-(1-phenethyl-3-(trifluoromethyl)-4,5-dihydro-1H-pyrazolo[3,4-c]pyridin-6(7H)-yl)ethyl)cyclohexanecarboxylic acid,
trans-4-(2-(1-((5-chlorothiophen-2-yl)methyl)-3-(trifluoromethyl)-4,5-dihydro-1H-pyrazolo[3,4-c]pyridin-6(7H)-yl)-2-oxoethyl)cyclohexanecarboxylic acid,
(2S)-1-(tert-Butoxycarbonyl)-4-(2-(1-(4-chloro-2-fluorobenzyl)-3-(trifluoromethyl)-4,5-dihydro-1H-pyrazolo[3,4-c]pyridin-6(7H)-yl)-2-oxoethyl)pyrrolidine-2-carboxylic acid,
trans-4-(2-(1-(1-(4-Fluorophenyl)ethyl)-3-(trifluoromethyl)-4,5-dihydro-1H-pyrazolo[3,4-c]pyridin-6(7H)-yl)-2-oxoethyl)cyclohexanecarboxylic acid,
cis-4-(2-(1-(1-(4-Fluorophenyl)ethyl)-3-(trifluoromethyl)-4,5-dihydro-1H-pyrazolo[3,4-c]pyridin-6(7H)-yl)-2-oxoethyl)cyclohexanecarboxylic acid,
cis-4-(2-Oxo-2-(1-phenyl-3-(trifluoromethyl)-4,5-dihydro-1H-pyrazolo[3,4-c]pyridin-6(7H)-yl)ethyl)cyclohexanecarboxylic acid,
4-(2-(1-(3-Fluorobenzyl)-3-(trifluoromethyl)-4,5-dihydro-1H-pyrazolo[3,4-c]pyridin-6(7H)-yl)-2-oxoethyl)cyclohexanecarboxylic acid,
4-(2-Oxo-2-(3-(trifluoromethyl)-1-(4-(trifluoromethyl)benzyl)-4,5-dihydro-1H-pyrazolo[3,4-c]pyridin-6(7H)-yl)ethyl)cyclohexanecarboxylic acid,
4-(2-(1-(2-Fluorobenzyl)-3-(trifluoromethyl)-4,5-dihydro-1H-pyrazolo[3,4-c]pyridin-6(7H)-yl)-2-oxoethyl)cyclohexanecarboxylic acid, 4-(1-(1-(4-Chloro-2-fluorobenzyl)-3-(trifluoromethyl)-4,5-dihydro-1H-pyrazolo[3,4-c]pyridin-6(7H)-yl)-1-oxopropan-2-yl)cyclohexanecarboxylic acid, 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)-1-methylcyclohexanecarboxylic acid, 3-(2-(1-(4-Chloro-2-fluorobenzyl)-3-(trifluoromethyl)-4,5-dihydro-1H-pyrazolo[3,4-c]pyridin-6(7H)-yl)-2-oxoethyl)cyclopentanecarboxylic acid, 3-(2-(1-(4-Fluorobenzyl)-3-(trifluoromethyl)-4,5-dihydro-1H-pyrazolo[3,4-c]pyridin-6(7H)-yl)-2-oxoethyl)cyclopentanecarboxylic acid, 3-(2-(1-(4-Chloro-2-fluorobenzyl)-3-(trifluoromethyl)-4,5-dihydro-1H-pyrazolo[3,4-c]pyridin-6(7H)-yl)-2-oxoethyl)cyclobutanecarboxylic acid, 3-(2-(1-(4-Fluorobenzyl)-3-(trifluoromethyl)-4,5-dihydro-1H-pyrazolo[3,4-c]pyridin-6(7H)-yl)-2-oxoethyl)cyclobutanecarboxylic acid, 8-(2-(1-(4-Chloro-2-fluorobenzyl)-3-(trifluoromethyl)-4,5-dihydro-1H-pyrazolo[3,4-c]pyridin-6(7H)-yl)-2-oxoethyl)bicyclo[3.2.1]octane-3-carboxylic acid, 4-(2-(1-(4-Fluorobenzyl)-3-(trifluoromethyl)-4,5-dihydro-1H-pyrazolo[3,4-c]pyridin-6(7H)-yl)-2-oxoethyl)-1-methylcyclohexanecarboxylic acid, 6-(2-(1-(4-Chloro-2-fluorobenzyl)-3-(trifluoromethyl)-4,5-dihydro-1H-pyrazolo[3,4-c]pyridin-6(7H)-yl)-2-oxoethyl)spiro[3.3]heptane-2-carboxylic acid, 6-(2-(1-(4-Fluorobenzyl)-3-(trifluoromethyl)-4,5-dihydro-1H-pyrazolo[3,4-c]pyridin-6(7H)-yl)-2-oxoethyl)spiro[3.3]heptane-2-carboxylic acid, 3-(2-(1-(4-Chloro-2-fluorobenzyl)-3-(trifluoromethyl)-4,5-dihydro-1H-pyrazolo[3,4-c]pyridin-6(7H)-yl)-2-oxoethyl)-2,2-dimethylcyclobutanecarboxylic acid, 3-(2-(1-(4-Fluorobenzyl)-3-(trifluoromethyl)-4,5-dihydro-1H-pyrazolo[3,4-c]pyridin-6(7H)-yl)-2-oxoethyl)-2,2-dimethylcyclobutanecarboxylic acid, (3R,4R)-5-(2-(1-(4-Chloro-2-fluorobenzyl)-3-(trifluoromethyl)-4,5-dihydro-1H-pyrazolo[3,4-c]pyridin-6(7H)-yl)-2-oxoethyl)tricyclo[2.2.1.02,6]heptane-3-carboxylic acid, (3R,4R)-5-(2-(1-(4-Fluorobenzyl)-3-(trifluoromethyl)-4,5-dihydro-1H-pyrazolo[3,4-c]pyridin-6(7H)-yl)-2-oxoethyl)tricyclo[2.2.1.02,6]heptane-3-carboxylic acid, trans-4-(2-(1-(4-Fluorobenzyl)-3-(trifluoromethyl)-4,5-dihydro-1H-pyrazolo[3,4-c]pyridin-6(7H)-yl)-2-oxoethyl)cyclohexanecarboxylic acid, cis-4-(2-(1-(4-fluorobenzyl)-3-(trifluoromethyl)-4,5-dihydro-1H-pyrazolo[3,4-c]pyridin-6(7H)-yl)-2-oxoethyl)cyclohexanecarboxylic acid, trans-4-(2-(1-(4-Chloro-2-fluorobenzyl)-4,5-dihydro-1H-pyrazolo[3,4-c]pyridin-6(7H)-yl)-2-oxoethyl)cyclohexanecarboxylic acid, cis-4-(2-(1-(4-chloro-2-fluorobenzyl)-4,5-dihydro-1H-pyrazolo[3,4-c]pyridin-6(7H)-yl)-2-oxoethyl)cyclohexanecarboxylic acid, trans-4-(2-(1-(4-Chlorobenzyl)-3-(trifluoromethyl)-4,5-dihydro-1H-pyrazolo[3,4-c]pyridin-6(7H)-yl)-2-oxoethyl)cyclohexanecarboxylic acid, cis-4-(2-(1-(4-chlorobenzyl)-3-(trifluoromethyl)-4,5-dihydro-1H-pyrazolo[3,4-c]pyridin-6(7H)-yl)-2-oxoethyl)cyclohexanecarboxylic acid, trans-4-(2-(1-(2,4-Dichlorobenzyl)-3-(trifluoromethyl)-4,5-dihydro-1H-pyrazolo[3,4-c]pyridin-6(7H)-yl)-2-oxoethyl)cyclohexanecarboxylic acid, cis-4-(2-(1-(2,4-dichlorobenzyl)-3-(trifluoromethyl)-4,5-dihydro-1H-pyrazolo[3,4-c]pyridin-6(7H)-yl)-2-oxoethyl)cyclohexanecarboxylic acid, cis-4-((1-(4-Chloro-2-fluorobenzyl)-3-(trifluoromethyl)-4,5,6,7-tetrahydro-1H-pyrazolo[3,4-c]pyridine-6-carbonyl)oxy)cyclohexanecarboxylic acid, trans-4-((1-(4-chloro-2-fluorobenzyl)-3-(trifluoromethyl)-4,5,6,7-tetrahydro-1H-pyrazolo[3,4-c]pyridine-6-carbonyl)oxy)cyclohexanecarboxylic acid, trans-4-(2-(1-Benzyl-3-(trifluoromethyl)-4,5-dihydro-1H-pyrazolo[3,4-c]pyridin-6(7H)-yl)-2-oxoethyl)cyclohexanecarboxylic acid, cis-4-(2-(1-benzyl-3-(trifluoromethyl)-4,5-dihydro-1H-pyrazolo[3,4-c]pyridin-6(7H)-yl)-2-oxoethyl)cyclohexanecarboxylic acid, trans-4 4-(2-(1-(cyclohexylmethyl)-3-(trifluoromethyl)-4,5-dihydro-1H-pyrazolo[3,4-c]pyridin-6(7H)-yl)-2-oxoethyl)cyclohexanecarboxylic acid, cis-4 4-(2-(1-(cyclohexylmethyl)-3-(trifluoromethyl)-4,5-dihydro-1H-pyrazolo[3,4-c]pyridin-6(7H)-yl)-2-oxoethyl)cyclohexanecarboxylic acid, trans-4-(2-(1-(4-Fluorobenzyl)-4,5-dihydro-1H-pyrazolo[3,4-c]pyridin-6(7H)-yl)-2-oxoethyl)cyclohexanecarboxylic acid, cis-4-(2-(1-(4-Fluorobenzyl)-4,5-dihydro-1H-pyrazolo[3,4-c]pyridin-6(7H)-yl)-2-oxoethyl)cyclohexanecarboxylic acid, trans-4-(1-(4-Fluorobenzyl)-3-(trifluoromethyl)-4,5,6,7-tetrahydro-1H-pyrazolo[3,4-c]pyridine-6-carbonyl)cyclohexanecarboxylic acid, cis-4-(1-(4-fluorobenzyl)-3-(trifluoromethyl)-4,5,6,7-tetrahydro-1H-pyrazolo[3,4-c]pyridine-6-carbonyl)cyclohexanecarboxylic acid, trans-4-(2-(1-cyclohexyl-3-(trifluoromethyl)-4,5-dihydro-1H-pyrazolo[3,4-c]pyridin-6(7H)-yl)-2-oxoethyl)cyclohexanecarboxylic acid, cis-4-(2-(1-cyclohexyl-3-(trifluoromethyl)-4,5-dihydro-1H-pyrazolo[3,4-c]pyridin-6(7H)-yl)-2-oxoethyl)cyclohexanecarboxylic acid, cis-4-(2-(1-(2-Cyclohexylethyl)-3-(trifluoromethyl)-4,5-dihydro-1H-pyrazolo[3,4-c]pyridin-6(7H)-yl)-2-oxoethyl)cyclohexanecarboxylic acid, trans-4-(2-(1-(2-cyclohexylethyl)-3-(trifluoromethyl)-4,5-dihydro-1H-pyrazolo[3,4-c]pyridin-6(7H)-yl)-2-oxoethyl)cyclohexanecarboxylic acid, tert-Butyl 3-(2-(1-(4-chloro-2-fluorobenzyl)-3-(trifluoromethyl)-4,5-dihydro-1H-pyrazolo[3,4-c]pyridin-6(7H)-yl)-2-oxoethyl)-8-azabicyclo[3.2.1]octane-8-carboxylate, tert-Butyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)piperidine-1-carboxylate, tert-Butyl 3-(2-(1-(4-chloro-2-fluorobenzyl)-3-(trifluoromethyl)-4,5-dihydro-1H-pyrazolo[3,4-c]pyridin-6(7H)-yl)-2-oxoethyl)azetidine-1-carboxylate, tert-Butyl 3-(2-(1-(4-fluorobenzyl)-3-(trifluoromethyl)-4,5-dihydro-1H-pyrazolo[3,4-c]pyridin-6(7H)-yl)-2-oxoethyl)piperidine-1-carboxylate, tert-Butyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)-2-methylpiperidine-1-carboxylate, tert-Butyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)-2,2-dimethylpiperidine-1-carboxylate, tert-Butyl 4-(2-(1-(4-chloro-2-fluorobenzyl)-3-(trifluoromethyl)-4,5-dihydro-1H-pyrazolo[3,4-c]pyridin-6(7H)-yl)-2-oxoethyl)-2-(trifluoromethyl)piperidine-1-carboxylate, 2-(8-Aza-bicyclo[3.2.1]octan-3-yl)-1-(1-(4-chloro-2-fluorobenzyl)-3-(trifluoromethyl)-4,5-dihydro-1H-pyrazolo[3,4-c]pyridin-6(7H)-yl)ethanone, 1-(1-(4-Chloro-2-fluorobenzyl)-3-(trifluoromethyl)-4,5-dihydro-1H-pyrazolo[3,4-c]pyridin-6(7H)-yl)-2-(piperidin-4-yl)ethanone, 2-(Azetidin-3-yl)-1-(1-(4-chloro-2-fluorobenzyl)-3-(trifluoromethyl)-4,5-dihydro-1H-pyrazolo[3,4-c]pyridin-6(7H)-yl)ethanone, 1-(1-(4-Fluorobenzyl)-3-(trifluoromethyl)-4,5-dihydro-1H-pyrazolo[3,4-c]pyridin-6(7H)-yl)-2-(piperidin-3-yl)ethanone, 1-(1-(4-Chloro-2-fluorobenzyl)-3-(trifluoromethyl)-4,5-dihydro-1H-pyrazolo[3,4-c]pyridin-6(7H)-yl)-2-(2-methylpiperidin-4-yl)ethanone, 1-(1-(4-Chloro-2-fluorobenzyl)-3-(trifluoromethyl)-4,5-dihydro-1H-pyrazolo[3,4-c]pyridin-6(7H)-yl)-2-(2,2-dimethylpiperidin-4-yl)ethanone, 1-(1-(4-Chloro-2-fluorobenzyl)-3-(trifluoromethyl)-4,5-dihydro-1H-pyrazolo[3,4-c]pyridin-6(7H)-yl)-2-(2-(trifluoromethyl)piperidin-4-yl)ethanone, (2s)-4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)pyrrolidine-2-carboxylic acid, 1-(1-(4-Chloro-2-fluorobenzyl)-3-(trifluoromethyl)-4,5-dihydro-1H-pyrazolo[3,4-c]pyridin-6(7H)-yl)-2-(8-methyl-8-aza-bicyclo[3.2.1]octan-3-yl)ethanone, 1-(1-(4-Chloro-2-fluorobenzyl)-3-(trifluoromethyl)-4,5-dihydro-1H-pyrazolo[3,4-c]pyridin-6(7H)-yl)-2-(1,2-dimethylpiperidin-4-yl)ethanone, 1-(1-(4-Chloro-2-fluorobenzyl)-3-(trifluoromethyl)-4,5-dihydro-1H-pyrazolo[3,4-c]pyridin-6(7H)-yl)-2-(1,2,2-trimethylpiperidin-4-yl)ethanone, 1-(1-(4-Chloro-2-fluorobenzyl)-3-(trifluoromethyl)-4,5-dihydro-1H-pyrazolo[3,4-c]pyridin-6(7H)-yl)-2-(1-methyl-2-(trifluoromethyl)piperidin-4-yl)ethanone, 1-(1-(4-Fluorobenzyl)-3-(trifluoromethyl)-4,5-dihydro-1H-pyrazolo[3,4-c]pyridin-6(7H)-yl)-2-(1-methylpiperidin-3-yl)ethanone formate, 1-(1-(4-Chloro-2-fluorobenzyl)-3-(trifluoromethyl)-4,5-dihydro-1H-pyrazolo[3,4-c]pyridin-6(7H)-yl)-2-(1-isopropylpiperidin-4-yl)ethanone, 1-(1-(4-Chloro-2-fluorobenzyl)-3-(trifluoromethyl)-4,5-dihydro-1H-pyrazolo[3,4-c]pyridin-6(7H)-yl)-2-(1-ethylpiperidin-4-yl)ethanone, 1-(1-(4-Fluorobenzyl)-3-(trifluoromethyl)-4,5-dihydro-1H-pyrazolo[3,4-c]pyridin-6(7H)-yl)-2-(1-isopropylpiperidin-3-yl)ethanone formate, Methyl 1-(2-(1-(4-fluorobenzyl)-3-(trifluoromethyl)-4,5-dihydro-1H-pyrazolo[3,4-c]pyridin-6(7H)-yl)-2-oxoethyl)piperidine-4-carboxylate, 1-(1-(4-Chloro-2-fluorobenzyl)-3-(trifluoromethyl)-4,5-dihydro-1H-pyrazolo[3,4-c]pyridin-6(7H)-yl)-2-(piperidin-1-yl)ethanone, Ethyl 1-(2-(1-(4-chloro-2-fluorobenzyl)-3-(trifluoromethyl)-4,5-dihydro-1H-pyrazolo[3,4-c]pyridin-6(7H)-yl)-2-oxoethyl)piperidine-3-carboxylate, Methyl 8-(2-(1-(4-chloro-2-fluorobenzyl)-3-(trifluoromethyl)-4,5-dihydro-1H-pyrazolo[3,4-c]pyridin-6(7H)-yl)-2-oxoethyl)-8-azabicyclo[3.2.1]octane-3-carboxylate, Ethyl 1-(2-(1-(4-fluorobenzyl)-3-(trifluoromethyl)-4,5-dihydro-1H-pyrazolo[3,4-c]pyridin-6(7H)-yl)-2-oxoethyl)piperidine-3-carboxylate, Ethyl 1-(1-(1-(4-chloro-2-fluorobenzyl)-3-(trifluoromethyl)-4,5-dihydro-1H-pyrazolo[3,4-c]pyridin-6(7H)-yl)-1-oxopropan-2-yl)piperidine-4-carboxylate, Methyl 1-(2-(1-(4-fluorobenzyl)-3-(trifluoromethyl)-4,5-dihydro-1H-pyrazolo[3,4-c]pyridin-6(7H)-yl)-2-oxoethyl)pyrrolidine-3-carboxylate, 1-(1-(4-Chloro-2-fluorobenzyl)-3-(trifluoromethyl)-4,5-dihydro-1H-pyrazolo[3,4-c]pyridin-6(7H)-yl)-2-(4-(trifluoromethyl)piperidin-1-yl)ethanone, Ethyl 3-(2-(1-(4-fluorobenzyl)-3-(trifluoromethyl)-4,5-dihydro-1H-pyrazolo[3,4-c]pyridin-6(7H)-yl)-2-oxoethylamino)propanoate, 1-(2-(1-(4-Fluorobenzyl)-3-(trifluoromethyl)-4,5-dihydro-1H-pyrazolo[3,4-c]pyridin-6(7H)-yl)-2-oxoethyl)piperidine-4-carboxylic acid, 1-(2-(1-(4-Chloro-2-fluorobenzyl)-3-(trifluoromethyl)-4,5-dihydro-1H-pyrazolo[3,4-c]pyridin-6(7H)-yl)-2-oxoethyl)piperidine-4-carboxylic acid, 1-(2-(1-(4-Chloro-2-fluorobenzyl)-3-(trifluoromethyl)-4,5-dihydro-1H-pyrazolo[3,4-c]pyridin-6(7H)-yl)-2-oxoethyl)piperidine-3-carboxylic acid, 8-(2-(1-(4-Chloro-2-fluorobenzyl)-3-(trifluoromethyl)-4,5-dihydro-1H-pyrazolo[3,4-c]pyridin-6(7H)-yl)-2-oxoethyl)-8-azabicyclo[3.2.1]octane-3-carboxylic acid, 8-(2-(1-(4-Fluorobenzyl)-3-(trifluoromethyl)-4,5-dihydro-1H-pyrazolo[3,4-c]pyridin-6(7H)-yl)-2-oxoethyl)-8-azabicyclo[3.2.1]octane-3-carboxylic acid, 9-(2-(1-(4-Fluorobenzyl)-3-(trifluoromethyl)-4,5-dihydro-1H-pyrazolo[3,4-c]pyridin-6(7H)-yl)-2-oxoethyl)-9-azabicyclo[3.3.1]nonane-3-carboxylic acid, 1-(2-(1-(4-Fluorobenzyl)-3-(trifluoromethyl)-4,5-dihydro-1H-pyrazolo[3,4-c]pyridin-6(7H)-yl)-2-oxoethyl)piperidine-3-carboxylic acid, 1-(1-(1-(4-Chloro-2-fluorobenzyl)-3-(trifluoromethyl)-4,5-dihydro-1H-pyrazolo[3,4-c]pyridin-6(7H)-yl)-1-oxopropan-2-yl)piperidine-4-carboxylic acid, 2-(2-(1-(4-Chloro-2-fluorobenzyl)-3-(trifluoromethyl)-4,5-dihydro-1H-pyrazolo[3,4-c]pyridin-6(7H)-yl)-2-oxoethyl)octahydrocyclopenta[c]pyrrole-5-carboxylic acid, 2-(2-(1-(4-Fluorobenzyl)-3-(trifluoromethyl)-4,5-dihydro-1H-pyrazolo[3,4-c]pyridin-6(7H)-yl)-2-oxoethyl)octahydrocyclopenta[c]pyrrole-5-carboxylic acid, 3-((2-(1-(4-Chloro-2-fluorobenzyl)-3-(trifluoromethyl)-4,5-dihydro-1H-pyrazolo[3,4-c]pyridin-6(7H)-yl)-2-oxoethyl)amino)-2,2-dimethylcyclobutanecarboxylic acid, 1-(2-(1-(4-Fluorobenzyl)-3-(trifluoromethyl)-4,5-dihydro-1H-pyrazolo[3,4-c]pyridin-6(7H)-yl)-2-oxoethyl)pyrrolidine-3-carboxylic acid, 2-(1-(2-(1-(4-Chloro-2-fluorobenzyl)-3-(trifluoromethyl)-4,5-dihydro-1H-pyrazolo[3,4-c]pyridin-6(7H)-yl)-2-oxoethyl)piperidin-4-yl)acetic acid, 3-((2-(1-(4-Fluorobenzyl)-3-(trifluoromethyl)-4,5-dihydro-1H-pyrazolo[3,4-c]pyridin-6(7H)-yl)-2-oxoethyl)amino)-2,2-dimethylcyclobutanecarboxylic acid, 2-(1-(2-(1-(4-Fluorobenzyl)-3-(trifluoromethyl)-4,5-dihydro-1H-pyrazolo[3,4-c]pyridin-6(7H)-yl)-2-oxoethyl)piperidin-4-yl)acetic acid, 3-(2-(1-(4-Fluorobenzyl)-3-(trifluoromethyl)-4,5-dihydro-1H-pyrazolo[3,4-c]pyridin-6(7H)-yl)-2-oxoethylamino)propanoic acid, 6-(1-(4-Chloro-2-fluorobenzyl)-3-(trifluoromethyl)-4,5-dihydro-1H-pyrazolo[3,4-c]pyridin-6(7H)-yl)-6-oxohexanoic acid, 5-(1-(4-Chloro-2-fluorobenzyl)-3-(trifluoromethyl)-4,5-dihydro-1H-pyrazolo[3,4-c]pyridin-6(7H)-yl)-5-oxopentanoic acid, 4-(1-(4-Chloro-2-fluorobenzyl)-3-(trifluoromethyl)-4,5-dihydro-1H-pyrazolo[3,4-c]pyridin-6(7H)-yl)-4-oxobutanoic acid, 2-(4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)piperidin-1-yl)acetic acid, 3-(3-(1-(4-Fluorobenzyl)-3-(trifluoromethyl)-4,5,6,7-tetrahydro-1H-pyrazolo[3,4-c]pyridine-6-carbonyl)pyrrolidin-1-yl)propanoic acid, 3-(3-(1-(4-chloro-2-fluorobenzyl)-3-(trifluoromethyl)-4,5,6,7-tetrahydro-1H-pyrazolo[3,4-c]pyridine-6-carbonyl)pyrrolidin-1-yl)propanoic acid, Methyl 3-(2-(1-(4-fluorobenzyl)-3-(trifluoromethyl)-4,5-dihydro-1H-pyrazolo[3,4-c]pyridin-6(7H)-yl)- 2-oxoethyl)piperidine-1-carboxylate, Methyl 3-(2-(1-(4-fluorobenzyl)-3-(trifluoromethyl)-4,5-dihydro-1H-pyrazolo[3,4-c]pyridin-6(7H)-yl)-2-oxoethyl)piperidine-1-carboxylate, and 1-(1-(4-Fluorobenzyl)-3-(trifluoromethyl)-4,5-dihydro-1H-pyrazolo[3,4-c]pyridin-6(7H)-yl)-2-(1-(pyrimidin-2-yl)piperidin-4-yl)ethanone, or a pharmaceutically acceptable salt thereof.

21. The compound of claim 1, wherein the compound is selected from:

1-(1-(4-Chloro-2-fluorobenzyl)-3-(trifluoromethyl)-4,5-dihydro-1H-pyrazolo[3,4-c]pyridin-6(7H)-yl)-2-(tetrahydro-2H-pyran-4-yl)ethanone;

1-(1-(4-Fluorobenzyl)-3-(trifluoromethyl)-4,5-dihydro-1H-pyrazolo[3,4-c]pyridin-6(7H)-yl)-2-(tetrahydro-2H-pyran-4-yl)ethanone;

1-(1-(4-Chloro-2-fluorobenzyl)-3-(trifluoromethyl)-4,5-dihydro-1H-pyrazolo[3,4-c]pyridin-6(7H)-yl)-3-(1H-tetrazol-5-yl)propan-1-one;

1-(1-(4-Fluorobenzyl)-3-(trifluoromethyl)-4,5-dihydro-1H-pyrazolo[3,4-c]pyridin-6(7H)-yl)-3-(1H-tetrazol-5-yl)propan-1-one;

1-(1-(4-Chloro-2-fluorobenzyl)-3-(trifluoromethyl)-4,5-dihydro-1H-pyrazolo[3,4-c]pyridin-6(7H)-yl)-2-(octahydroindolizin-7-yl)ethanone;

1-(1-(4-Fluorobenzyl)-3-(trifluoromethyl)-4,5-dihydro-1H-pyrazolo[3,4-c]pyridin-6(7H)-yl)-2-(octahydroindolizin-7-yl)ethanone;

(1-(4-Fluorobenzyl)-3-(trifluoromethyl)-4,5-dihydro-1H-pyrazolo[3,4-c]pyridin-6(7H)-yl)(quinuclidin-3-yl)methanone;

(1-(4-Fluorobenzyl)-3-(trifluoromethyl)-4,5-dihydro-1H-pyrazolo[3,4-c]pyridin-6(7H)-yl)(quinuclidin-4-yl)methanone;

1-(1-(4-Fluorobenzyl)-3-(trifluoromethyl)-4,5-dihydro-1H-pyrazolo[3,4-c]pyridin-6(7H)-yl)-2-(quinuclidin-3-yl)ethanone;

trans-Ethyl 4-(2-(3-(difluoromethyl)-1-(4-fluorobenzyl)-4,5-dihydro-1H-pyrazolo[3,4-c]pyridin-6(7H)-yl)-2-oxoethyl)cyclohexanecarboxylate;

trans-Ethyl 4-(2-(3-cyclopropyl-1-(4-fluorobenzyl)-4,5-dihydro-1H-pyrazolo[3,4-c]pyridin-6(7H)-yl)-2-oxoethyl)cyclohexanecarboxylate;

Ethyl 6-(2-(trans-4-(ethoxycarbonyl)cyclohexyl)acetyl)-1-(4-fluorobenzyl)-4,5,6,7-tetrahydro-1H-pyrazolo[3,4-c]pyridine-3-carboxylate;

trans-Ethyl-4-(2-(1-(4-fluorobenzyl)-3-(hydroxymethyl)-4,5-dihydro-1H-pyrazolo[3,4-c]pyridin-6(7H)-yl)-2-oxoethyl)cyclohexanecarboxylate;

trans-Ethyl-4-(2-oxo-2-(1-(thiophen-3-ylmethyl)-3-(trifluoromethyl)-4,5-dihydro-1H-pyrazolo[3,4-c]pyridin-6(7H)-yl)ethyl)cyclohexanecarboxylate;

trans-Ethyl-4-(2-oxo-2-(1-(thiophen-2-ylmethyl)-3-(trifluoromethyl)-4,5-dihydro-1H-pyrazolo[3,4-c]pyridin-6(7H)-yl)ethyl)cyclohexanecarboxylate;

trans-Ethyl 4-(2-oxo-2-(1-(thiazol-5-ylmethyl)-3-(trifluoromethyl)-4,5-dihydro-1H-pyrazolo[3,4-c]pyridin-6(7H)-yl)ethyl)cyclohexanecarboxylate;

trans-Ethyl 4-(2-(1-((4-methylcyclohexyl)methyl)-3-(trifluoromethyl)-4,5-dihydro-1H-pyrazolo[3,4-c]pyridin-6(7H)-yl)-2-oxoethyl)cyclohexanecarboxylate;

trans-Ethyl 4-(2-(1-(2,4-difluorobenzyl)-3-(trifluoromethyl)-4,5-dihydro-1H-pyrazolo[3,4-c]pyridin-6(7H)-yl)-2-oxoethyl)cyclohexanecarboxylate;

trans-4-(2-Oxo-2-(1-(pyridin-3-ylmethyl)-3-(trifluoromethyl)-4,5-dihydro-1H-pyrazolo[3,4-c]pyridin-6(7H)-yl)ethyl)cyclohexanecarboxylic acid;

trans-4-(2-Oxo-2-(1-(pyridin-2-ylmethyl)-3-(trifluoromethyl)-4,5-dihydro-1H-pyrazolo[3,4-c]pyridin-6(7H)-yl)ethyl)cyclohexanecarboxylic acid;

trans-4-(2-Oxo-2-(1-(pyridin-4-ylmethyl)-3-(trifluoromethyl)-4,5-dihydro-1H-pyrazolo[3,4-c]pyridin-6(7H)-yl)ethyl)cyclohexanecarboxylic acid;

cis-4-(2-(1-((5-Chlorothiophen-2-yl)methyl)-3-(trifluoromethyl)-4,5-dihydro-1H-pyrazolo[3,4-c]pyridin-6(7H)-yl)-2-oxoethyl)cyclohexanecarboxylic acid;

trans-4-(2-Oxo-2-(1-(thiophen-2-ylmethyl)-3-(trifluoromethyl)-4,5-dihydro-1H-pyrazolo[3,4-c]pyridin-6(7H)-yl)ethyl)cyclohexanecarboxylic acid;

trans-4-(2-Oxo-2-(1-(thiophen-3-ylmethyl)-3-(trifluoromethyl)-4,5-dihydro-1H-pyrazolo[3,4-c]pyridin-6(7H)-yl)ethyl)cyclohexanecarboxylic acid;

trans-4-(2-Oxo-2-(1-(thiazol-5-ylmethyl)-3-(trifluoromethyl)-4,5-dihydro-1H-pyrazolo[3,4-c]pyridin-6(7H)-yl)ethyl)cyclohexanecarboxylic acid;

trans-4-(2-Oxo-2-(1-(pyrimidin-5-ylmethyl)-3-(trifluoromethyl)-4,5-dihydro-1H-pyrazolo[3,4-c]pyridin-6(7H)-yl)ethyl)cyclohexanecarboxylic acid;

trans-4-(2-(1-(2,4-Difluorobenzyl)-3-(trifluoromethyl)-4,5-dihydro-1H-pyrazolo[3,4-c]pyridin-6(7H)-yl)-2-oxoethyl)cyclohexanecarboxylic acid;

trans-4-(2-(1-(3,4-Difluorobenzyl)-3-(trifluoromethyl)-4,5-dihydro-1H-pyrazolo[3,4-c]pyridin-6(7H)-yl)-2-oxoethyl)cyclohexanecarboxylic acid;

trans-4-(2-(1-(2,4,5-Trifluorobenzyl)-3-(trifluoromethyl)-4,5-dihydro-1H-pyrazolo[3,4-c]pyridin-6(7H)-yl)-2-oxoethyl)cyclohexanecarboxylic acid;

trans-4-(2-(1-(3,4,5-Trifluorobenzyl)-3-(trifluoromethyl)-4,5-dihydro-1H-pyrazolo[3,4-c]pyridin-6(7H)-yl)-2-oxoethyl)cyclohexanecarboxylic acid;

cis-4-(2-(1-(2,4-Difluorobenzyl)-3-(trifluoromethyl)-4,5-dihydro-1H-pyrazolo[3,4-c]pyridin-6(7H)-yl)-2-oxoethyl)cyclohexanecarboxylic acid;

cis-4-(2-(1-(4-Cyanobenzyl)-3-(trifluoromethyl)-4,5-dihydro-1H-pyrazolo[3,4-c]pyridin-6(7H)-yl)-2-oxoethyl)cyclohexanecarboxylic acid;

trans-4-(2-(1-((4-Methylcyclohexyl)methyl)-3-(trifluoromethyl)-4,5-dihydro-1H-pyrazolo[3,4-c]pyridin-6(7H)-yl)-2-oxoethyl)cyclohexanecarboxylic acid;

trans-4-(2-(3-Cyclopropyl-1-(4-fluorobenzyl)-4,5-dihydro-1H-pyrazolo[3,4-c]pyridin-6(7H)-yl)-2-oxoethyl)cyclohexanecarboxylic acid;

trans-4-(2-(3-(Difluoromethyl)-1-(4-fluorobenzyl)-4,5-dihydro-1H-pyrazolo[3,4-c]pyridin-6(7H)-yl)-2-oxoethyl)cyclohexanecarboxylic acid;

trans-4-(2-(1-(4-Fluorobenzyl)-3-(hydroxymethyl)-4,5-dihydro-1H-pyrazolo[3,4-c]pyridin-6(7H)-yl)-2-oxoethyl)cyclohexanecarboxylic acid;

2-(trans-4-(2-(1-(4-Fluorobenzyl)-3-(trifluoromethyl)-4,5-dihydro-1H-pyrazolo[3,4-c]pyridin-6(7H)-yl)-2-oxoethyl)cyclohexyl)acetic acid;

2-(cis-4-(2-(1-(4-Fluorobenzyl)-3-(trifluoromethyl)-4,5-dihydro-1H-pyrazolo[3,4-c]pyridin-6(7H)-yl)-2-oxoethyl)cyclohexyl)acetic acid;

4-(1-(4-Fluorobenzyl)-3-(trifluoromethyl)-4,5,6,7-tetrahydro-1H-pyrazolo[3,4-c]pyridine-6-carbonyl)bicyclo[2.2.1]heptane-1-carboxylic acid;

4-(1-(4-Fluorobenzyl)-3-(trifluoromethyl)-4,5,6,7-tetrahydro-1H-pyrazolo[3,4-c]pyridine-6-carbonyl)bicyclo[2.2.1]heptane-1-carboxylic acid;

4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)bicyclo[2.2.1]heptane-1-carboxylic acid;

4-(2-(1-(4-Fluorobenzyl)-3-(trifluoromethyl)-4,5-dihydro-1H-pyrazolo[3,4-c]pyridin-6(7H)-yl)-2-oxoethyl)bicyclo[2.2.1]heptane-1-carboxylic acid;

4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)adamantancarboxylic acid;

1-(1-(4-Fluorobenzyl)-3-(trifluoromethyl)-4,5-dihydro-1H-pyrazolo[3,4-c]pyridin-6(7H)-yl)-2-(2-azaspiro[3.3]heptan-6-yl)adamantane carboxylic acid;

(2R)-1-(tert-Butoxycarbonyl)-4-(2-(1-(4-chloro-2-fluorobenzyl)-3-(trifluoromethyl)-4,5-dihydro-1H-pyrazolo[3,4-c]pyridin-6(7H)-yl)-2-oxoethyl)pyrrolidine-2-carboxylic acid;

3-(2-(1-(4-Chloro-2-fluorobenzyl)-3-(trifluoromethyl)-4,5-dihydro-1H-pyrazolo[3,4-c]pyridin-6(7H)-yl)-2-oxoethyl)-1-methylcyclobutanecarboxylic acid;

cis-3-(2-(1-(4-Fluorobenzyl)-3-(trifluoromethyl)-4,5-dihydro-1H-pyrazolo[3,4-c]pyridin-6(7H)-yl)-2-oxoethyl)-1-methylcyclobutanecarboxylic acid;

trans-3-(2-(1-(4-fluorobenzyl)-3-(trifluoromethyl)-4,5-dihydro-1H-pyrazolo[3,4-c]pyridin-6(7H)-yl)-2-oxoethyl)-1-methylcyclobutanecarboxylic acid;

cis-4-(2-(1-(4-fluorobenzyl)-3-(trifluoromethyl)-4,5-dihydro-1H-pyrazolo[3,4-c]pyridin-6(7H)-yl)-2-oxoethyl)-1-methylcyclohexanecarboxylic acid;

trans-4-(2-(1-(4-fluorobenzyl)-3-(trifluoromethyl)-4,5-dihydro-1H-pyrazolo[3,4-c]pyridin-6(7H)-yl)-2-oxoethyl)-1-methylcyclohexanecarboxylic acid;

trans-4-(2-(1-(4-fluorobenzyl)-3-(trifluoromethyl)-4,5-dihydro-1H-pyrazolo[3,4-c]pyridin-6(7H)-yl)-2-oxoethyl)-1-methylcyclohexanecarboxylic acid;

tert-Butyl 2-ethyl-4-(2-(1-(4-fluorobenzyl)-3-(trifluoromethyl)-4,5-dihydro-1H-pyrazolo[3,4-c]pyridin-6(7H)-yl)-2-oxoethyl)piperidine-1-carboxylate;

tert-Butyl 4-(2-(1-(4-fluorobenzyl)-3-(trifluoromethyl)-4,5-dihydro-1H-pyrazolo[3,4-c]pyridin-6(7H)-yl)-2-oxoethyl)-2-propylpiperidine-1-carboxylate;

tert-Butyl 4-(1-(4-fluorobenzyl)-3-(trifluoromethyl)-4,5,6,7-tetrahydro-1H-pyrazolo[3,4-c]pyridine-6-carbonyl)bicyclo[2.2.2]octan-1-ylcarbamate;

(4-Aminobicyclo[2.2.2]octan-1-yl)(1-(4-fluorobenzyl)-3-(trifluoromethyl)-4,5-dihydro-1H-pyrazolo[3,4-c]pyridin-6(7H)-yl)methanone;

2-(4-Aminobicyclo[2.2.2]octan-1-yl)-1-(1-(4-fluorobenzyl)-3-(trifluoromethyl)-4,5-dihydro-1H-pyrazolo[3,4-c]pyridin-6(7H)-yl)ethanone;

2-(2-Ethylpiperidin-4-yl)-1-(1-(4-fluorobenzyl)-3-(trifluoromethyl)-4,5-dihydro-1H-pyrazolo[3,4-c]pyridin-6(7H)-yl)ethanone;

1-(1-(4-Fluorobenzyl)-3-(trifluoromethyl)-4,5-dihydro-1H-pyrazolo[3,4-c]pyridin-6(7H)-yl)-2-(2-propylpiperidin-4-yl)ethanone acid;

1-(1-(4-Fluorobenzyl)-3-(trifluoromethyl)-4,5-dihydro-1H-pyrazolo[3,4-c]pyridin-6(7H)-yl)-2-(2-(trifluoromethyl)piperidin-4-yl)ethanone;

(2R)-4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)pyrrolidine-2-carboxylic acid;

1-(1-(4-Chloro-2-fluorobenzyl)-3-(trifluoromethyl)-4,5-dihydro-1H-pyrazolo[3,4-c]pyridin-6(7H)-yl)-2-(morpholin-2-yl)ethanone;

1-(1-(4-Fluorobenzyl)-3-(trifluoromethyl)-4,5-dihydro-1H-pyrazolo[3,4-c]pyridin-6(7H)-yl)-2-(morpholin-2-yl)ethanone;

2-(cis-4-Aminocyclohexyl)-1-(1-(4-chloro-2-fluorobenzyl)-3-(trifluoromethyl)-4,5-dihydro-1H-pyrazolo[3,4-c]pyridin-6(7H)-yl)ethanone;

2-(cis-4-Aminocyclohexyl)-1-(1-(4-fluorobenzyl)-3-(trifluoromethyl)-4,5-dihydro-1H-pyrazolo[3,4-c]pyridin-6(7H)-yl)ethanone;

2-(trans-4-aminocyclohexyl)-1-(1-(4-chloro-2-fluorobenzyl)-3-(trifluoromethyl)-4,5-dihydro-1H-pyrazolo[3,4-c]pyridin-6(7H)-yl)ethanone;

2-(trans-4-Aminocyclohexyl)-1-(1-(4-fluorobenzyl)-3-(trifluoromethyl)-4,5-dihydro-1H-pyrazolo[3,4-c]pyridin-6(7H)-yl)ethanone;

1-(1-(4-Chloro-2-fluorobenzyl)-3-(trifluoromethyl)-4,5-dihydro-1H-pyrazolo[3,4-c]pyridin-6(7H)-yl)-2-(octahydrocyclopenta[c]pyrrol-5-yl)ethanone;

(1-(4-Fluorobenzyl)-3-(trifluoromethyl)-4,5-dihydro-1H-pyrazolo[3,4-c]pyridin-6(7H)-yl)(4-(methylamino)bicyclo[2.2.2]octan-1-yl)methanone;

1-(1-(4-Fluorobenzyl)-3-(trifluoromethyl)-4,5-dihydro-1H-pyrazolo[3,4-c]pyridin-6(7H)-yl)-2-(pyrrolidin-3-yl)ethanone;

1-(1-(4-Fluorobenzyl)-3-(trifluoromethyl)-4,5-dihydro-1H-pyrazolo[3,4-c]pyridin-6(7H)-yl)-2-(1-methylpyrrolidin-3-yl)ethanone;

1-(1-(4-Fluorobenzyl)-3-(trifluoromethyl)-4,5-dihydro-1H-pyrazolo[3,4-c]pyridin-6(7H)-yl)-2-(1-isopropylpyrrolidin-3-yl)ethanone;

2-(2-Ethyl-1-methylpiperidin-4-yl)-1-(1-(4-fluorobenzyl)-3-(trifluoromethyl)-4,5-dihydro-1H-pyrazolo[3,4-c]pyridin-6(7H)-yl)ethanone;

1-(1-(4-Fluorobenzyl)-3-(trifluoromethyl)-4,5-dihydro-1H-pyrazolo[3,4-c]pyridin-6(7H)-yl)-2-(1-methyl-2-propylpiperidin-4-yl)ethanone acid;

1-(1-(4-Fluorobenzyl)-3-(trifluoromethyl)-4,5-dihydro-1H-pyrazolo[3,4-c]pyridin-6(7H)-yl)-2-(1-methyl-2-propylpiperidin-4-yl)ethanone acid;

(2R)-4-(2-(1-(4-chloro-2-fluorobenzyl)-3-(trifluoromethyl)-4,5-dihydro-1H-pyrazolo[3,4-c]pyridin-6(7H)-yl)-2-oxoethyl)-1-methylpyrrolidine-2-carboxylic acid;

(2S)-4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)-1-methylpyrrolidine-2-carboxylic acid;

(2S)-4-(2-(1-(4-Chloro-2-fluorobenzyl)-3-(trifluoromethyl)-4,5-dihydro-1H-pyrazolo[3,4-c]pyridin-6(7H)-yl)-2-oxoethyl)-1-isopropylpyrrolidine-2-carboxylic acid;

1-(2-(1-(4-Fluorobenzyl)-3-(trifluoromethyl)-4,5-dihydro-1H-pyrazolo[3,4-c]pyridin-6(7H)-yl)-2-oxoethyl)piperidine-4-carbonitrile;
1-(2-(1-(4-Fluorobenzyl)-3-(trifluoromethyl)-4,5-dihydro-1H-pyrazolo[3,4-c]pyridin-6(7H)-yl)-2-oxoethyl)pyrrolidine-3-carbonitrile;
1-(2-(1-(4-Fluorobenzyl)-3-(trifluoromethyl)-4,5-dihydro-1H-pyrazolo[3,4-c]pyridin-6(7H)-yl)-2-oxoethyl)azetidine-3-carbonitrile;
1-(1-(4-Chloro-2-fluorobenzyl)-3-(trifluoromethyl)-4,5-dihydro-1H-pyrazolo[3,4-c]pyridin-6(7H)-yl)-2-(4-methylpiperidin-1-yl)ethanone;
1-(1-(4-Fluorobenzyl)-3-(trifluoromethyl)-4,5-dihydro-1H-pyrazolo[3,4-c]pyridin-6(7H)-yl)-2-(4-methylpiperidin-1-yl)ethanone;
1-(1-(4-Fluorobenzyl)-3-(trifluoromethyl)-4,5-dihydro-1H-pyrazolo[3,4-c]pyridin-6(7H)-yl)-2-(4-(trifluoromethyl)piperidin-1-yl)ethanone;
Ethyl 1-(2-(1-(4-fluorobenzyl)-3-(trifluoromethyl)-4,5-dihydro-1H-pyrazolo[3,4-c]pyridin-6(7H)-yl)-2-oxoethyl)azepane-4-carboxylate;
Ethyl 1-(2-(1-(4-fluorobenzyl)-3-(trifluoromethyl)-4,5-dihydro-1H-pyrazolo[3,4-c]pyridin-6(7H)-yl)-2-oxoethyl)azepane-4-carboxylate;
Methyl 9-(2-(1-(4-fluorobenzyl)-3-(trifluoromethyl)-4,5-dihydro-1H-pyrazolo[3,4-c]pyridin-6(7H)-yl)-2-oxoethyl)-3-oxa-9-azabicyclo[3.3.1]nonane-7-carboxylate;
Methyl 2-(1-(2-(1-(4-fluorobenzyl)-3-(trifluoromethyl)-4,5-dihydro-1H-pyrazolo[3,4-c]pyridin-6(7H)-yl)-2-oxoethyl)azetidin-3-yl)acetate;
1-(2-(1-(4-Chloro-2-fluorobenzyl)-3-(trifluoromethyl)-4,5-dihydro-1H-pyrazolo[3,4-c]pyridin-6(7H)-yl)-2-oxoethyl)azetidine-3-carboxylic acid;
1-(2-(1-(4-Fluorobenzyl)-3-(trifluoromethyl)-4,5-dihydro-1H-pyrazolo[3,4-c]pyridin-6(7H)-yl)-2-oxoethyl)azetidine-3-carboxylic acid;
1-(2-(1-(4-Fluorobenzyl)-3-(trifluoromethyl)-4,5-dihydro-1H-pyrazolo[3,4-c]pyridin-6(7H)-yl)-2-oxoethyl)azepane-4-carboxylic acid;
1-(2-(1-(4-Chloro-2-fluorobenzyl)-3-(trifluoromethyl)-4,5-dihydro-1H-pyrazolo[3,4-c]pyridin-6(7H)-yl)-2-oxoethyl)azepane-4-carboxylic acid;
2-(2-(1-(4-Chloro-2-fluorobenzyl)-3-(trifluoromethyl)-4,5-dihydro-1H-pyrazolo[3,4-c]pyridin-6(7H)-yl)-2-oxoethyl)-2-azaspiro[3.3]heptane-6-carboxylic acid;
2-(1-(2-(1-(4-Chloro-2-fluorobenzyl)-3-(trifluoromethyl)-4,5-dihydro-1H-pyrazolo[3,4-c]pyridin-6(7H)-yl)-2-oxoethyl)azetidin-3-yl)acetic acid;
2-(1-(2-(1-(4-Fluorobenzyl)-3-(trifluoromethyl)-4,5-dihydro-1H-pyrazolo[3,4-c]pyridin-6(7H)-yl)-2-oxoethyl)azetidin-3-yl)acetic acid;
2-(1-(2-(1-(4-Chloro-2-fluorobenzyl)-3-(trifluoromethyl)-4,5-dihydro-1H-pyrazolo[3,4-c]pyridin-6(7H)-yl)-2-oxoethyl)pyrrolidin-3-yl)acetic acid;
2-(1-(2-(1-(4-Fluorobenzyl)-3-(trifluoromethyl)-4,5-dihydro-1H-pyrazolo[3,4-c]pyridin-6(7H)-yl)-2-oxoethyl)pyrrolidin-3-yl)acetic acid;
9-(2-(1-(4-Fluorobenzyl)-3-(trifluoromethyl)-4,5-dihydro-1H-pyrazolo[3,4-c]pyridin-6(7H)-yl)-2-oxoethyl)-3-oxa-9-azabicyclo[3.3.1]nonane-7-carboxylic acid;
9-(2-(1-(4-Chloro-2-fluorobenzyl)-3-(trifluoromethyl)-4,5-dihydro-1H-pyrazolo[3,4-c]pyridin-6(7H)-yl)-2-oxoethyl)-3-oxa-9-azabicyclo[3.3.1]nonane-7-carboxylic acid;
cis-3-(2-(1-(4-Fluorobenzyl)-3-(trifluoromethyl)-4,5-dihydro-1H-pyrazolo[3,4-c]pyridin-6(7H)-yl)-2-oxoethylamino)cyclobutanecarboxylic acid;
trans-3-(2-(1-(4-Fluorobenzyl)-3-(trifluoromethyl)-4,5-dihydro-1H-pyrazolo[3,4-c]pyridin-6(7H)-yl)-2-oxoethylamino)cyclobutanecarboxylic acid;
cis-4-(2-(1-(4-Fluorobenzyl)-3-(trifluoromethyl)-4,5-dihydro-1H-pyrazolo[3,4-c]pyridin-6(7H)-yl)-2-oxoethylamino)cyclohexanecarboxylic acid;
trans-4-(2-(1-(4-Fluorobenzyl)-3-(trifluoromethyl)-4,5-dihydro-1H-pyrazolo[3,4-c]pyridin-6(7H)-yl)-2-oxoethylamino)cyclohexanecarboxylic acid;
3-(2-(1-(4-Chloro-2-fluorobenzyl)-3-(trifluoromethyl)-4,5-dihydro-1H-pyrazolo[3,4-c]pyridin-6(7H)-yl)-2-oxoethylamino)propanoic acid;
2-(3-(1-(4-Fluorobenzyl)-3-(trifluoromethyl)-4,5,6,7-tetrahydro-1H-pyrazolo[3,4-c]pyridine-6-carbonyl)pyrrolidin-1-yl)acetic acid;
2-(3-(1-(4-Chloro-2-fluorobenzyl)-3-(trifluoromethyl)-4,5,6,7-tetrahydro-1H-pyrazolo[3,4-c]pyridine-6-carbonyl)pyrrolidin-1-yl)acetic acid;
1-(1-(4-Fluorobenzyl)-3-(trifluoromethyl)-4,5-dihydro-1H-pyrazolo[3,4-c]pyridin-6(7H)-yl)-2-(1-(pyridin-2-yl)piperidin-4-yl)ethanone;
1-(1-(4-Fluorobenzyl)-3-(trifluoromethyl)-4,5-dihydro-1H-pyrazolo[3,4-c]pyridin-6(7H)-yl)-2-(1-(pyrimidin-4-yl)piperidin-4-yl)ethanone;
1-(1-(4-Fluorobenzyl)-3-(trifluoromethyl)-4,5-dihydro-1H-pyrazolo[3,4-c]pyridin-6(7H)-yl)-2-(1-(pyridin-4-yl)piperidin-4-yl)ethanone;
trans-4-(2-(1-(4-Fluorobenzyl)-3-(trifluoromethyl)-4,5-dihydro-1H-pyrazolo[3,4-c]pyridin-6(7H)-yl)-2-oxoethyl)-N (methylsulfonyl)cyclohexane-carboxamide;
trans-4-(2-(1-(4-Fluorobenzyl)-3-(trifluoromethyl)-4,5-dihydro-1H-pyrazolo[3,4-c]pyridin-6(7H)-yl)-2-oxoethyl)-N-(methylsulfonyl)cyclohexanecarboxamide;
cis-4-(2-(1-(4-Fluorobenzyl)-3-(trifluoromethyl)-4,5-dihydro-1H-pyrazolo[3,4-c]pyridin-6(7H)-yl)-2-oxoethyl)cyclohexanecarboxamide;
trans-4-(2-(1-(4-Fluorobenzyl)-3-(trifluoromethyl)-4,5-dihydro-1H-pyrazolo[3,4-c]pyridin-6(7H)-yl)-2-oxoethyl)cyclohexanecarboxamide;
cis-4-(2-(1-(4-Fluorobenzyl)-3-(trifluoromethyl)-4,5-dihydro-1H-pyrazolo[3,4-c]pyridin-6(7H)-yl)-2-oxoethyl)cyclohexanecarbonitrile;
trans-4-(2-(1-(4-Fluorobenzyl)-3-(trifluoromethyl)-4,5-dihydro-1H-pyrazolo[3,4-c]pyridin-6(7H)-yl)-2-oxoethyl)cyclohexanecarbonitrile;
2-(3-(Azetidin-1-yl)cyclobutyl)-1-(1-(4-fluorobenzyl)-3-(trifluoromethyl)-4,5-dihydro-1H-pyrazolo[3,4-c]pyridin-6(7H)-yl)ethanone;
1-(1-(4-Fluorobenzyl)-3-(trifluoromethyl)-4,5-dihydro-1H-pyrazolo[3,4-c]pyridin-6(7H)-yl)-2-(octahydroindolizin-7-yl)ethanone;
1-(1-(4-Fluorobenzyl)-3-(trifluoromethyl)-4,5-dihydro-1H-pyrazolo[3,4-c]pyridin-6(7H)-yl)-2-(3-(pyrrolidin-1-yl)cyclobutyl)ethanone;
1-(1-(4-Fluorobenzyl)-3-(trifluoromethyl)-4,5-dihydro-1H-pyrazolo[3,4-c]pyridin-6(7H)-yl)-2-(3-(piperidin-1-yl)cyclobutyl)ethanone;
1-(1-(4-Fluorobenzyl)-3-(trifluoromethyl)-4,5-dihydro-1H-pyrazolo[3,4-c]pyridin-6(7H)-yl)-2-(3-morpholinocyclobutyl)ethanone;
2-(4-(Azetidin-1-yl)cyclohexyl)-1-(1-(4-fluorobenzyl)-3-(trifluoromethyl)-4,5-dihydro-1H-pyrazolo[3,4-c]pyridin-6(7H)-yl)ethanone;

2-(cis-4-(3,3-Difluoroazetidin-1-yl)cyclohexyl)-1-(1-(4-fluorobenzyl)-3-(trifluoromethyl)-4,5-dihydro-1H-pyrazolo[3,4-c]pyridin-6(7H)-yl)ethanone;

2-(trans-4-(3,3-difluoroazetidin-1-yl)cyclohexyl)-1-(1-(4-fluorobenzyl)-3-(trifluoromethyl)-4,5-dihydro-1H-pyrazolo[3,4-c]pyridin-6(7H)-yl)ethanone;

1-(1-(4-Fluorobenzyl)-3-(trifluoromethyl)-4,5-dihydro-1H-pyrazolo[3,4-c]pyridin-6(7H)-yl)-2-(4-(pyrrolidin-1-yl)cyclohexyl)ethanone; and 1-(1-(4-Fluorobenzyl)-3-(trifluoromethyl)-4,5-dihydro-1H-pyrazolo[3,4-c]pyridin-6(7H)-yl)-2-(4-morpholinocyclohexyl)ethanone;

or a pharmaceutically acceptable salt thereof.

* * * * *